US010869798B2

(12) United States Patent
Jackson et al.

(10) Patent No.: US 10,869,798 B2
(45) Date of Patent: Dec. 22, 2020

(54) PATIENT POSITIONING SUPPORT APPARATUS WITH VIRTUAL PIVOT-SHIFT PELVIC PADS, UPPER BODY STABILIZATION AND FAIL-SAFE TABLE ATTACHMENT MECHANISM

(71) Applicant: WARSAW ORTHOPEDIC, INC., Warsaw, IN (US)

(72) Inventors: Roger P. Jackson, Prairie Village, KS (US); Lawrence E. Guerra, Mission, KS (US); Trevor A. Waggoner, Kansas City, KS (US); Steven R. Walton, Olathe, KS (US); Michael A. Herron, Overland Park, KS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 516 days.

(21) Appl. No.: 15/421,994

(22) Filed: Feb. 1, 2017

(65) Prior Publication Data

US 2017/0181908 A1 Jun. 29, 2017

Related U.S. Application Data

(63) Continuation of application No. 14/012,434, filed on Aug. 28, 2013, now Pat. No. 9,642,760, which is a (Continued)

(51) Int. Cl.
*A61G 13/04* (2006.01)
*A61G 13/06* (2006.01)
(Continued)

(52) U.S. Cl.
CPC ............ *A61G 13/04* (2013.01); *A61B 5/4836* (2013.01); *A61B 5/704* (2013.01); *A61B 5/7425* (2013.01);
(Continued)

(58) Field of Classification Search
CPC ........ A61G 13/02; A61G 13/04; A61G 13/06; A61G 13/08; A61G 13/00; A61G 13/10;
(Continued)

(56) References Cited

U.S. PATENT DOCUMENTS

| 377,377 A | 2/1888 | Ferry |
| 392,743 A | 11/1888 | Millen |

(Continued)

FOREIGN PATENT DOCUMENTS

| CN | 2467091 Y | 12/2001 | |
| EP | 1498096 A1 * | 1/2005 | ............. A61G 13/02 |

(Continued)

OTHER PUBLICATIONS

Brochure of Smith & Nephew on Spinal Positioning System, 2003, 2004.

(Continued)

*Primary Examiner* — Nicholas F Polito

(57) ABSTRACT

A patient support apparatus for supporting a patient in a prone position during a surgical procedure is provided, including an open fixed frame suspended above a floor and a pair of spaced opposed radially sliding joints cooperating with the frame, each joint including a virtual pivot point and an arc of motion spaced from the virtual pivot point, the joints being movable along the arc providing a pivot ship mechanism for a pair of pelvic pads attached to the joints. A base for supporting and suspending a patient support structure above the floor, for supporting a patient during a surgical procedure, the base including a pair of spaced opposed vertical translation subassemblies reversibly attachable to a patient support structure, a cross-bar, and a rotation subassembly having two degrees of rotational freedom;

(Continued)

wherein a location of each vertical translation subassembly is substantially constant during operation of the patient support structure.

28 Claims, 259 Drawing Sheets

Related U.S. Application Data continuation-in-part of application No. 13/956,704, filed on Aug. 1, 2013, now Pat. No. 9,468,576, and a continuation-in-part of application No. 13/694,392, filed on Nov. 28, 2012, now abandoned.

(60) Provisional application No. 61/742,098, filed on Aug. 2, 2012, provisional application No. 61/852,199, filed on Mar. 15, 2013, provisional application No. 61/849,016, filed on Jan. 17, 2013, provisional application No. 61/849,035, filed on Jan. 17, 2013, provisional application No. 61/795,649, filed on Oct. 22, 2012, provisional application No. 61/743,240, filed on Aug. 29, 2012, provisional application No. 61/629,815, filed on Nov. 28, 2011.

(51) Int. Cl.
| | |
|---|---|
| *A61G 13/08* | (2006.01) |
| *A61G 13/10* | (2006.01) |
| *A61G 13/00* | (2006.01) |
| *A61G 13/12* | (2006.01) |
| *A61G 13/02* | (2006.01) |
| *G06F 19/00* | (2018.01) |
| *A61B 5/00* | (2006.01) |
| *A61G 7/00* | (2006.01) |
| *A61G 7/005* | (2006.01) |
| *A61G 7/008* | (2006.01) |
| *A61G 7/012* | (2006.01) |
| *A61G 7/015* | (2006.01) |
| *A61G 7/018* | (2006.01) |
| *G06F 3/0484* | (2013.01) |
| *A61B 17/00* | (2006.01) |
| *A61G 7/002* | (2006.01) |

(52) U.S. Cl.
CPC .............. *A61G 7/001* (2013.01); *A61G 7/005* (2013.01); *A61G 7/008* (2013.01); *A61G 7/012* (2013.01); *A61G 7/015* (2013.01); *A61G 7/018* (2013.01); *A61G 13/0036* (2013.01); *A61G 13/0054* (2016.11); *A61G 13/02* (2013.01); *A61G 13/06* (2013.01); *A61G 13/08* (2013.01); *A61G 13/101* (2013.01); *A61G 13/104* (2013.01); *A61G 13/121* (2013.01); *A61G 13/122* (2013.01); *A61G 13/123* (2013.01); *A61G 13/1205* (2013.01); *A61G 13/1235* (2013.01); *G06F 3/04842* (2013.01); *G06F 19/32* (2013.01); *A61B 2017/00022* (2013.01); *A61G 7/002* (2013.01)

(58) Field of Classification Search
CPC ............ A61G 13/1285; A61G 13/0036; A61G 13/101
See application file for complete search history.

(56) References Cited

U.S. PATENT DOCUMENTS

| | | |
|---|---|---|
| 430,635 A | 6/1890 | Fox |
| 769,415 A | 9/1904 | Smock |
| 987,423 A | 3/1911 | Barnett |
| 1,032,743 A | 7/1912 | Courtney |
| 1,046,430 A | 12/1912 | Beitz |
| 1,098,209 A | 5/1914 | Allen |
| 1,098,477 A | 6/1914 | Cashman |
| 1,143,618 A | 6/1915 | Ewald |
| 1,160,451 A | 11/1915 | Sanford |
| 1,171,713 A | 2/1916 | Gilkerson |
| 1,356,467 A | 10/1920 | Payne |
| 1,404,482 A | 1/1922 | Sawyer |
| 1,482,439 A | 2/1924 | McCullough |
| 1,524,399 A | 1/1925 | Krueger |
| 1,528,835 A | 3/1925 | McCullough |
| 1,667,982 A | 5/1928 | Pearson |
| 1,780,399 A | 11/1930 | Munson |
| 1,799,692 A | 4/1931 | Knott |
| 1,938,006 A | 12/1933 | Blanchard |
| 1,990,357 A | 2/1935 | Ward |
| 2,188,592 A | 1/1940 | Hosken et al. |
| 2,261,297 A | 11/1941 | Seib |
| 2,411,768 A | 11/1946 | Welch |
| 2,475,003 A | 7/1949 | Black |
| 2,636,793 A | 4/1953 | Meyer |
| 2,688,410 A | 9/1954 | Nelson |
| 2,792,945 A | 5/1957 | Brenny |
| 3,046,071 A | 7/1962 | Shampaine et al. |
| 3,049,726 A | 8/1962 | Getz |
| 3,281,141 A | 10/1966 | Smiley et al. |
| 3,302,218 A | 2/1967 | Stryker |
| 3,584,321 A | 6/1971 | Buchanan |
| 3,599,964 A | 8/1971 | Magni |
| 3,640,416 A | 2/1972 | Temple |
| 3,766,384 A | 10/1973 | Anderson |
| 3,814,414 A | 6/1974 | Chapa |
| 3,827,089 A | 8/1974 | Grow |
| 3,832,742 A | 9/1974 | Stryker |
| 3,868,103 A | 2/1975 | Pageot et al. |
| 3,937,054 A | 2/1976 | Hortvet et al. |
| 3,988,790 A | 11/1976 | Mracek et al. |
| 4,101,120 A | 7/1978 | Seshima |
| 4,131,802 A | 12/1978 | Braden et al. |
| 4,144,880 A | 3/1979 | Daniels |
| 4,148,472 A | 4/1979 | Rais et al. |
| 4,175,550 A | 11/1979 | Leininger et al. |
| 4,186,917 A | 2/1980 | Rais et al. |
| 4,195,829 A | 4/1980 | Reser |
| 4,227,269 A | 10/1980 | Johnston |
| 4,230,100 A | 10/1980 | Moon |
| 4,244,358 A | 1/1981 | Pyers |
| 4,292,962 A | 10/1981 | Krause |
| 4,391,438 A | 7/1983 | Heffington, Jr. |
| 4,435,861 A | 3/1984 | Lindley |
| 4,474,364 A | 10/1984 | Brendgord |
| 4,503,844 A | 3/1985 | Siczek |
| 4,552,346 A | 11/1985 | Schnelle et al. |
| 4,712,781 A | 12/1987 | Watanabe |
| 4,715,073 A | 12/1987 | Butler |
| 4,718,077 A | 1/1988 | Moore et al. |
| 4,763,643 A | 8/1988 | Vrzalik |
| 4,771,785 A | 9/1988 | Duer |
| 4,830,337 A | 5/1989 | Ichiro et al. |
| 4,850,775 A | 7/1989 | Lee et al. |
| 4,862,529 A | 9/1989 | Peck |
| 4,872,656 A | 10/1989 | Brendgord et al. |
| 4,872,657 A | 10/1989 | Lussi |
| 4,887,325 A | 12/1989 | Tesch |
| 4,937,901 A | 7/1990 | Brennan |
| 4,939,801 A | 7/1990 | Schaal et al. |
| 4,944,500 A | 7/1990 | Mueller et al. |
| 4,953,245 A | 9/1990 | Jung |
| 4,970,737 A | 11/1990 | Sagel |
| 4,989,848 A | 2/1991 | Monroe |
| 5,013,018 A | 5/1991 | Sicek et al. |
| 5,088,706 A | 2/1992 | Jackson |
| 5,131,103 A | 7/1992 | Thomas et al. |
| 5,131,105 A | 7/1992 | Harrawood et al. |
| 5,131,106 A | 7/1992 | Jackson |
| 5,161,267 A | 11/1992 | Smith |
| 5,163,890 A | 11/1992 | Perry, Jr. |

(56) References Cited

U.S. PATENT DOCUMENTS

| | | |
|---|---|---|
| 5,181,289 A | 1/1993 | Kassai |
| 5,208,928 A | 5/1993 | Kuck et al. |
| 5,210,887 A | 5/1993 | Kershaw |
| 5,210,888 A | 5/1993 | Canfield |
| 5,230,112 A | 7/1993 | Harrawood et al. |
| 5,231,741 A | 8/1993 | Maguire |
| 5,239,716 A | 8/1993 | Fisk |
| 5,274,862 A | 1/1994 | Palmer, Jr. |
| 5,294,179 A | 3/1994 | Rudes et al. |
| 5,333,334 A | 8/1994 | Kassai |
| 5,393,018 A | 2/1995 | Roth et al. |
| 5,444,882 A | 8/1995 | Andrews et al. |
| 5,461,740 A | 10/1995 | Pearson |
| 5,468,216 A | 11/1995 | Johnson et al. |
| 5,487,195 A | 1/1996 | Ray |
| 5,499,408 A | 3/1996 | Nix |
| 5,524,304 A | 6/1996 | Shutes |
| 5,544,371 A | 8/1996 | Fuller |
| 5,579,550 A | 12/1996 | Bathrick et al. |
| 5,588,705 A | 12/1996 | Chang |
| 5,613,254 A | 3/1997 | Clayman et al. |
| 5,640,730 A | 6/1997 | Godette |
| 5,645,079 A | 7/1997 | Zahiri et al. |
| 5,658,315 A * | 8/1997 | Lamb .................. A61F 5/04 |
| | | 602/32 |
| 5,659,909 A | 8/1997 | Pfeuffer et al. |
| 5,673,443 A | 10/1997 | Marmor |
| 5,737,781 A | 4/1998 | Votel |
| 5,754,997 A | 5/1998 | Lussi et al. |
| 5,774,914 A | 7/1998 | Johnson et al. |
| 5,794,286 A | 8/1998 | Scott |
| 5,829,077 A | 11/1998 | Neige |
| 5,862,549 A | 1/1999 | Morton et al. |
| 5,870,784 A | 2/1999 | Elliott |
| 5,890,238 A | 4/1999 | Votel |
| 5,901,388 A | 5/1999 | Cowan |
| 5,937,456 A | 8/1999 | Norris |
| 5,940,911 A | 8/1999 | Wang |
| 5,996,151 A | 12/1999 | Bartow et al. |
| 6,000,076 A | 12/1999 | Webster et al. |
| 6,035,465 A | 3/2000 | Rogozinski |
| 6,049,923 A | 4/2000 | Ochiai |
| 6,058,532 A | 5/2000 | Allen |
| 6,109,424 A | 8/2000 | Doan |
| 6,212,713 B1 | 4/2001 | Kuck et al. |
| 6,224,037 B1 | 5/2001 | Novick |
| 6,240,582 B1 | 6/2001 | Reinke |
| 6,260,220 B1 * | 7/2001 | Lamb ................ A61G 13/02 |
| | | 5/601 |
| 6,282,736 B1 | 9/2001 | Hand et al. |
| 6,282,738 B1 | 9/2001 | Heimbrock et al. |
| 6,286,164 B1 | 9/2001 | Lamb et al. |
| 6,287,241 B1 | 9/2001 | Ellis |
| 6,295,666 B1 | 10/2001 | Takaura |
| 6,295,671 B1 | 10/2001 | Reesby et al. |
| 6,315,564 B1 | 11/2001 | Levisman |
| 6,322,251 B1 | 11/2001 | Ballhaus et al. |
| 6,438,777 B1 | 8/2002 | Bender |
| 6,496,991 B1 | 12/2002 | Votel |
| 6,499,162 B1 | 12/2002 | Lu |
| 6,505,365 B1 | 1/2003 | Hanson et al. |
| 6,526,610 B1 | 3/2003 | Hand et al. |
| 6,634,043 B2 | 10/2003 | Lamb et al. |
| 6,638,299 B2 | 10/2003 | Cox |
| 6,662,388 B2 | 12/2003 | Friel |
| 6,668,396 B2 | 12/2003 | Wei |
| 6,681,423 B2 | 1/2004 | Zachrisson |
| 6,701,553 B1 | 3/2004 | Hand et al. |
| 6,779,210 B1 | 8/2004 | Kelly |
| 6,791,997 B2 | 9/2004 | Beyer et al. |
| 6,794,286 B2 | 9/2004 | Aoyama et al. |
| 6,817,363 B2 | 11/2004 | Biondo et al. |
| 6,854,137 B2 | 2/2005 | Johnson |
| 6,857,144 B1 | 2/2005 | Huang |
| 6,862,759 B2 | 3/2005 | Hand et al. |
| 6,885,165 B2 | 4/2005 | Henley et al. |
| 6,971,131 B2 | 12/2005 | Bannister |
| 6,971,997 B1 | 12/2005 | Ryan et al. |
| 7,003,828 B2 | 2/2006 | Roussy |
| 7,055,195 B2 | 6/2006 | Roussy |
| 7,089,612 B2 | 8/2006 | Rocher et al. |
| 7,103,931 B2 | 9/2006 | Somasundaram et al. |
| 7,137,160 B2 | 11/2006 | Hand et al. |
| 7,152,261 B2 | 12/2006 | Jackson |
| 7,171,709 B2 | 2/2007 | Weismiller |
| 7,189,214 B1 | 3/2007 | Saunders |
| 7,197,778 B2 | 4/2007 | Sharps |
| 7,213,279 B2 | 5/2007 | Weismiller et al. |
| 7,234,180 B2 | 6/2007 | Horton et al. |
| 7,290,302 B2 | 11/2007 | Sharps |
| 7,331,557 B2 | 2/2008 | Dewert |
| 7,343,635 B2 | 3/2008 | Jackson |
| 7,428,760 B2 | 9/2008 | McCrimmon |
| 7,437,785 B2 | 10/2008 | Farooqui |
| 7,552,490 B2 | 6/2009 | Saracen et al. |
| 7,565,708 B2 | 7/2009 | Jackson |
| 7,596,820 B2 | 10/2009 | Nielsen et al. |
| 7,653,953 B2 | 2/2010 | Lopez-Sansalvador |
| 7,669,262 B2 | 3/2010 | Skripps et al. |
| 7,739,762 B2 | 6/2010 | Lamb et al. |
| 7,874,030 B2 | 1/2011 | Cho et al. |
| 7,874,695 B2 | 1/2011 | Jensen |
| 7,882,583 B2 | 2/2011 | Skripps |
| 8,056,163 B2 | 11/2011 | Lemire et al. |
| 8,060,960 B2 | 11/2011 | Jackson |
| 8,381,331 B2 | 2/2013 | Sharps et al. |
| 8,584,281 B2 | 11/2013 | Diel et al. |
| 8,635,725 B2 | 1/2014 | Tannoury et al. |
| 8,677,529 B2 | 3/2014 | Jackson |
| 8,707,476 B2 | 4/2014 | Sharps |
| 8,707,484 B2 | 4/2014 | Jackson |
| 8,719,979 B2 | 5/2014 | Jackson |
| 8,826,474 B2 | 9/2014 | Jackson |
| 8,826,475 B2 | 9/2014 | Jackson |
| 8,839,471 B2 | 9/2014 | Jackson |
| 8,844,077 B2 | 9/2014 | Jackson et al. |
| 8,856,986 B2 | 10/2014 | Jackson |
| D720,076 S | 12/2014 | Sharps et al. |
| 8,938,826 B2 | 1/2015 | Jackson |
| 8,978,180 B2 | 3/2015 | Jackson |
| 9,180,062 B2 | 11/2015 | Jackson |
| 9,186,291 B2 | 11/2015 | Jackson et al. |
| 9,198,817 B2 | 12/2015 | Jackson |
| 9,205,013 B2 | 12/2015 | Jackson |
| 9,211,223 B2 | 12/2015 | Jackson |
| 9,265,680 B2 | 2/2016 | Sharps et al. |
| 9,295,433 B2 | 3/2016 | Jackson et al. |
| 2001/0037524 A1 | 11/2001 | Truwit |
| 2002/0170116 A1 | 11/2002 | Borders et al. |
| 2003/0074735 A1 | 4/2003 | Zachrisson |
| 2003/0145383 A1 | 8/2003 | Schwaegerle |
| 2004/0098804 A1 | 5/2004 | Varadharajulu et al. |
| 2004/0133983 A1 | 7/2004 | Newkirk et al. |
| 2004/0168253 A1 | 9/2004 | Hand et al. |
| 2004/0219002 A1 | 11/2004 | Lenaers |
| 2006/0248650 A1 | 11/2006 | Skripps |
| 2007/0056105 A1 | 3/2007 | Hyre et al. |
| 2007/0107126 A1 | 5/2007 | Koch et al. |
| 2007/0157385 A1 | 7/2007 | Lemire et al. |
| 2007/0174965 A1 | 8/2007 | Lemire et al. |
| 2007/0192960 A1 * | 8/2007 | Jackson ................ A61G 7/001 |
| | | 5/618 |
| 2007/0266516 A1 | 11/2007 | Cakmak |
| 2008/0216241 A1 | 9/2008 | Mangiardi |
| 2009/0126116 A1 | 5/2009 | Lamb et al. |
| 2009/0139030 A1 * | 6/2009 | Yang .................. A61B 6/0457 |
| | | 5/619 |
| 2009/0235456 A1 | 9/2009 | Bock |
| 2010/0037397 A1 | 2/2010 | Wood |
| 2010/0107790 A1 | 5/2010 | Yamaguchi |
| 2010/0192300 A1 | 8/2010 | Tannoury et al. |
| 2010/0223728 A1 | 9/2010 | Hutchison et al. |
| 2011/0107517 A1 | 5/2011 | Lamb et al. |
| 2011/0197361 A1 | 8/2011 | Hornbach et al. |

(56) References Cited

U.S. PATENT DOCUMENTS

| | | |
|---|---|---|
| 2012/0005832 A1 | 1/2012 | Turner et al. |
| 2012/0144589 A1 | 6/2012 | Skripps et al. |
| 2012/0174319 A1 | 7/2012 | Menkedick |
| 2012/0198625 A1 | 8/2012 | Jackson |
| 2012/0246829 A1 | 10/2012 | Lamb et al. |
| 2012/0246830 A1 | 10/2012 | Hornbach |
| 2013/0111666 A1 | 5/2013 | Jackson |
| 2013/0133137 A1 | 5/2013 | Jackson |
| 2013/0198958 A1 | 8/2013 | Jackson et al. |
| 2013/0219623 A1 | 8/2013 | Jackson |
| 2013/0254995 A1 | 10/2013 | Jackson |
| 2013/0269710 A1 | 10/2013 | Hight et al. |
| 2013/0282234 A1 | 10/2013 | Roberts et al. |
| 2013/0312187 A1 | 11/2013 | Jackson |
| 2013/0312188 A1 | 11/2013 | Jackson |
| 2014/0007349 A1 | 1/2014 | Jackson |
| 2014/0020181 A1 | 1/2014 | Jackson |
| 2014/0033436 A1 | 2/2014 | Jackson |
| 2014/0068861 A1 | 3/2014 | Jackson et al. |
| 2014/0082842 A1 | 3/2014 | Jackson |
| 2014/0109316 A1 | 4/2014 | Jackson et al. |
| 2014/0173826 A1 | 6/2014 | Jackson |
| 2014/0196212 A1 | 7/2014 | Jackson |
| 2014/0201913 A1 | 7/2014 | Jackson |
| 2014/0201914 A1 | 7/2014 | Jackson |
| 2014/0208512 A1 | 7/2014 | Jackson |
| 2014/0317847 A1 | 10/2014 | Jackson |
| 2015/0007391 A1 | 1/2015 | Xu |
| 2015/0059094 A1 | 3/2015 | Jackson |
| 2015/0113733 A1 | 4/2015 | Diel et al. |
| 2015/0150743 A1 | 6/2015 | Jackson |
| 2016/0000620 A1 | 1/2016 | Koch |
| 2016/0000621 A1 | 1/2016 | Jackson et al. |
| 2016/0000626 A1 | 1/2016 | Jackson et al. |
| 2016/0000627 A1 | 1/2016 | Jackson et al. |
| 2016/0000629 A1 | 1/2016 | Jackson et al. |
| 2016/0008201 A1 | 1/2016 | Jackson |
| 2016/0038364 A1 | 2/2016 | Jackson |
| 2016/0136027 A1 | 5/2016 | Jackson |
| 2016/0166452 A1 | 6/2016 | Jackson et al. |
| 2016/0213542 A1 | 7/2016 | Jackson |
| 2016/0296393 A1 | 10/2016 | Jackson et al. |
| 2016/0296395 A1 | 10/2016 | Jackson et al. |
| 2016/0317372 A1 | 11/2016 | Jackson |
| 2016/0317373 A1 | 11/2016 | Jackson et al. |
| 2016/0346148 A1 | 12/2016 | Jackson et al. |
| 2016/0346149 A1 | 12/2016 | Jackson et al. |

FOREIGN PATENT DOCUMENTS

| | | |
|---|---|---|
| EP | 2226010 B1 | 6/2014 |
| GB | 569758 | 6/1945 |
| GB | 810956 | 3/1959 |
| JP | S53763 | 1/1978 |
| JP | 2000-060995 | 2/2000 |
| JP | 2000-116733 | 4/2000 |
| WO | WO99/07320 | 2/1999 |
| WO | WO 00/07537 | 2/2000 |
| WO | WO2000/062731 | 10/2000 |
| WO | WO2001/060308 | 8/2001 |
| WO | WO 02/078589 A1 | 10/2002 |
| WO | WO2003/070145 | 8/2003 |
| WO | WO 2007/130679 A2 | 11/2007 |
| WO | WO2009/054969 | 4/2009 |
| WO | WO2009/100692 | 8/2009 |
| WO | WO2010/051303 A1 | 5/2010 |

OTHER PUBLICATIONS

Complaint for Patent Infringement, *Jackson v. Mizuho Orthopedic Sys., Inc.*, No. 4:12-CV-01031 (W.D. Mo. Aug. 7, 2012).
First Amended Complaint for Patent Infringement and Correction of Inventorship, *Jackson v. Mizuho Orthopedic Sys., Inc.*, No. 4:12-CV-01031 (W.D. Mo. Sep. 21, 2012).
Defendant Mizuho Orthopedic Systems, Inc.'s Answer to First Amended Complaint and Counterclaims, *Jackson v. Mizuho Orthopedic Sys., Inc.*, No. 4:12-CV-01031 (W.D. Mo. Nov. 1, 2012).
Plaintiff Roger P. Jackson, MD's, Reply to Counterclaims, *Jackson v. Mizuho Orthopedic Sys., Inc.*, No. 4:12-CV-01031 (W.D. Mo. Nov. 26, 2012).
Roger P. Jackson's Disclosure of Asserted Claims and Preliminary Infringement Contentions, *Jackson v. Mizuho Orthopedic Sys., Inc.*, No. 4:12-CV-01031 (W.D. Mo. Jan. 4, 2013).
Second Amended Complaint for Patent Infringement, for Correction of Inventorship, for Breach of a Non-Disclosure and Confidentiality Agreement, and for Misappropriation of Dr. Jackson's Right of Publicity, *Jackson v. Mizuho Orthopedic Sys., Inc.*, No. 4:12-CV-01031 (W.D. Mo. Jan. 28, 2013).
Defendant Mizuho Orthopedic Systems, Inc.'s Answer to Second Amended Complaint and Counterclaims, *Jackson v. Mizuho Orthopedic Sys., Inc.*, No. 4:12-CV-01031 (W.D. Mo. Feb. 19, 2013).
Defendant Mizuho Osi's Invalidity Contentions Pursuant to the Parties' Joint Scheduling Order, *Jackson v. Mizuho Orthopedic Sys., Inc.*, No. 4:12-CV-01031 (W.D. Mo. Feb. 22, 2013).
Plaintiff Roger P. Jackson, MD's, Reply to Second Counterclaims, *Jackson v. Mizuho Orthopedic Sys., Inc.*, No. 4:12-CV-01031 (W.D. Mo. Mar. 12, 2013).
Roger P. Jackson, MD's Disclosure of Proposed Terms to Be Construed, *Jackson v. Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).
Mizuho Orthopedic Systems, Inc.'s Disclosure of Proposed Claim Constructions and Extrinsic Evidence, *Jackson v. Mizuho Orthopedic Sys., Inc.*, No. 4:12-CV-01031 (W.D. Mo. May 13, 2013).
Plaintiff Roger P. Jackson, MD's Disclosure of Preliminary Proposed Claim Constructions, *Jackson v. Mizuho Orthopedic Sys., Inc.*, No. 4:12-CV-01031 (W.D. Mo. May 13, 2013).
Defendant Mizuho Osi's Amended Invalidity Contentions Pursuant to the Parties' Joint Scheduling Order, *Jackson v. Mizuho Orthopedic Sys., Inc.*, No. 4:12-CV-01031 (W.D. Mo. May 15, 2013).
Joint Claim Construction Chart and Joint Prehearing Statement, *Jackson v. Mizuho Orthopedic Sys., Inc.*, No. 4:12-CV-01031 (W.D. Mo. Jun. 7, 2013).
Defendant Mizuho Orthopedic Systems, Inc.'s Objections and Responses to Plaintiff's First Set of Interrogatories, *Jackson v. Mizuho Orthopedic Sys., Inc.*, No. 4:12-CV-01031 (W.D. Mo. Jun. 24, 2013).
Defendant Mizuho Orthopedic Systems, Inc.'s Opening Claim Construction Brief, *Jackson v. Mizuho Orthopedic Sys., Inc.*, No. 4:12-CV-01031 (W.D. Mo. Jul. 31, 2013).
Plaintiff Roger P. Jackson, MD's Opening Claim Construction Brief, *Jackson v. Mizuho Orthopedic Sys., Inc.*, No. 4:12-CV-01031 (W.D. Mo. Jul. 31, 2013).
Appendix A Amended Infringement Contentions Claim Chart for Mizuho's Axis System Compared to U.S. Pat. No. 7,565,708, *Jackson v. Mizuho Orthopedic Sys., Inc.*, No. 4:12-CV-01031 (W.D. Mo. Aug. 12, 2013).
Appendix B Amended Infringement Contentions Claim Chart for Mizuho's Axis System Compared to U.S. Pat. No. 8,060,960, *Jackson v. Mizuho Orthopedic Sys., Inc.*, No. 4:12-CV-01031 (W.D. Mo. Aug. 12, 2013).
Appendix C Amended Infringement Contentions Claim Chart for Mizuho's Proaxis System Compared to U.S. Pat. No. 7,565,708, *Jackson v. Mizuho Orthopedic Sys., Inc.*, No. 4:12-CV-01031 (W.D. Mo. Aug. 12, 2013).
Appendix D Amended Infringement Contentions Claim Chart for Mizuho's Proaxis System Compared to U.S. Pat. No. 8,060,960, *Jackson v. Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson v. Mizuho Orthopedic Sys., Inc.*, No. 4:12-CV-01031 (W.D. Mo. Aug. 16, 2013).

(56) References Cited

OTHER PUBLICATIONS

Defendant Mizuho Orthopedic Systems, Inc's Brief in Response to Plaintiff's Opening Claim Construction Brief, *Jackson* v. *Mizuho Orthopedic Sys., Inc.*, No. 4:12-CV-01031 (W.D. Mo. Aug. 16, 2013).
Plaintiff Roger P. Jackson, Md's Suggestions in Support of His Motion to Strike Exhibit A of Mizuho's Opening Claim Construction Brief, *Jackson* v. *Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiff's Motion to Strike, *Jackson* v. *Mizuho Orthopedic Sys., Inc.*, No. 4:12-CV-01031 (W.D. Mo. Sep. 3, 2013).
Transcript of Claim Construction Hearing, *Jackson* v. *Mizuho Orthopedic Sys., Inc.*, No. 4:12-CV-01031 (W.D. Mo. Oct. 11, 2013).
Plaintiff Roger P. Jackson, MD's Claim Construction Presentation for U.S. District Judge Nanette K. Laughrey, *Jackson* v. *Mizuho Orthopedic Sys., Inc.*, No. 4:12-CV-01031 (W.D. Mo. Oct. 11, 2013).
Mizuho's Claim Construction Argument, *Jackson* v. *Mizuho Orthopedic Sys., Inc.*, No. 4:12-CV-01031 (W.D. Mo. Oct. 11, 2013).
Order, *Jackson* v. *Mizuho Orthopedic Sys., Inc.*, No. 4:12-CV-01031 (W.D. Mo. Apr. 4, 2014).
Brochure of OSI on Modular Table System 90D, pp. 1-15, date of first publication: Unknown.
Pages from website http://www.schaerermayfieldusa.com, pp. 1-5, date of first publication: Unknown.
European Search Report, EP11798501.0, dated Mar. 30, 2015.
Canadian Office Action, CA2803110, dated Mar. 5, 2015.
Chinese Office Action, CN 201180039162.0, dated Jan. 19, 2015.
Japanese Office Action, JP 2014-142074, dated Jun. 18, 2015.
Japanese Office Action, JP 2014-132463, dated Jun. 18, 2015.
Quayle Action, U.S. Appl. No. 14/792,216, dated Sep. 9, 2015.
Australian Patent Examination Report No. 2, AU2014200274, dated Oct. 9, 2015.
European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.
Japanese Office Action, JP 2016-041088, dated Apr. 12, 2016.
U.S. Appl. No. 15/341,167, filed Nov. 2, 2016, Jackson et al.
U.S. Appl. No. 15/431,439, filed Feb. 13, 2017, Jackson.

\* cited by examiner

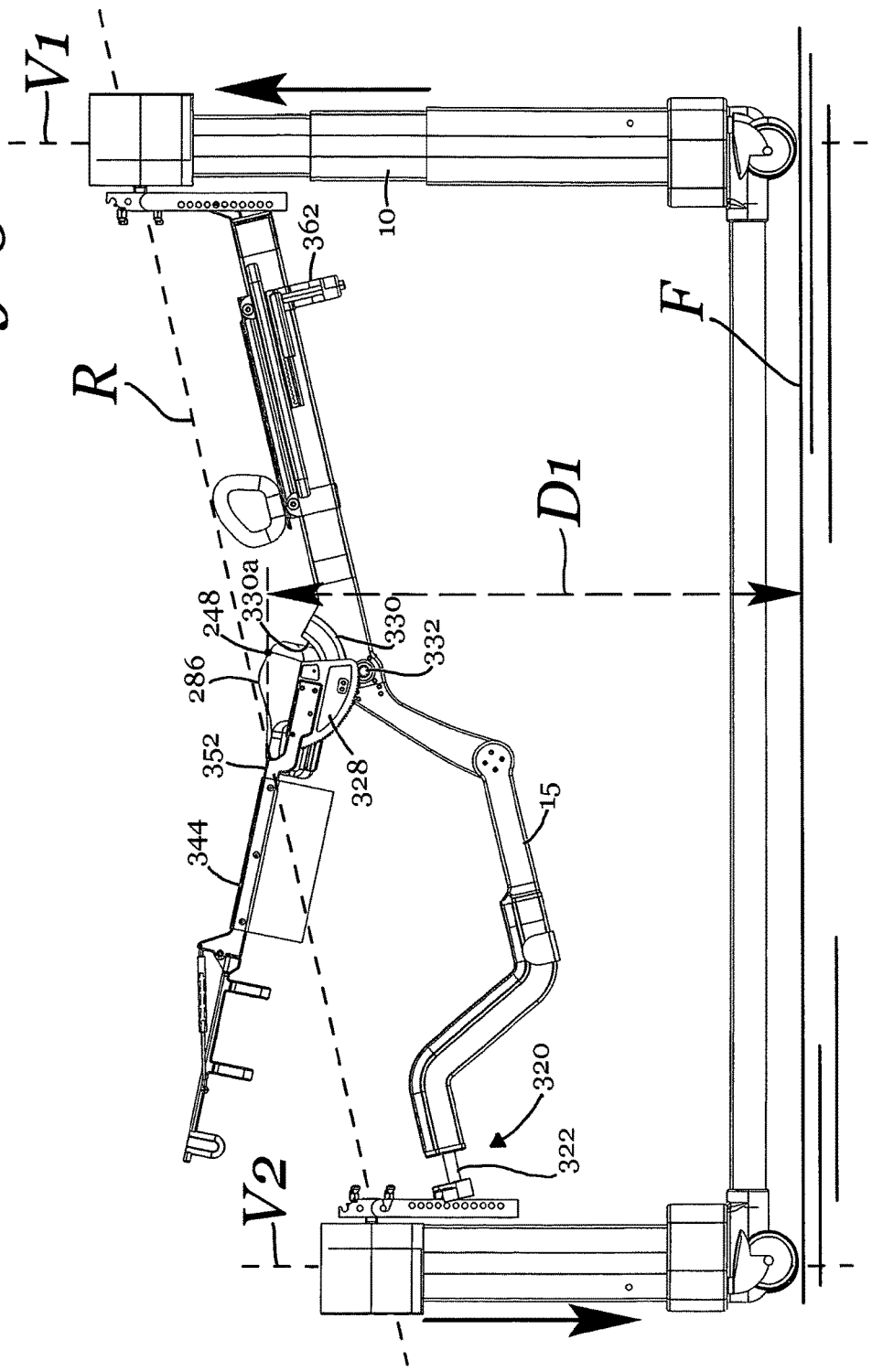

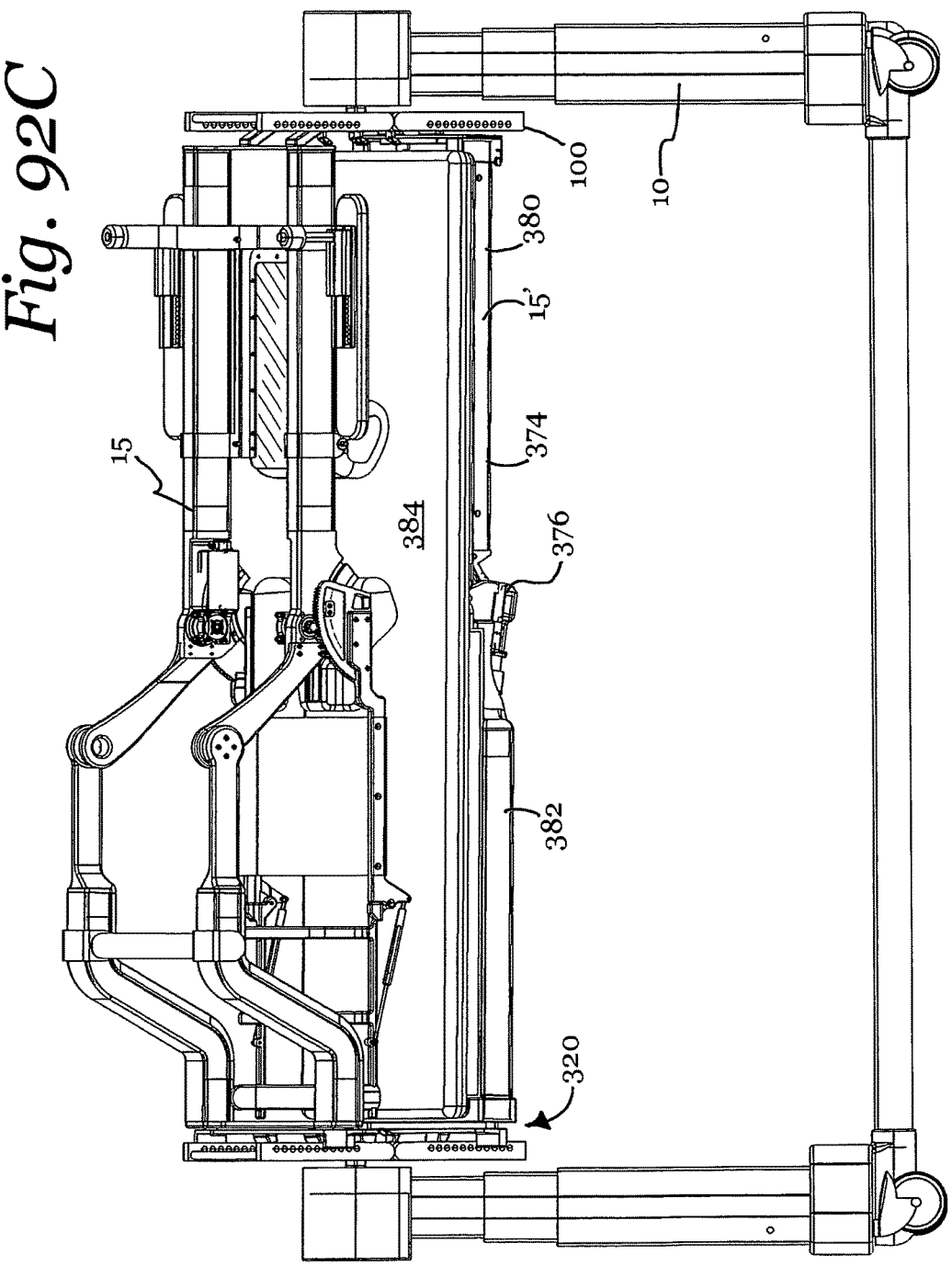

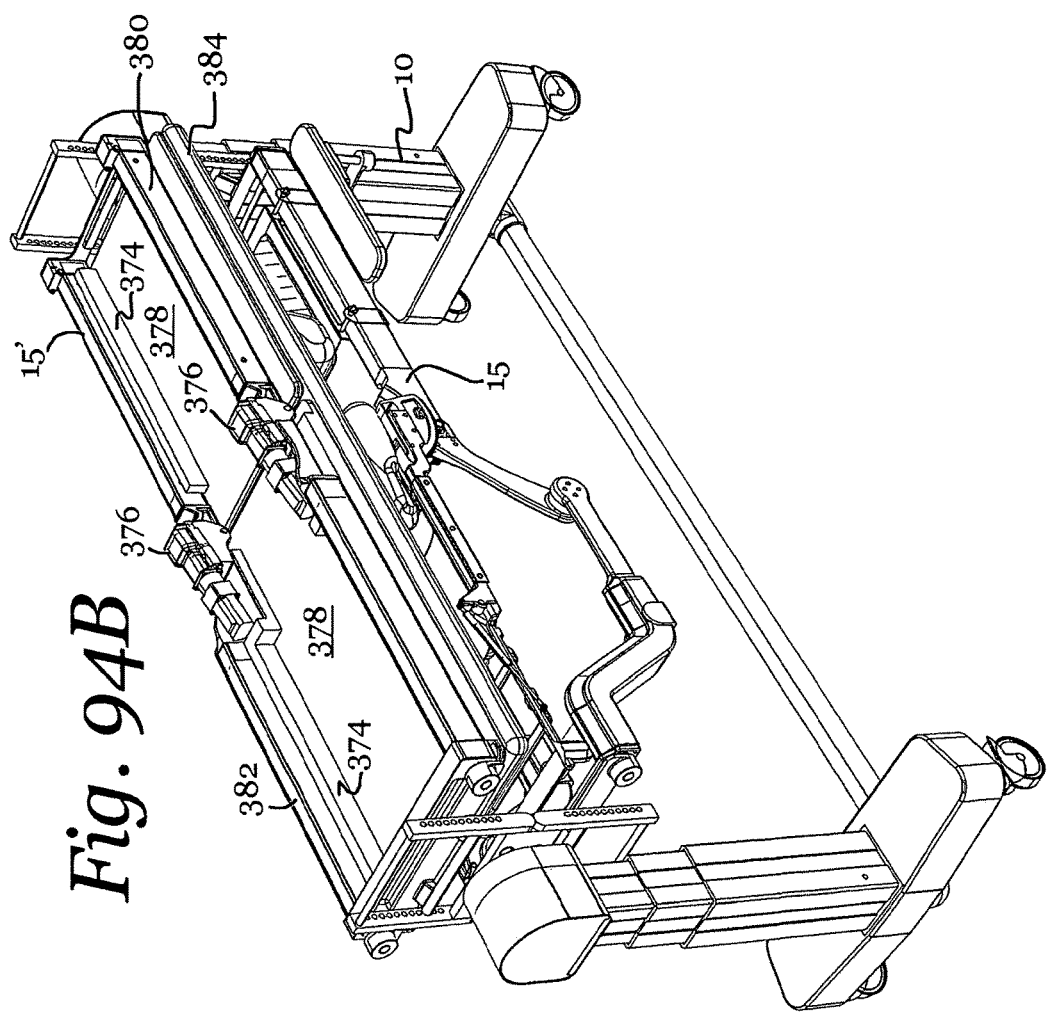

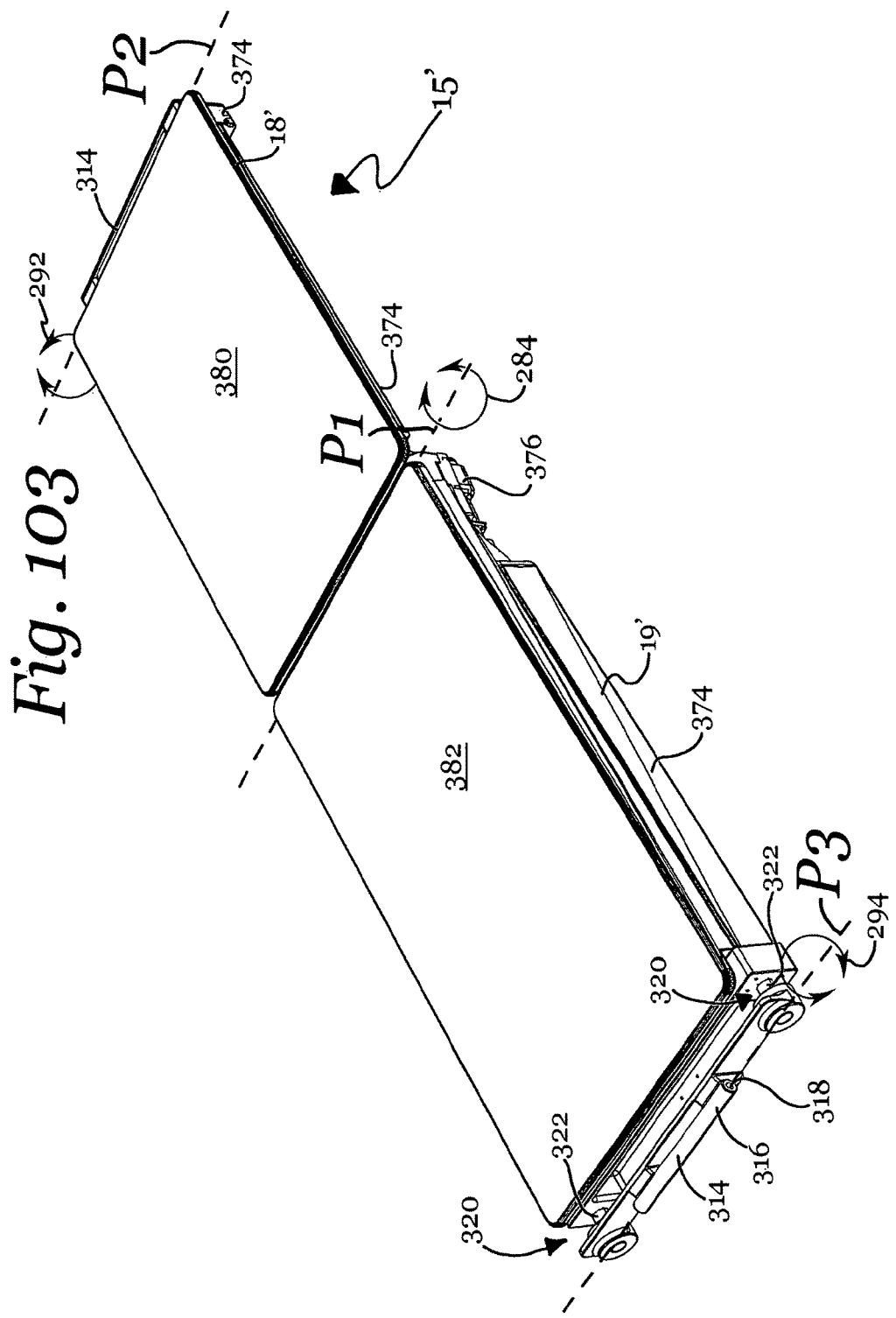

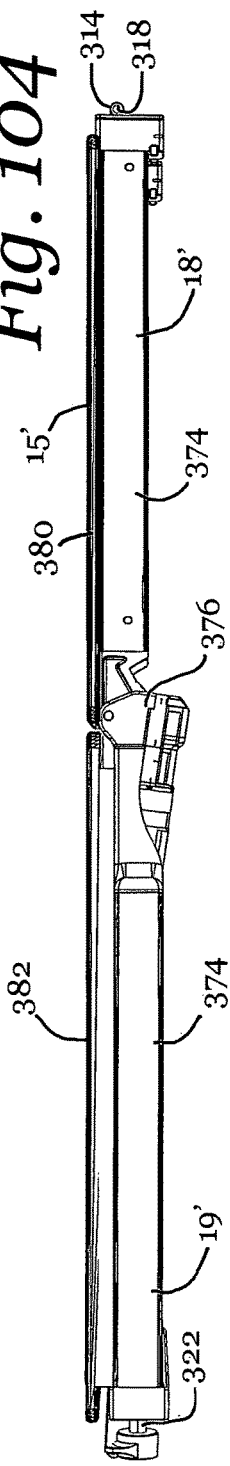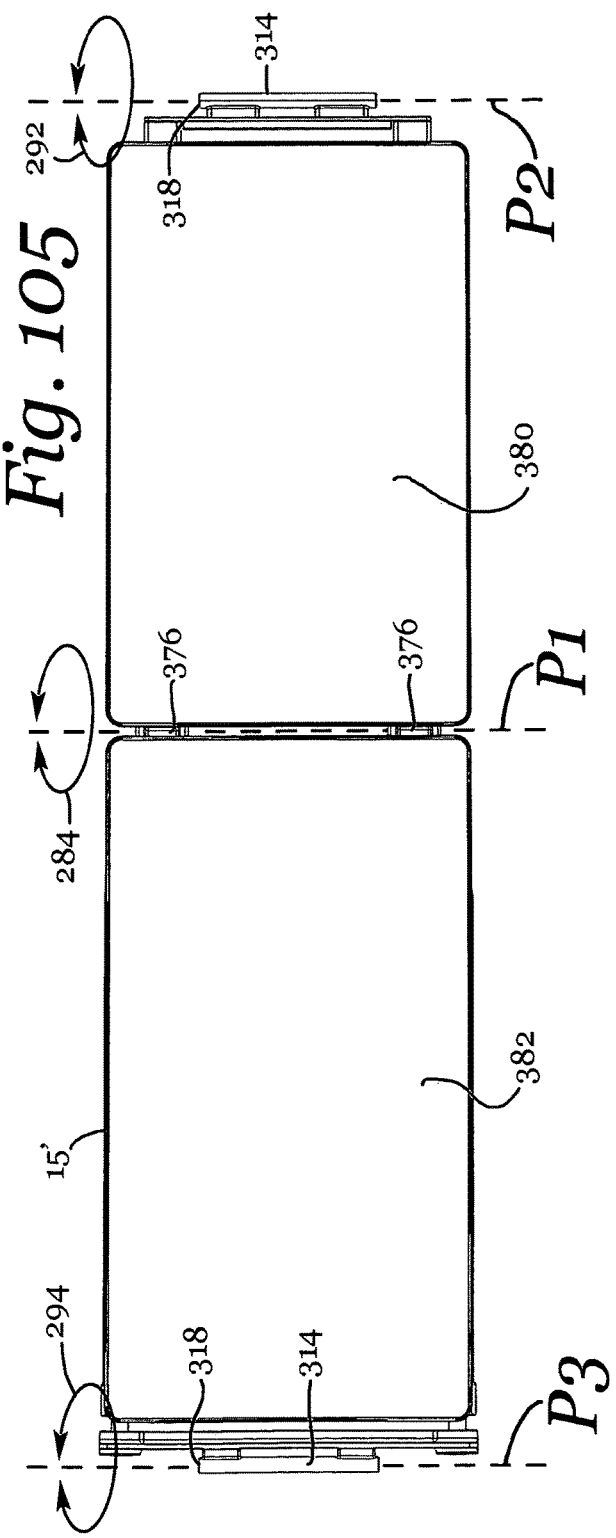

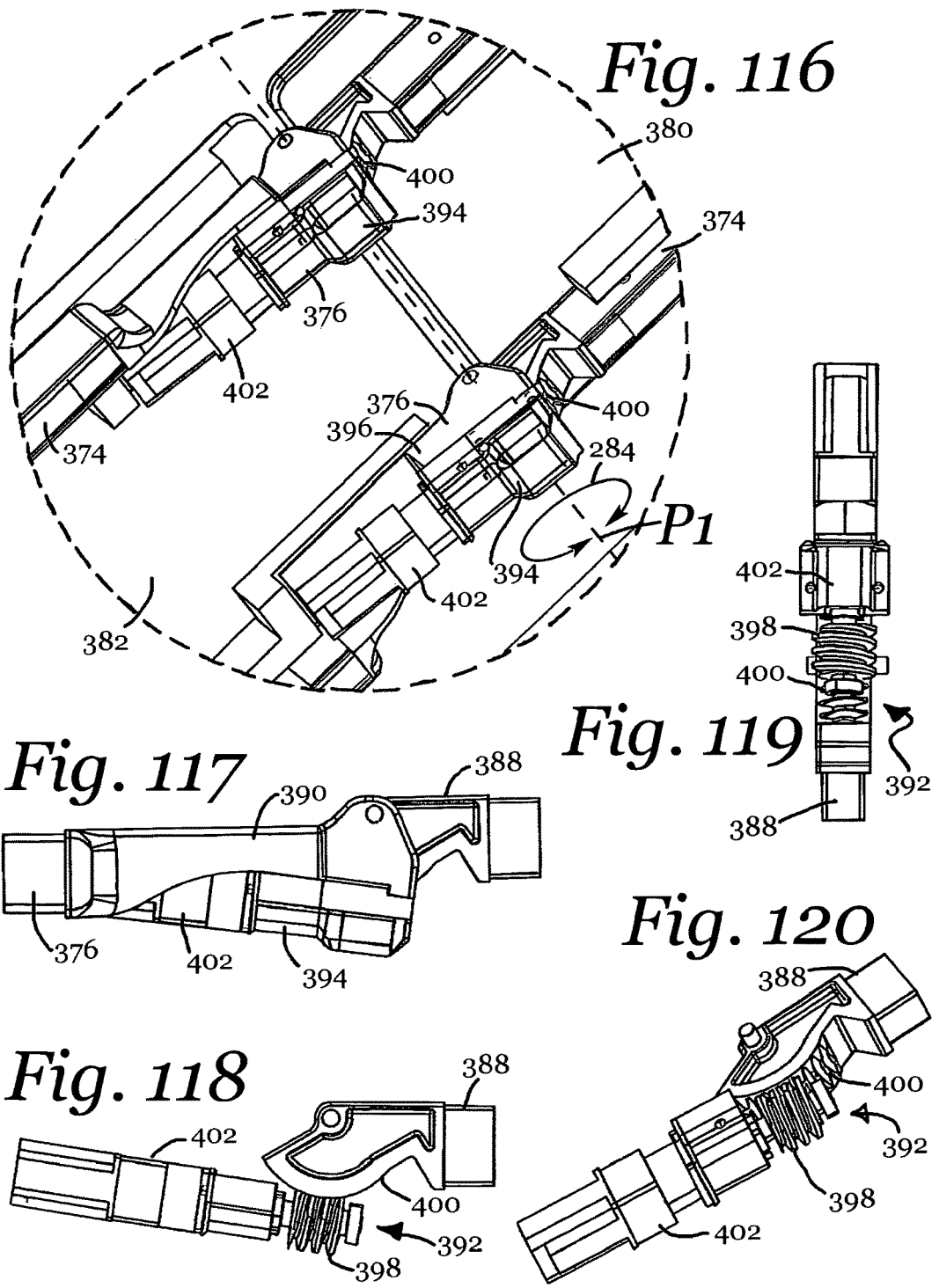

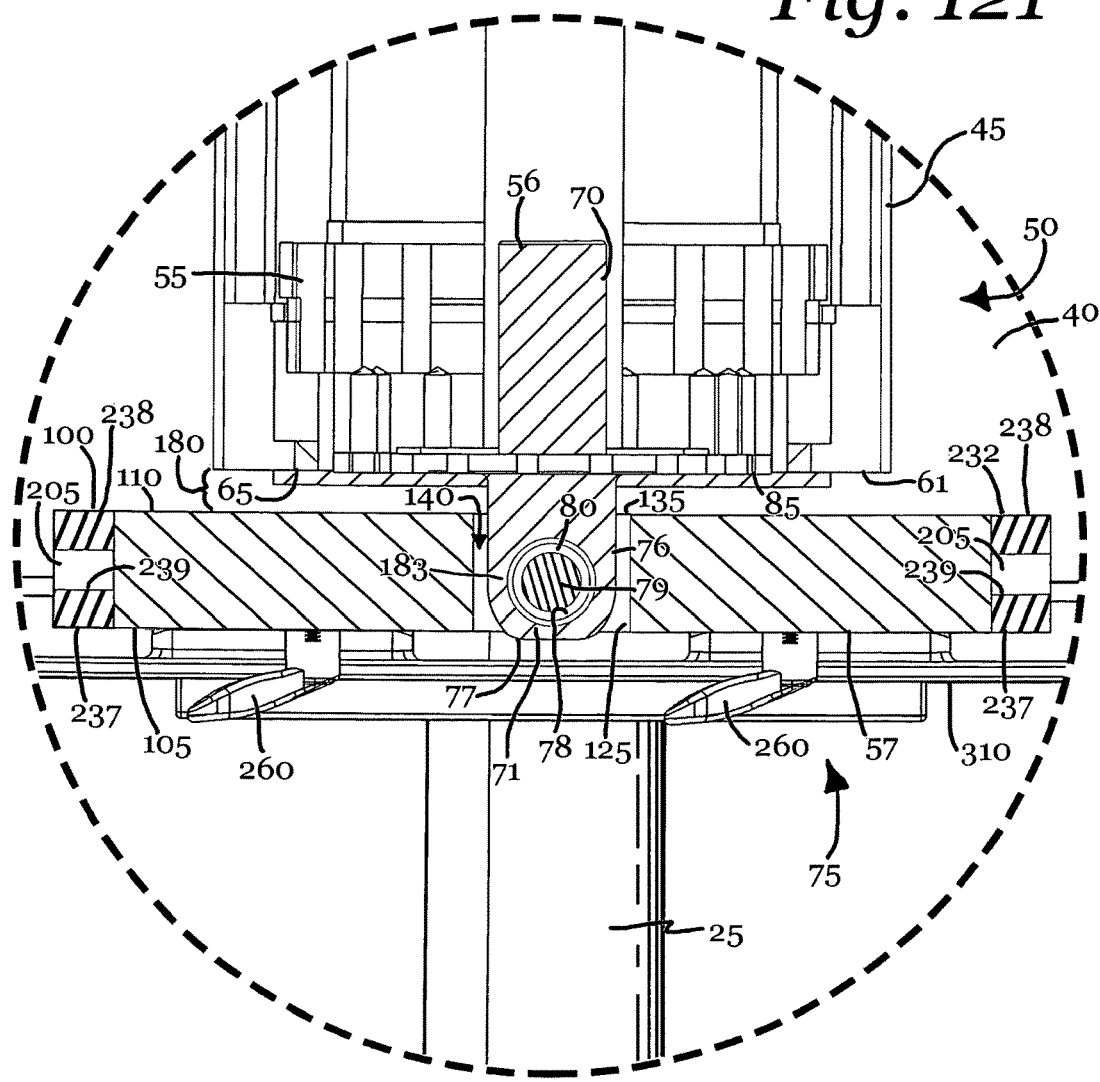

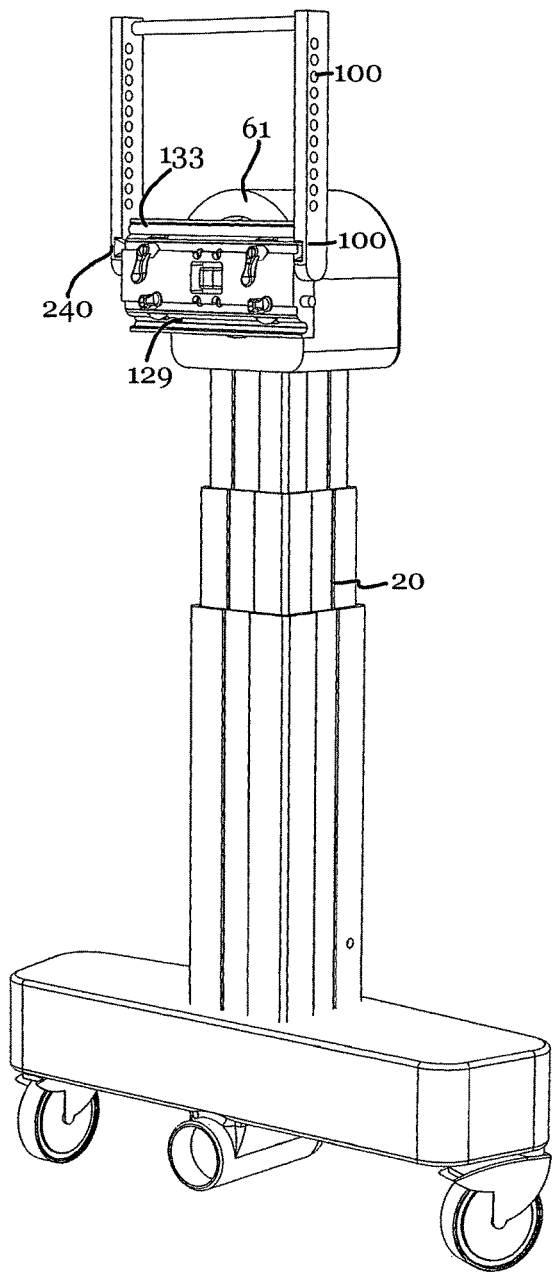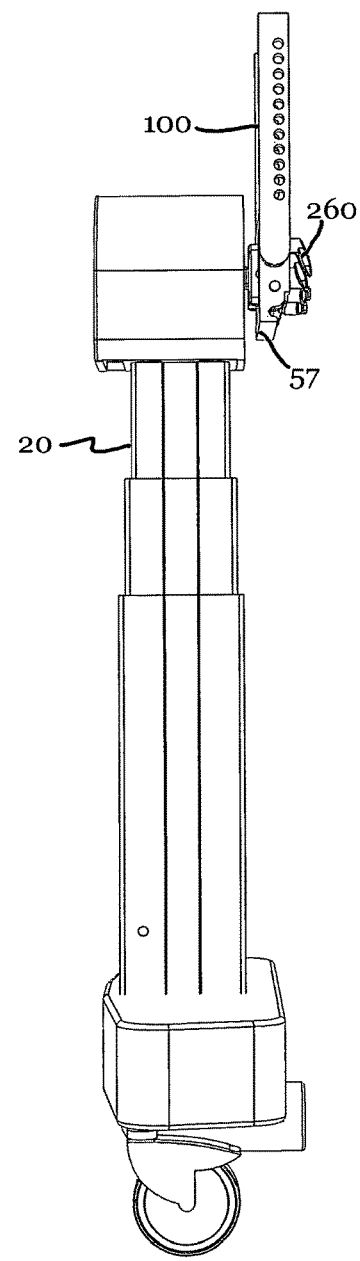

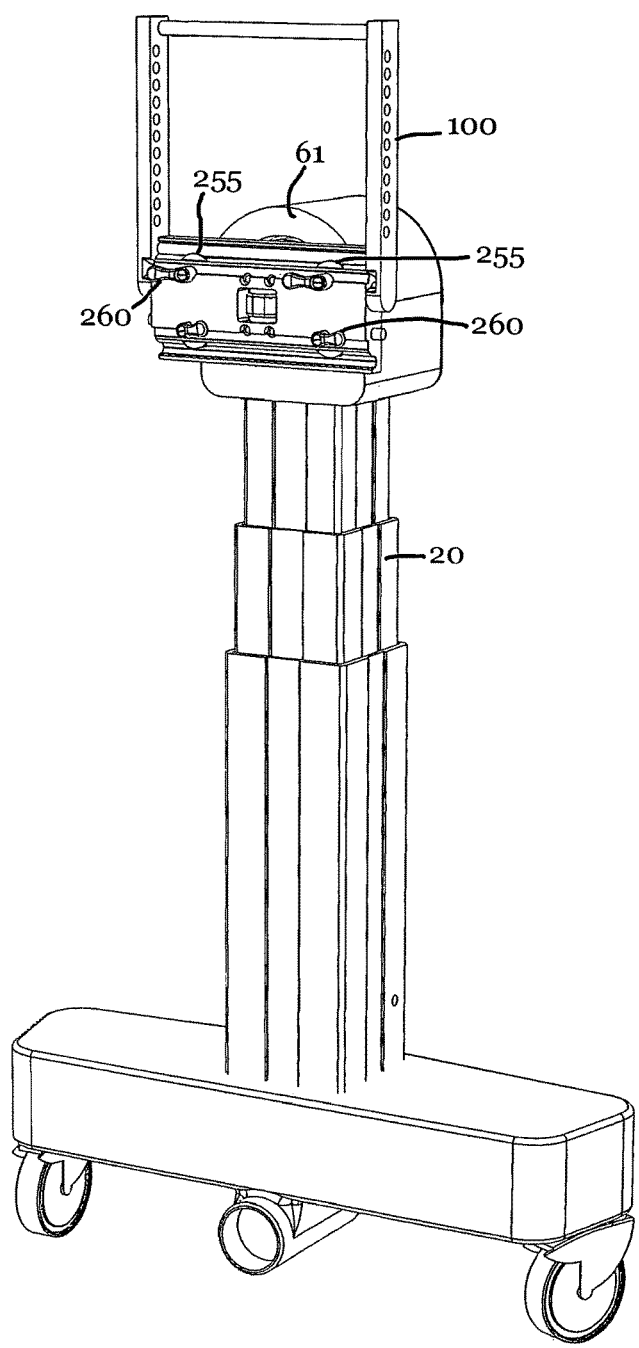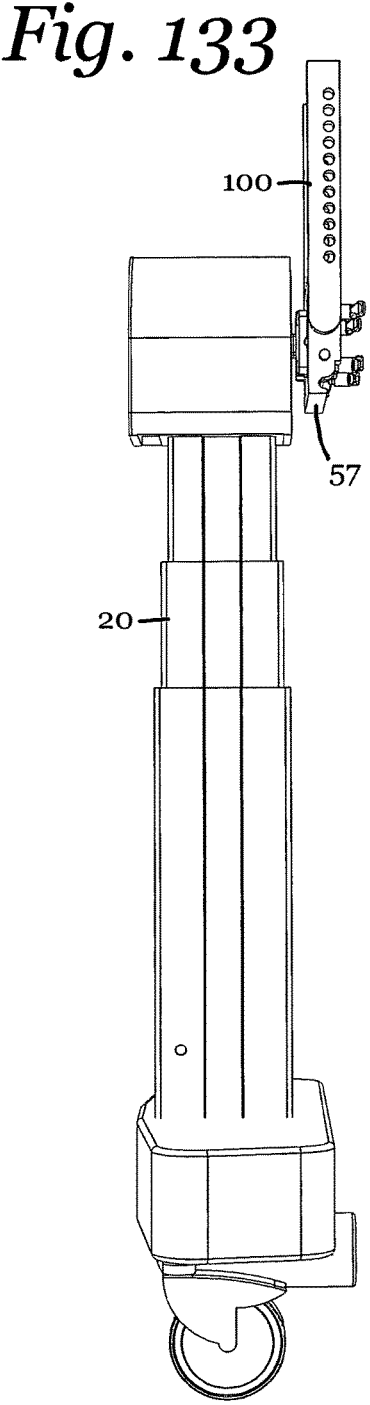

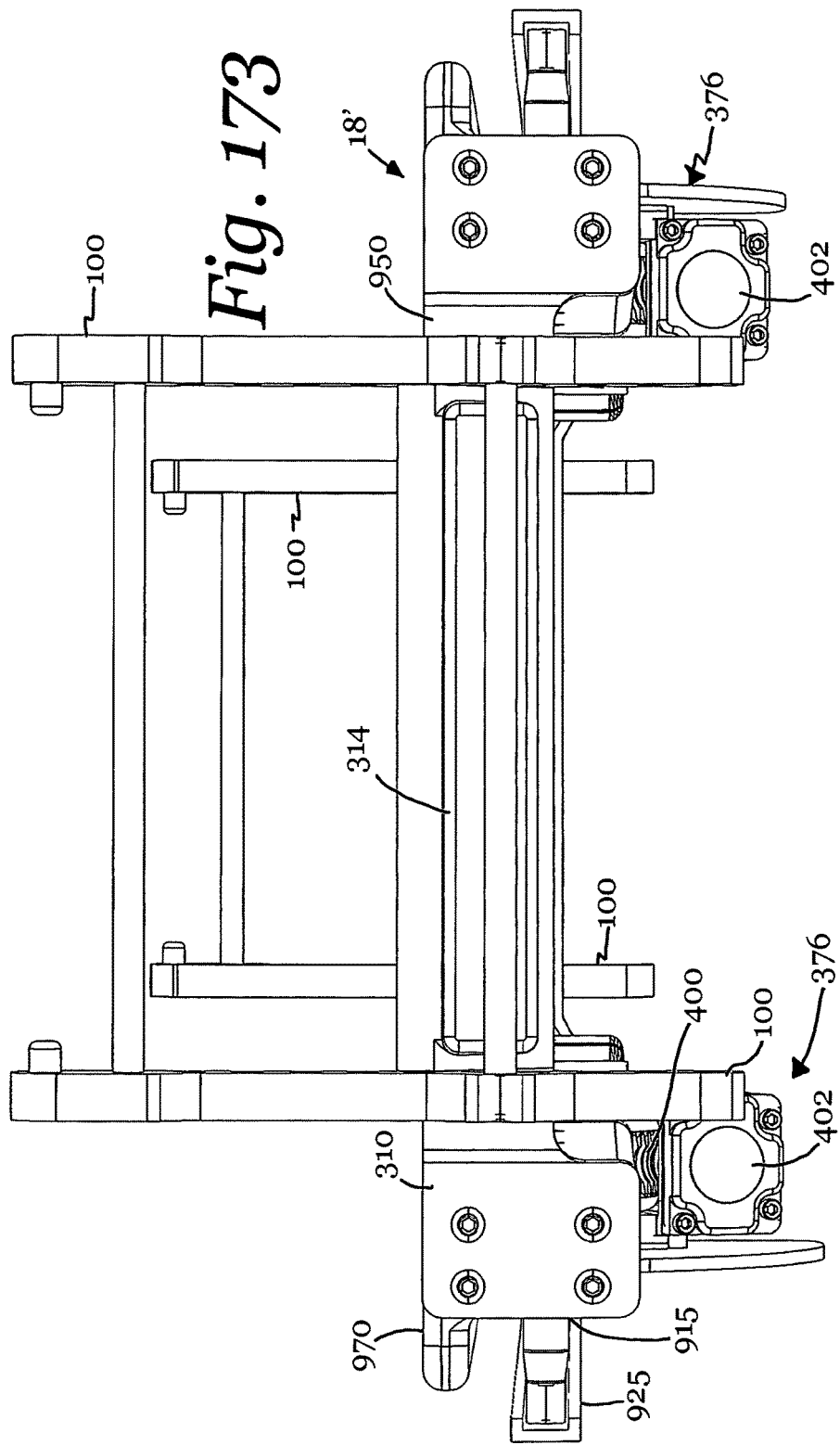

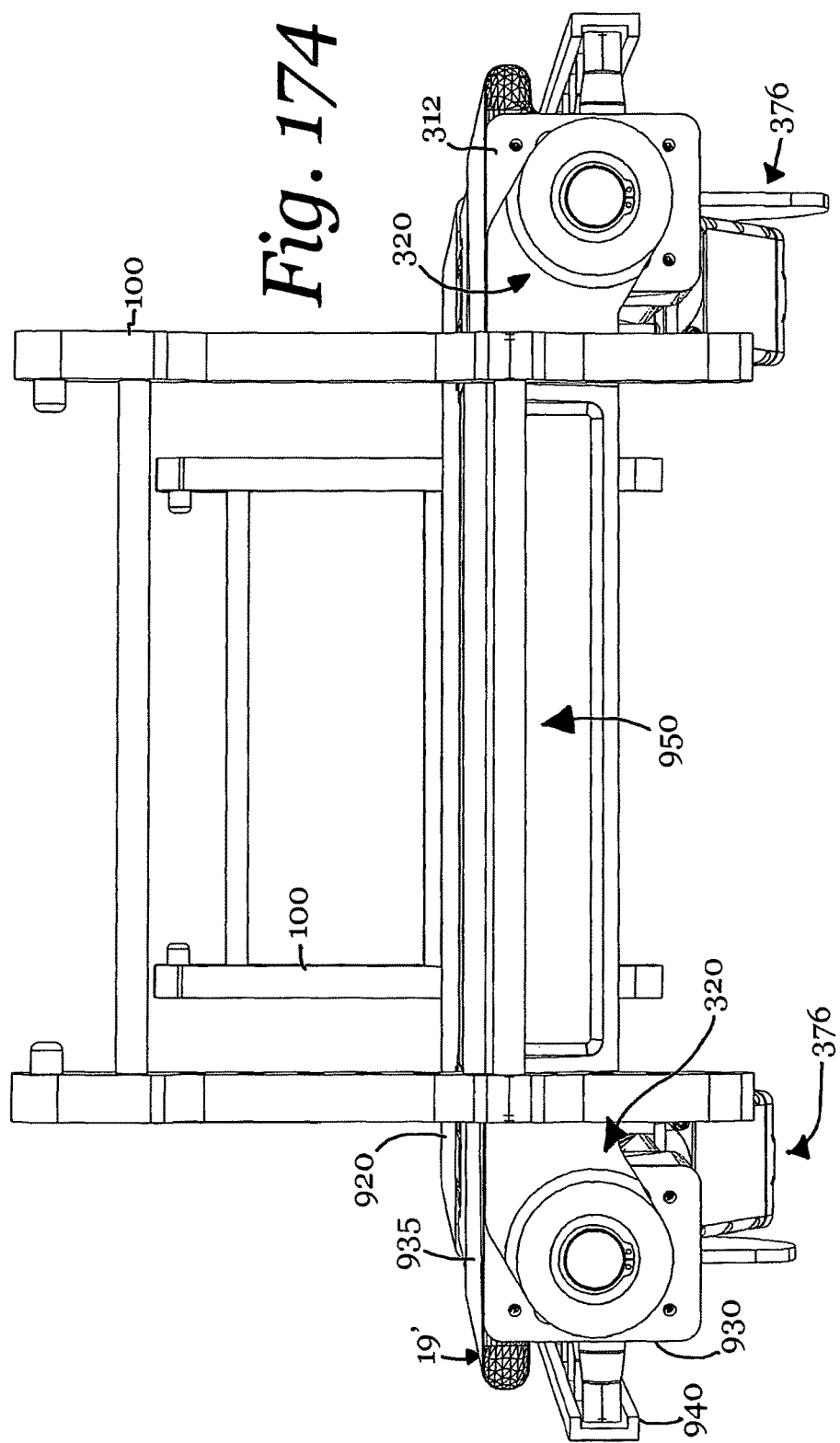

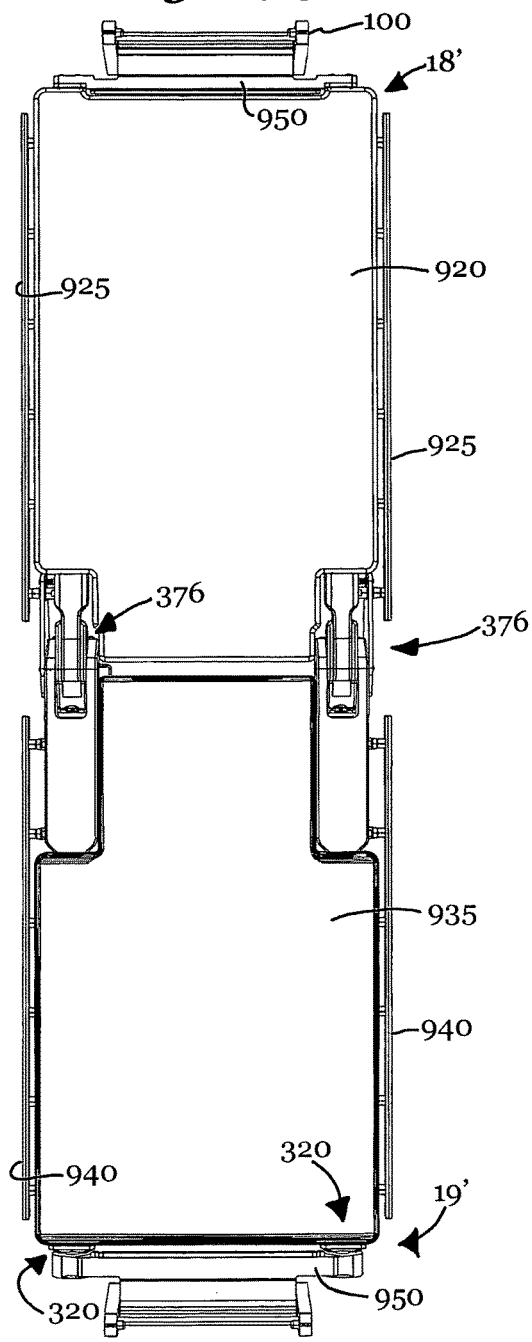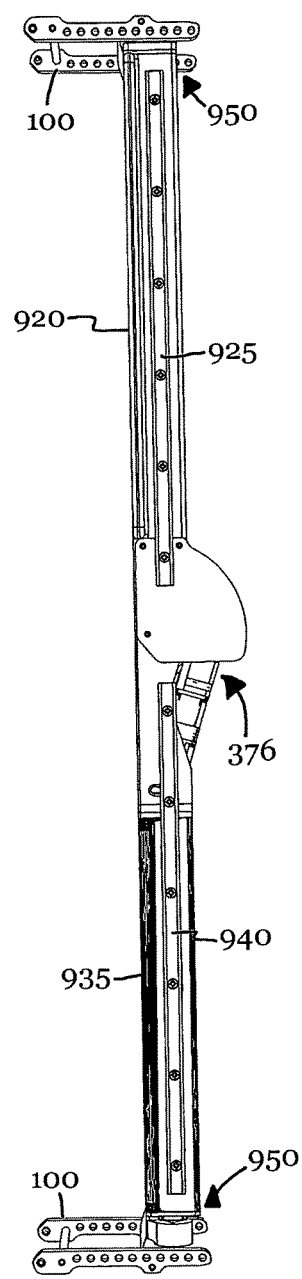

Fig. 186
Fig. 187
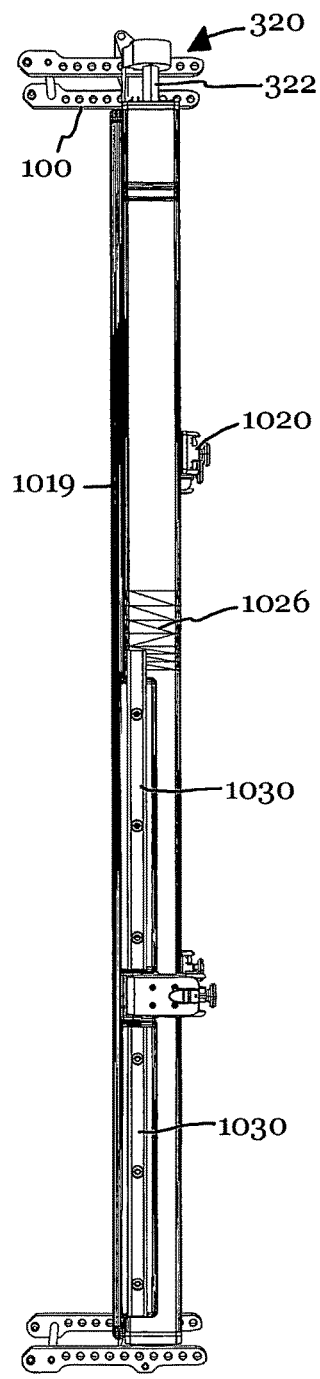
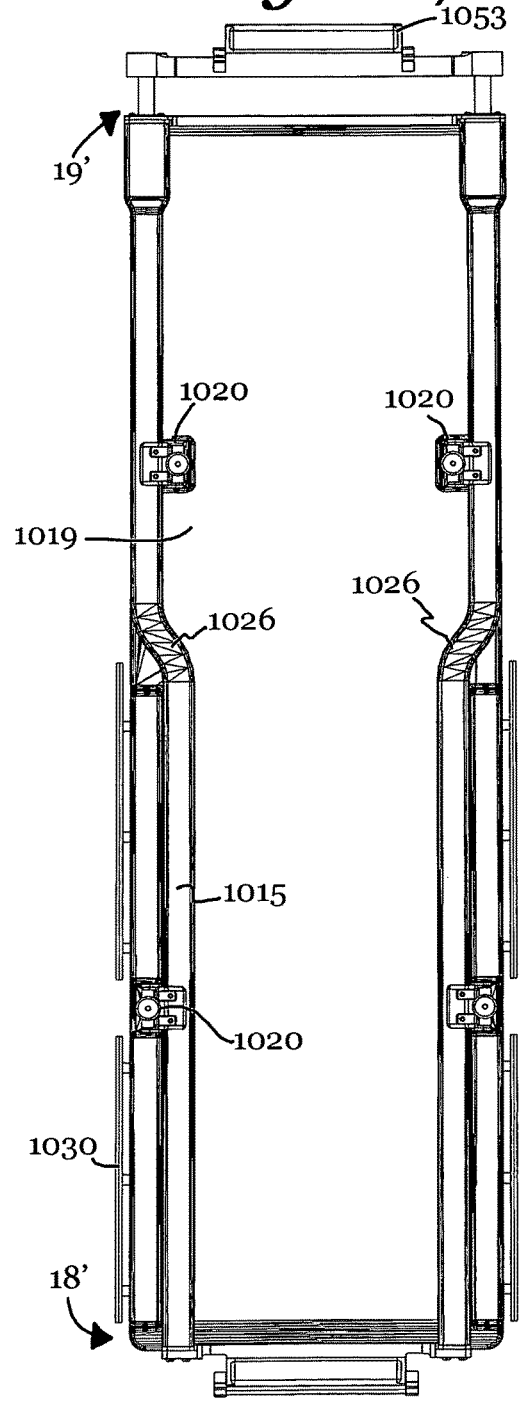

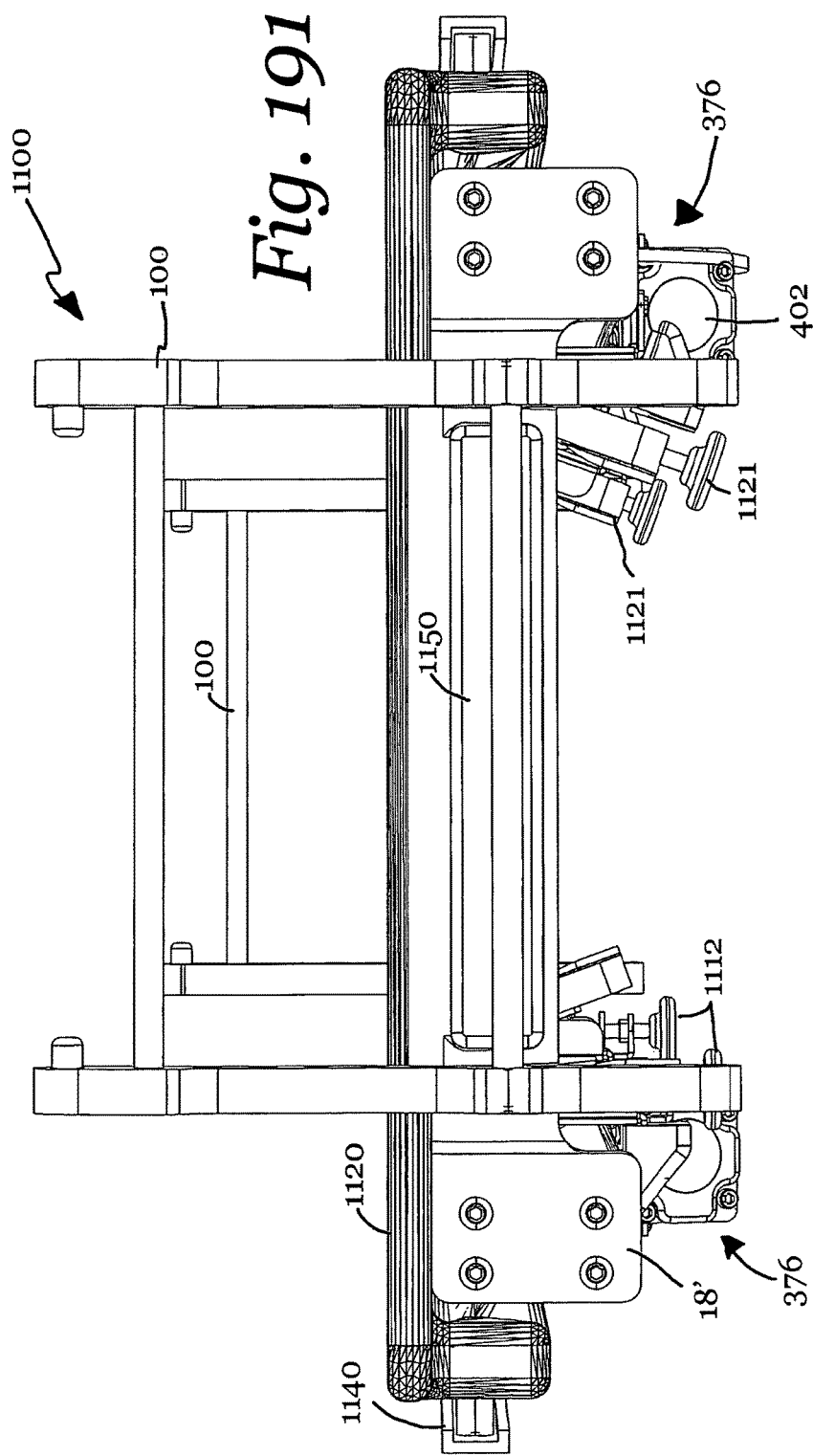

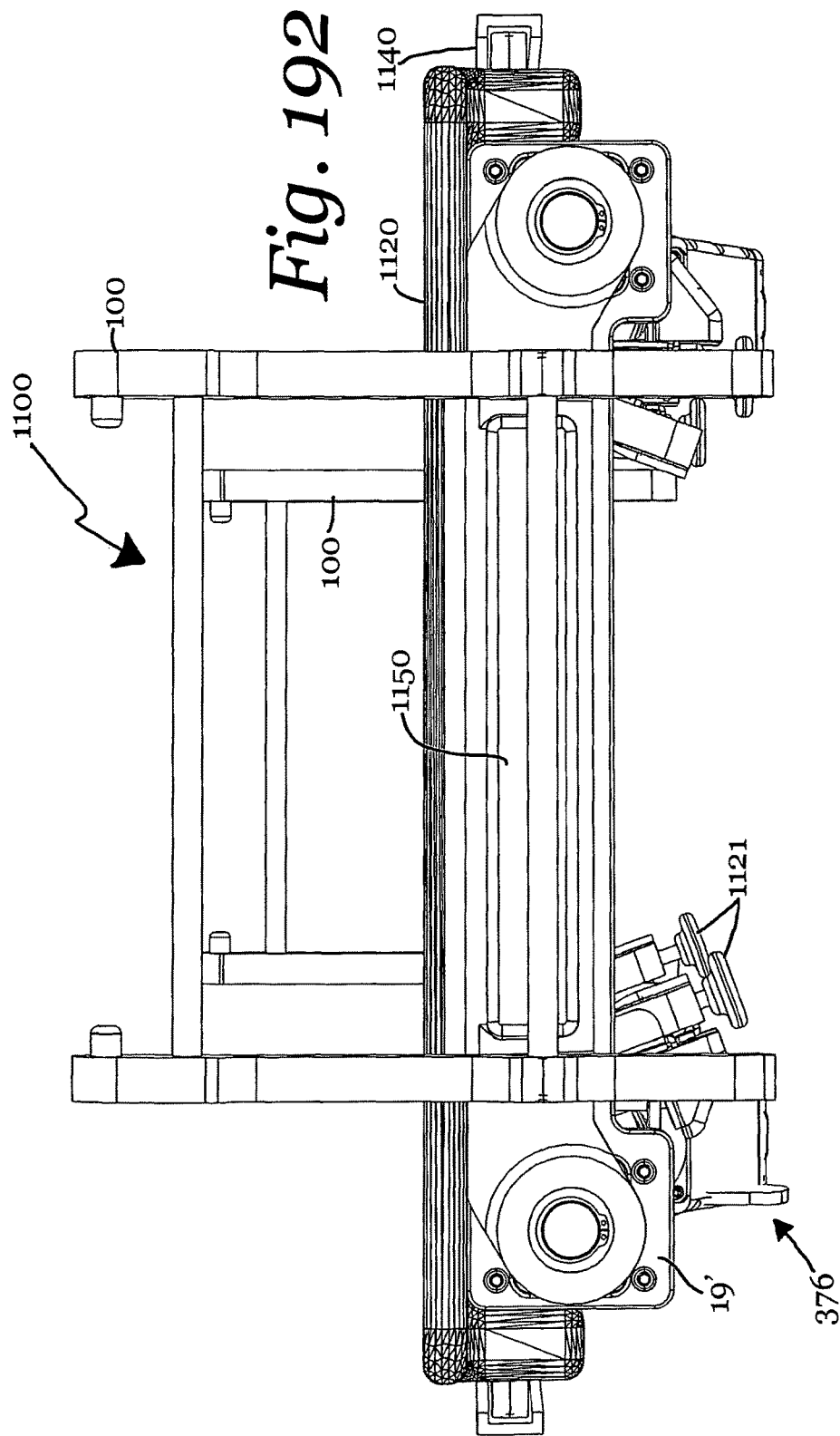

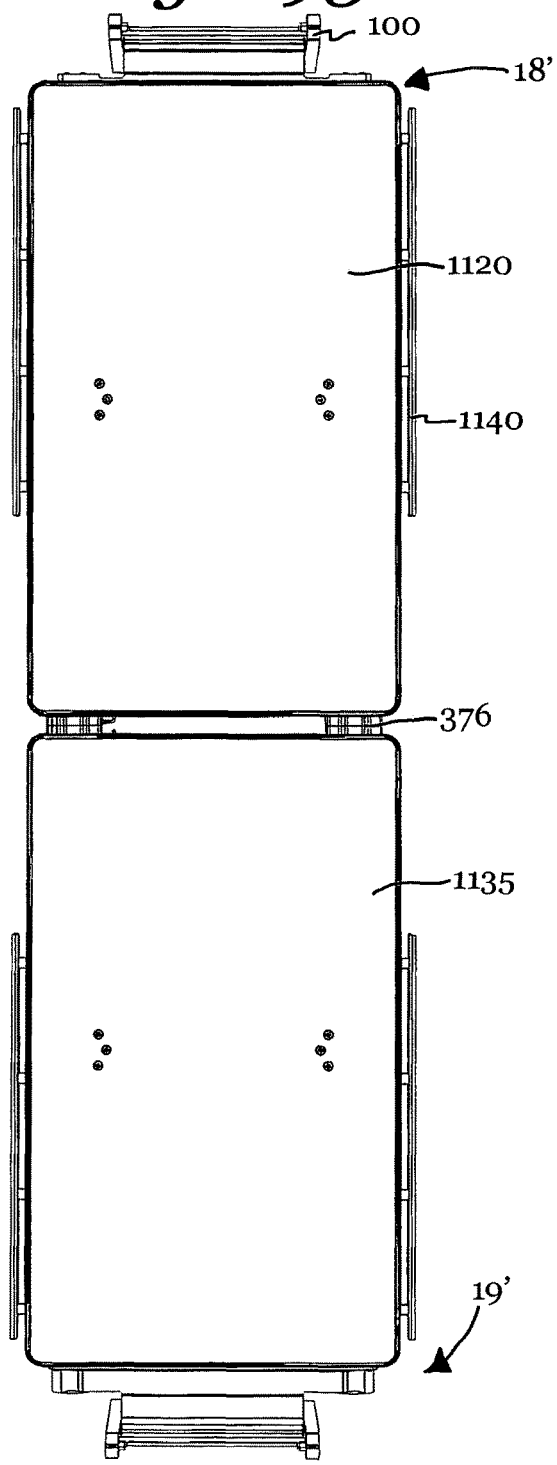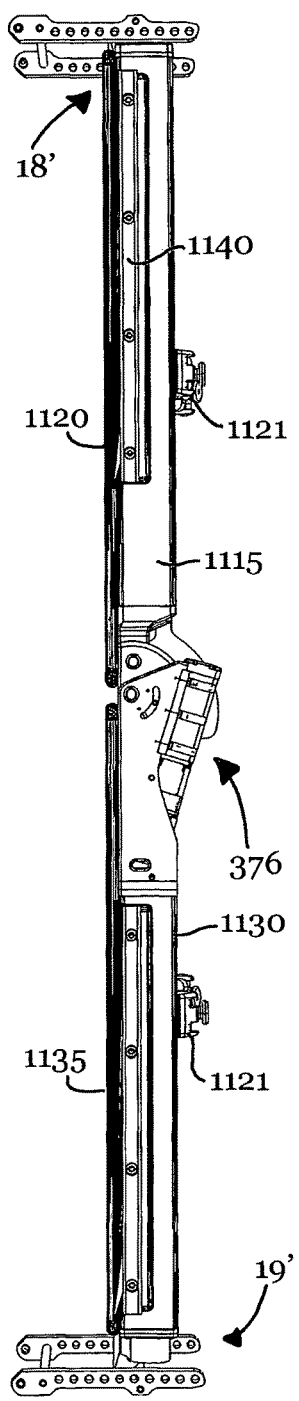

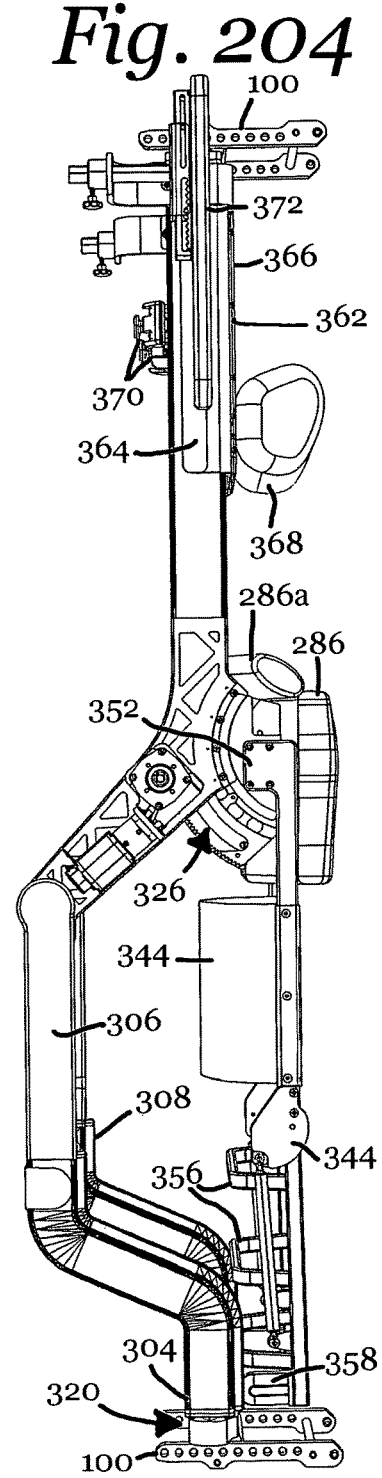
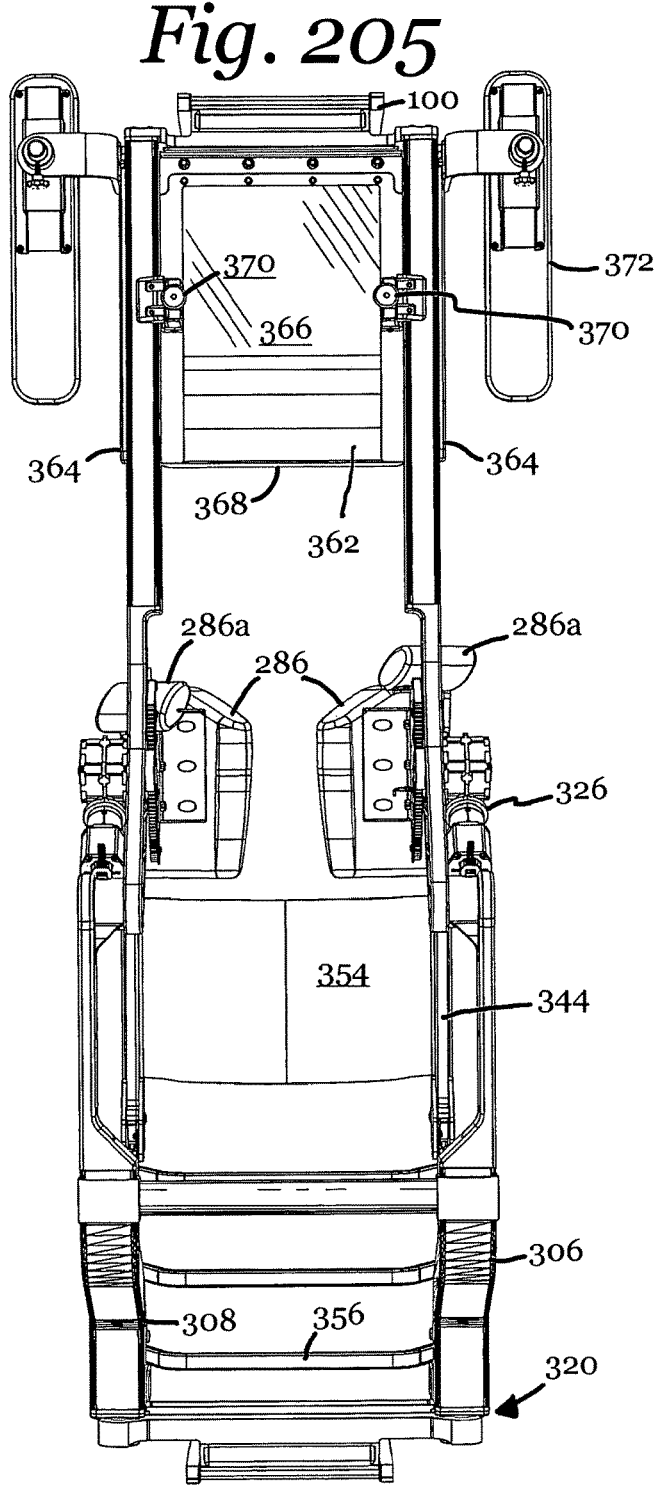

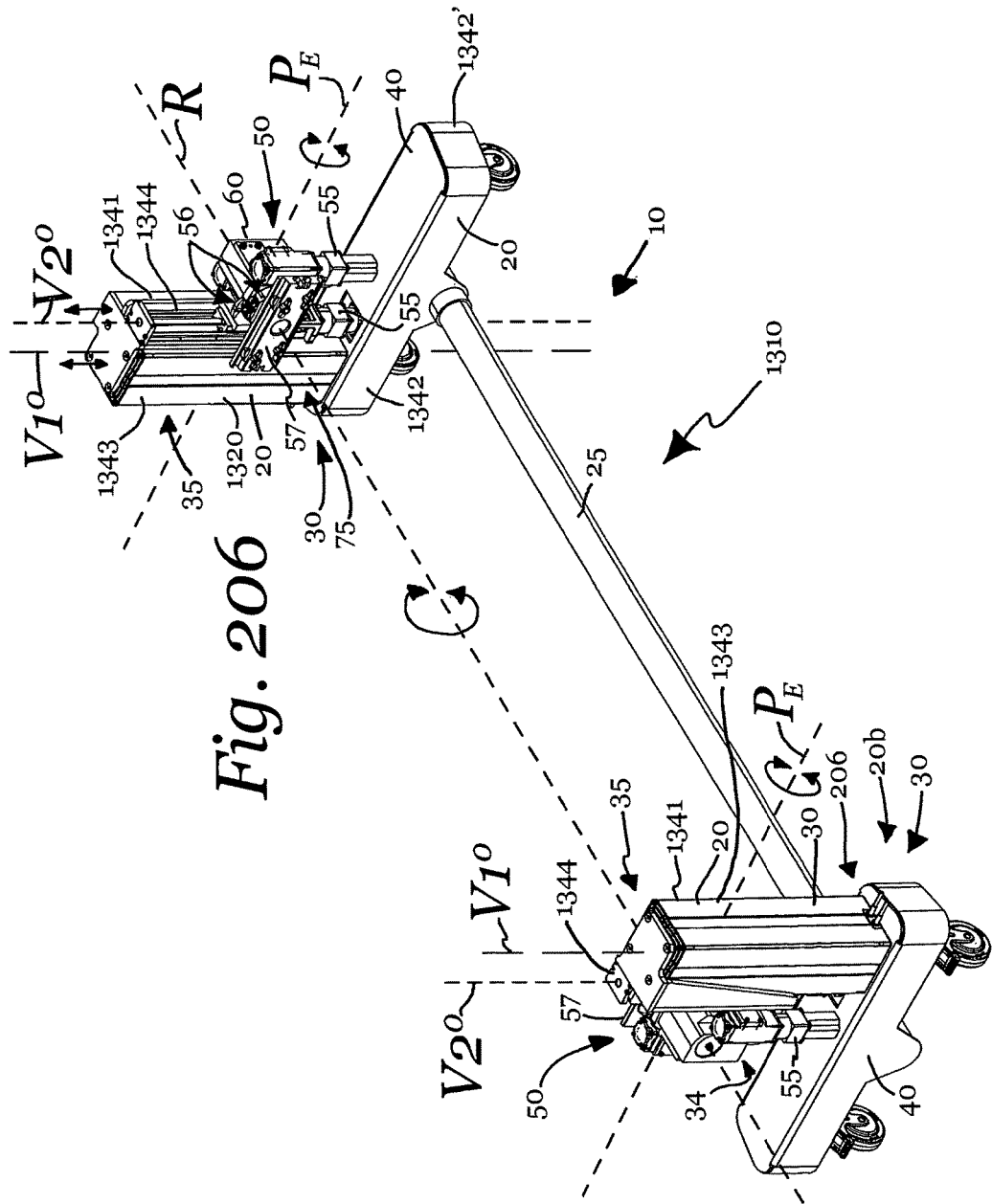

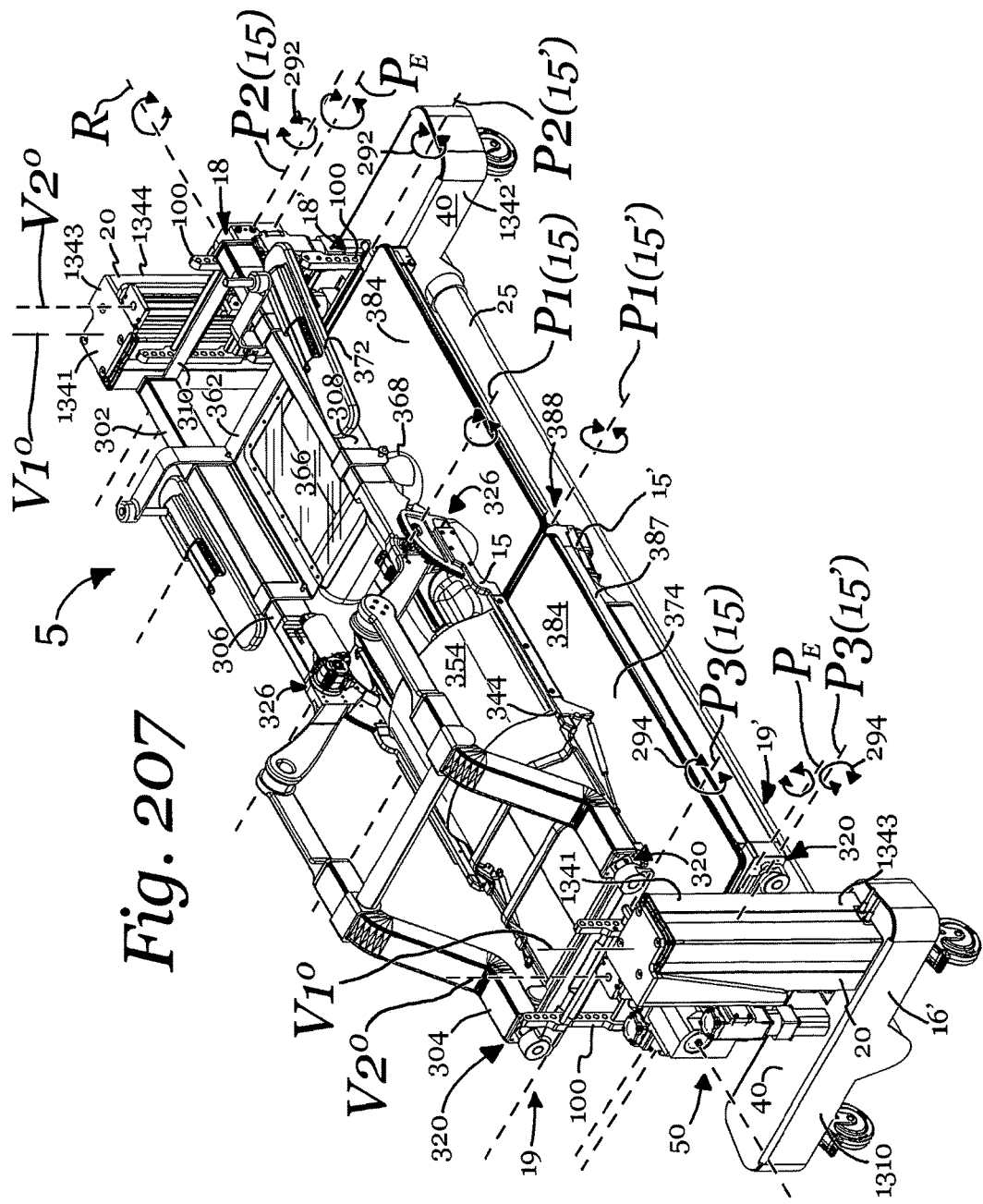

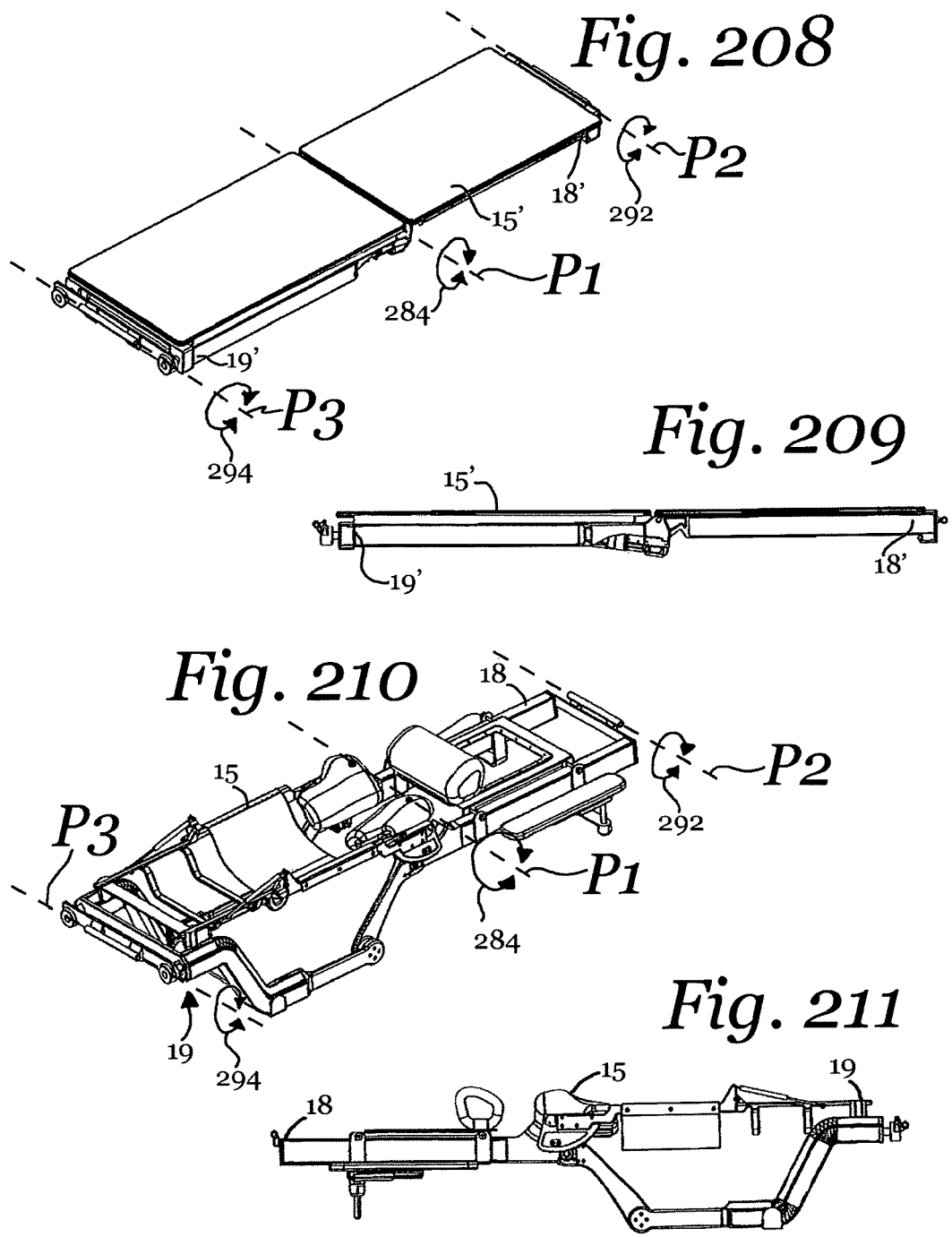

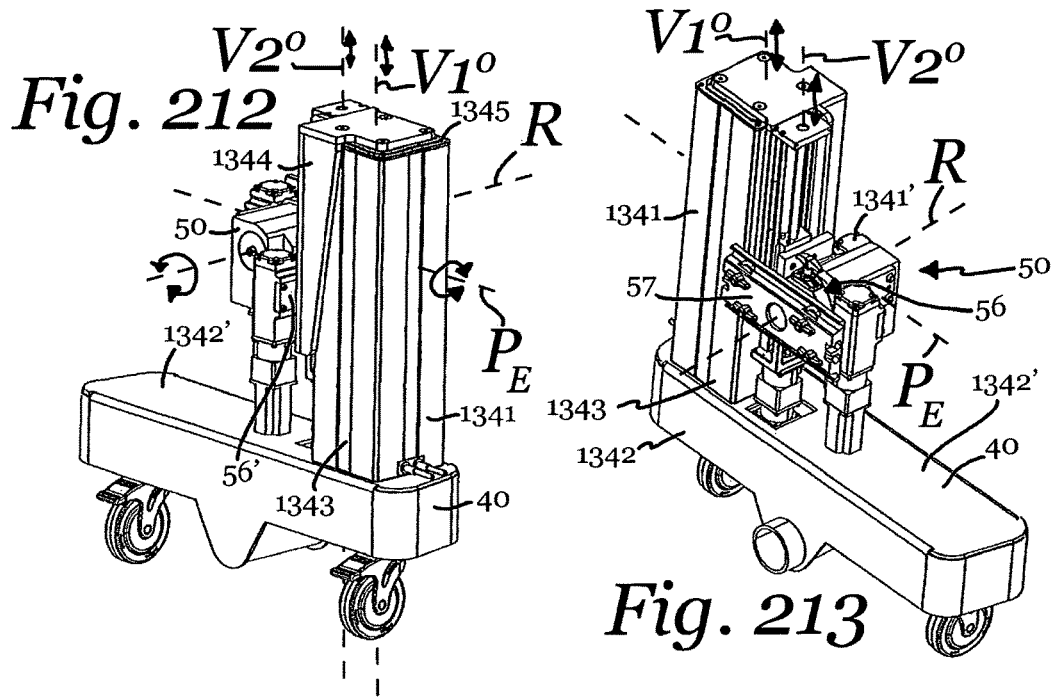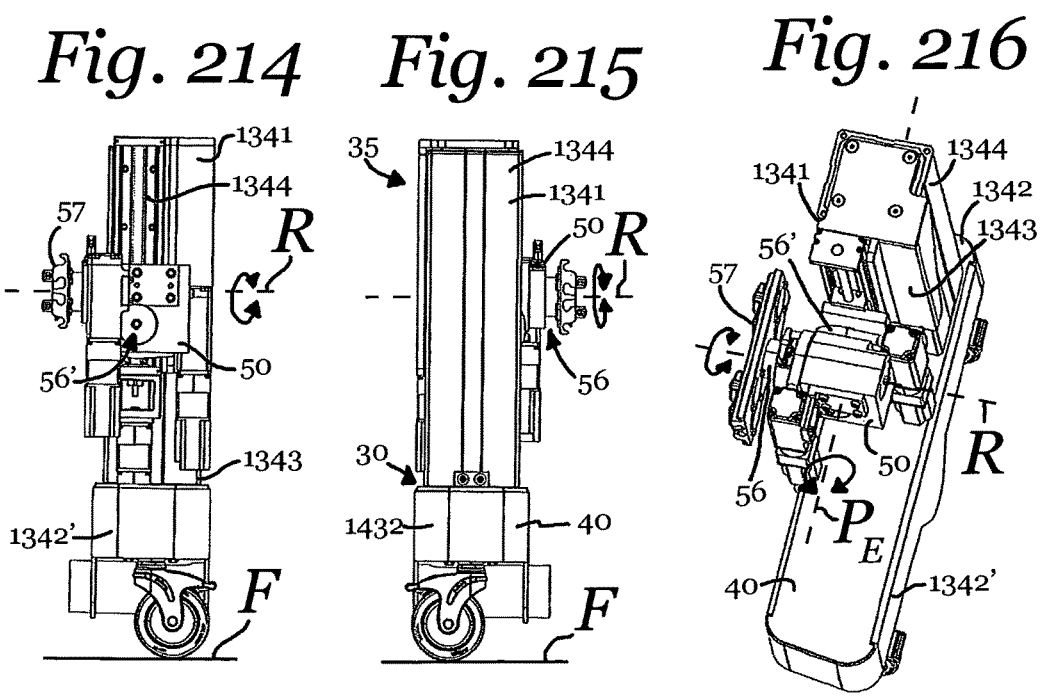

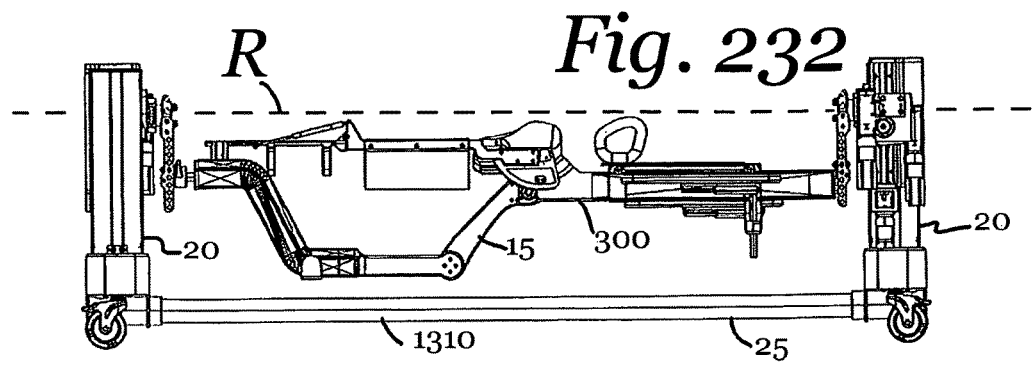
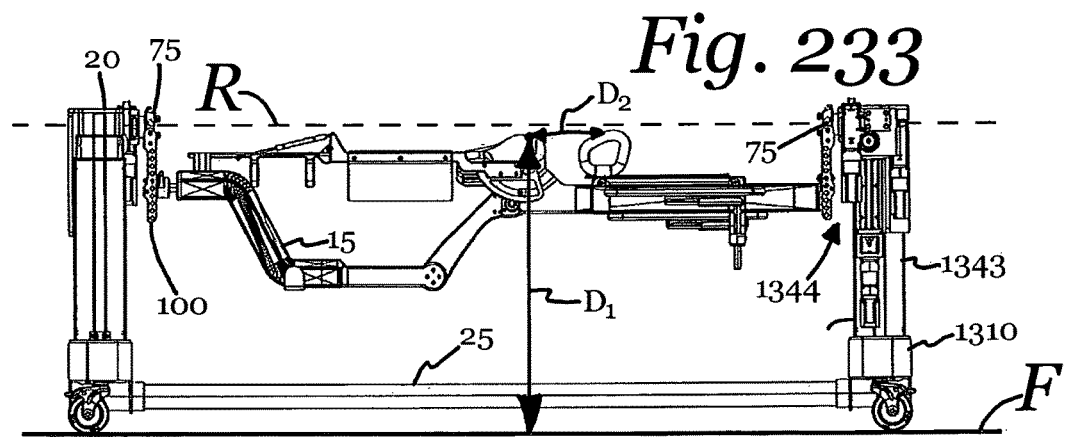
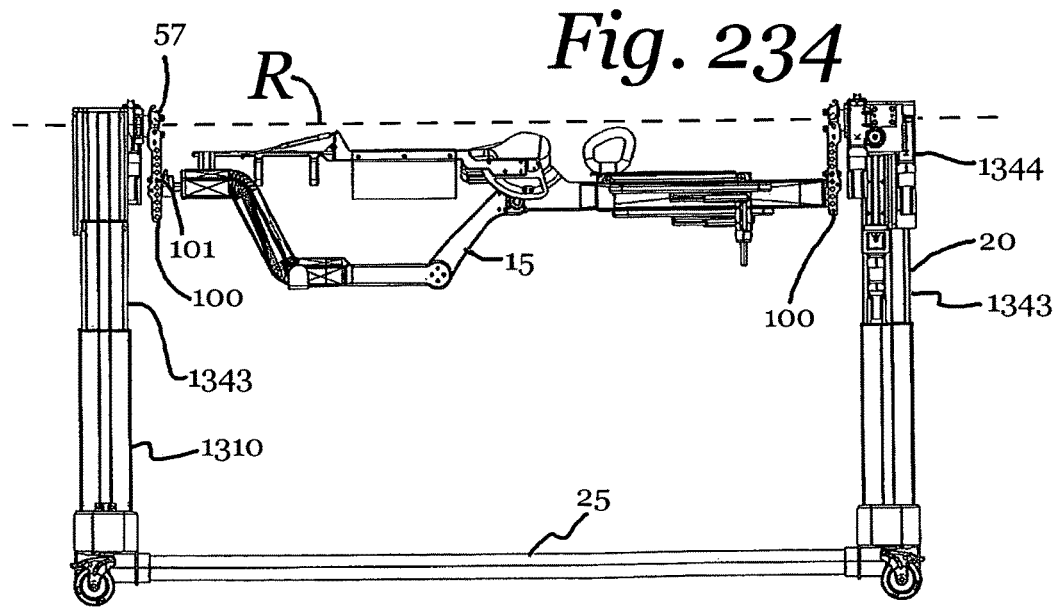

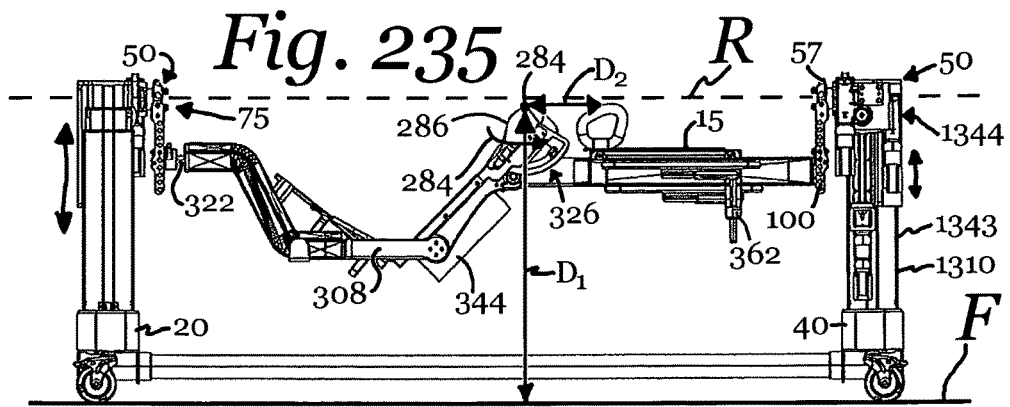
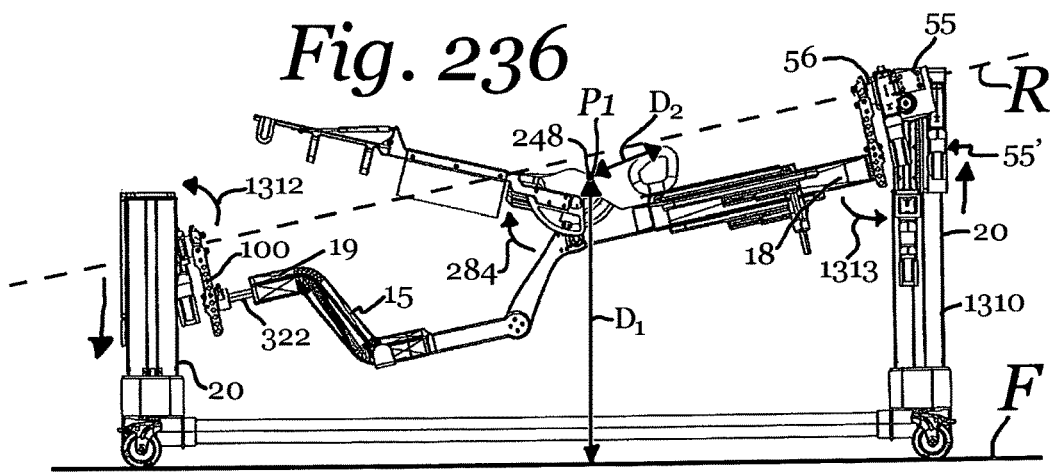
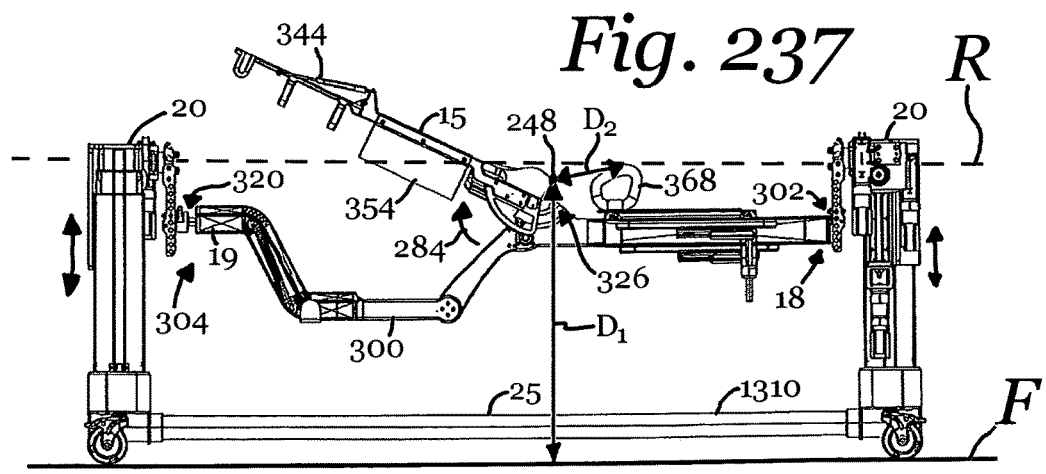

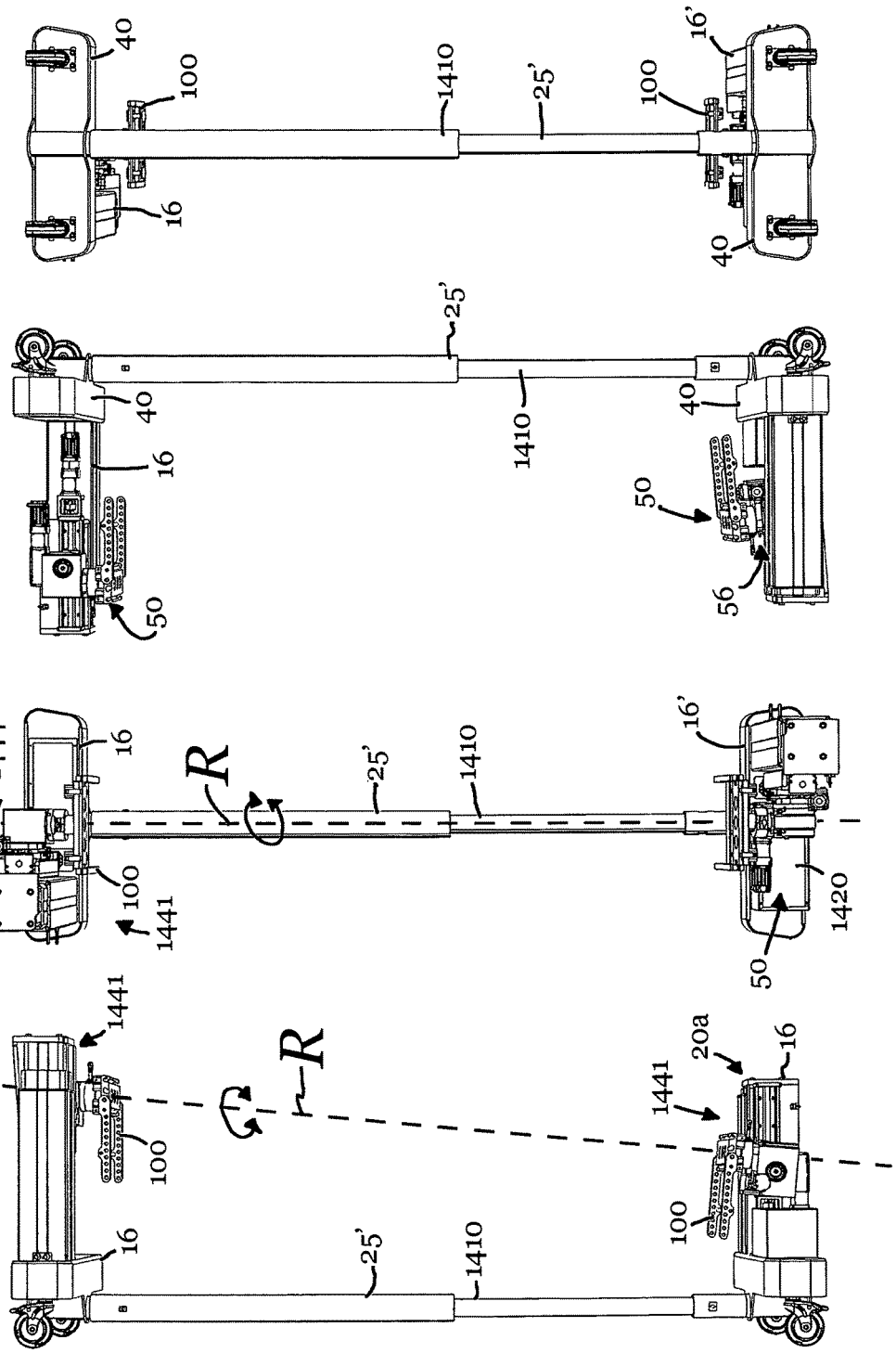

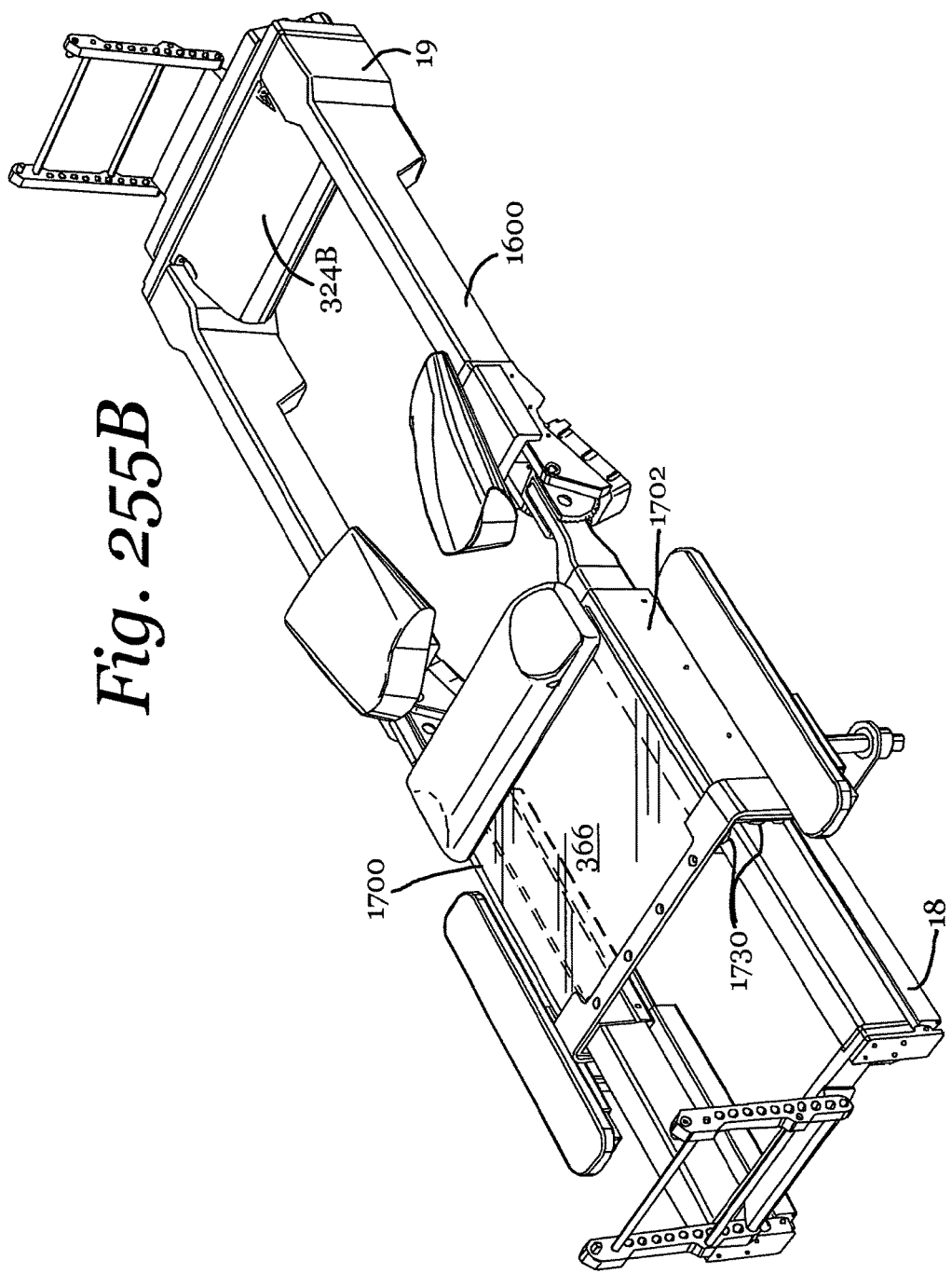

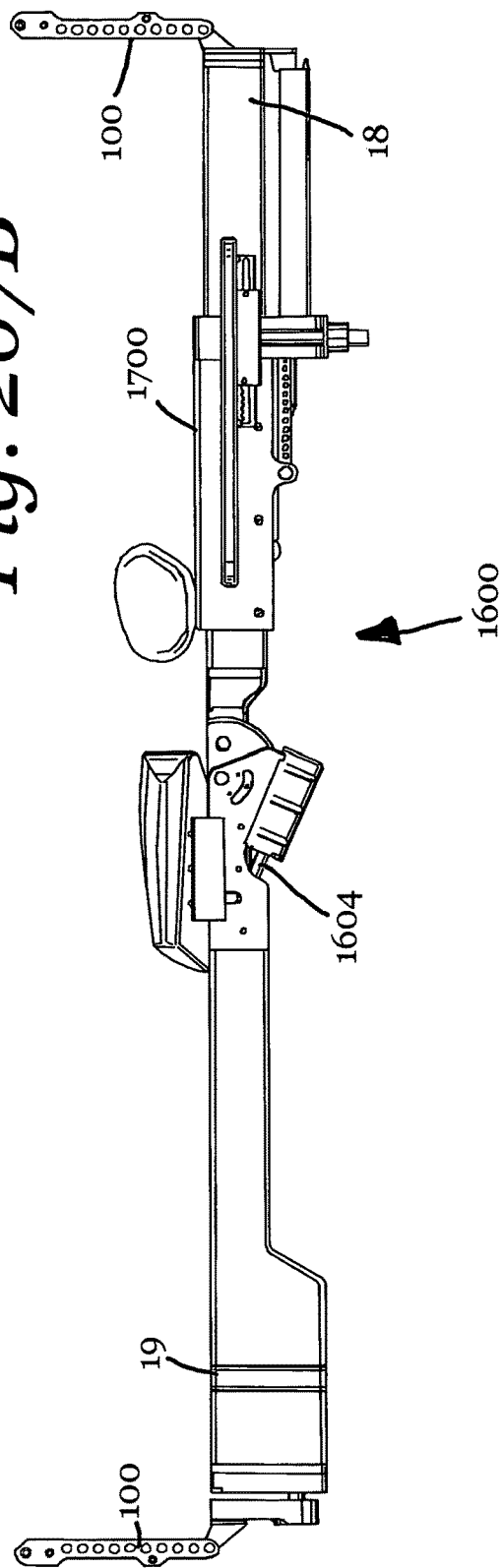

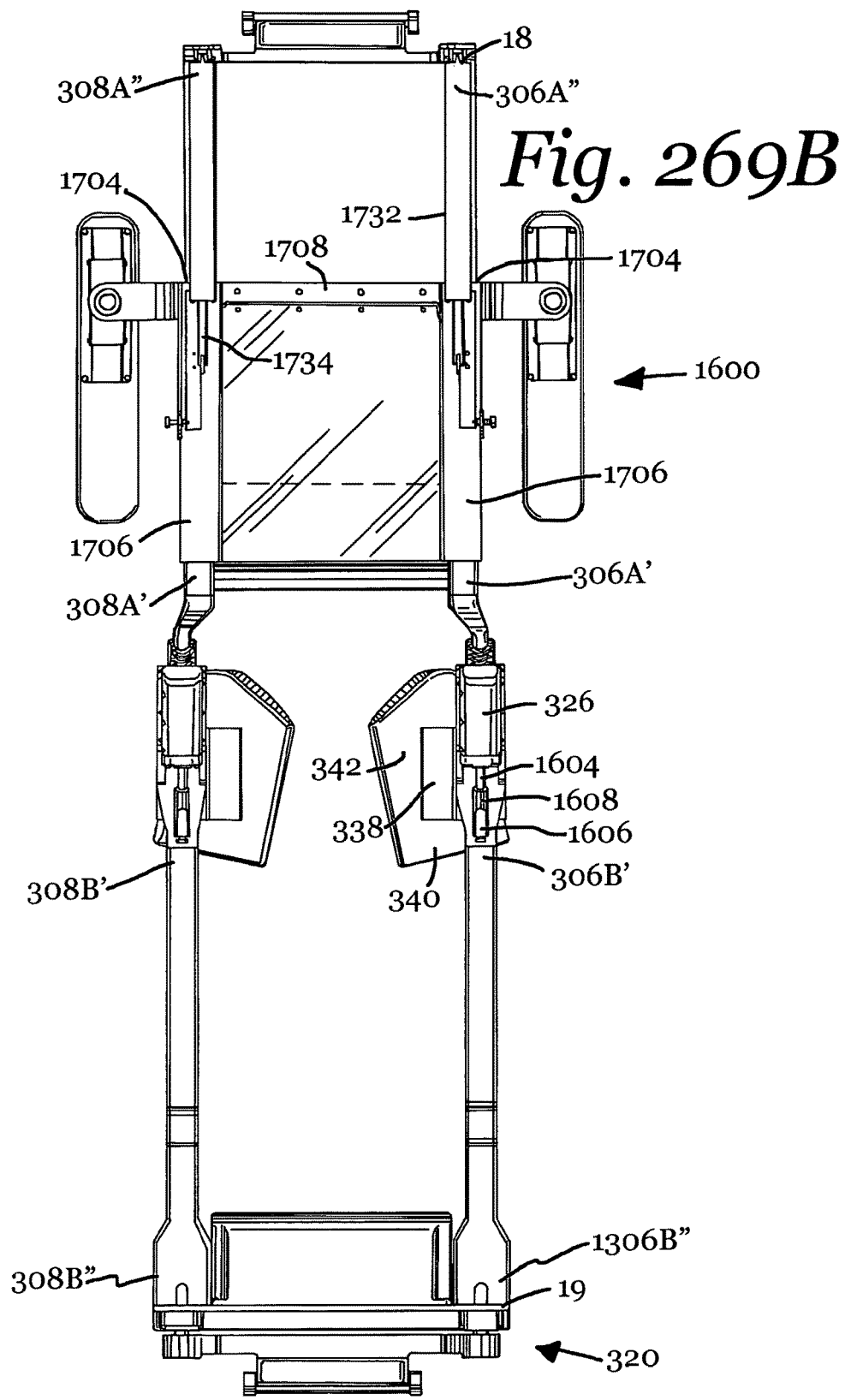

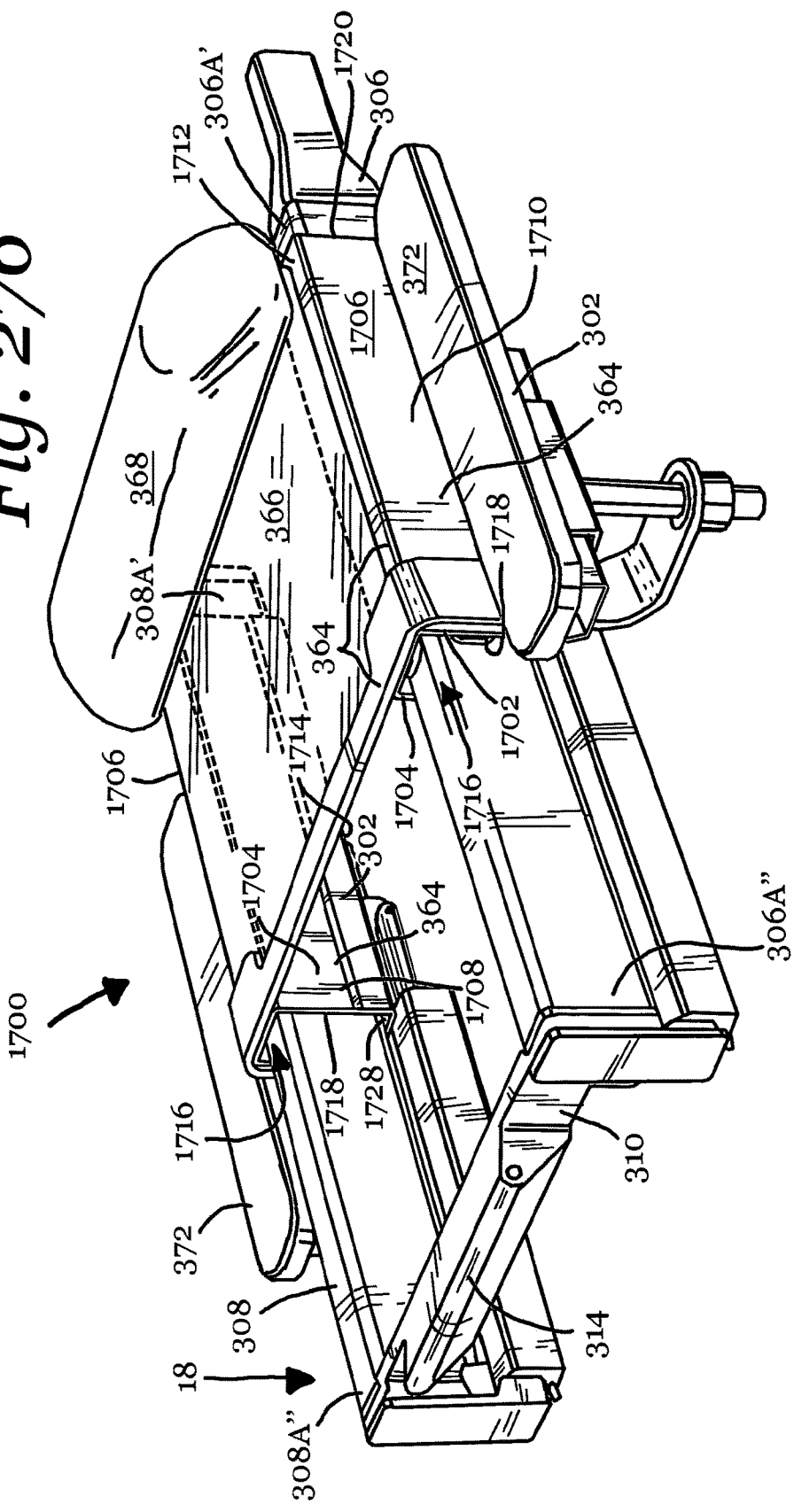

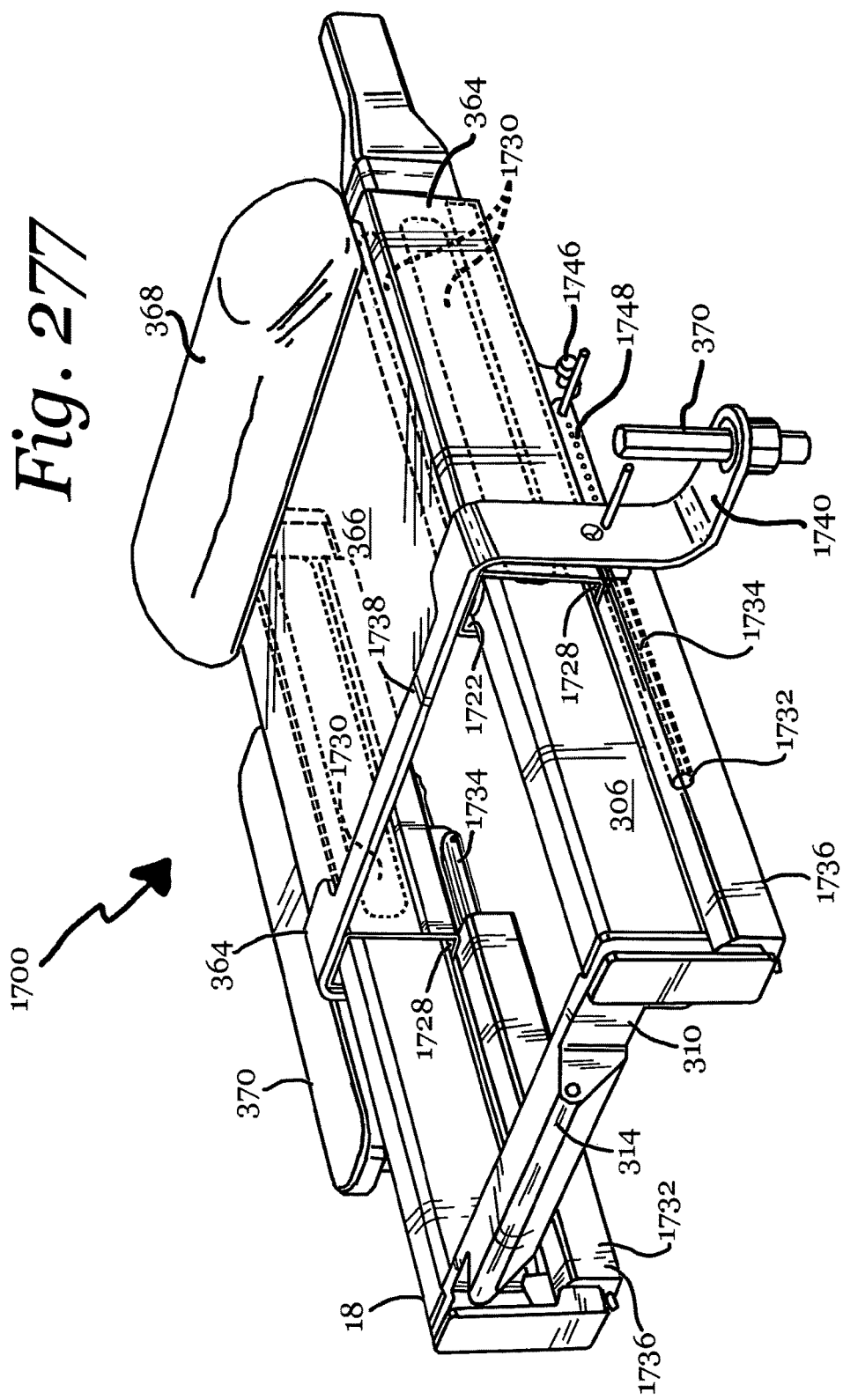

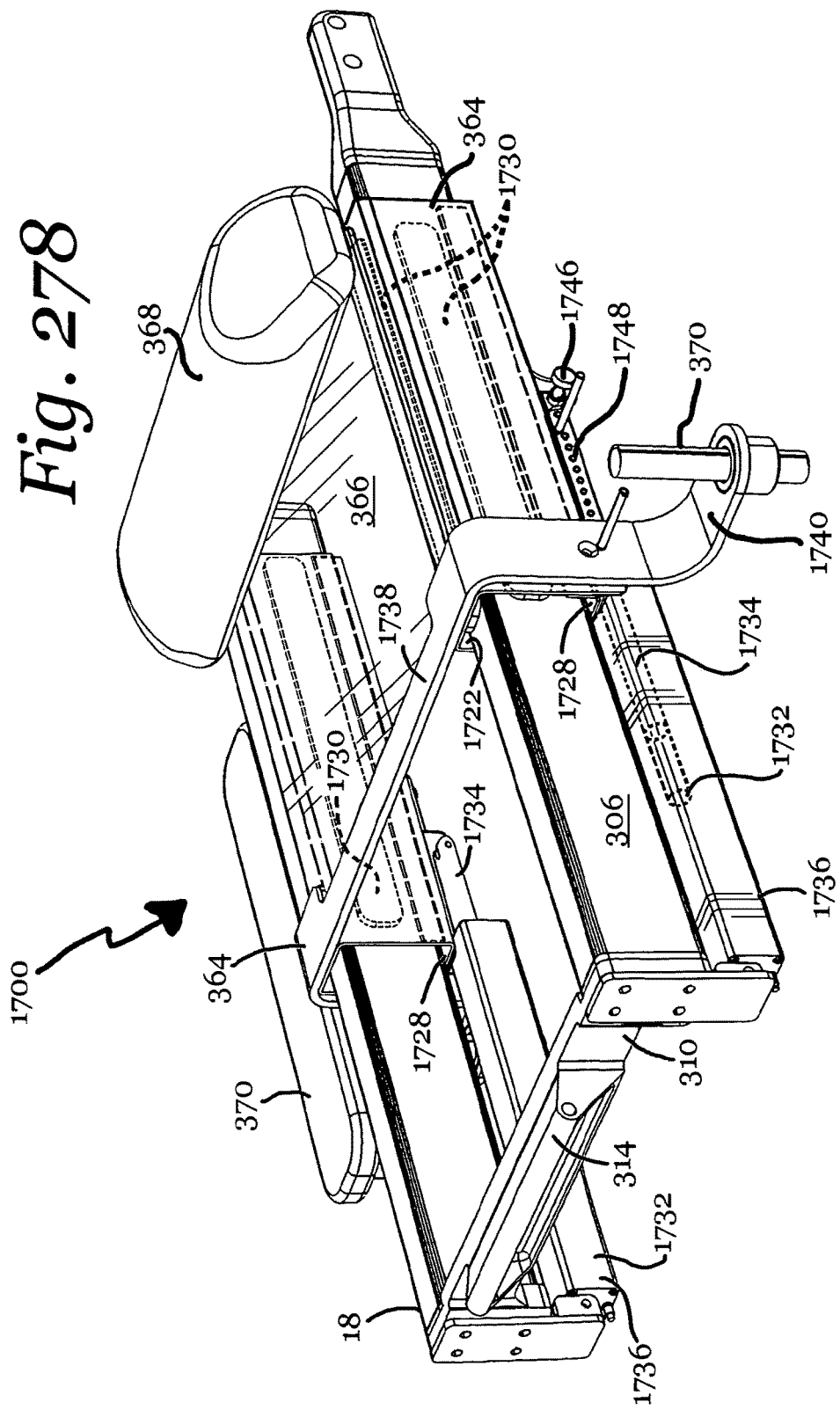

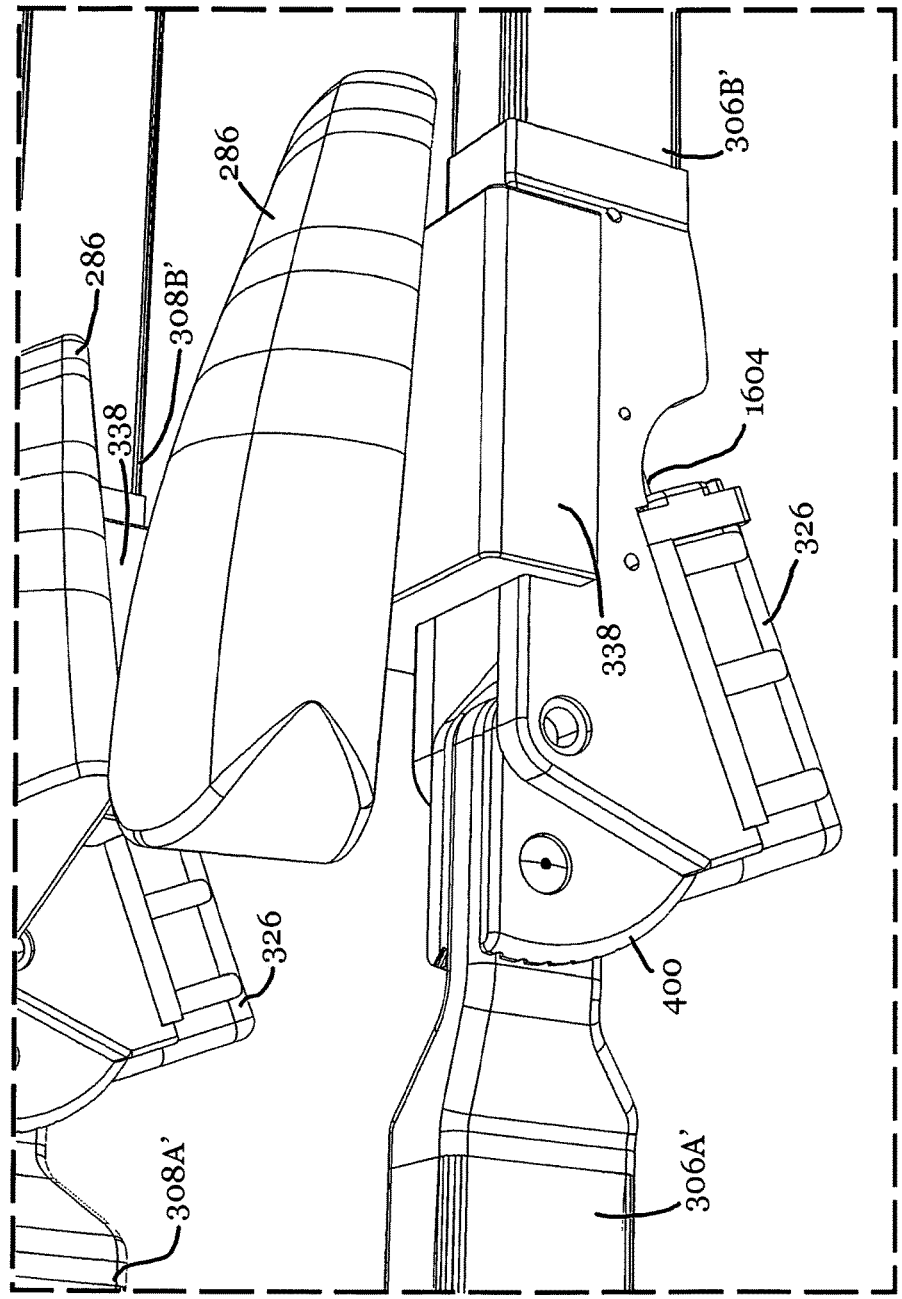

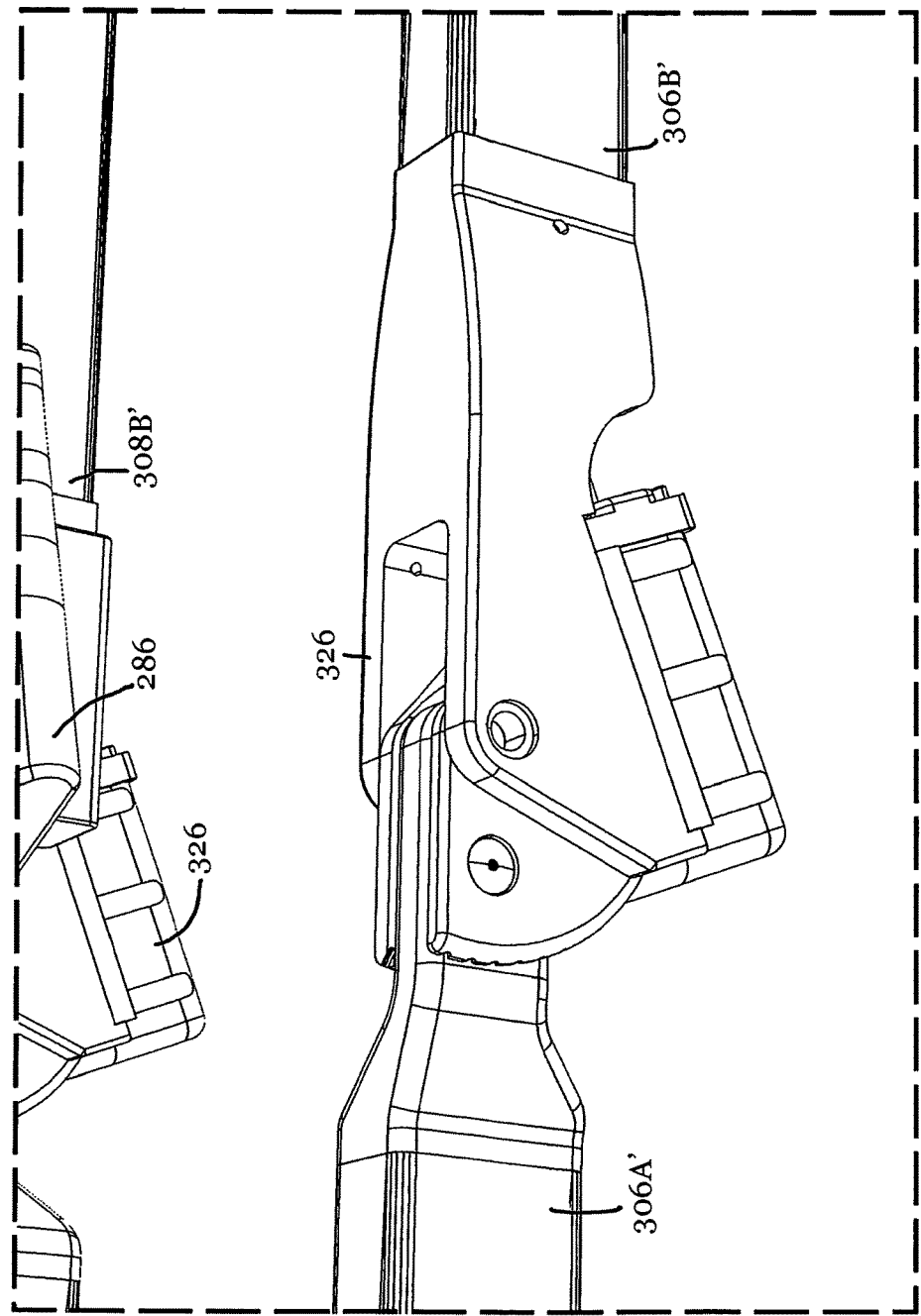

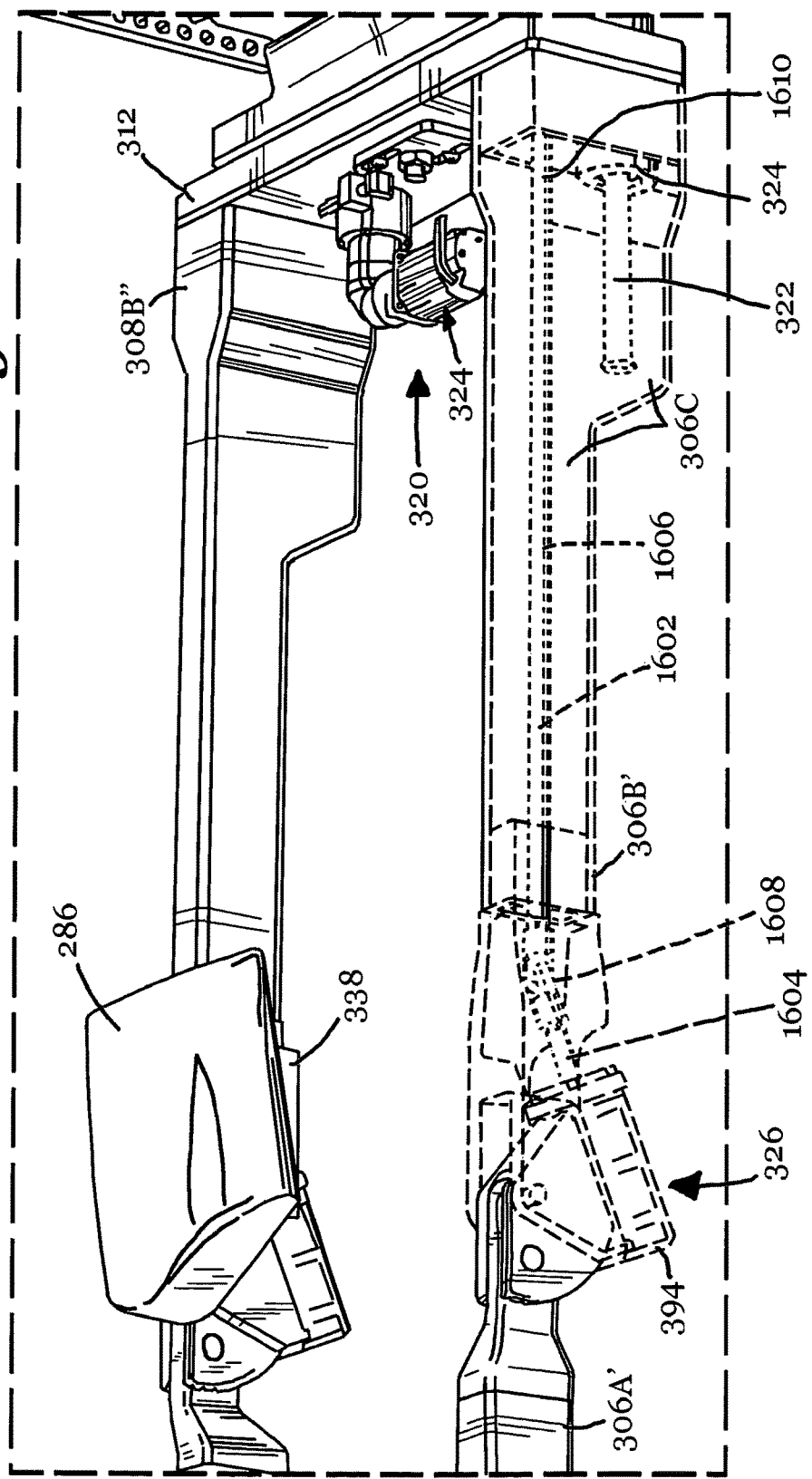

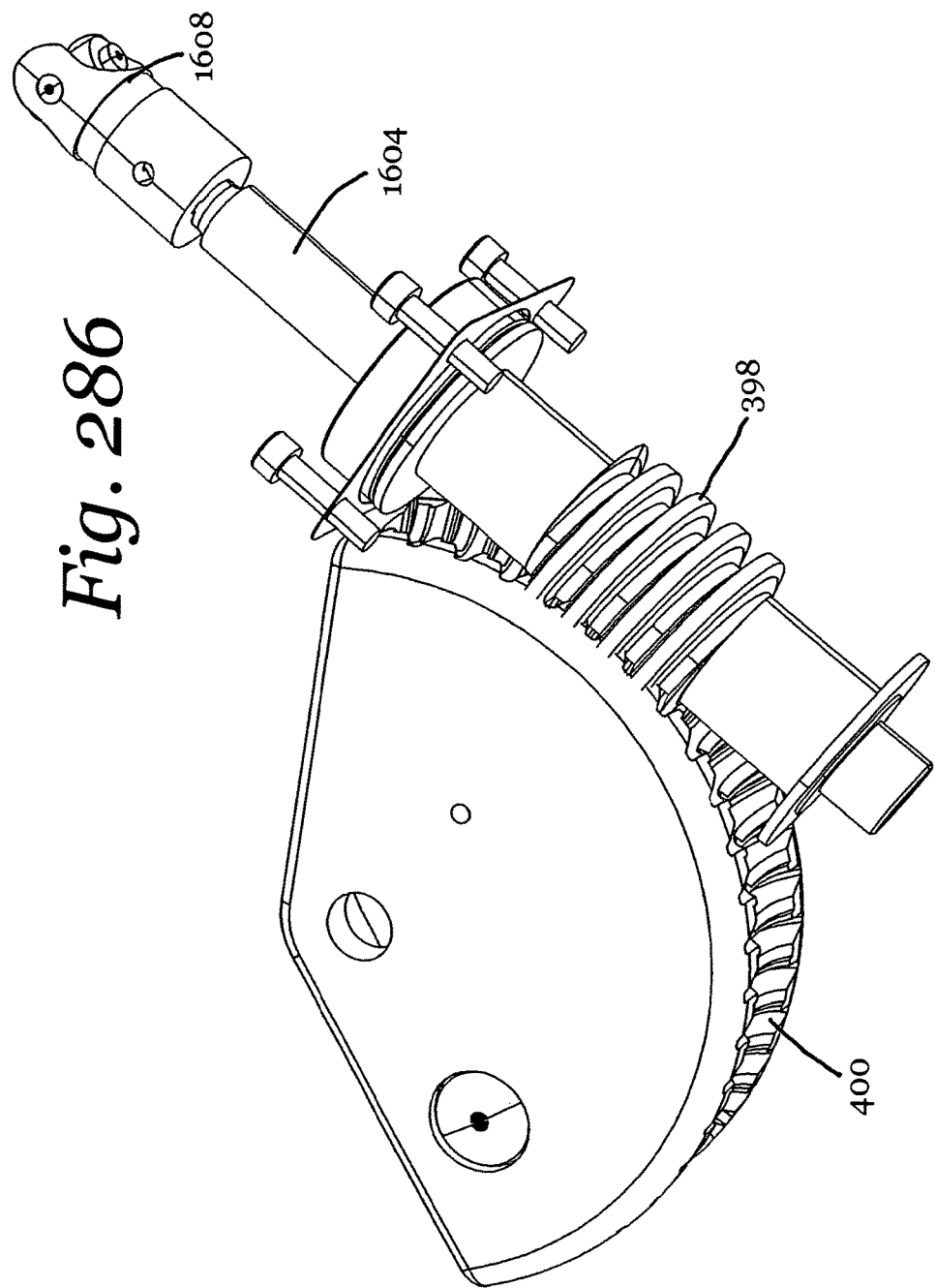

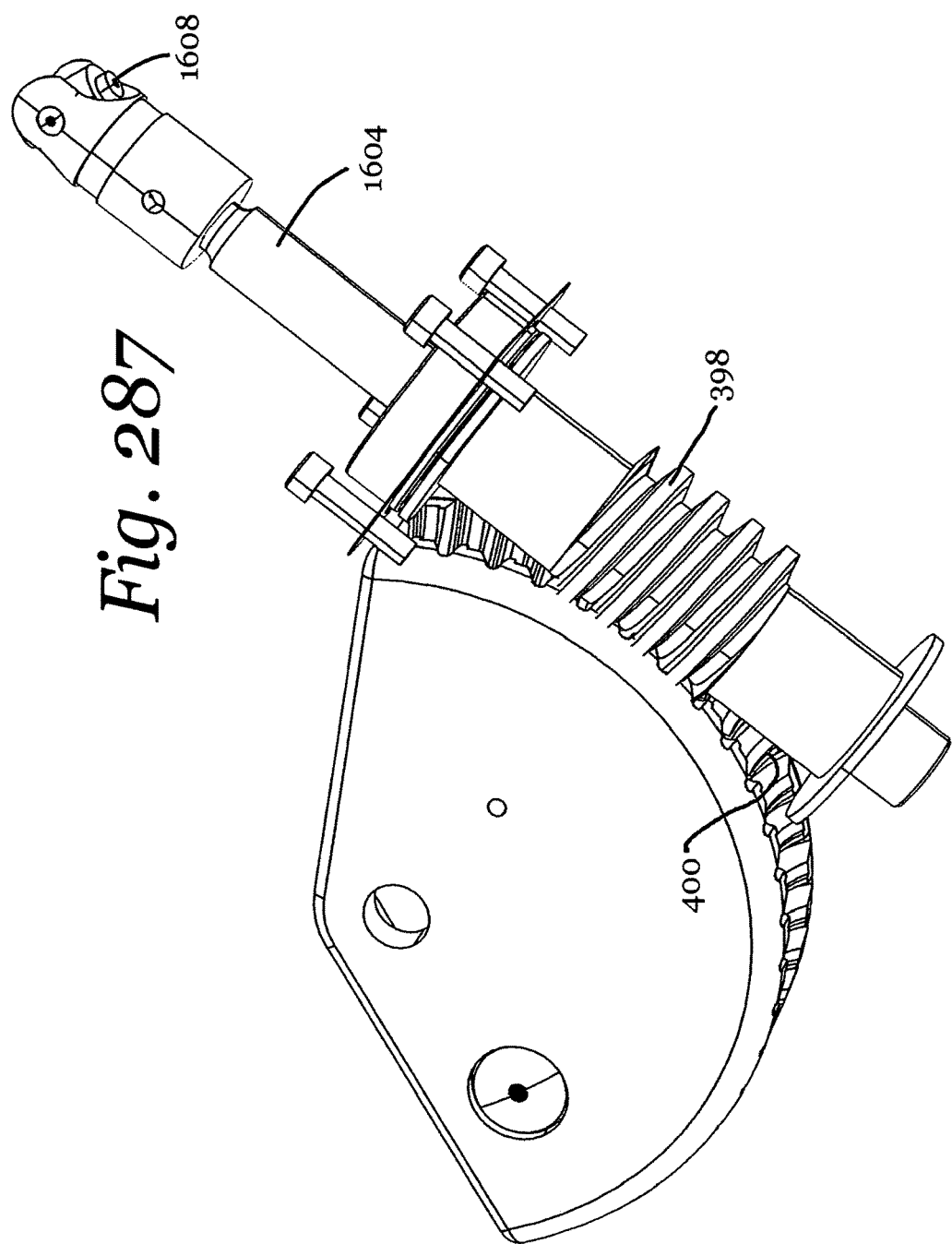

PATIENT POSITIONING SUPPORT APPARATUS WITH VIRTUAL PIVOT-SHIFT PELVIC PADS, UPPER BODY STABILIZATION AND FAIL-SAFE TABLE ATTACHMENT MECHANISM

CROSS-REFERENCE TO RELATED APPLICATIONS

The present application is a continuation application of U.S. patent application Ser. No. 14/012,434, entitled "PATIENT POSITIONING SUPPORT APPARATUS WITH VIRTUAL PIVOT-SHIFT PELVIC PADS, UPPER BODY STABILIZATION AND FAIL-SAFE TABLE ATTACHMENT MECHANISM", filed Aug. 28, 2013, the entirety of which is incorporated by reference herein.

Application Ser. No. 14/012,434 is a continuation-in-part application of U.S. patent application Ser. No. 13/956,704, entitled "PATIENT SUPPORT APPARATUS WITH BODY SLIDE POSITION DIGITALLY COORDINATED WITH HINGE ANGLE", filed Aug. 1, 2013, the entirety of which is incorporated by reference herein. Application Ser. No. 13/956,704 claimed the benefit of U.S. Provisional Patent Application Nos.: 61/742,098, filed Aug. 2, 2012; 61/852,199, filed Mar. 15, 2013; 61/849,016, filed Jan. 17, 2013; 61/849,035, filed Jan. 17, 2013; 61/795,649, filed Oct. 22, 2012; and 61/743,240, filed Aug. 29, 2012. The entirety of all patent applications are incorporated by reference herein in their entireties.

Application Ser. No. 14/012,434 is also a continuation-in-part application of U.S. patent application Ser. No. 13/694,392, entitled "PATIENT POSITIONING SUPPORT STRUCTURE WITH COORDINATED CONTINUOUS NONSEGMENTED ARTICULATION, ROTATION AND LIFT, AND LOCKING FAIL-SAFE DEVICE", filed Nov. 28, 2012, which claimed the benefit of U.S. Provisional Patent Application No. 61/629,815, filed Nov. 28, 2011, the entirety of which are incorporated herein by reference.

TECHNICAL FIELD

The present disclosure relates to patient positioning support structures.

BACKGROUND OF THE INVENTION

The present invention is direct to structures for supporting a patient in a desired position during examination and treatment, including medical procedures such as imaging and surgery and in particular to such a structure that allows a surgeon to selectively position the patient for convenient access to the surgery site and providing for manipulation of the patient during surgery including the tilting, pivoting, angulating or bending of a trunk and additionally or alternatively joint of a patient in a supine, prone or lateral-decubitus position, while simultaneously maintaining the patient's head in a convenient location for anesthesia and substantially preventing undesired stretching or compression of the patient's spine and the patient's skin.

Current surgical procedures and approaches incorporate imaging techniques and technologies that facilitate the surgical plan and improve outcomes and that provide for more rapid patient recovery. For example, minimally invasive surgical techniques, such as percutaneous insertion of spinal implants, involve small incisions that are guided by continuous or repeated intra-operative imaging and that are frequently associated with navigation technologies. These imaging and navigation techniques can be processed using computer software programs that produce two or three dimensional images for reference by the surgeon during the course of the procedure. If the patient support structure, apparatus, system or device is not radiolucent or configured to be compatible with the imaging technologies, it may be necessary to interrupt the surgery periodically in order to remove the patient to a separate structure for imaging followed by transfer back to the operating support structure for resumption of the surgical procedure. Such patient transfers for imaging purposes may be avoided by employing radiolucent and other imaging and navigation compatible systems. The patient support system should also be constructed to permit unobstructed movement of the imaging equipment and other surgical equipment around, over and under the patient throughout the course of the surgical procedure without contamination of the sterile field.

It is also necessary that the patient support structure be constructed to provide optimum access to the surgical field by the surgery team. Some procedures require positioning of portions of the patient's body in different ways at different times during the procedure. Some procedures, for example, spinal surgery, involve access through more than one surgical site or field. Since all of these fields may not be in the same plane or anatomical location, the patient support surfaces should be adjustable and capable of providing support in different planes for different parts of the patient's body as well as different positions or alignments for a given part of the body. Preferably, the patient support should be adjustable to provide support in separate planes and in different alignments for the head and upper trunk portion of the patient's body, the lower trunk and pelvic portion of the body as well as each of the limbs independently.

Certain types of surgery, such as orthopedic surgery, may require that the patient or a part of the patient be repositioned during the procedure while in some cases maintaining the sterile field. Where surgery is directed toward motion preservation procedures, such as by installation of artificial joints, soft or dynamic stabilization implants, spinal ligaments and total disc prostheses, for example, the surgeon must be able to manipulate certain joints while supporting selected portions of the patient's body during surgery in order to facilitate the procedure. It is also desirable to be able to test the range of motion of the surgically repaired or stabilized joint and to observe the gliding movement of the reconstructed articulating prosthetic surfaces or the tension and flexibility of artificial ligaments, cords, spacers and other types of dynamic stabilizers before the wound is closed. Such manipulation can be used, for example, to verify the correct positioning and function of an implanted prosthetic disc, spinal dynamic longitudinal connecting member, interspinous spacer or joint replacement during a surgical procedure. Where manipulation discloses binding, sub-optimal position or even crushing of the adjacent vertebrae, for example, as may occur with osteoporosis, the prosthesis can be removed and the adjacent vertebrae fused or otherwise treated while the patient remains anesthetized. Injury which might otherwise have resulted from a "trial" use of the implant post-operatively will be avoided, along with the need for a second round of anesthesia and surgery to remove the implant or prosthesis and perform the revision, fusion or corrective surgery.

There is also a need for a patient support structure that can be rotated, articulated and angulated so that the patient can be moved or rolled from a supine position to a prone position, or from a lateral-decubitus to a supine position, or from a prone position to a position with the hips and knees flexed or extended, and whereby intra-operative extension and flexion of at least a portion of the spinal column can be achieved to change lumbar lordosis. The patient support structure must also be capable of cooperating with the biomechanics of the patient for easy, selective adjustment without necessitating removal of the patient or causing substantial interruption of the procedure.

For certain types of surgical procedures, for example spinal surgeries, it may be desirable to position the patient for sequential anterior, posterior and additionally or alternatively lateral procedures. The patient support structure should also be capable of rotation about an axis in order to provide correct positioning of the patient and optimum accessibility for the surgeon as well as imaging equipment during such sequential procedures, and also without translating the patient's head, which could disrupt connection of the patient with anesthesia equipment, and also without undesirably distracting or compressing the patient's spine during angulation or rotation of the patient's pelvis around the hips.

Orthopedic procedures involving fractures and other trauma may require the use of traction equipment such as cables, tongs, pulleys and weights. The patient support system must include structure and accessories for anchoring such equipment and it must provide adequate support to withstand unequal forces generated by traction against such equipment.

Orthopedic procedures, especially spine surgery, may also require the use of an open frame, instead of a closed table top, that allows a prone patient's belly to hang downwardly therebetween so as to prevent compression of internal organs against the anterior side of the patient's spine and prevent compression of the patient's vessels to decrease blood loss.

Articulated robotic arms are increasingly employed to perform surgical techniques. These units are generally designed to move short distances and to perform very precise work. Reliance on the patient support structure to perform any necessary gross movement of the patient can be beneficial, especially if the movements are synchronized or coordinated. Such units require a surgical support surface capable of smoothly performing the multi-directional movements which would otherwise be performed by trained medical personnel. There is thus a need in this application as well for integration between the robotics technology and the patient positioning technology.

While conventional operating tables generally include structure that permits tilting or rotation of a patient support surface about a longitudinal axis, previous surgical support devices have attempted to address the need for access by providing a cantilevered patient support surface on one end. Such designs typically employ either a massive base to counterbalance the extended support member or a large overhead frame structure to provide support from above. The enlarged base members associated with such cantilever designs are problematic in that they can and do obstruct the movement of C-arm and O-arm mobile fluoroscopic imaging devices and other equipment. Surgical tables with overhead frame structures are bulky and may require the use of dedicated operating rooms, since in some cases they cannot be moved easily out of the way. Neither of these designs is easily portable or storable. More recent orthopedic surgical tables require complicated mechanisms to provide translation of the patient's trunk while manipulating the patient's lower body during surgery.

More recent and advanced articulating surgical tables are available, and include an open frame patient support for positioning with upper and lower body support portions joined by centrally located and spaced apart hinges. However, while these surgical tables enable bending the patient at the waist or hips, maintaining the vertical height of the surgical site can be difficult. These tables can also cause significant translation of the patient's trunk toward and away from anesthesia, which is undesirable. These tables also require complex translation compensation structural mechanisms to prevent potential patient injury.

Thus, there remains a need for a patient support structure that provides easy access for personnel and equipment, that can be easily and quickly positioned and repositioned in multiple planes without the use of massive counterbalancing support structure, that can maintain the patient's head at a convenient location for anesthesia during positioning of the patient, that does not cause undesired stretching or compression of the patient's spine and skin and that does not require use of a dedicated operating room.

SUMMARY OF THE INVENTION

The present invention is directed to a patient support structure that permits adjustable positioning, repositioning and selectively lockable support of a patient's head and upper body, lower body and limbs in up to a plurality of individual planes while permitting tilting, rotation, flexion, extension, angulation, articulation and bending, and other manipulations as well as full and free access to the patient by medical personnel and equipment. The apparatus of the present invention may be cantilevered or non-cantilevered, such as in the case of a dual-column base, and includes at least a prone patient support structure that is suspended above a floor, that is adapted to cooperate with the patient's biomechanics so as to allow positioning of the patient's hips and knees in a neutral position, a flexed position and an extended position. The apparatus allows positioning of the patient parallel with the floor or in Trendelenburg or reverse Trendelenburg surgical positions, and optionally while also tilting or rolling the patient with respect to the floor, along a horizontal axis, and while simultaneously maintaining the patient's head in a suitable location for anesthesia, without substantial horizontal translation, and also while preventing undesired spinal distraction or compression. The patient support structure of the present invention includes an open frame that allows the patient's belly to fall, extend, depend or hang downwardly therethrough between a pair of spaced opposed and somewhat centrally located radially sliding or gliding joints that enable flexion and extension of the prone patient's hips and knees with respect to a virtual pivot point located on or above patient pelvic support pads. The pelvic pads are sized, shaped and configured to follow an arc of motion associated with the joint and defined by a radius. The joint joins the pelvic pads with a lower body or lower extremity support structure or frame. The prone patient support structure includes one or more hip-thigh or pelvic pads attached to one or both of the joints and an adjustable torso support with a chest pad slidingly attached to a fixed rigid outer frame. The torso support, chest pad and hip-thigh pads are substantially radiolucent, so as to not interfere with imaging when the patient is on the patient positioning support system 5.

The apparatus of the present invention may also include a supine patient support structure comprised of two sections and suspended above the floor. The sections are connected at a pair of spaced opposed hinges that angulate and translate. The supine patient support structure is size, shaped and configured for positioning the patient in an angulated or articulated and non-articulated prone, supine or lateral position and for performing a sandwich-and-roll procedure, wherein the patient is rolled over 180-degrees between supine and prone positions.

The surgical table of the present invention may also include a base that is sized, shaped and configured to hold the prone and supine patient supports above the floor and also to provide for vertical translation or height adjustment of one or both of the patient support structures as well as three degrees of freedom with respect to movement of the patient support structure relative to a roll axis, a pitch axis and a yaw axis.

The surgical table of the present invention may also include a fail-safe connection mechanism for connecting a patient support structure to the base while simultaneously preventing incorrect disconnection of a patient support structure from the base, which could cause the support structure to collapse and result in patient injury. The patient support structure can also provide for a length adjustment with respect to the base when the structure is angulated or the ends are pivoted so as to put the structure into a Trendelenburg or reverse Trendelenburg position.

In an embodiment of the present invention, a patient support apparatus for supporting a patient in a prone position during a surgical procedure is provided, wherein the apparatus includes an open fixed frame that is suspended above a floor, and a pair of spaced opposed radially sliding joints that cooperate with the frame, wherein each joint includes a virtual pivot point and an arc of motion spaced from the virtual pivot point, and the joints are movable along the arc so as to provide a pivot shift mechanism for a pair of pelvic pads attached to the joints.

In a further embodiment, the joints are movable between a first position and a second position with respect to the virtual pivot point, the arc of motion and the floor.

In a further embodiment, the virtual pivot point is located within a patient supported on the apparatus.

In a further embodiment, the virtual pivot point is located at a contact point between a patient supported on the apparatus and a hip-thigh pad.

In some embodiments, the hip-thigh pad is joined with a joint.

In some embodiments, the virtual pivot point is located adjacent to a spine of a patient supported on the apparatus.

In a further embodiment, the virtual pivot point includes a height above the floor; wherein the height is substantially constant during movement of the joint with respect to the virtual pivot point.

In a further embodiment, the height is adjustable.

In a further embodiment, the virtual pivot point is associated with a first pitch axis, such as an axis of articulation or angulation.

In a further embodiment, each joint includes a radius that extends from the virtual pivot point in a plane substantially perpendicular to the first pitch axis, such that the radius defines at least a portion of the arc of motion.

In a further embodiment, the apparatus further includes a hip-thigh pad joined with one of the joints so as to be movable about the virtual pivot point and with respect to the arc of motion.

In a further embodiment, at least a portion of the hip-thigh pad glides along the arc of motion.

In a further embodiment, the apparatus further includes a lower extremity support structure joined with the joints such that the lower extremity support structure is movable with respect to the virtual pivot point and between a first position and a second position.

In a further embodiment, the apparatus further includes a chest pad attachable to a head-end portion of the frame.

In a further embodiment, the apparatus further includes a hip-thigh pad associated with a lower-body side of the joint; wherein the chest pad is associated with an upper-body side of the joint, so as to be opposed to and spaced a distance from the hip-thigh pad.

In a further embodiment, the distance between the chest pad and the hip-thigh pad is substantially constant during movement of the joint between a first position and a second position.

In a further embodiment, the distance between the chest pad and the hip-thigh pad is slightly variable during movement of the joint.

In a further embodiment, the hip-thigh pad translates laterally during movement of the joint, such as but not limited toward or away from the head-end of the base when moving between neutral and angulated positions.

In a further embodiment, the apparatus further includes a lower extremity support structure joined with the joints such that the lower extremity support structure is movable with respect to the virtual pivot point.

In a further embodiment, the lower extremity support structure includes a femoral support and a lower leg cradle.

In a further embodiment, the femoral support includes an adjustable sling.

In a further embodiment, the femoral support and the lower leg cradle are pivotably connected so as to be movable between a first position and a second position; and wherein when in the first position, the femoral support and the lower leg cradle are in a neutral position; and when in the second position, the femoral support and the lower leg cradle are in a flexed position.

In a further embodiment, the lower leg cradle is non-incrementally adjustable with respect to the femoral support and between the neutral position and a maximally flexed position.

In a further embodiment, the lower leg cradle is continuously adjustable with respect to the femoral support and between the neutral position and a maximally flexed position.

In a further embodiment, the lower leg cradle is incrementally adjustable with respect to the femoral support.

In a further embodiment, the femoral support and the lower leg cradle are joined by a pair of spaced opposed lower leg hinges.

In a further embodiment, the chest pad is slidably adjustable with respect to a length of the frame.

In a further embodiment, the chest pad is attachable to the frame.

In a further embodiment, the chest pad is lockable.

In a further embodiment, the chest pad is located adjacent to the joints.

In a further embodiment, the chest pad includes at least two chest pads.

In a further embodiment, the frame includes head-end portion; and the chest pad is adjustable along a length of the frame head-end portion and between a first location adjacent to an outer-end of the frame head-end portion and a second location adjacent to the joints.

In a further embodiment, the chest pad is substantially radiolucent.

In a further embodiment, the hip-thigh pad includes a pair of hip-thigh pads spaced apart with respect to the frame so as to provide a space for at least a portion of a patient's body to be positioned therebetween.

In a further embodiment, the hip-thigh pad is substantially radiolucent.

In a further embodiment, the apparatus further includes a base.

In a further embodiment, the base includes a pair of laterally spaced vertical translator subassemblies, each vertical translator subassembly including an upper end portion and a lower end portion; and a crossbar joining the lower end portions of the vertical translator subassemblies such that the vertical translator subassemblies are spaced apart a constant distance; wherein the frame is suspended from upper end portions of the vertical translator subassemblies.

In a further embodiment, the base includes a pair of connection subassemblies, each of connection subassemblies including: a ladder attachment structure or connector portion; and a ladder or attachment upright attached to the ladder attachment structure.

In a further embodiment, the ladder is removably attached to the ladder attachment structure.

In a further embodiment, the ladder is lockably attached to the ladder attachment structure.

In a further embodiment, the ladder includes a set of ladders, the set of ladders including a pair of standard length ladders.

In a further embodiment, the ladder includes at least one additional ladder selected from the group consisting of standard length ladders and extended-length ladders.

In a further embodiment, the apparatus further includes a T-pin associated with at least one of a second pitch axis and a third pitch axis; wherein the T-pin joins an outer end of the frame with the base.

In a further embodiment, the frame is pivotable about the T-pin with respect to a joined vertical translator subassembly in response to vertical movement of the joined vertical translator subassembly.

In a further embodiment, the frame is positionable in a Trendelenburg position and a Reverse Trendelenburg position.

In a further embodiment, at least one of the vertical translator subassembly upper end portions includes a rotation subassembly.

In a further embodiment, at least a portion of the frame is cantilevered.

In a further embodiment, the frame foot-end portion includes: a translation compensation subassembly.

In a further embodiment, the frame includes: a longitudinally extending roll axis.

In a further embodiment, the frame is rotatable about the roll axis an amount of between about 1-degree and about 237-degrees.

In a further embodiment, the frame is continuously adjustable with respect to the roll axis and between a non-rolled orientation and an orientation associated with rolling an amount of about 237-degrees about the roll axis.

In a further embodiment, the frame is adapted to rotate with respect to the roll axis so as to be rolled an amount of about 180-degrees, so as to be positioned in an inverted orientation or position.

In a further embodiment, the frame is non-incrementally rotatable, pivotable or rollable about or around the roll axis.

In a further embodiment, the frame is lockable in a rolled position.

In a further embodiment, the apparatus further includes a supine patient support structure suspended above the floor.

In a further embodiment, the supine patient support structure includes an open frame that is articulatable at a pair of spaced opposed hinges; and at least one of a set of body support pads and a closed table-top.

In a further embodiment, the body support pads, the elongate table pad and the table-top are substantially radiolucent.

In a further embodiment, the supine patient support structure is positionable in a decubitus position.

In a further embodiment, the supine patient support structure is spaced from and opposed to the frame.

In a further embodiment, at least one of the vertical translation subassemblies includes a rotation subassembly adapted to roll the frame about a longitudinally extending roll axis.

In a further embodiment, the hip-thigh pad includes a hip-thigh pad mount joining the hip-thigh pad with one of the joints.

In a further embodiment, the apparatus includes a fail-safe mechanism.

In another embodiment, a method of positioning a patient on a patient support in a prone position is provided, the method comprising the steps of placing a patient on a supine patient support suspended above a floor, such that the patient is in a substantially supine position; sandwiching the patient between the supine patient support and a prone patient support suspended above the supine patient support; and rolling the patient an amount of about 180-degrees with respect to a longitudinally extending roll axis, such that the patient is in a substantially prone position.

In a further embodiment, the method includes removing the supine patient support.

In a further embodiment, the step of sandwiching the patient between the supine patient support and a prone patient support includes attaching the prone patient support to a pair of spaced opposed ladder attachment structures.

Therefore, the patient positioning support structure of the present invention is configured and arranged to overcome one or more of the problems with patient support systems described above. In some embodiments, the present invention provides a prone patient support structure that avoids a pair of spaced opposed hinges that translate and angulate, while cooperating with the patient's biomechanics to position the patient in and to move the patient's spine between neutral, flexed and extended positions while substantially preventing vertical and horizontal translation of the patient's torso. In some embodiments, the present invention provides such structures that allow for simultaneous rolling or tilting of the patient. In some embodiments, the present invention provides such structure wherein the base support is located at an end of the patient support structure, so as to allow for patient positioning and clearance for access to the patient in a wide variety of orientations. In some embodiments, the present invention provides such structure that may be rotated about an axis as well as moved upwardly or downwardly at either end thereof. In some embodiments, the present invention provides a fail-safe structure that prevents patient injury due to certain operator errors. In some embodiments, the present invention provides such apparatus and methods that are easy to use and especially adapted for the intended use thereof and wherein the apparatus are comparatively inexpensive to make and suitable for use.

In yet another embodiment, present invention is directed to a base for supporting and suspending a patient support structure above the floor, such as for supporting a patient during a surgical procedure. The base includes a pair of spaced opposed vertical translation subassemblies reversibly attachable to a patient support structure, a cross-bar, and a rotation subassembly that includes two degrees of rotational freedom. The location of each vertical translation subassembly is substantially constant during operation of the patient support structure, such that the vertical translation subassemblies do not move closer or farther apart during table operation.

Each of the vertical translation subassemblies includes a base portion and an off-set elevator subassembly that extends upwardly from the base portion. The vertical translation subassemblies each include an elevator, such as a primary elevator and a rotation subassembly.

In a further embodiment, the base includes a longitudinally extending roll axis and a pitch axis that extends perpendicularly to the roll axis and is also parallel to the floor.

In a further embodiment, each of the rotation subassemblies includes first and second rotation motor subassemblies. The first rotation motor subassembly includes a first shaft that extends parallel to the cross-bar and is adapted for releasable attachment of the patient support structure thereto. The second rotation motor subassembly includes a second shaft that joins the first rotation motor subassembly with an elevator of a respective vertical translation subassembly, such that the second rotation motor subassembly can rotate the first rotation motor subassembly with respect to a pitch axis that extends perpendicular to a roll axis and is also parallel with the floor.

The drawings constitute a part of this specification and include exemplary embodiments of the present invention and illustrate various objects and features thereof.

BRIEF DESCRIPTION OF THE DRAWINGS

FIG. 11A is an enlarged cross-sectional view of a portion of the T-pin to show greater detail of positioning of the locking portion thereof, the cross-section being taken along line 11A-11A of FIG. 11.

FIG. 56 is right side view of the patient positioning support system of FIG. 55.

FIG. 92C is a right-side view of the patient positioning support system of FIG. 92A.

FIG. 94B is a perspective view of the patient positioning support system of FIG. 94A.

FIG. 103 is perspective view of a supine patient support structure of the present invention, in one embodiment.

FIG. 104 is a right-side view of the supine patient support structure of FIG. 103.

FIG. 105 is a top view of the supine patient support structure of FIG. 103.

FIG. 112 is a right-side view of the patient positioning support structure of FIG. 110, wherein the supine patient support structure is in a lateral-decubitus position.

FIG. 113 is a head-end view of the patient positioning support structure of FIG. 112.

FIG. 114 is a right-side view of the patient positioning support structure of FIG. 110, wherein the supine patient support structure is in a hinge down position.

FIG. 115 is a head-end view of the patient positioning support structure of FIG. 114.

FIG. 116 is an enlarged bottom perspective view of a portion of the supine patient support structure of FIG. 102 showing the spaced opposed hinges.

FIG. 117 is a side view of one the spaced opposed hinges of FIG. 116.

FIG. 118 is a side view of the spaced opposed hinge of FIG. 117 with shrouding not shown, so as to show detail of the worm gear drive of the hinge.

FIG. 119 is a bottom view of the hinge of FIG. 118.

FIG. 120 is a perspective view of the hinge of FIG. 118.

FIG. 121 is a cross-sectional view of the head-end of the patient positioning support structure of FIG. 5, the cross-section being taken along the line 121-121 of FIG. 7.

FIG. 122 is an enlarged left side view of the head-end of the patient positioning support structure of FIG. 23.

FIG. 123 is an enlarged top view of the patient positioning support structure of FIG. 122.

Figure 23:
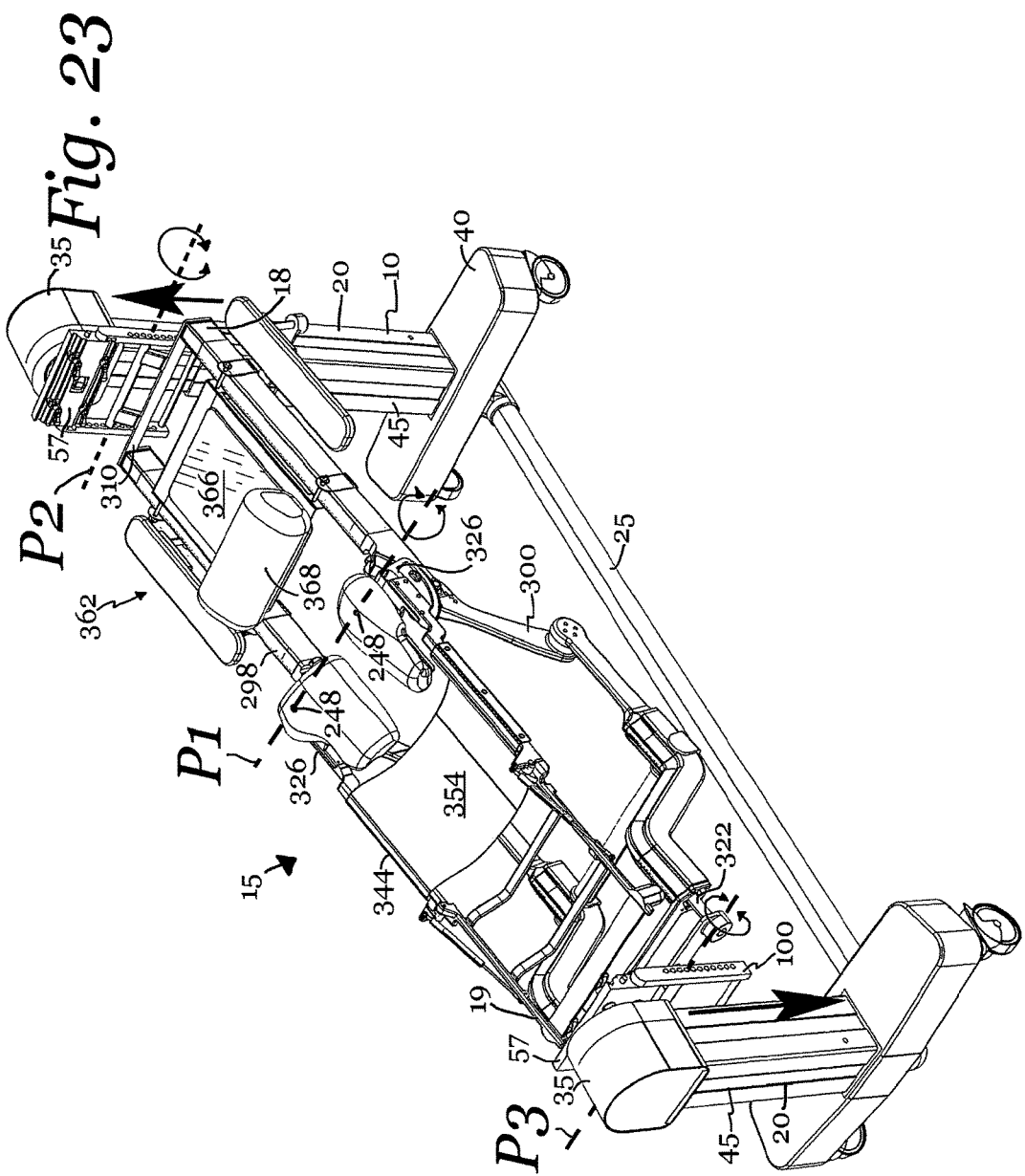
FIG. 23 is a reduced perspective view of the patient positioning support system of FIG. 1, with the patient support structure in a reverse Trendelenburg position.
Figure 124:
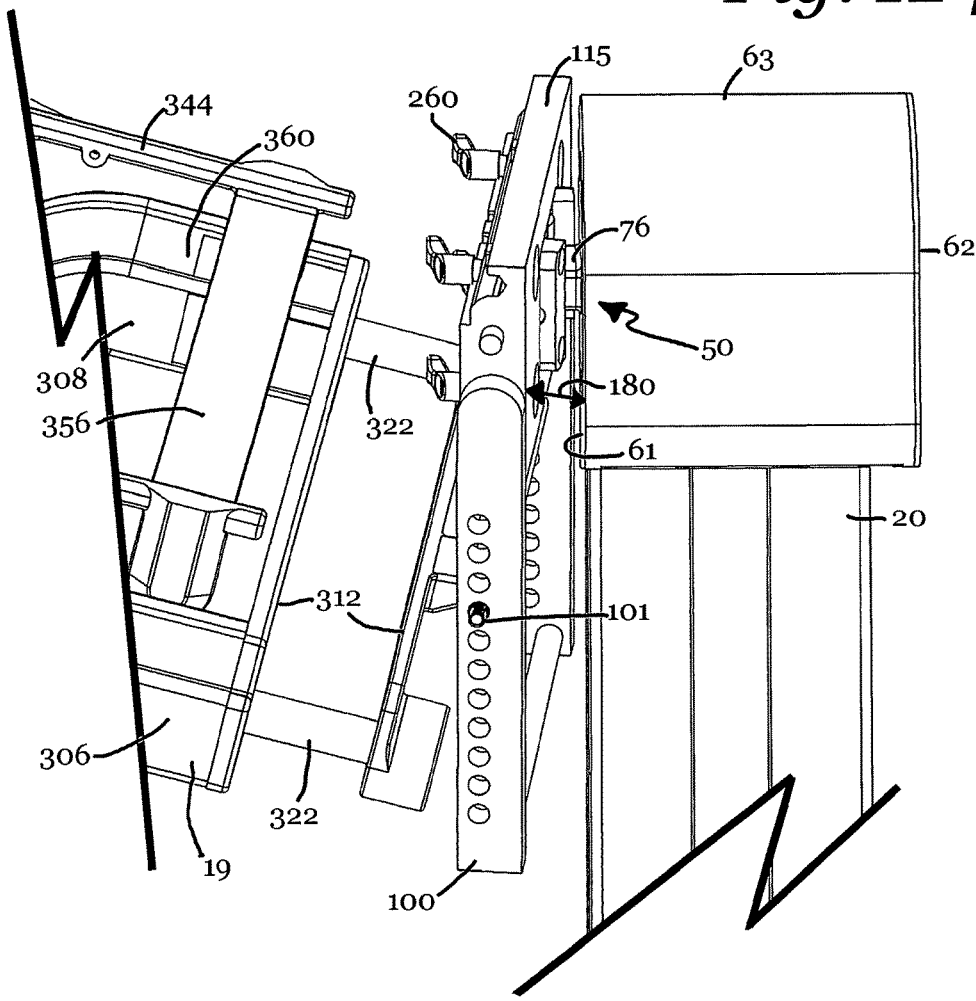

FIG. 124 is an enlarged left side view of the foot-end of the patient positioning support structure of FIG. 23.

Figure 125:
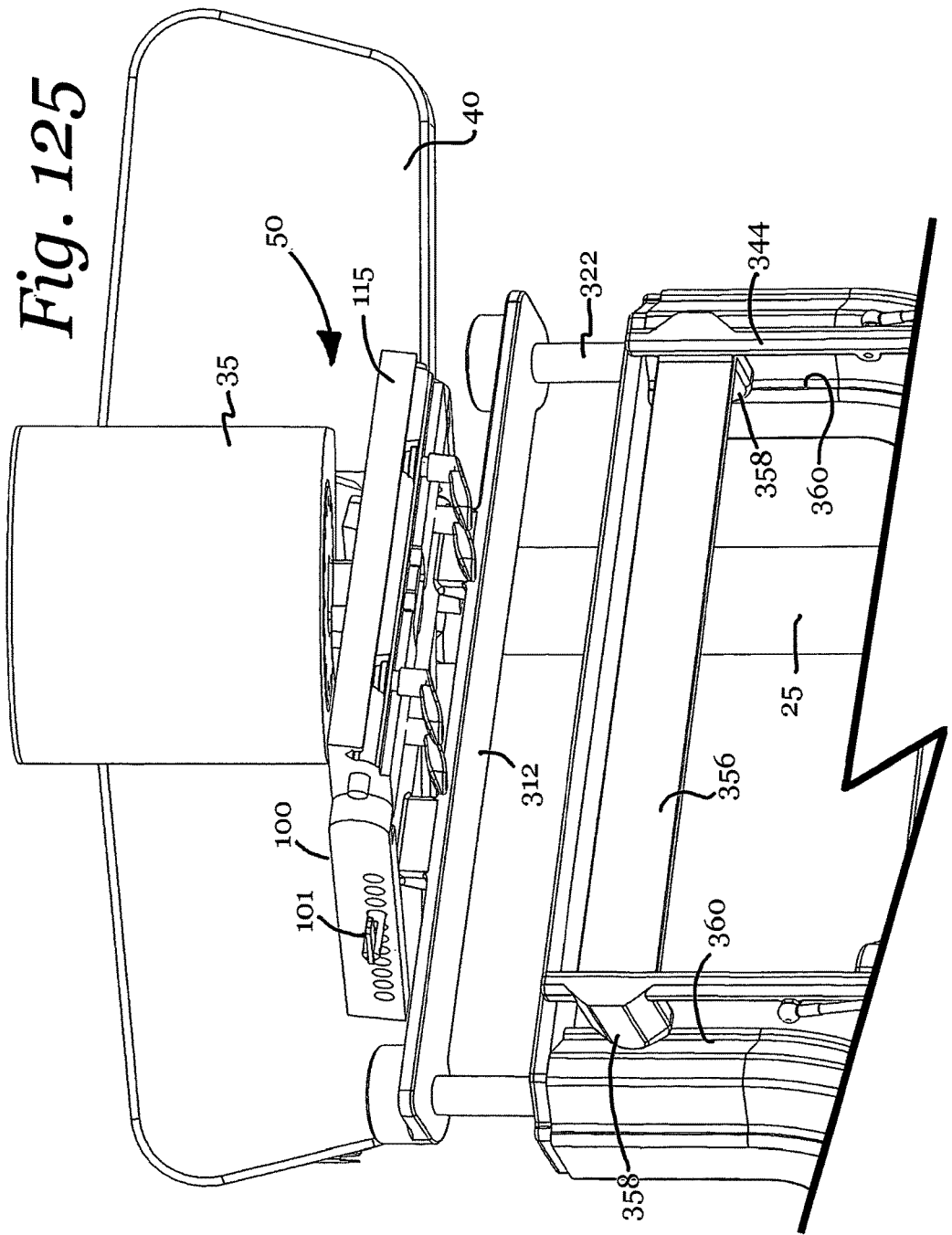

FIG. 125 is an enlarged top view of the patient positioning support structure of FIG. 124.

Figure 2:
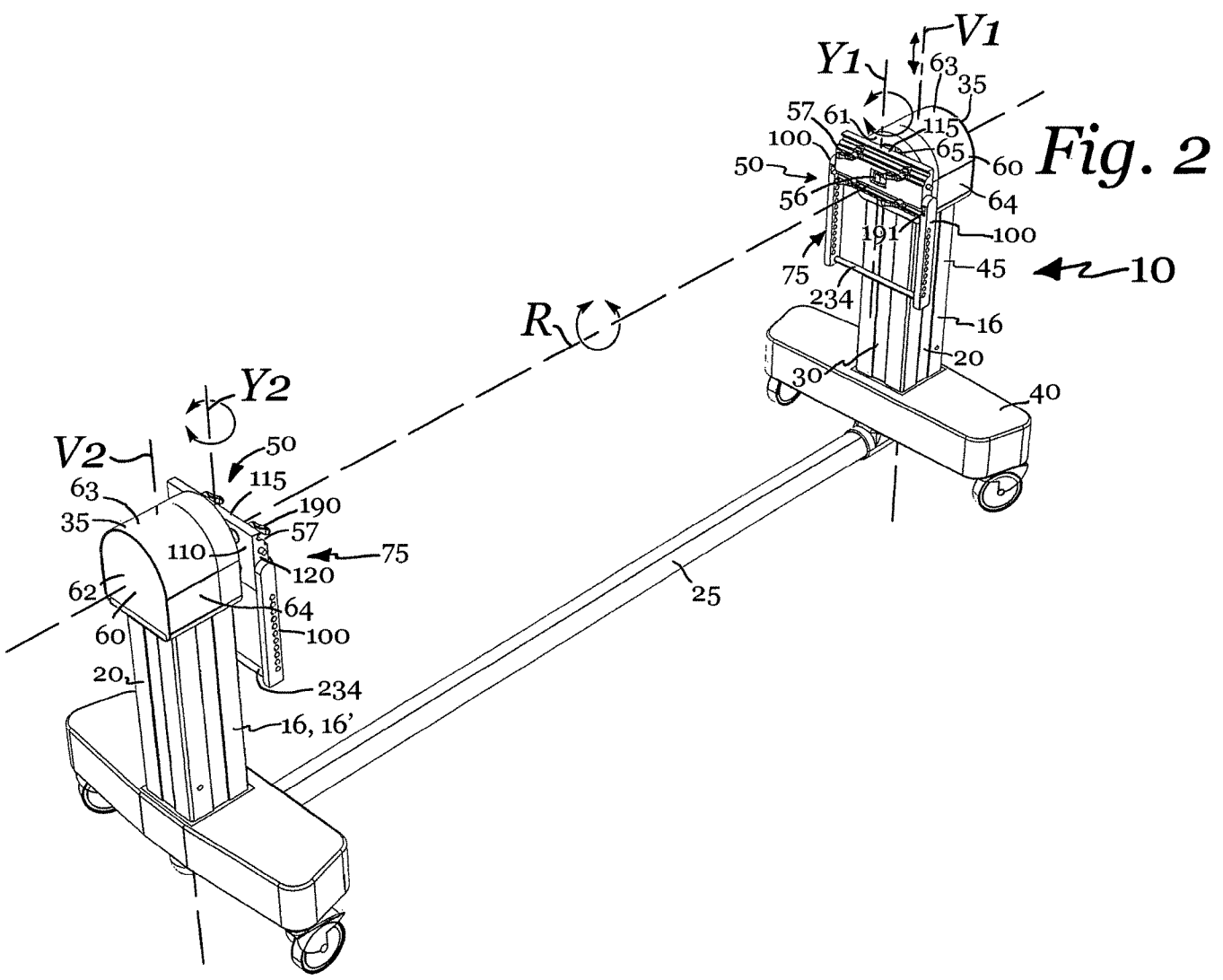
FIG. 2 is a perspective view of a base of the patient positioning support system of FIG. 1, including a pair of laterally spaced opposed vertical translator subassemblies.
Figure 126:
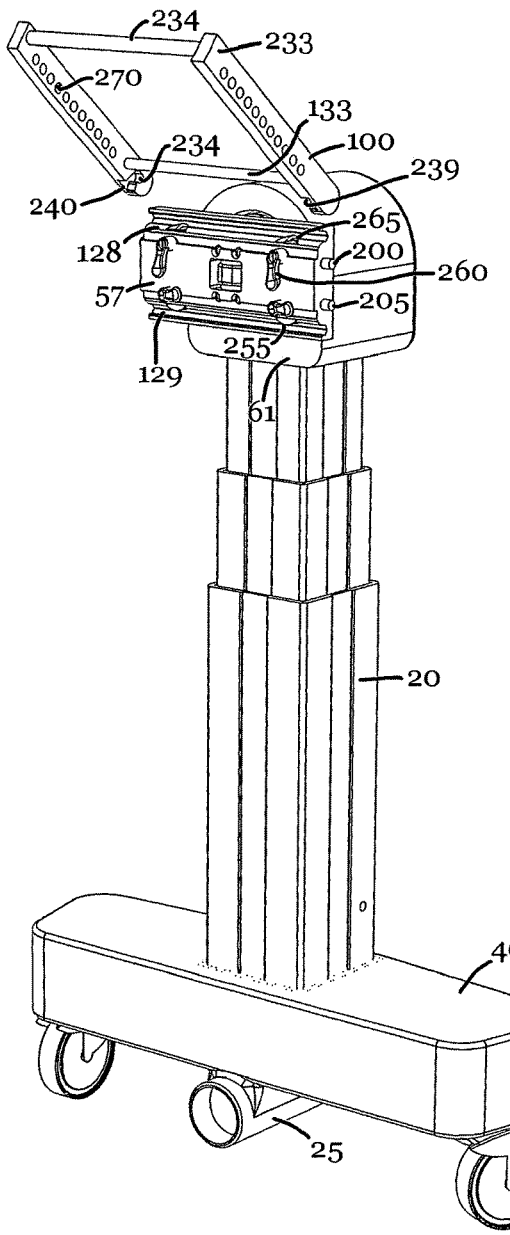

FIG. 126 an enlarged perspective view of a vertical translation subassembly of the base of FIG. 2 showing a first step in attaching a standard length ladder to the vertical translation subassembly.

Figure 127:
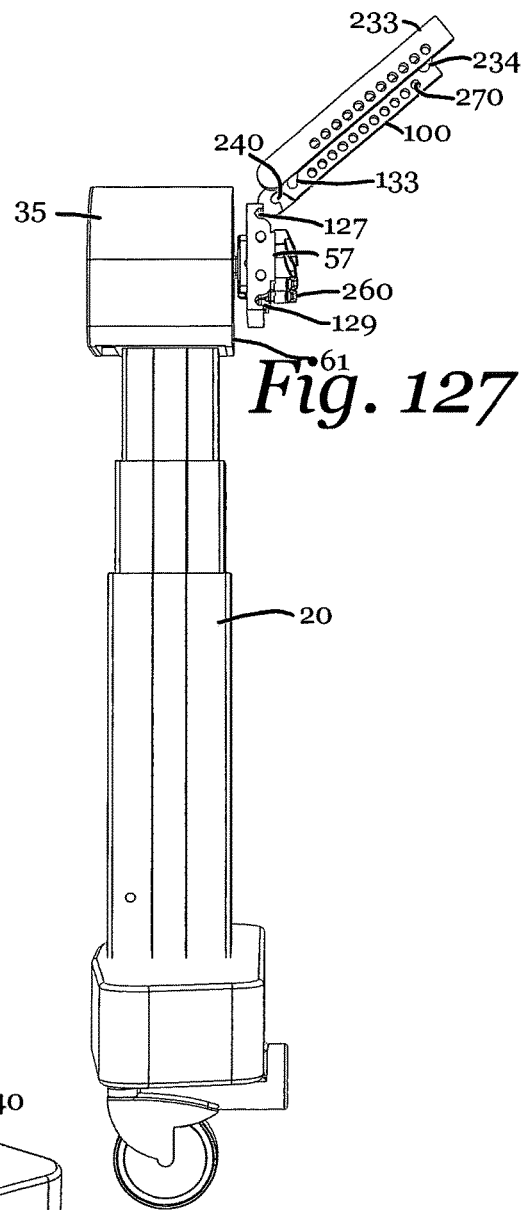

FIG. 127 is a side view of the vertical translation subassembly of FIG. 126.

Figure 128:
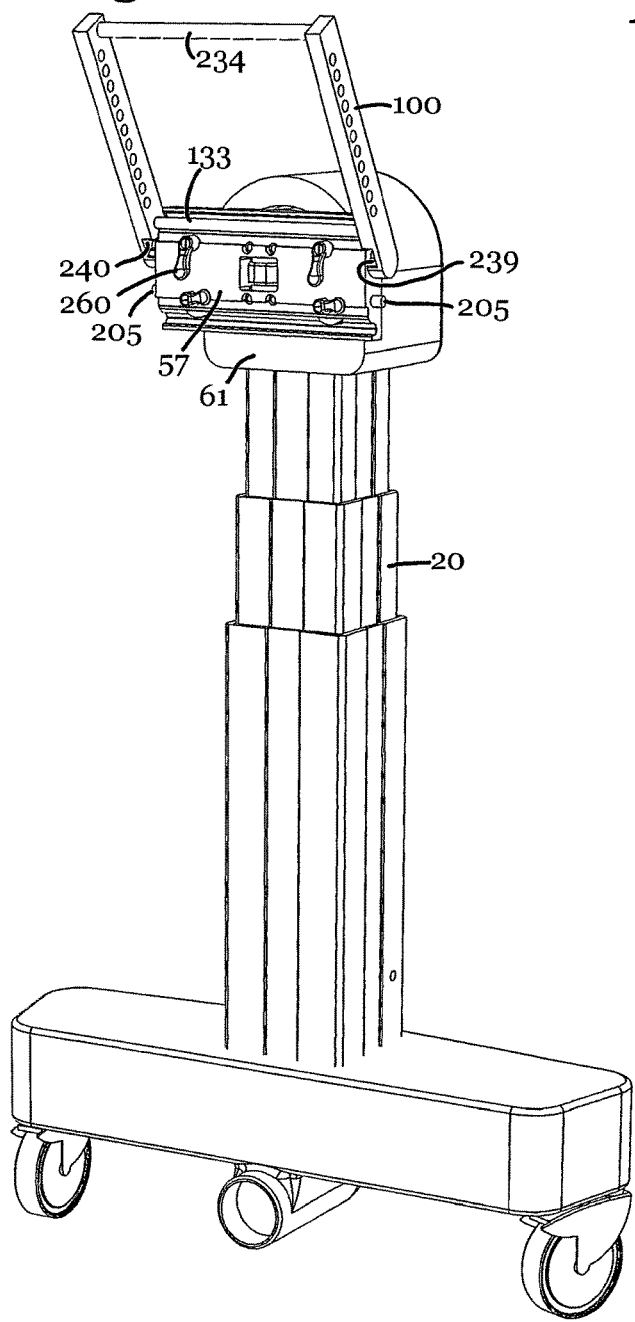

FIG. 128 is a perspective view of the vertical translation subassembly of FIG. 126 showing a second step in attaching the ladder to the vertical translation subassembly.

Figure 129:
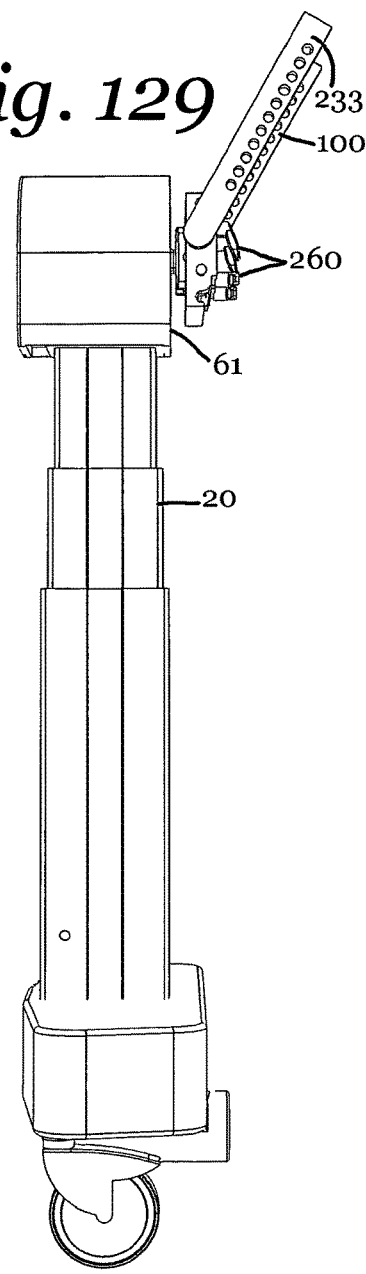

FIG. 129 is a side view of the vertical translation subassembly of FIG. 128.

FIG. 130 is a perspective view of the vertical translation subassembly of FIG. 126 showing a third step in attaching the ladder to the vertical translation subassembly.

FIG. 131 is a side view of the vertical translation subassembly of FIG. 130.

FIG. 132 is a perspective view of the vertical translation subassembly of FIG. 126 showing a fourth step in attaching the ladder to the vertical translation subassembly.

FIG. 133 is a side view of the vertical translation subassembly of FIG. 132.

Figure 3:
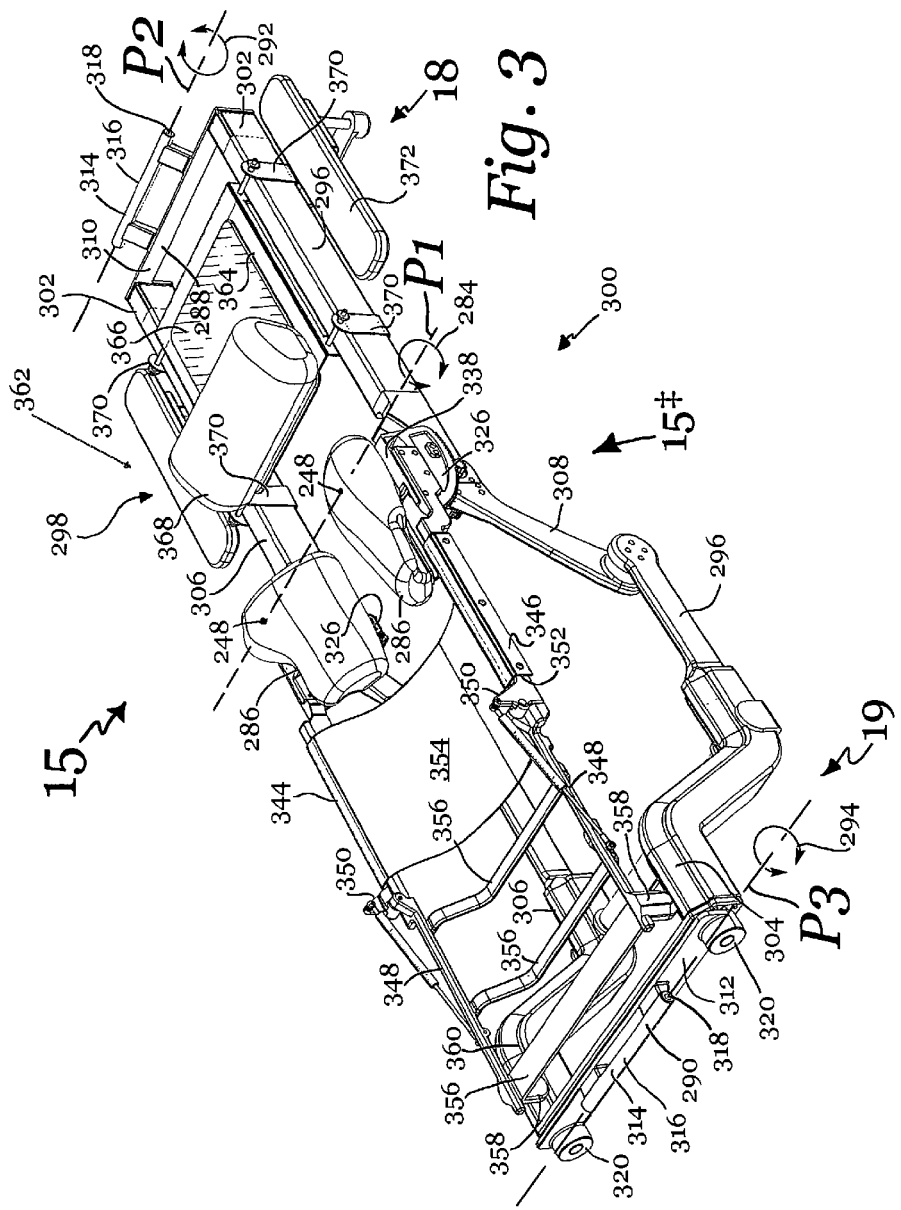
FIG. 3 is a perspective view of a prone patient support structure of the patient positioning support system of FIG. 1.
Figure 134:
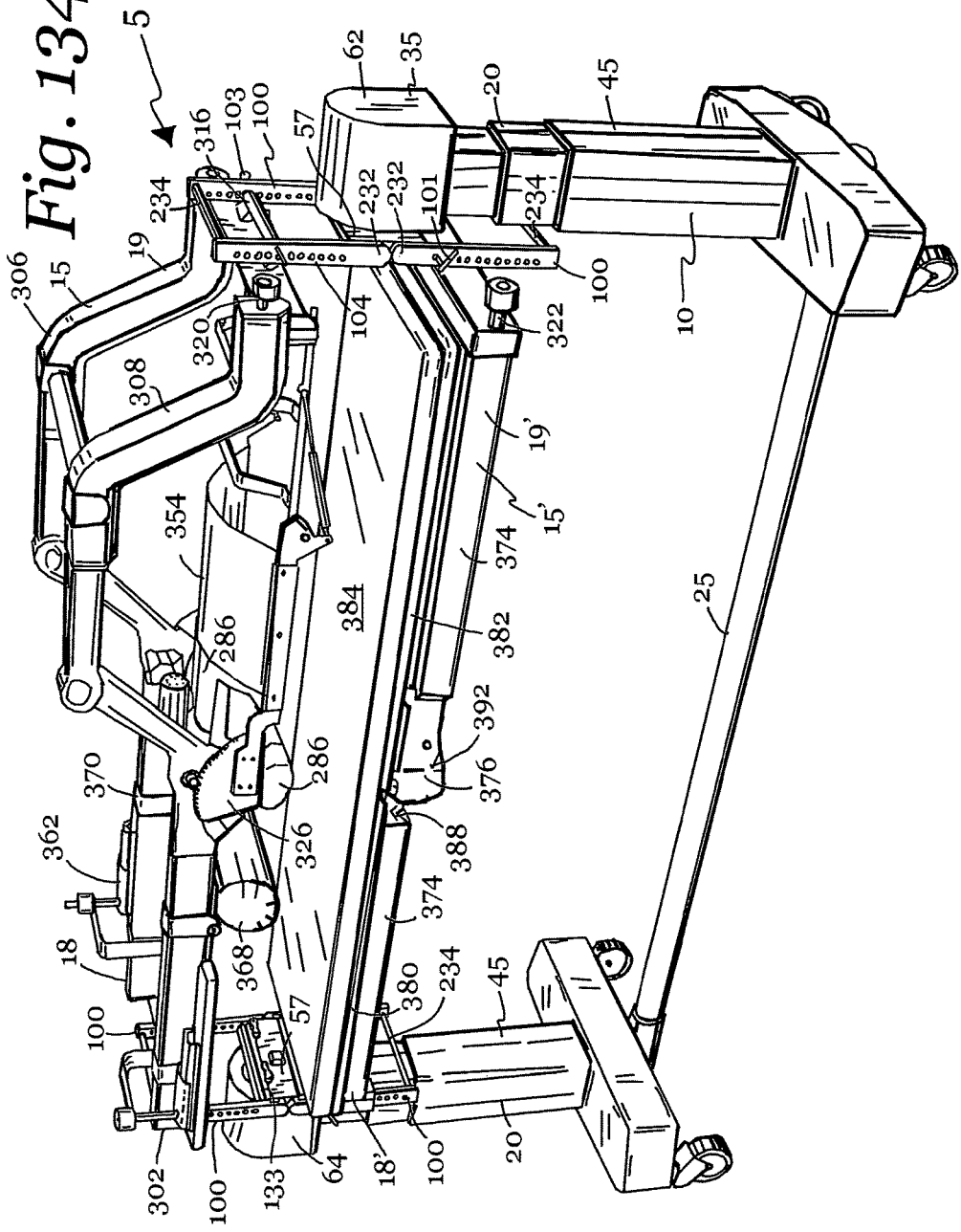

FIG. 134 is an illustration showing a perspective view of a patient positioning support system of the present invention, in another embodiment, wherein the patient positioning support system is positioned to begin a sandwich-and-roll procedure, so as to turn over a patient from a supine position, on the supine patient support structure of FIG. 103, to a prone position, on the prone patient support structure of FIG. 3.

Figure 135:
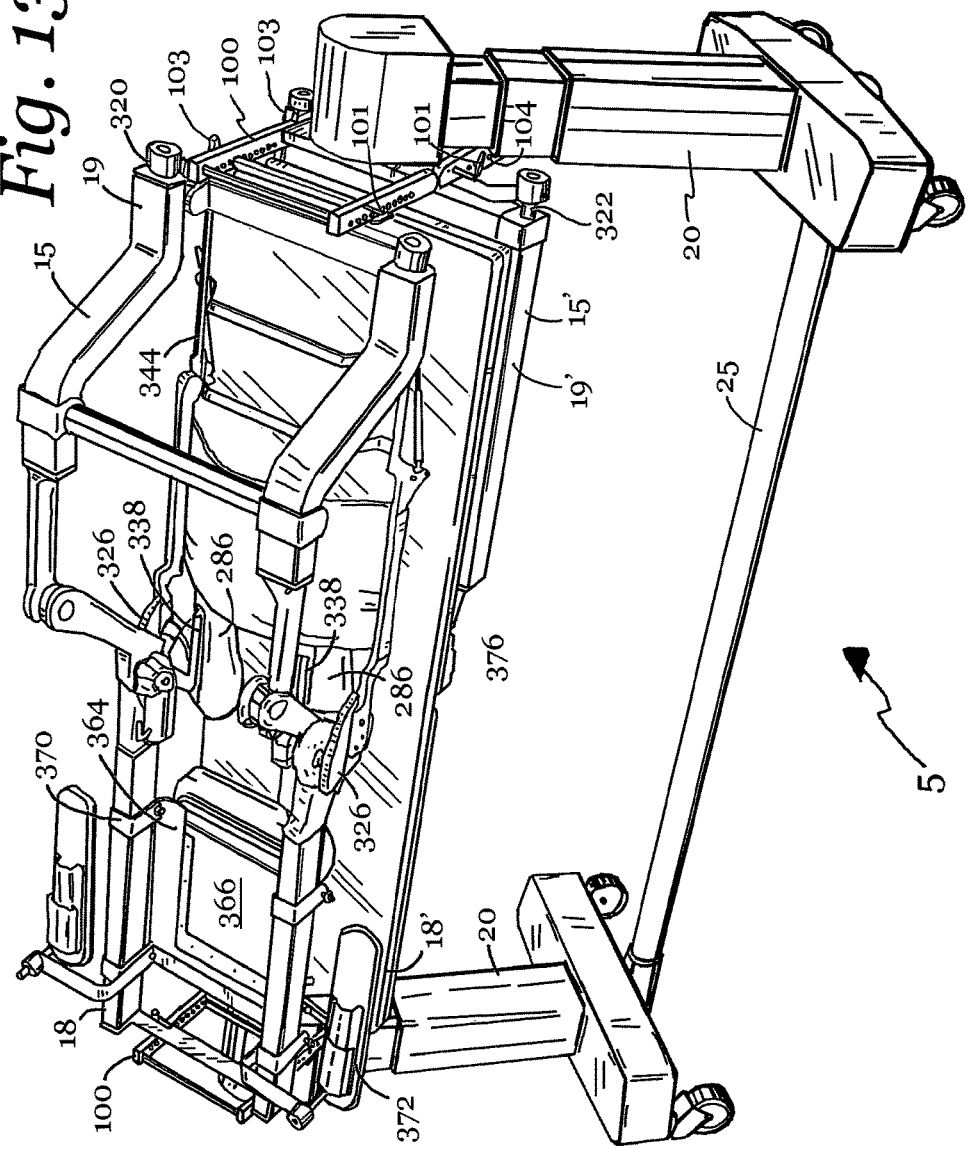

FIG. 135 is an illustration showing the patient positioning support structure of FIG. 134 after a 180-degree roll has been initiated.

Figure 136:
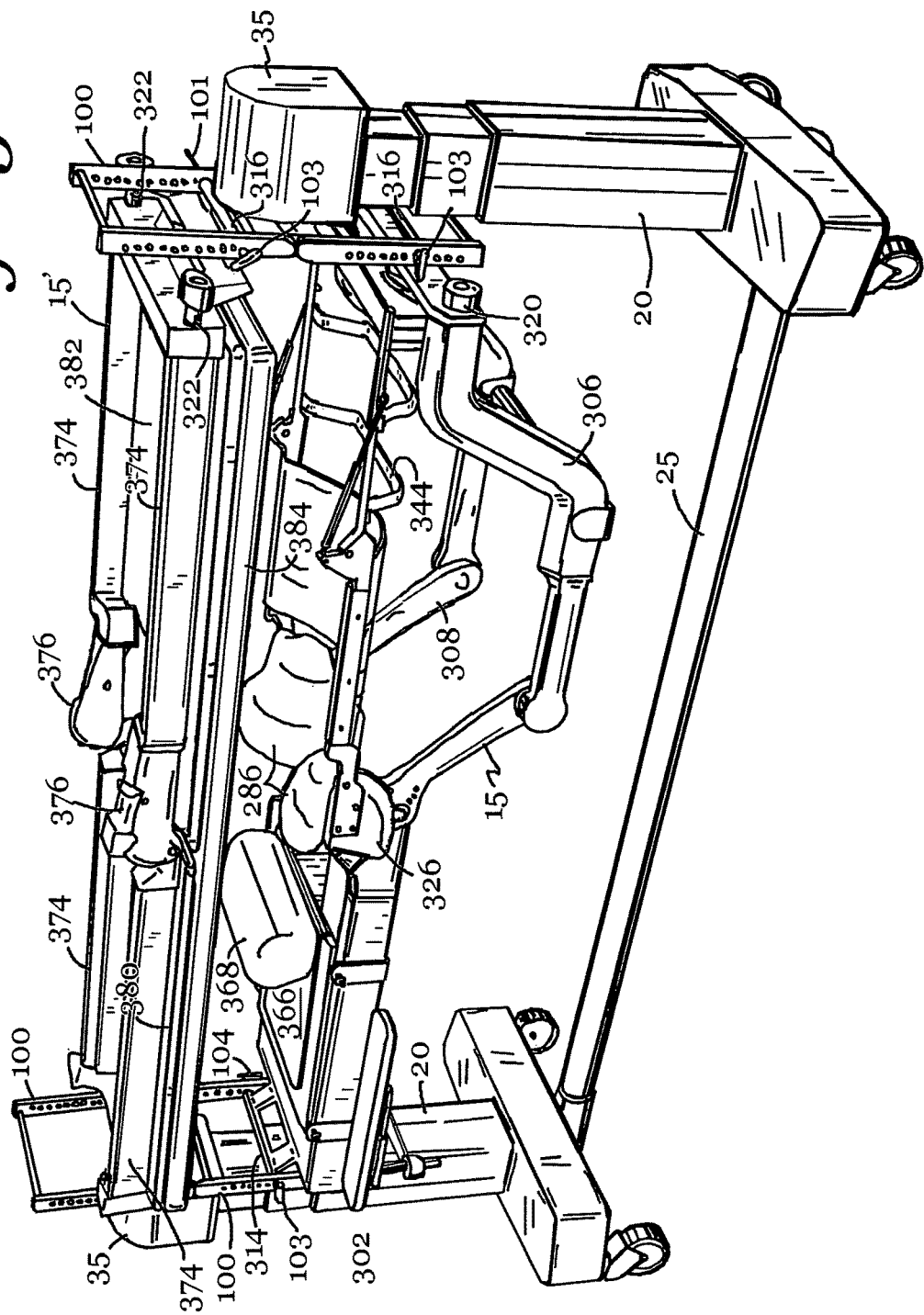

FIG. 136 is an illustration showing the patient positioning support structure of FIG. 134 after the 180-degree roll has been completed.

Figure 137:
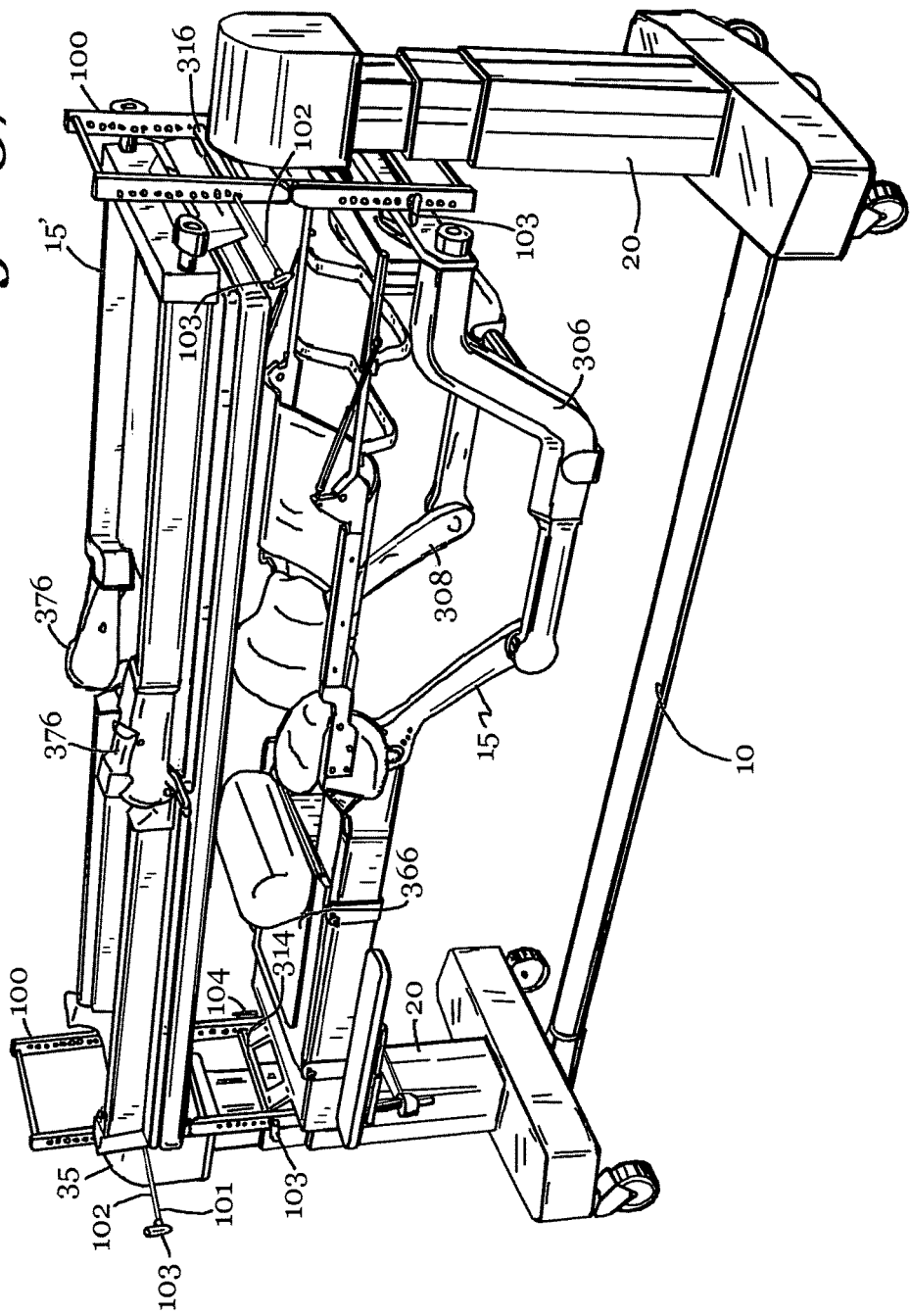

FIG. 137 is an illustration showing the patient positioning support structure of FIG. 136 showing removal of a first of the T-pins attaching the supine patient support structure to the base.

Figure 138:
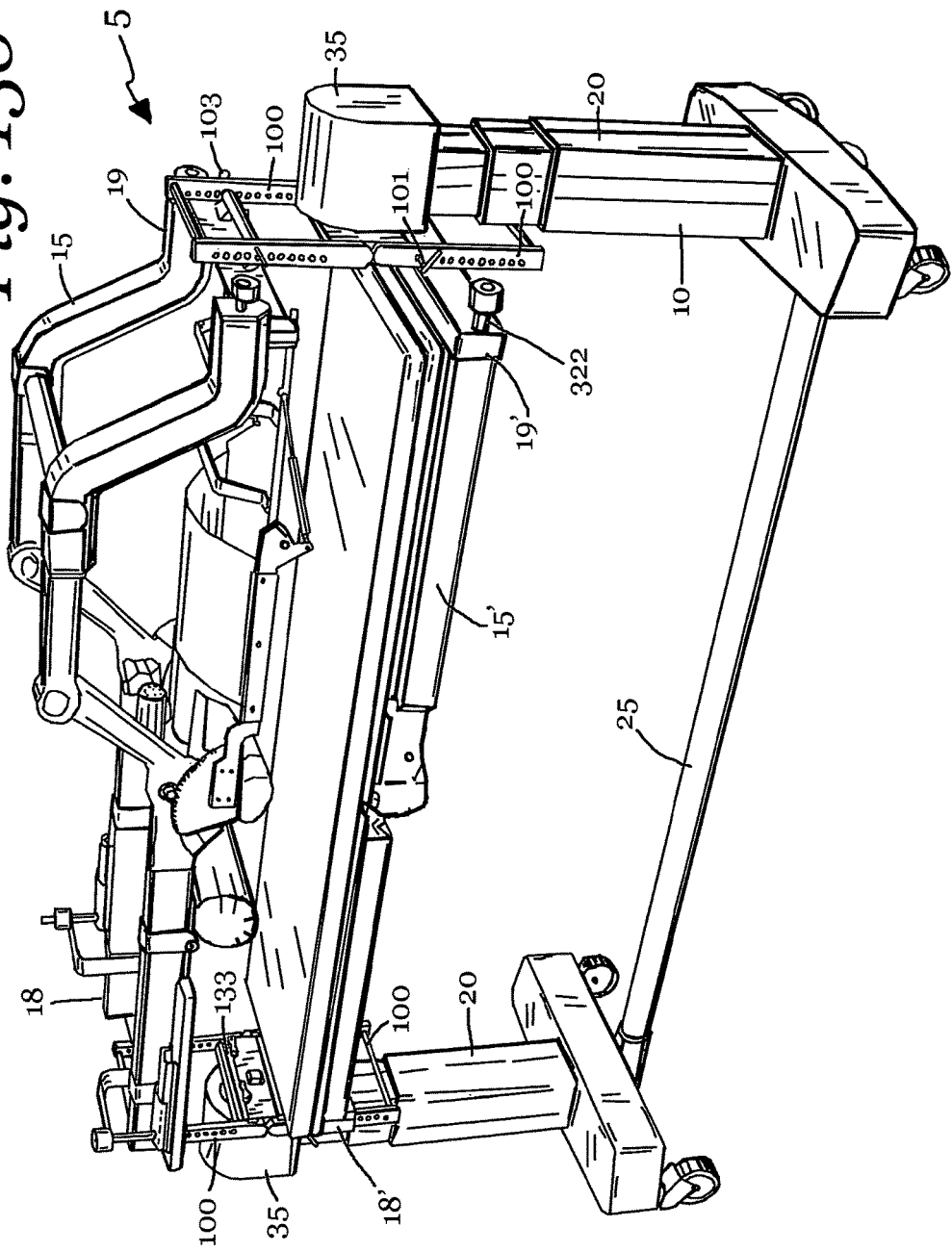

FIG. 138 is an illustration showing the patient positioning support structure of FIG. 137 showing removal of a second of the T-pins attaching the supine patient support structure to the base.

Figure 139:
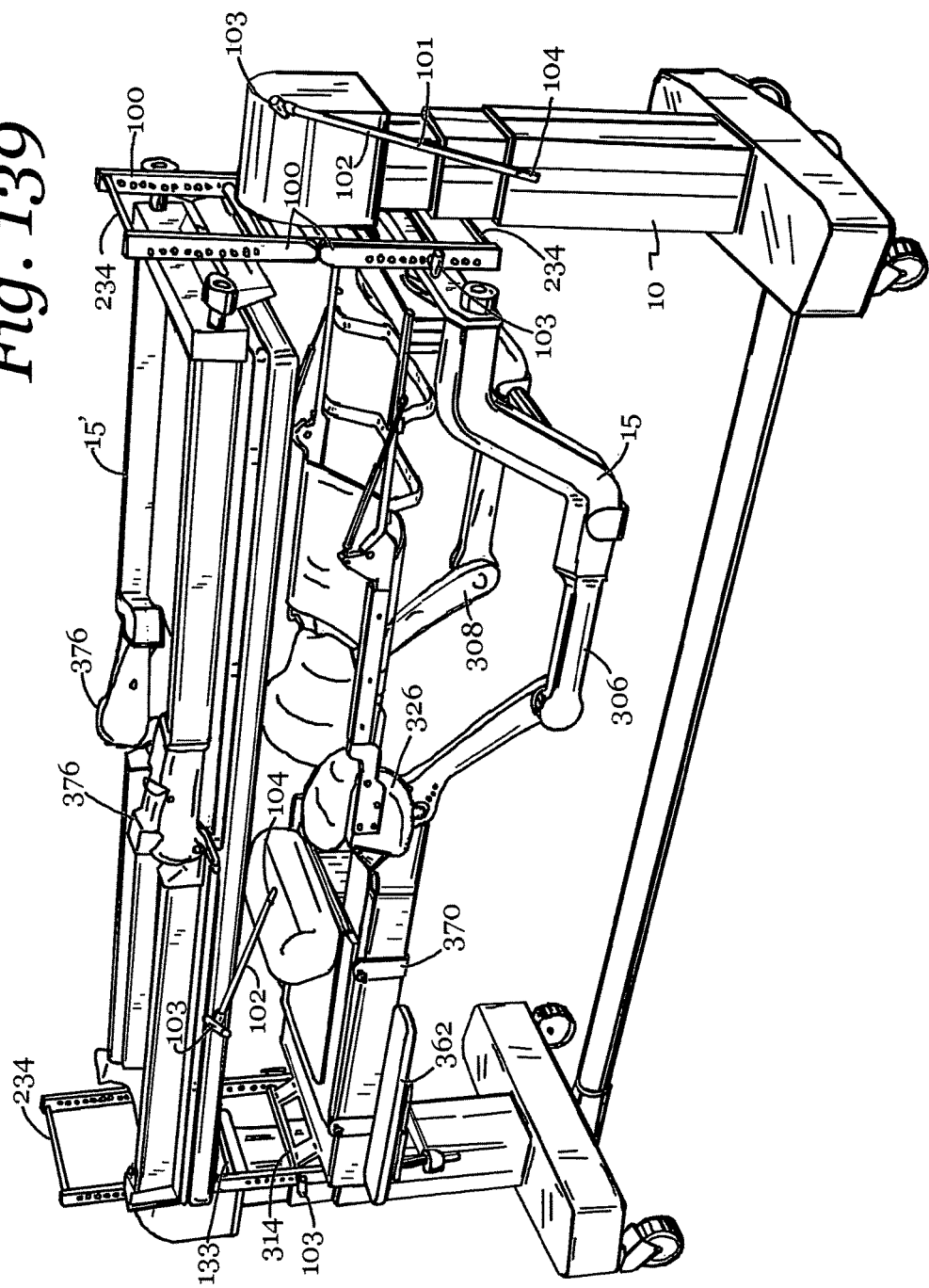

FIG. 139 is an illustration showing the patient positioning support structure of FIG. 138 showing a beginning step in removing the supine patient support structure from the base.

Figure 140:
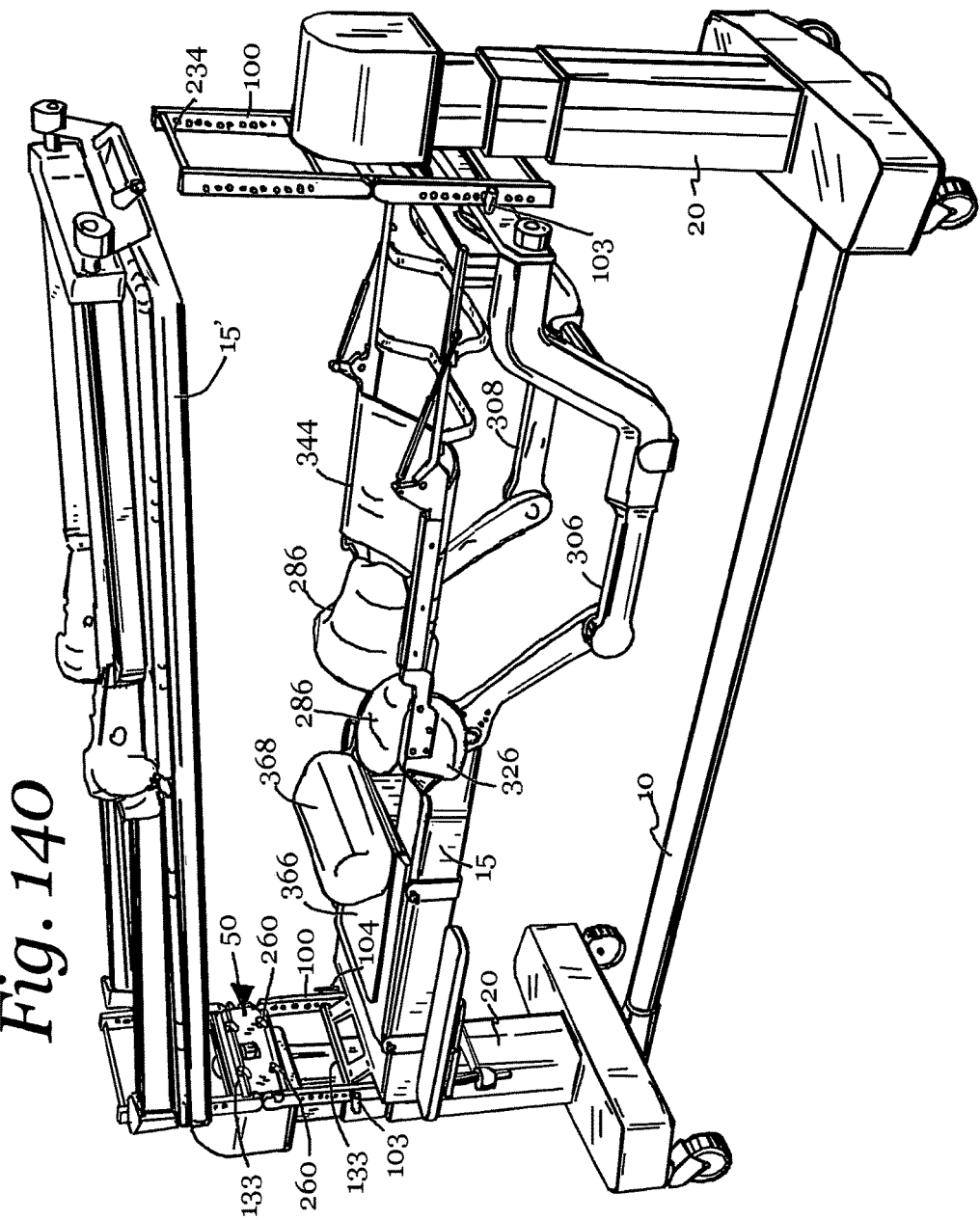

FIG. 140 is an illustration showing the patient positioning support structure of FIG. 139 showing an intermediate step in removing the supine patient support structure from the base.

Figure 141:
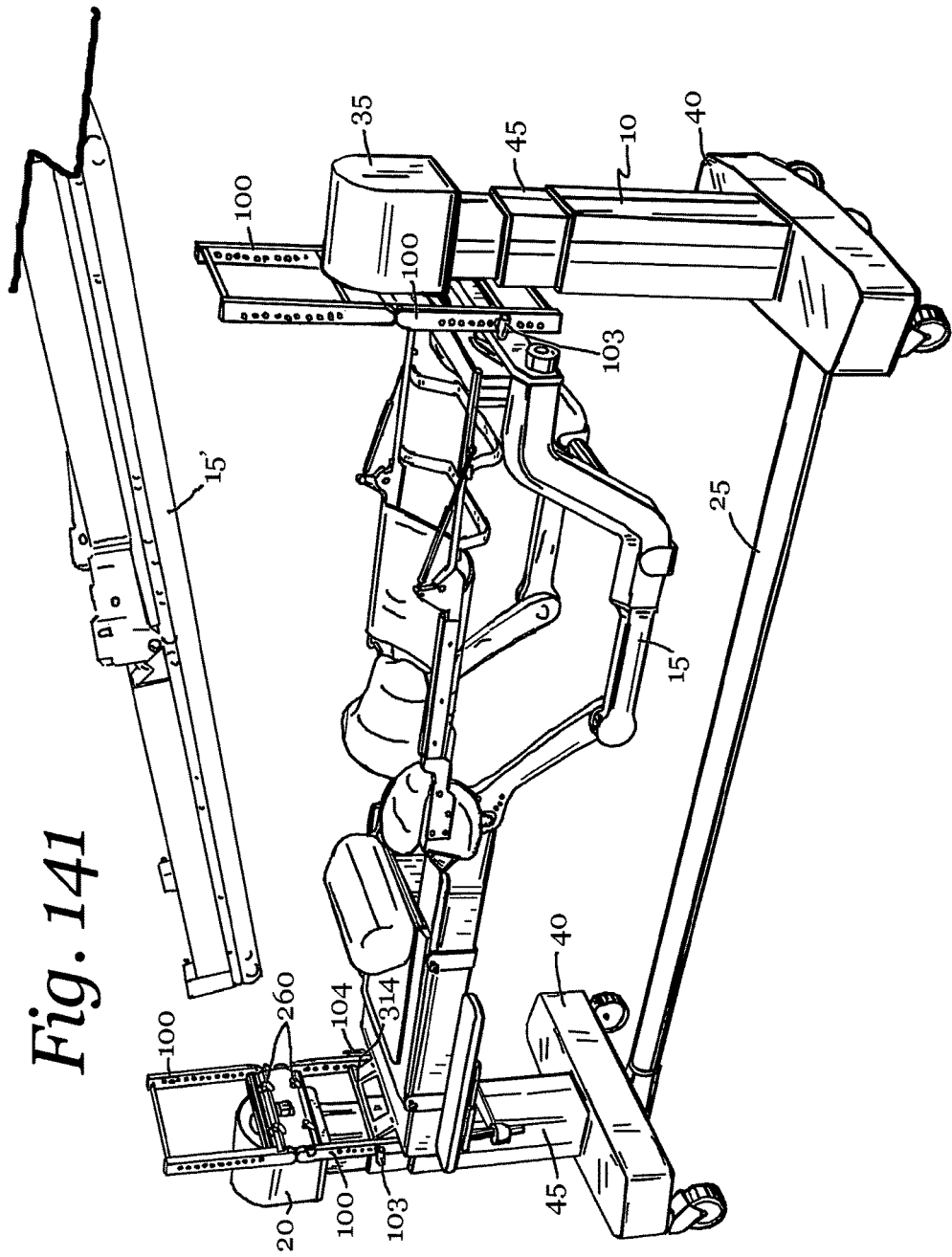

FIG. 141 is an illustration showing the patient positioning support structure of FIG. 140 showing the supine patient support structure fully removed from the base.

Figure 142:
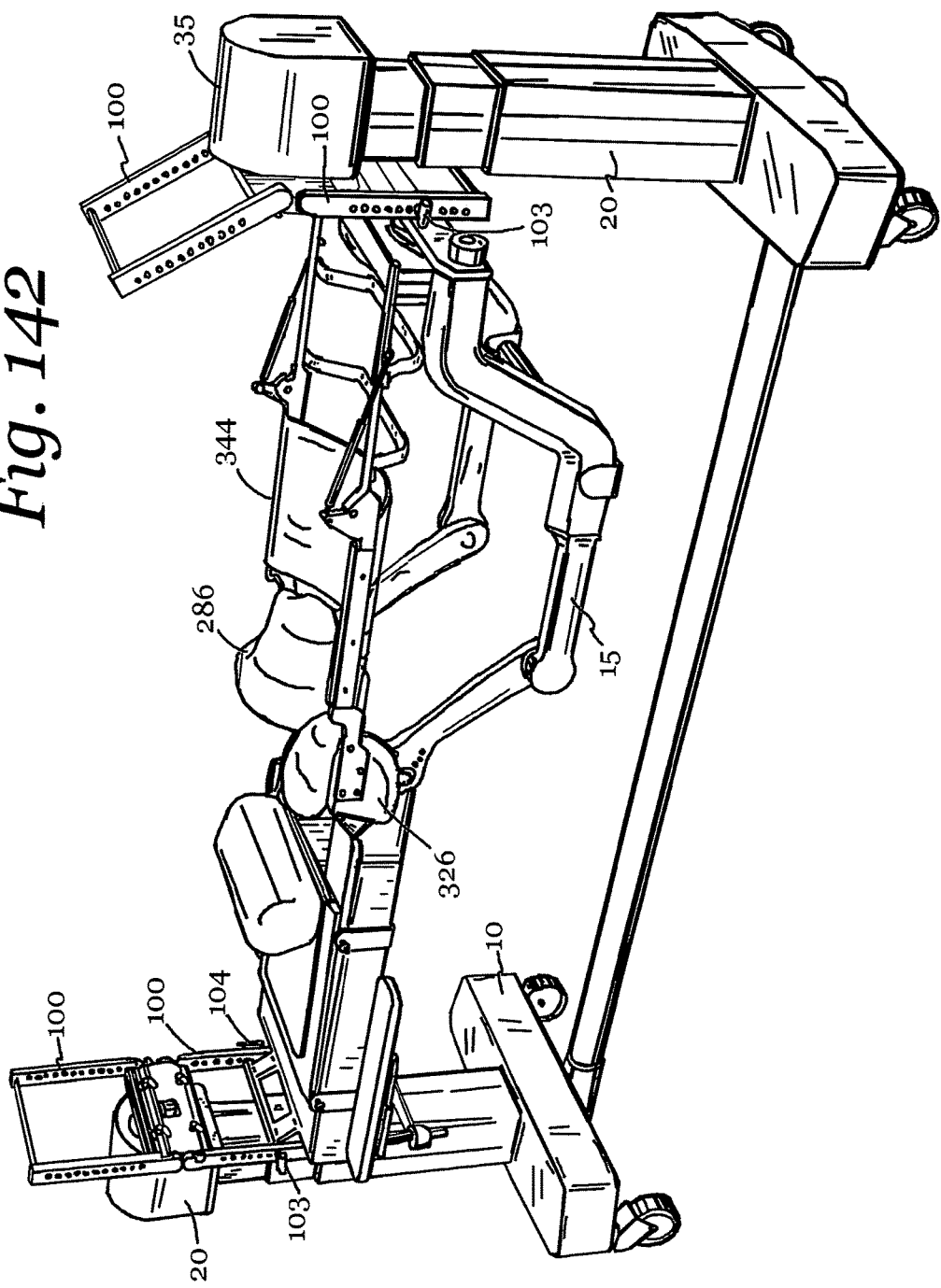

FIG. 142 is an illustration showing the patient positioning support structure of FIG. 141 showing an intermediate step in removing a first of the standard length ladders from the base.

Figure 143:
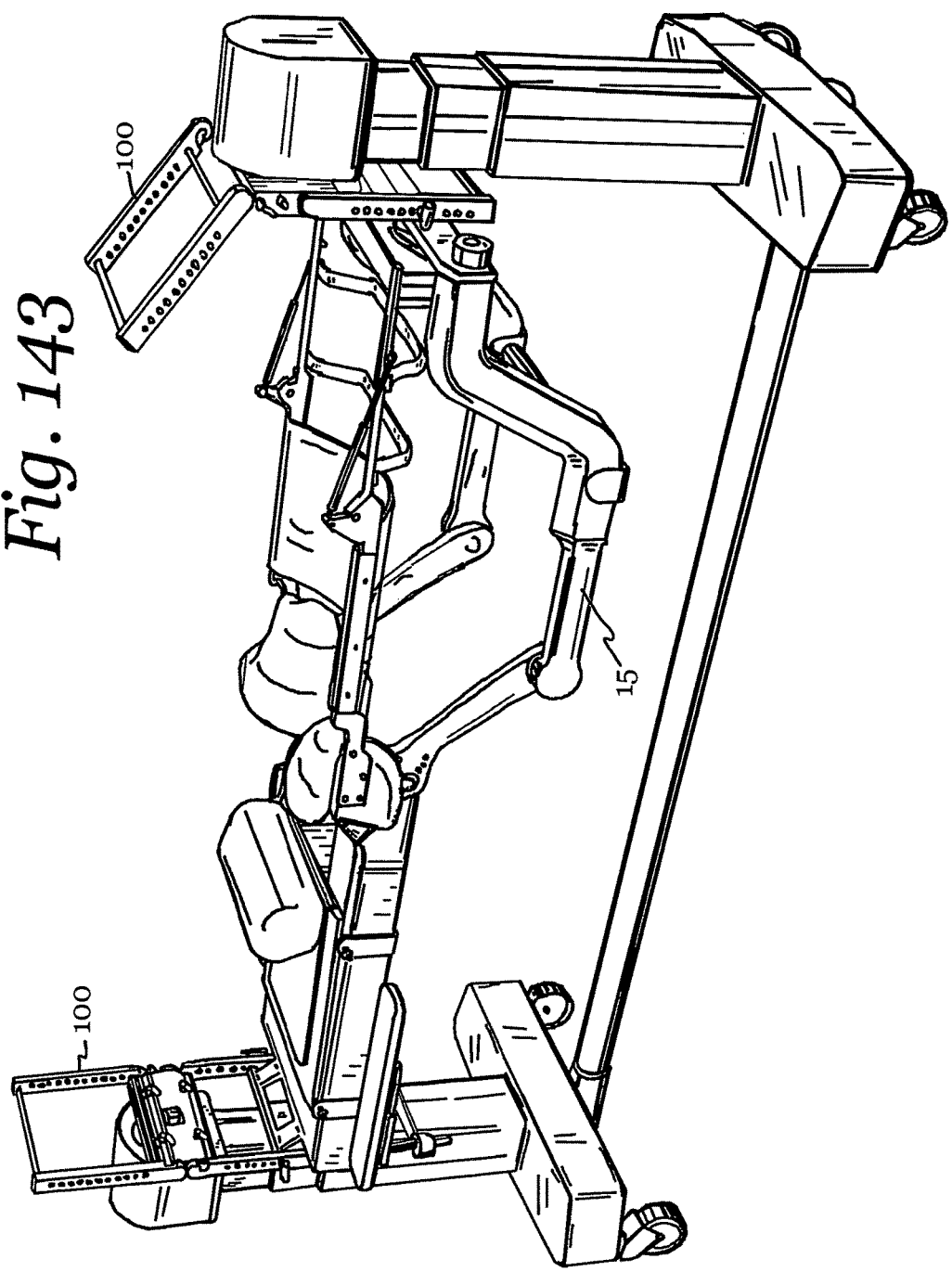

FIG. 143 is an illustration showing the patient positioning support structure of FIG. 142 showing a further intermediate step in removing the first ladder from the base.

Figure 144:
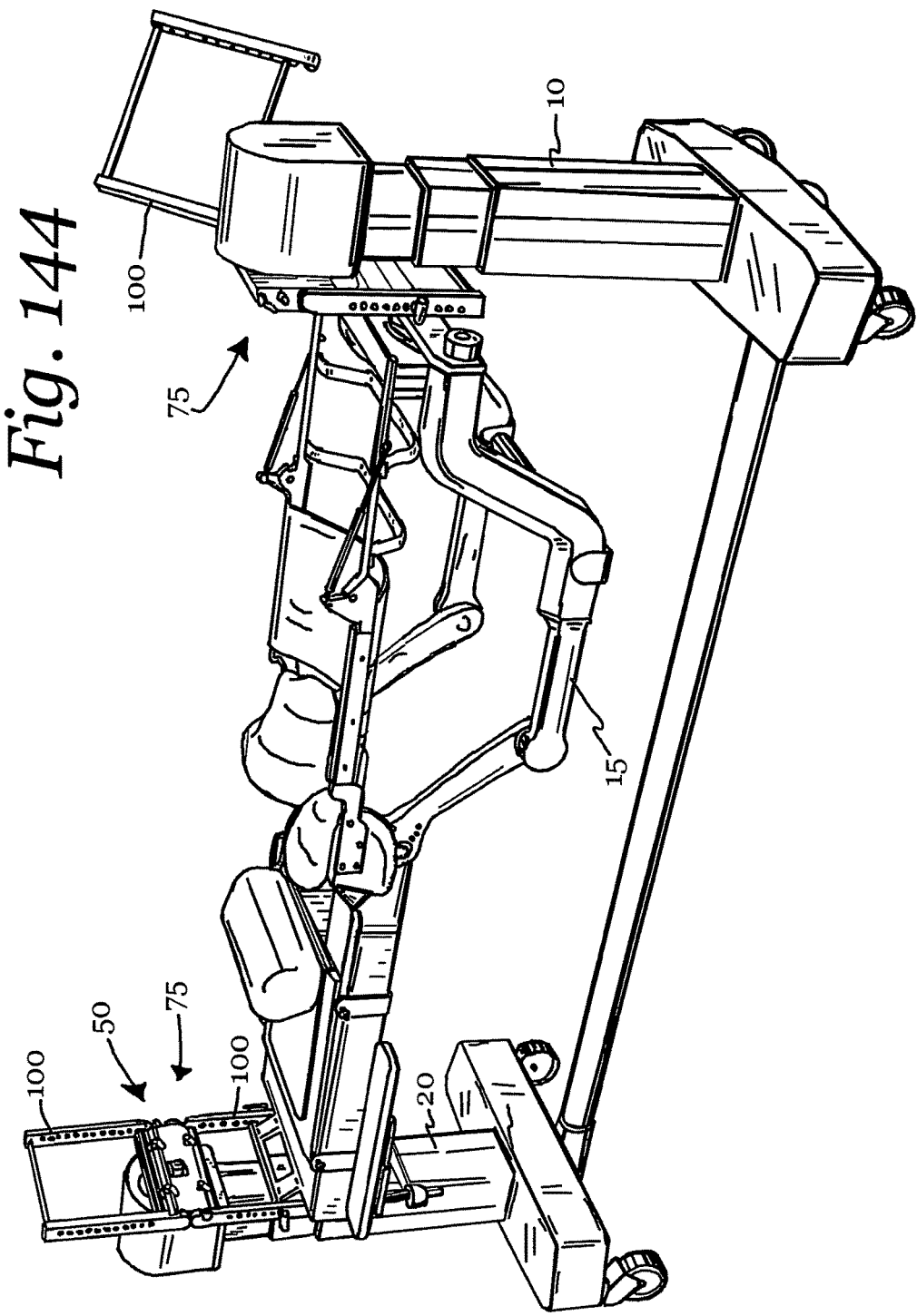

FIG. 144 is an illustration showing the patient positioning support structure of FIG. 144 showing the first ladder removed from the base.

Figure 145:
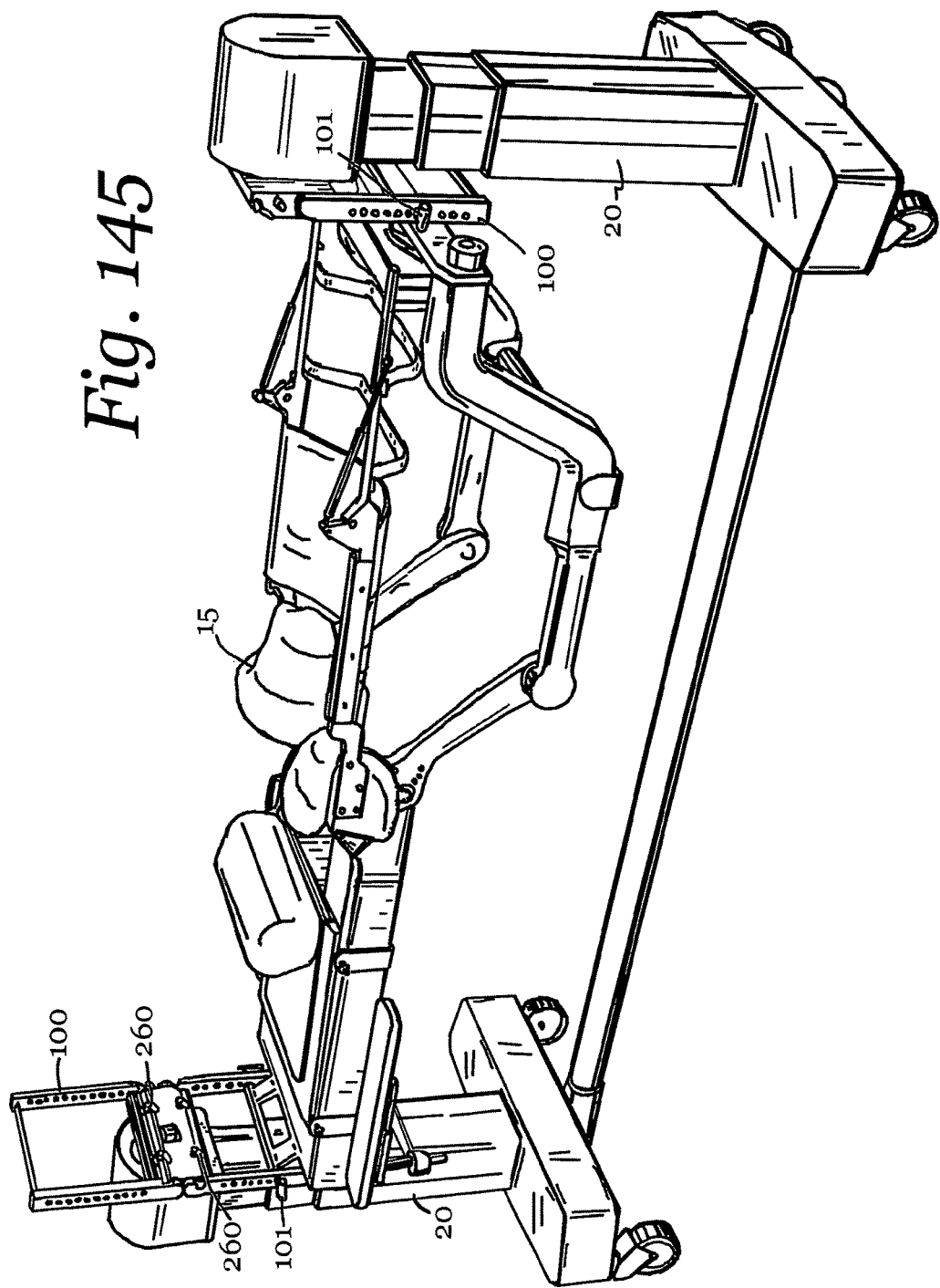
Figure 146:
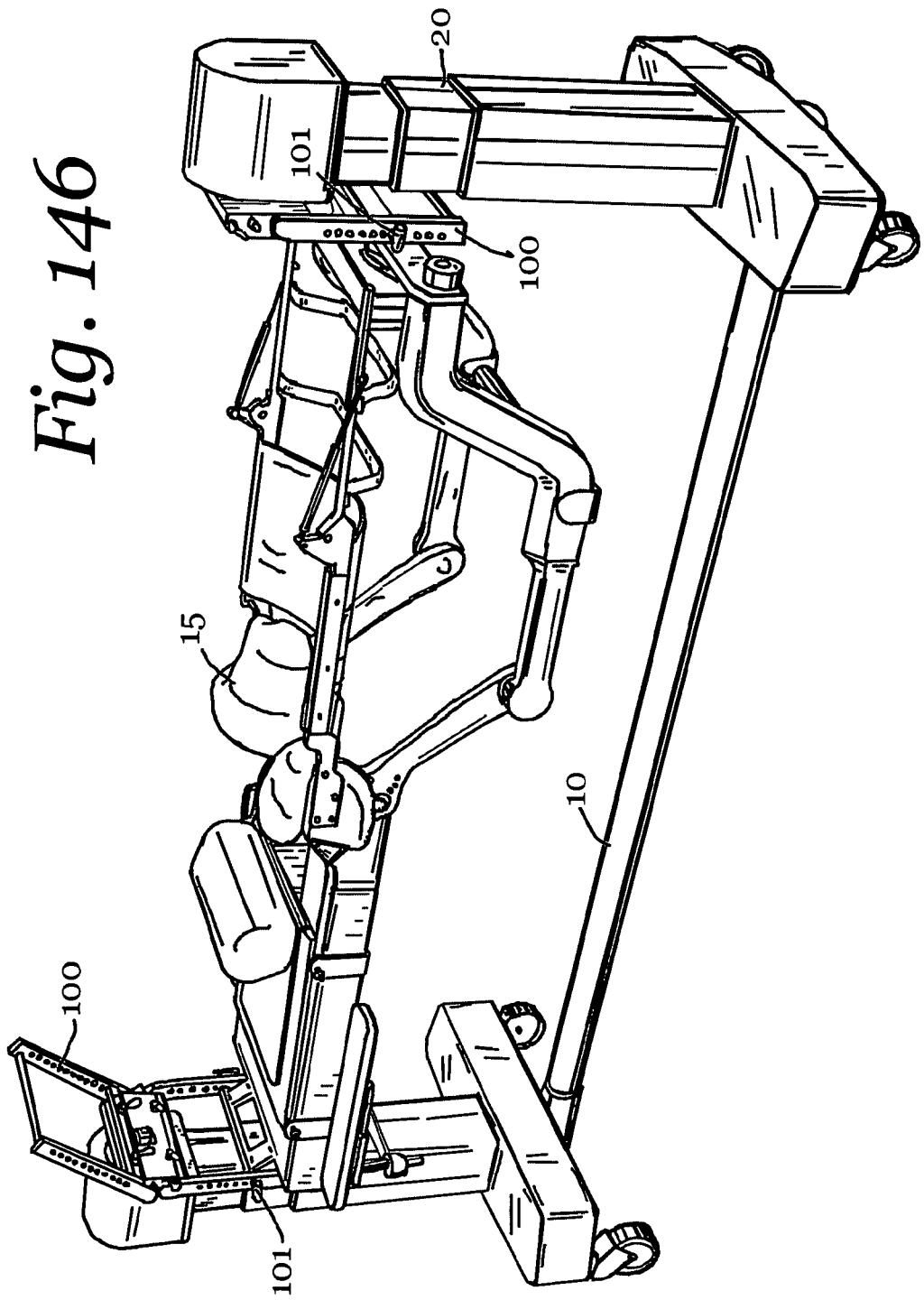

FIG. 145 is an illustration showing the patient positioning support structure of FIG. 146 showing an intermediate step in removing a second of the standard length ladders from the base.

FIG. 146 is an illustration showing the patient positioning support structure of FIG. 145 showing a further intermediate step in removing the second ladder from the base.

Figure 147:
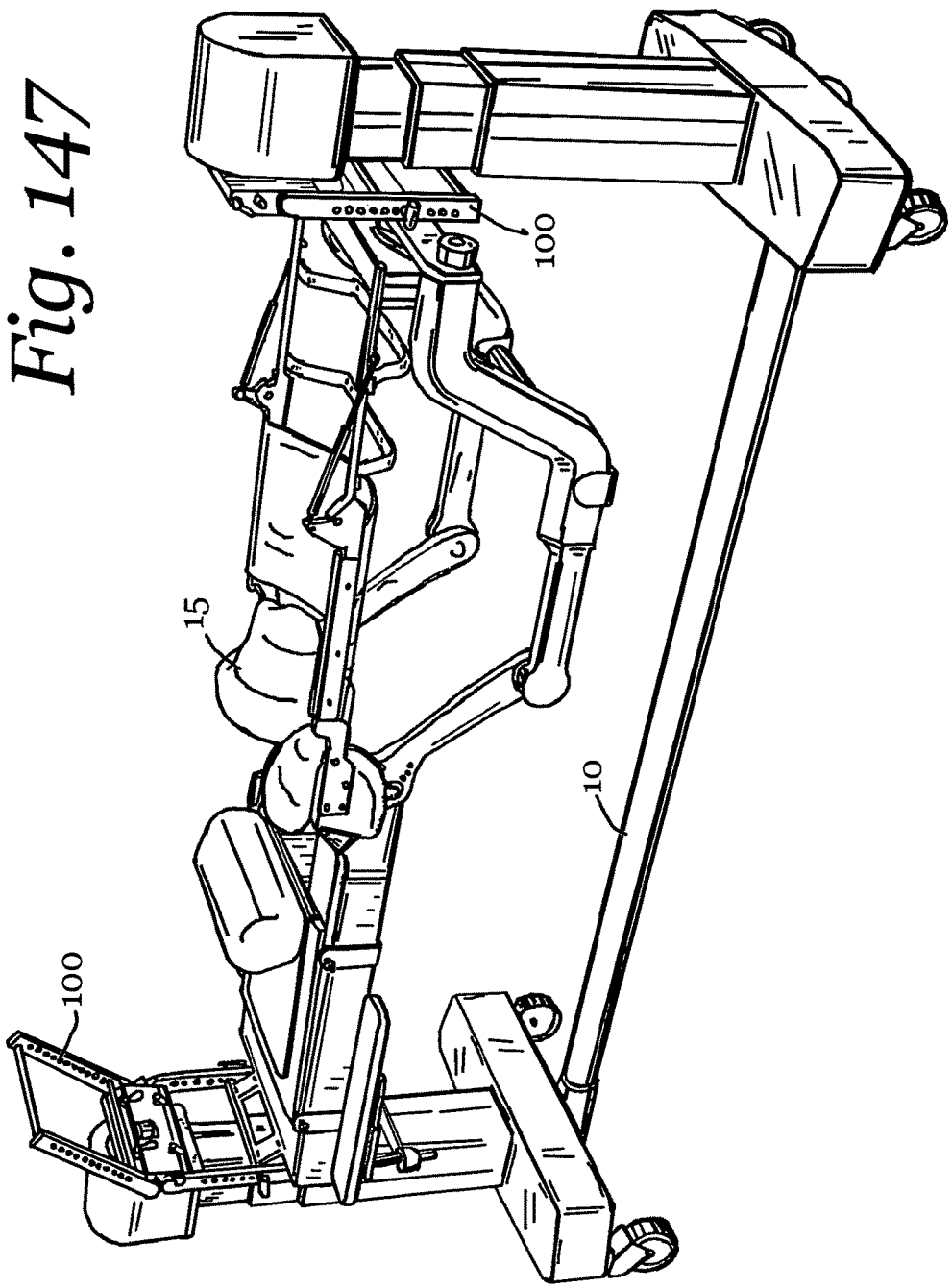

FIG. 147 is an illustration showing the patient positioning support structure of FIG. 146 showing an even further intermediate step in removing the second ladder from the base.

Figure 148:
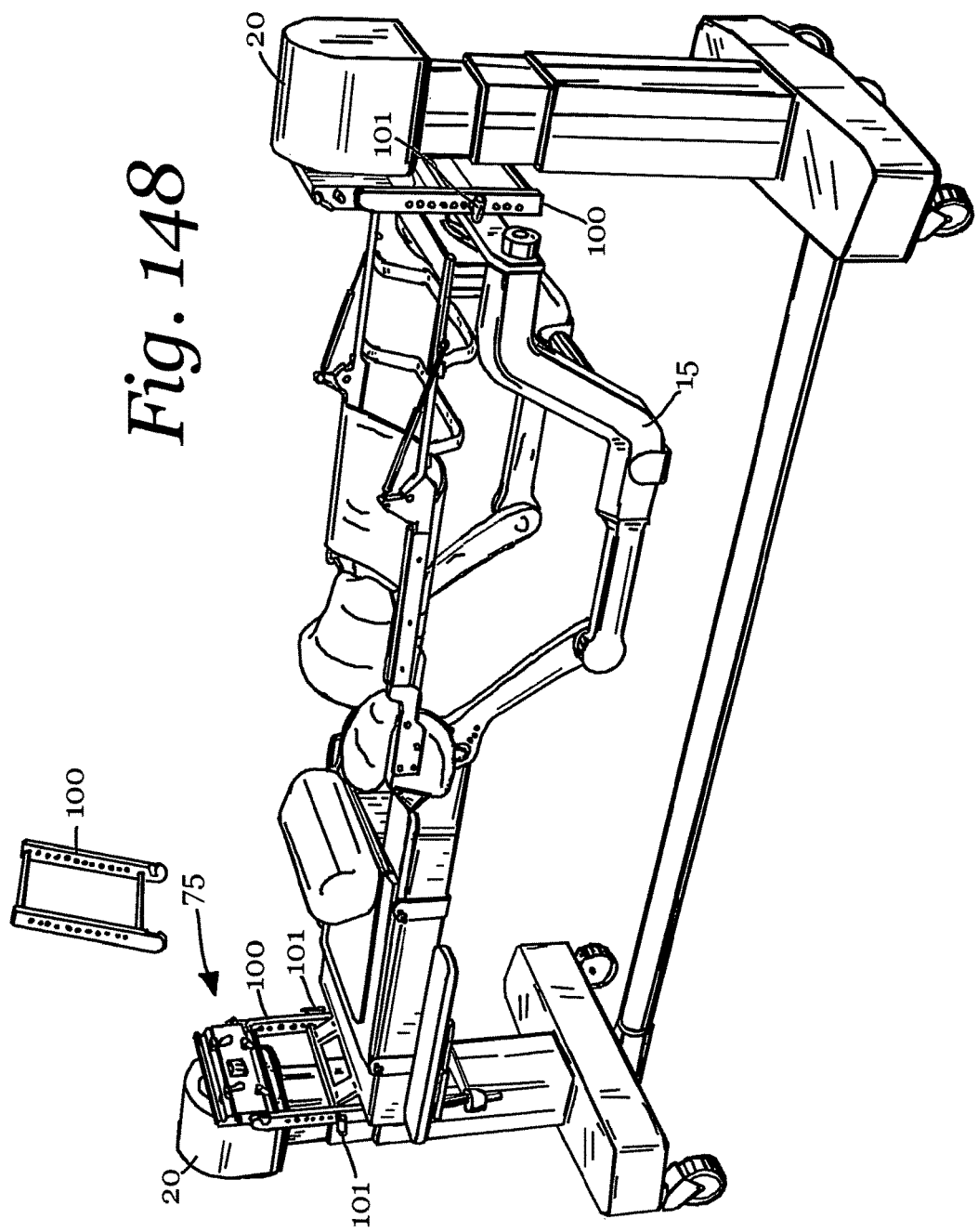

FIG. 148 is an illustration showing the patient positioning support structure of FIG. 147 showing both the first and second ladders removed from the base.

Figure 149:
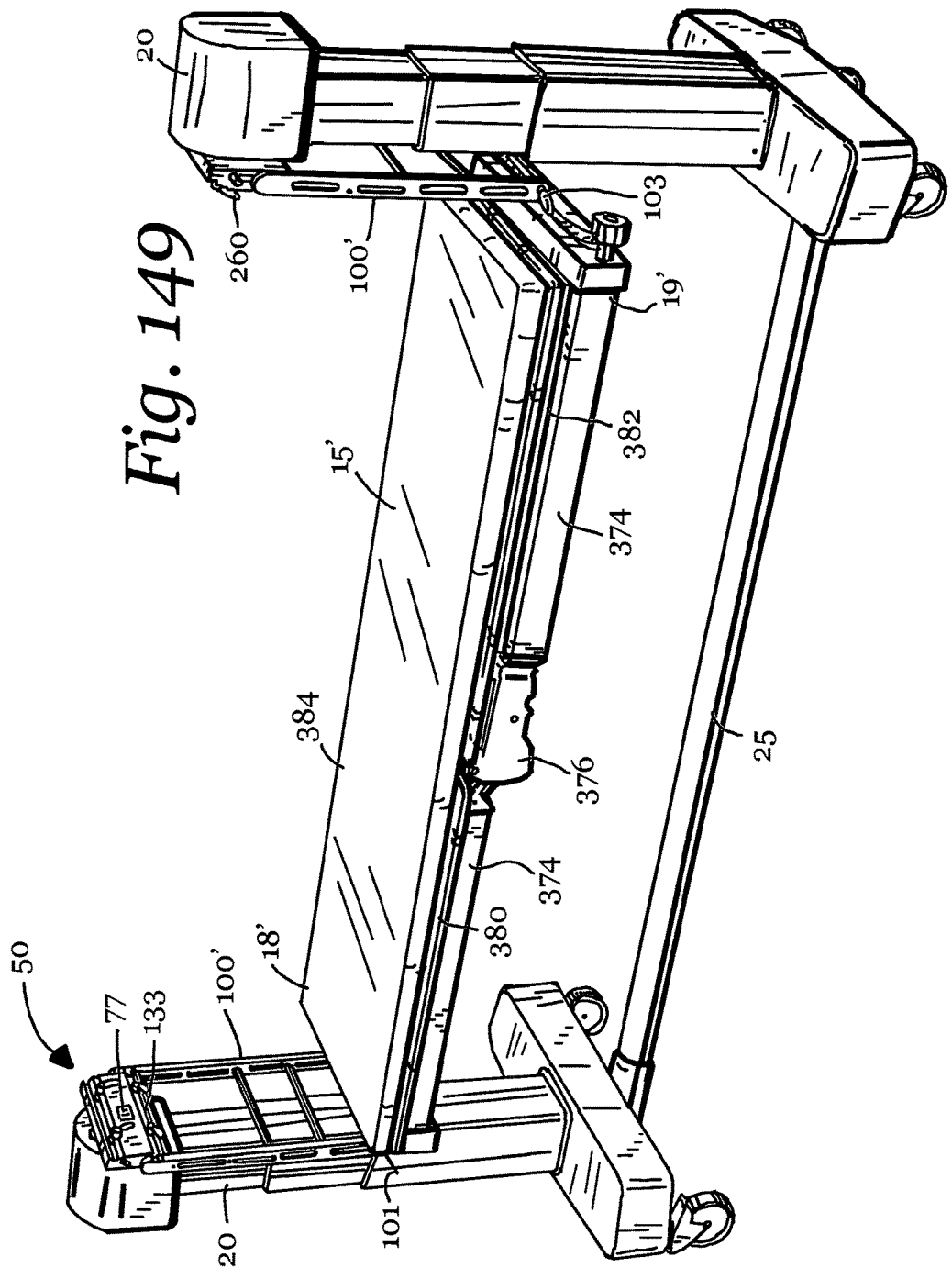

FIG. 149 is an illustration showing a perspective view of a patient positioning support system of the present invention, in still another embodiment, including a supine patient support structure attached to a base by a pair of extended-length ladders.

Figure 150:
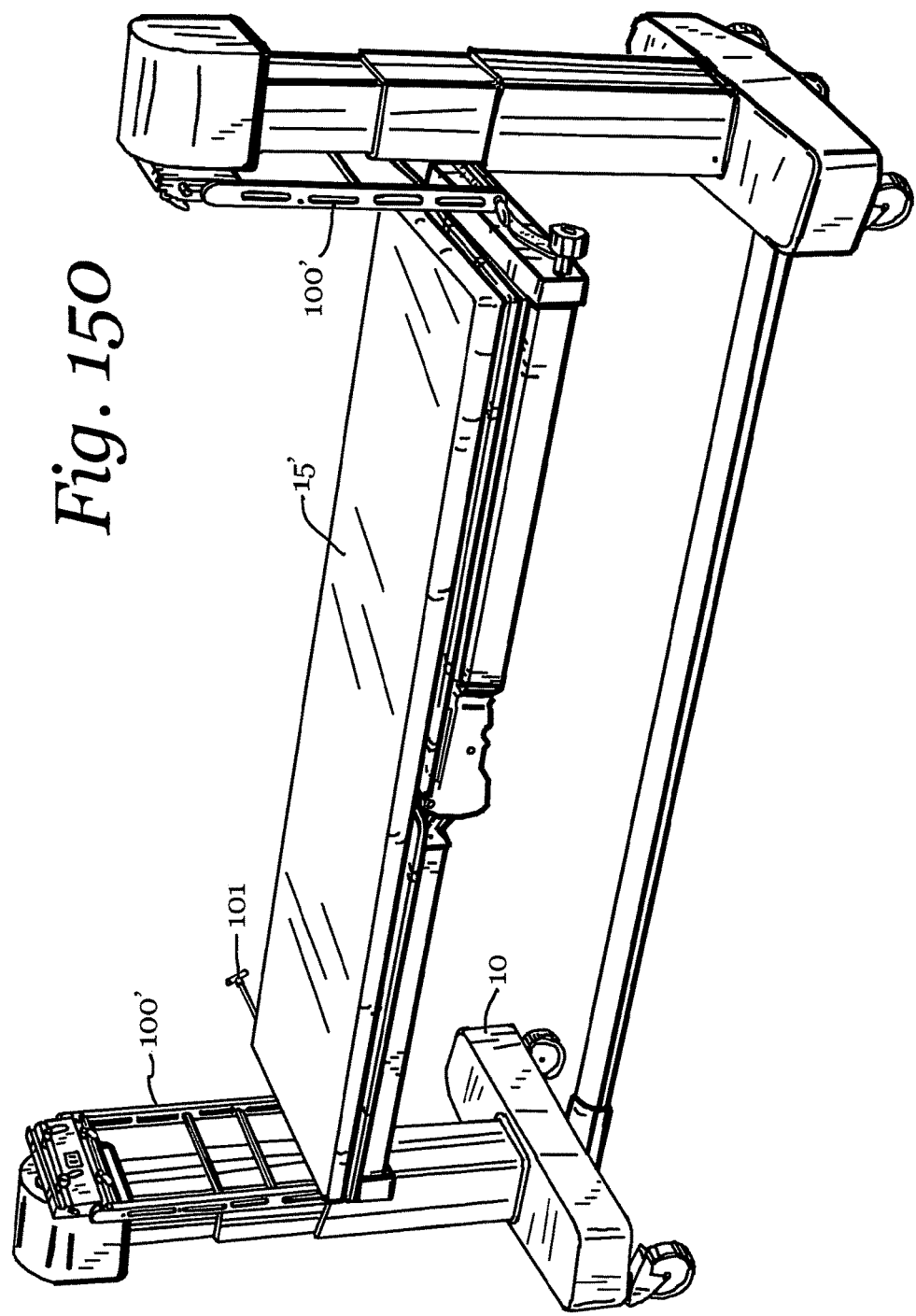

FIG. 150 is an illustration showing the patient positioning support system of FIG. 149, wherein a first of the T-pins has been removed to disconnect the head-end of the supine patient support structure from the base.

Figure 151:
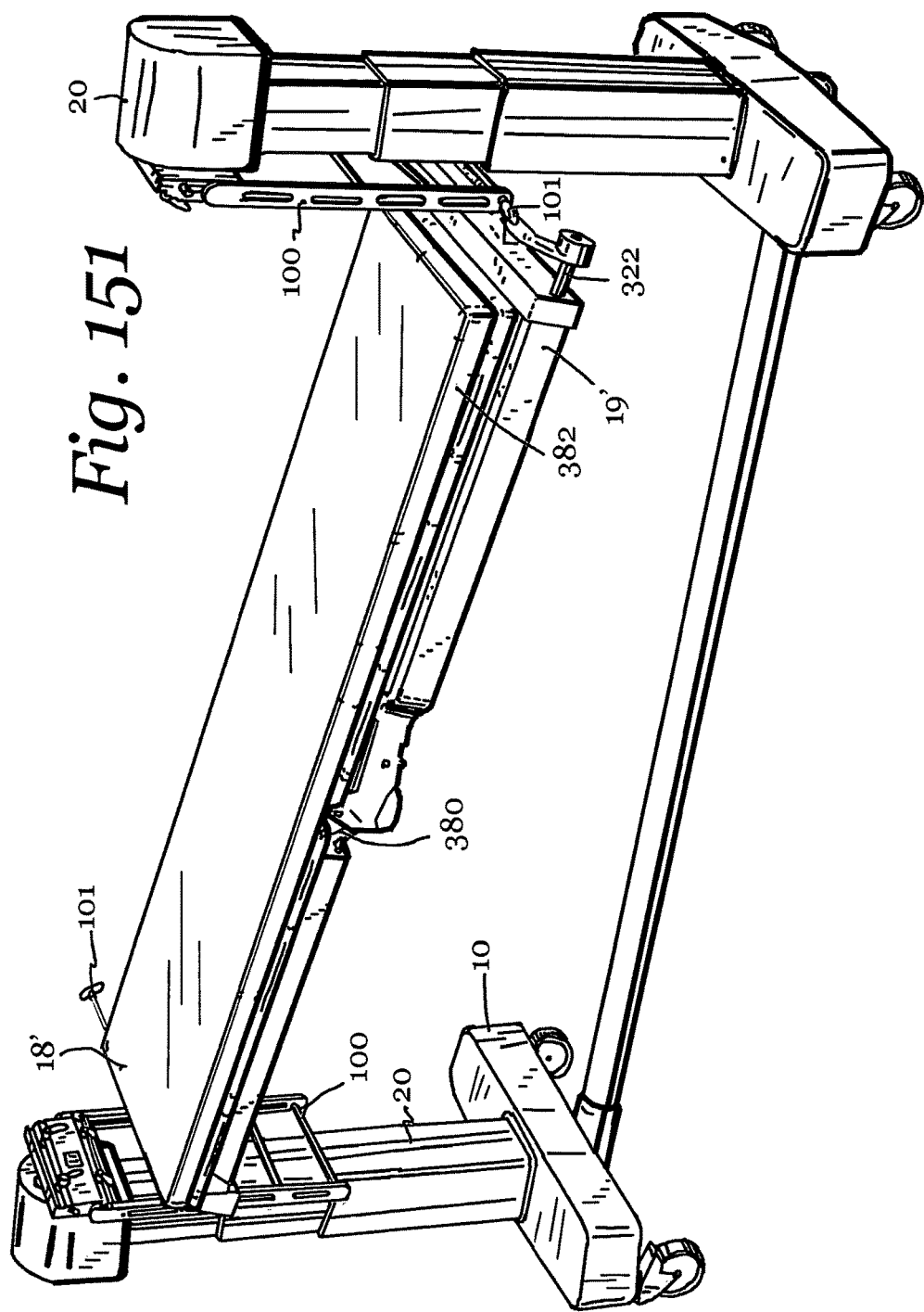

FIG. 151 is an illustration showing the patient positioning support system of FIG. 150, wherein the head-end of the supine patient support structure has been raised to a height suitable for a sandwich-and-roll procedure and the T-pin is being inserted to reconnect the supine patient support structure to the base.

Figure 152:
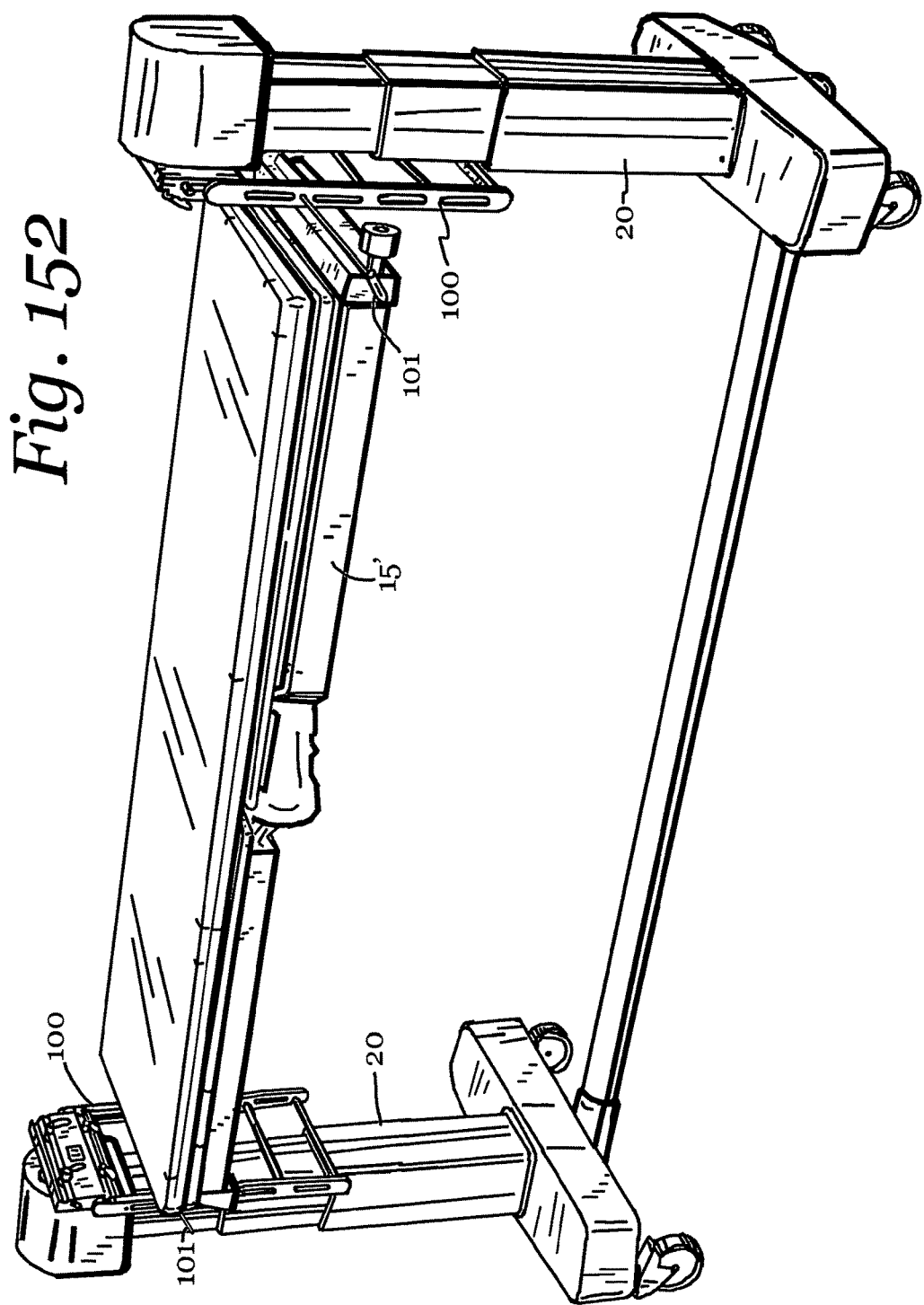

FIG. 152 is an illustration showing the patient positioning support system of FIG. 151, wherein the foot-end of the supine patient support structure has been raised to the height suitable for the sandwich-and-roll procedure and reconnected to the base.

Figure 153:
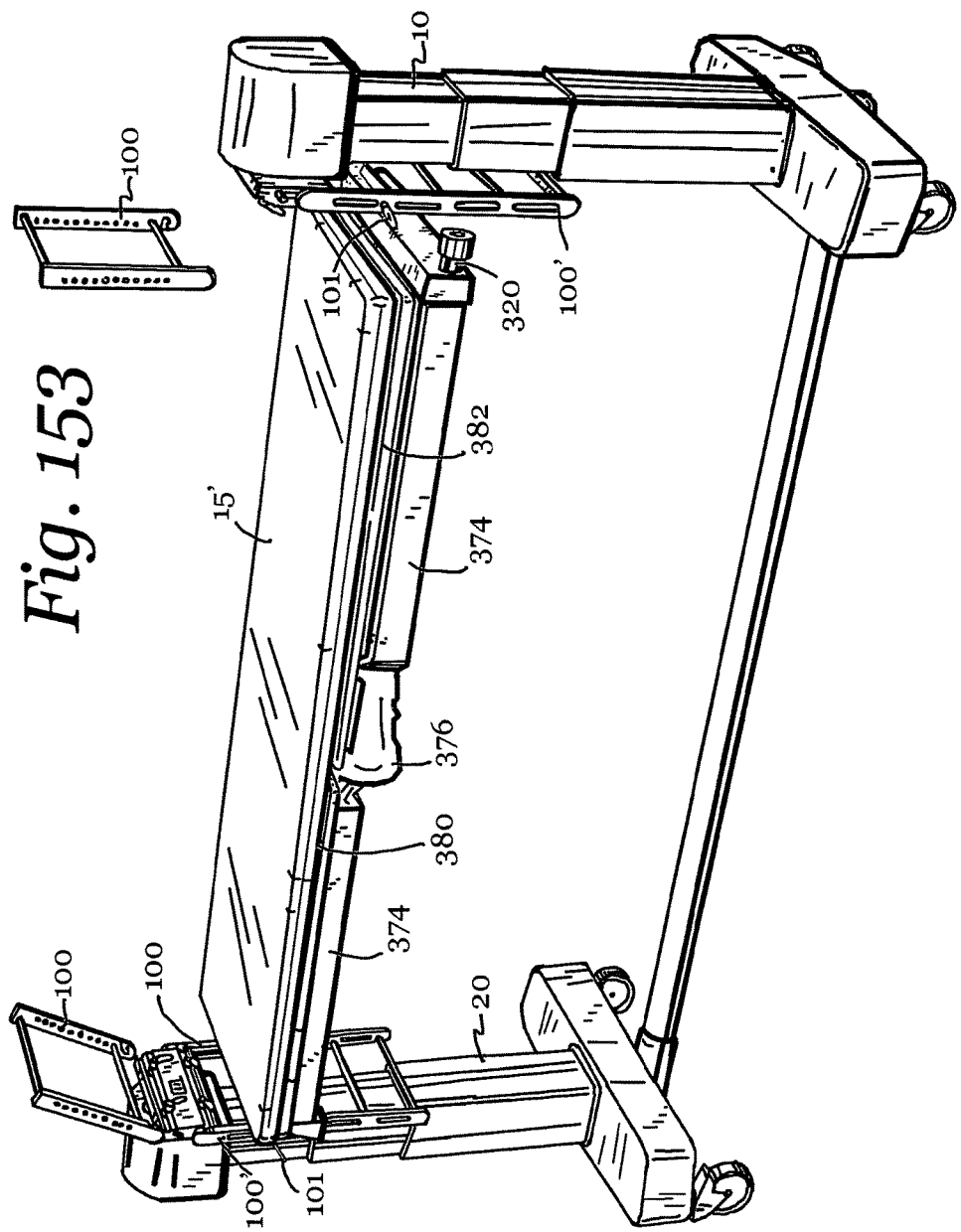

FIG. 153 is an illustration showing the patient positioning support system of FIG. 152, in an intermediate step of connecting a first of a pair of standard length ladders to the base, wherein the standard length ladders are opposed to the extended length ladders.

Figure 154:
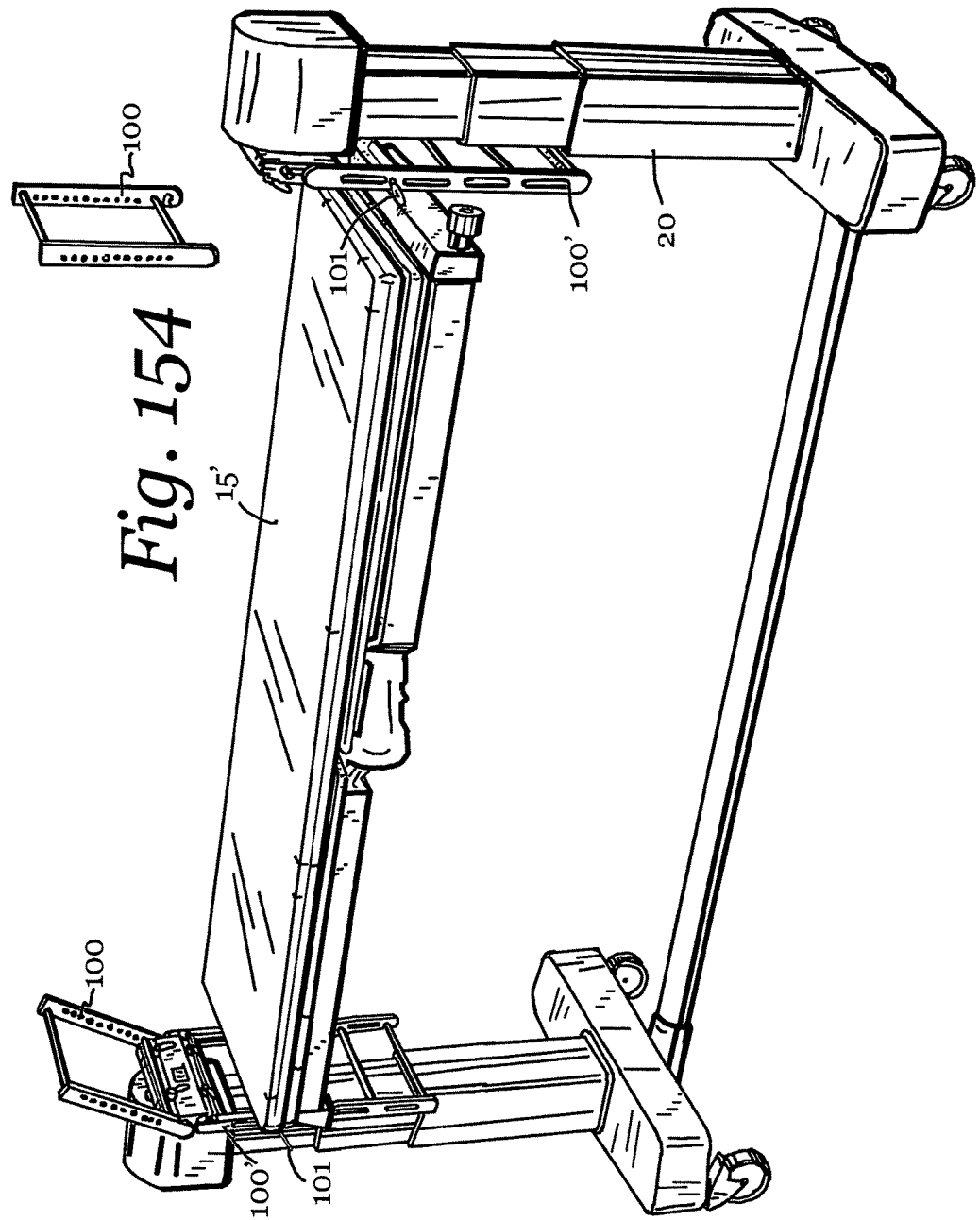

FIG. 154 is an illustration showing the patient positioning support system of FIG. 153, in a further intermediate step of connecting the first standard length ladder to the base.

Figure 155:
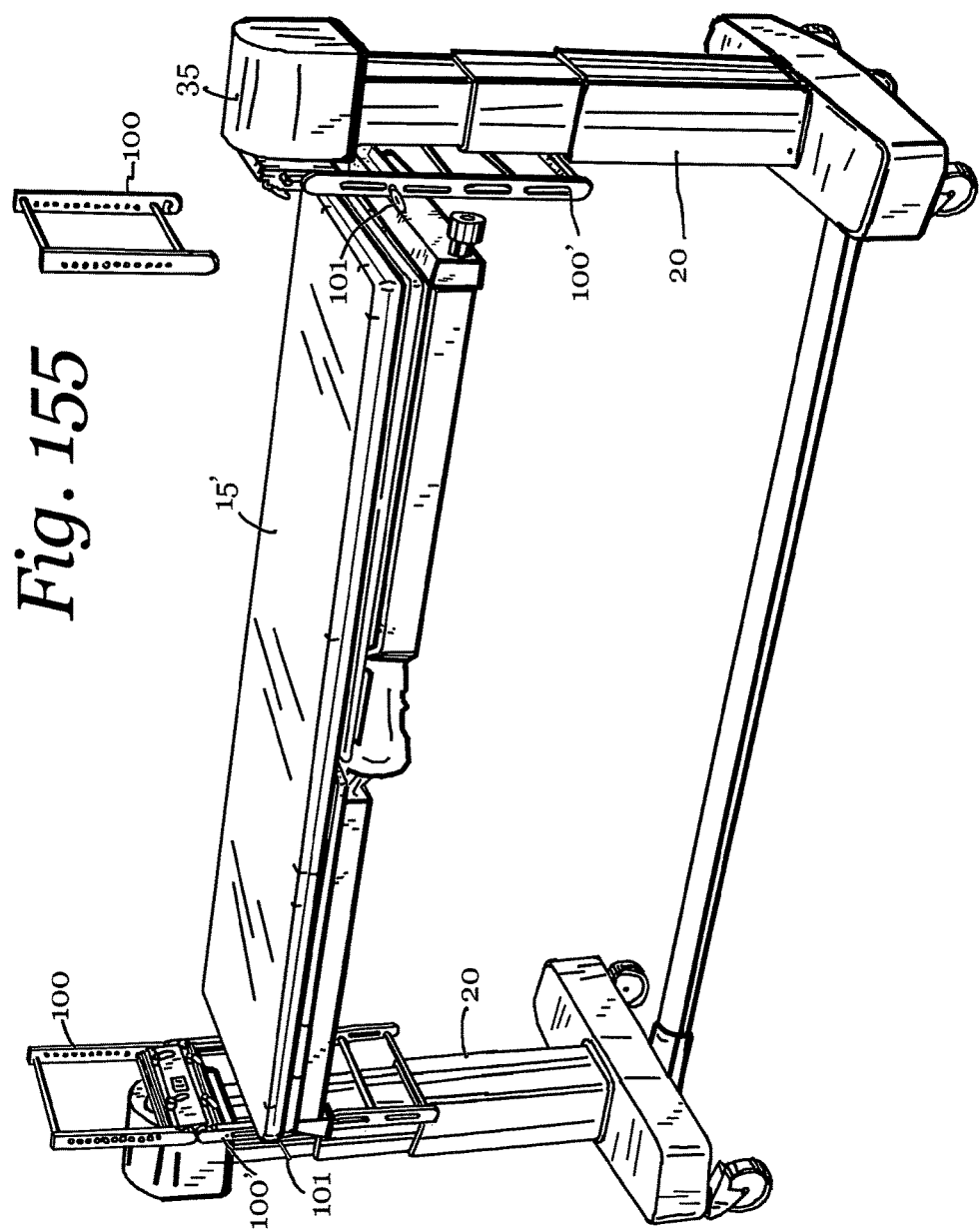

FIG. 155 is an illustration showing the patient positioning support system of FIG. 154, wherein the first standard length ladder is connected to the base.

Figure 156:
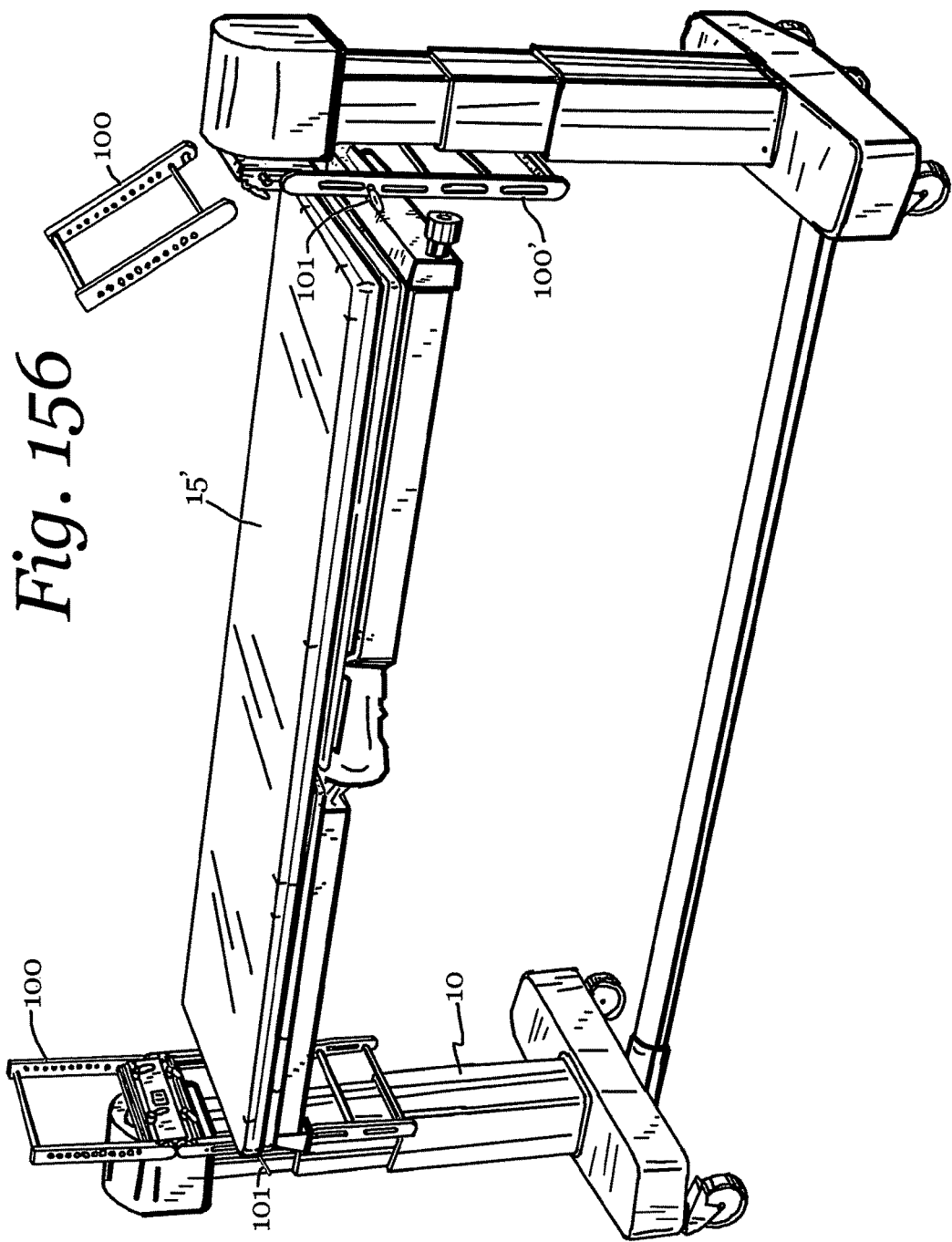

FIG. 156 is an illustration showing the patient positioning support system of FIG. 155, in an intermediate step of connecting the second standard length ladder to the base.

Figure 157:
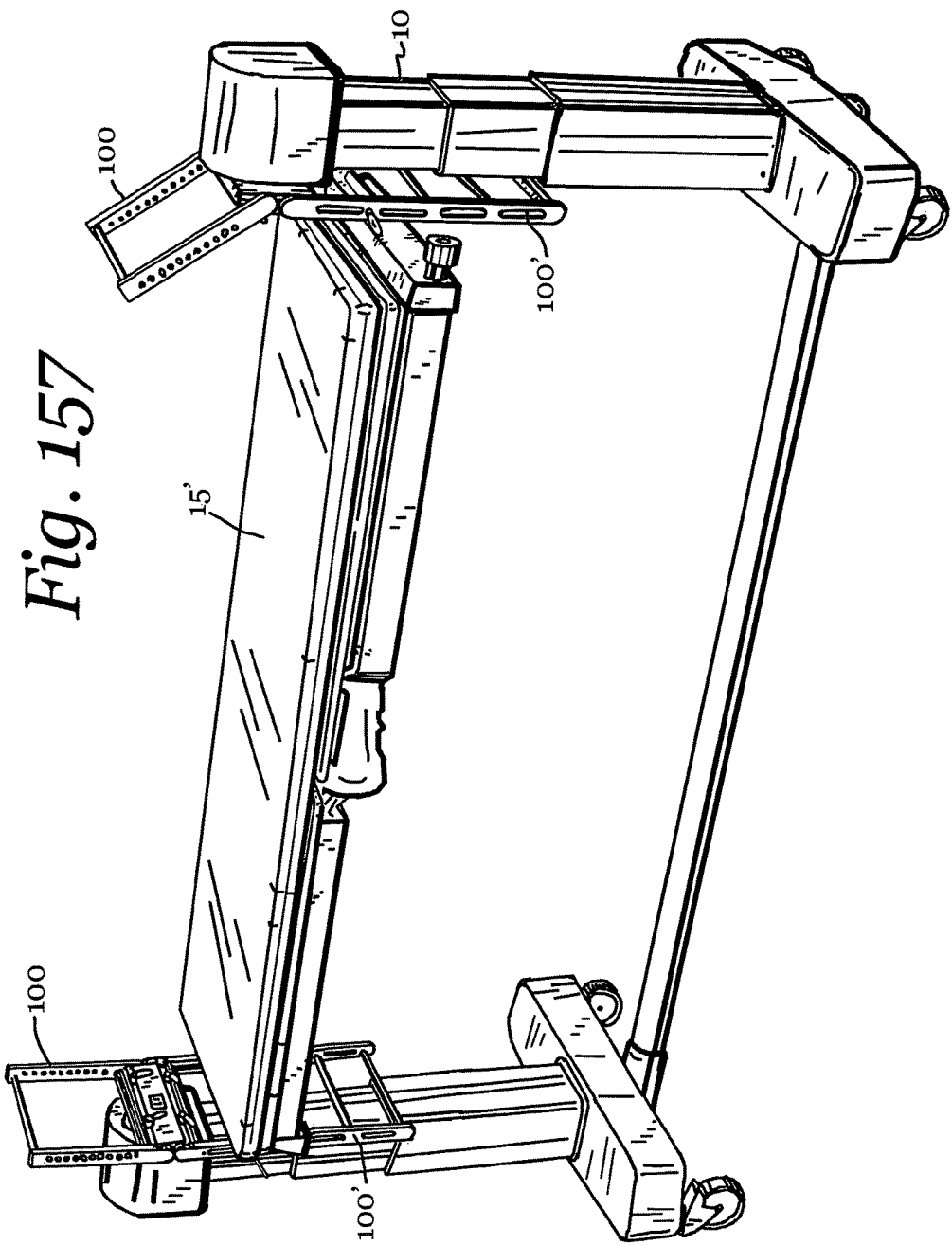

FIG. 157 is an illustration showing the patient positioning support system of FIG. 156, showing a further intermediate step of connecting the second standard length ladder to the base.

Figure 158:
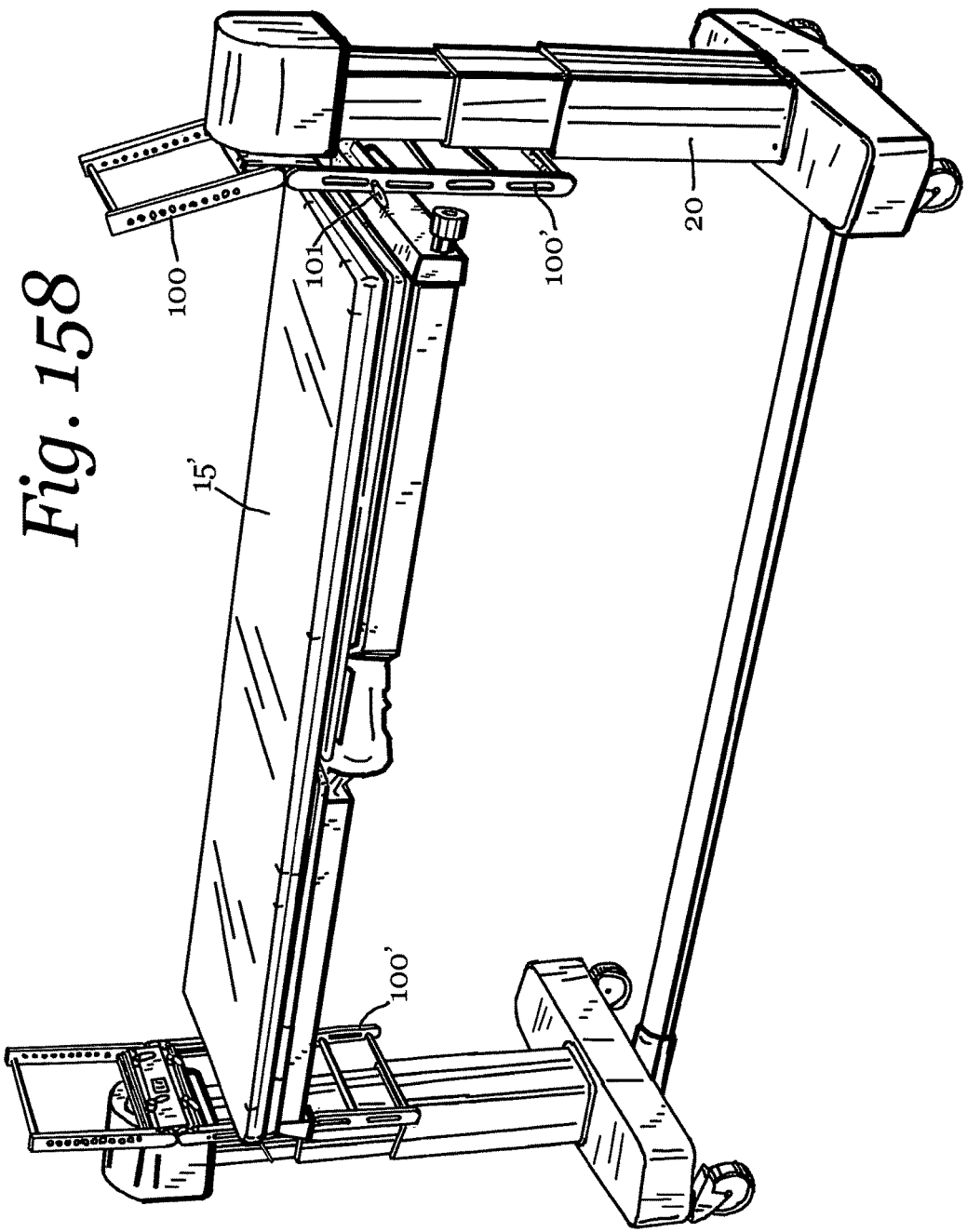

FIG. 158 is an illustration showing the patient positioning support system of FIG. 157, showing a still further intermediate step of connecting the second standard length ladder to the base.

Figure 159:
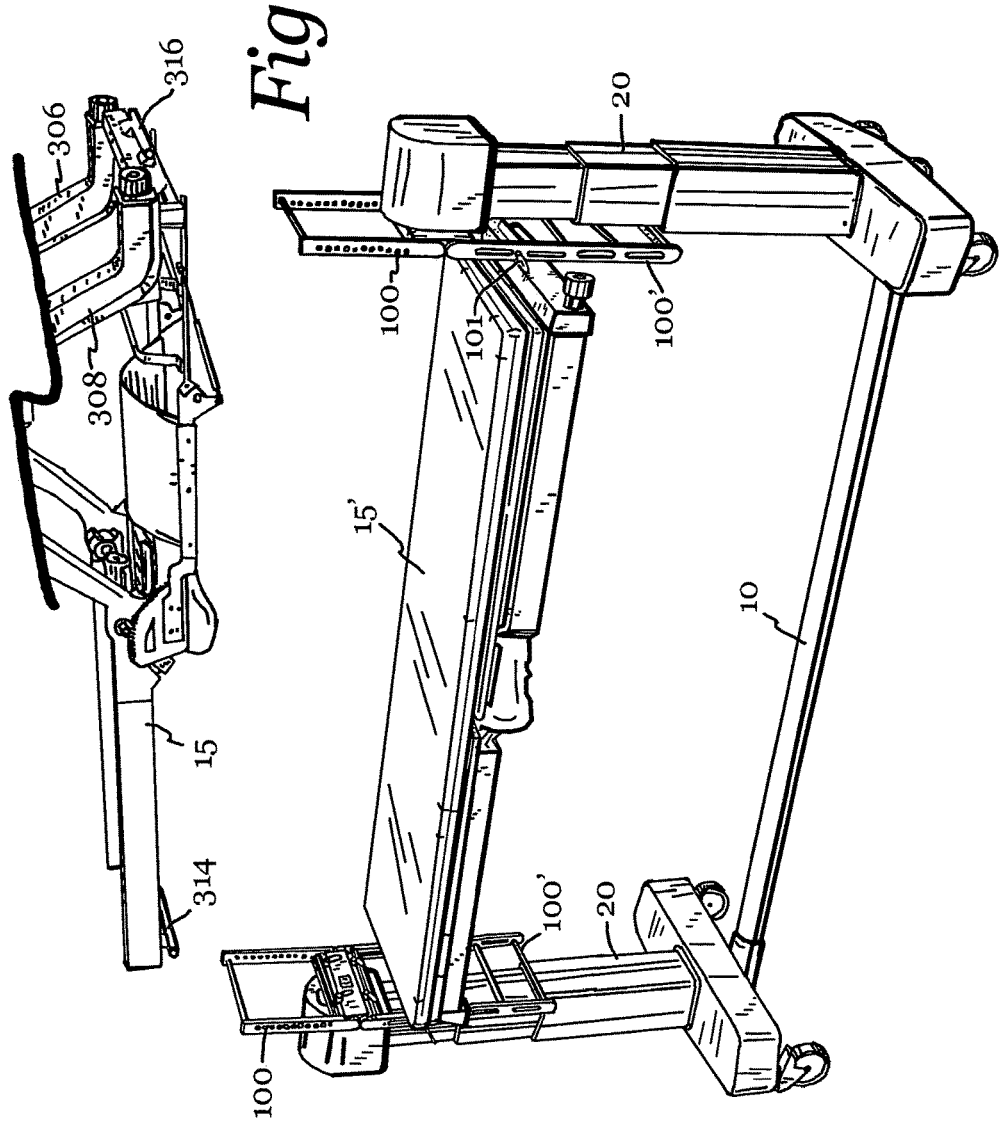

FIG. 159 is an illustration showing the patient positioning support system of FIG. 158, showing the standard length ladders both attached to the base and bringing in the prone patient support structure to be attached to the standard length ladders.

Figure 160:
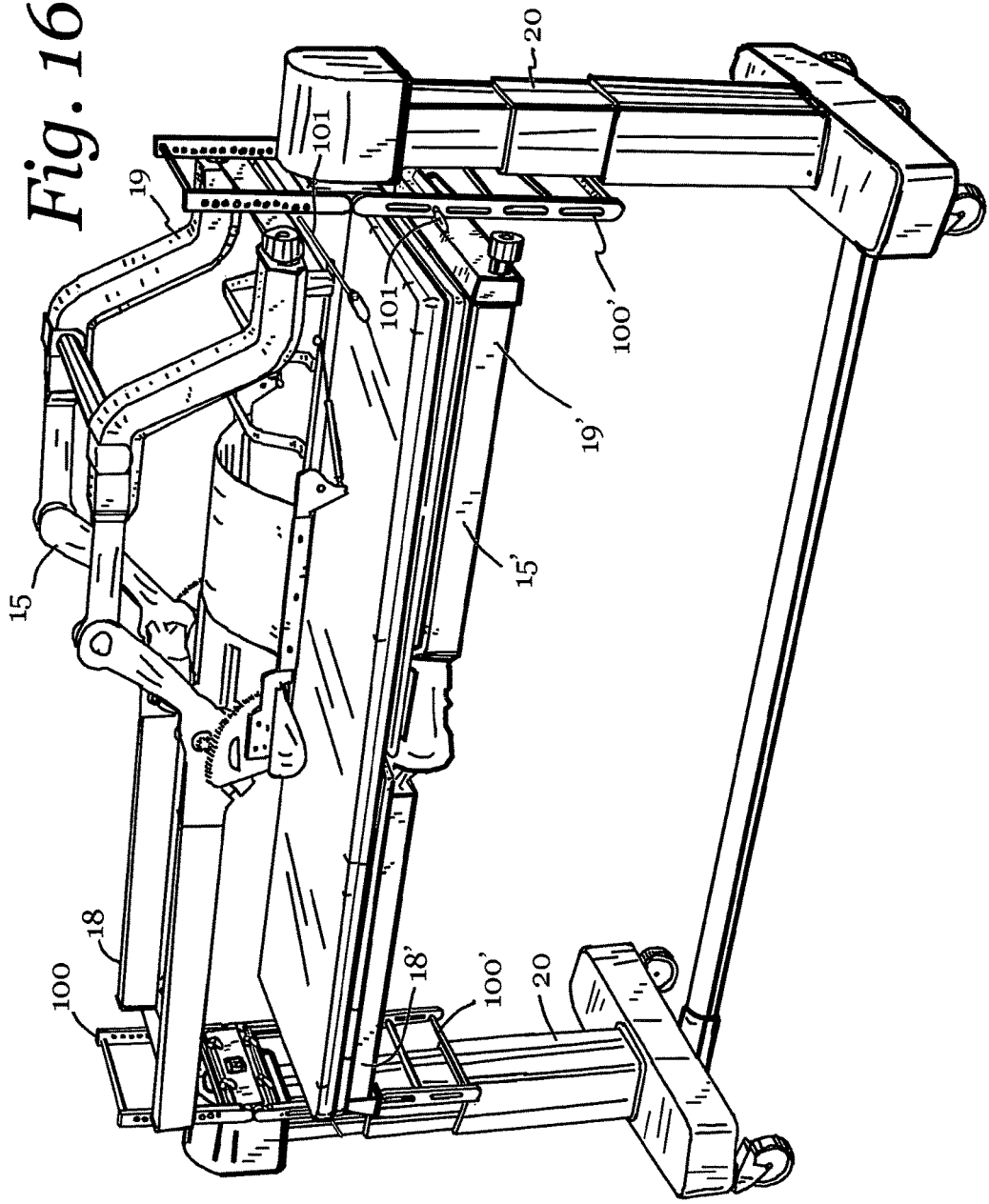

FIG. 160 is an illustration showing the patient positioning support system of FIG. 159, showing connecting the foot-end of the prone patient support structure to a ladder using a T-pin, such that the foot-ends of the prone and supine patient support structures are attached to the same end of the base.

Figure 161:
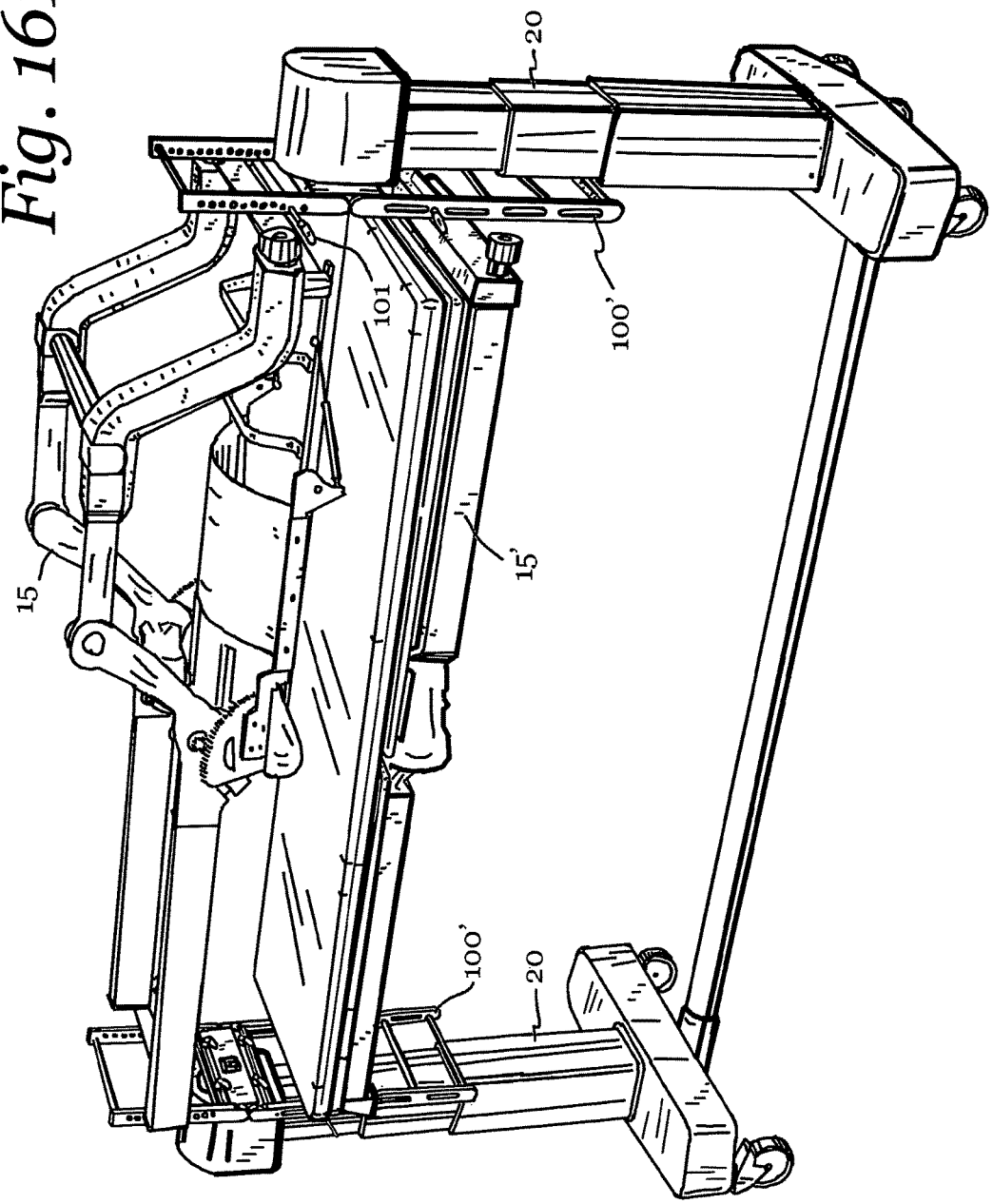

FIG. 161 is an illustration showing the patient positioning support system of FIG. 160, showing connecting the head-end of the prone patient support structure to the second standard length ladder using another T-pin.

Figure 162:
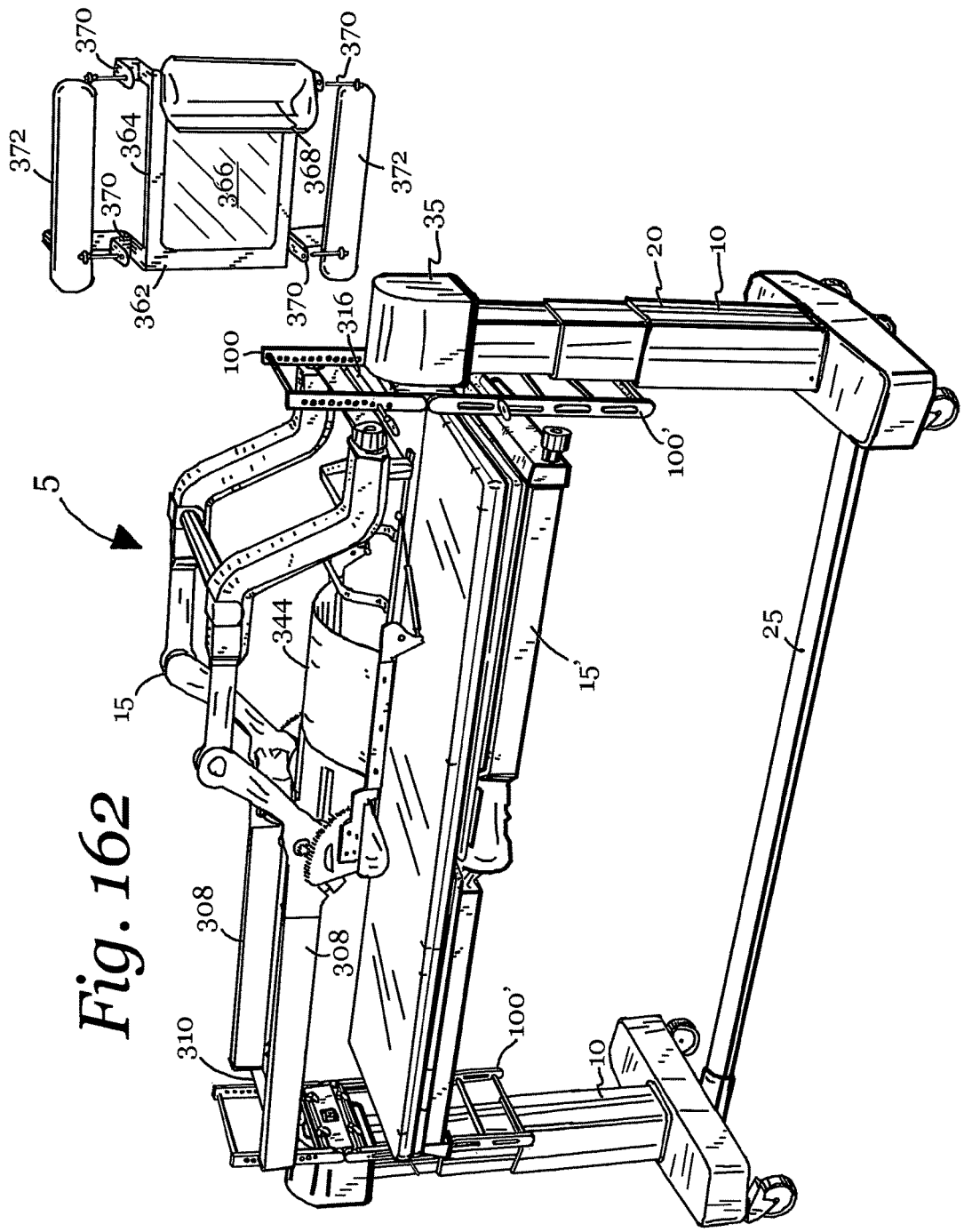

FIG. 162 is an illustration showing the patient positioning support system of FIG. 161, showing the prone patient support structure fully connected to the base and bringing in the torso support structure.

Figure 163:
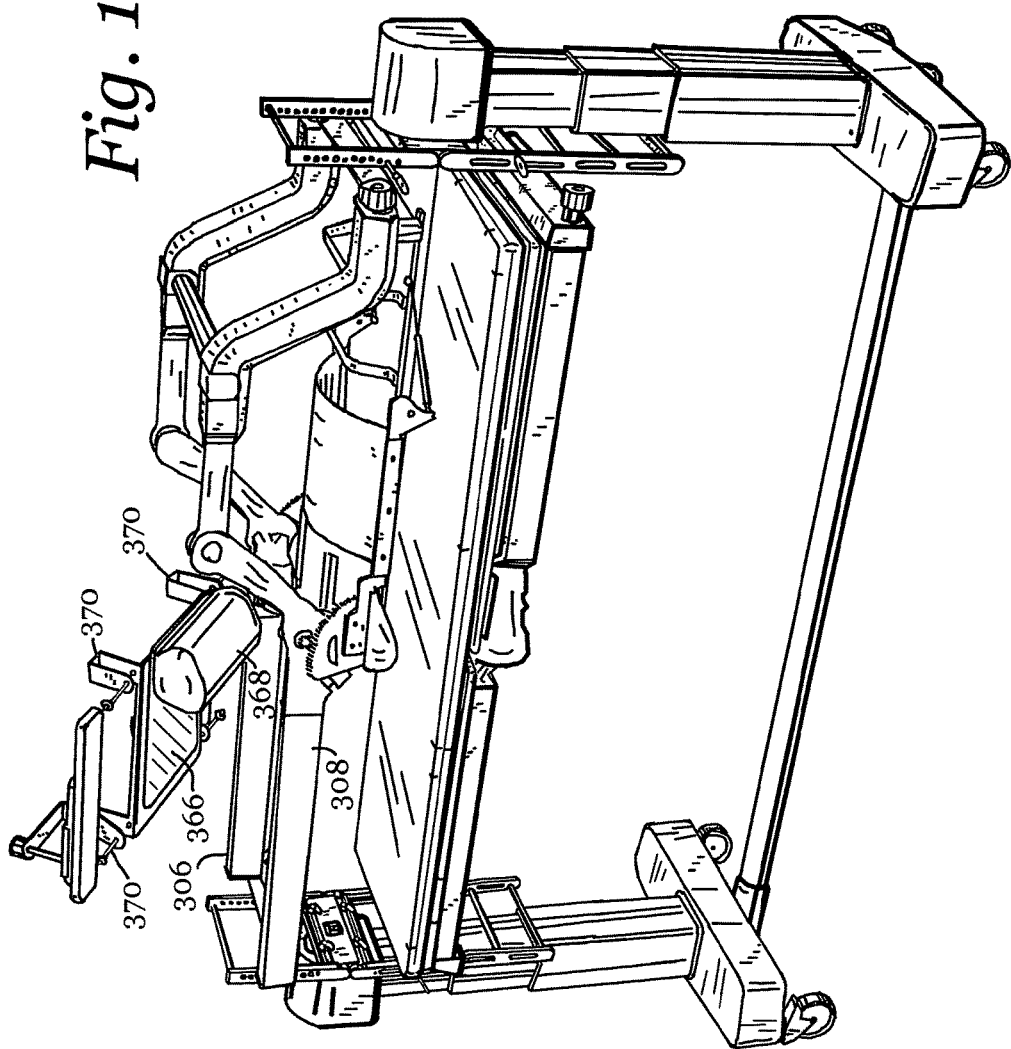

FIG. 163 is an illustration showing the patient positioning support system of FIG. 162, showing an initial step in attaching a torso support structure to the prone patient support structure.

Figure 164:
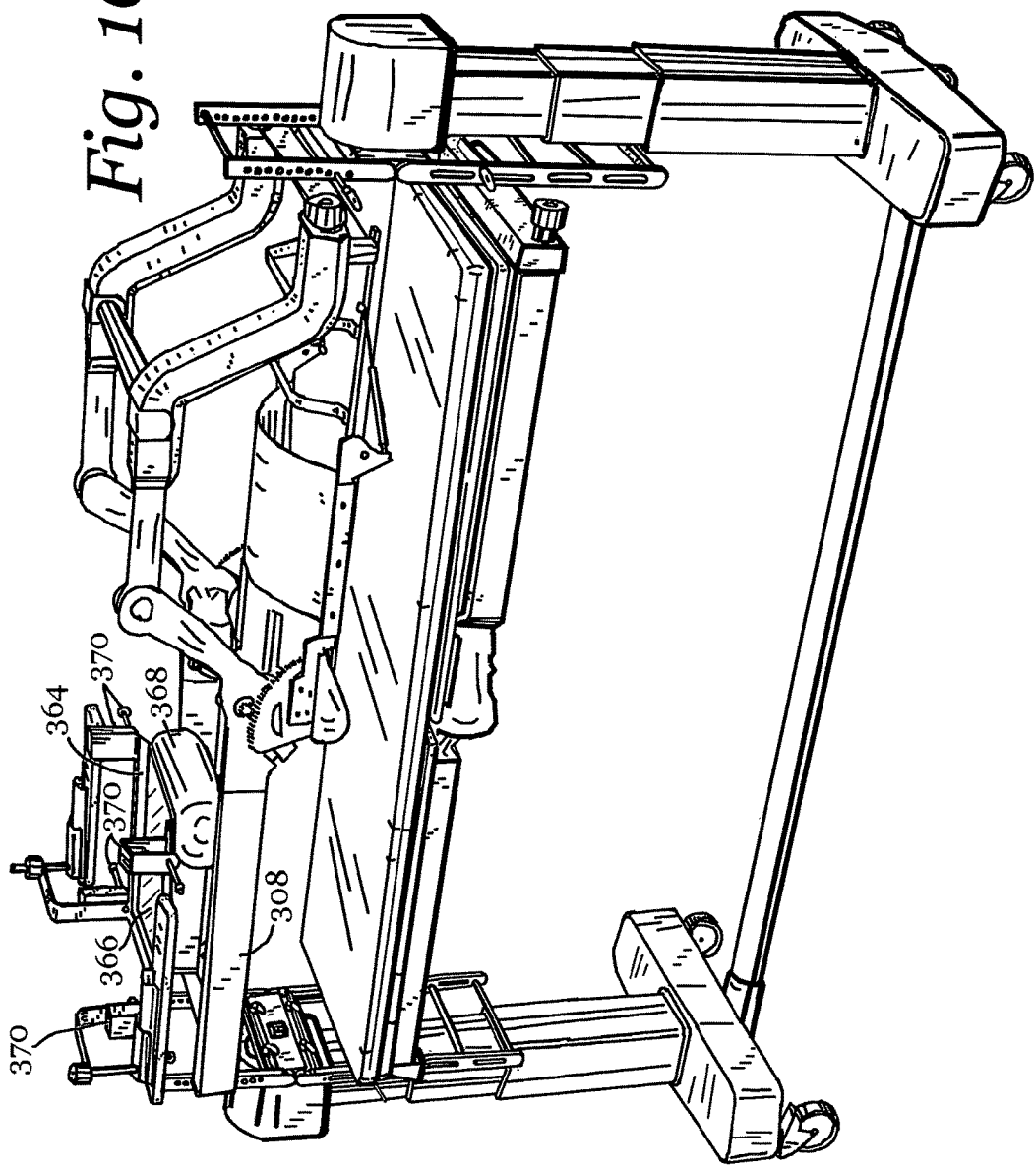

FIG. 164 is an illustration showing the patient positioning support system of FIG. 163, showing an intermediate step in attaching the torso support structure to the prone patient support structure.

Figure 165:
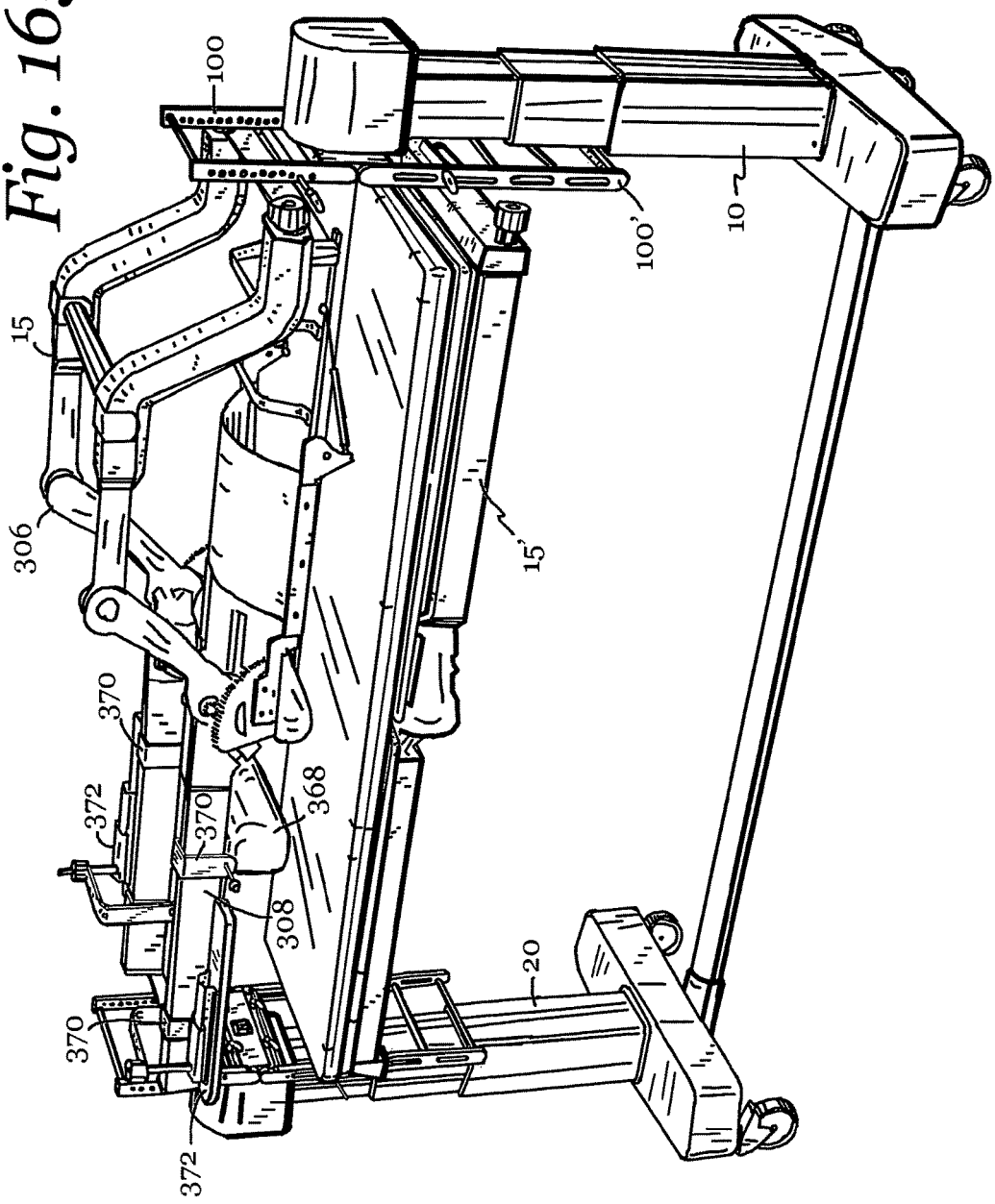

FIG. 165 is an illustration showing the patient positioning support system of FIG. 164, showing the torso support structure attached to the prone patient support structure, wherein the patient positioning support system is configured and arranged to begin the sandwich-and-roll procedure, such as to roll over a supine patient, on the supine patient support structure, to a prone position on the prone patient support structure.

Figure 166:
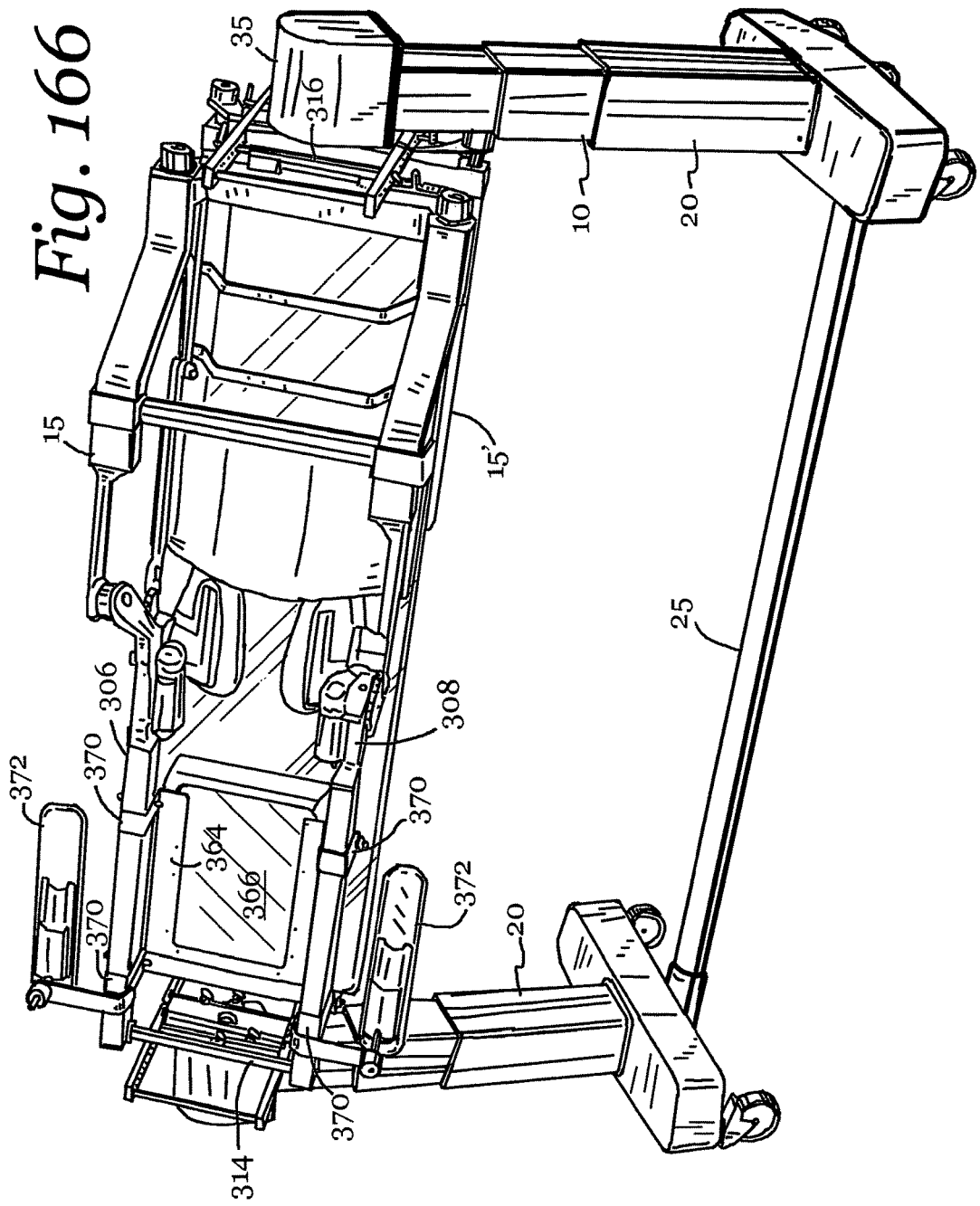

FIG. 166 is an illustration showing the patient positioning support system of FIG. 165, showing an intermediate step in such a sandwich-and-roll procedure.

Figure 167:
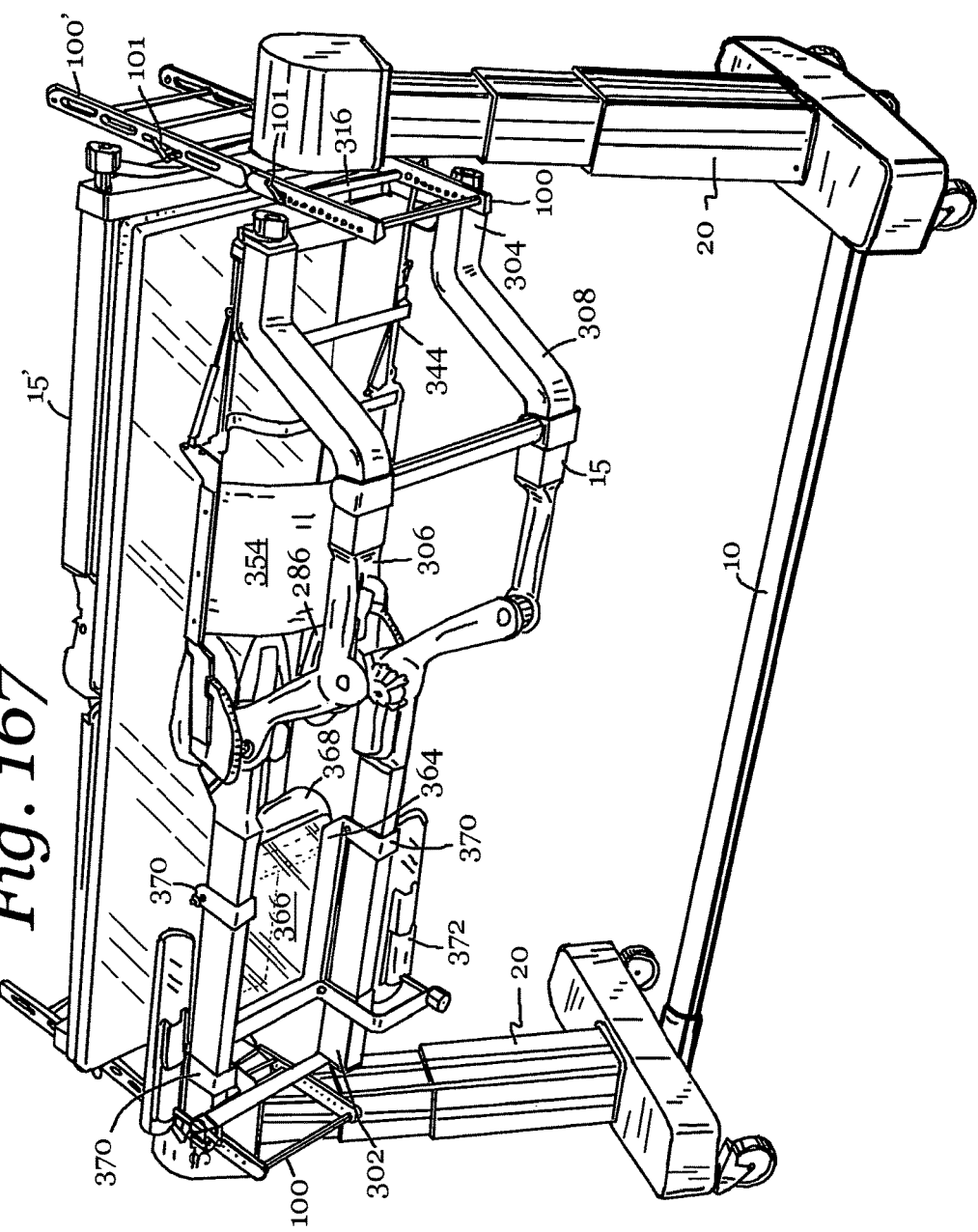

FIG. 167 is an illustration showing the patient positioning support system of FIG. 166, showing another intermediate step in the sandwich-and-roll procedure, wherein the roll has progressed farther than that shown in FIG. 166.

Figure 168:
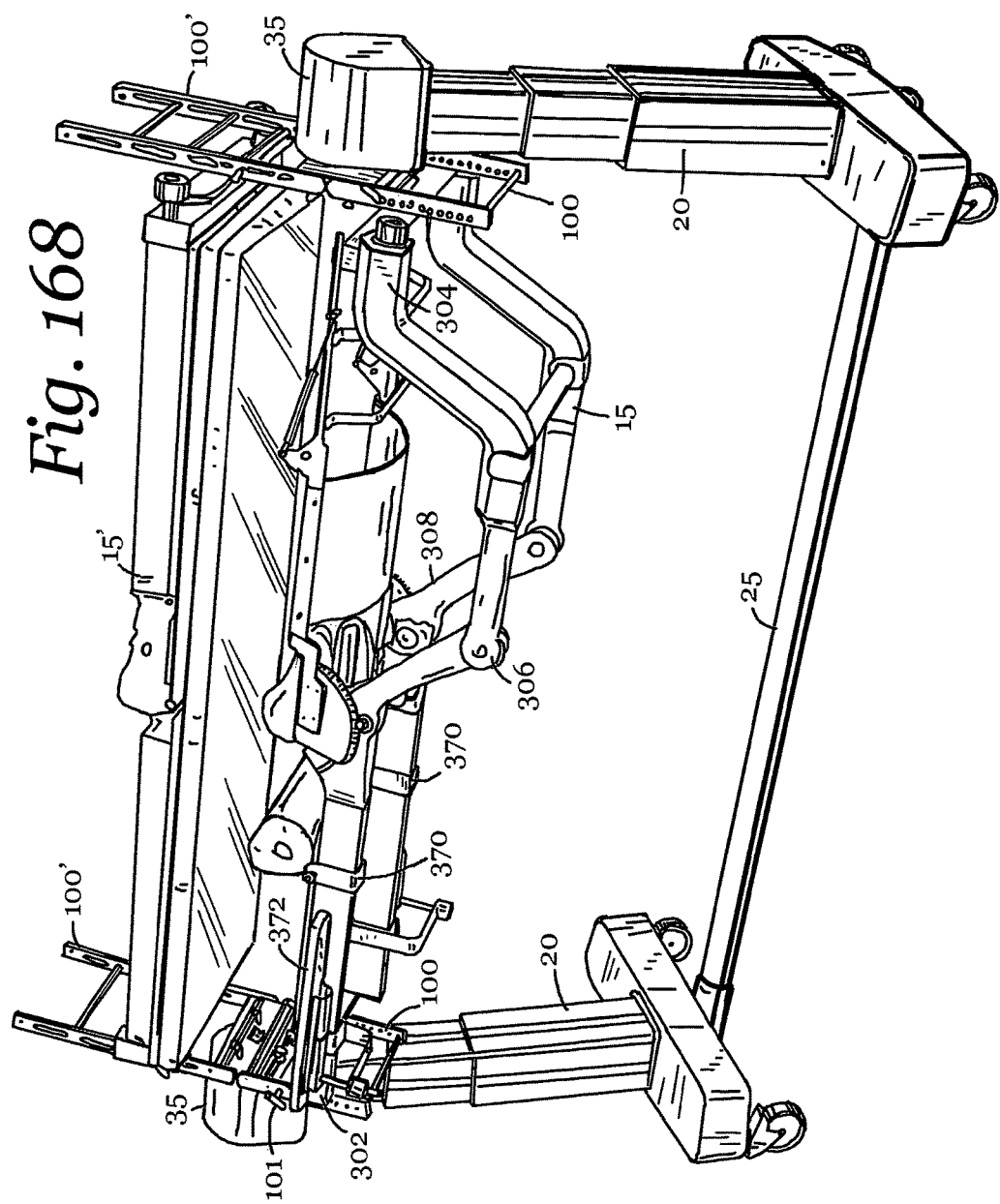

FIG. 168 is an illustration showing the patient positioning support system of FIG. 167, showing yet another intermediate step in the sandwich-and-roll procedure, wherein the roll has progressed farther than that shown in FIG. 167.

Figure 169:
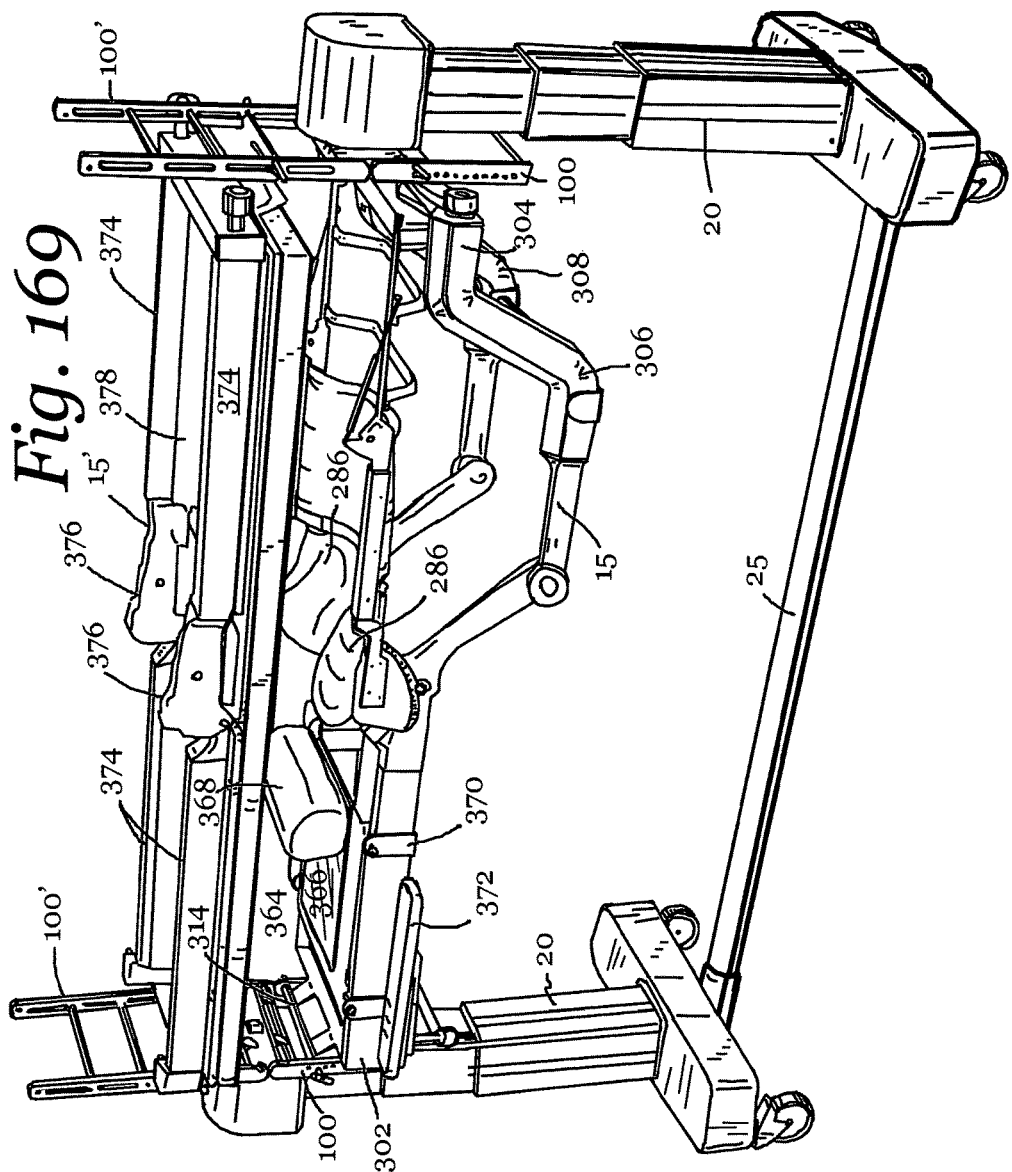

FIG. 169 is an illustration showing the patient positioning support system of FIG. 168 after the sandwich-and-roll procedure has been completed.

Figure 170:
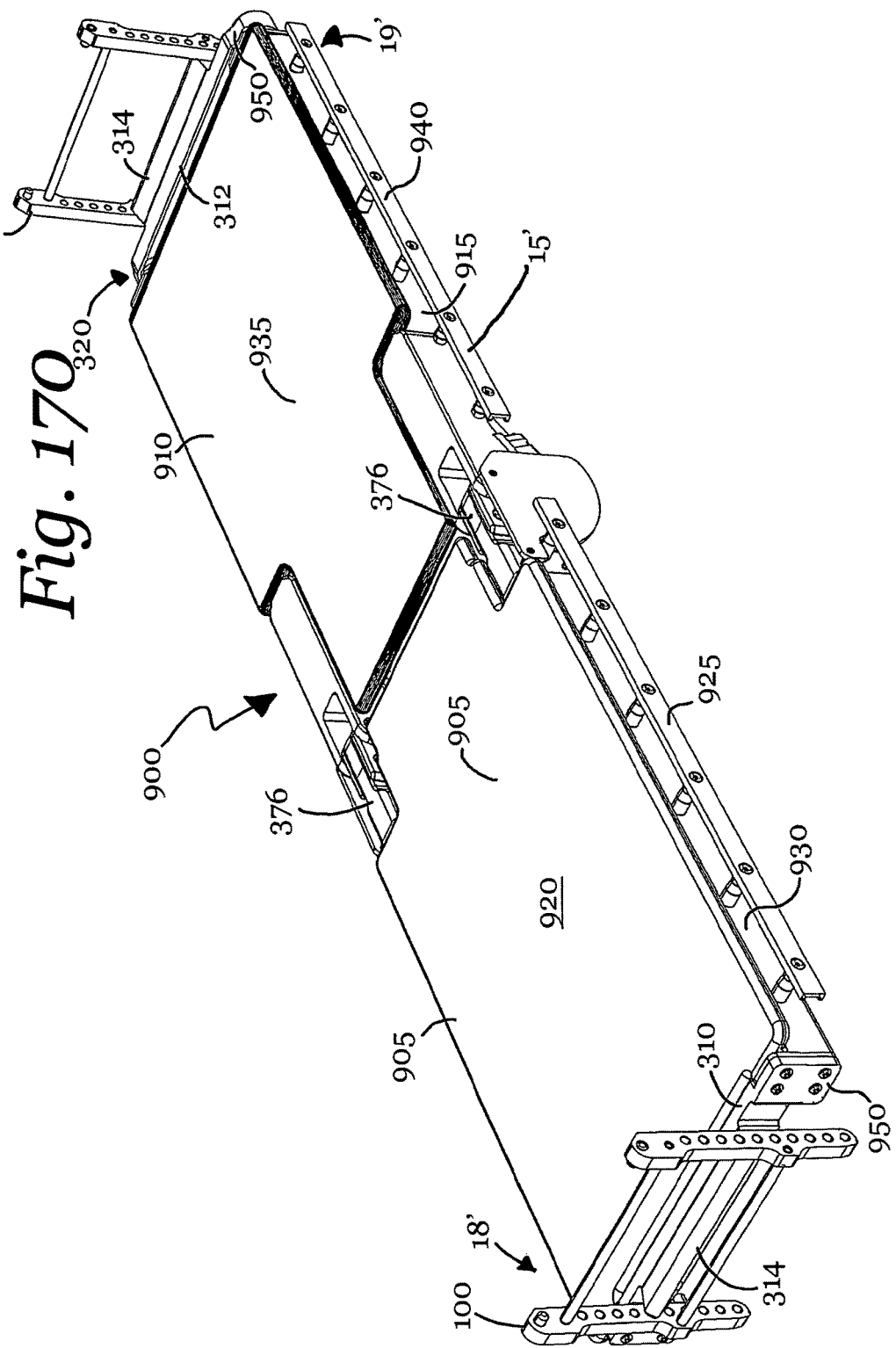

FIG. 170 is a head-end top perspective view of a supine lateral patient support in an embodiment.

Figure 171:
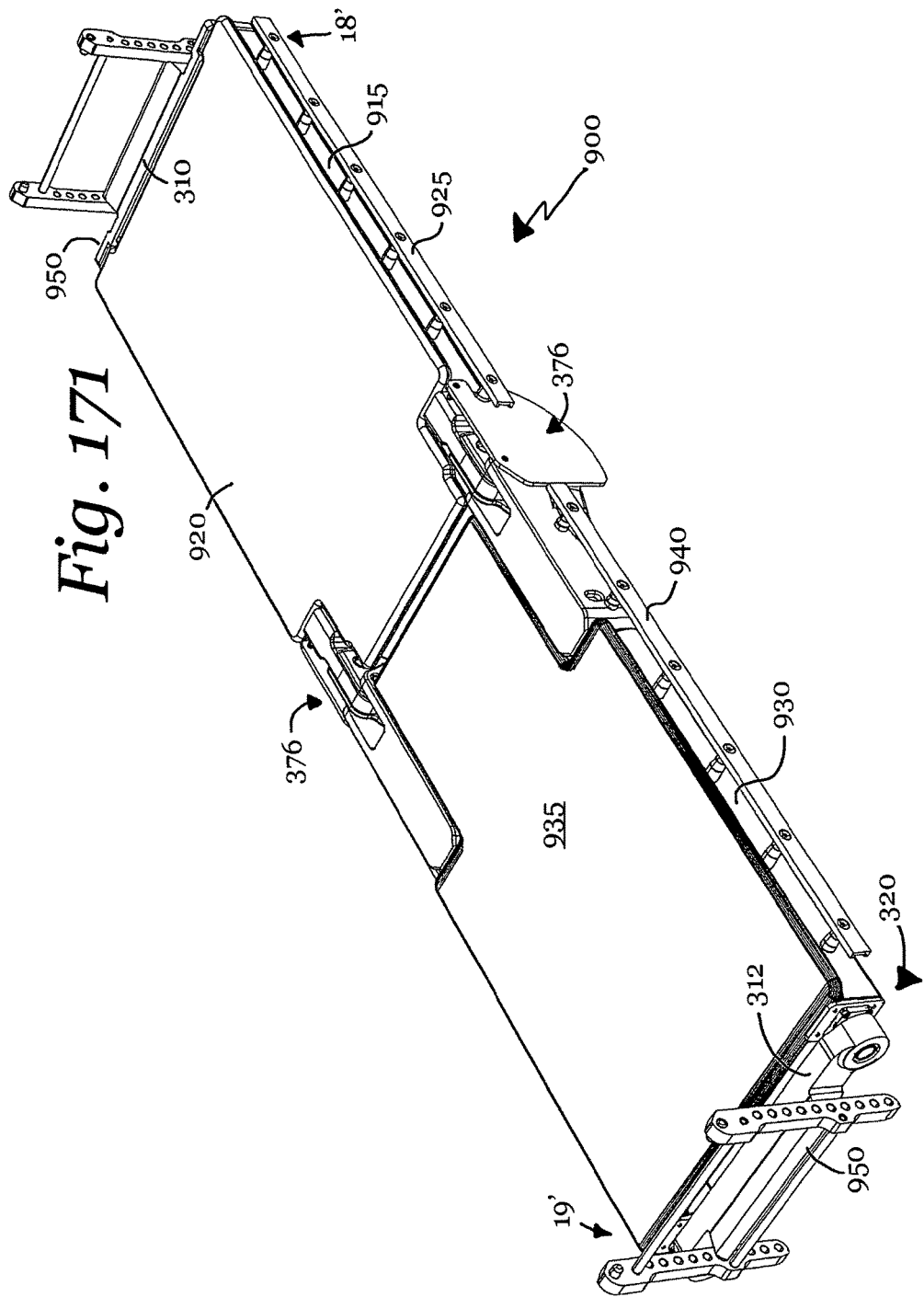

FIG. 171 is a foot-end top perspective view of the supine lateral patient support of FIG. 170.

Figure 172:
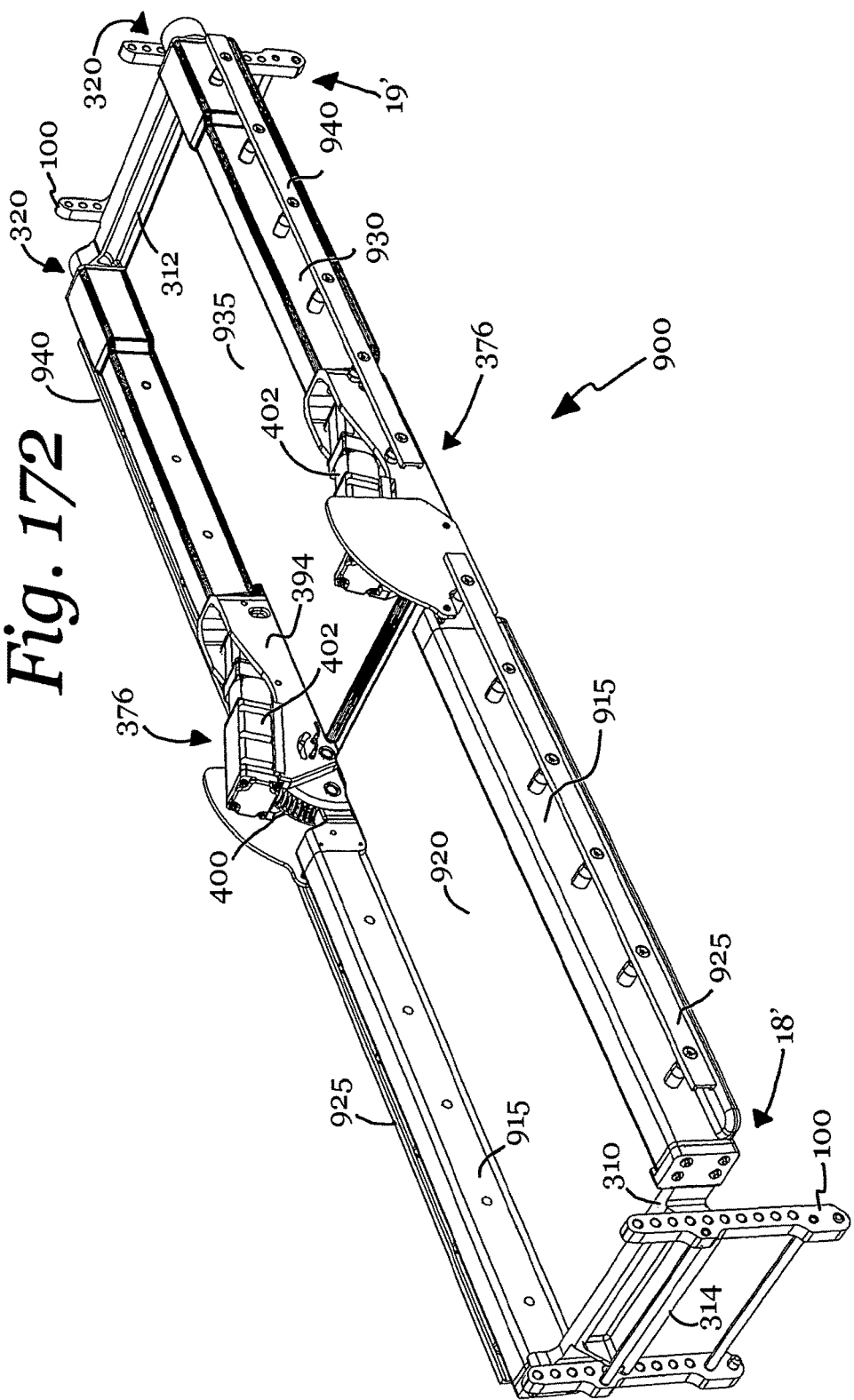

FIG. 172 is a head-end bottom perspective view of the supine lateral patient support of FIG. 170.

FIG. 173 is an enlarge head-end view of the supine lateral patient support of FIG. 170.

FIG. 174 is an enlarged foot-end view of the supine lateral patient support of FIG. 170.

FIG. 175 is an enlarged top view of the supine lateral patient support of FIG. 170.

FIG. 176 is an enlarged right side view of the supine lateral patient support of FIG. 170.

Figure 177:
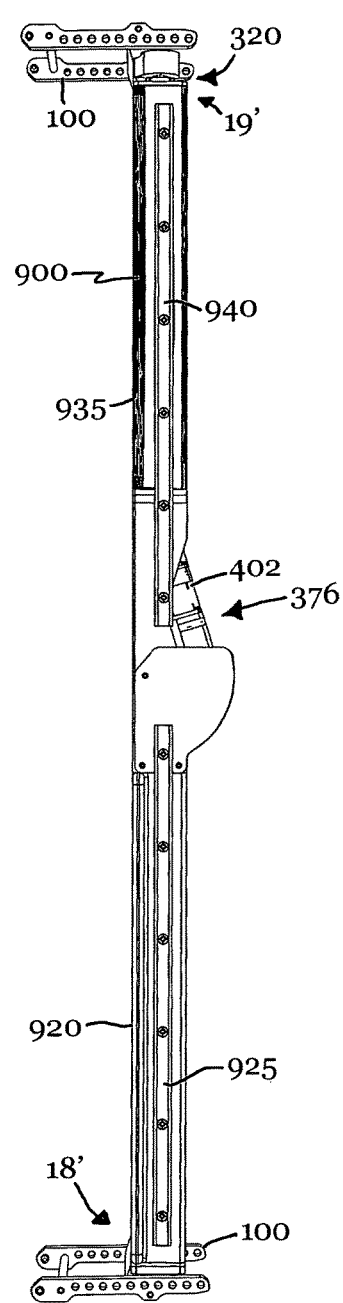

FIG. 177 is an enlarged left side view of the supine lateral patient support of FIG. 170.

Figure 178:
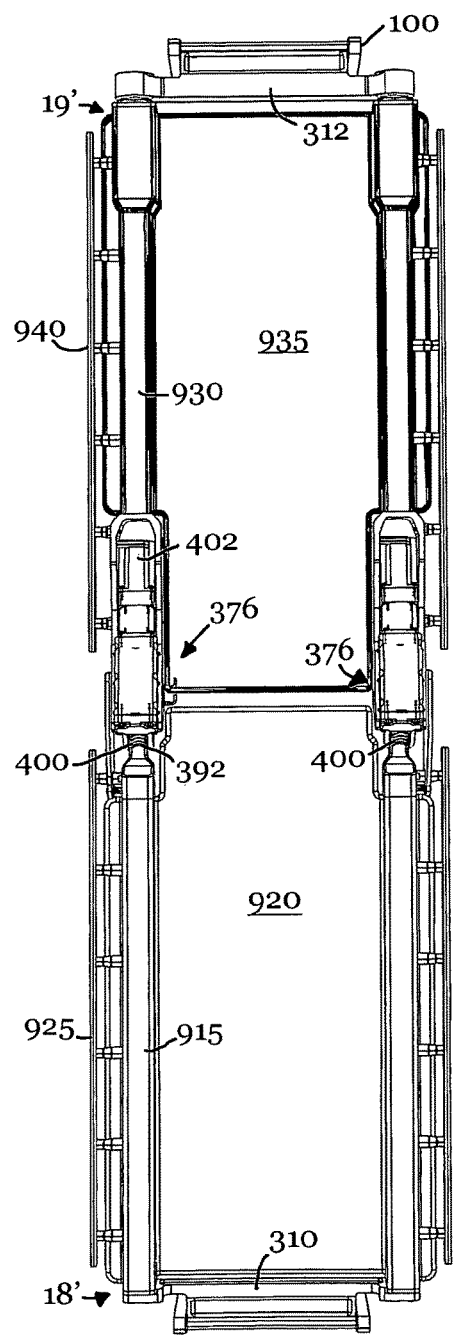

FIG. 178 is an enlarged bottom view of the supine lateral patient support of FIG. 170.

Figure 179:
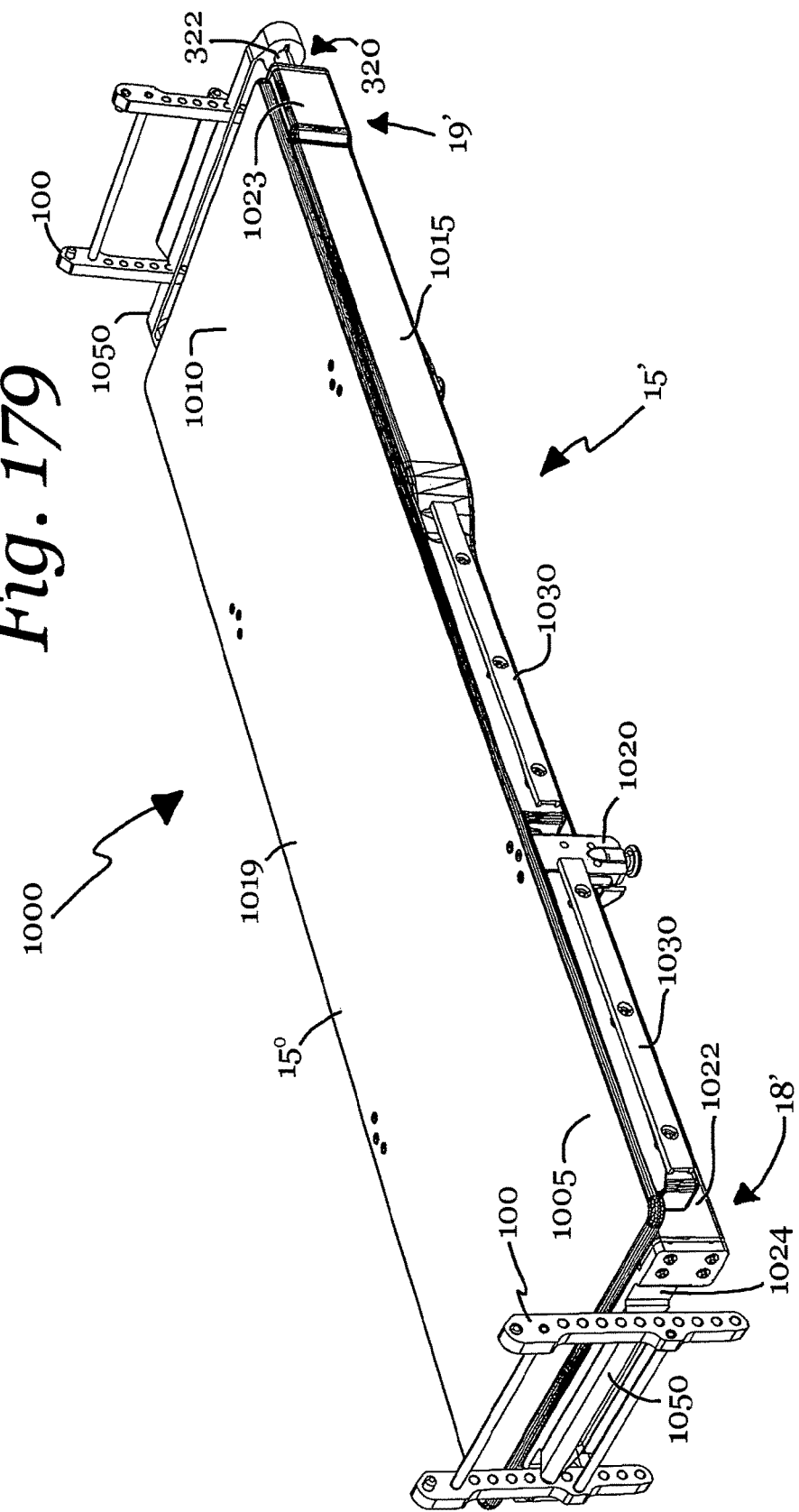

FIG. 179 is a head-end top perspective view of a non-breaking supine lateral patient support in one embodiment.

Figure 180:
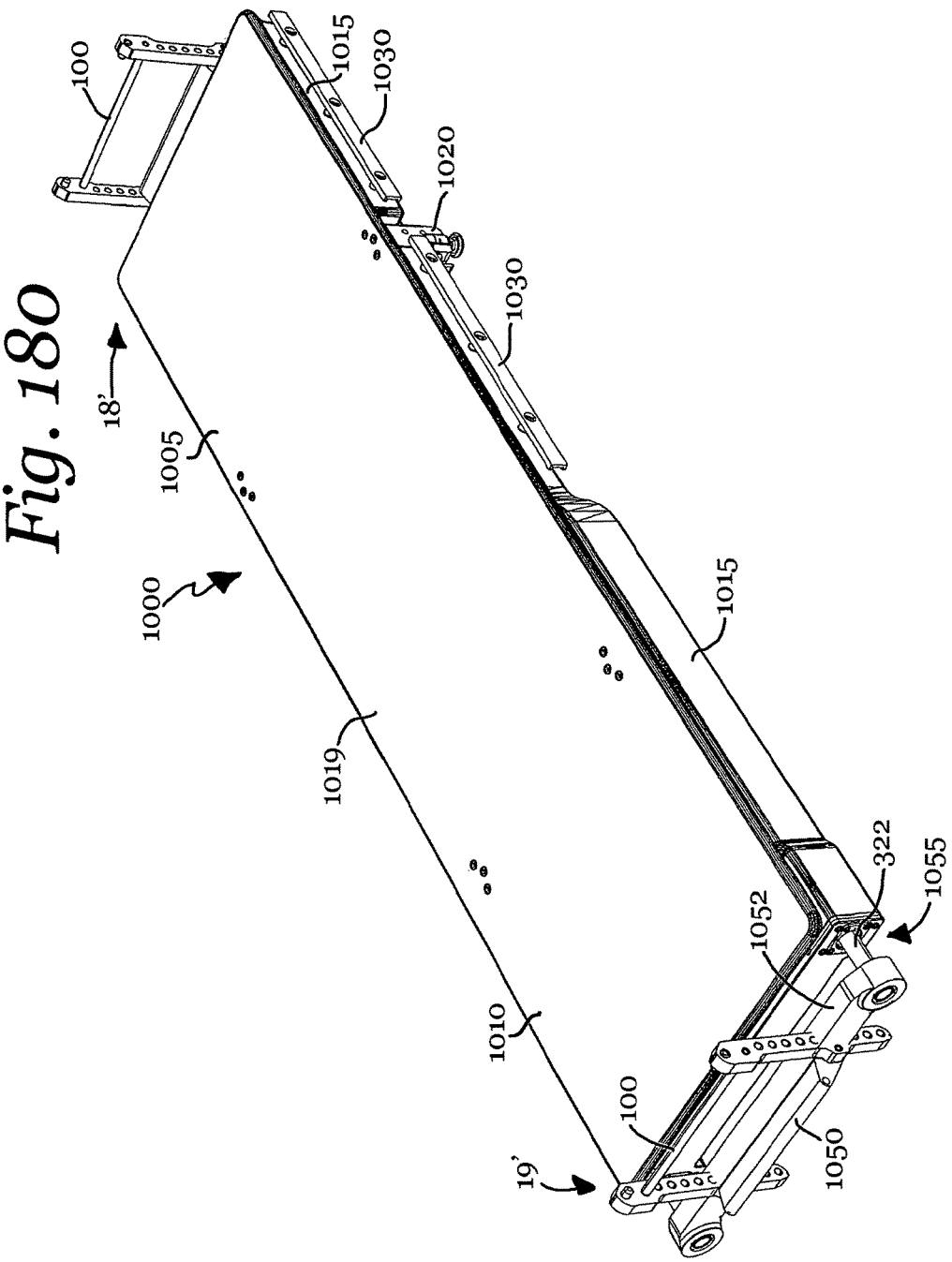

FIG. 180 is a foot-end top perspective view of the non-breaking supine lateral patient support of FIG. 179.

Figure 181:
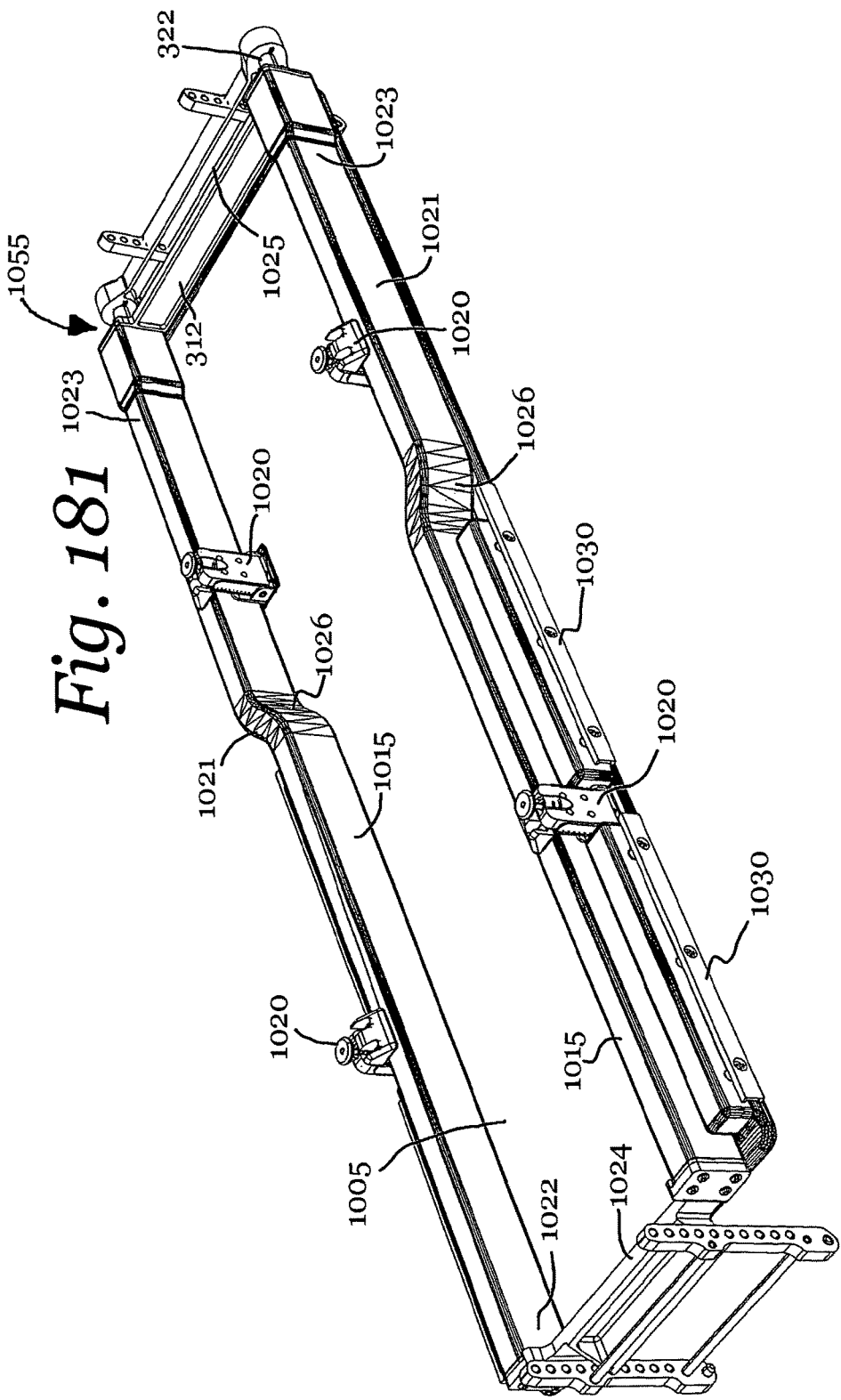

FIG. 181 is a head-end bottom perspective view of the non-breaking supine lateral patient support of FIG. 179.

Figure 182:
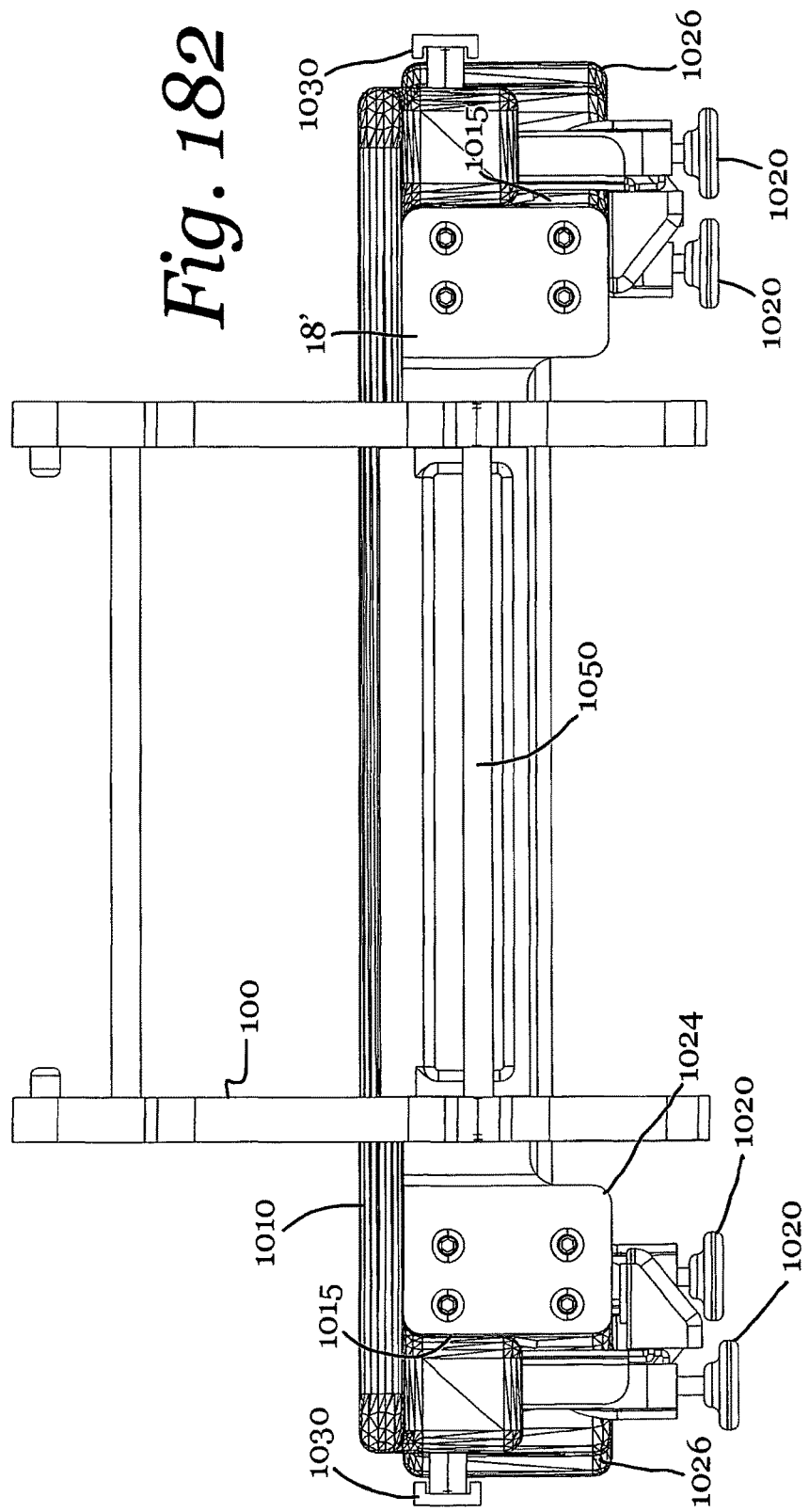

FIG. 182 is an enlarge head-end view of the non-breaking supine lateral patient support of FIG. 179.

Figure 183:
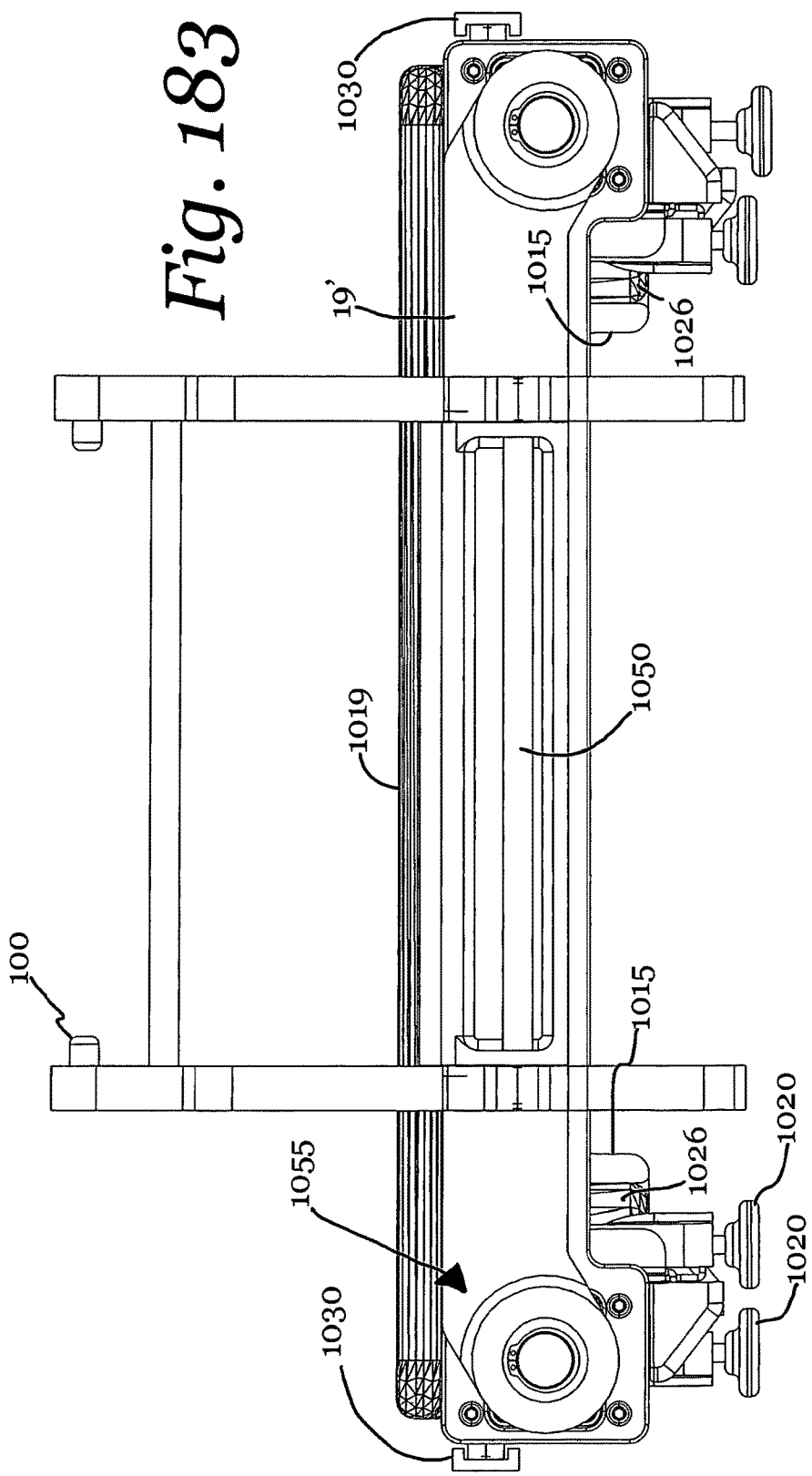

FIG. 183 is an enlarged foot-end view of the non-breaking supine lateral patient support of FIG. 179.

Figure 184:
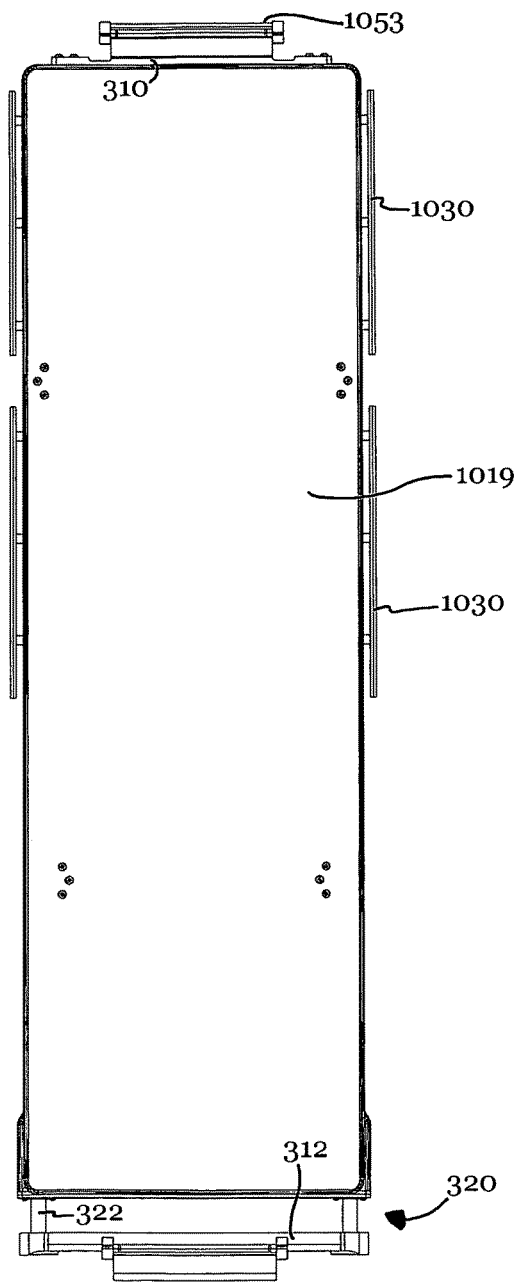

FIG. 184 is an enlarged top view of the non-breaking supine lateral patient support of FIG. 179.

Figure 185:
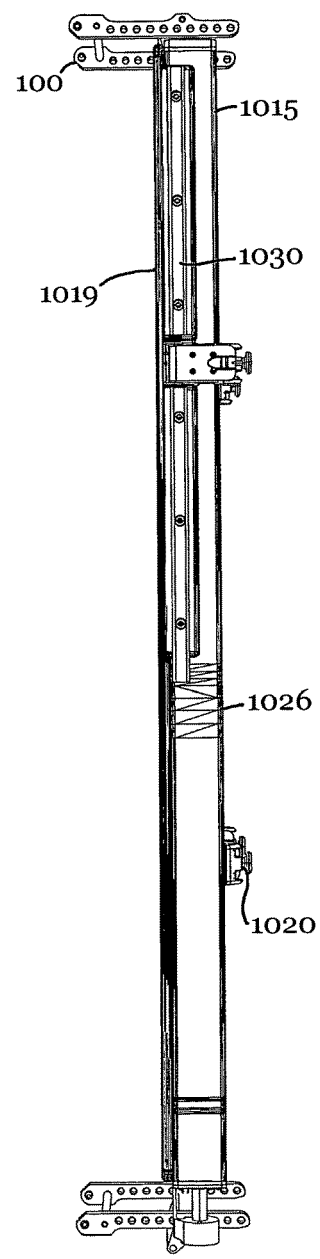

FIG. 185 is an enlarged right side view of the non-breaking supine lateral patient support of FIG. 179.

FIG. 186 is an enlarged left side view of the non-breaking supine lateral patient support of FIG. 179.

FIG. 187 is an enlarged bottom view of the non-breaking supine lateral patient support of FIG. 179.

Figure 188:
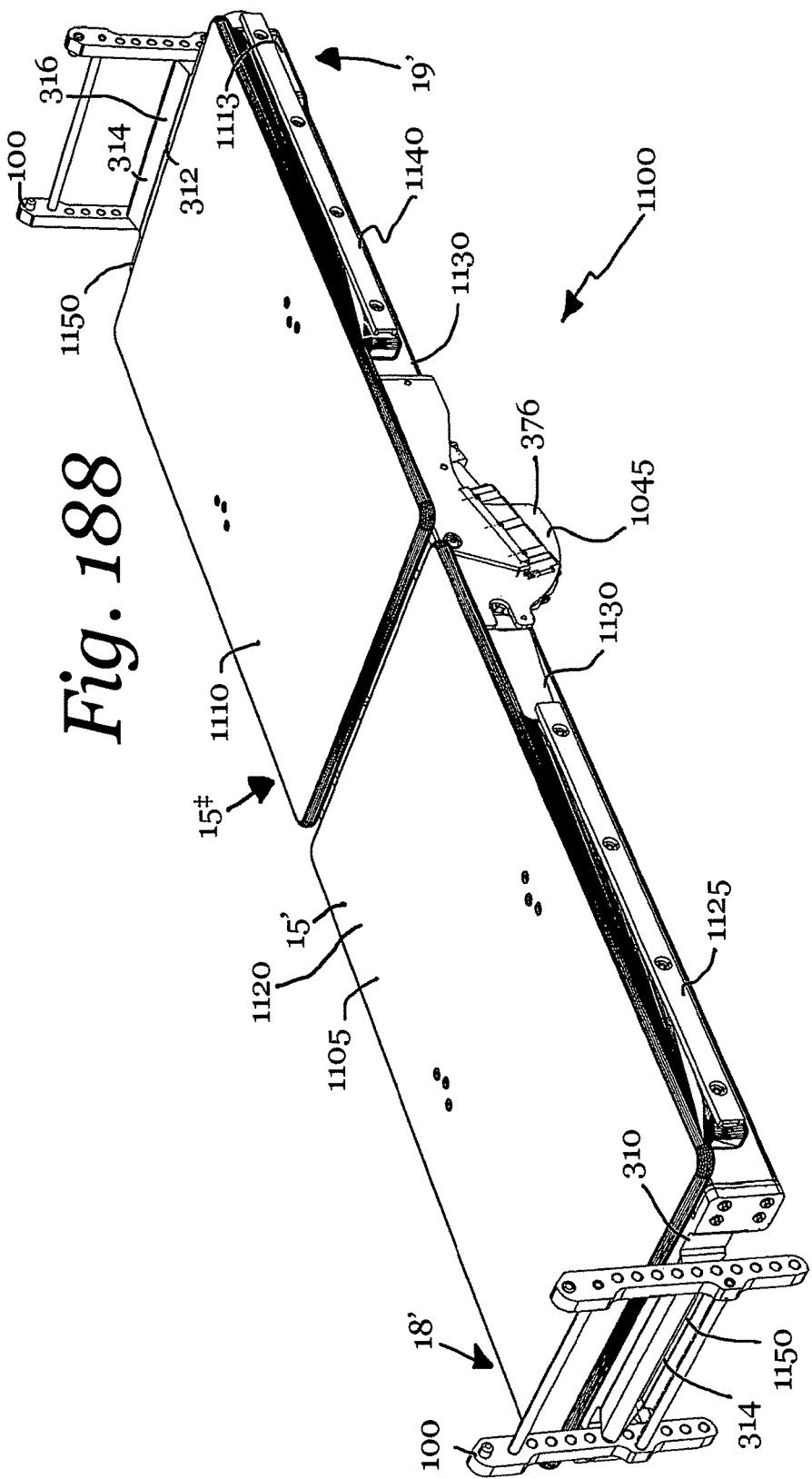

FIG. 188 is a head-end top perspective view of a breaking supine lateral patient support in an embodiment.

Figure 189:
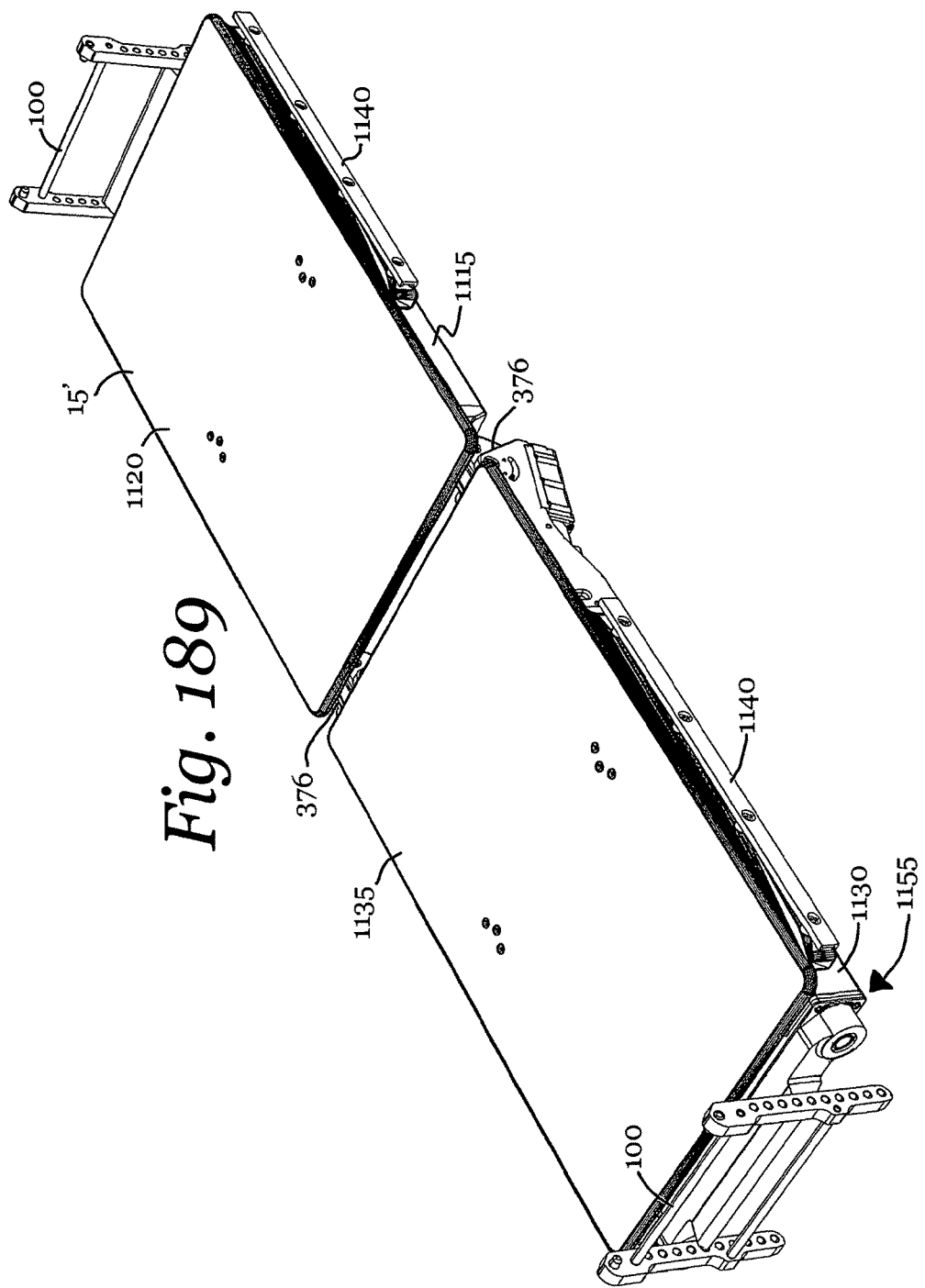

FIG. 189 is a foot-end top perspective view of the breaking supine lateral patient support of FIG. 188.

Figure 190:
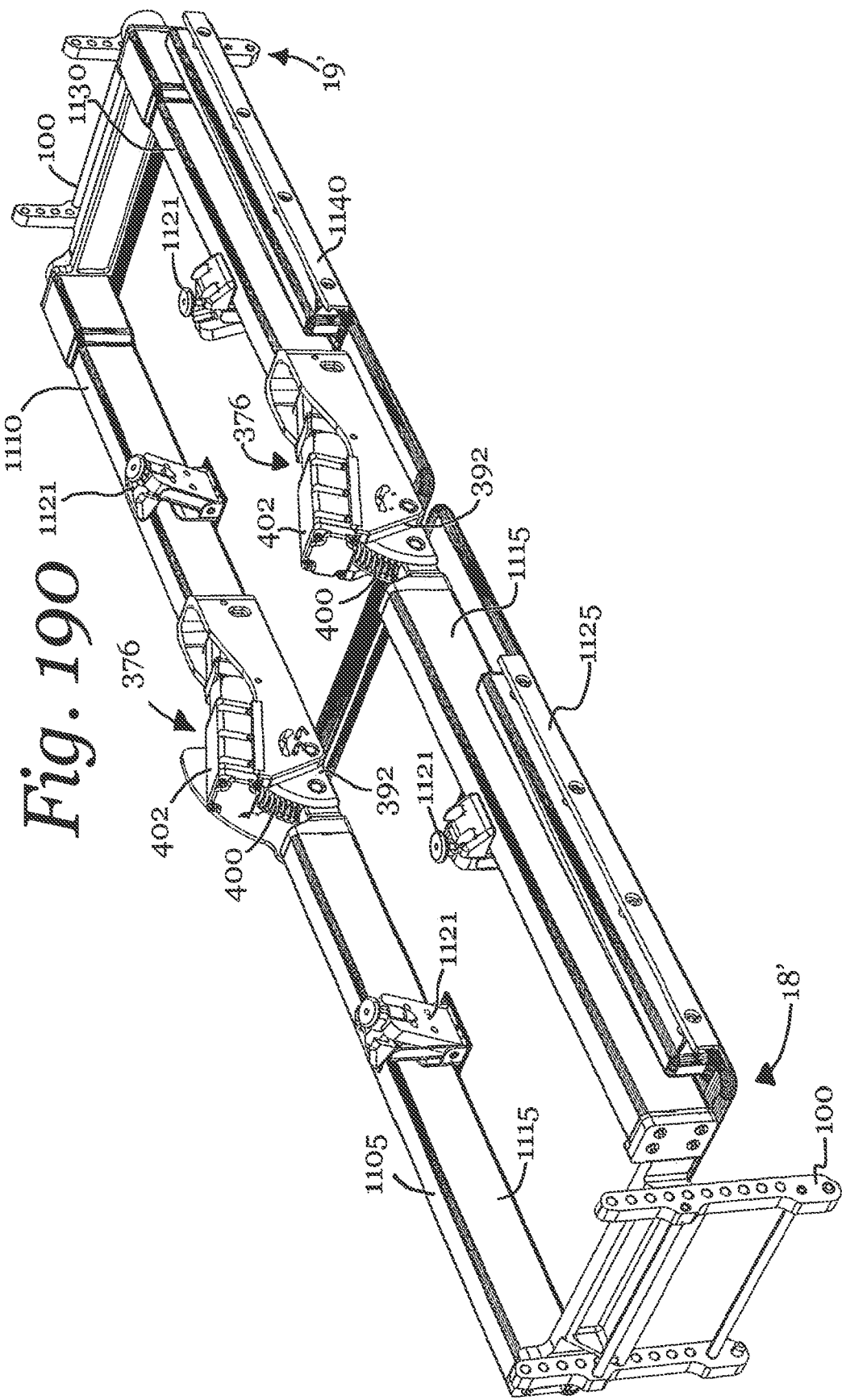

FIG. 190 is a head-end bottom perspective view of the breaking supine lateral patient support of FIG. 188.

FIG. 191 is an enlarge head-end view of the breaking supine lateral patient support of FIG. 188.

FIG. 192 is an enlarged foot-end view of the breaking supine lateral patient support of FIG. 188.

FIG. 193 is an enlarged top view of the breaking supine lateral patient support of FIG. 188.

FIG. 194 is an enlarged right side view of the breaking supine lateral patient support of FIG. 188.

Figure 195:
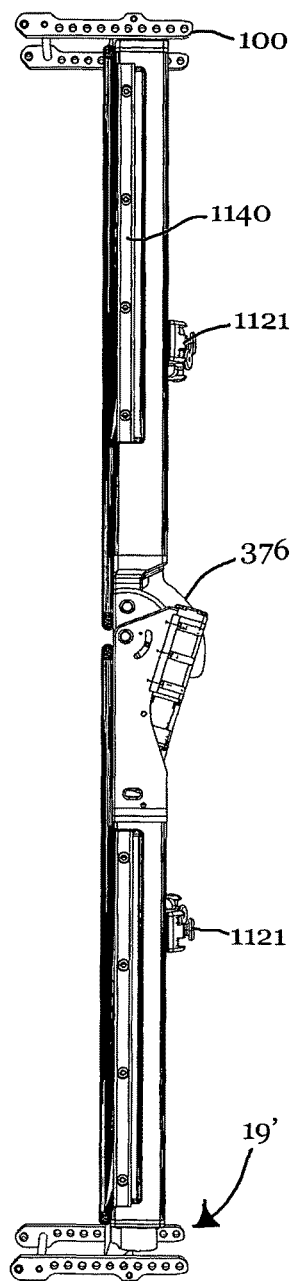

FIG. 195 is an enlarged left side view of the breaking supine lateral patient support of FIG. 188.

Figure 196:
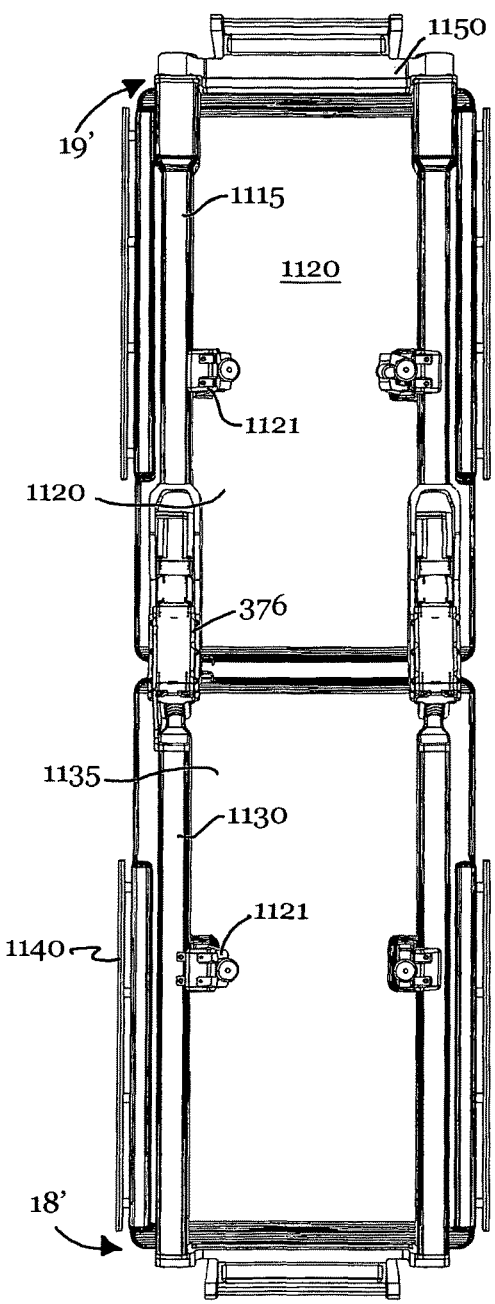

FIG. 196 is an enlarged bottom view of the breaking supine lateral patient support of FIG. 188.

Figure 197:
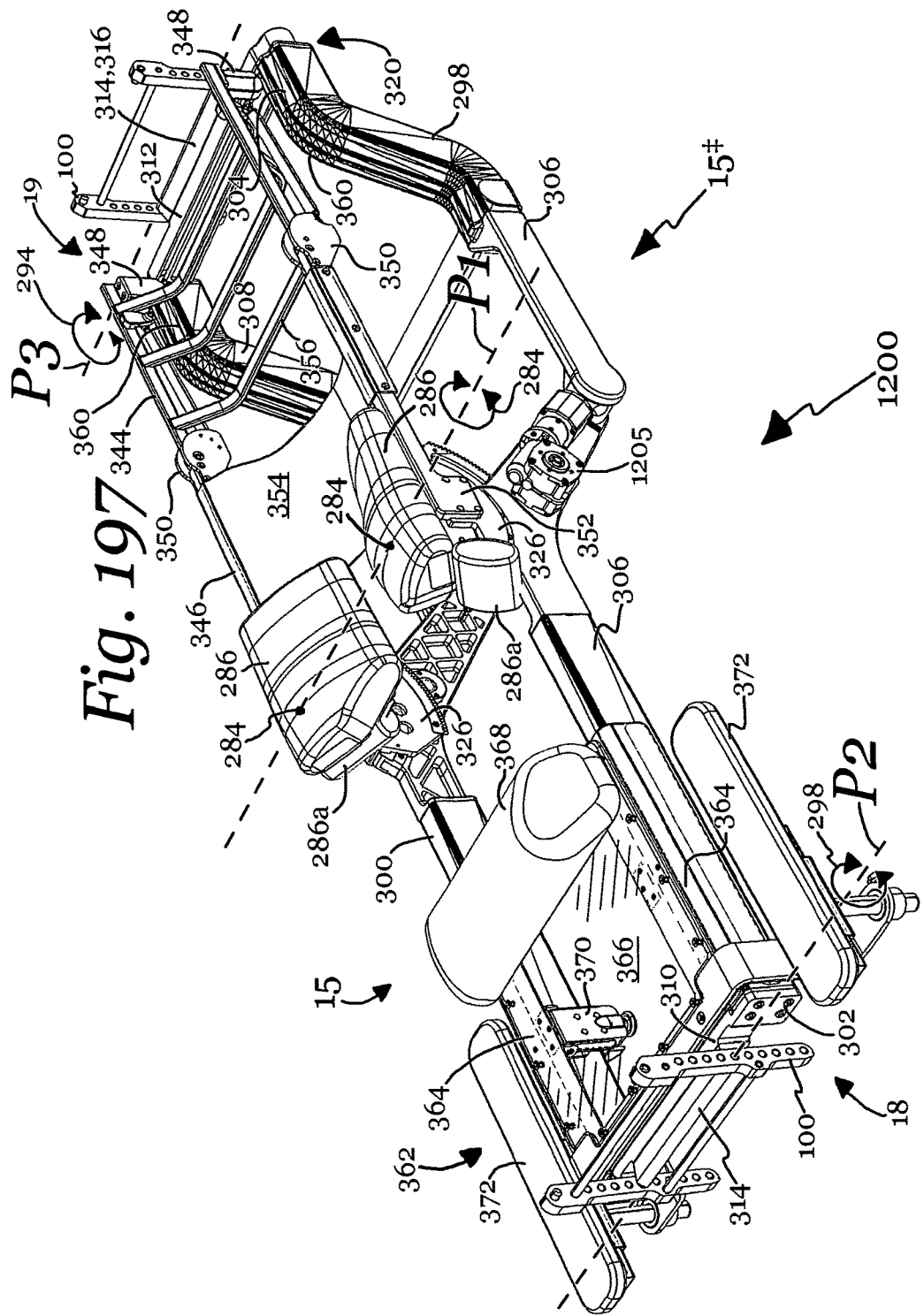

FIG. 197 is a head-end top perspective view of a prone lateral patient support in an embodiment.

Figure 198:
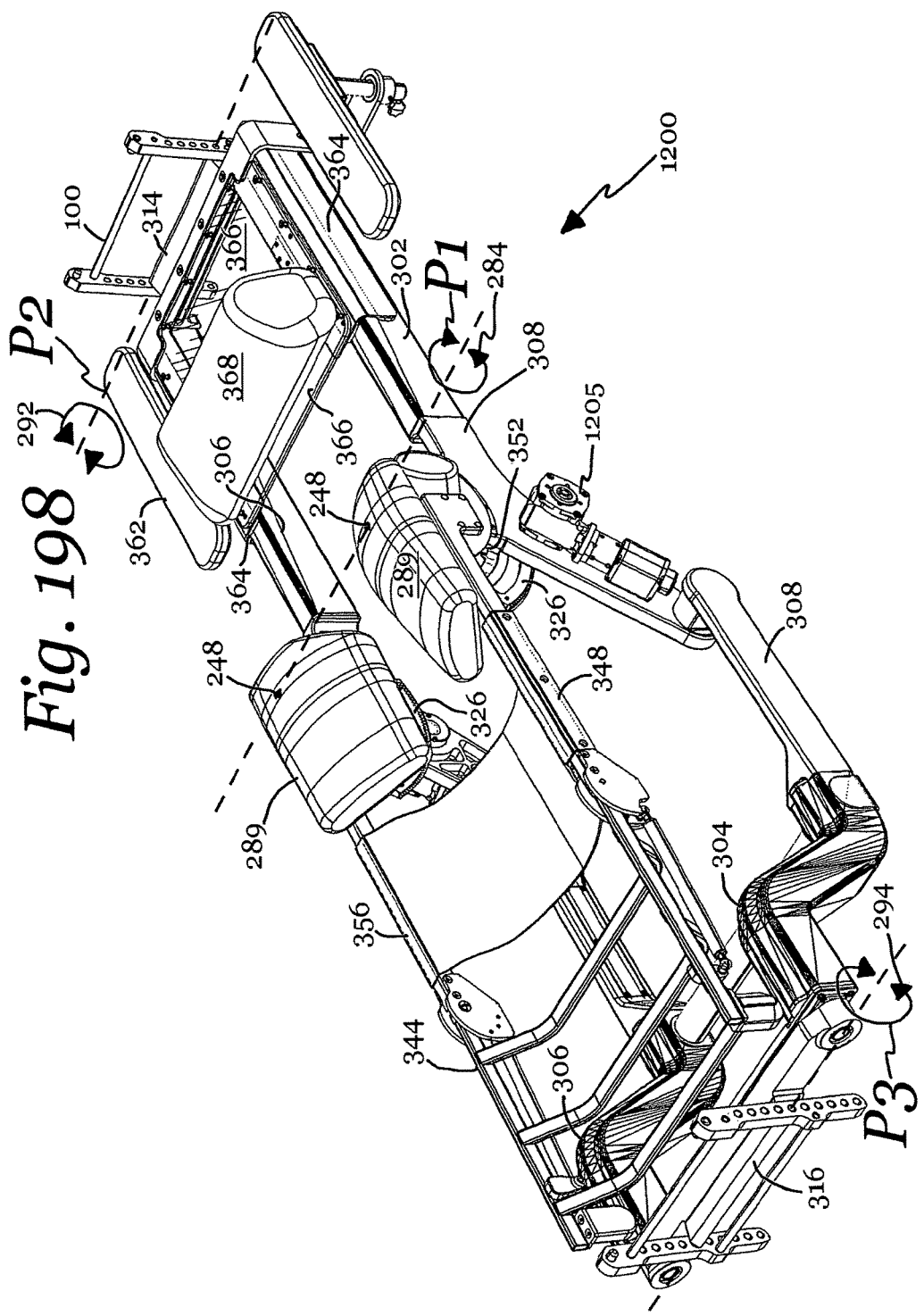

FIG. 198 is a foot-end top perspective view of the prone lateral patient support of FIG. 197.

Figure 199:
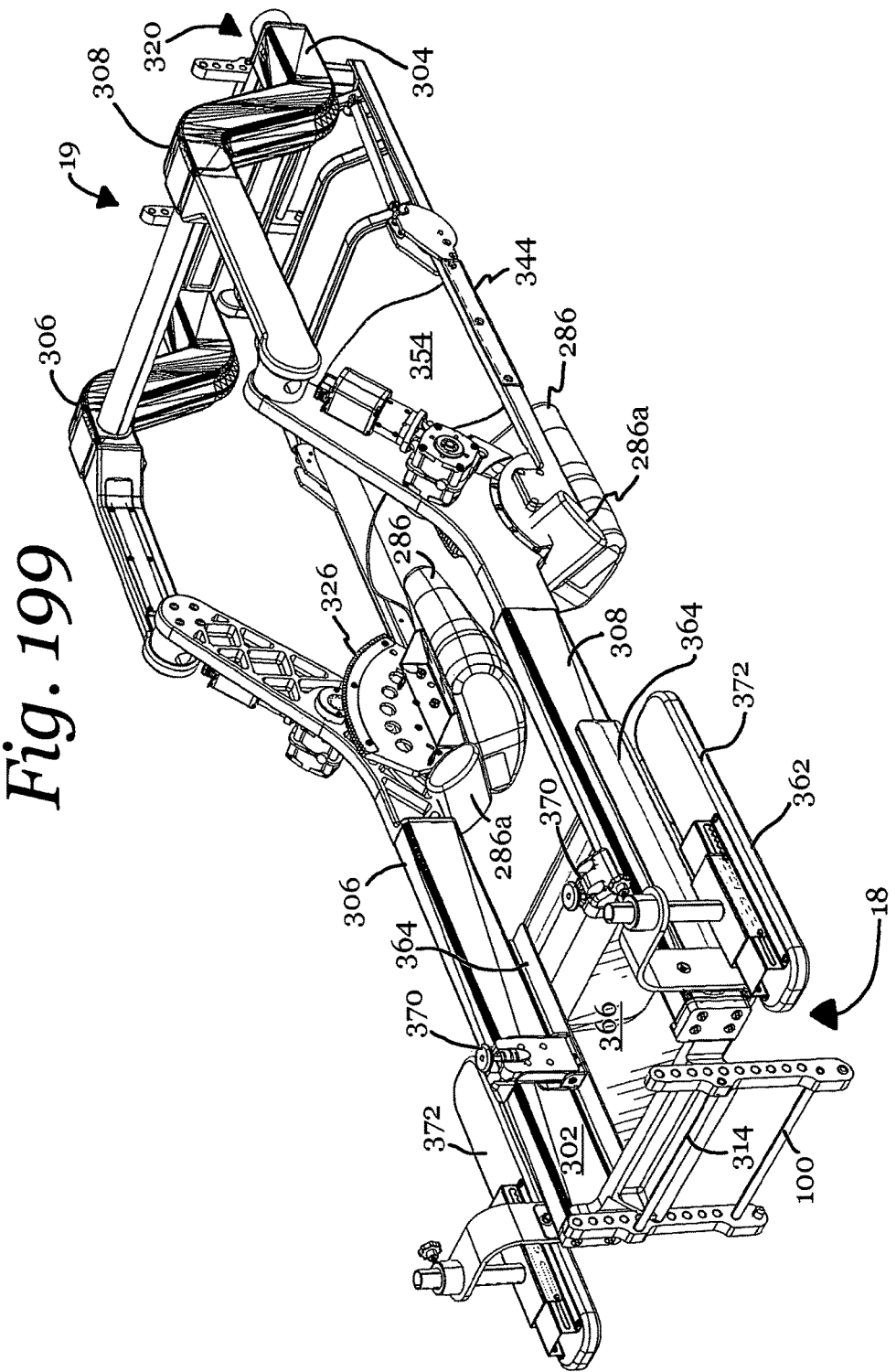

FIG. 199 is a head-end bottom perspective view of the prone lateral patient support of FIG. 197.

Figure 200:
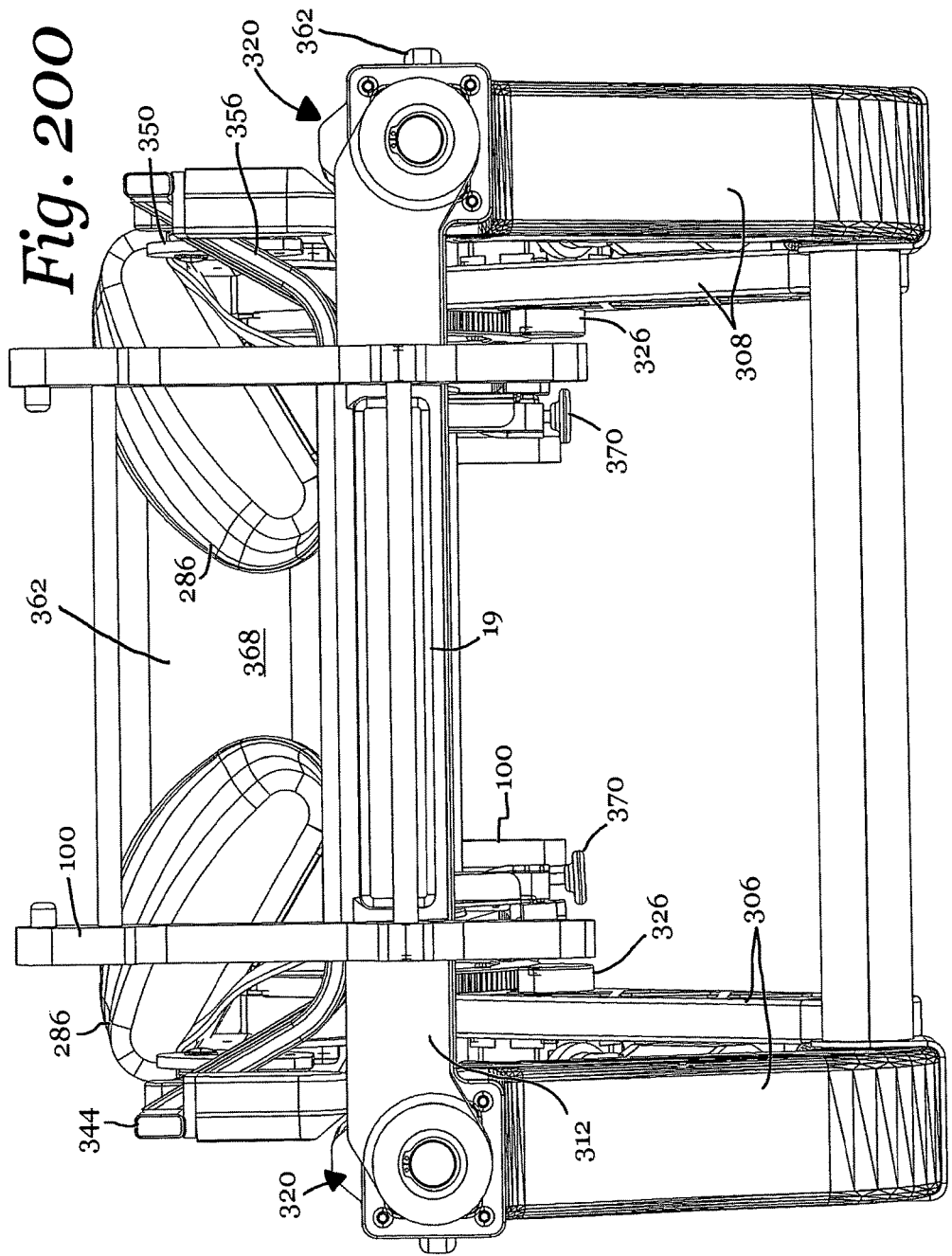

FIG. 200 is an enlarge head-end view of the prone lateral patient support of FIG. 197.

Figure 201:
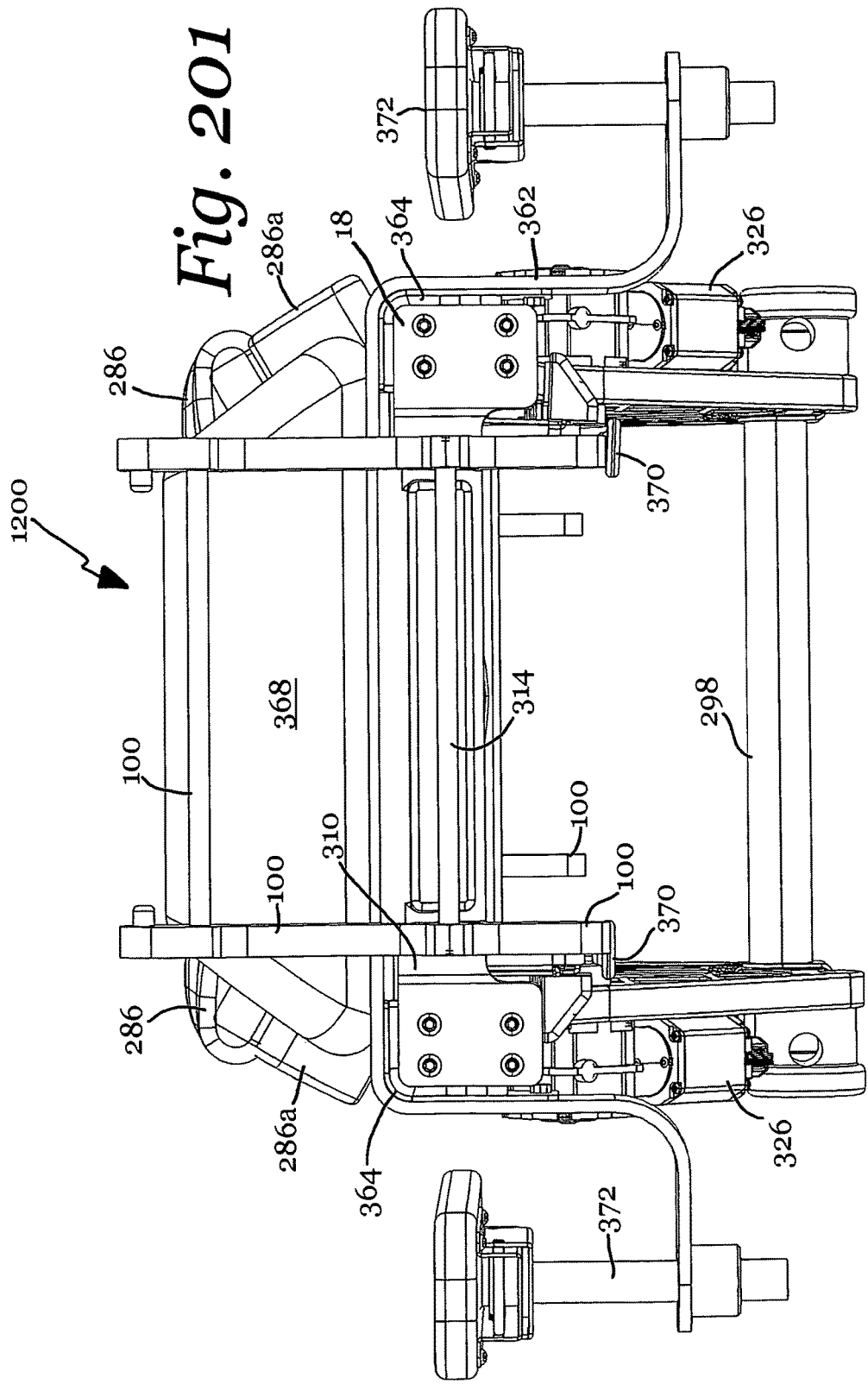

FIG. 201 is an enlarged foot-end view of the prone lateral patient support of FIG. 197.

Figure 202:
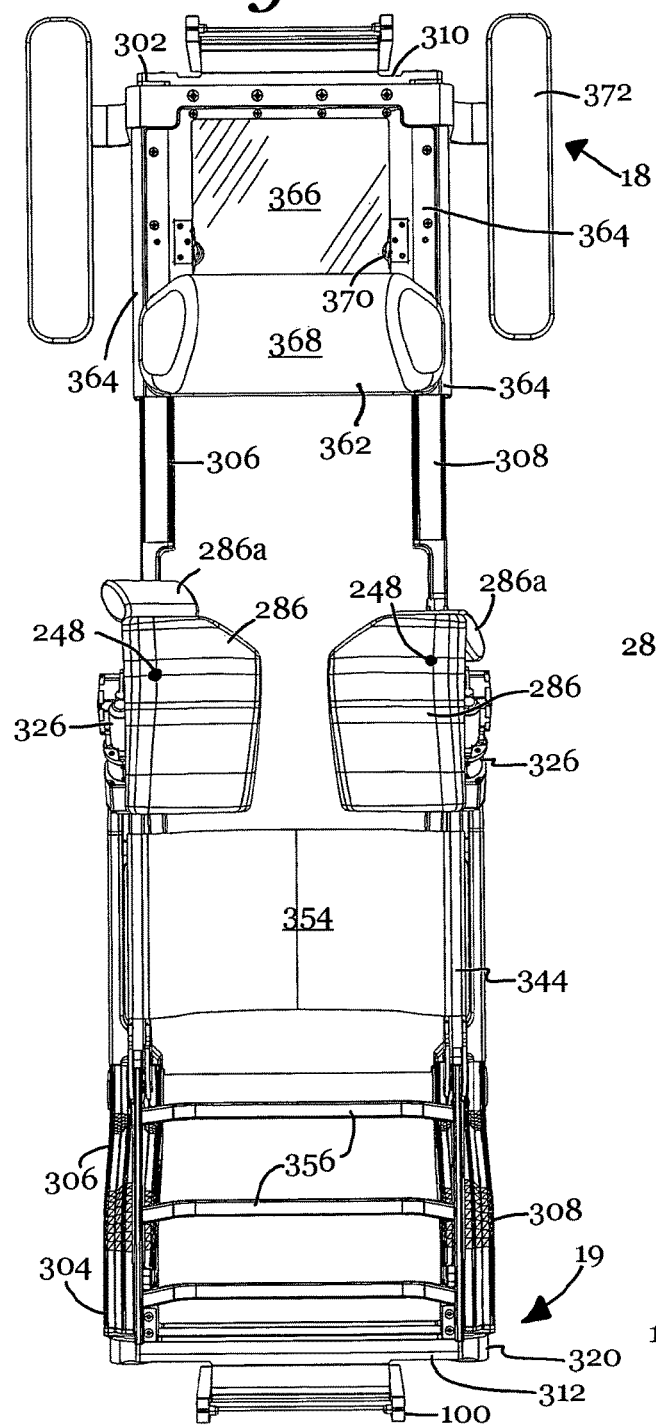

FIG. 202 is an enlarged top view of the prone lateral patient support of FIG. 197.

Figure 203:
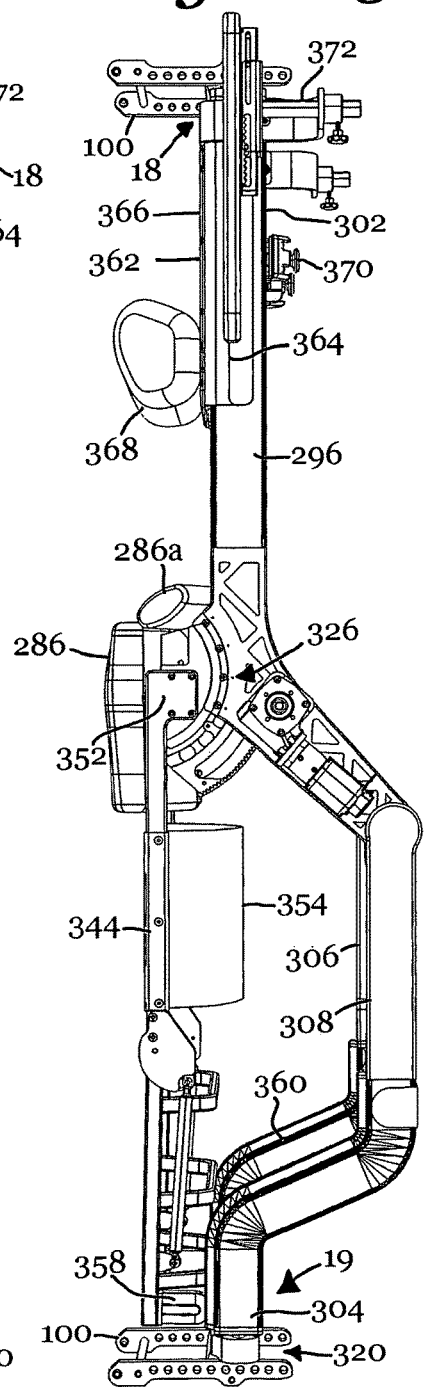

FIG. 203 is an enlarged right side view of the prone lateral patient support of FIG. 197.

FIG. 204 is an enlarged left side view of the prone lateral patient support of FIG. 197.

FIG. 205 is an enlarged bottom view of the prone lateral patient support of FIG. 197.

FIG. 206 is a perspective view of a base of the present invention.

FIG. 207 is a perspective view of the base of FIG. 206, including an attached prone patient support structure and an attached supine patient support structure.

FIG. 208 is a perspective view of a supine patient support structure for attachment to the base of FIG. 206.

FIG. 209 is a side view of the supine patient support structure of FIG. 208.

FIG. 210 is a perspective view of a prone patient support structure for attachment to the base of FIG. 206.

FIG. 211 is a side view of the prone patient support structure of FIG. 210.

FIG. 212 is an enlarged outboard perspective view of a vertical translation subassembly of FIG. 206.

FIG. 213 is an enlarged inboard perspective view of a vertical translation subassembly of FIG. 206.

FIG. 214 is an enlarged side view of a vertical translation subassembly of FIG. 206.

FIG. 215 is another enlarged side view of a vertical translation subassembly of FIG. 206.

FIG. 216 is an enlarged top perspective view of a vertical translation subassembly of FIG. 206.

Figure 217:
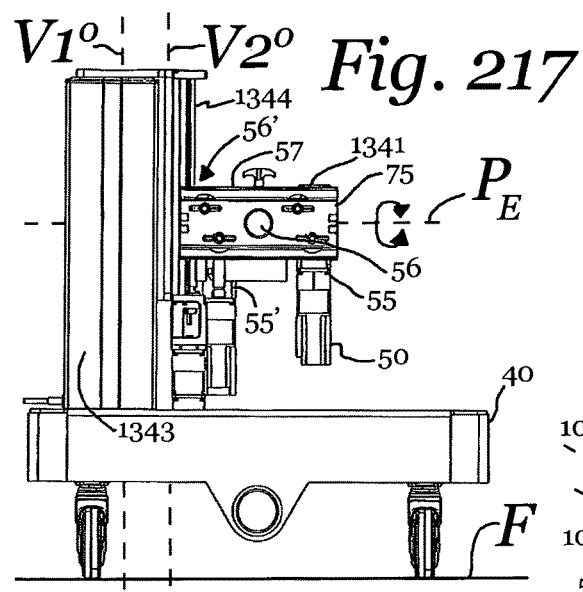

FIG. 217 is an enlarged inboard view of a vertical translation subassembly of FIG. 206.

Figure 218:
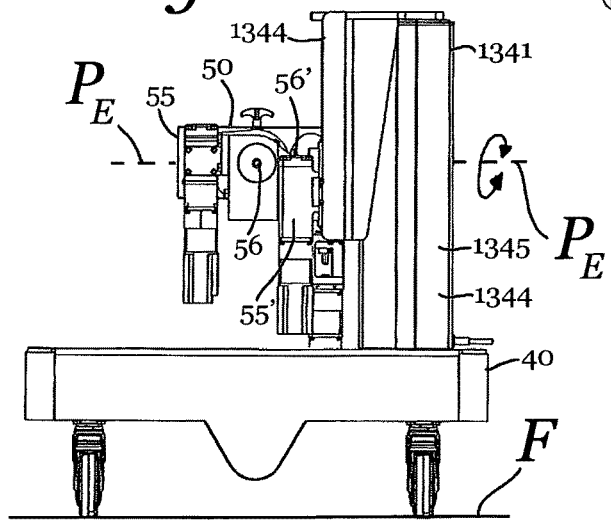

FIG. 218 is an enlarged outboard view of a vertical translation subassembly of FIG. 206.

Figure 219:
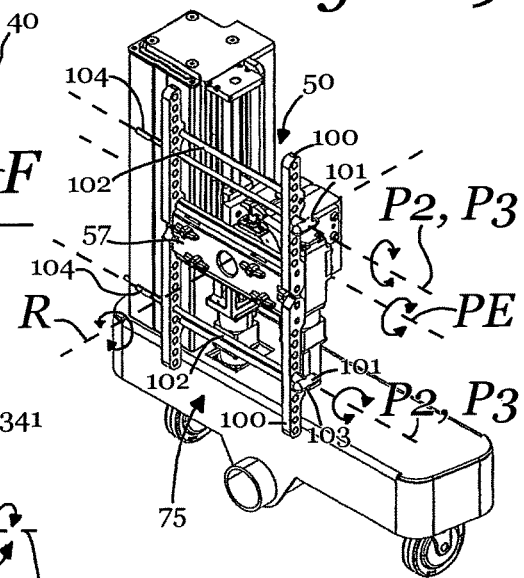

FIG. 219 is another enlarged inboard perspective view of a vertical translation subassembly of FIG. 206, with attachment ladders attached.

Figure 220:
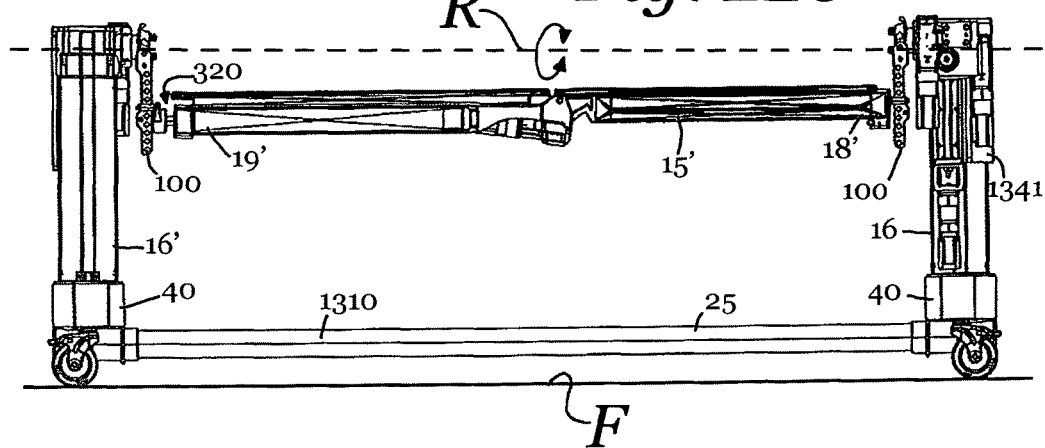

FIG. 220 is a side view of the base of FIG. 206, including an attached supine patient support structure, wherein the primary elevators are equally partially outwardly telescoped, the secondary elevators are equally raised to the highest point, and the supine patient support structure is substantially parallel with the floor.

Figure 221:
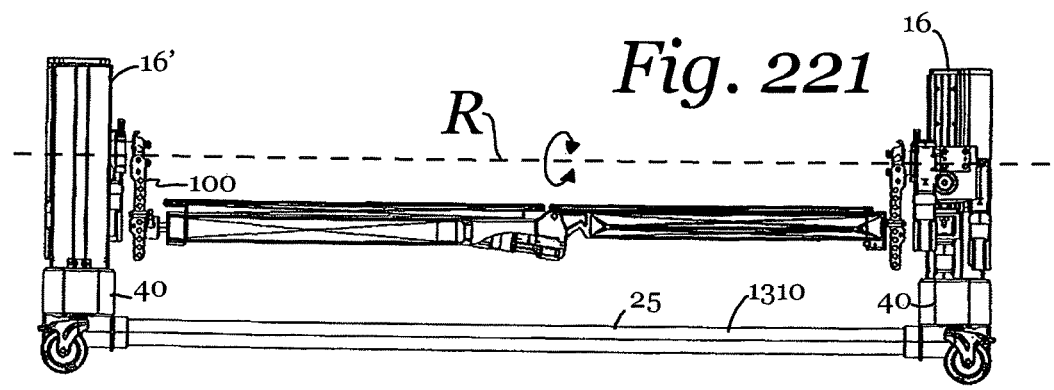

FIG. 221 is a side view of the base of FIG. 220, wherein the primary elevators are equally fully inwardly telescoped or closed, the secondary elevators are equally lowered to the lowest possible point, and the patient support structure is lowered to the lowest possible position and is also substantially parallel with the floor.

Figure 222:
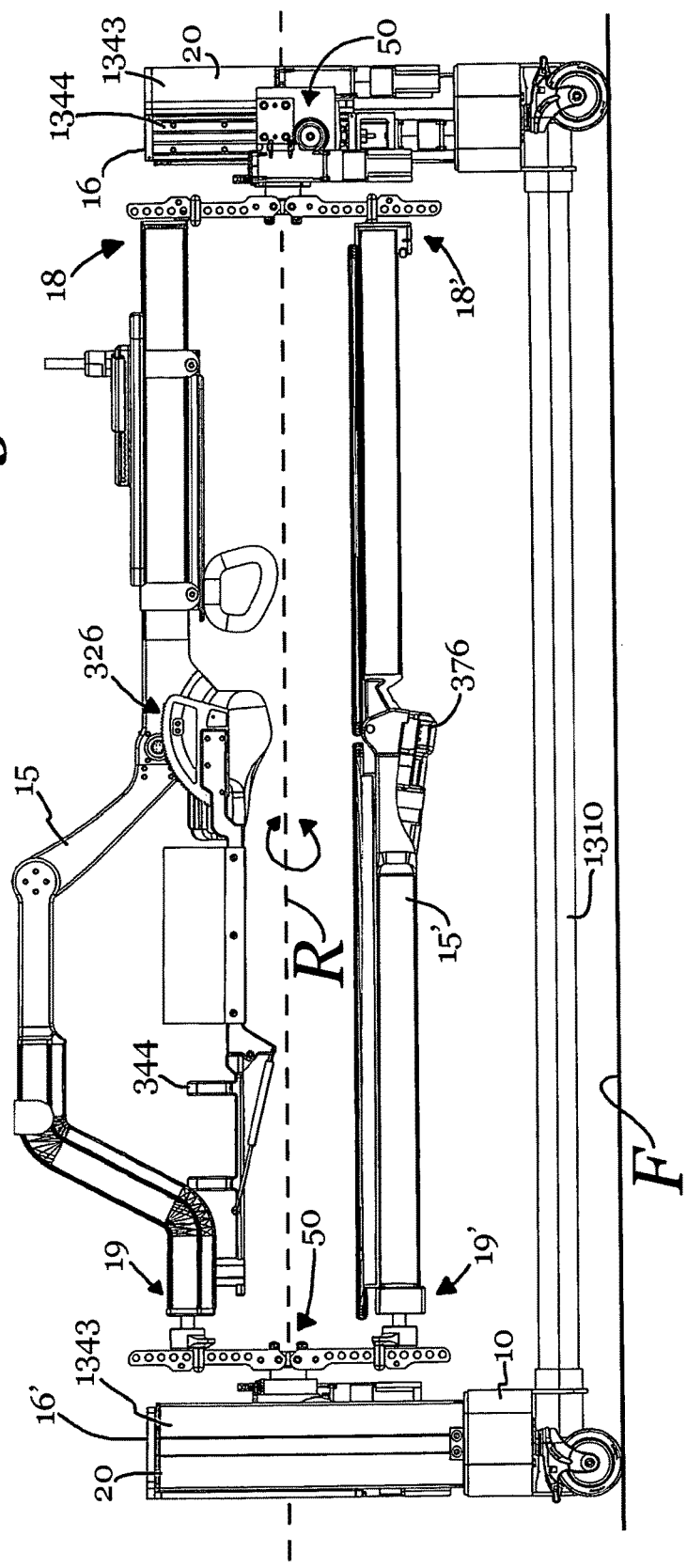

FIG. 222 is a side view of the base of FIG. 221, including an attached prone patient support structure, so as to support a patient for a sandwich-and-roll procedure to transfer a patient between the prone and supine patient support structures.

Figure 223:
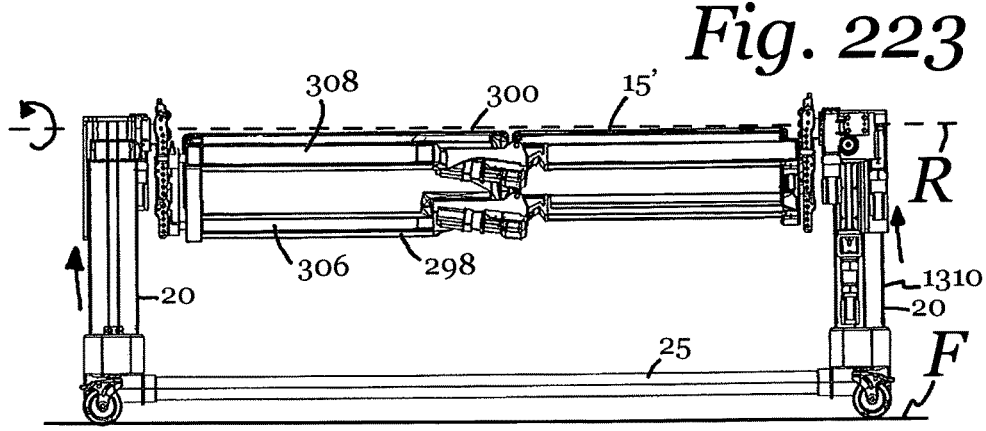

FIG. 223 is a side view of the base and supine patient support structure of FIG. 219, showing the patient support structure tilted in a first orientation.

Figure 224:
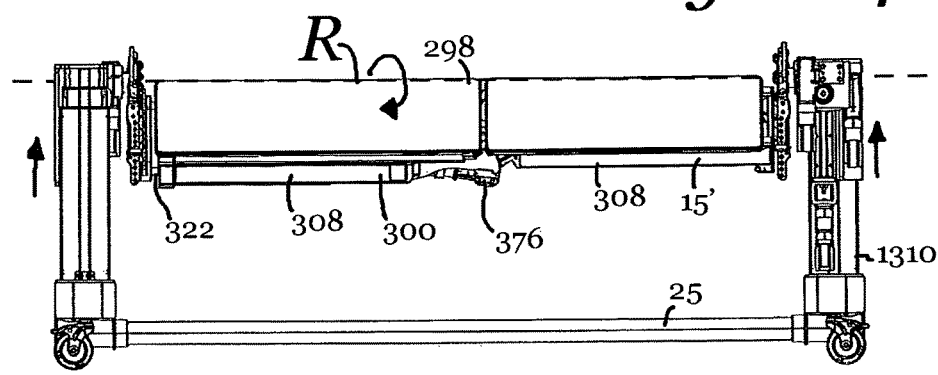

FIG. 224 is a side view of the base and supine patient support structure of FIG. 220, showing the patient support structure tilted in a second orientation that is opposite to the orientation shown in FIG. 223.

Figure 225:
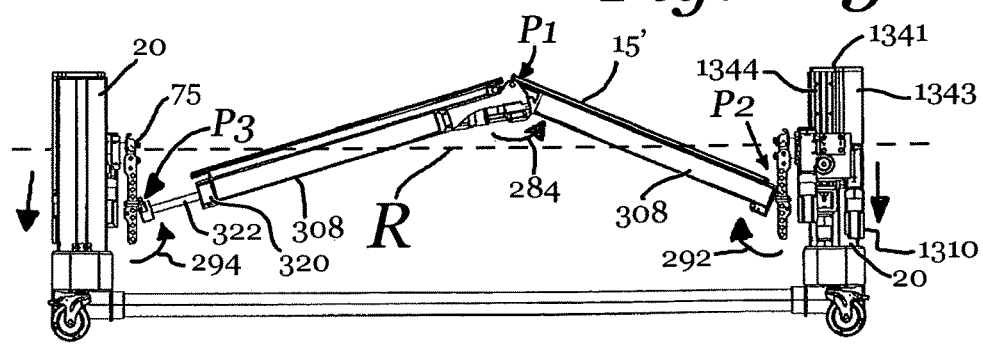

FIG. 225 is a side view of the base and supine patient support structure of FIG. 220, showing the patient support structure positioned so as to be substantially parallel with the floor and also in an upward articulated or breaking position, and also wherein the primary elevators are equally fully inwardly telescoped or closed, the secondary elevators are equally lowered to the lowest possible point, and the patient support structure is lowered to the lowest possible position and is also substantially parallel with the floor.

Figure 226:
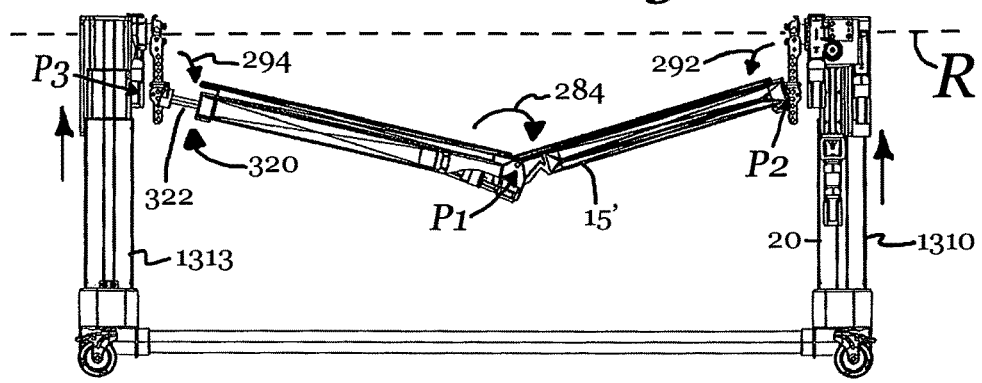

FIG. 226 is a side view of the base and supine patient support structure of FIG. 220, showing the patient support structure positioned so as to be substantially parallel with the floor and also in a downwardly articulated or breaking position, and also wherein the primary elevators are equally fully outwardly telescoped or opened, the secondary elevators are equally raised to the highest possible point, and the patient support structure is raised to the highest possible position and is also substantially parallel with the floor.

Figure 227:
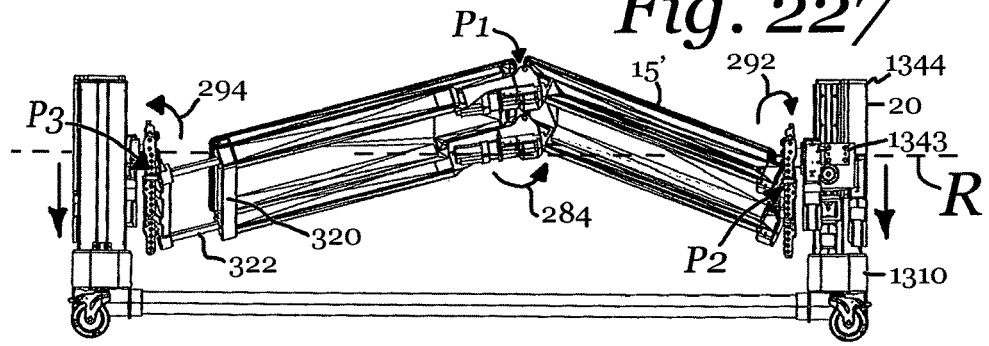

FIG. 227 is a side view of the base and supine patient support structure of FIG. 225, showing the patient support structure tilted in the first orientation.

Figure 228:
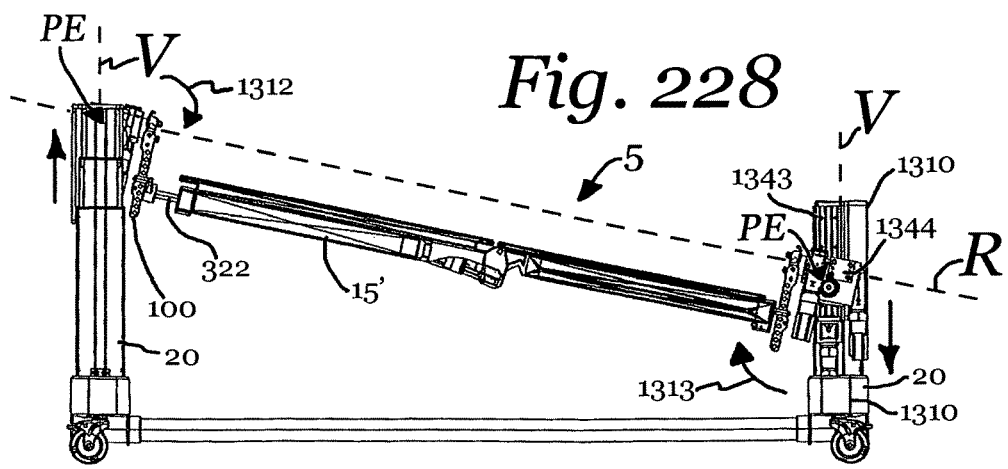

FIG. 228 is a side view of the base and supine patient support structure of FIG. 220, showing the patient support structure in a Trendelenburg position.

Figure 229:
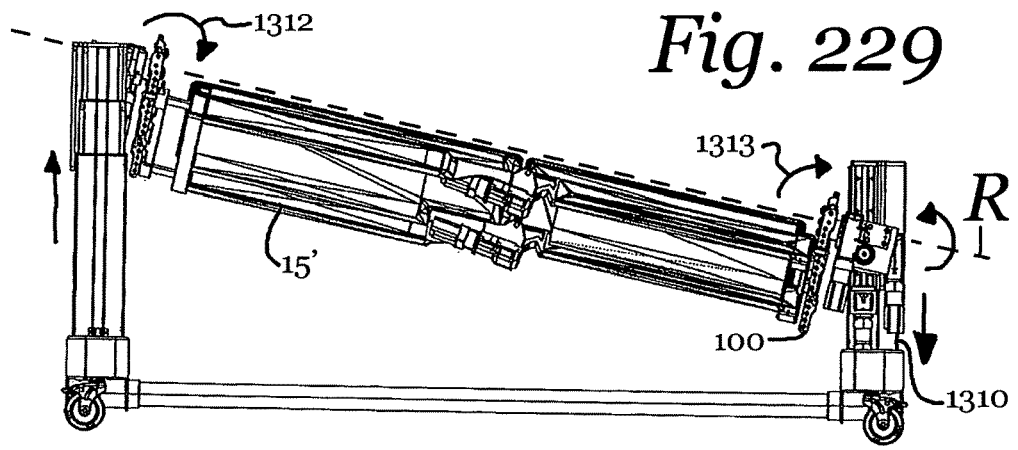

FIG. 229 is a side view of the base and supine patient support structure of FIG. 220, showing the patient support structure in a Trendelenburg position and also tilted in a first orientation.

Figure 230:
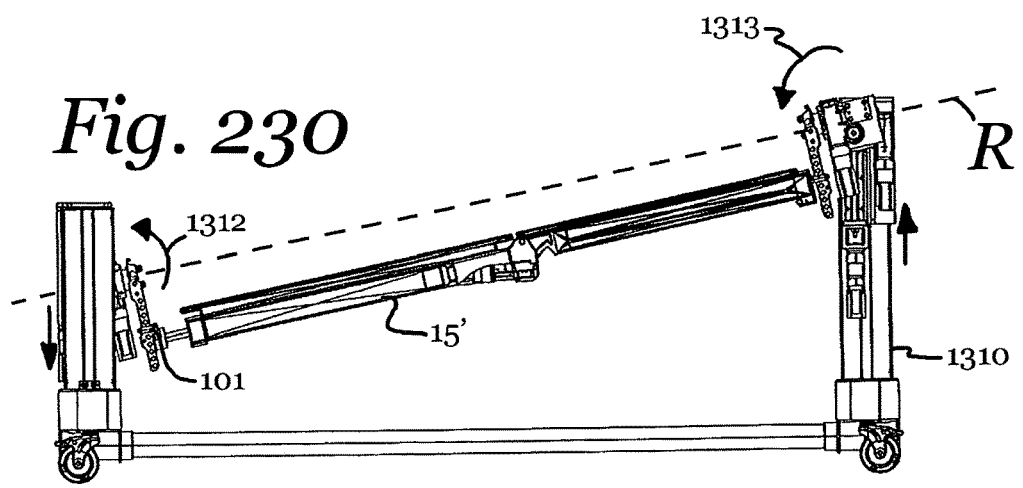

FIG. 230 is a side view of the base and supine patient support structure of FIG. 220, showing the patient support structure in a reverse Trendelenburg position.

Figure 231:
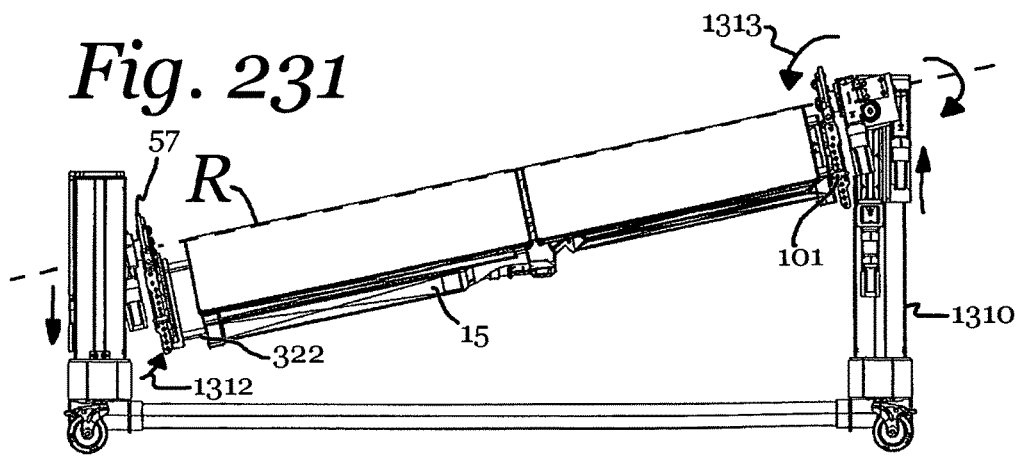

FIG. 231 is a side view of the base and supine patient support structure of FIG. 220, showing the patient support structure in a reverse Trendelenburg position and also tilted in a second orientation opposite to the first orientation of FIG. 229.

FIG. 232 is a side view of the base of FIG. 206, including an attached prone patient support structure, wherein the primary elevators are equally telescoped closed, the secondary elevators are equally raised, and the prone patient support structure is substantially parallel with the floor.

FIG. 233 is a side view of the base of FIG. 232, wherein the primary elevators are equally partially telescoped open, the secondary elevators are fully raised to the highest possible point, and the prone patient support structure is substantially parallel with the floor.

FIG. 234 is a side view of the base of FIG. 232, wherein both the primary and secondary elevators are raised as high as possible, and the prone patient support structure is substantially parallel with the floor.

FIG. 235 is a side view of the base of FIG. 233, showing the prone patient support structure in a flexed position wherein the hips and knees of a patient supported thereon would be flexed.

FIG. 236 is a side view of the base of FIG. 233, showing the prone patient support structure in an extended position wherein the hips and knees of a patient supported thereon would be extended.

FIG. 237 is another side view of the base of FIG. 233, showing the prone patient support structure in an extended position wherein the hips and knees of a patient supported thereon would be extended.

Figure 238:
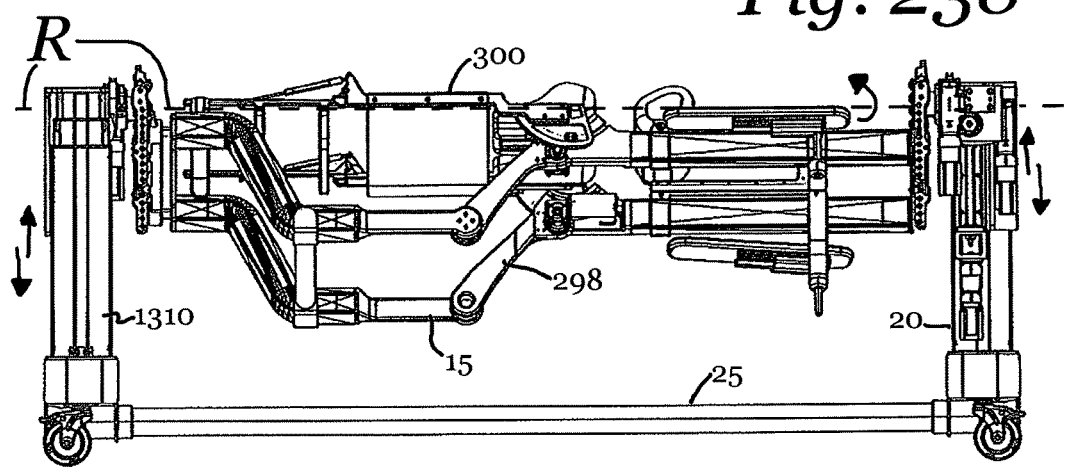

FIG. 238 is a side view of the base of FIG. 233, wherein the prone patient support structure is tilted in a first orientation.

Figure 239:
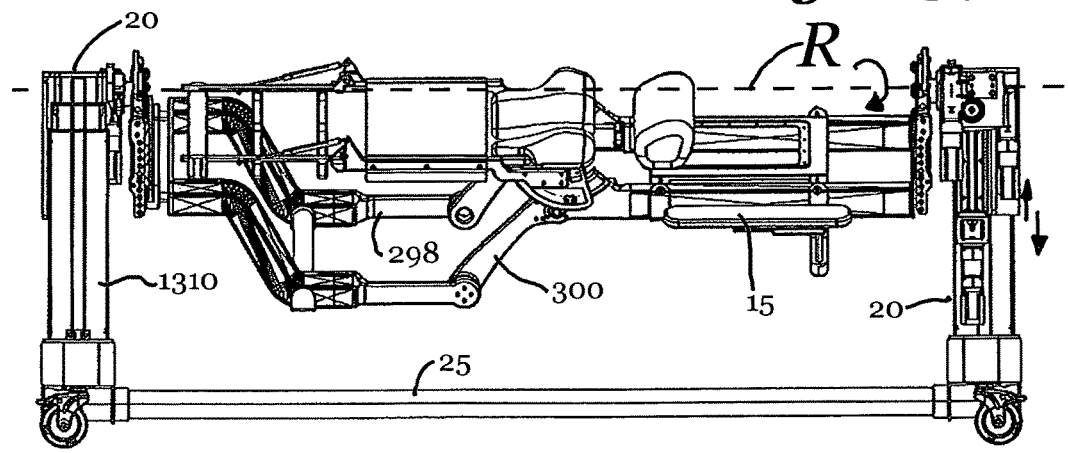

FIG. 239 is a side view of the base of FIG. 233, wherein the prone patient support structure is tilted in a second orientation that is opposite to the first orientation of FIG. 238.

Figure 240:
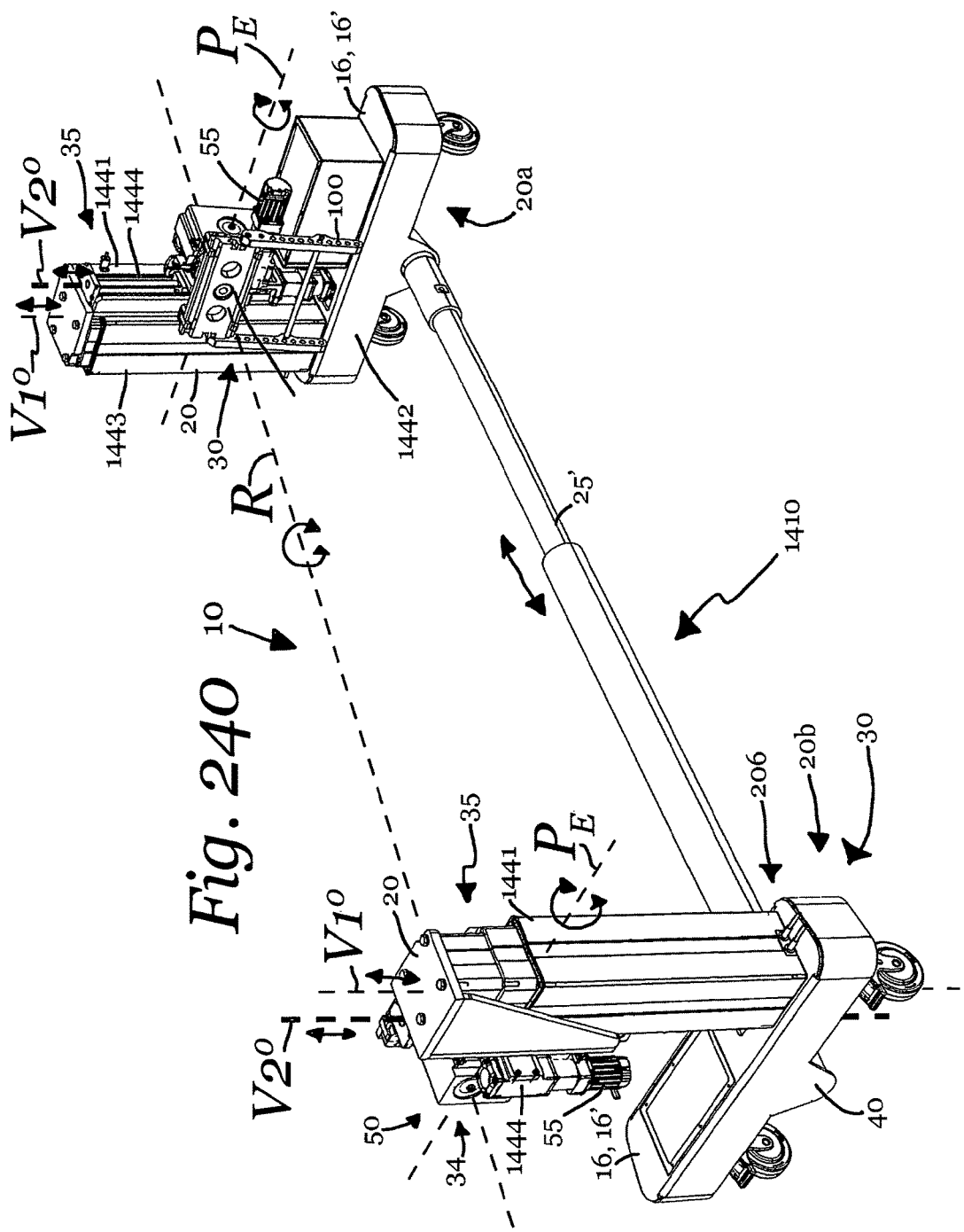

FIG. 240 is a head-end perspective view of a base for supporting a patient support structure in another embodiment.

Figure 241:
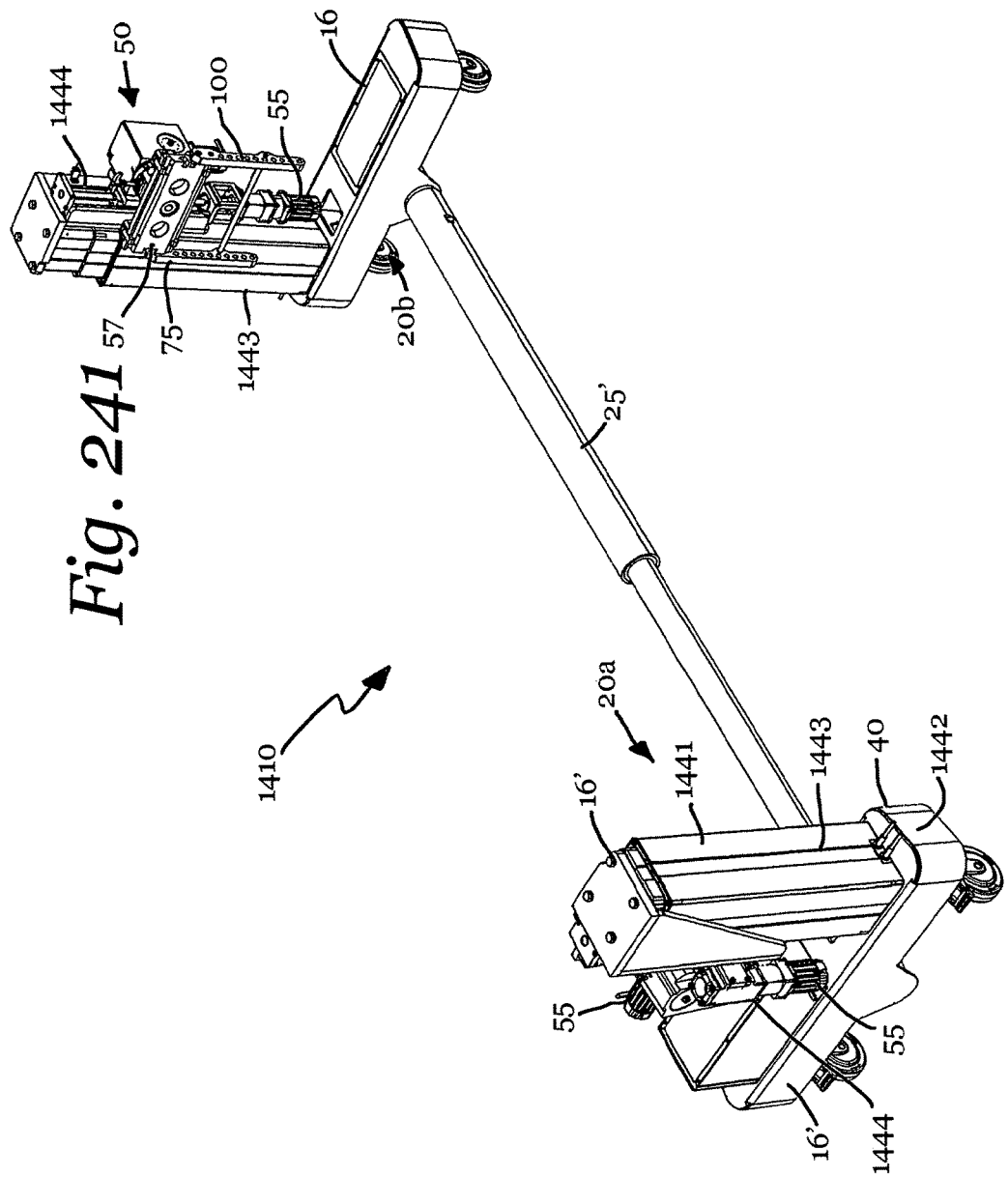

FIG. 241 is a foot-end perspective view of the base of FIG. 240.

FIG. 242 is an enlarged side view of the base of FIG. 240.

FIG. 243 is an enlarged top view of the base of FIG. 240.

FIG. 244 is another enlarged side view of the base of FIG. 240.

FIG. 245 is an enlarged bottom view of the base of FIG. 240.

Figure 246:
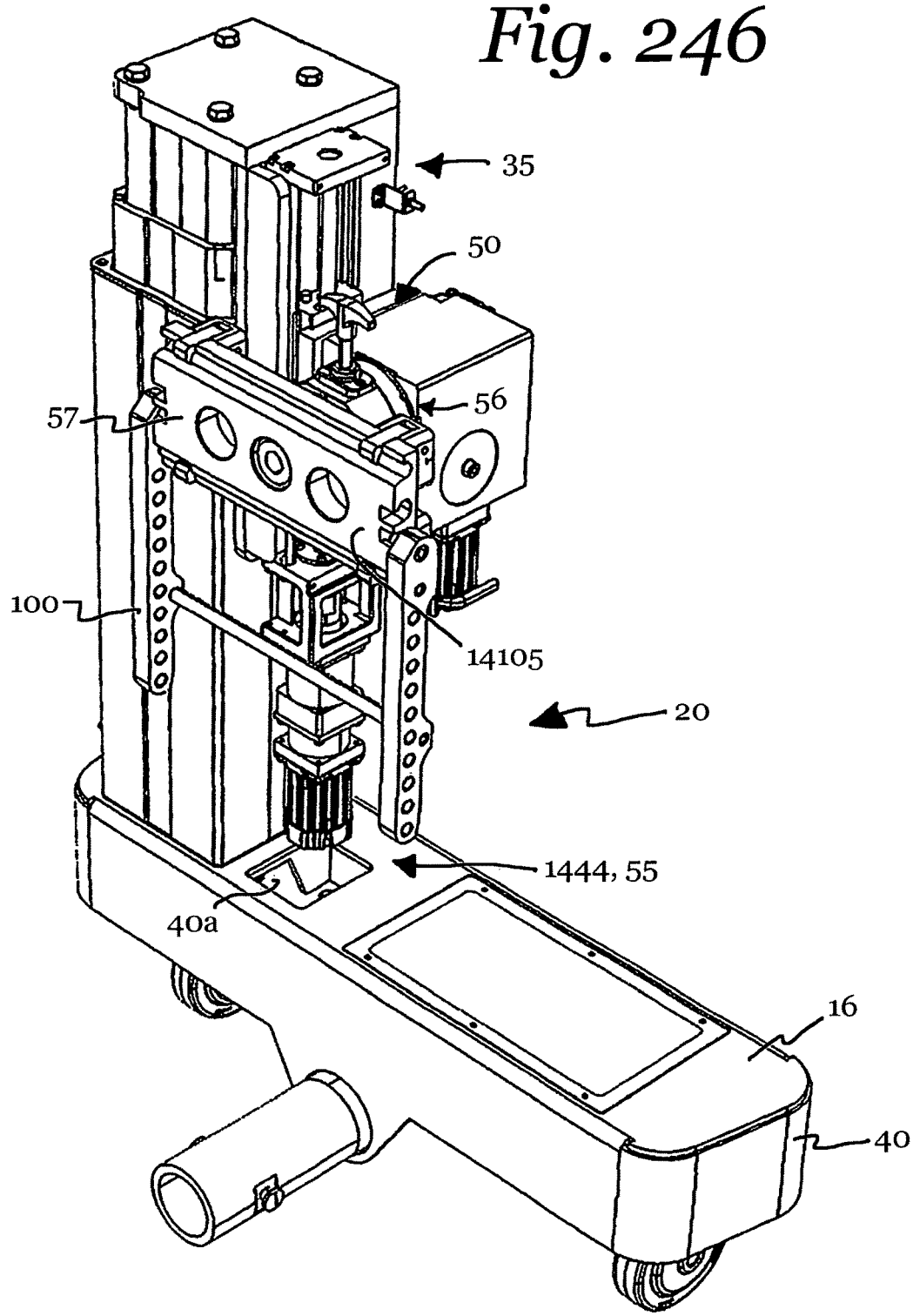

FIG. 246 is an enlarged inboard perspective view of the head-end vertical translation subassembly of the base of FIG. 240.

Figure 247:
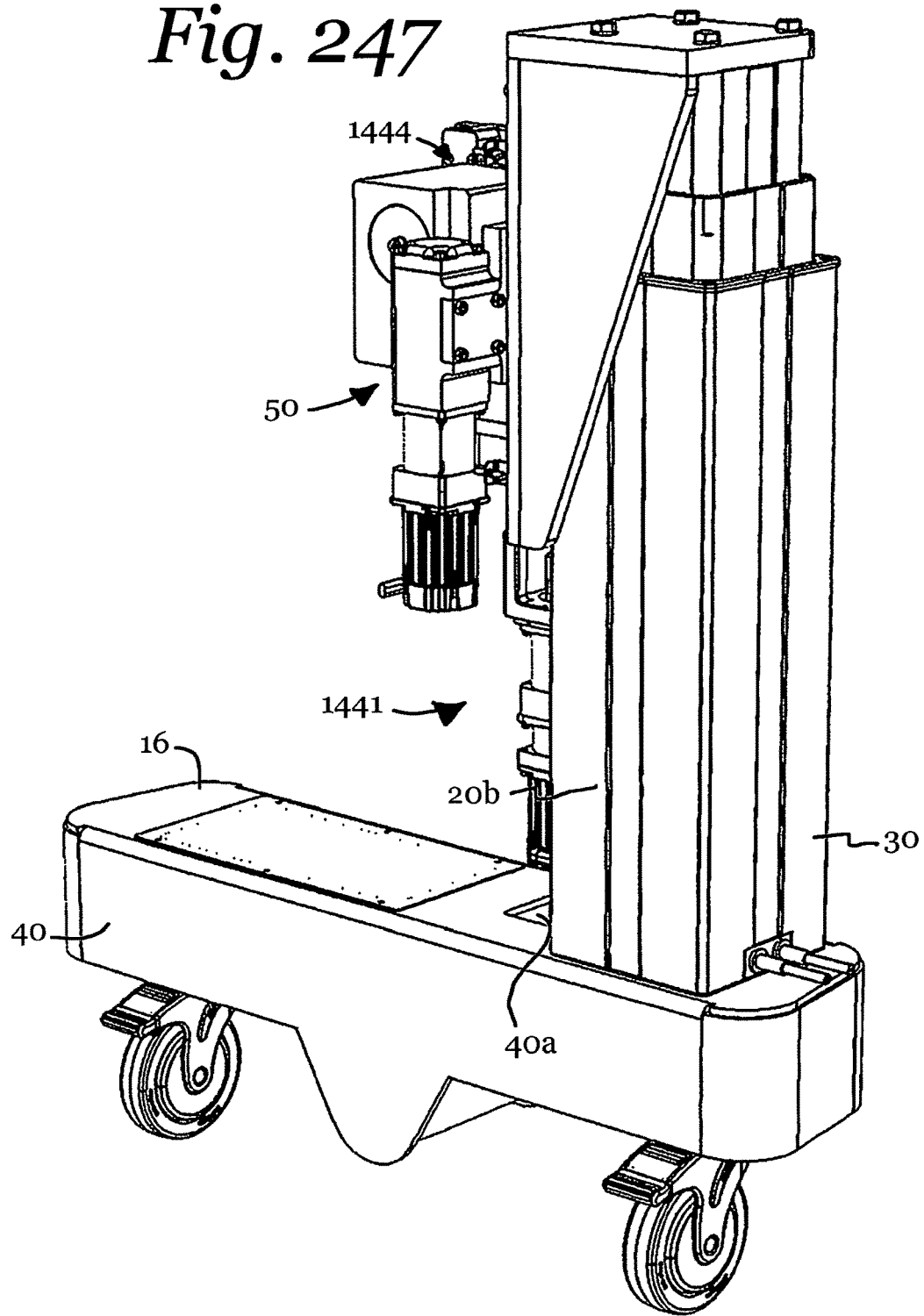

FIG. 247 is an enlarged outboard perspective view of the head-end vertical translation subassembly of the base of FIG. 240.

Figure 248:
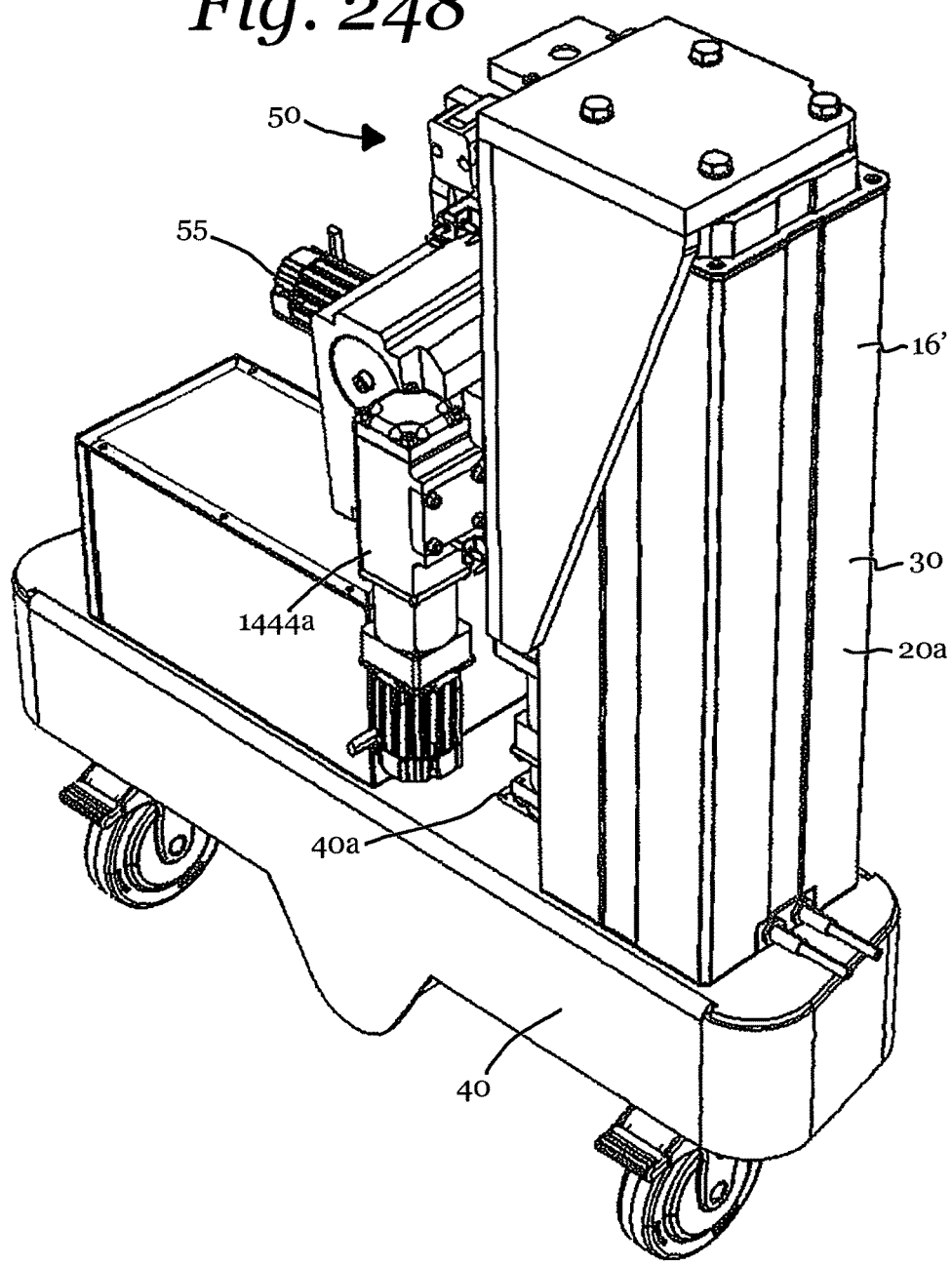

FIG. 248 is an enlarged inboard perspective view of the foot-end vertical translation subassembly of the base of FIG. 240.

Figure 249:
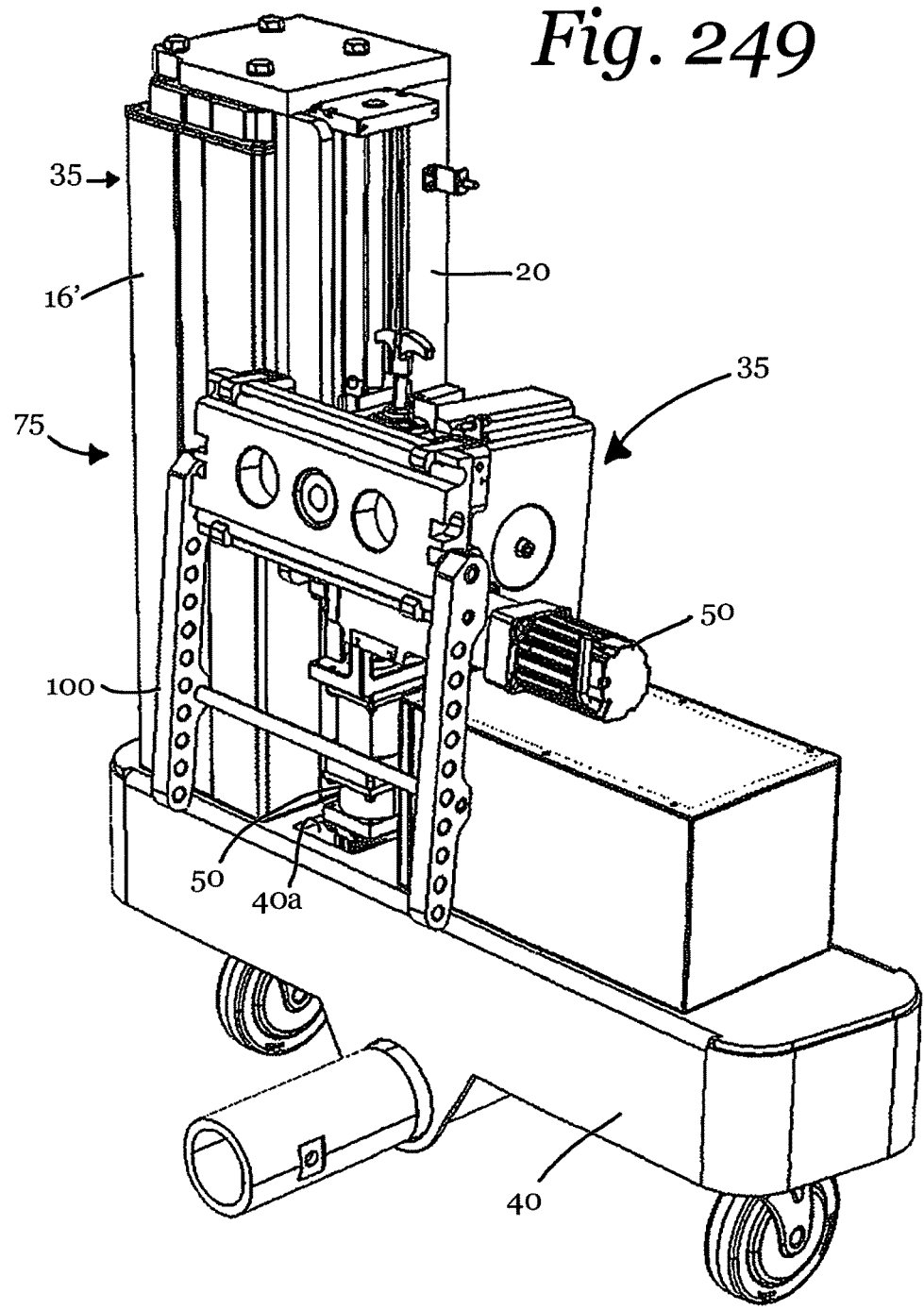

FIG. 249 is an enlarged outboard perspective view of the foot-end vertical translation subassembly of the base of FIG. 240.

Figure 250:
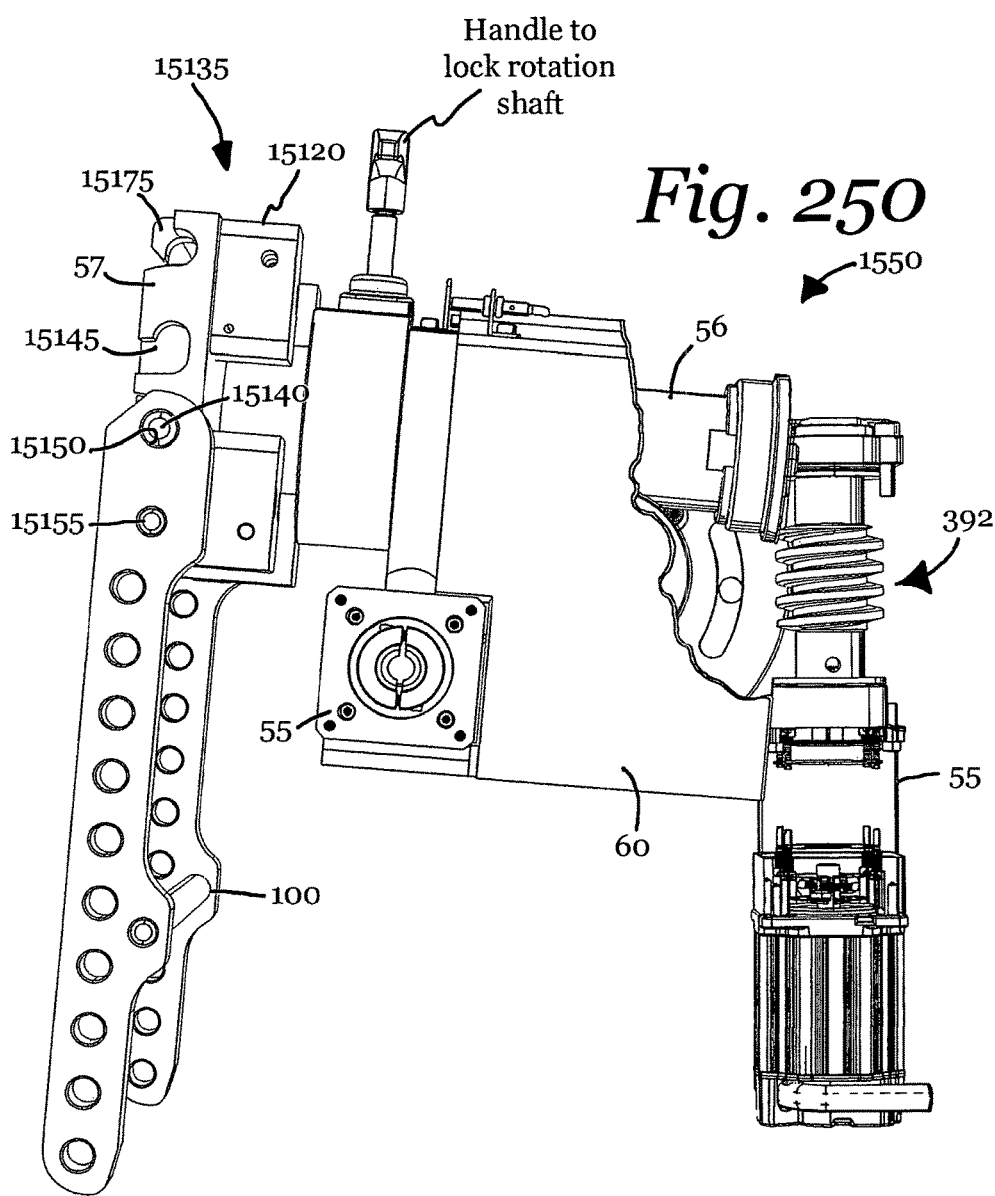

FIG. 250 is an enlarged side view of portions of the rotation subassembly and the secondary elevator portion, with portions broken away to show greater detail thereof, of the base of FIG. 240.

Figure 251:
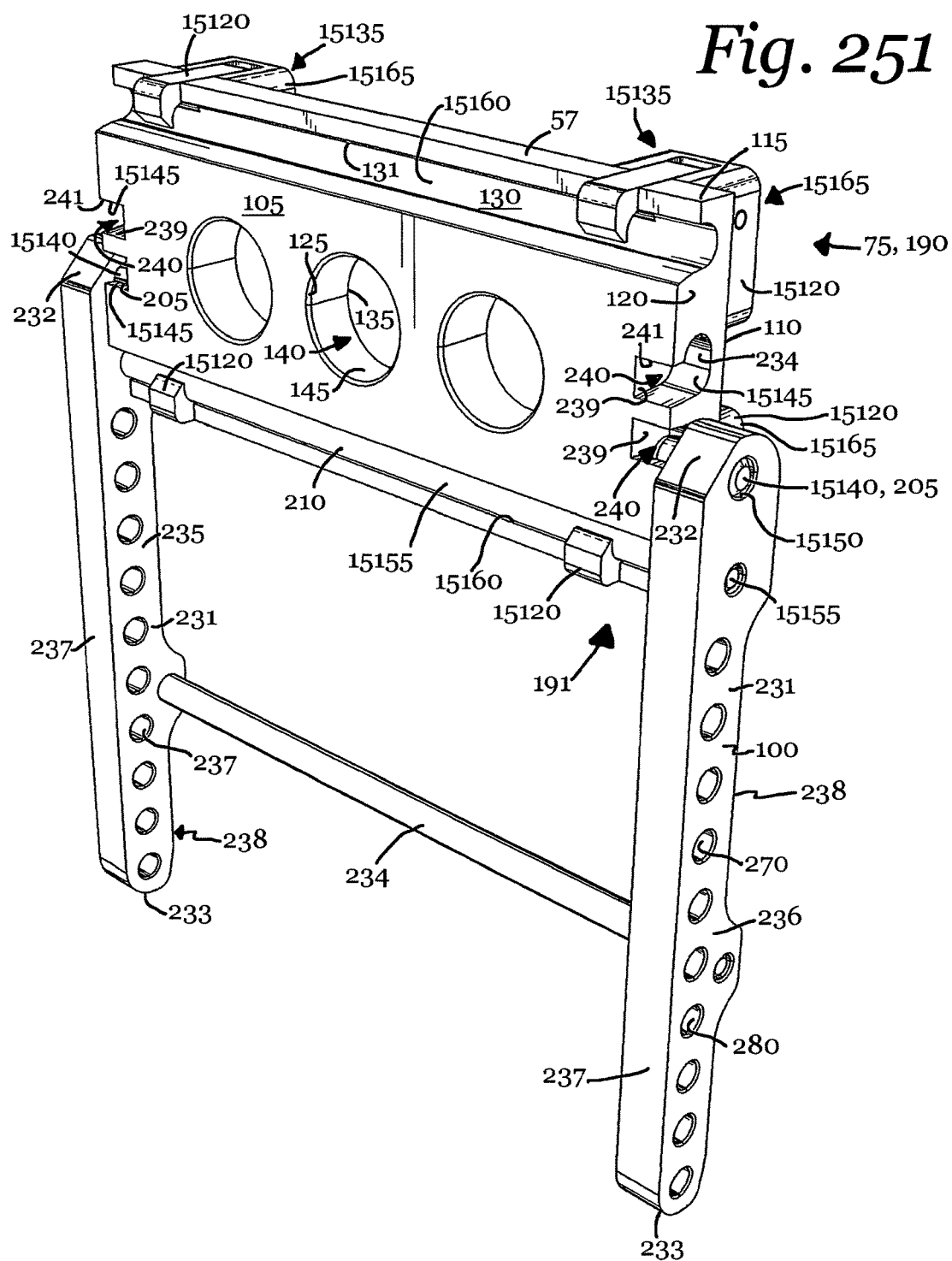

FIG. 251 is an enlarged inboard perspective view of a rotation block and a standard length ladder connected thereto of the base of FIG. 240.

Figure 252:
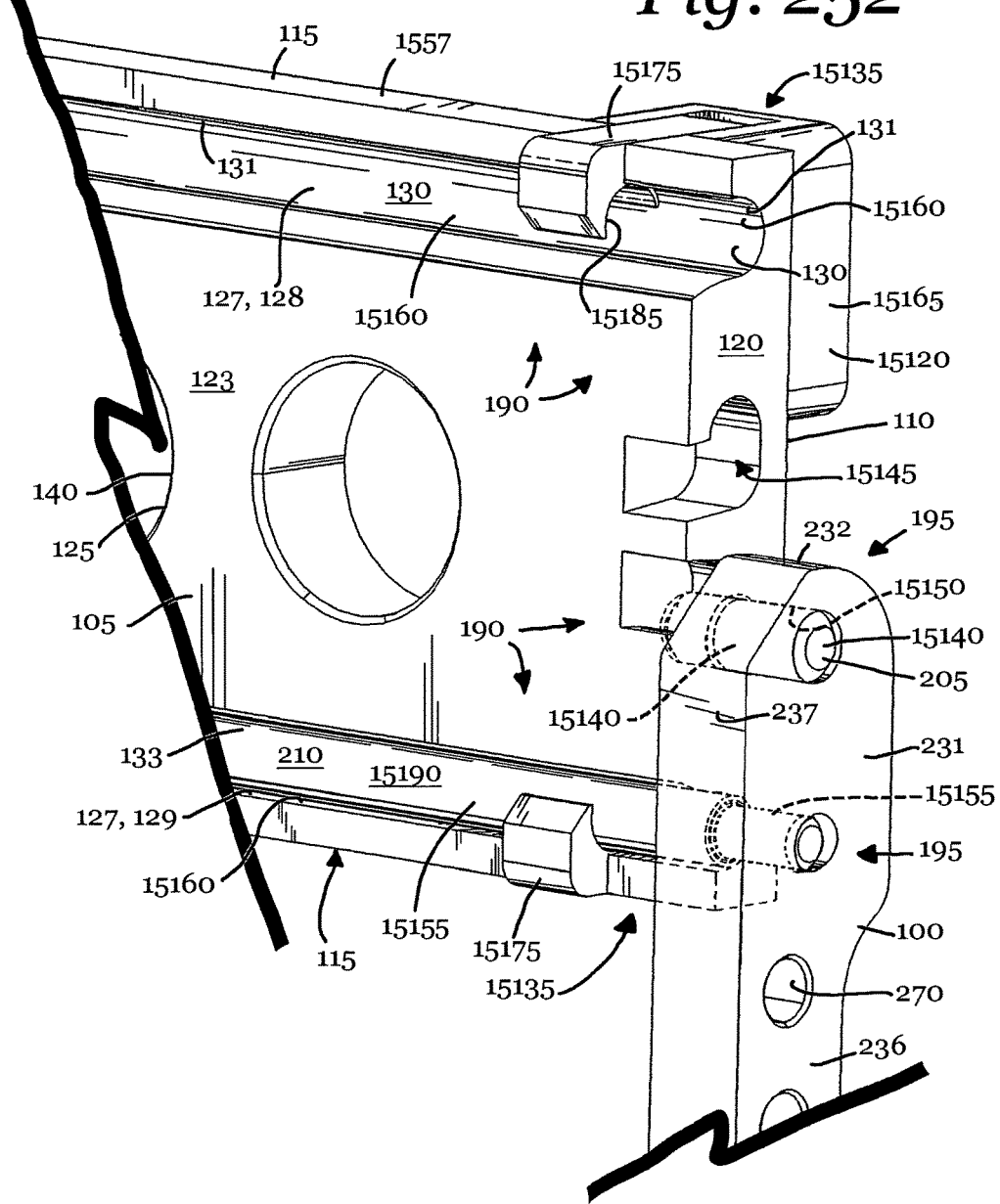

FIG. 252 is an enlarged view of the rotation block and the standard length ladder of FIG. 241, with portions shown in phantom.

Figure 253:
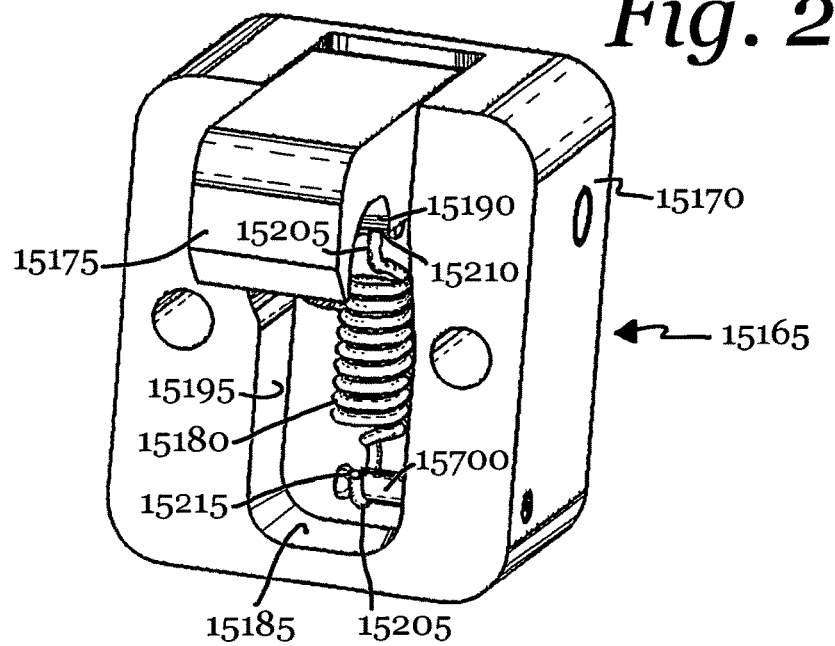

FIG. 253 is an enlarged view of an upper reversibly locking ladder attachment member of the rotation block FIG. 241.

Figure 254:
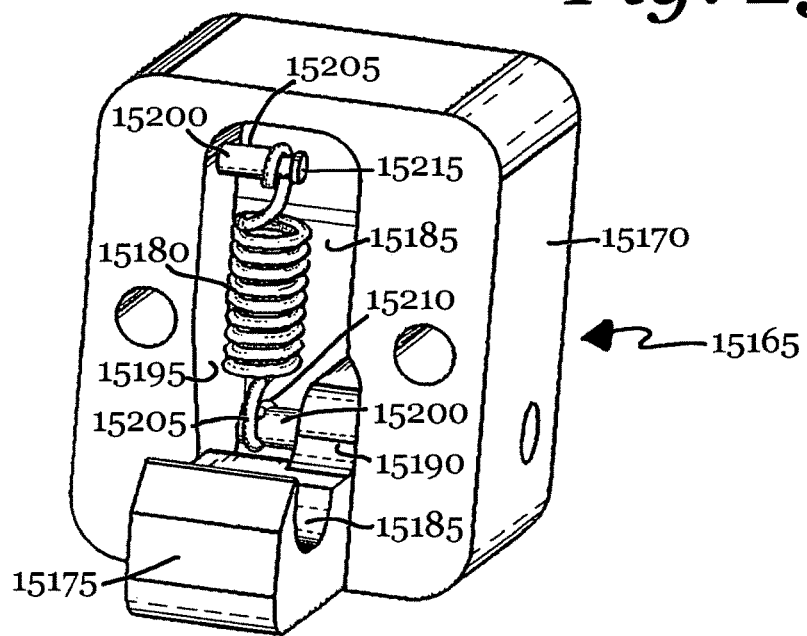

FIG. 254 is an enlarged view of lower reversibly locking ladder attachment member of the rotation block FIG. 241.

Figure 255A:
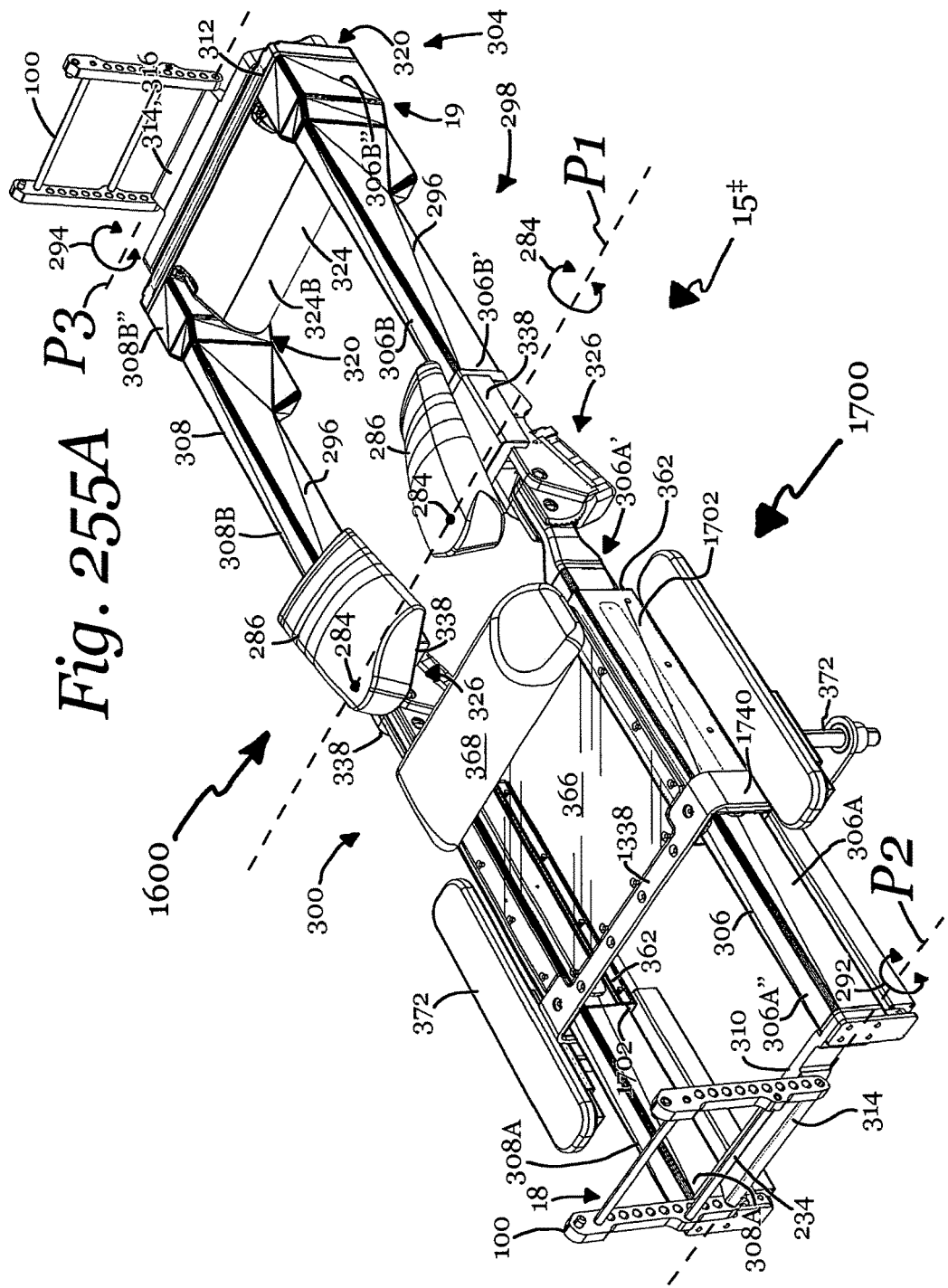

FIG. 255A is a head-end top perspective view of a prone patient support structure in another embodiment, including a torso support structure.

FIG. 255B is another head-end top perspective view of the prone patient support structure of FIG. 255A.

Figure 256:
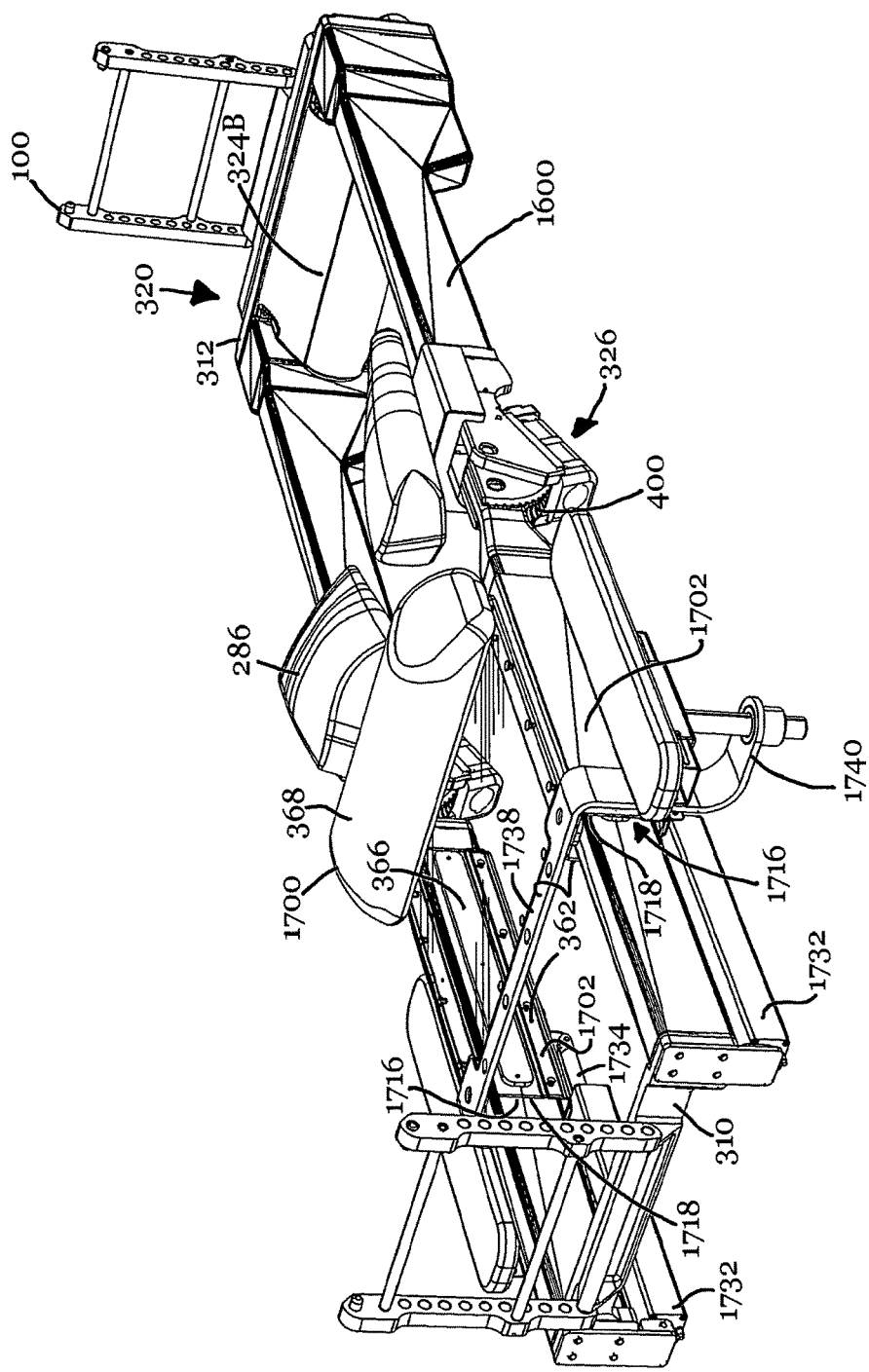

FIG. 256 is another head-end top perspective view of the prone patient support structure of FIG. 255A.

Figure 257:
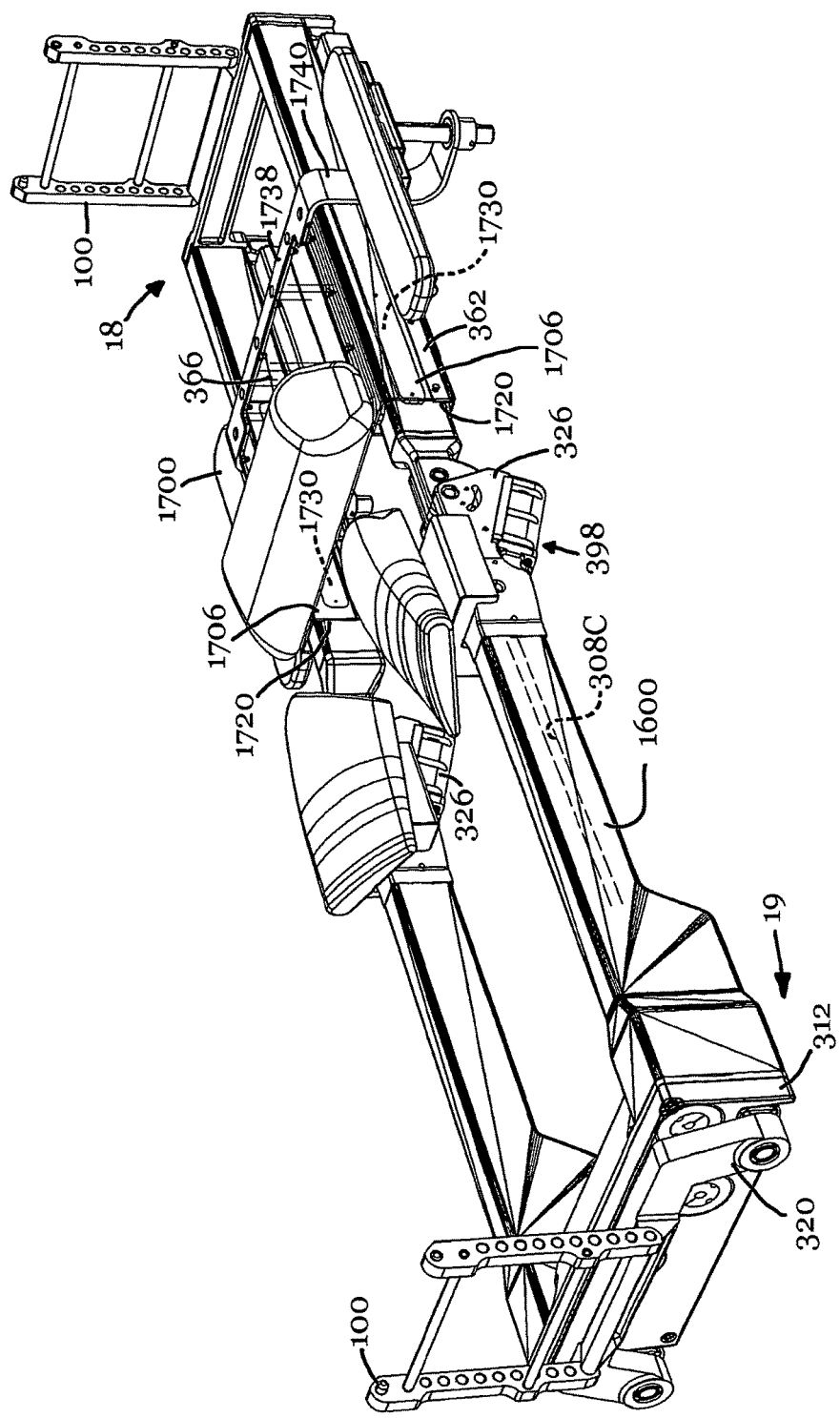

FIG. 257 is a foot-end top perspective view of the prone patient support structure of FIG. 255A.

Figure 258:
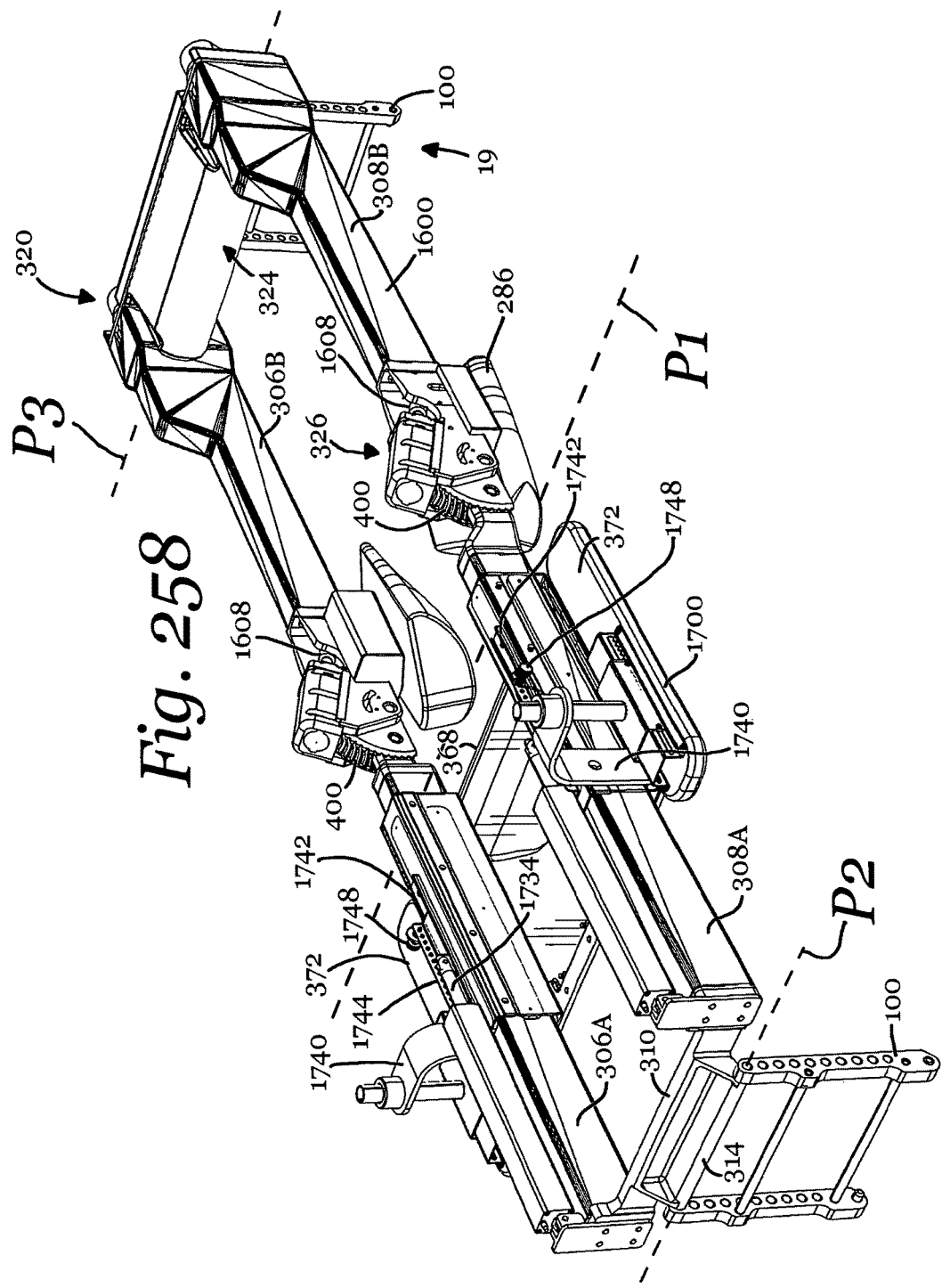

FIG. 258 is a head-end bottom perspective view of the prone patient support structure of FIG. 255A.

Figure 259:
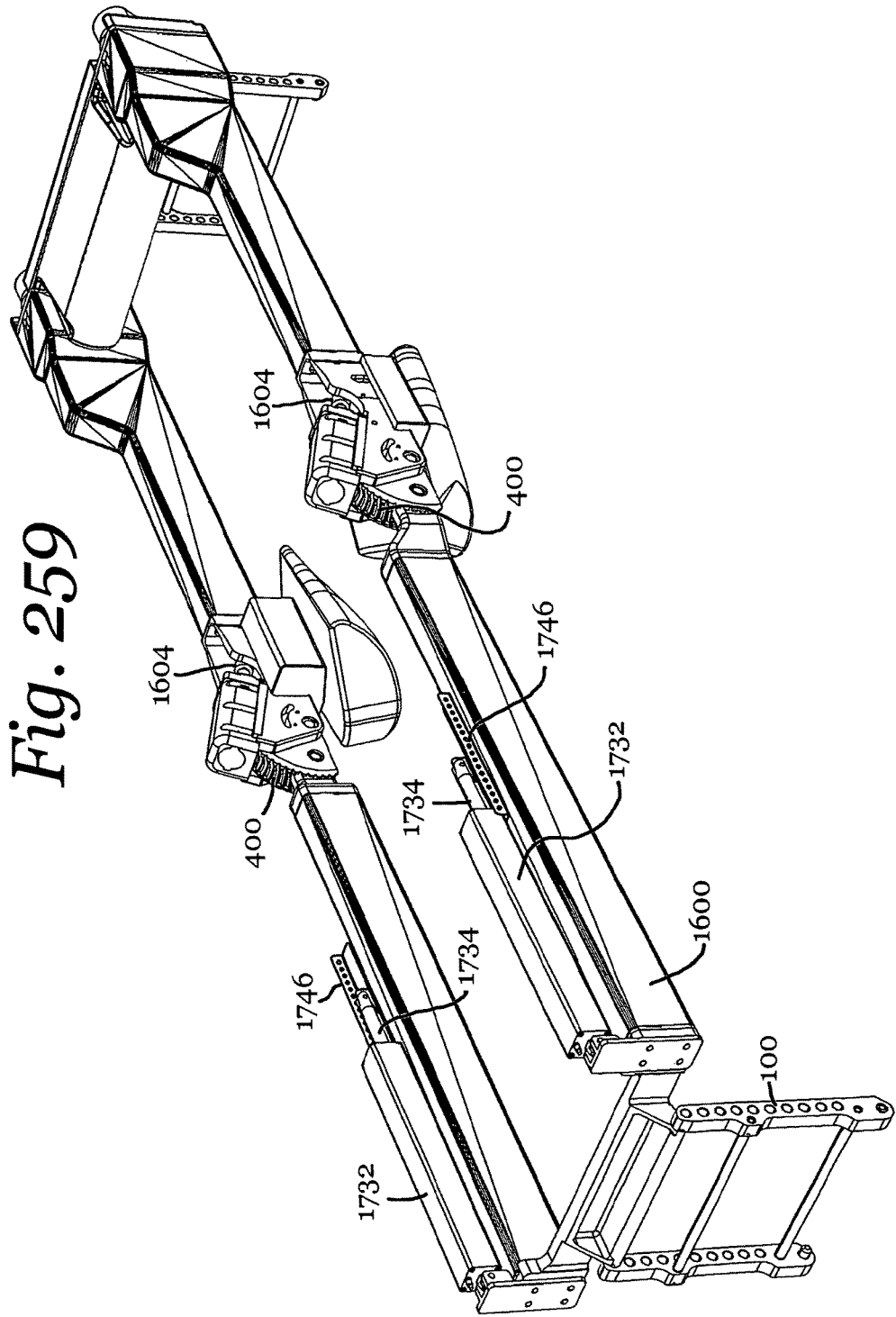

FIG. 259 is another head-end bottom perspective view of the prone patient support structure of FIG. 255A.

Figure 260:
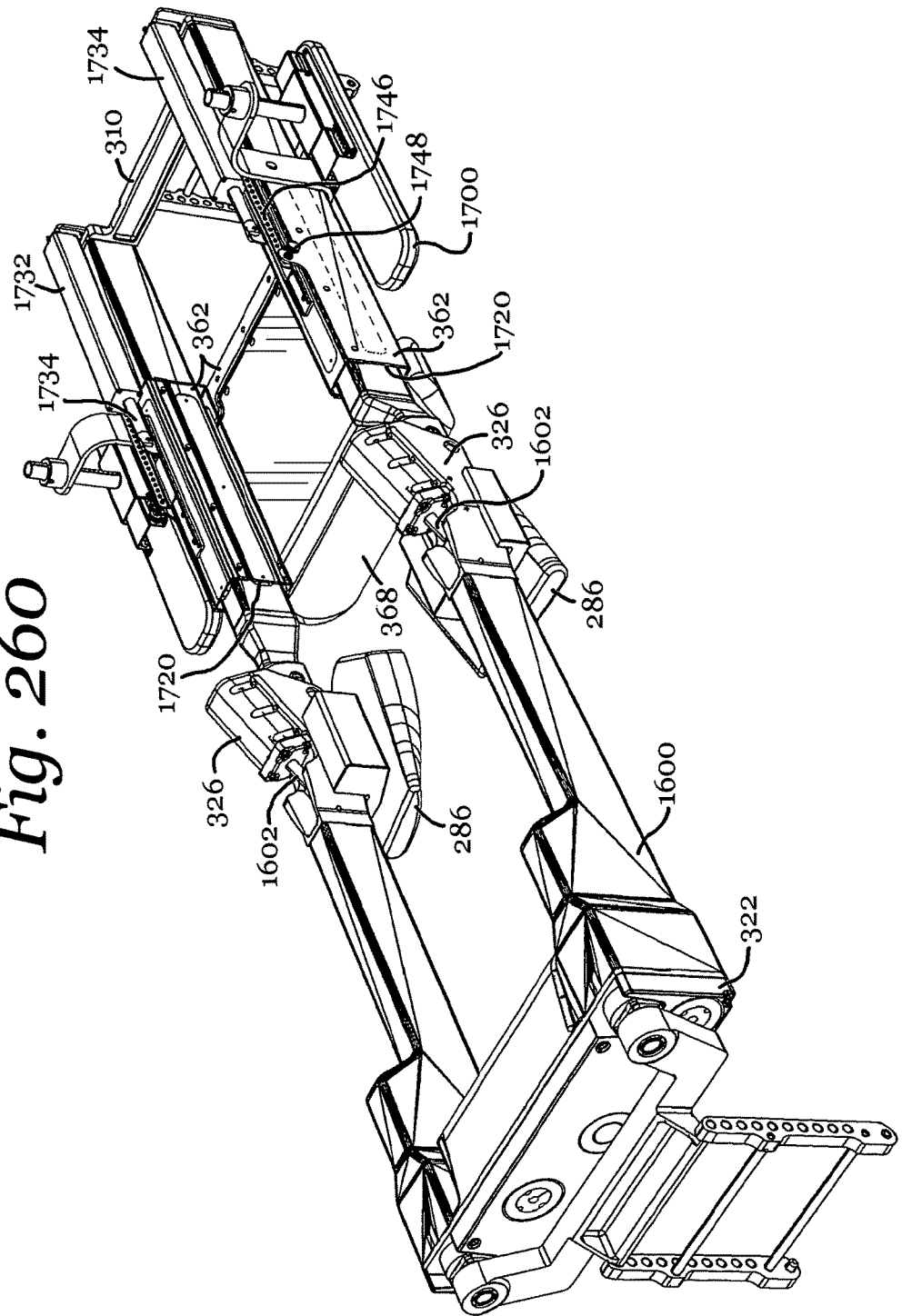

FIG. 260 is a foot-end bottom perspective view of the prone patient support structure of FIG. 255A.

Figure 261:
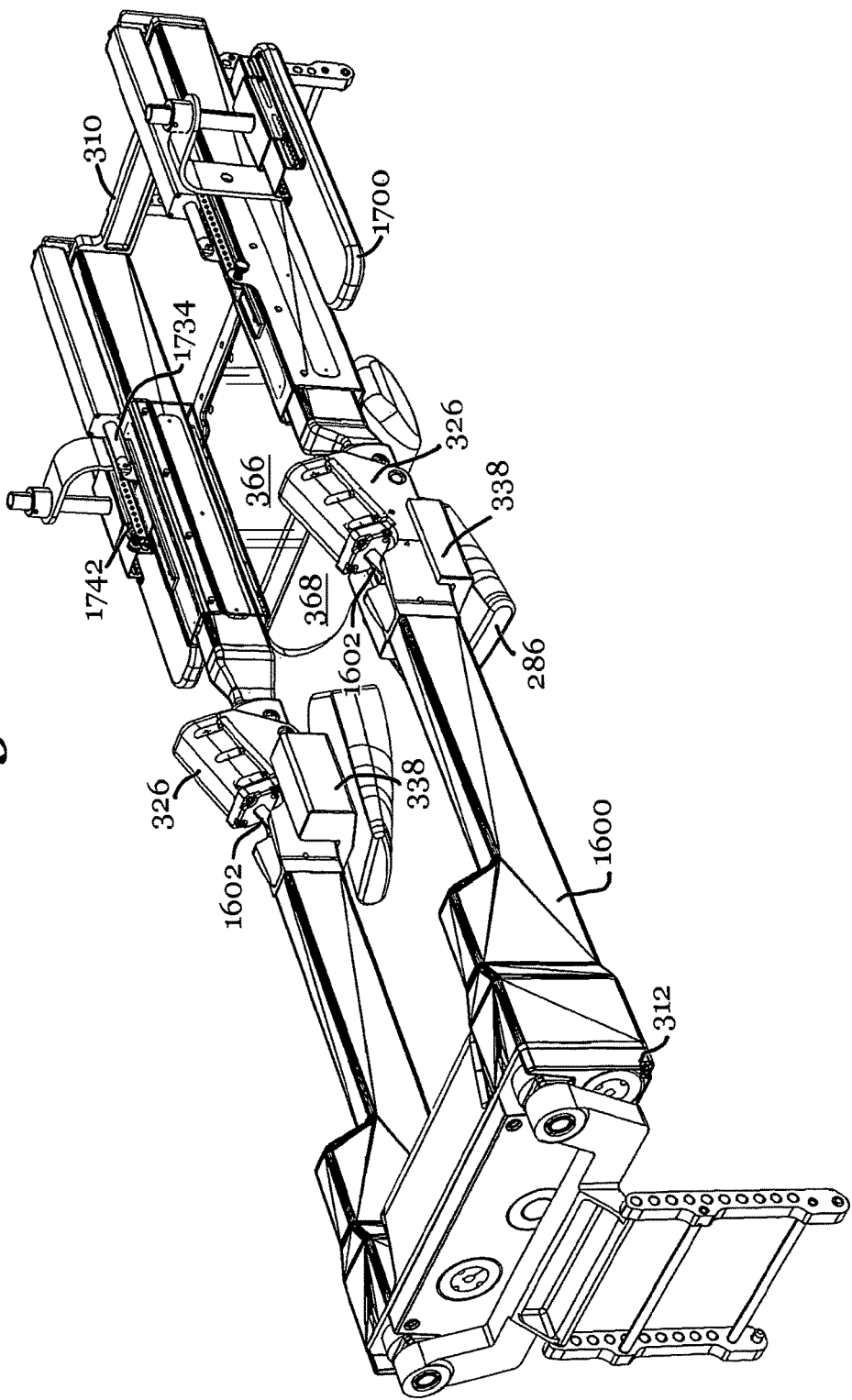

FIG. 261 is another foot-end bottom perspective view of the prone patient support structure of FIG. 255A.

Figure 262A:
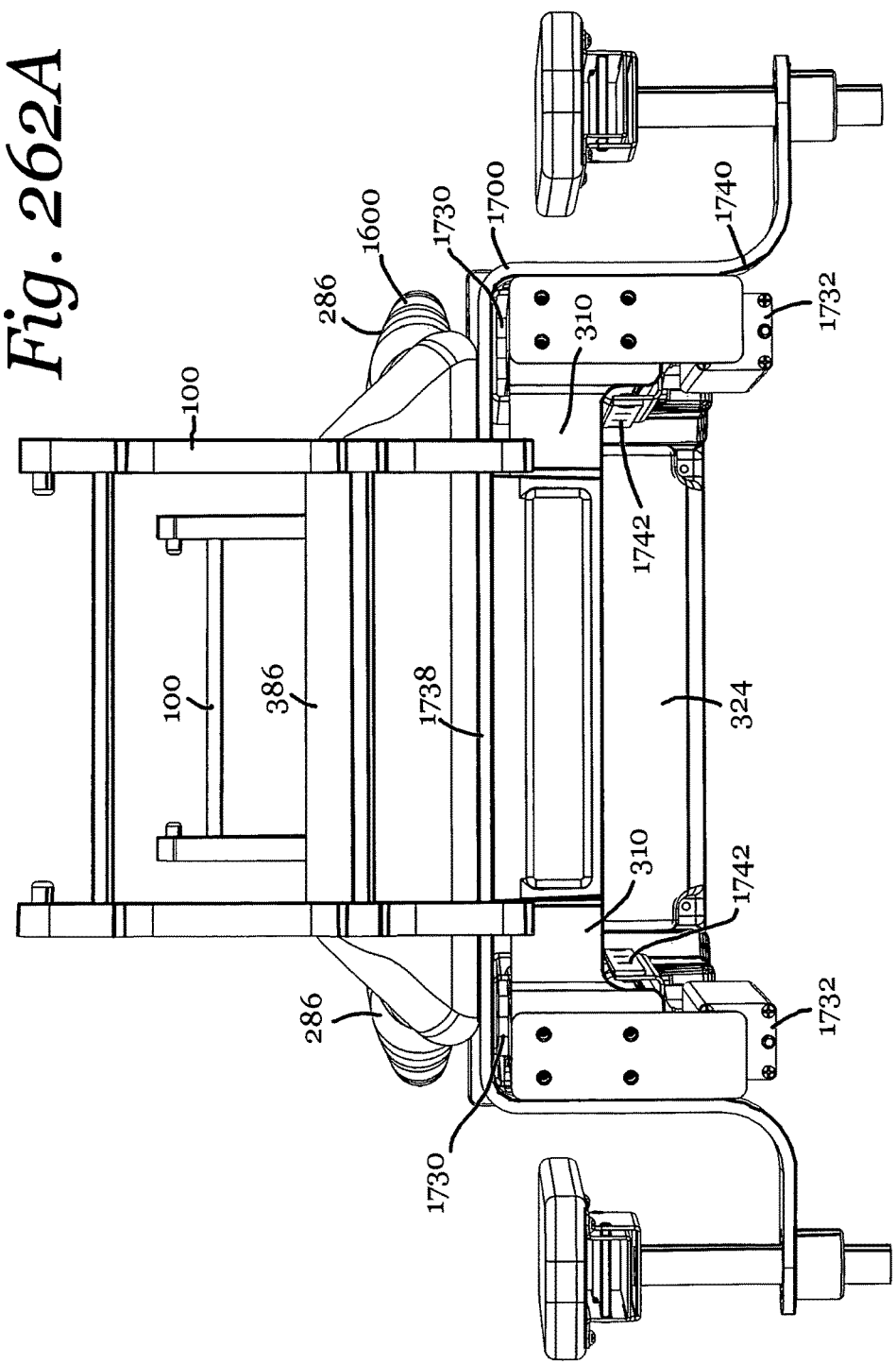

FIG. 262A is an enlarged head-end view of the prone patient support structure of FIG. 255A.

Figure 262B:
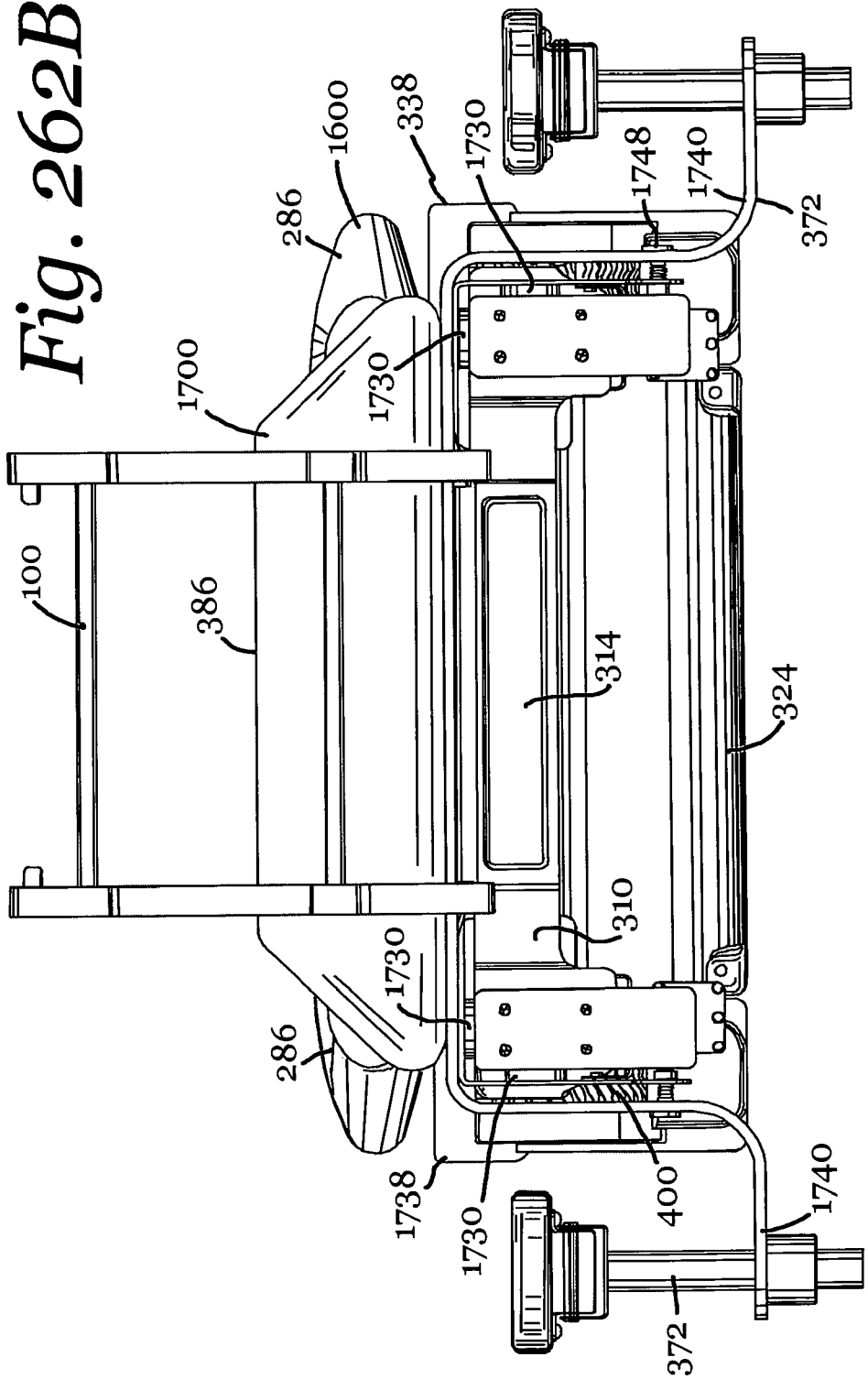

FIG. 262B is another enlarged head-end view of the prone patient support structure of FIG. 255A.

Figure 263:
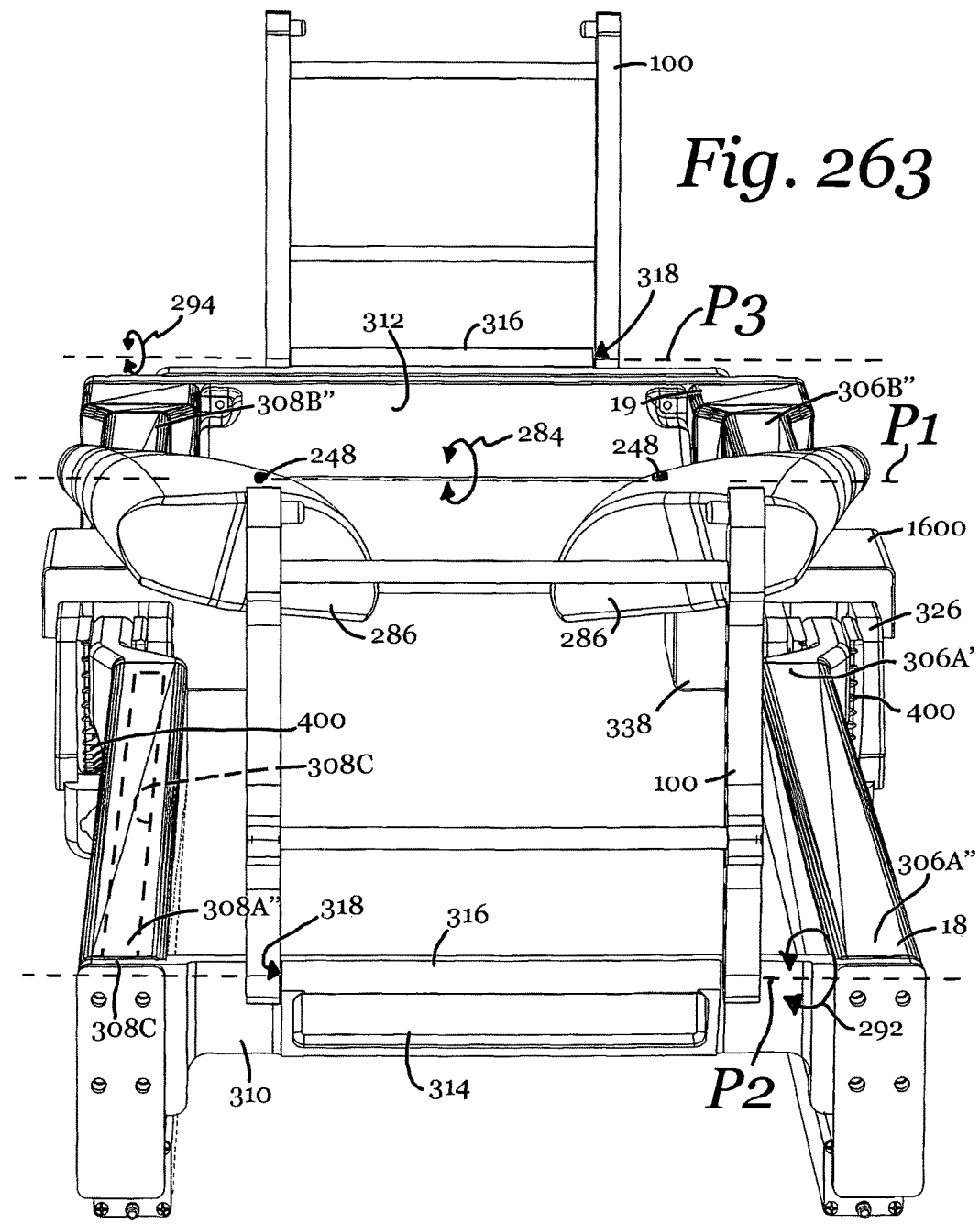

FIG. 263 is an enlarged head-end top view of the prone patient support structure of FIG. 255A.

Figure 264A:
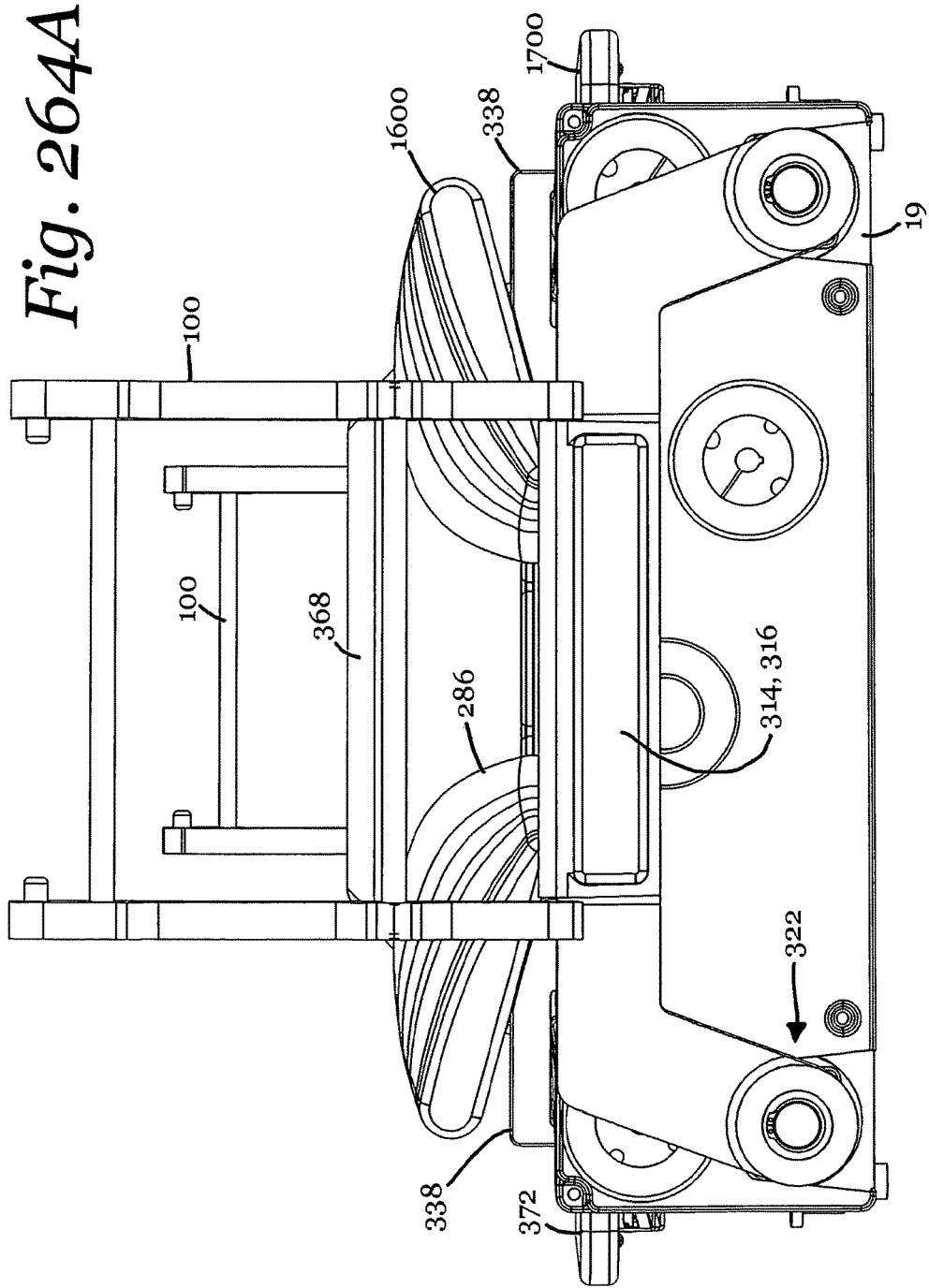

FIG. 264A is an enlarged foot-end view of the prone patient support structure of FIG. 255A.

Figure 264B:
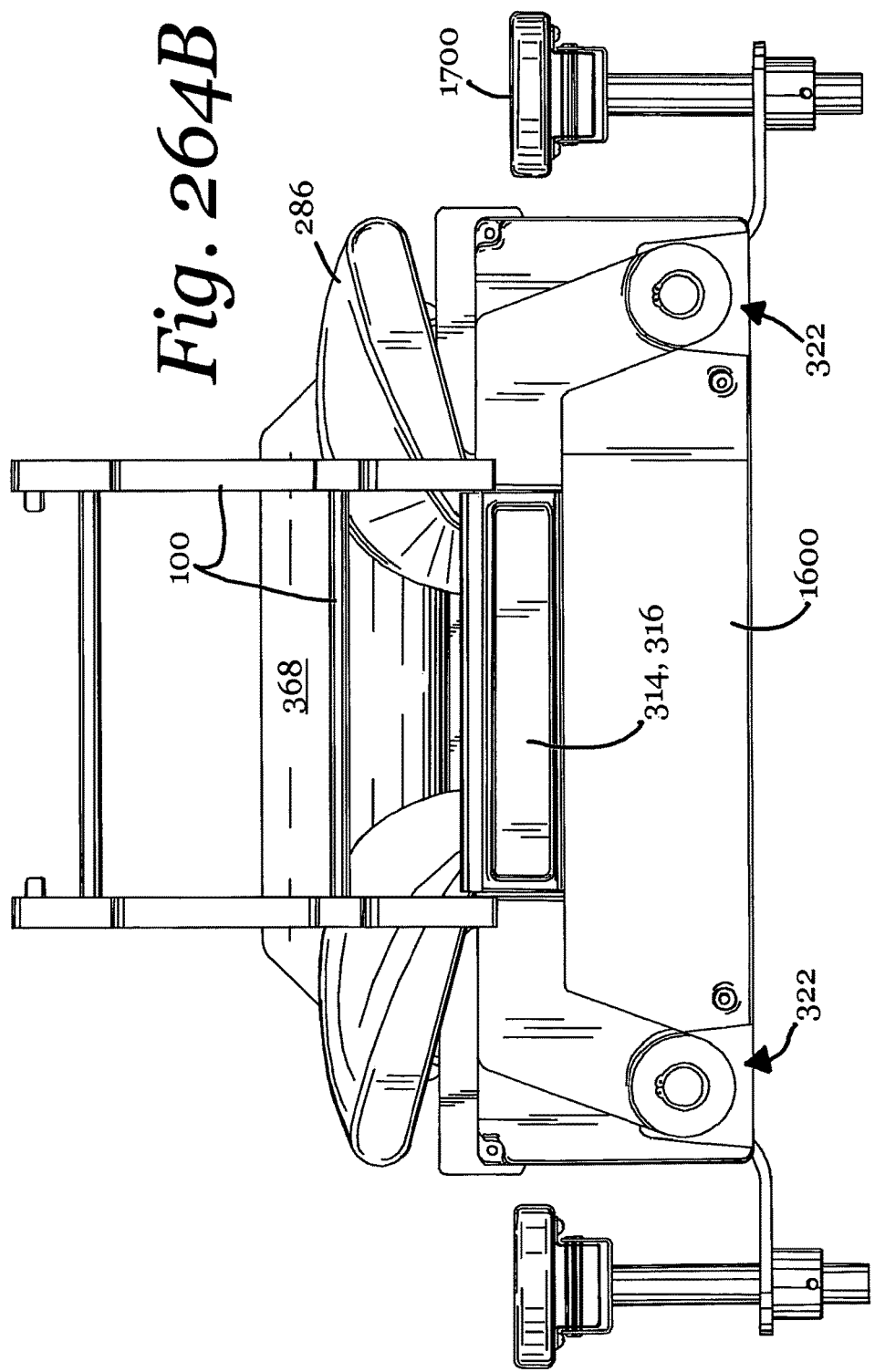

FIG. 264B is another enlarged foot-end view of the prone patient support structure of FIG. 255A.

Figure 265:
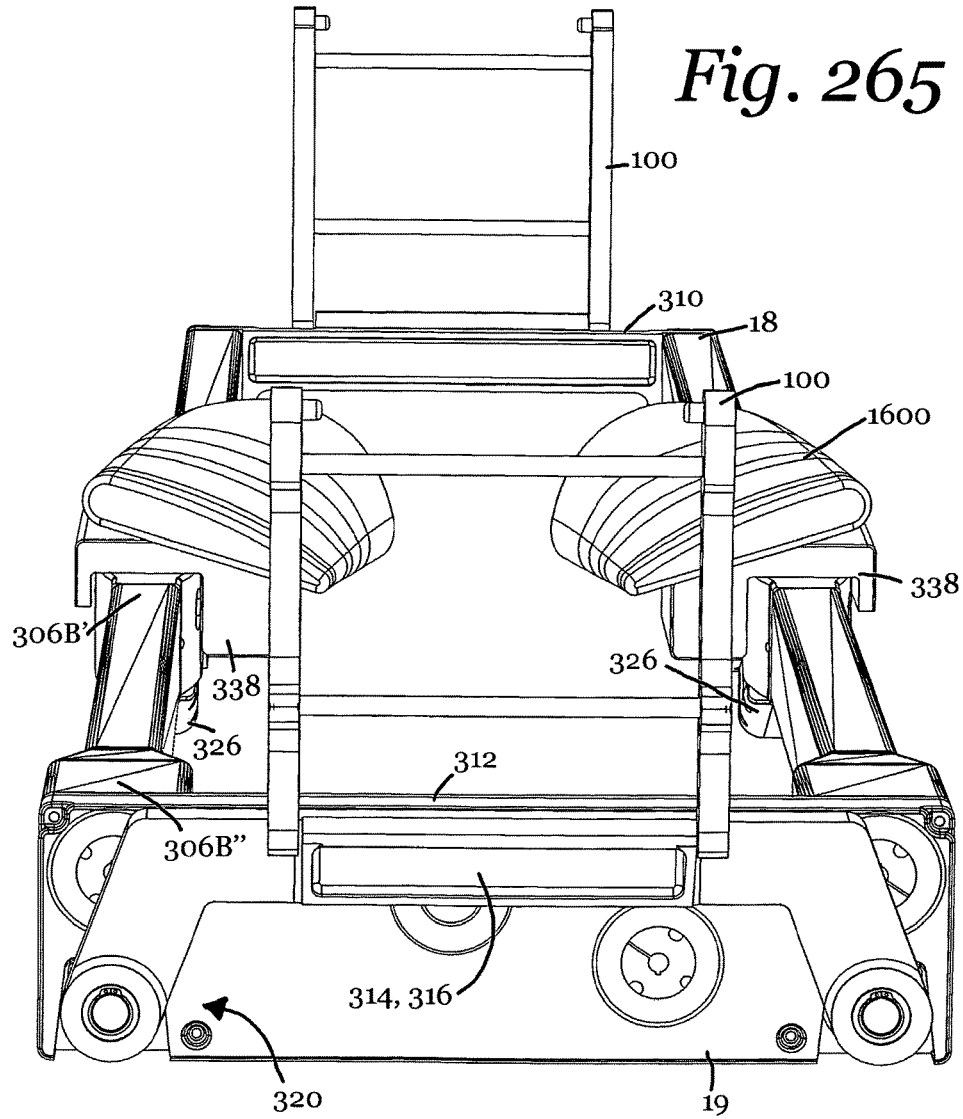

FIG. 265 is an enlarged foot-end top view of the prone patient support structure of FIG. 255A.

Figure 266A:
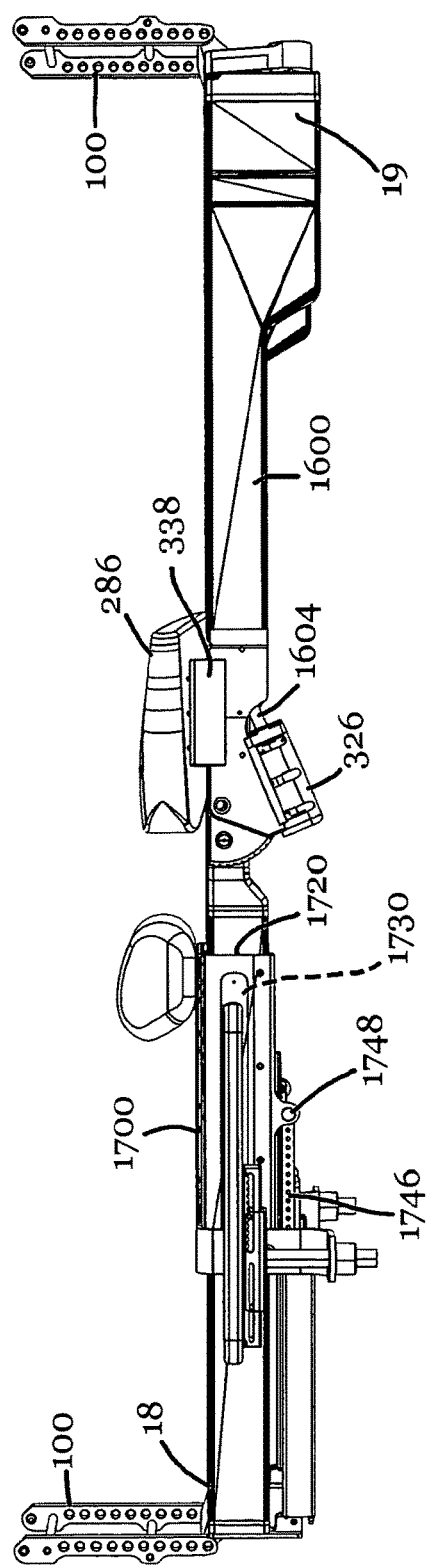

FIG. 266A is a reduced left side view of the prone patient support structure of FIG. 255A.

Figure 266B:
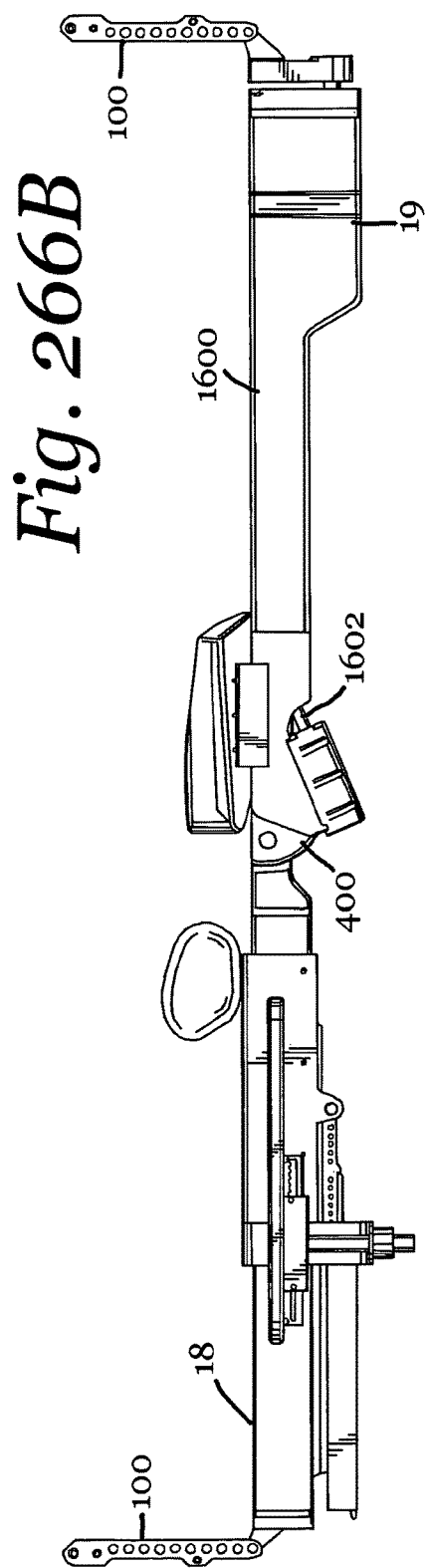

FIG. 266B is another reduced left side view of the prone patient support structure of FIG. 255A.

Figure 267A:
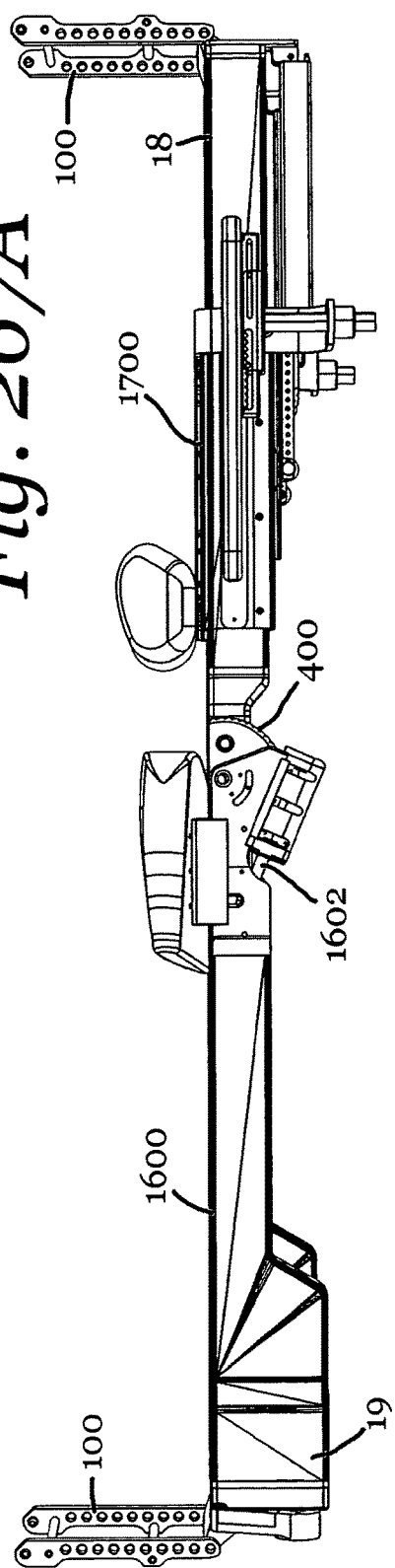

FIG. 267A is a reduced right side view of the prone patient support structure of FIG. 255A.

FIG. 267B is another reduced right side view of the prone patient support structure of FIG. 255A.

Figure 268A:
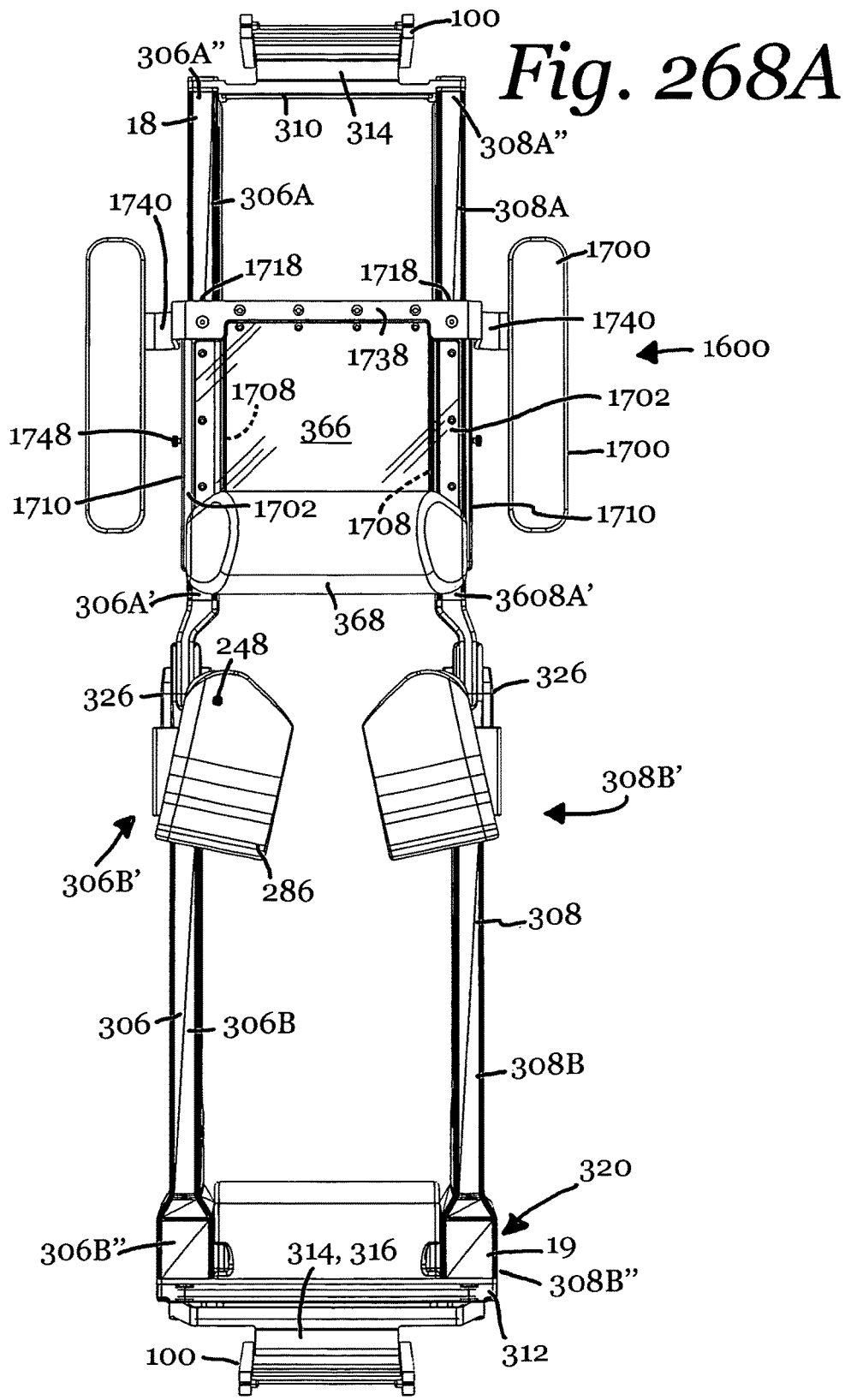

FIG. 268A is a reduced top view of the prone patient support structure of FIG. 255A.

Figure 268B:
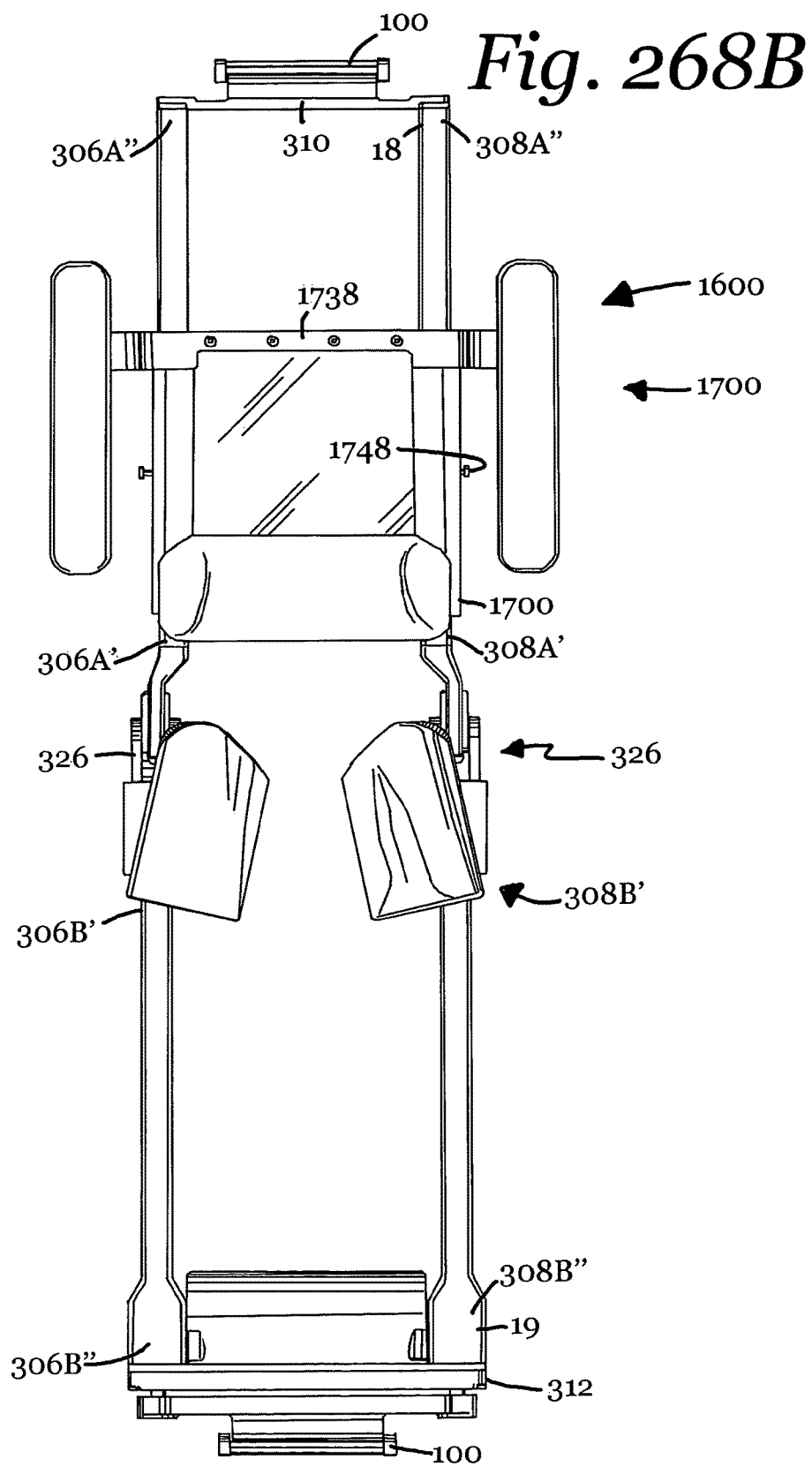

FIG. 268B is another reduced top view of the prone patient support structure of FIG. 255A.

Figure 269A:
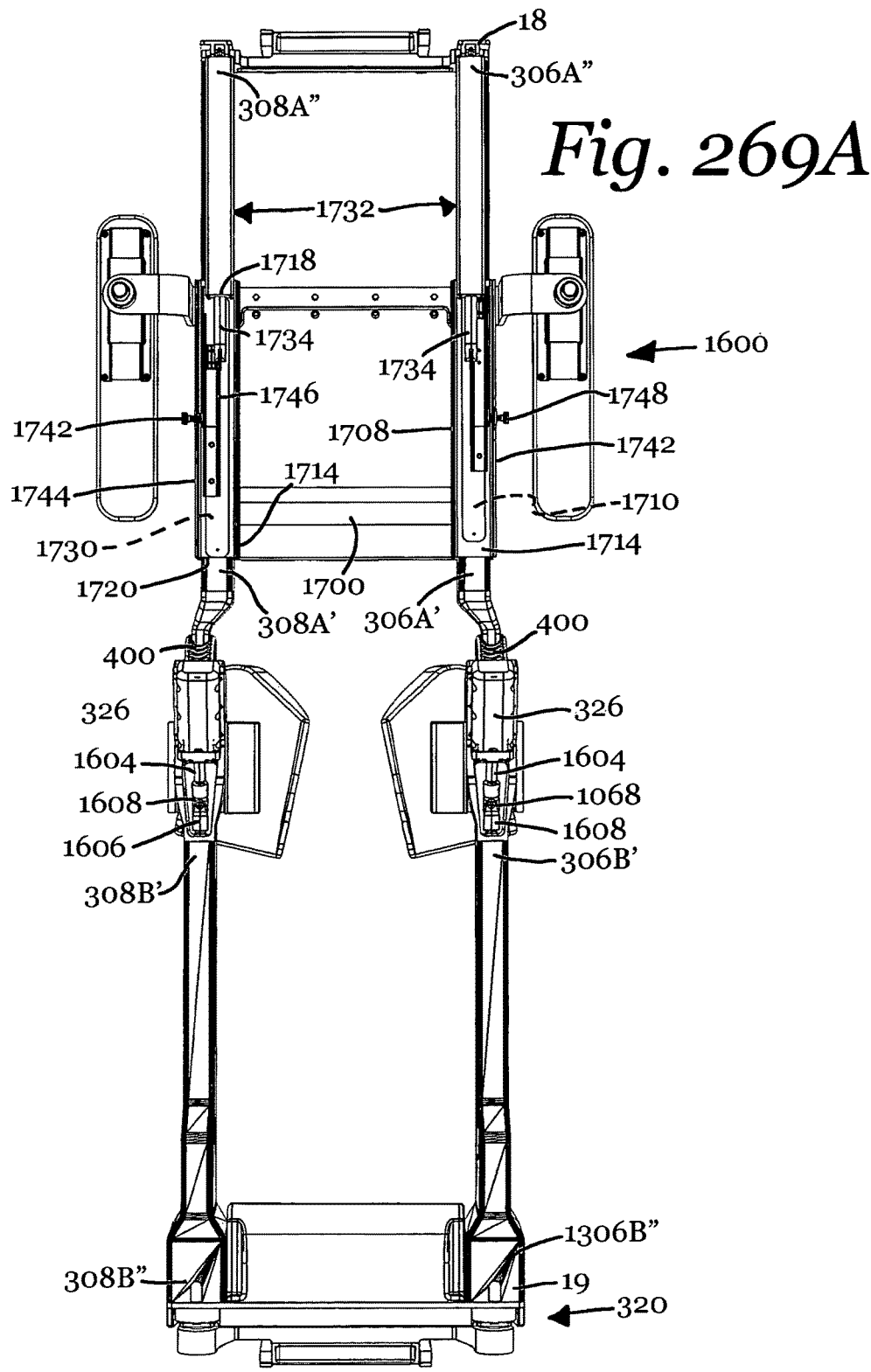

FIG. 269A is a reduced bottom view of the prone patient support structure of FIG. 255A.

FIG. 269B is another reduced bottom view of the prone patient support structure of FIG. 255A.

Figure 270:
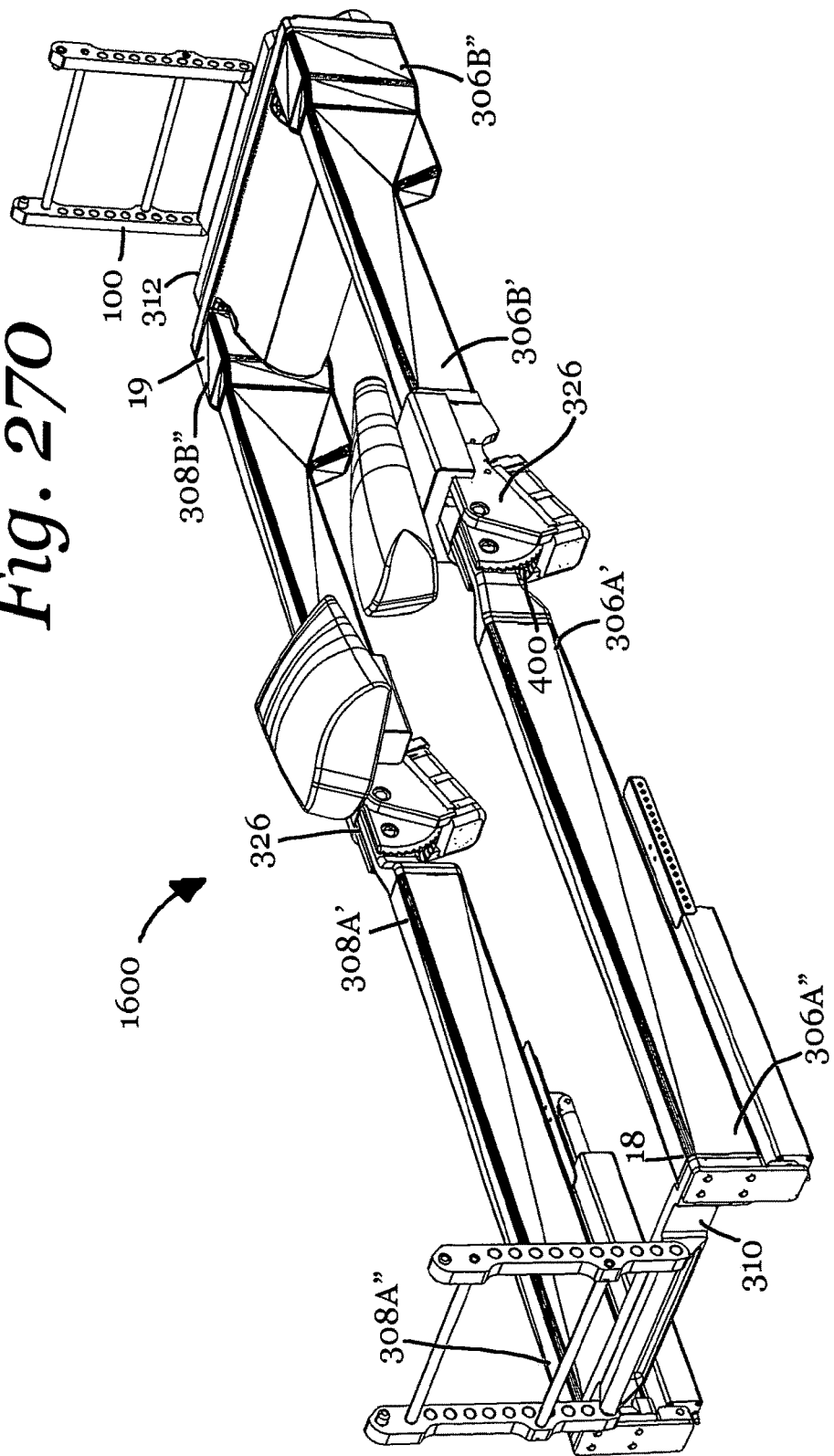

FIG. 270 is another head-end top perspective view of the prone patient support structure of FIG. 255A, with portions of the torso support structure removed to show greater detail of the frame.

Figure 271:
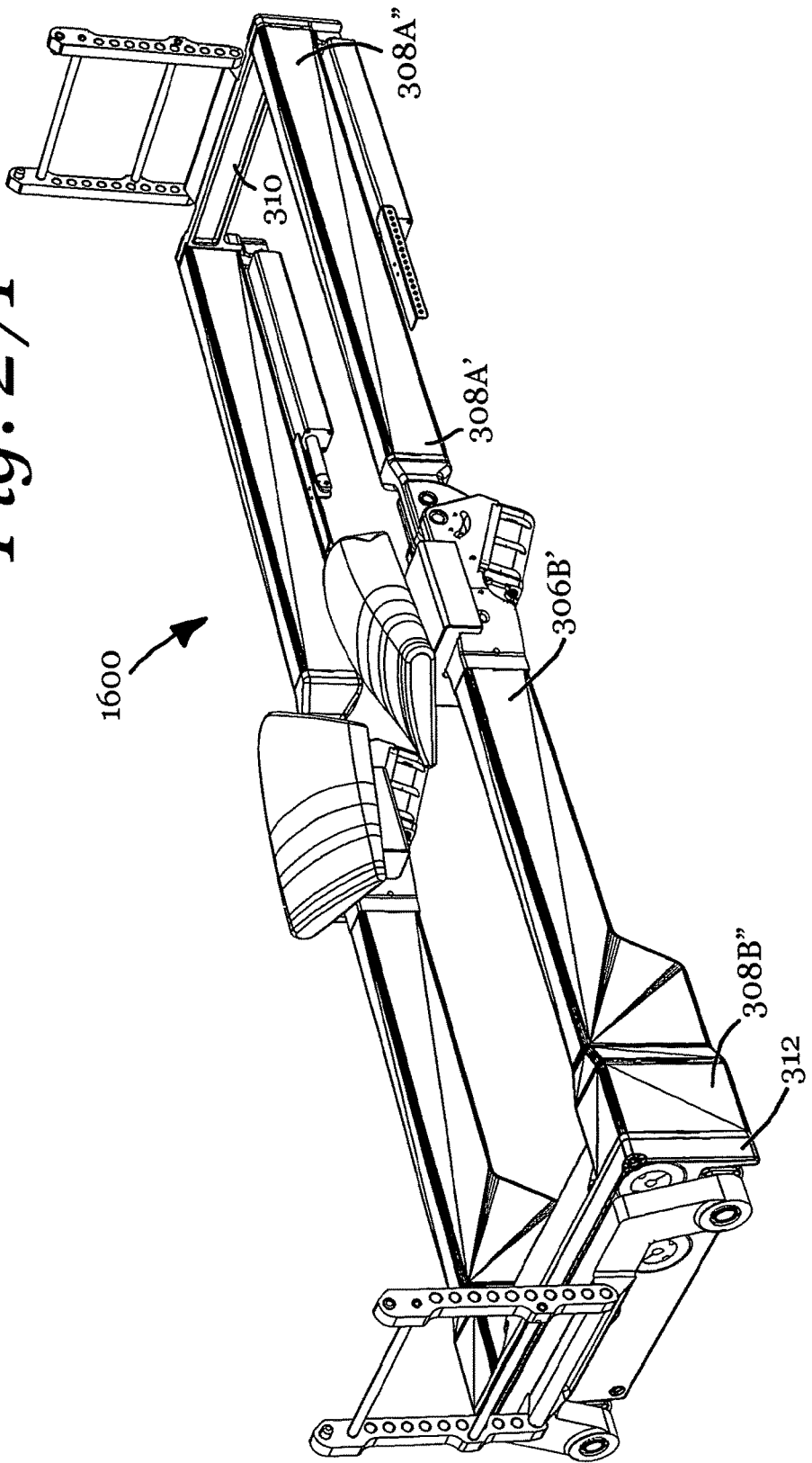

FIG. 271 is a foot-end top perspective view of the prone patient support structure of FIG. 270.

Figure 272:
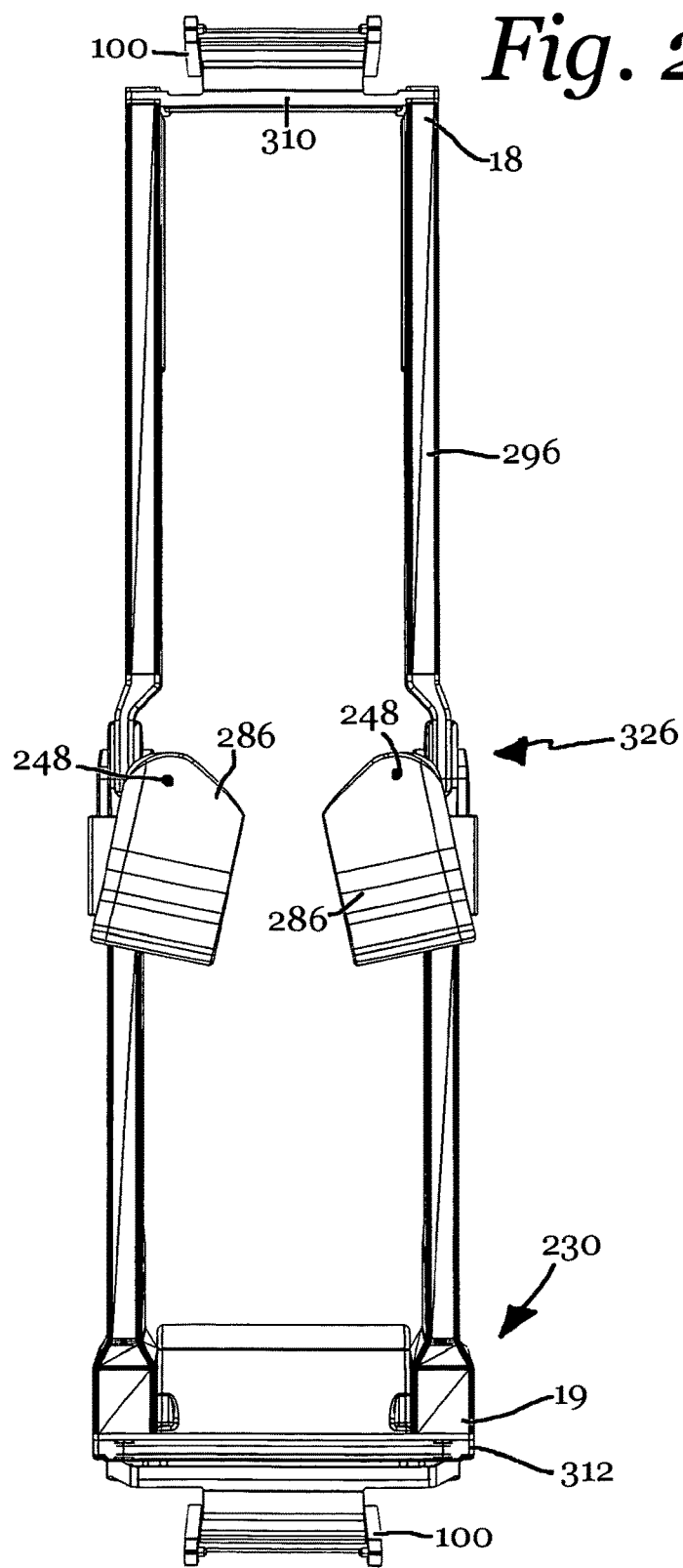

FIG. 272 is a reduced top view of the prone patient support structure of FIG. 270.

Figure 273:
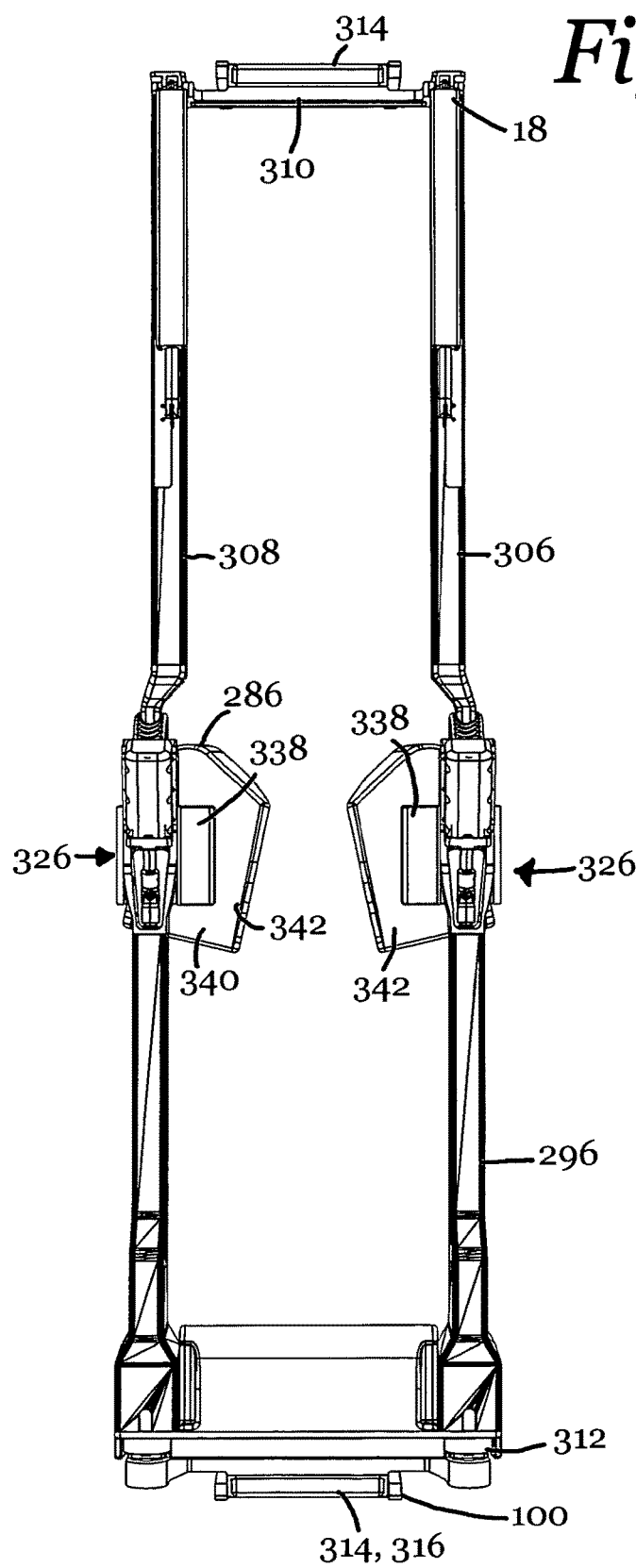

FIG. 273 is a reduced bottom view of the prone patient support structure of FIG. 270.

Figure 274:
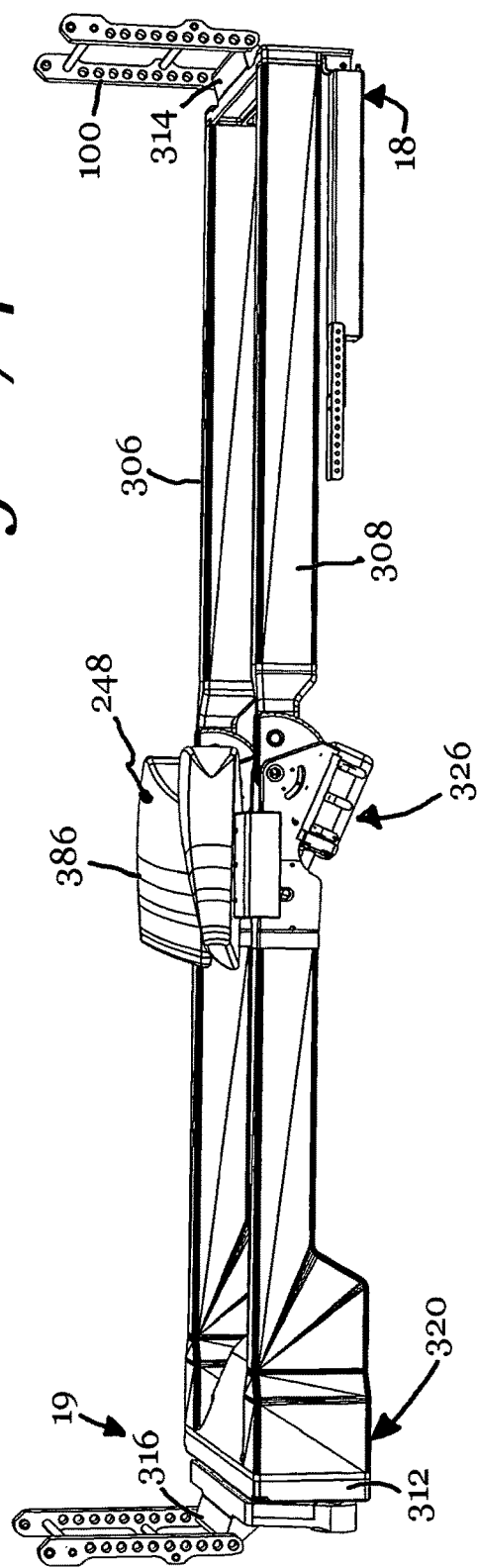

FIG. 274 is a reduced right side view of the prone patient support structure of FIG. 270.

Figure 275:
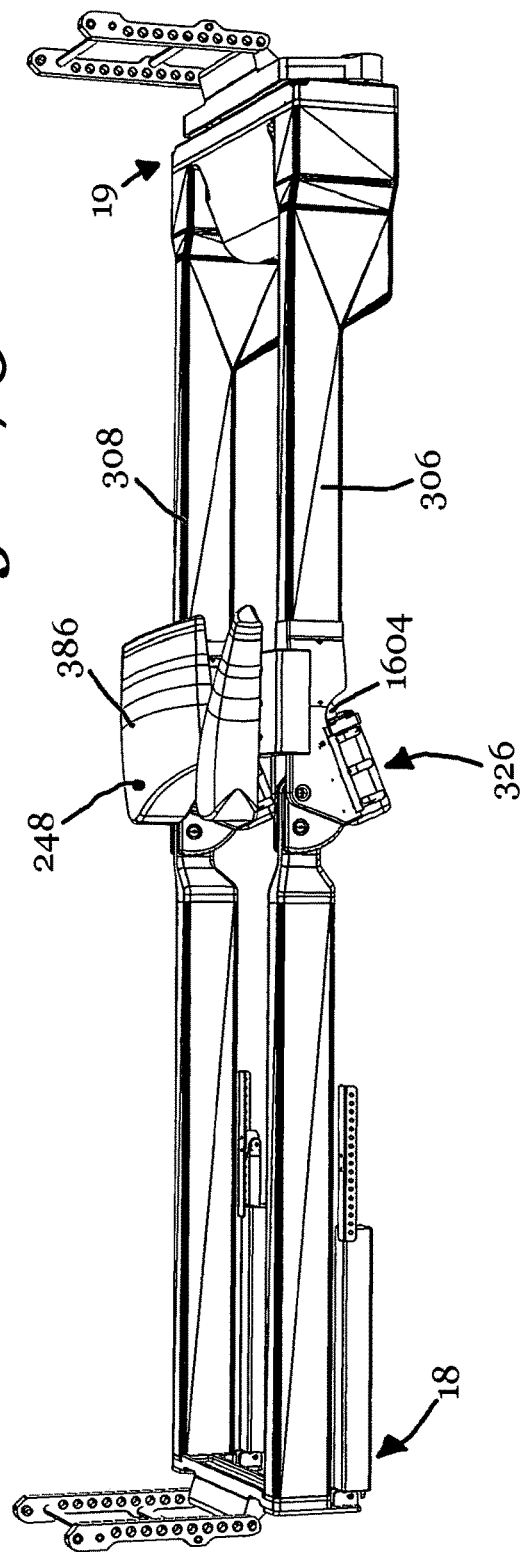

FIG. 275 is a reduced left side view of the prone patient support structure of FIG. 270.

FIG. 276 is an enlarged head-end top perspective view of the head-end portion of the prone patient support structure of FIG. 255A, and the torso support structure showing greater detail thereof.

FIG. 277 is another enlarged head-end top perspective view of the head-end portion of the prone patient support structure of FIG. 255A, and the torso support structure, with portions cut away and in phantom, to show greater detail thereof.

FIG. 278 is another enlarged head-end top perspective view of the head-end portion of the prone patient support structure of FIG. 255A, and the torso support structure, with portions cut away and in phantom, to show greater detail thereof.

Figure 279A:
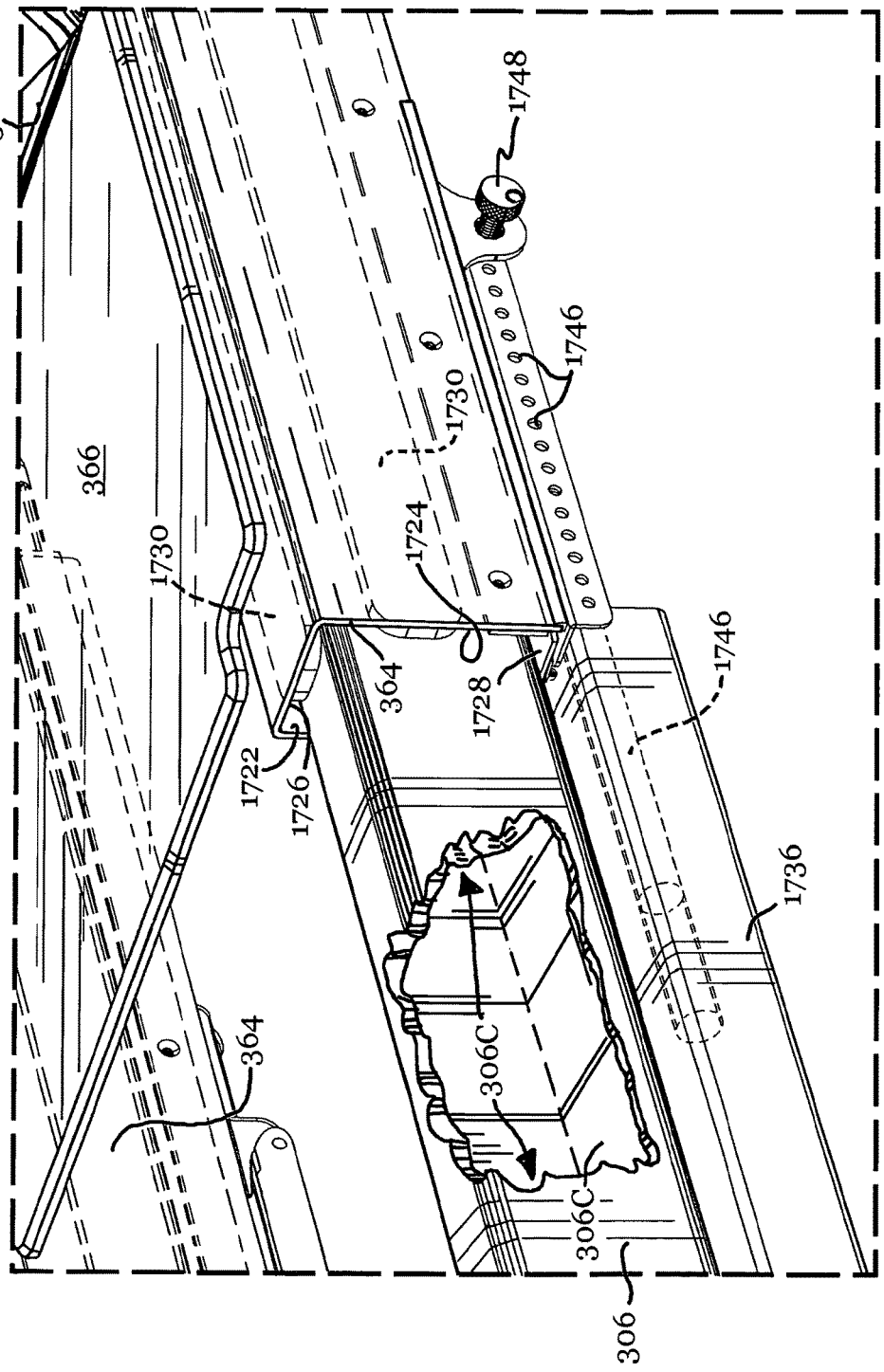

FIG. 279A is an enlarged view of a portion of the head-end portion of the prone patient support structure of FIG. 278.

Figure 279B:
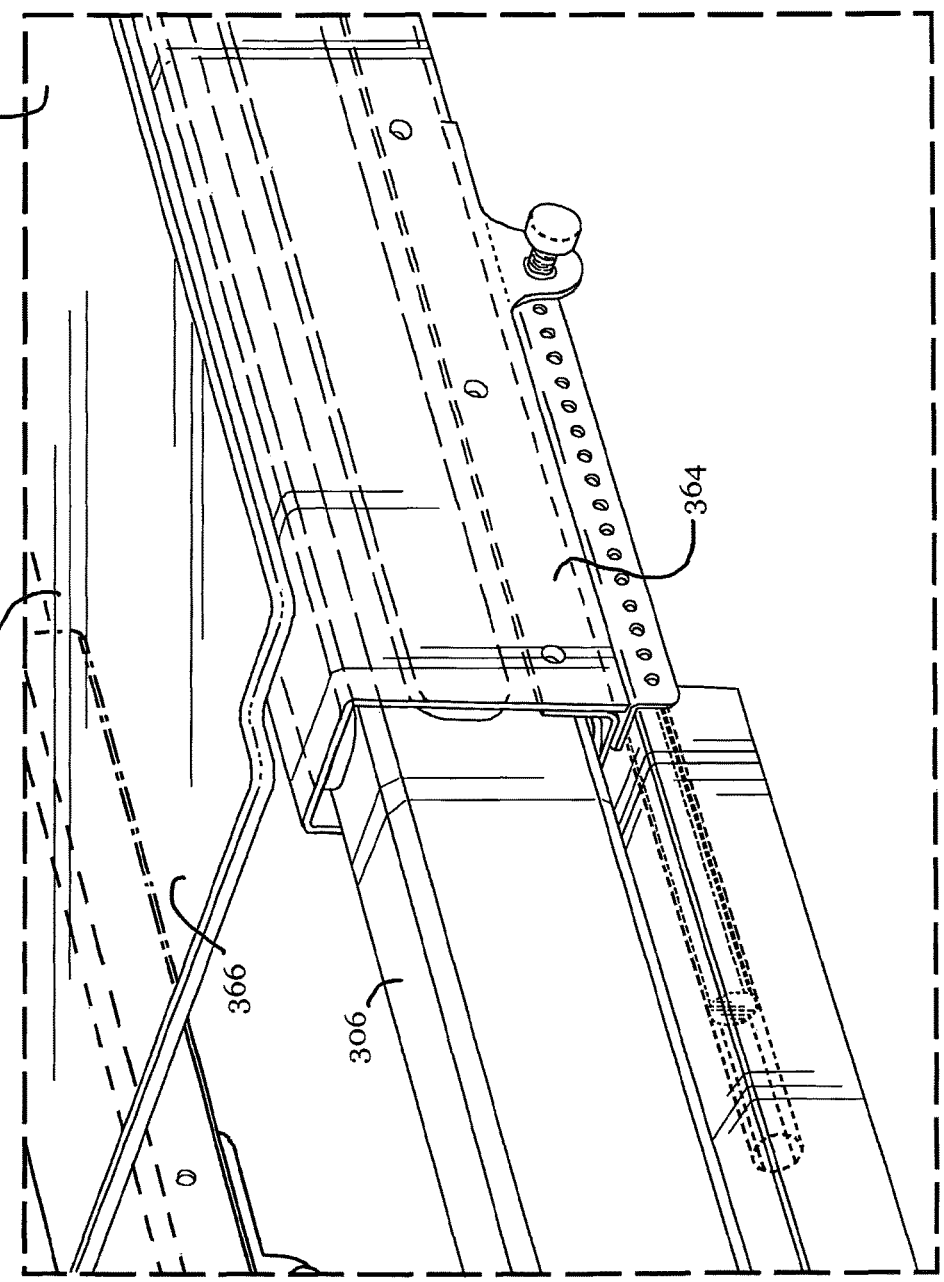

FIG. 279B is another enlarged view of a portion of the head-end portion of the prone patient support structure of FIG. 278.

FIG. 280 is an enlarged view of a hip-thigh pad attached to a pad mount of a joint of the prone patient support structure of FIG. 255A.

FIG. 281A is an enlarged view of a joint of the prone patient support structure of FIG. 255A.

Figure 281B:
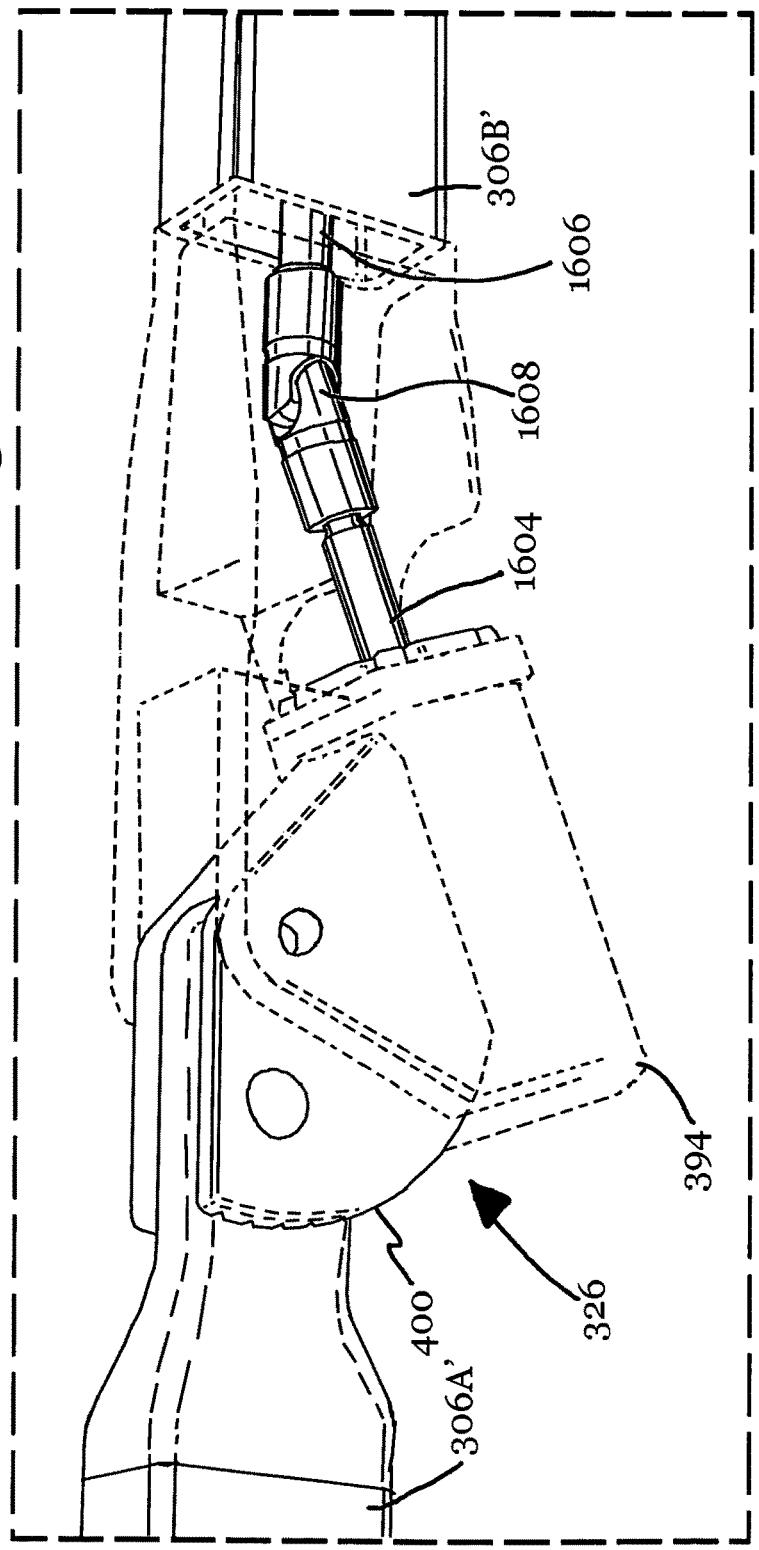

FIG. 281B is a view of the joint of FIG. 281A with portions shown in phantom.

FIG. 282 is an enlarged side perspective view of the prone patient support structure of FIG. 255A with portions broken away and portions shown in phantom to show greater detail thereof.

Figure 283:
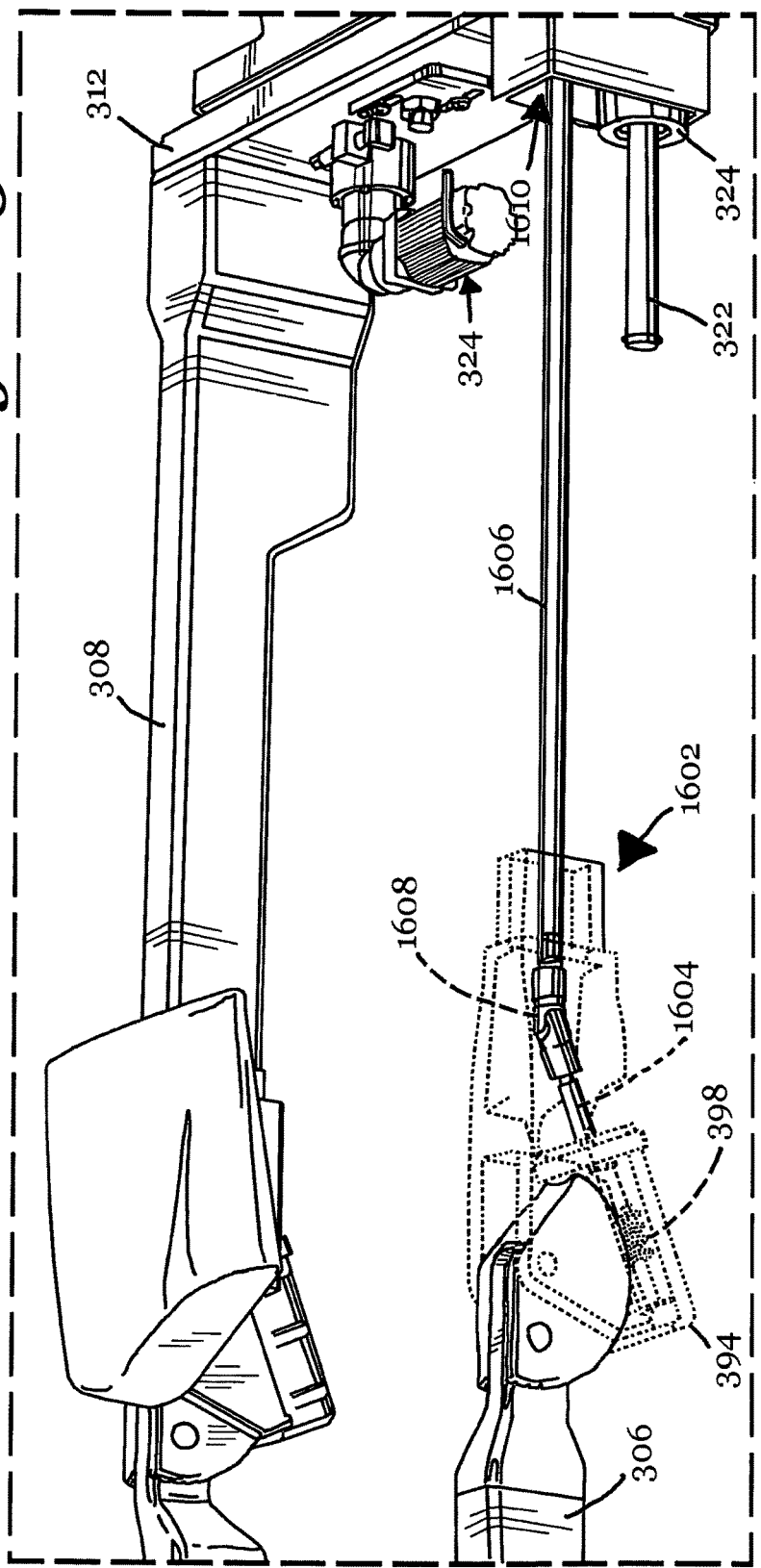

FIG. 283 is an view of the prone patient support structure of FIG. 282 with portions broken away and portions shown in phantom to show greater detail thereof.

Figure 284A:
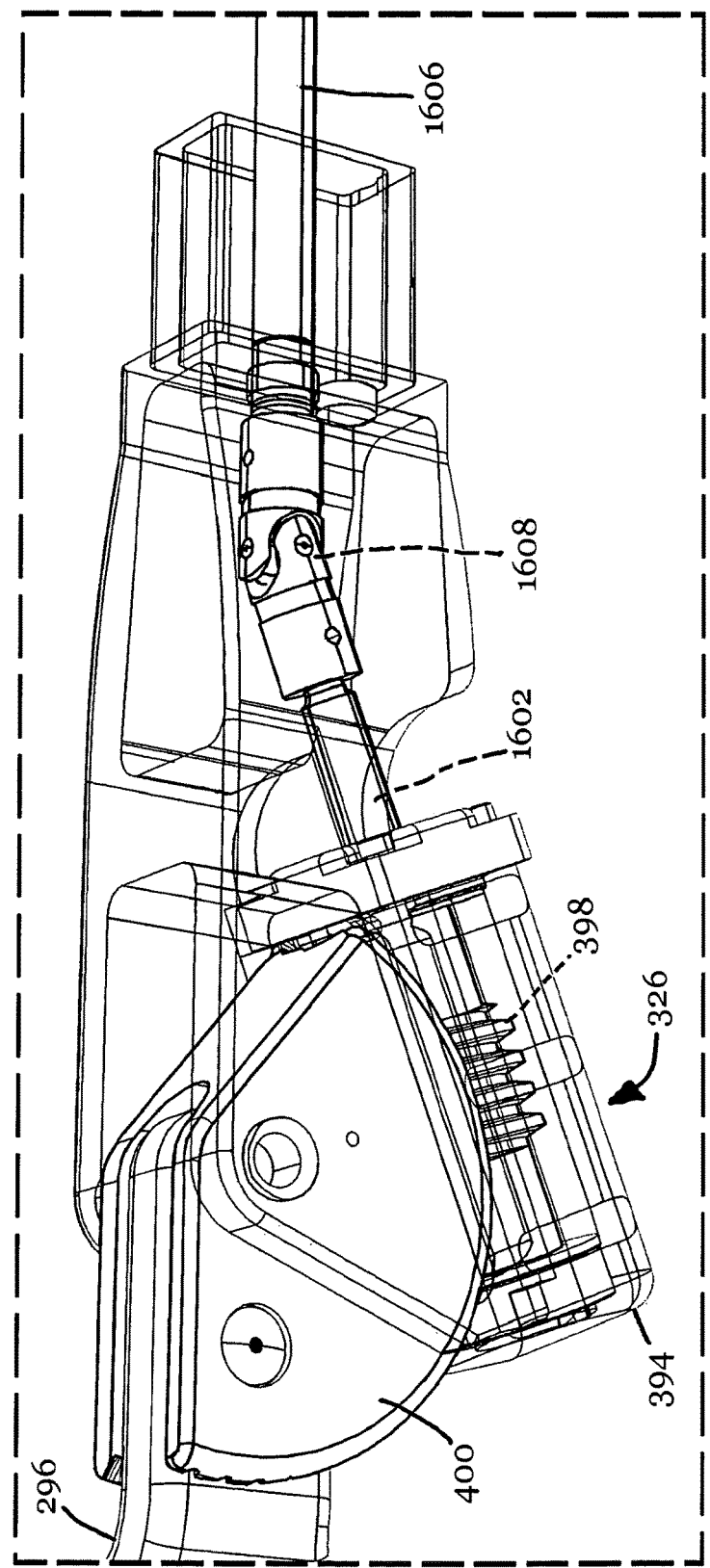

FIG. 284A is an enlarged view of joint of the prone patient support structure of FIG. 282 with portions shown in phantom to show greater detail thereof.

Figure 284B:
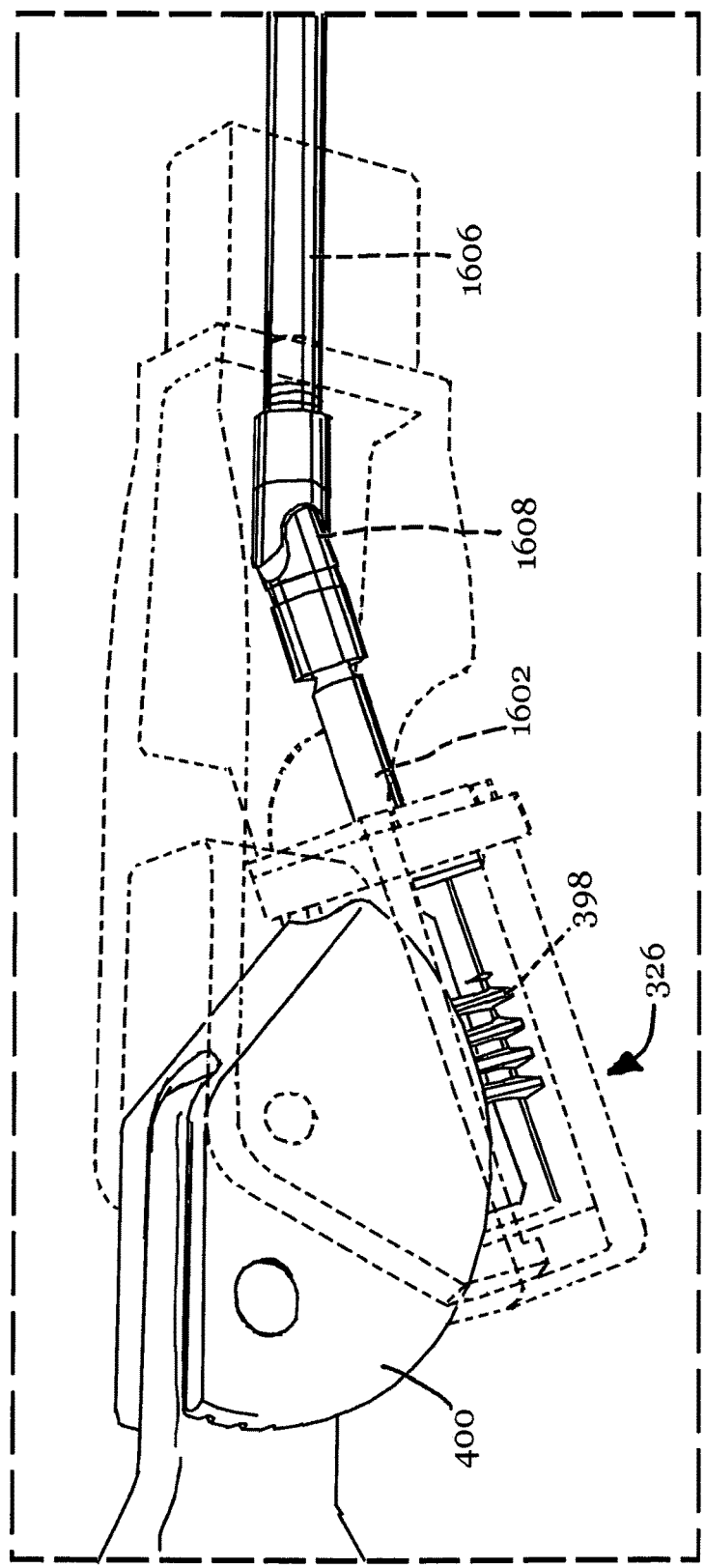

FIG. 284B is another enlarged view of joint of the prone patient support structure of FIG. 282 with portions shown in phantom to show greater detail thereof.

Figure 284C:
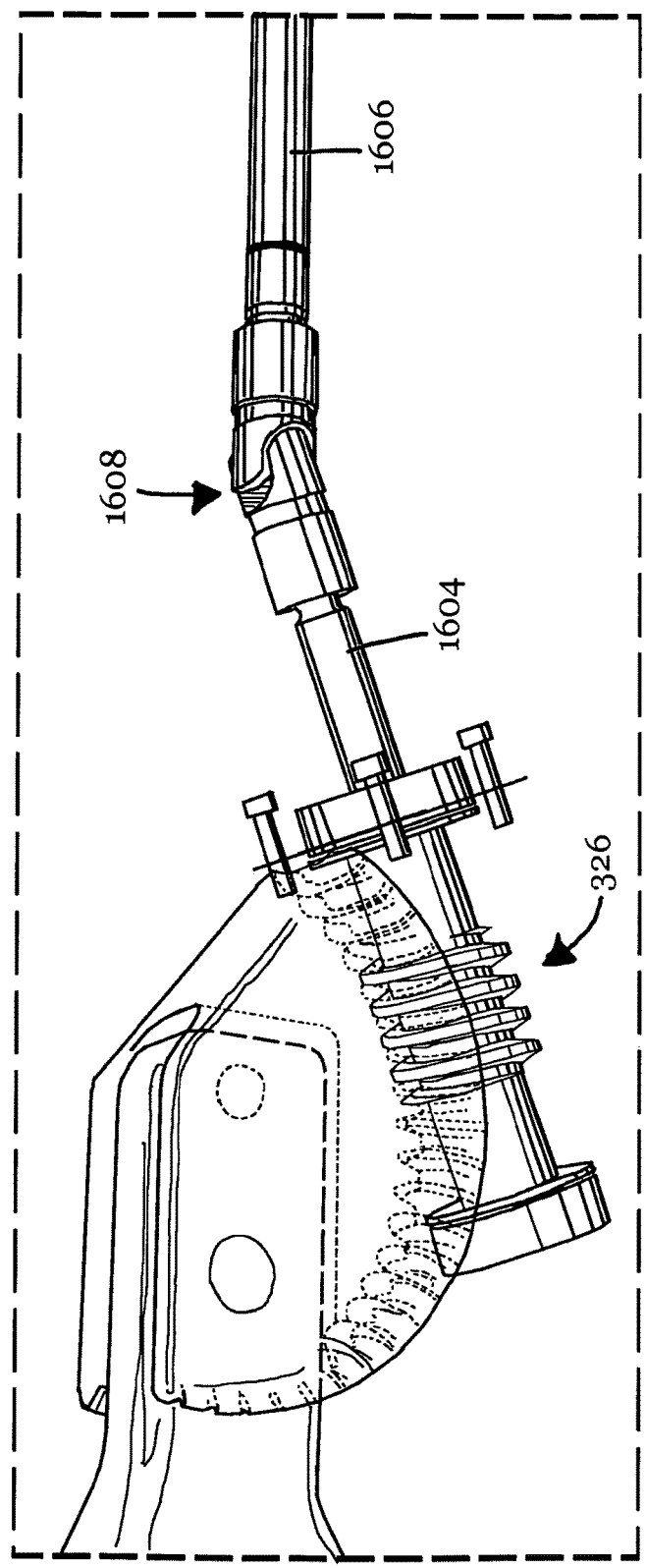

FIG. 284C is another enlarged view of joint of the prone patient support structure of FIG. 282 with portions broken away to show greater detail thereof.

Figure 285A:
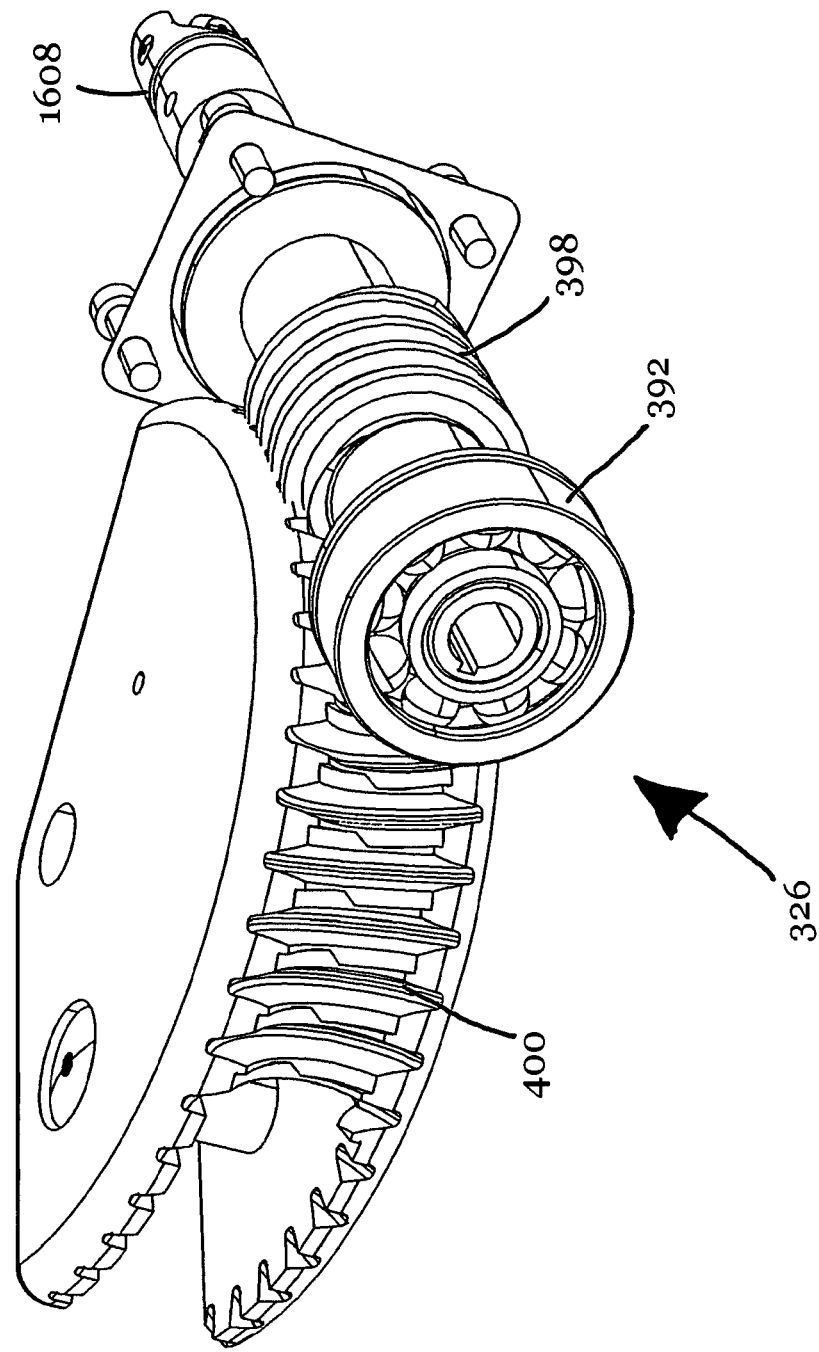

FIG. 285A is an enlarged perspective view of a portion of the joint of the prone patient support structure of FIG. 282.

Figure 285B:
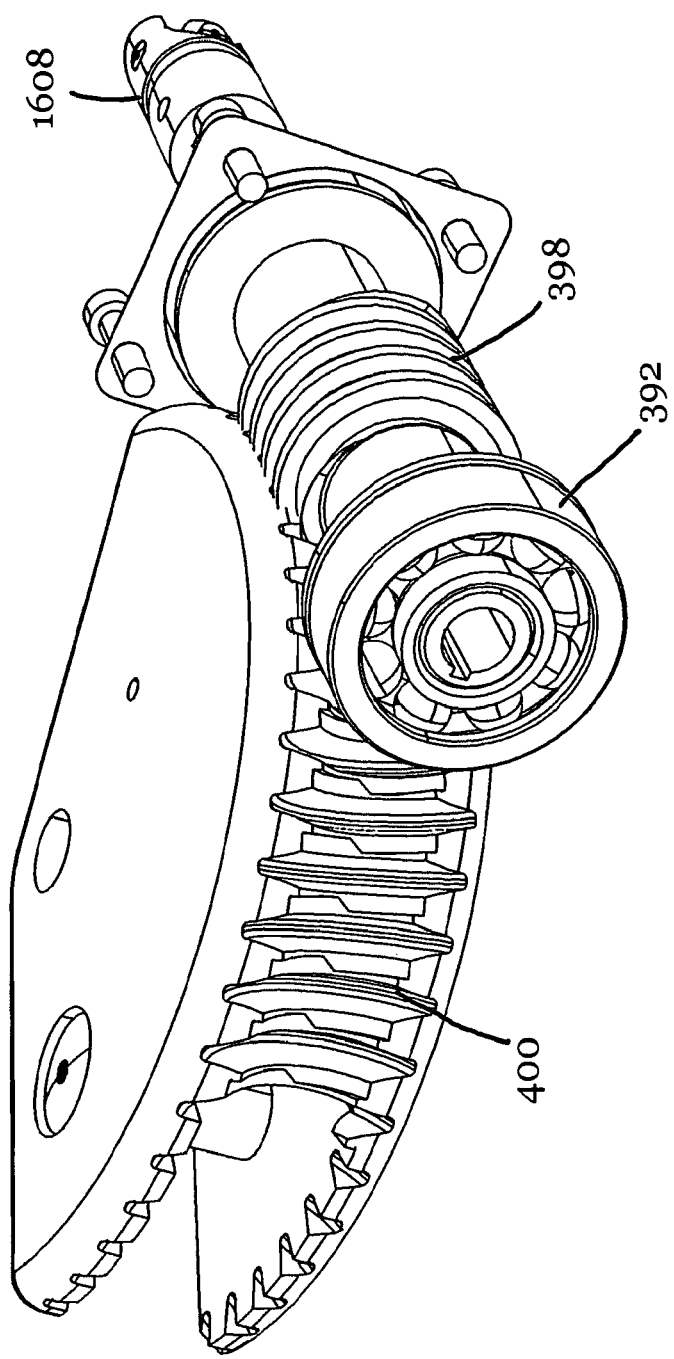

FIG. 285B is another view of the joint of FIG. 285A.

FIG. 286 is another perspective view of the joint of FIG. 285A.

FIG. 287 is another perspective view of the joint of FIG. 285A.

DETAILED DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to various employ the present invention in virtually any appropriately detailed structure.

Patient Positioning Support System Components and Operation

Figure 1:
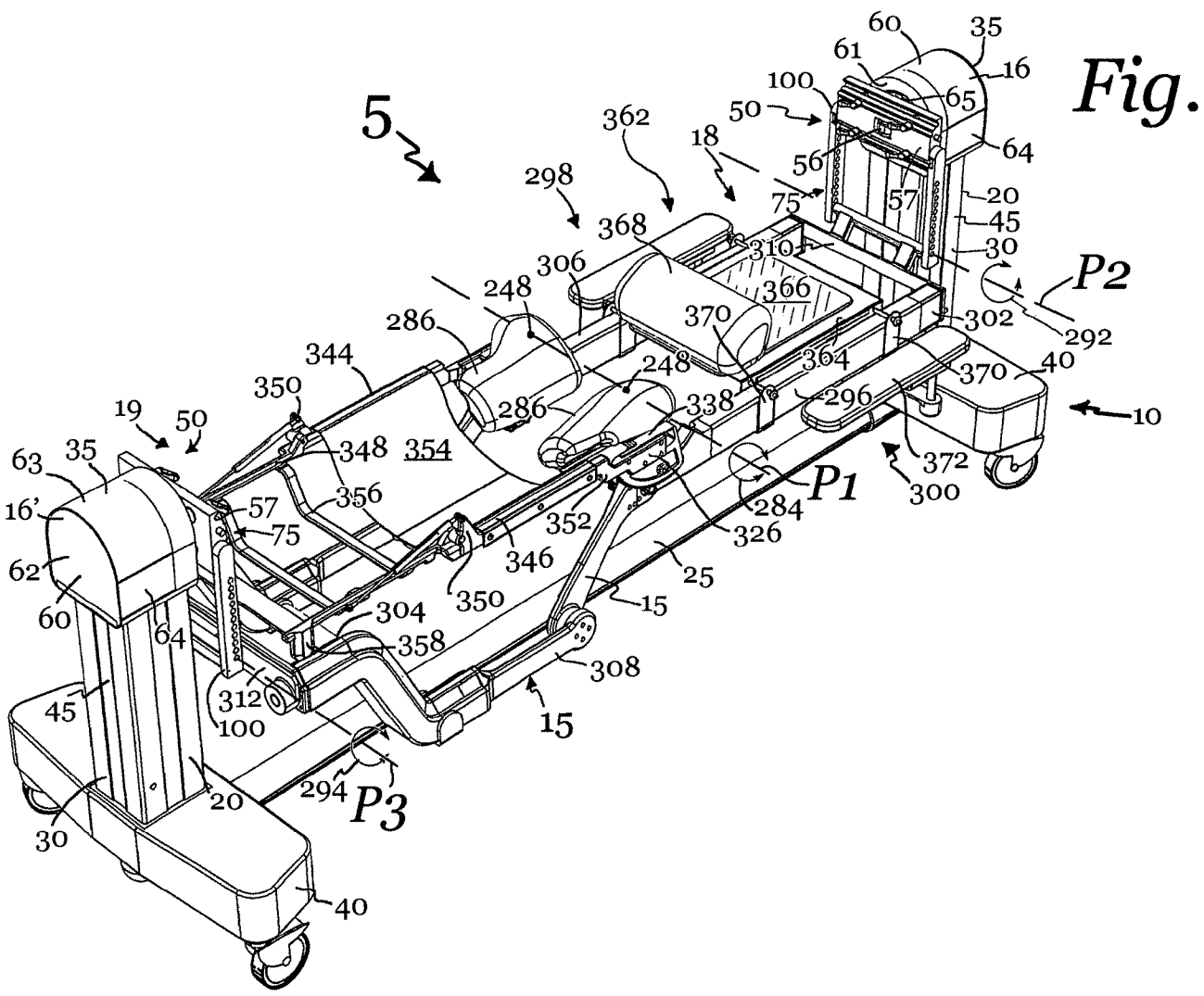
FIG. 1 is a perspective view of a patient positioning support system of the present invention in one embodiment, including a base and a prone patient support structure.

Referring now to FIGS. 1-119, a patient positioning support system, structure, apparatus or table according to the invention is generally designated by the reference numeral 5, in one embodiment. FIG. 1 is a top perspective view of the patient positioning support system 5 of the present invention, which includes a base, generally 10, and a patient support structure or table top, generally $15^0$, such as but not limited to at least one of a prone patient support structure 15, a supine patient support structure 15' and an alternatively sized, shaped and configured patient support structure. The patient positioning support system 5 includes head and foot-ends, left and right-hand sides, and top and bottom sides, which for discussion purposes are denoted relative to the sides of a patient's body when the patient is positioned in a prone position on the prone patient support structure 15.

The patient support system 5 also includes a plurality of axes, including but not limited to roll, pitch, yaw and vertical translation axes, which are respectively denoted by R, Pn, Yn and Vn, wherein n denotes or identifies a specific axis, and all of which are most easily seen in FIGS. 1-3. The roll axis R extends longitudinally along a length of the patient support system 5, and intersects the head- and foot-ends 16 and 16', respectively, of the base 10. The base head-end 16 includes a first vertical translation axis V1 and a first yaw axis Y1. Similarly, the base foot-end 16' includes a second vertical translation axis V2 and a second yaw axis Y2. Finally, P1 the patient support structure $15^0$ includes three pitch axes, wherein the first pitch axis P1 is P1 associated with a patient's hips, the second pitch axis P2 is associated with the head-end 18 of the patient support structure $15^0$, and the third pitch axis P3 is associated with the foot-end 19 of the patient support structure $15^0$.

Generally, the roll, pitch and yaw axes, R, Pn and Yn, of the patient positioning support system 5 are axes about which rotational movement of at least a portion of the patient positioning support system 5 can occur, and therefore are functionally analogous to the roll, pitch and yaw axes of an airplane. The vertical translation axes Vn are associated with up and down lifting and lowering the head- and foot-ends 18, 19 of the patient support structure $15^0$.

In various embodiments, the movements of the patient positioning support system 5, with respect to the head and foot-ends, left and right-hand sides, and top and bottom sides, as well as with respect to the roll, pitch, yaw and vertical translation axes, R, Pn, Yn and Vn, respectively, can be one or more of synchronous or sequential, active or passive, powered or non-powered, mechanically linked or synchronized by software, and continuous (e.g., within a range) or incremental, and such as is described in greater detail below.

Base Structure and Function

FIG. 2 is a perspective view of a base 10 of the patient positioning support system 5, in an exemplary embodiment. The base 10 may also be referred to as a base structure or base subassembly. The base 10 is adapted to support the patient support structure 15° above the floor F. The base 10 includes structure that is adapted to lift and lower, tilt, roll, rotate and, additionally or alternatively, angulate at least a portion of the patient support structure 15° relative to the floor F, so as to position a patient's body in a desired position for a medical procedure, such as is described in greater detail below.

The base 10 includes at least one vertical translation subassembly 20, also referred to as a vertical elevator, a telescoping pier, a vertical translator, or the like. In an exemplary embodiment, such as that shown in FIGS. 2, 7, 8 and 24, the base includes a vertical translation subassembly 20 at each of its head- and foot-ends 16, 16'; wherein the pair of spaced opposed vertical translation subassemblies 20 joined by a longitudinally extending supportive cross-bar 25. In the illustrated embodiment, the vertical translation subassemblies 20 are generally identical and face one another, or are mirror images of one another, though this is not required in all embodiments. It is foreseen that one or both vertical translation subassemblies 20 may have an alternative structure. For example, the telescoping riser of the vertical translation subassemblies (described below) may be off-set, or not centered over the foot or base portion, such as is described elsewhere herein. In another example, one or both of the vertical translation subassemblies 20 may be constructed such as described in U.S. Pat. Nos. 7,152,261, 7,343,635, 7,565,708, 8,060,960, or U.S. Patent Application No. 60/798,288, U.S. patent application Ser. No. 12/803,173, U.S. patent application Ser. No. 12/803,192, or U.S. patent application Ser. No. 13/317,012, all of which are incorporated by reference herein in their entireties.

The cross-bar 25 is a substantially rigid support that joins and holds the vertical translation subassemblies 20 in spaced opposed relation to one. In a further embodiment, the cross-bar 25 is non-adjustable. However, in some other embodiments, the cross-bar 25 is removable or telescoping, so that the vertical translation subassemblies 20 can be moved closer together, such as for storage. In certain embodiments, the cross-bar 25 is longitudinally adjustable so that the vertical translation subassemblies 20 can be moved closer together or farther apart, such as, for example, to support or hold different patient support structures 15 of various lengths or configurations, such as but not limited to interchangeable or modular patient support structures 15. In certain other embodiments, there patient positioning support system 5 does not include a cross-bar 25. Numerous cross-bar 25 variations are foreseen. It is foreseen that the cross-bar 25 may be telescoping, and additionally or alternatively removable, such that the cross-bar 25 can be shortened, or removed, such as for storage of the base 10.

Regardless of the presence or absence of any such cross-bar 25 described herein or foreseen, the vertical translation subassemblies 20 are substantially laterally non-movable with respect to one another, either closer together or farther apart, once a patient support structure 15° has been attached to or joined with the base 10, and during use or operation of the patient positioning support system 5.

Referring again to FIG. 2, each vertical translation subassembly 20 includes a lower portion 30, an upper portion 35 and a vertical translation axis V1 or V2 that extends upwardly from the floor F so as to be substantially perpendicular thereto. The lower portion 30 includes a lower support structure 40, such as a base portion or a foot, and a riser assembly 45. The riser assembly 45 includes a mechanical drive system or mechanism (not shown), such as is known in the art that lifts and lowers the upper portion 35 along the respective vertical translation axis V1, V2 and relative to the floor F. As mentioned above, the riser assembly 45 may be off-set with respect to the lower support structure 40.

At least one of the vertical translation subassembly upper portions 35 includes a rotation subassembly, generally 50, that enables tilting and rolling of the patient support structure 15° about the roll axis R, such as is described below. As is described in greater detail below, the roll axis R extends longitudinally between the upper portions 35.

The rotation subassembly 50 includes a mechanical rotation motor 55, a rotation shaft 56 and a rotation or ladder connection block 57. The rotation motor 55 may be any motor known in the art that is strong enough to rotate the patient support structure 15° about the roll axis R and optionally to lock the patient support structure 15° in a tilted orientation with respect to the floor F. Harmonic motors are particularly useful as the rotation motor due to their strength. Alternatively, the rotation subassembly 50 may be constructed such as described in U.S. Pat. Nos. 7,152,261, 7,343,635, 7,565,708, 8,060,960, or U.S. Patent Application No. 60/798,288, U.S. patent application Ser. No. 12/803,173, U.S. patent application Ser. No. 12/803,192, or U.S. patent application Ser. No. 13/317,012, all of which are incorporated by reference herein in their entireties. Numerous variations are foreseen. Non-motorized rotation subassemblies 50 are also foreseen.

The motor 55 is enclosed or shrouded by a housing 60, with front and back portions 61, 62, a top portion 63, opposed side portions 64 and an optional front plate or rotation plate 65, so as to be protected thereby. Accordingly, the rotation shaft 56 extends through the housing front portion 61, as is described below.

Figure 4:
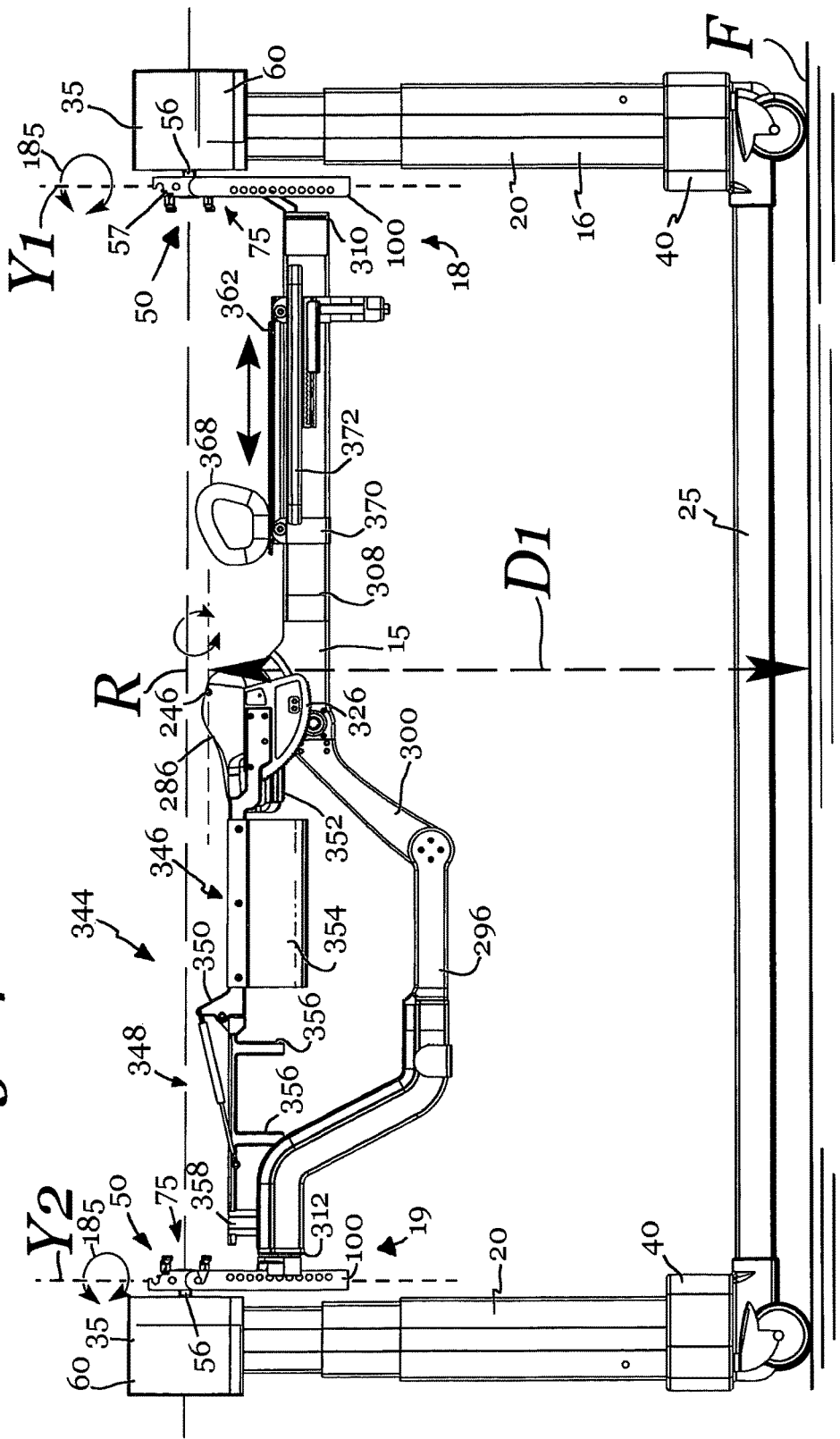
FIG. 4 is reduced right side view of the patient positioning support system of FIG. 1.
Figure 5:
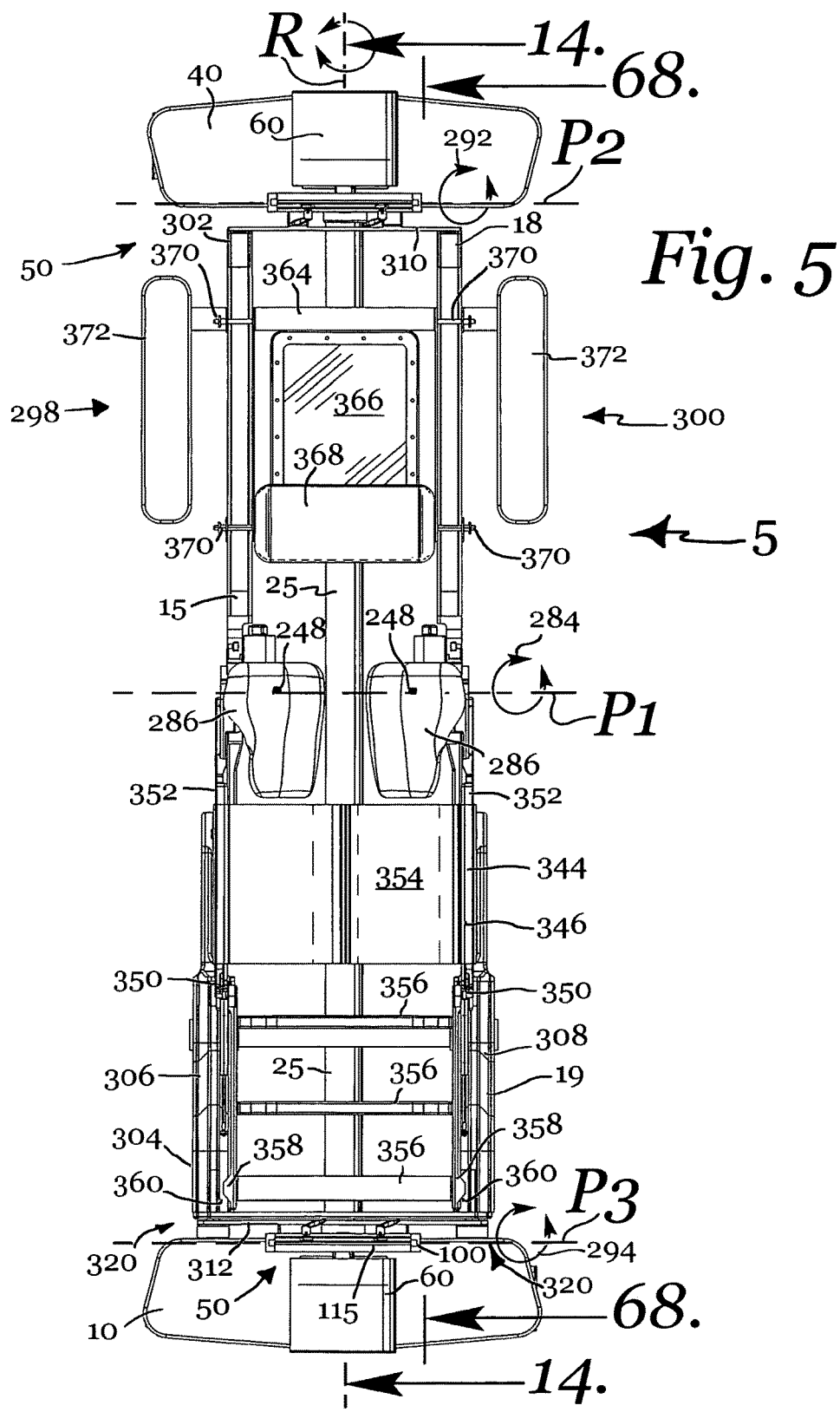
FIG. 5 is a top view of the patient positioning support system of FIG. 4.
Figure 6:
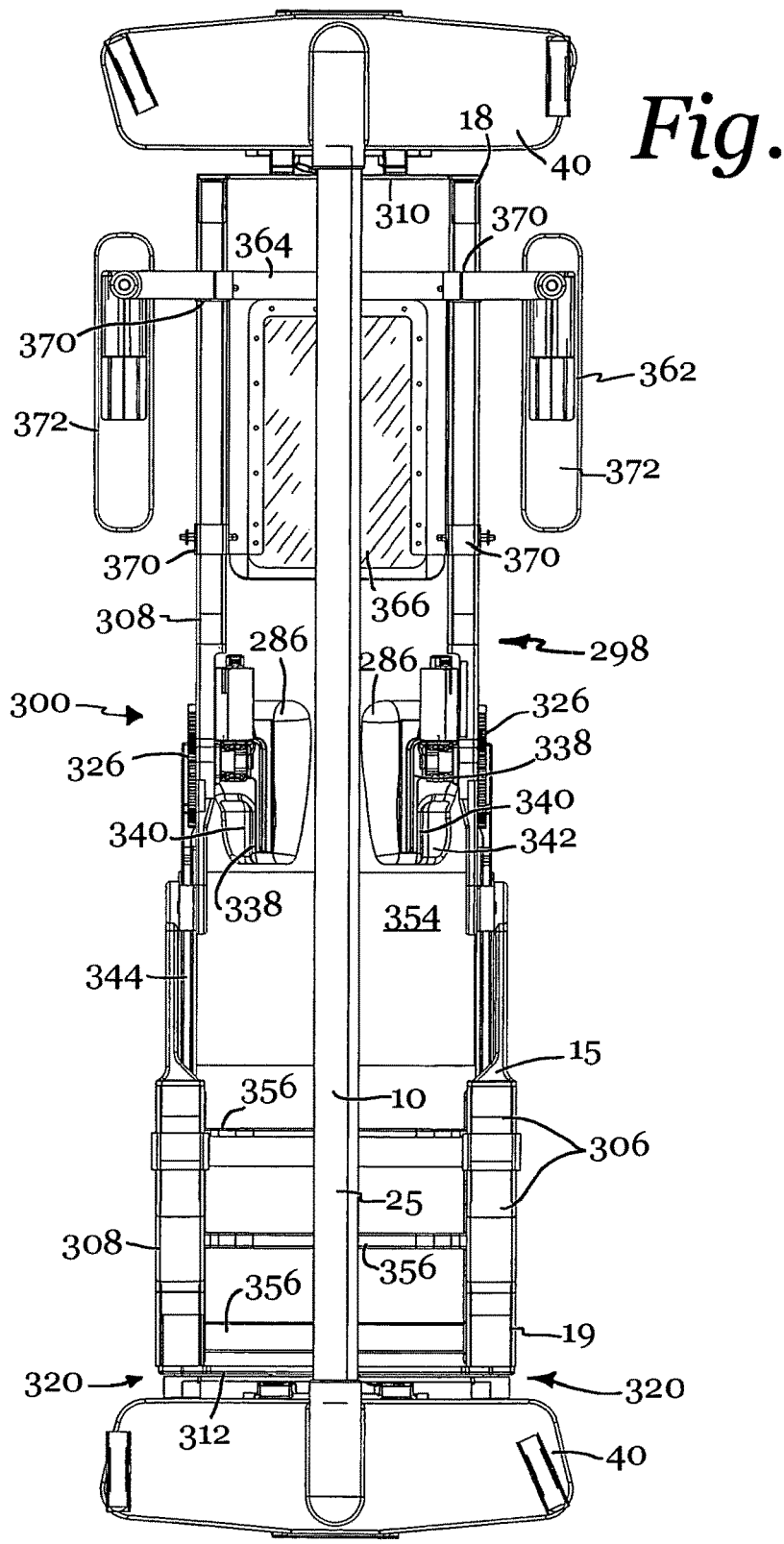
FIG. 6 is a bottom view of the patient positioning support system of FIG. 4.
Figure 7:
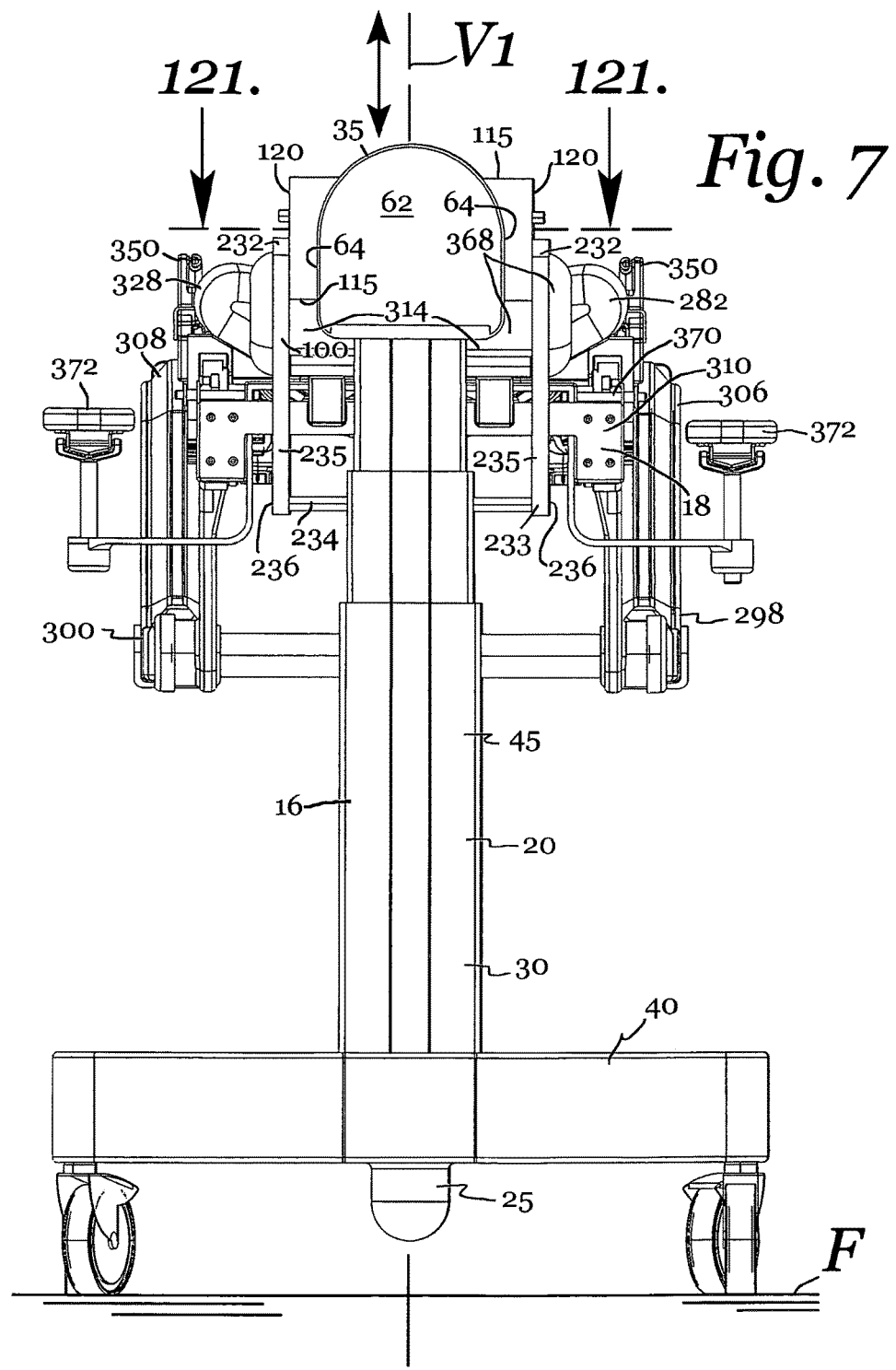
FIG. 7 is a head-end view of the patient positioning support system of FIG. 4.
Figure 8:
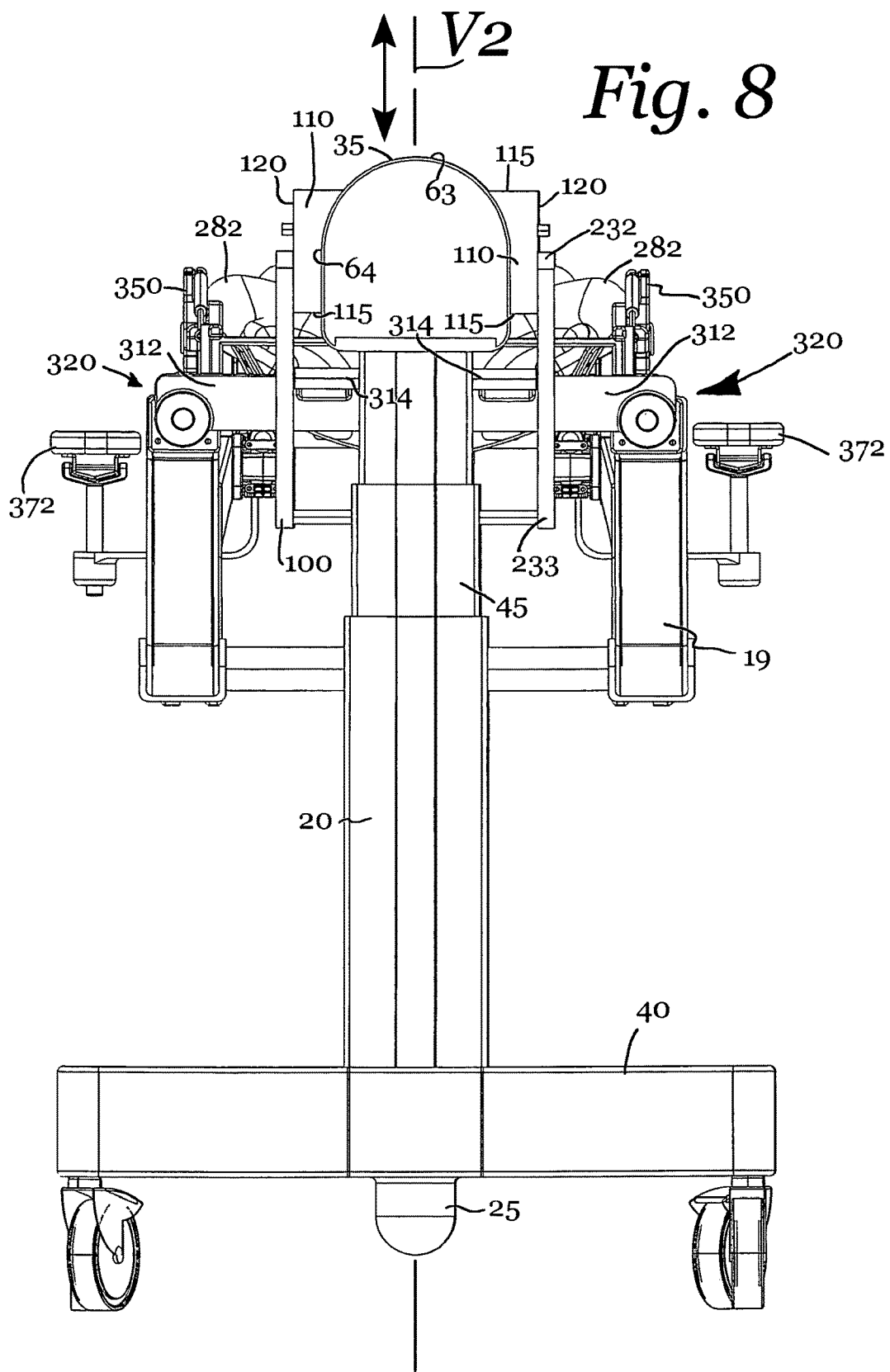
FIG. 8 is a foot-end view of the patient positioning support system of FIG. 4.
Figure 9:
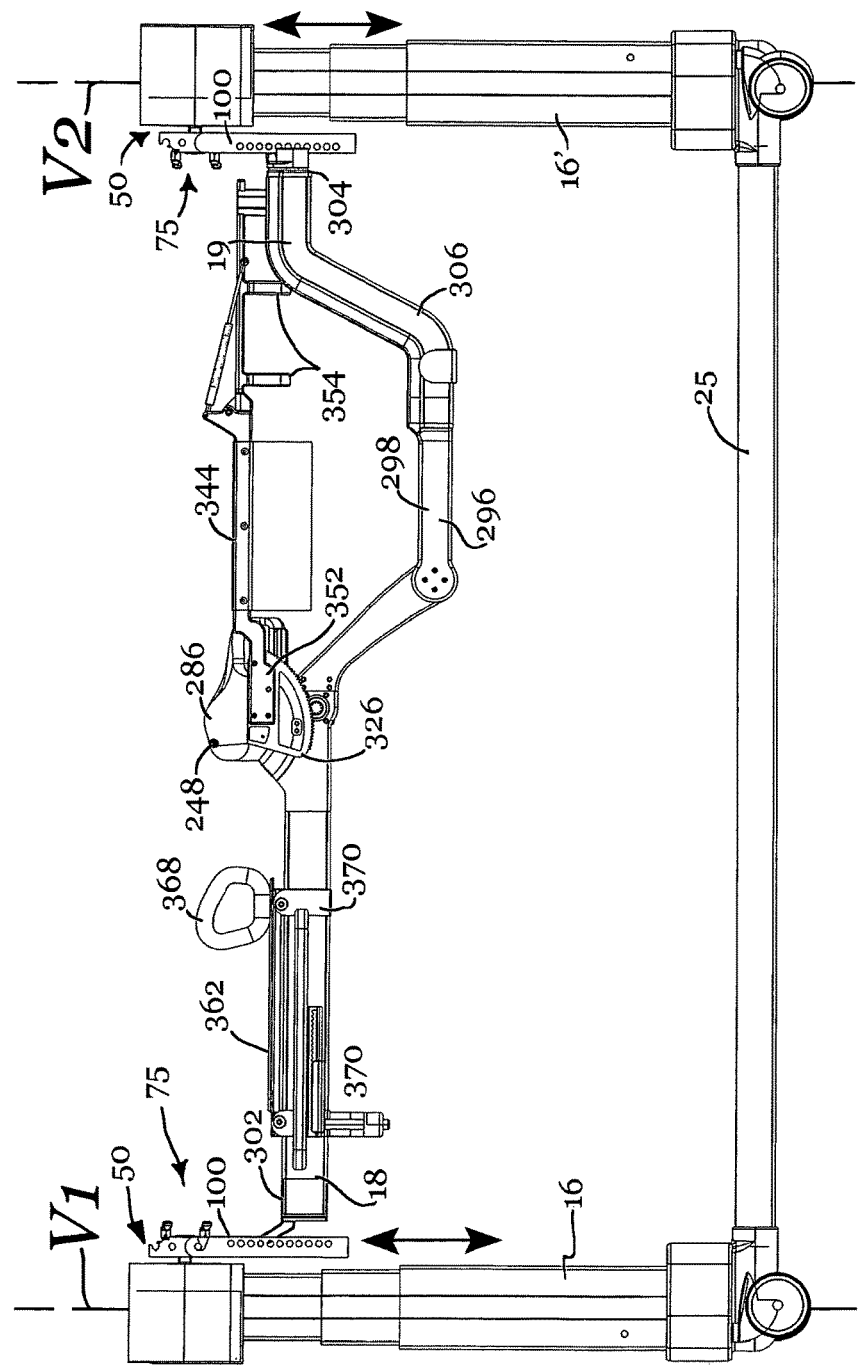
FIG. 9 is reduced left side view of the patient positioning support system of FIG. 1.
Figure 24:
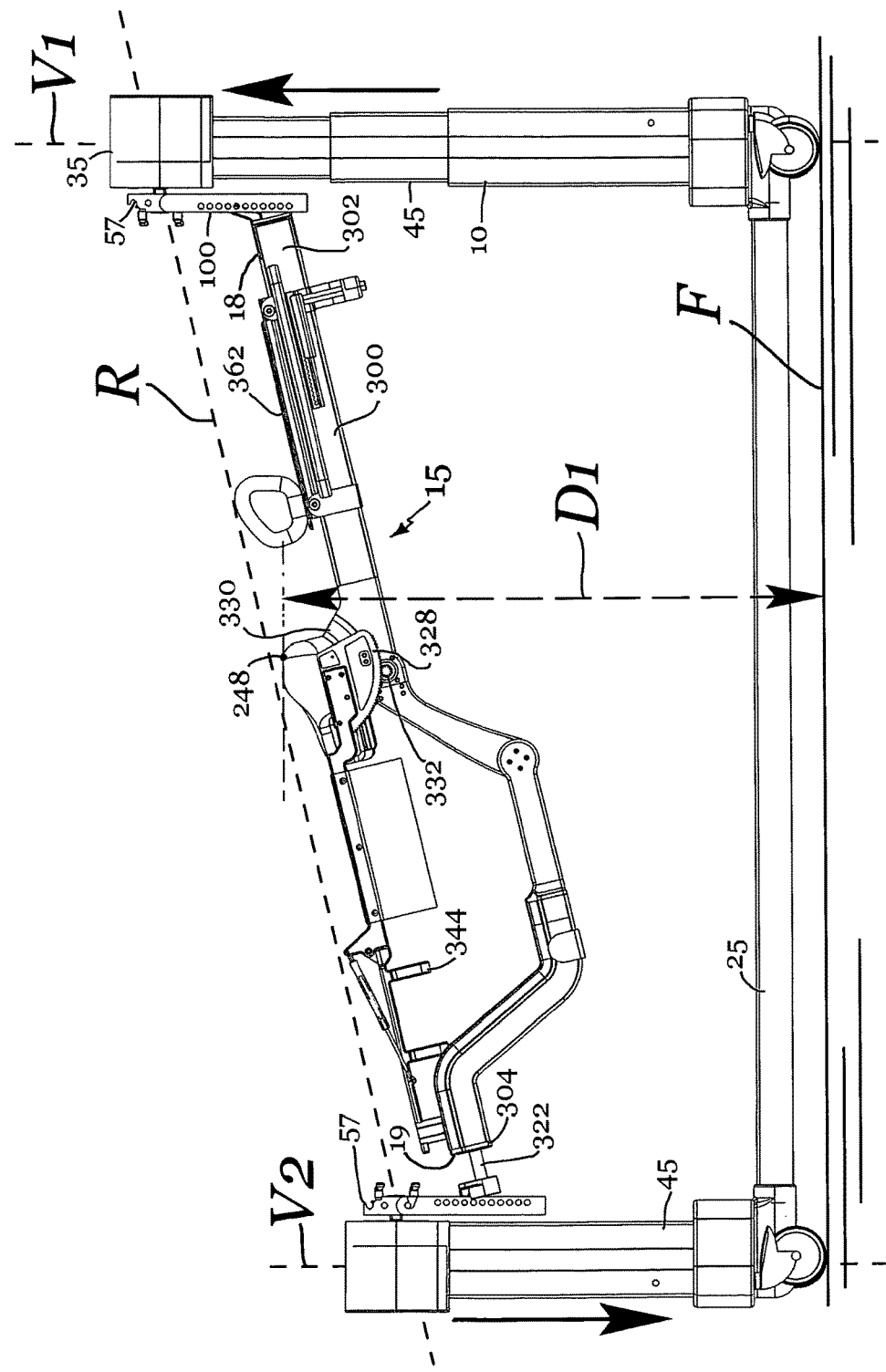
FIG. 24 is a right side view of the patient positioning support system of FIG. 23.
Figure 25:
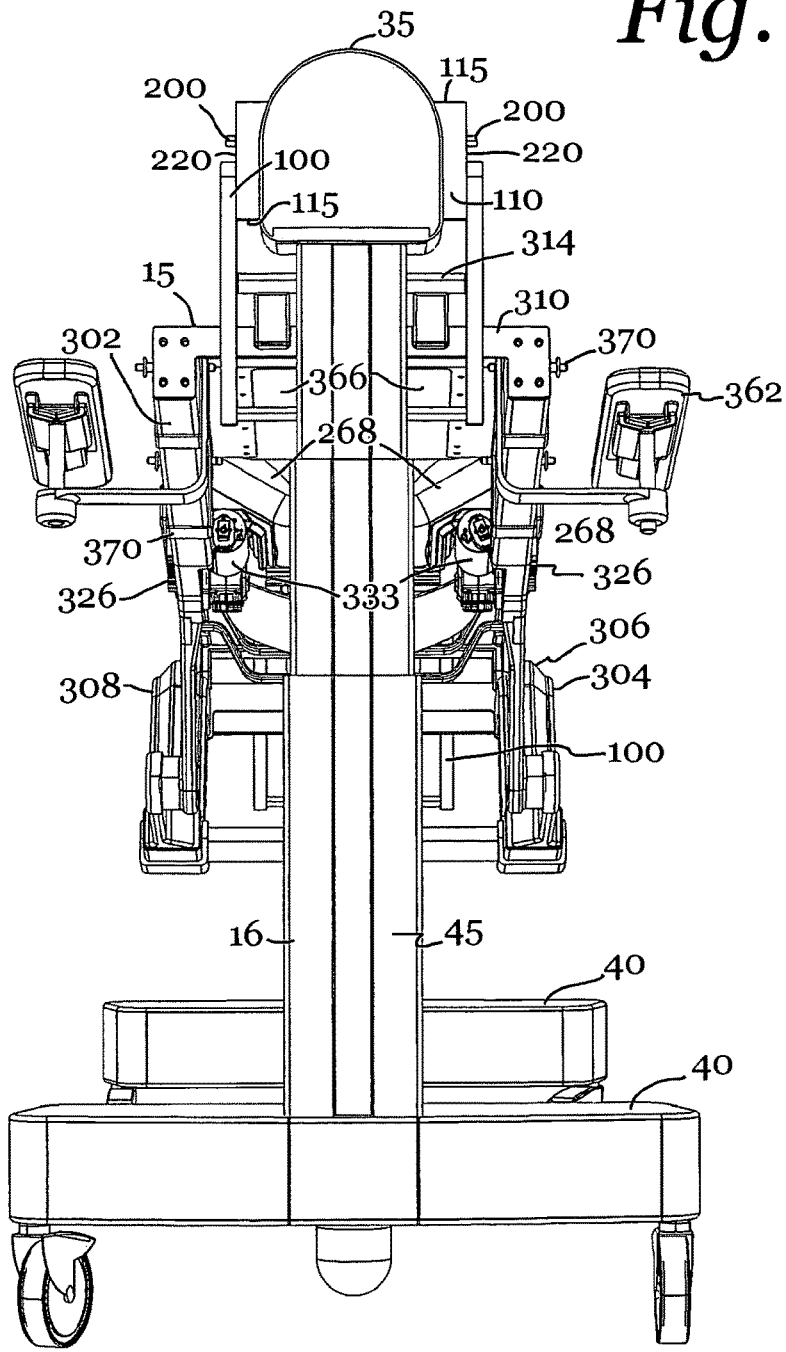
FIG. 25 is a head-end view of the patient positioning support system of FIG. 23.
Figure 26:
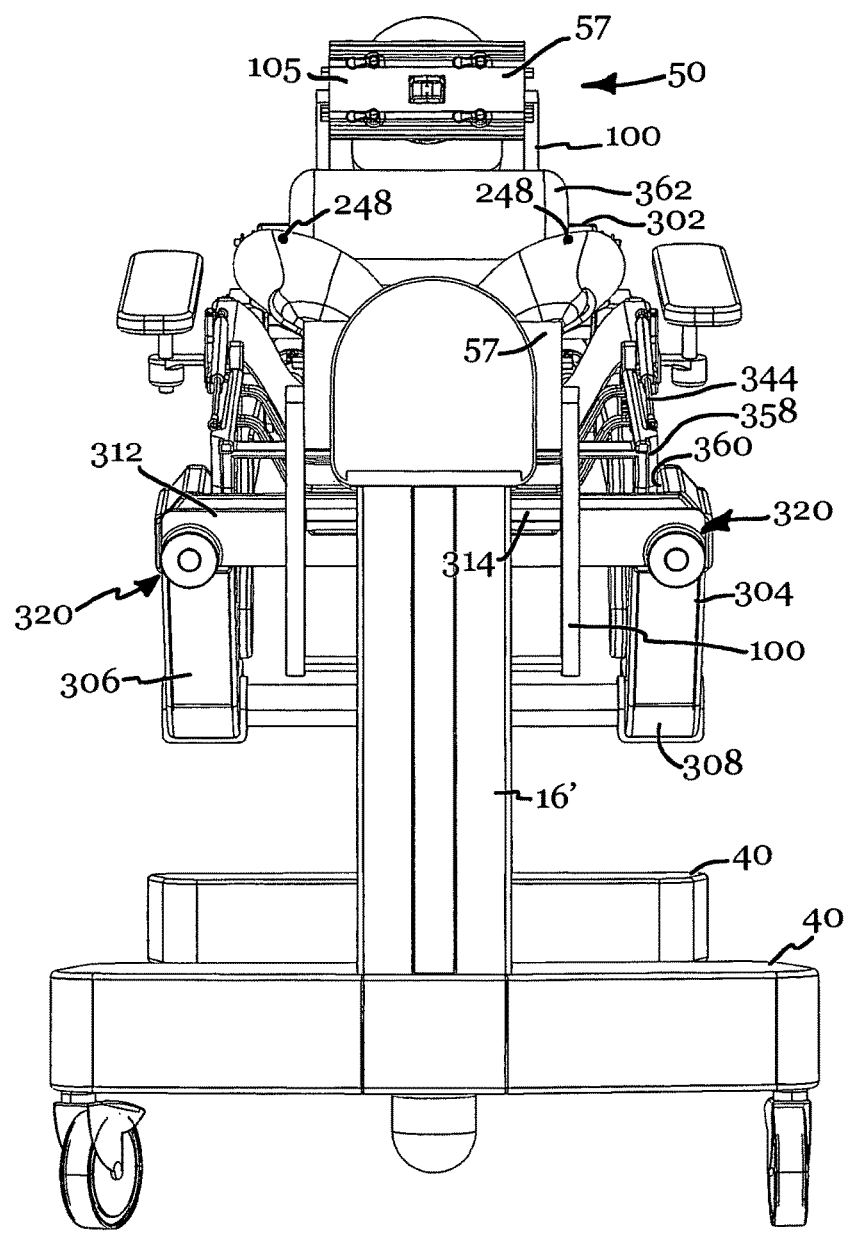
FIG. 26 is a foot-end view of the patient positioning support system of FIG. 23.
Figure 27:
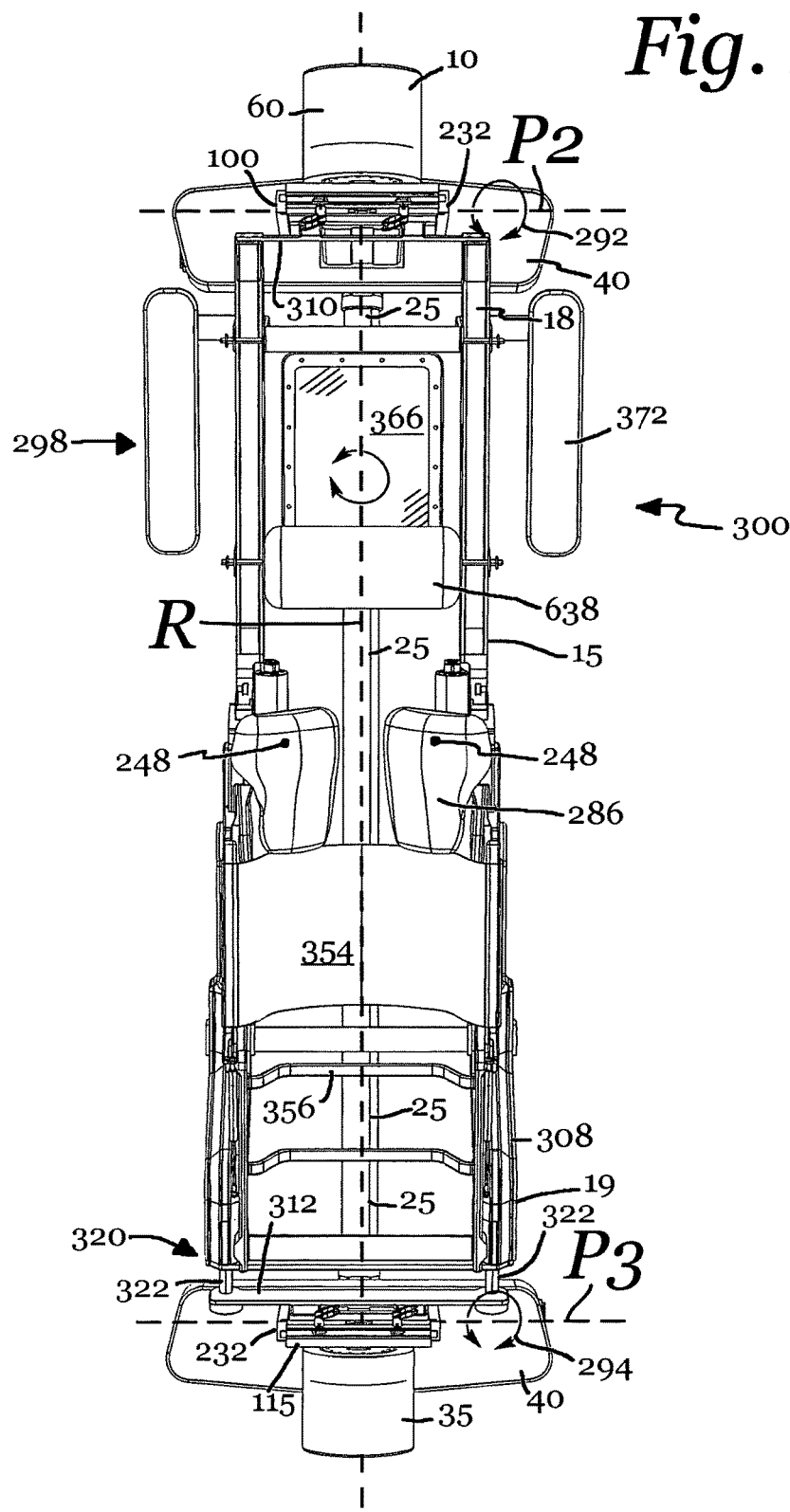
FIG. 27 is a top view of the patient positioning support system of FIG. 23.
Figure 32:
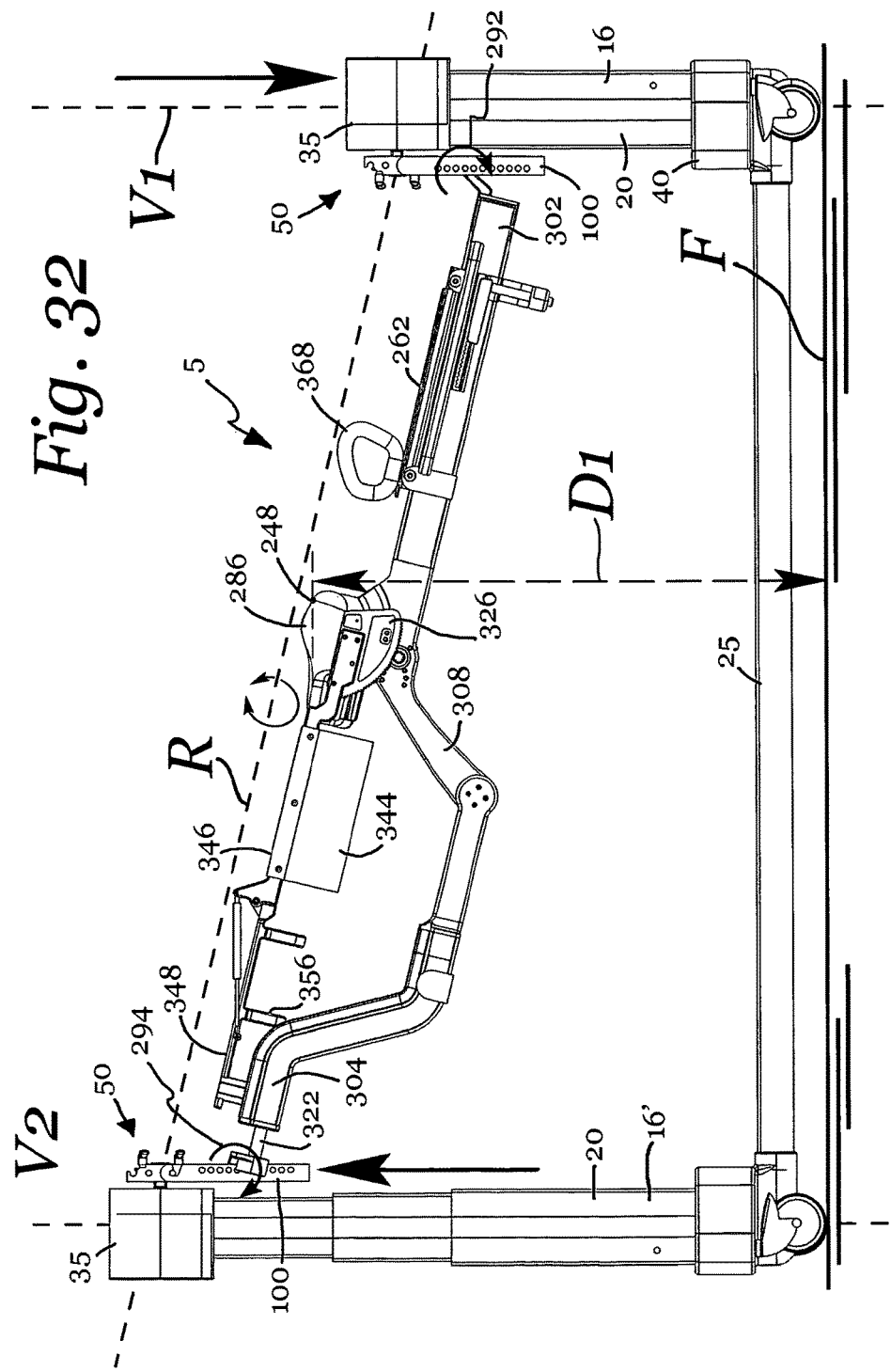
FIG. 32 is a right side view of the patient positioning support system of FIG. 31.
Figure 33:
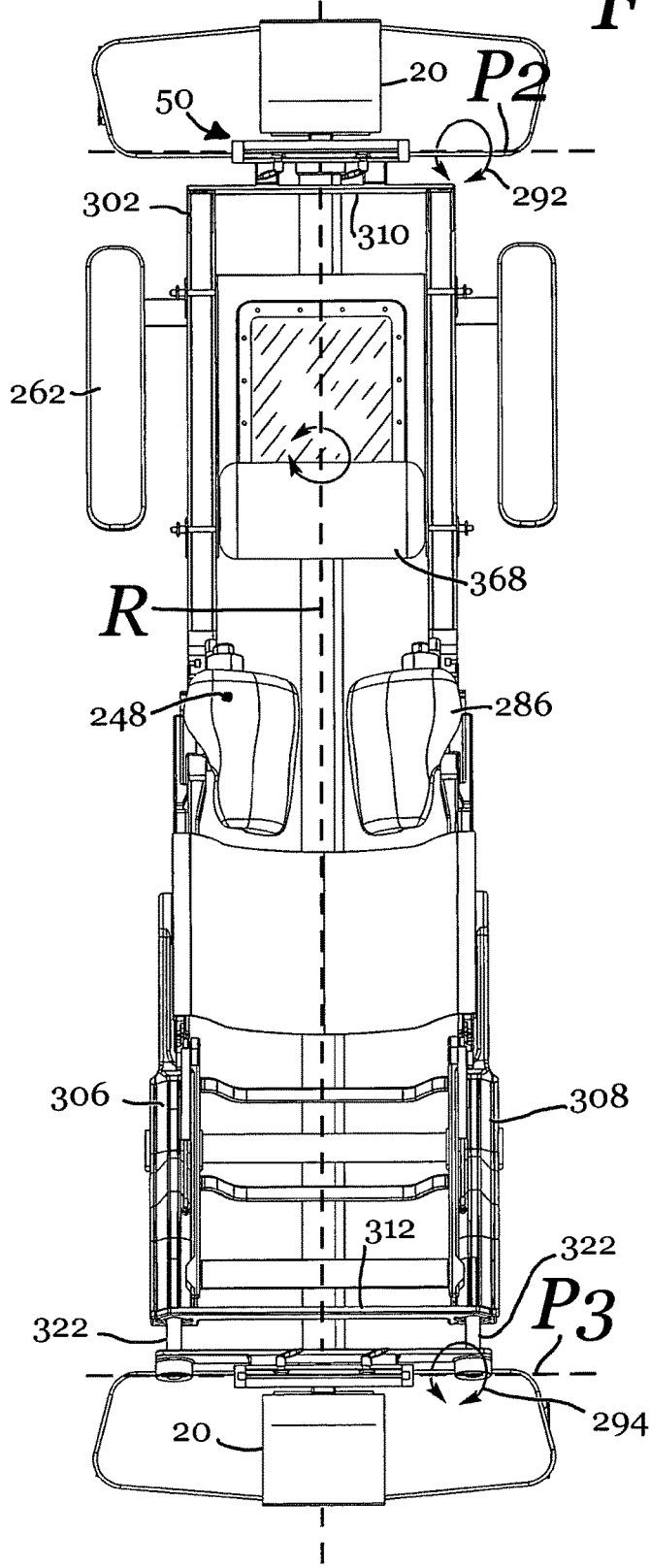
FIG. 33 is a head-end view of the patient positioning support system of FIG. 31.
Figure 34:
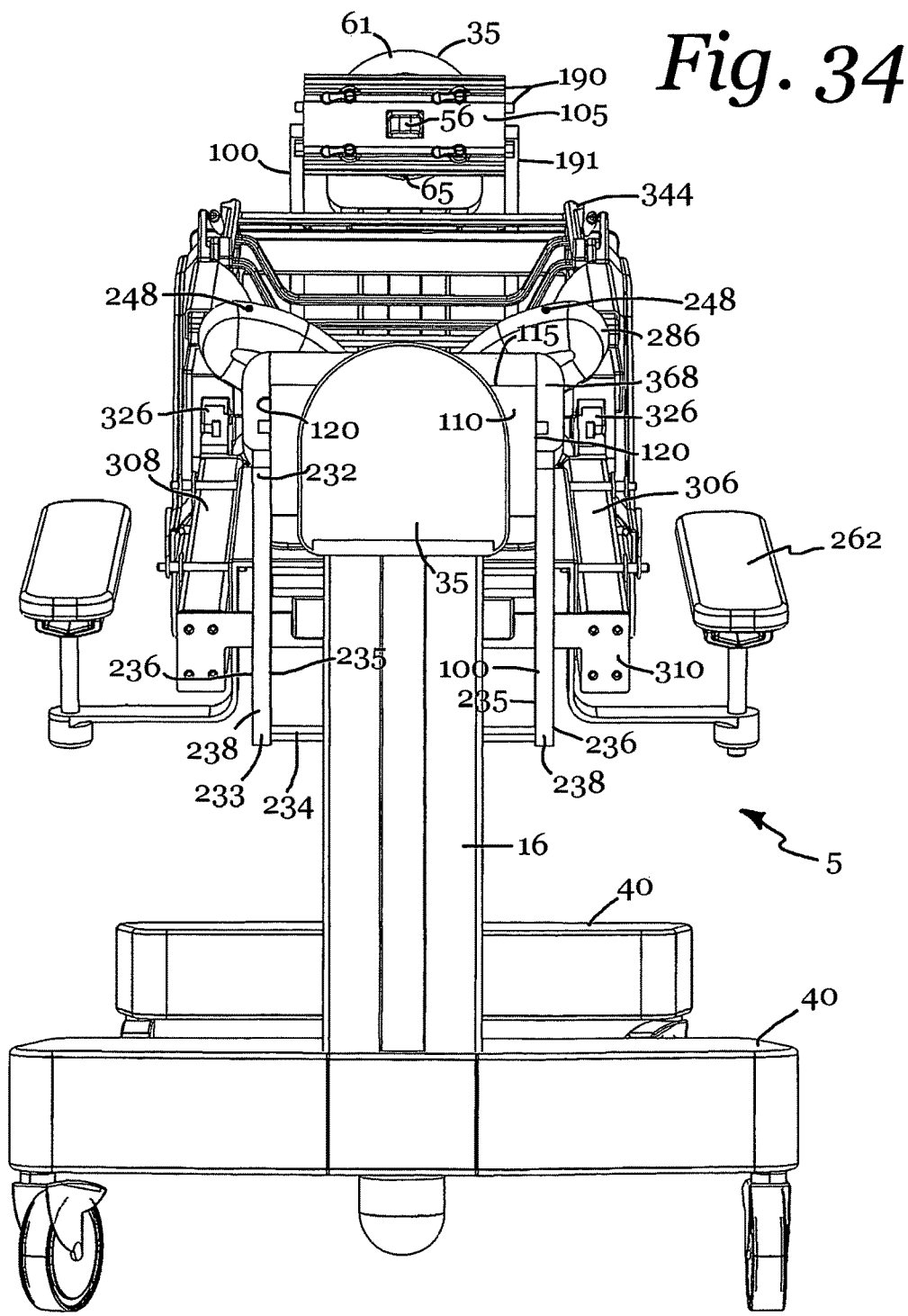
FIG. 34 is a foot-end view of the patient positioning support system of FIG. 31.
Figure 35:
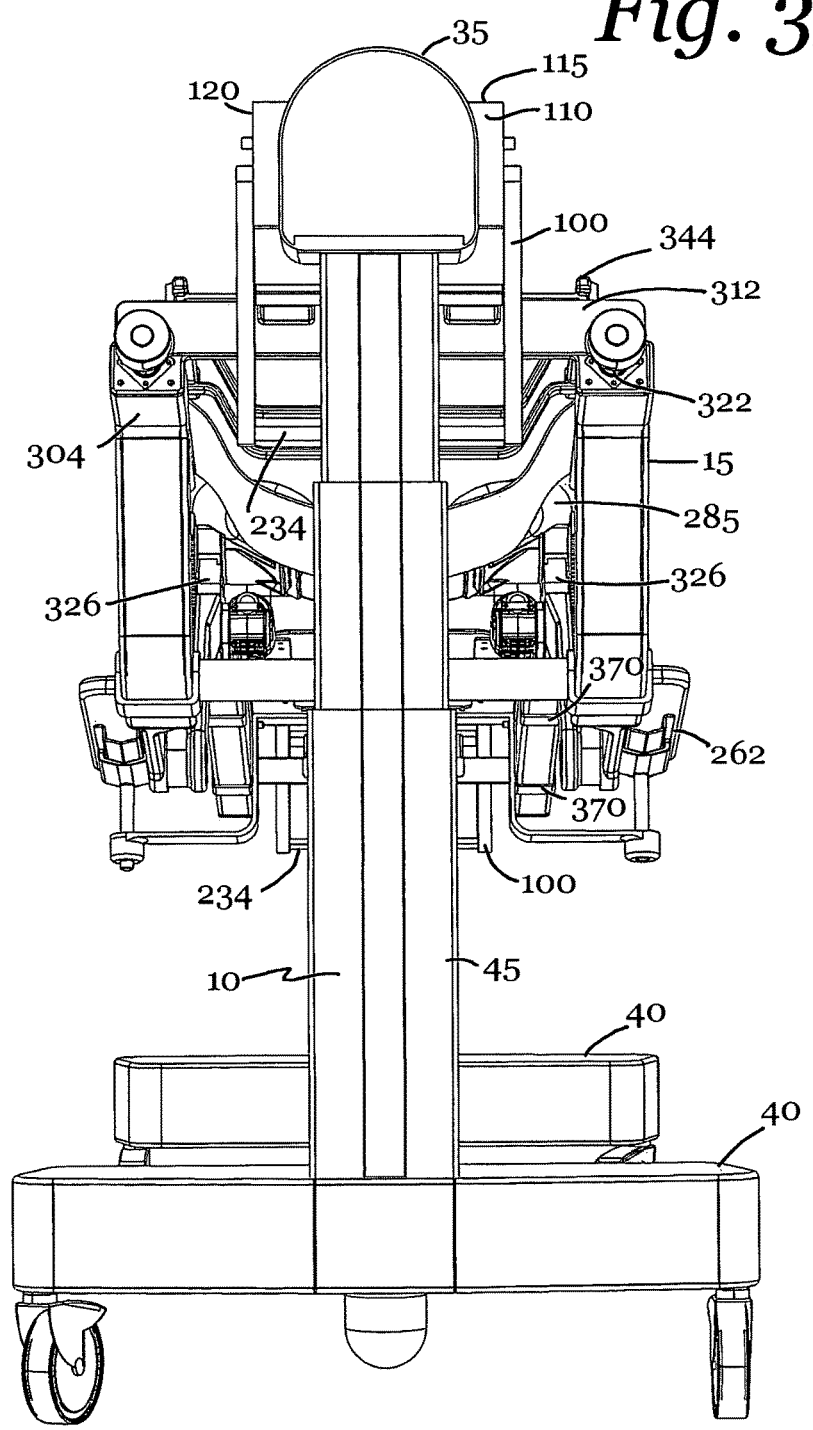
FIG. 35 is a top view of the patient positioning support system of FIG. 31.
Figure 40:
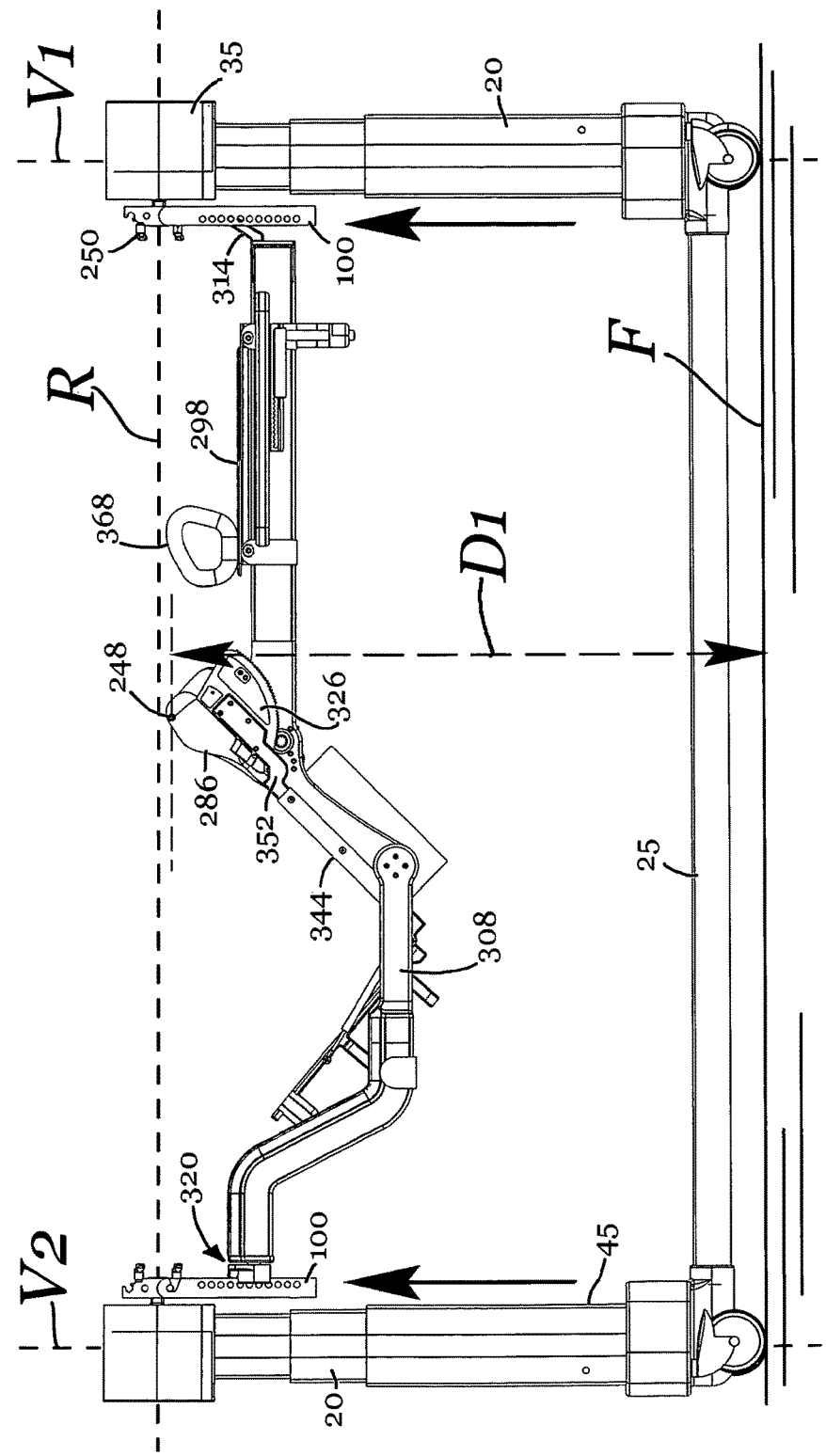
FIG. 40 is a right side view of the patient positioning support system of FIG. 39.
Figure 41:
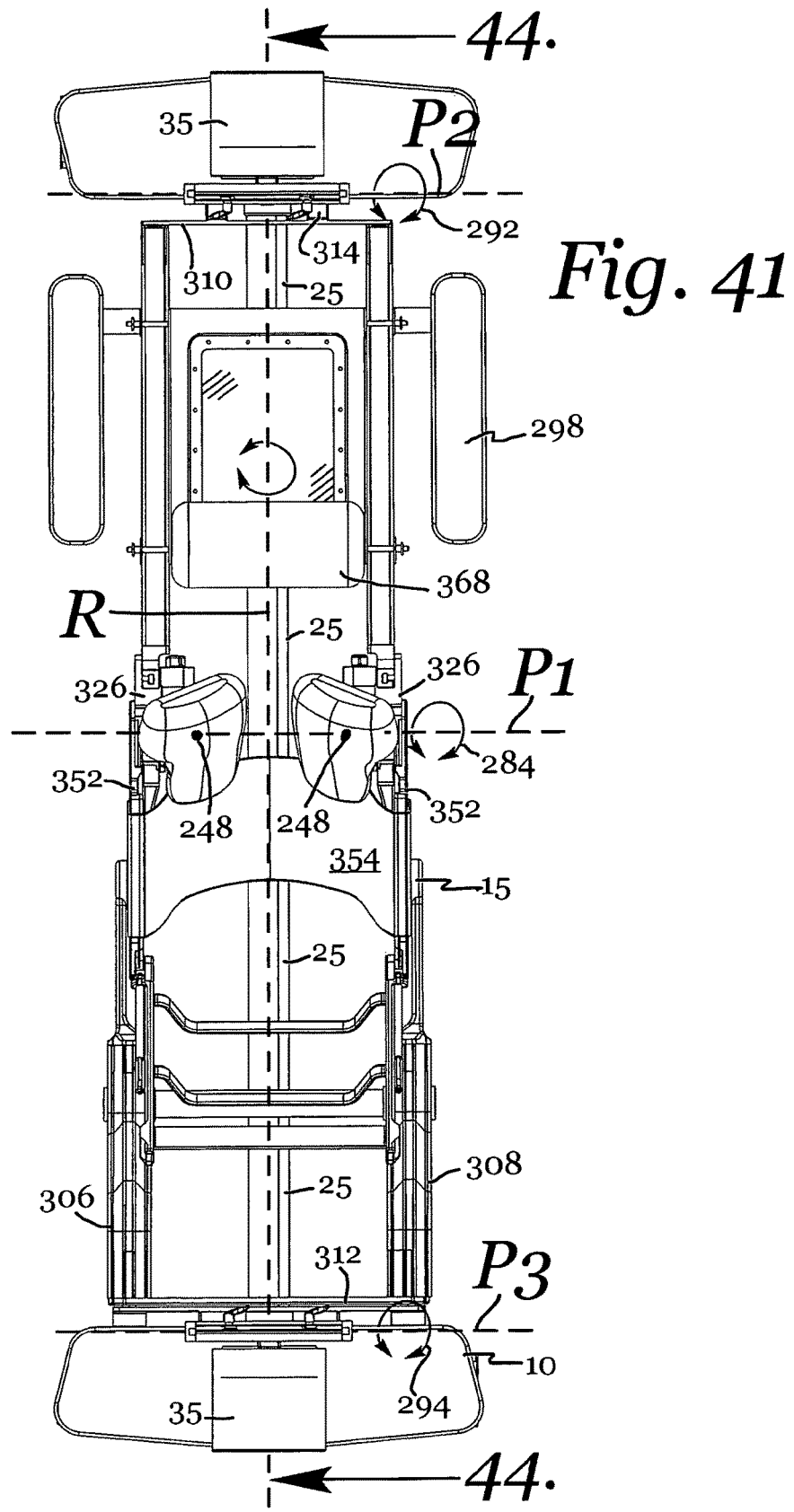
FIG. 41 is a top view of the patient positioning support system of FIG. 39.
Figure 42:
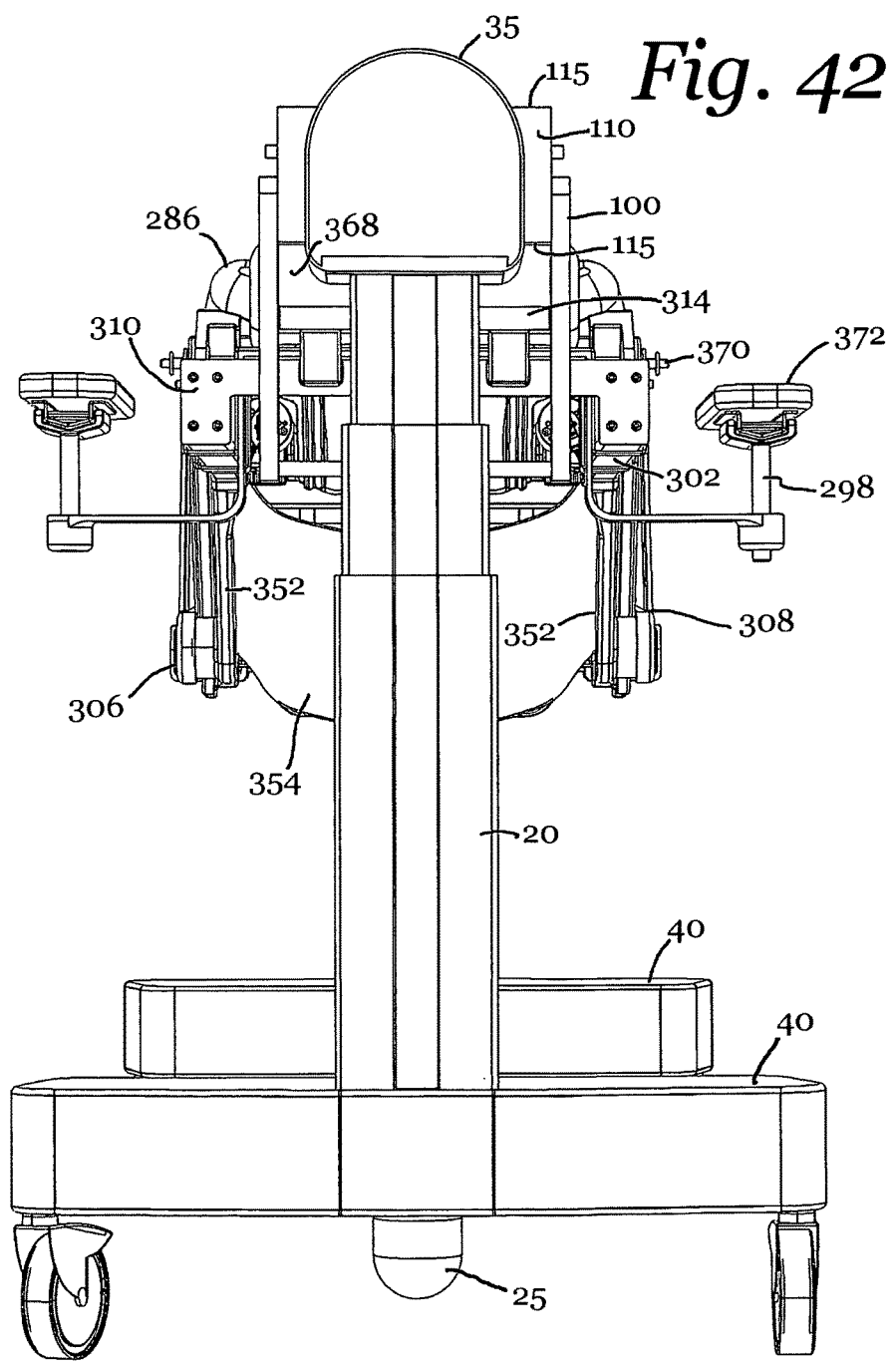
FIG. 42 is a head-end view of the patient positioning support system of FIG. 39.
Figure 43:
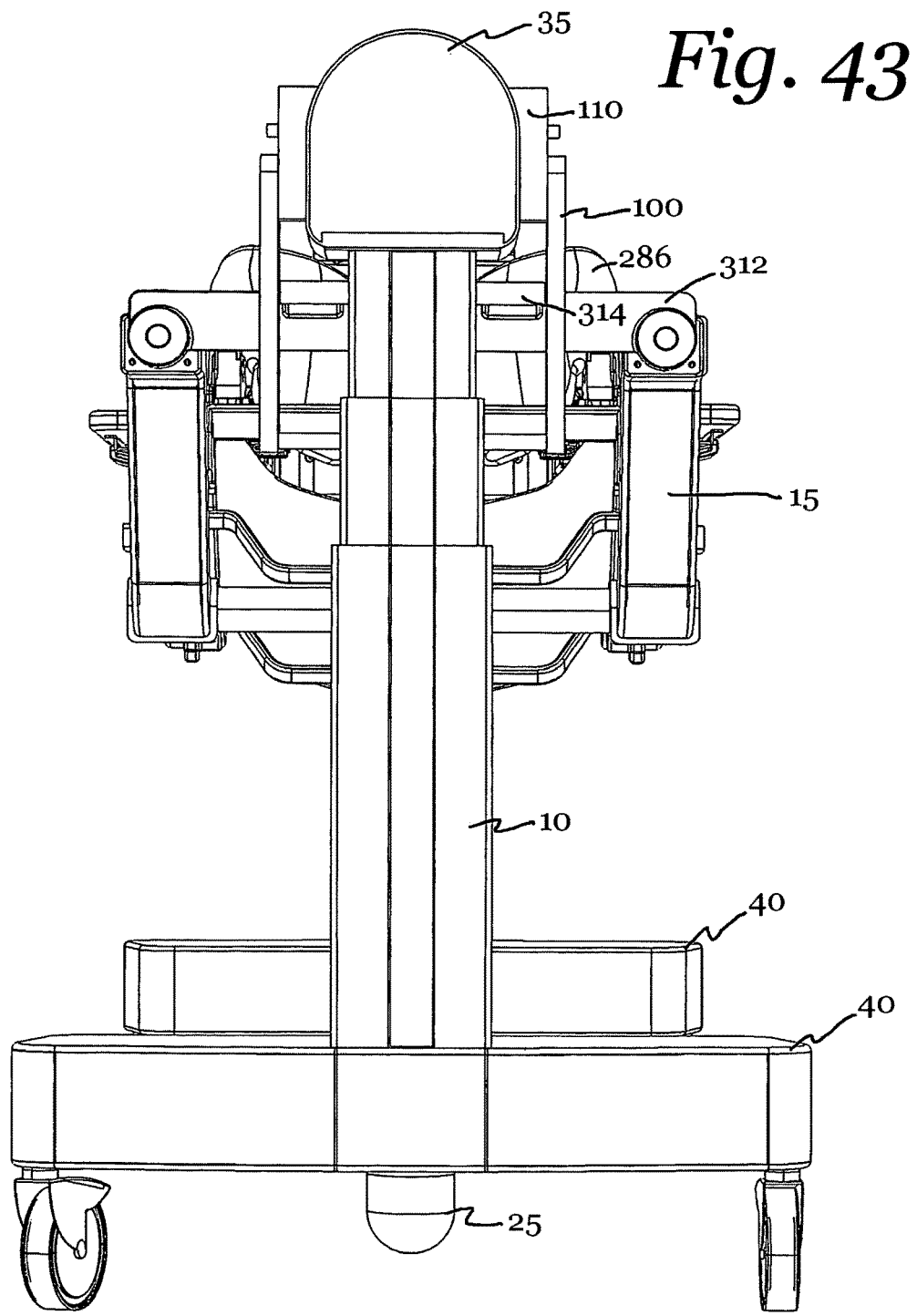
FIG. 43 is a foot-end view of the patient positioning support system of FIG. 39.
Figure 44:
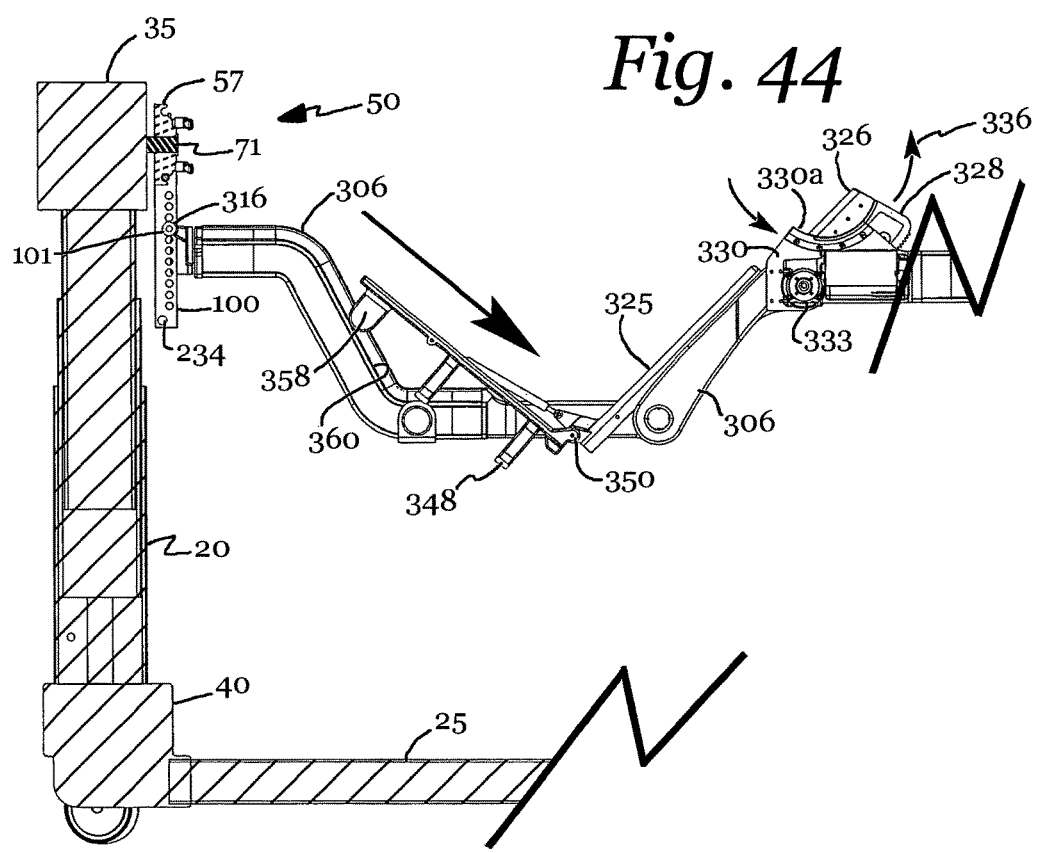
FIG. 44 is an enlarged cross-section of the patient positioning support system of FIG. 39, with the cross-section being taken along the line 44-44 of FIG. 41, and with portions broken away.

Referring now to FIG. 121, which is a top cross-section of the patient positioning support system 5 taken along line 121-121 of FIG. 7, the rotation shaft 56 is generally cylindrical in shape, with a circular cross-section, and is substantially parallel with the floor F. The rotation shafts 56, of the opposed vertical translation subassembly upper portions 35, are each movable with respect to an associated vertical translation axes V1 or V2, so as to be locatable or placeable at a selectable distance above the floor F. When the opposed rotation shafts 56, of two vertical translation subassemblies 20, are equally spaced above the floor F, such as is shown in FIGS. 4 and 40, the rotation shafts 56 are also substantially coaxial with the roll axis R. However, when the rotation shafts 56 is raised or lowered, such that the shafts 56 are no longer equally spaced from the floor F, such as is shown in FIGS. 24 and 32, the rotation shafts 56 intersect roll axis R but a not coaxial with the roll axis R.

Each rotation shaft 56 includes inner and outer portions, 70, 71, respectively. The rotation shaft inner portion 70 is engaged by and cooperates with the rotation motor 55, so as to be rotatable in either the clockwise or counter-clockwise directions, such as is illustrated in FIGS. 91a-94a, FIGS. 134-136, and FIGS. 165-169.

The outer portion 71 of the rotation shaft 56 includes a substantially cylindrical side surface 76 with opposed side surface openings (not shown), an outer or inboard face 77 and a through-channel 78 that joins the side surface openings and extends through the outer portion 71 so as to form a bore-like structure. Thus, the interior of the through-channel 78 is joined with the side surface 76 by the surface openings. As noted below, the through-channel 78 of the rotation shaft outer portion 71 is sized to receive a yaw pin therethrough, so as to join the shaft outer portion 71 with the associated rotation block 57.

The rotation shaft outer portion 71 extends out of the housing 60 and in an inboard direction toward the upper portion 35 of the opposed vertical translation subassembly 20. The outer portion 71 is joined with the rotation block 57, also referred to as a connection member or first portion, by a yaw pin 79, inner connector shaft, peg, post or connector, that extends through the shaft outer portion through-channel 78 and into the rotation block 57. Each yaw pin 79 is coaxial with a respective yaw axis Y1 or Y2, so as to enable the rotation block 57 to rotate at least a small amount the yaw axis Y1 or Y2. One or more bushings 80 sleeve at least a portion of the yaw pin 79, such as is shown in FIGS. 13-22 and 121, so as to reduce friction and to secure the yaw pin 79 to the shaft outer portion 71.

In some embodiments, a rotation plate 65 joins the inner and outer portions 70 and 71 of the rotation shaft 56. The rotation plate 65 may also be referred to as an optional front plate 65 of the housing 60. The rotation plate 65 may be integral with or separate from the rotation shaft 56. In some embodiments, the housing front portion 61 includes, and is optionally integral with, the rotation plate 65, which functions as a face plate that covers and protects the inboard side 85 of the rotation motor 55. It is foreseen that the patient positioning support system 5 may include no front or rotation plate 65.

The base 10 includes a pair of connection subassemblies 75, for reversible attachment with a patient support structure 15°. Each connection subassembly 75 includes a respective rotation block 57, a ladder 100 or 100' and a T-pin 101. The T-pin 101 includes a rod portion 102 and a handle portion 103. In the illustrated embodiment, connection subassemblies 57 are each joined with one of the vertical translation subassemblies 20, such as but not limited to by a respective rotation subassembly 50. The rotation block 57, also referred to as a ladder connection block 57, is reversibly attachable or connectable to at least one ladder structure 100, 100', which in turn is reversibly attachable to an end of the patient support structure 15°, such as is described below. The connection subassemblies 57 provide structure for removably connecting, attaching or joining the base 10 with a patient support structure 15°. In the illustrated embodiment, the head-end and foot-end rotation blocks 57 are substantially identical, or mirror images of one another; however, it is foreseen that one or both of the blocks 57 may have an alternative size, shape and additionally or alternatively configuration.

The connection subassemblies 57 provide structure for at least some vertical translation, or height adjustment, of an attached patient support structure 15°, such as is described below. Further, the two connection subassemblies 57 cooperate with each other and optionally with the patient support structure 15°, to provide structure for a fail-safe structure or mechanism, such as is described below. The fail-safe substantially blocks incorrect detachment of an attached patient support structure 15°, wherein such incorrect detachment can result in catastrophic collapse of at least a portion of the patient positioning support system 5 and patient injury.

Referring to FIGS. 13-22 and 121, each rotation block 57 is generally block-shaped and includes spaced opposed front and rear faces 105, 110, spaced opposed top and bottom faces 115 and spaced opposed end faces 120. The faces may also be referred to as sides, ends, surfaces or portions. In the illustrated embodiment, the faces of each pair of opposed faces, such as the front and rear faces 105, 110, the top and bottom faces 115, and the end faces 120, are substantially parallel with one another; but, it is foreseen that this may not be the case in other embodiments.

The rotation block front face 105 includes a front surface 123 with a centrally located front opening 125 and at least one rail-receiving groove 127 or channel. In the illustrated embodiment, the front 105 includes a pair of parallel rail-receiving grooves 127, which are denoted as first and second rail-receiving grooves 128 and 129, respectively, with reference to the figures. In some circumstances, the first rail-receiving groove 128 may also be referred to as an upper rail-receiving groove, and the second rail-receiving groove 129 may be referred to as a lower rail-receiving groove 129.

Each rail-receiving groove 127 includes a contoured inner surface 130 and an outer lip 131. The inner surface 130 and lip 131 are sized, shaped and configured to receive an upper rail 133 of a ladder 100, 100' therein. In the illustrated embodiment, the upper rail 133 is substantially cylindrical with a circular cross-section. Accordingly, the groove inner surface 130 and lip 131 are sized, shaped and configured to reversibly receive therein and to engage the cylindrical upper rail 133. In some embodiments, the contoured inner surface 130 is adapted to frictionally engage the upper rail 133. In an exemplary alternative embodiment, the ladder upper rail 133 is box-shaped with a square cross-section, and the rail-receiving groove 127 includes a complementary box shape with an inner surface 130 having planar surface portions and a lip 131 that are adapted to engage and retain the upper rail 133.

The rotation block rear face 110 includes a rear surface 134 and a centrally located rear opening 135. The surface 134 is generally flat and planar, but may include some non-planar portions, in some embodiments.

The block front and rear openings 125, 135 are joined by a block through-bore 140 or channel that is sized, shaped and adapted to receive at least a portion of the rotation shaft 56 therein, whereby by the block 57 is attached to the rotation shaft 56. In some embodiments, the rotation shaft 56 extends through the block through-bore 140.

Figure 15:
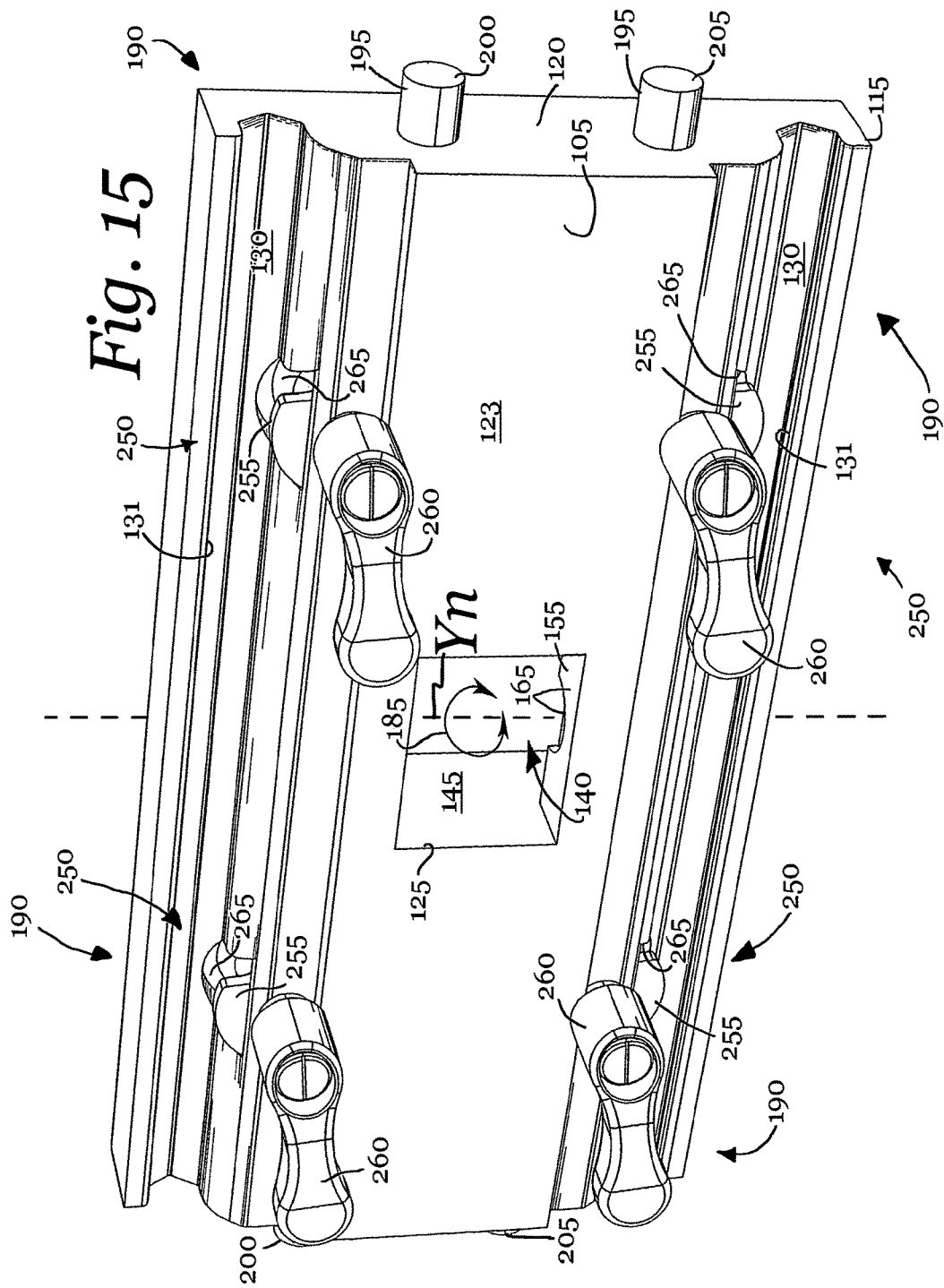
FIG. 15 is an enlarged perspective view of a ladder connection subassembly of the patient positioning support system of FIG. 1.
Figure 16:
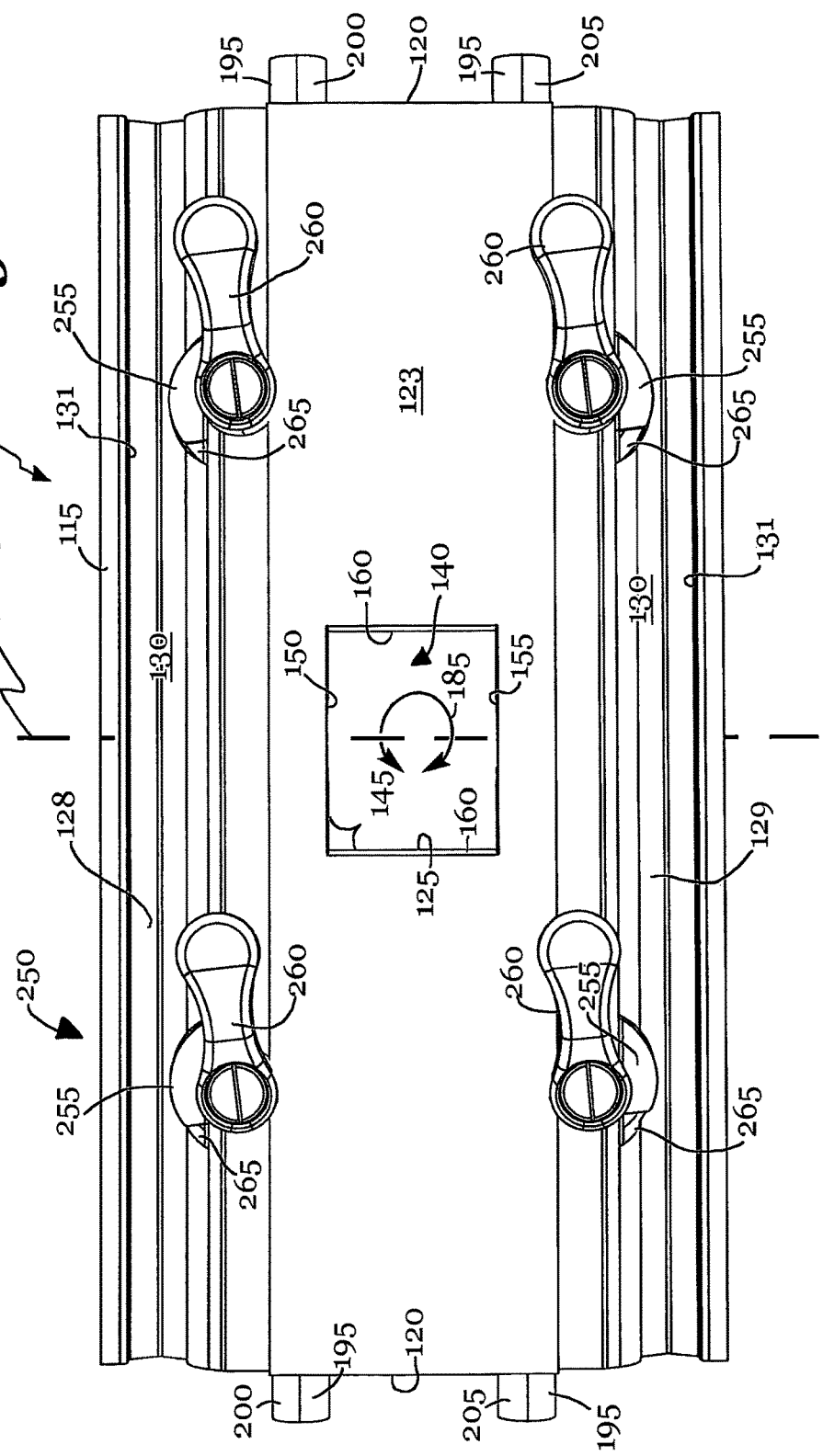
FIG. 16 is a front view of the ladder connection subassembly of FIG. 15.
Figure 17:
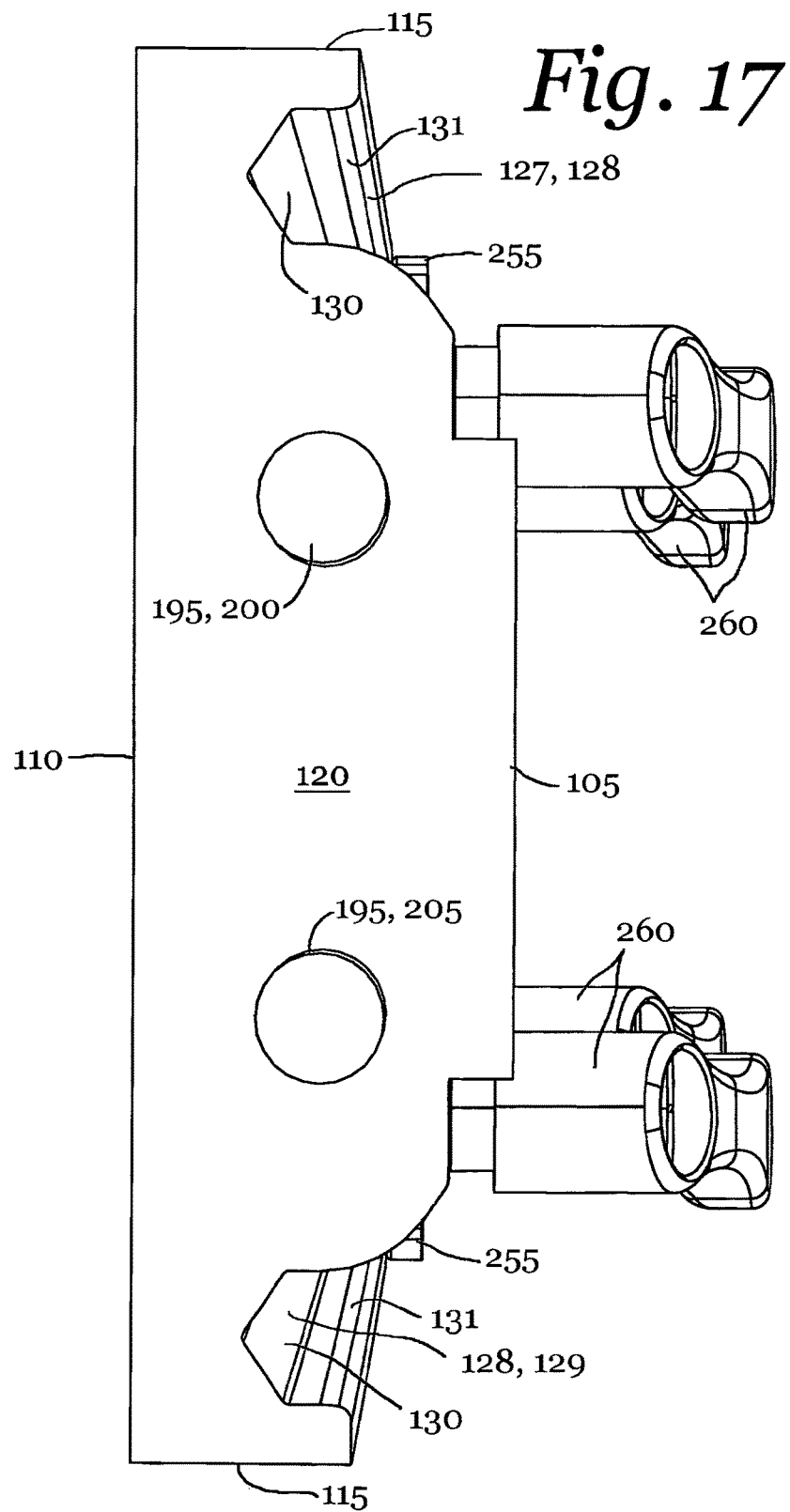
FIG. 17 is a first side view of the ladder connection subassembly of FIG. 15.
Figure 18:
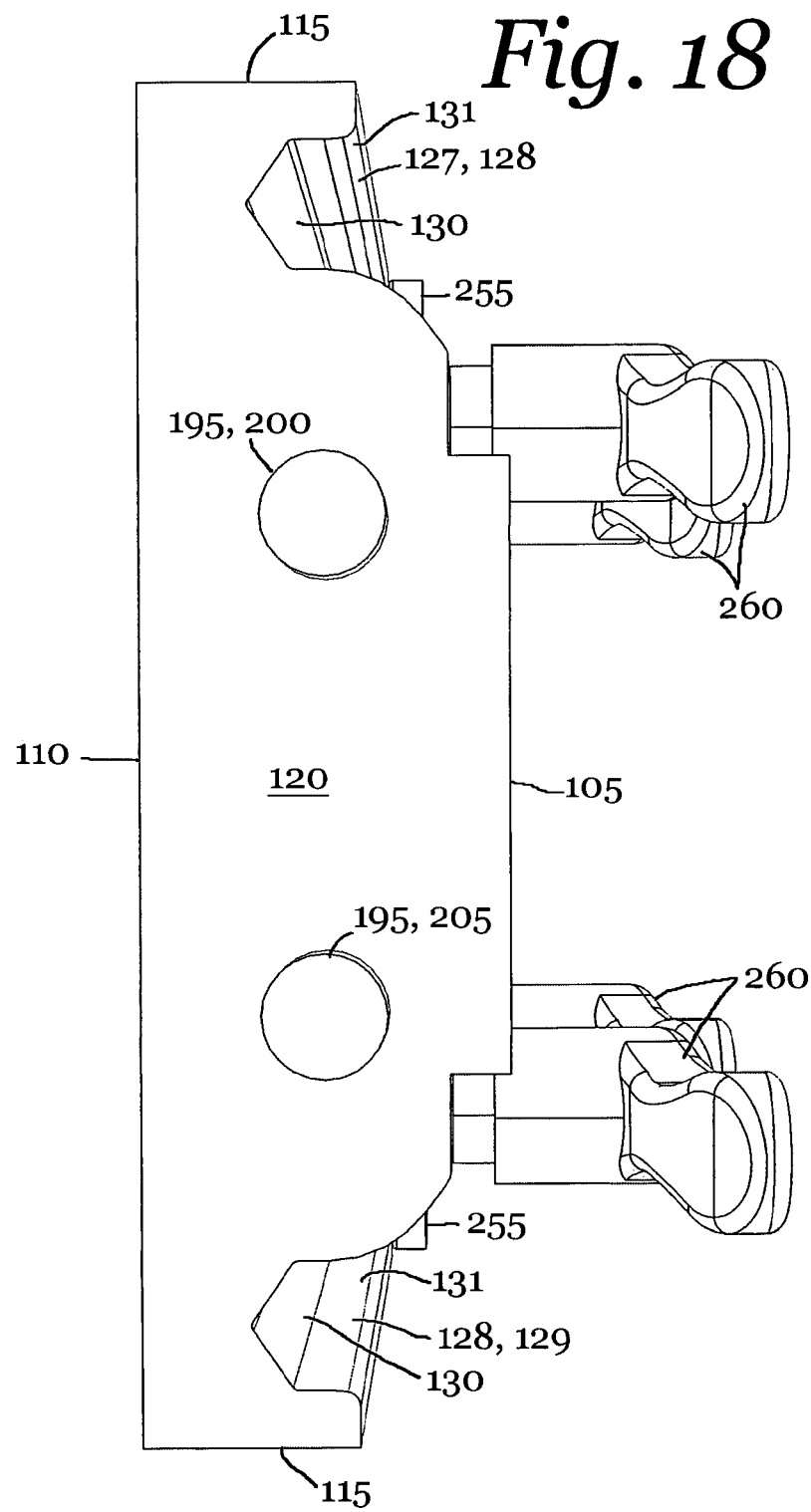
FIG. 18 is a second side view of the ladder connection subassembly of FIG. 15.
Figure 19:
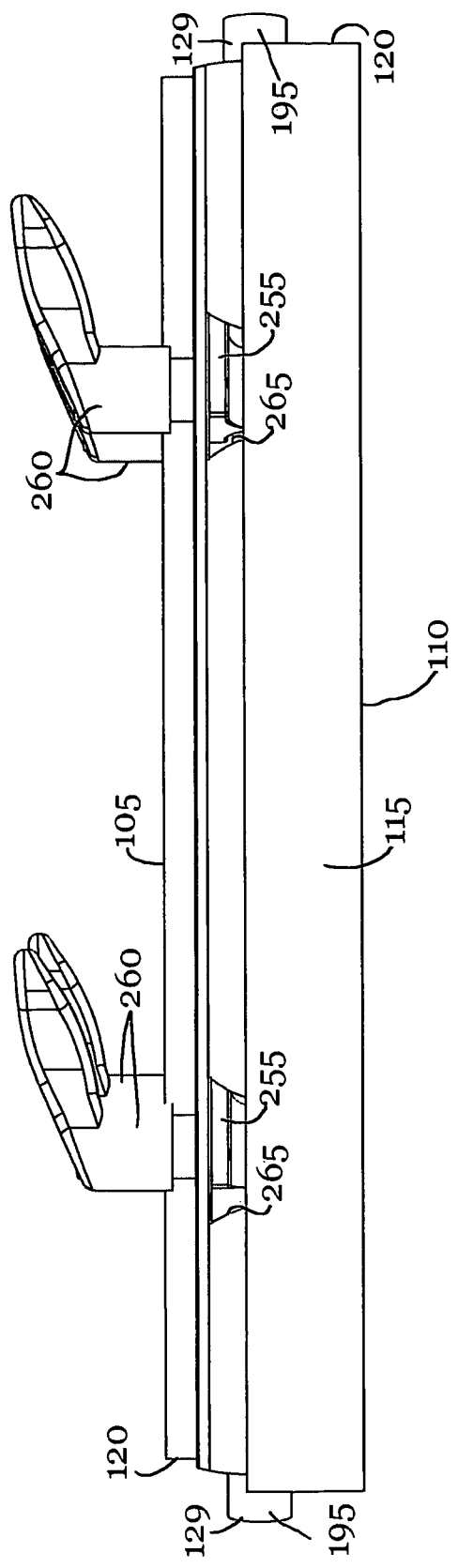
FIG. 19 is a top view of the ladder connection subassembly of FIG. 15.
Figure 20:
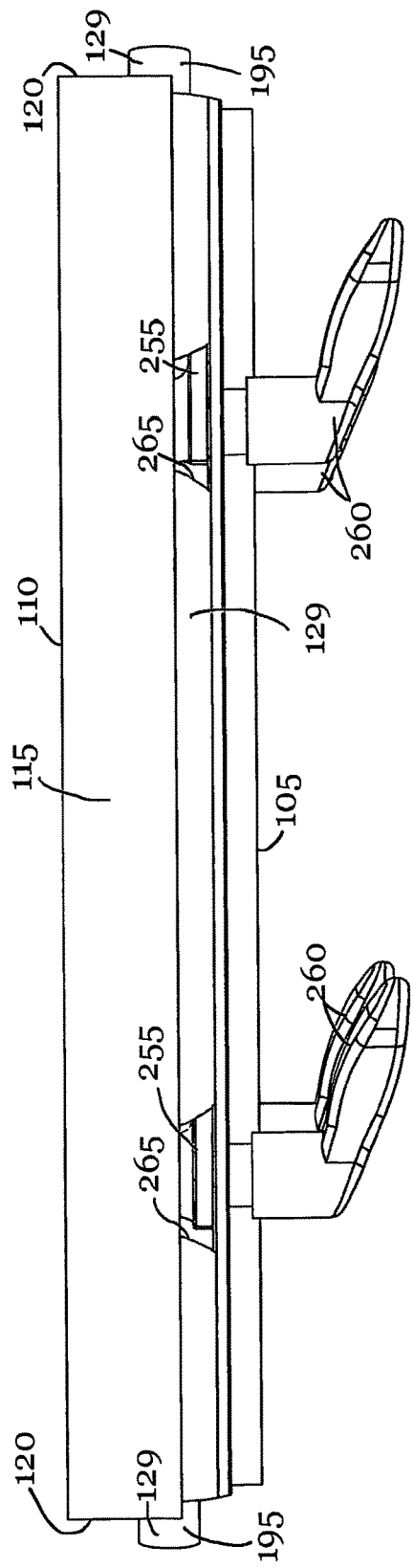
FIG. 20 is a bottom view of the ladder connection subassembly of FIG. 15.
Figure 21:
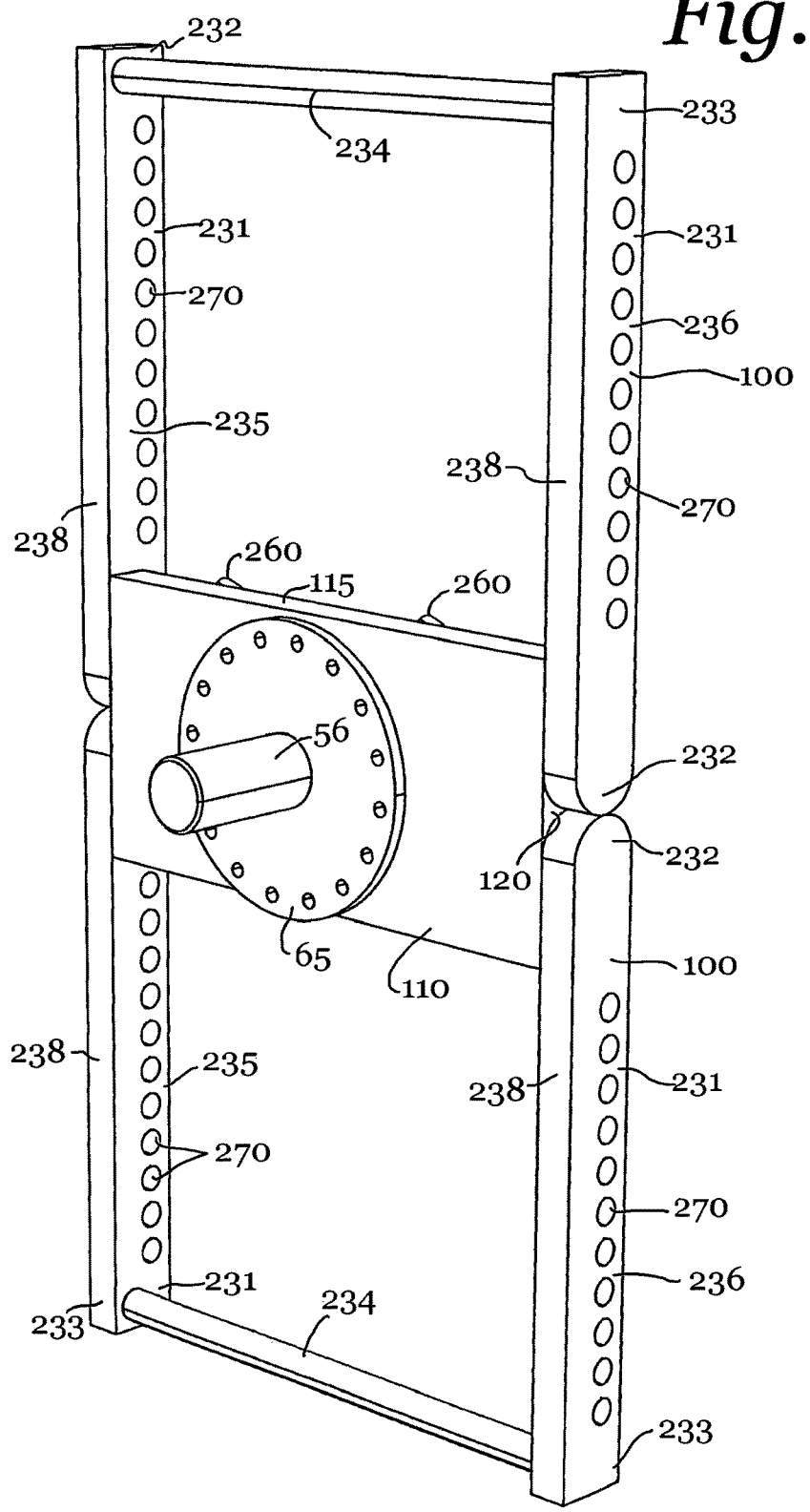
FIG. 21 is a reduced back perspective view of the ladder connection subassembly of FIG. 15, with a pair of ladders attached thereto and a portion of the rotation subassembly extending therefrom.
Figure 22:
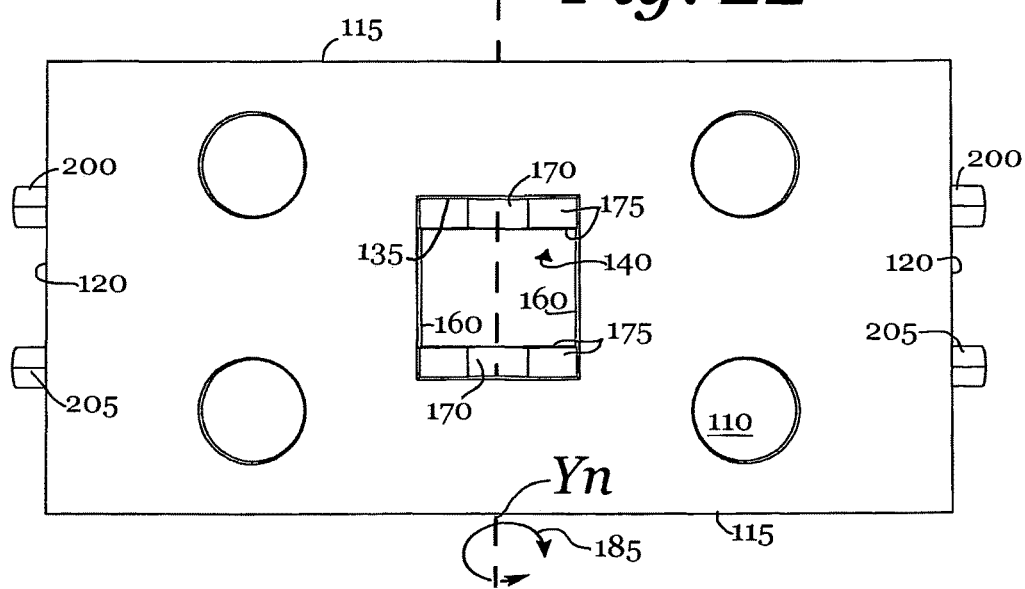
FIG. 22 is a back view of the ladder connection subassembly of FIG. 15.

The rotation block through-bore 140 includes an inner surface 145, with upper, lower and side surfaces 150, 155 and 160, respectively, and one or more engagement surfaces 165 that are shaped to engage one or more portions of the rotation subassembly 50, such as but not limited to the rotation shaft outer portion 71. For example, as shown in FIGS. 15, 16 and 22, the engagement surfaces 165 include at least one partially cylindrical bushing engagement surface 170 and an optional substantially planar engagement surface 175 (see FIGS. 15 and 22). While in the illustrated embodiment the rotation block through-bore 140 is generally box-shaped, it is foreseen that the through-bore 140 may have other shapes, such as but not limited to cylindrical, conical and prismatic shapes.

The rotation block 57 is joined with the rotation shaft outer portion 71. Namely, the shaft outer portion 71 extends into and optionally through the block through-bore 140. A yaw pin, peg or post 180 attaches the through-bore 140 with the shaft outer portion 71. The yaw pin 79 extends through the shaft through channel 78 and into the side surface 160 of the block through-bore 140. One or more of the engagement surfaces 165 contacts and engages the surface 183 of the yaw pin 79. One or more bushings 80 may be received over or around the yaw pin 79, so as to provide spacing.

Figure 14:
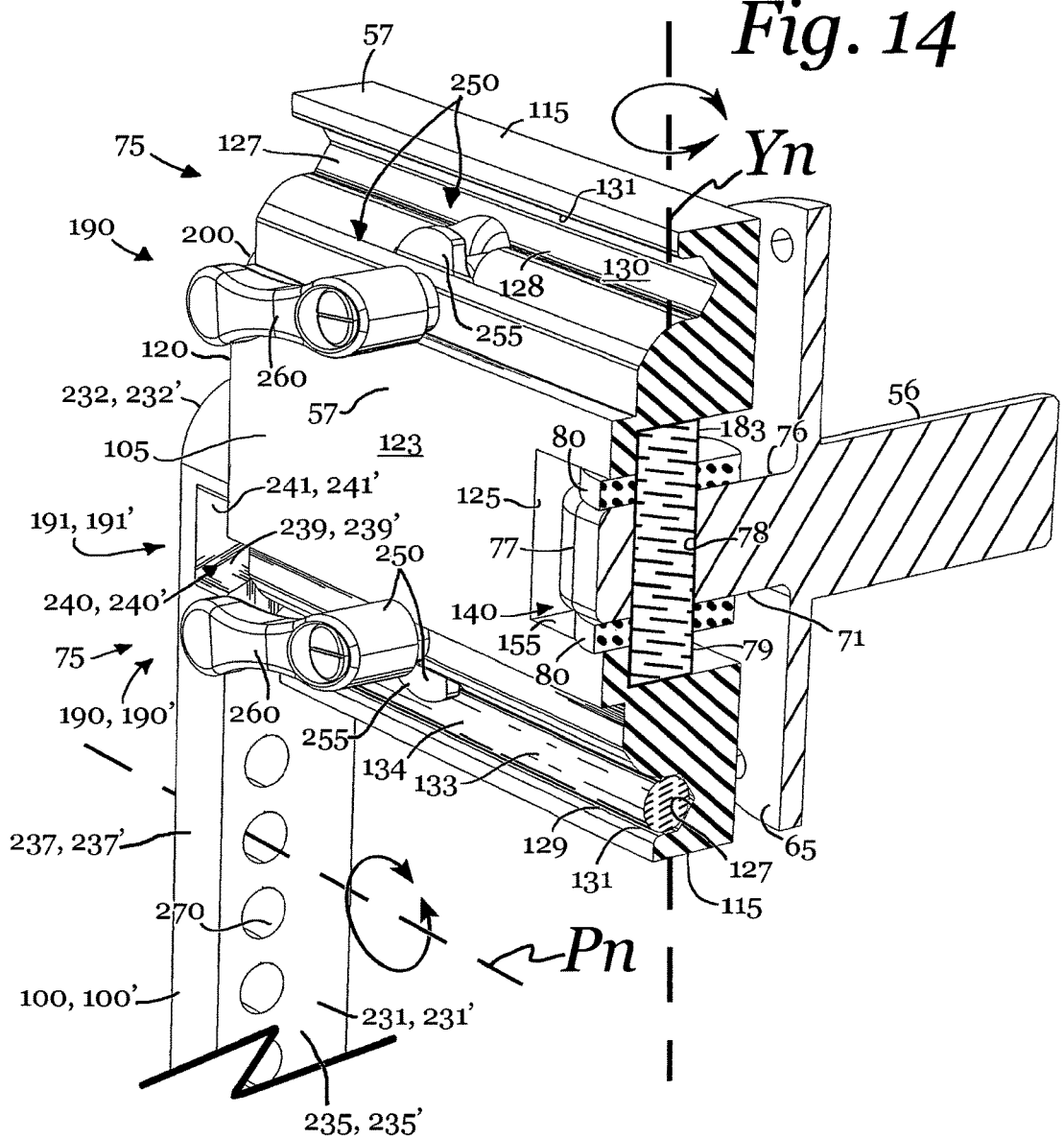
FIG. 14 is an enlarged cross-section of the patient positioning support system of FIG. 1, the cross-section being taken along the line 14-14 of FIG. 5, with portions broken away.

Returning to FIGS. 14, 22 and 121, in some embodiments, one or more bushings 80 are received over the yaw pin 79. The bushings 80 provide for at least some engagement between the yaw pin 79 and the bushing engagement surfaces 170 and optionally additional engagement surfaces 165, 175 of the block through-bore 140. As shown in FIG. 14, the bushings 80 space or separate the rotation shaft 56 from the inner surface 145 of the block through-bore 140. Further, the bushings 80 can provide a snug and secure fit or connection between the rotation shaft 56 and the rotation block 57. While the yaw pin 79 is substantially cylindrical with a circular cross-section, it is foreseen that the yaw pin 79 may be any other useful three-dimensional shape, such as a cone or a prism, optionally with a cylindrical portion.

The yaw pin 79 is coaxial with a respective yaw axis Y1 or Y2, and is adapted to enable or allow rotational movement of the rotation block 57 about the respective yaw axis Y1 or Y2. In addition, as shown in FIGS. 29-30 and 122-125, each of the rotation blocks 57 is attached to a respective shaft 75 so as to provide a space 180 or distance between the block rear face 110 and the housing front 61. This space 180 is particularly important, as described below, because the rotation block 57 is adapted to yaw or rotate about the associated yaw axis Y1 or Y2, such as is indicated by the double-headed directional arrow 185. This yaw motion brings a portion of the block rear face 110 closer to the housing front 61, and the space 180 must be sufficient to prevent the structures from contacting or bumping into each other, wherein such contact between the block rear face 110 and the housing front 61 could inhibit free, or smooth, rotation of the block 57 with respect to the roll axis R. Accordingly, in preferred embodiments, the space 180 is sufficient to substantially block or prevent contact between the block rear face 110 and the housing front 61 when the respective rotation block 57 rotates about the respective yaw axis Y1 or Y2.

Referring to FIGS. 13-22 and 121, each rotation block 57 is attached to or joined with a respective rotation shaft outer portion 71 of the vertical translation subassembly 20. The rotation shafts 56 of the opposed vertical translation subassemblies 20 are rotated in synchronization, toward either the left-hand side or right-hand side of the patient positioning support system 5 and also at the same speed. Each of the rotation shafts 56 rotates an attached block 57 clockwise or counter-clockwise, which in turn rotate a pair of attached ladders 100 or 100' about the roll axis R. As the ladders 100 or 100' rotated in unison, they cooperatively rotate a patient support structure 15⁰ that is attached or suspended therebetween.

The block through-bore 140 is located so as to enable the rotation shaft outer portion 71 to smoothly and evenly rotate the ladder connection block 57 with respect to the roll axis R. A shaft through-channel 78 pierces or extends through the shaft outer portion 71. The yaw pin 79 extends through both the rotation block through-bore 140 and the rotation shaft through-channel 78 so as to join the rotation shaft outer portion 71 with the ladder connection block 57.

Figure 28:
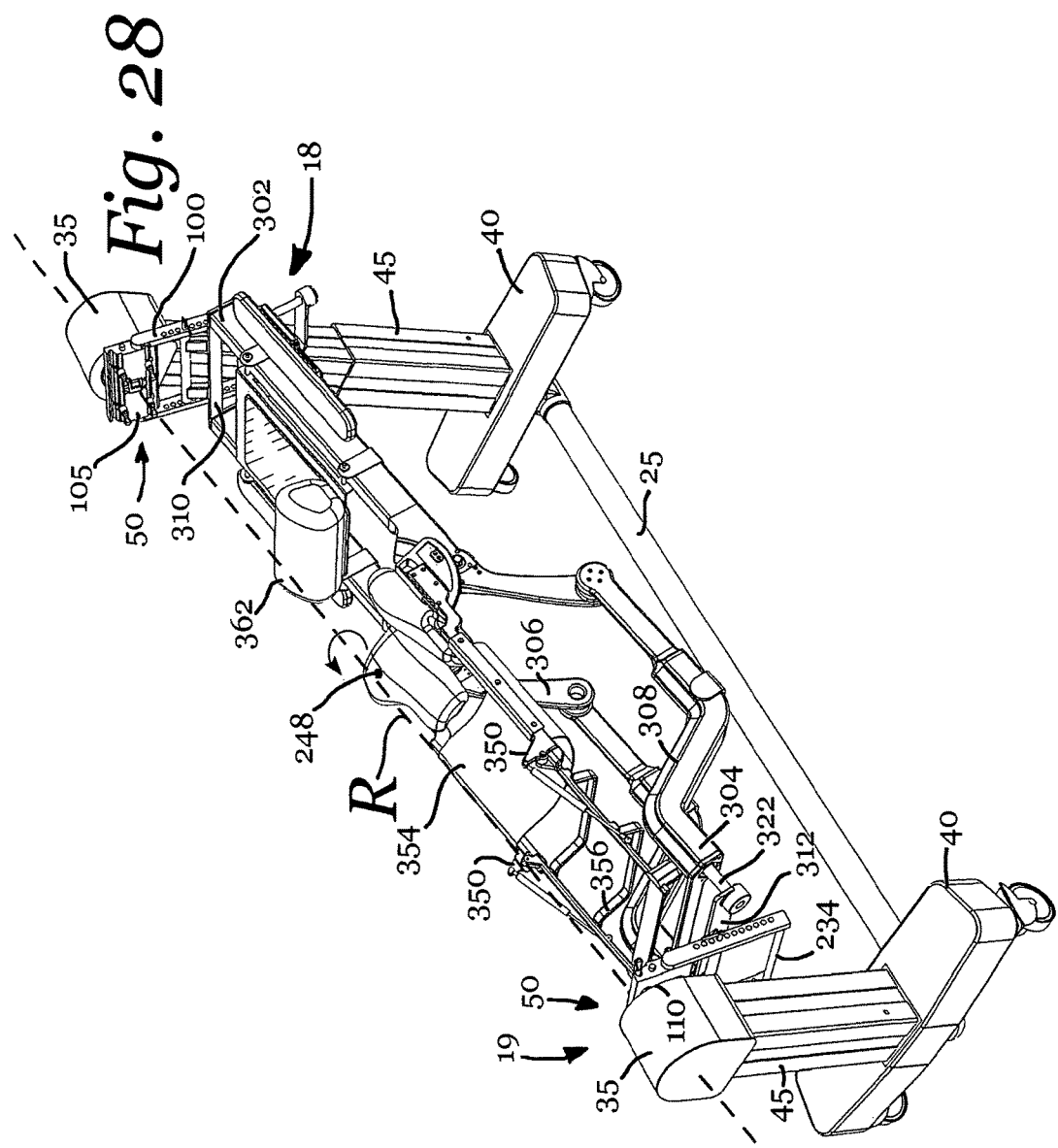
FIG. 28 is a right side view of the patient positioning support system of FIG. 23, wherein the patient support structure has been rolled 25-degrees toward the left side of the table.
Figure 29:
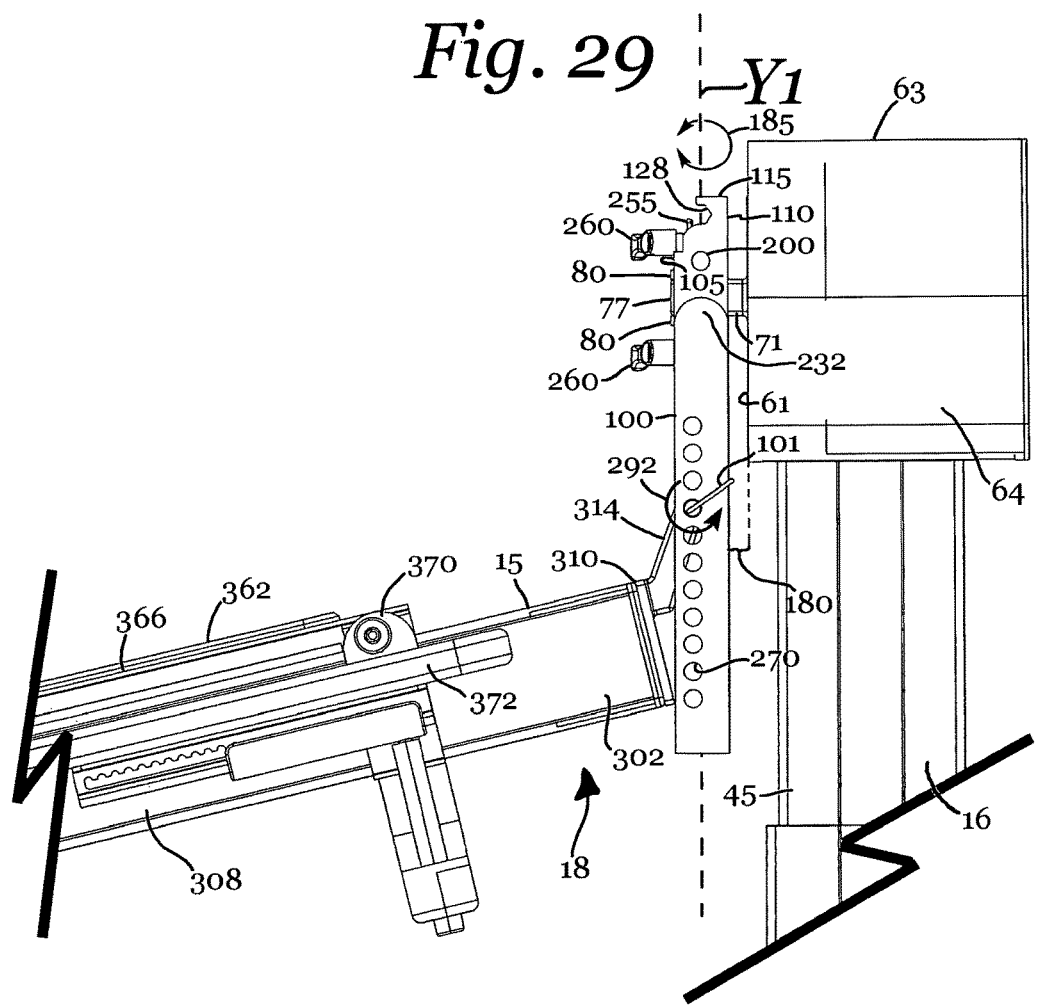
FIG. 29 is an enlarged view of the head-end of the patient positioning support system of FIG. 24, with portions broken away.
Figure 30:
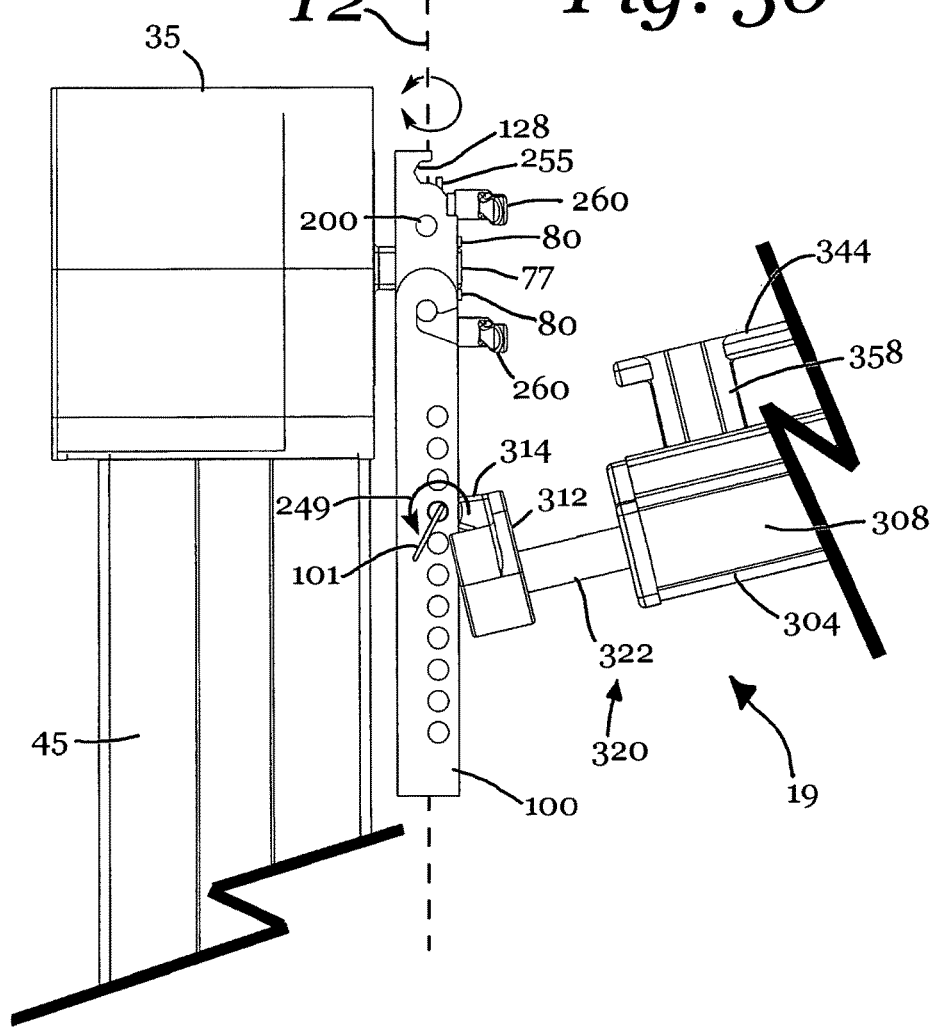
FIG. 30 is an enlarged view of the foot-end of the patient positioning support system of FIG. 24, with portions broken away.
Figure 36:
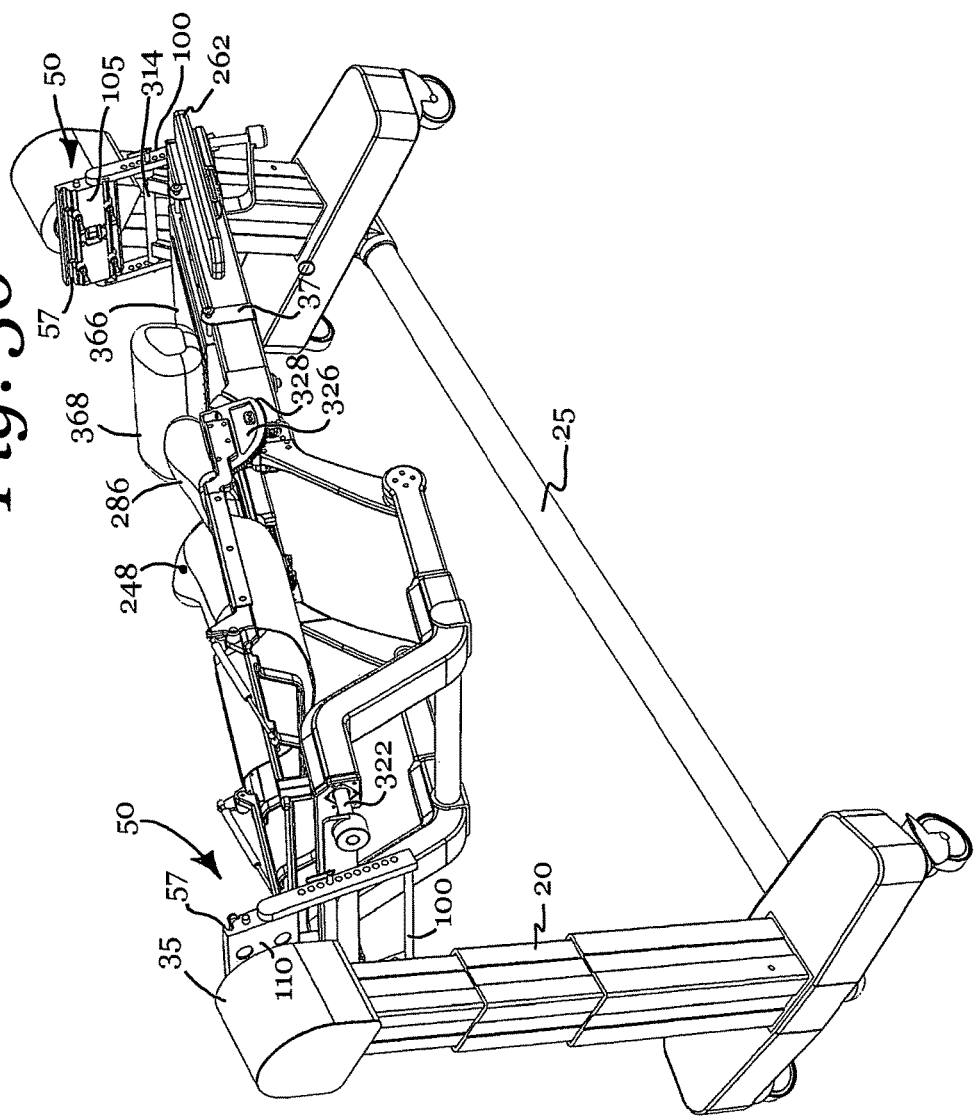
FIG. 36 is a right side view of the patient positioning support system of FIG. 31, wherein the patient support structure has been rolled 25-degrees toward the left side of the table.

The yaw pin 79 is substantially coaxial with the associated yaw axis Yn, so as to enable the ladder connection block 57 to be rotated, articulated or pivoted either clockwise or counter-clockwise about the associated yaw axis Yn, such as is indicated by directional arrow 185. For example, in FIGS. 19, 20 and 121, the yaw axis Yn extends out of the page, so as to be substantially perpendicular to the plane of the page. In the illustrated embodiment, the cylindrical yaw pin 79 includes a circular cross-section. It is foreseen that the yaw pin 79 may have any other shaped cross-section that enables the ladder connection block 57 to sufficiently pivot about the yaw axis Yn, and thereby to prevent buckling of the patient positioning support system 5 when the patient support structure 15⁰ is placed in a Trendelenburg or reverse Trendelenburg position and is also rolled or tilted about the roll axis R, such as is shown in FIGS. 28 and 36. For example, in some embodiments, a universal joint-like structure replaces or is substituted for the yaw pin 79.

Each rotation block 57 includes at least one ladder connection structure 190, or ladder connection subassembly, which is complementary in size, shape and configuration with a block connection structure 191, or block connection subassembly, of a ladder 100, 100'. The block connection structures 191, of the ladders 100, 100', are described below. Cooperation between the block's ladder connection structure 190 and the ladder's block connection structure 191 enables reversible attachment, engagement or mating of a ladder 100, 100' to the block 57.

Referring to FIGS. 13-22, the ladder connection structure 190, of the rotation block 57, includes a rail-receiving groove 127 (described above) and a pair of ladder engagement pegs 195. As shown in FIG. 16, each of the engagement pegs 195 extends outwardly from an associated rotation block end face 120. The pegs 195 are positioned on the end faces 120 so as to be coaxially aligned with one another. Further, the pair of pegs 195 are positioned so as to cooperate with the associated rail-receiving groove 127. In preferred embodiments, the rotation block 57 includes two ladder connection structures 190. Accordingly, the rotation block 57 includes two pairs of engagement pegs 195, such as upper and lower pairs 200, 205 of pegs 195, or a first pair 200 of pegs 195 and a second pair 205 of pegs 195. The upper pair 200 of pegs 195 is associated with the upper or first rail-receiving groove 128, and the lower pair 205 of pegs 195 is associated with the lower or second rail-receiving groove 129.

The engagement pegs 195 of each pair 200 or 205 of pegs 195 are aligned with one another and spaced from an adjacent ladder connection groove 201 so as to enable connection of a ladder 100 to the ladder connection block 57. For example, the upper pegs 200 are coaxial with one another and spaced from the first rail-receiving groove 128, and the lower pegs 205 are coaxial with one another and spaced from the second rail-receiving groove 129, such that a ladder 100 or 100' can be engaged either with the upper pair of pegs 200 and the upper groove 128 or with the lower pair of pegs 205 and the lower groove 129. Engagement or connection of a rotation block 57 and a ladder 100 or 100' is described in greater detail below.

The ladders 100, 100' are substantially rigid and facilitate or provide attachment of a patient support structure 15⁰, such as but not limited to a prone patient support structure 15 and a supine patient support structure 15', to the base 10 of the patient positioning support system 5.

Figure 10:
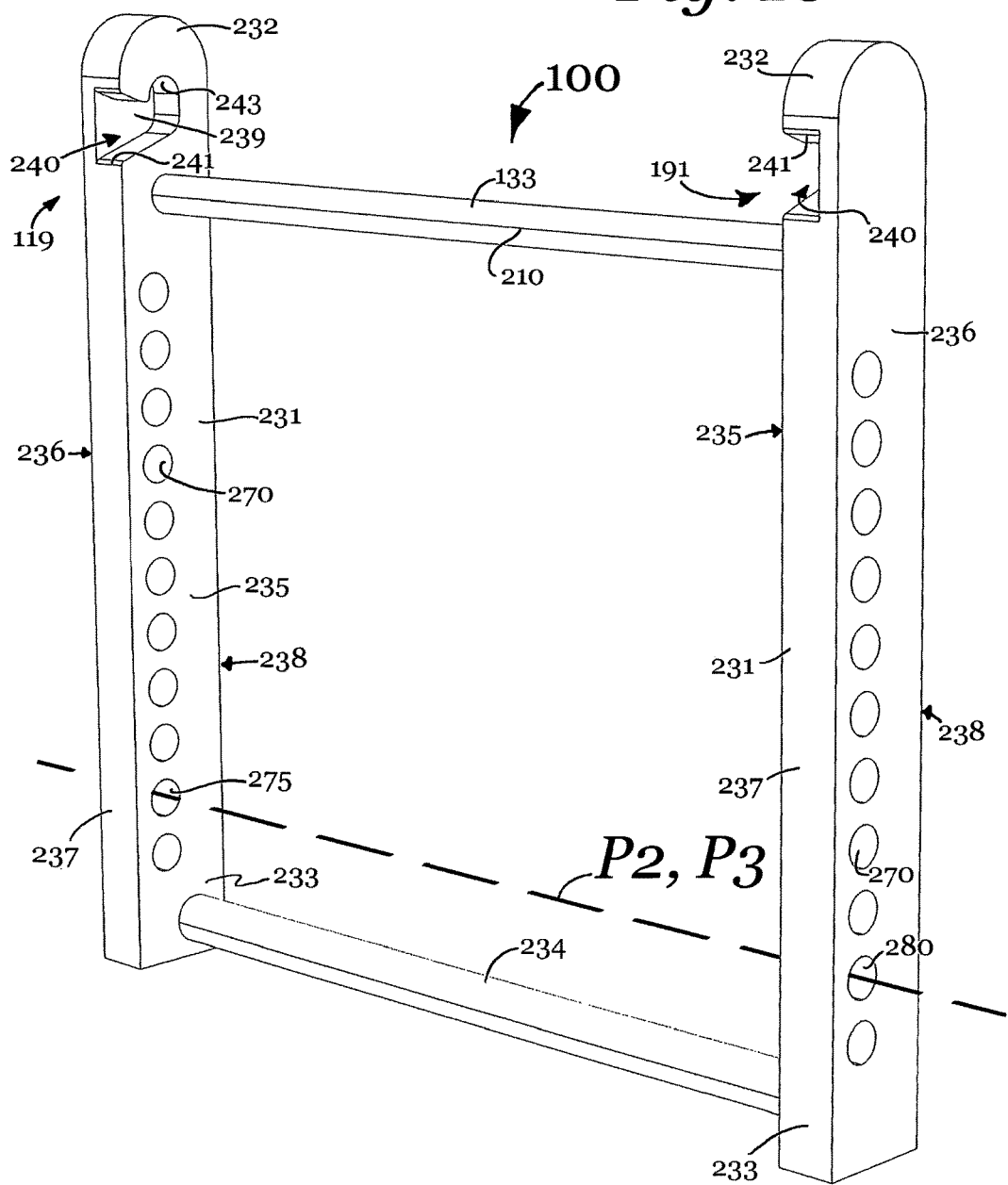
FIG. 10 is an enlarged perspective view of a ladder of the patient positioning support system of FIG. 1.

In the illustrated embodiment, the patient positioning support system 5 includes at least one pair of ladder structures or ladders. The ladders may be a provided in a variety of lengths, such as but not limited to a standard and non-standard lengths. Ladders having a standard length are denoted by the number 100, and ladders having a non-standard length are denoted by the number 100'. Non-standard length ladders 100' include a length that is relatively longer or shorter than a standard length ladder 100. FIG. 10 illustrates an exemplary standard length ladder 100. An exemplary pair of extended length ladders 100' is shown in FIGS. 110-115.

It is noted that in the illustrated embodiment, the ladders 100, 100' are provided in one of two lengths, a standard length ladder 100 and non-standard length ladder 100', wherein the non-standard length ladder 100' includes an extended length, or a length greater than that of the standard length ladder 100. It is foreseen that ladders 100' of other, non-standard lengths can be provided. In the illustrated embodiment, pairs of matched ladders 100 or 100', or two ladders 100 or 100' having substantially the same length, are attached to the opposed rotation blocks 57. It is foreseen that miss-matched pairs of ladders 100, 100' could be attached to the rotation blocks 57.

Each ladder 100, 100' includes a pair of rigid space opposed ladder side members, wherein standard length side members are denoted by the number 231 and non-standard length side members are denoted by the number 231'. The pair of ladder side members 231, 231' are joined at or near their upper ends 232 or 232' also referred to as connection ends, by the upper rail 133 described above. At their lower ends 233 or 233', the ladder side members 231, 231' are joined by a second or lower rail 234, 234'. In some embodiments, the ladder 100 or 100' may include additional stabilizing rails (not shown).

Figure 102:
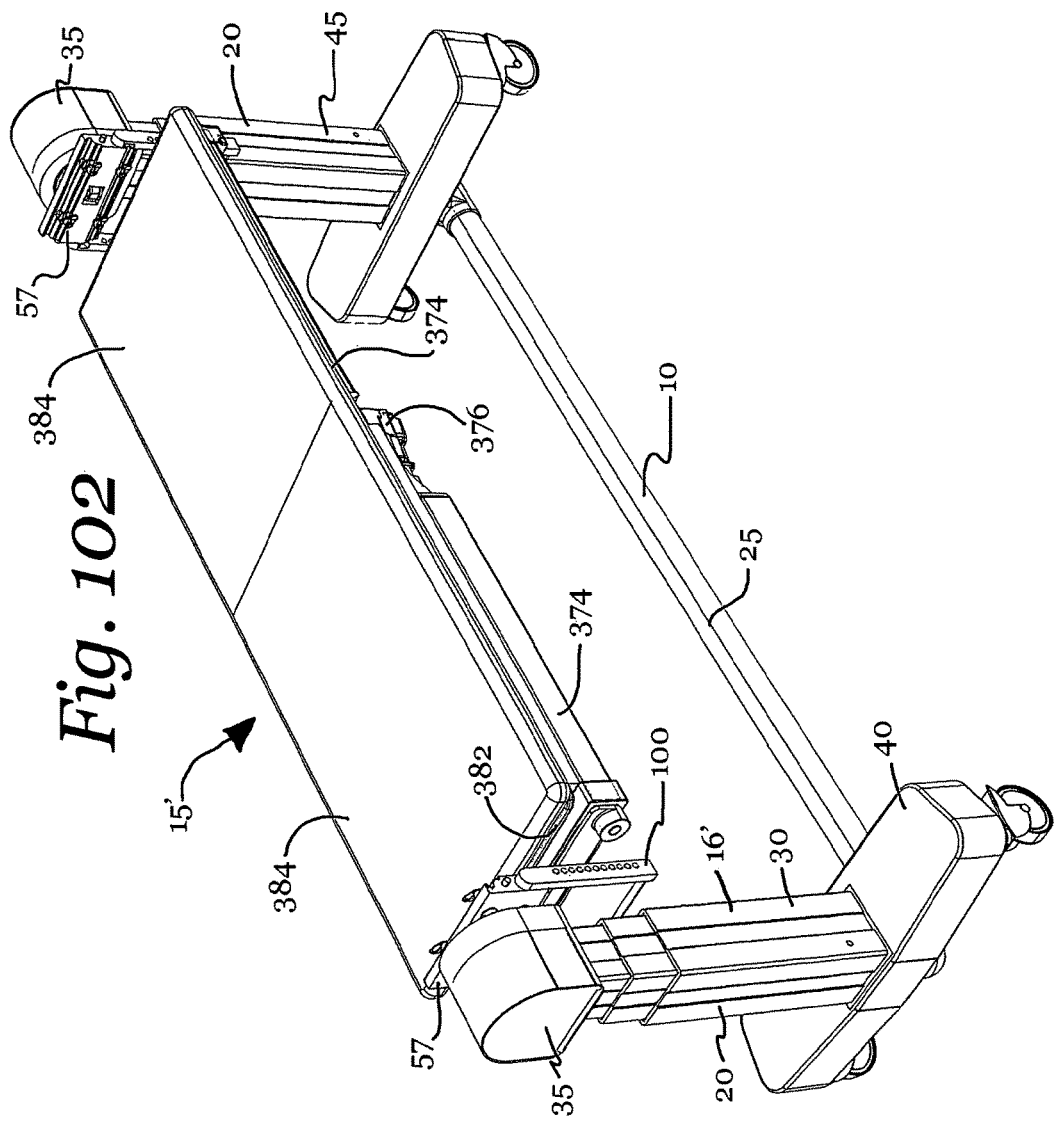
FIG. 102 is a perspective view of a patient positioning support system of the present invention, in another embodiment, including a supine patient support structure attached to a base using standard length ladders.
Figure 106:
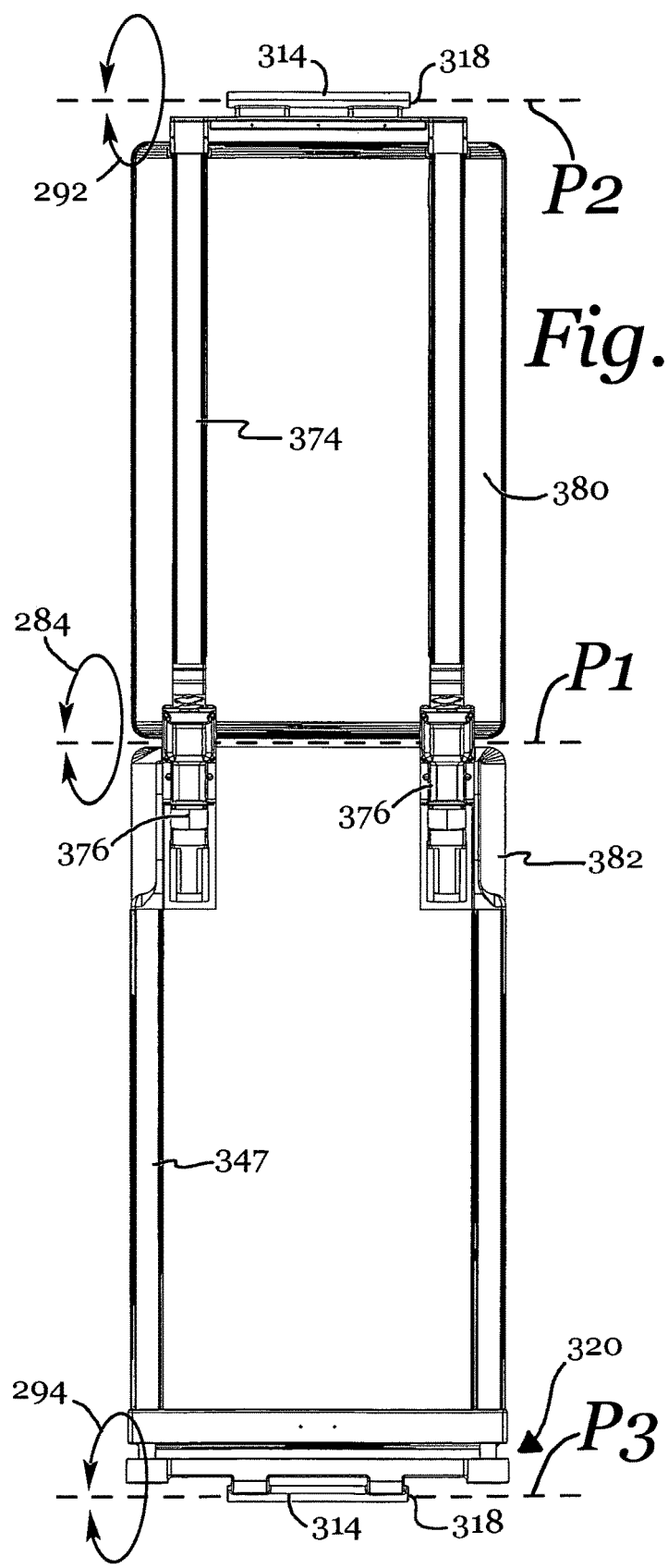
FIG. 106 is a bottom view of the supine patient support structure of FIG. 103.
Figure 107:
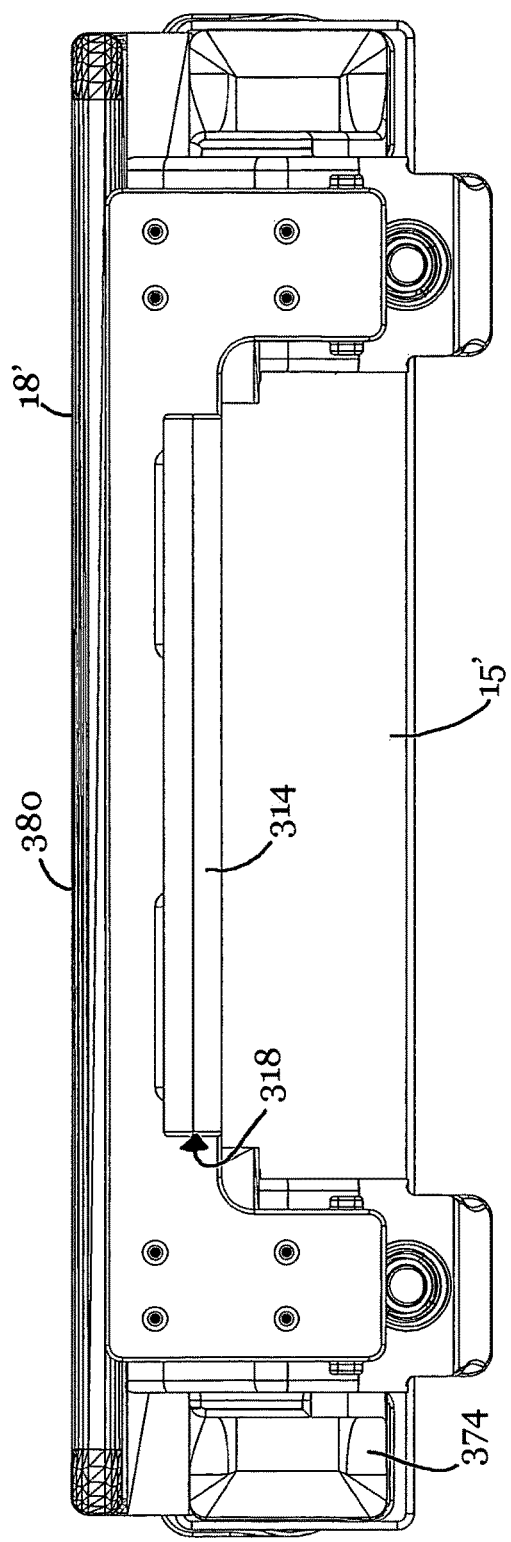
FIG. 107 is an enlarged head-end view of the supine patient support structure of FIG. 103.
Figure 108:
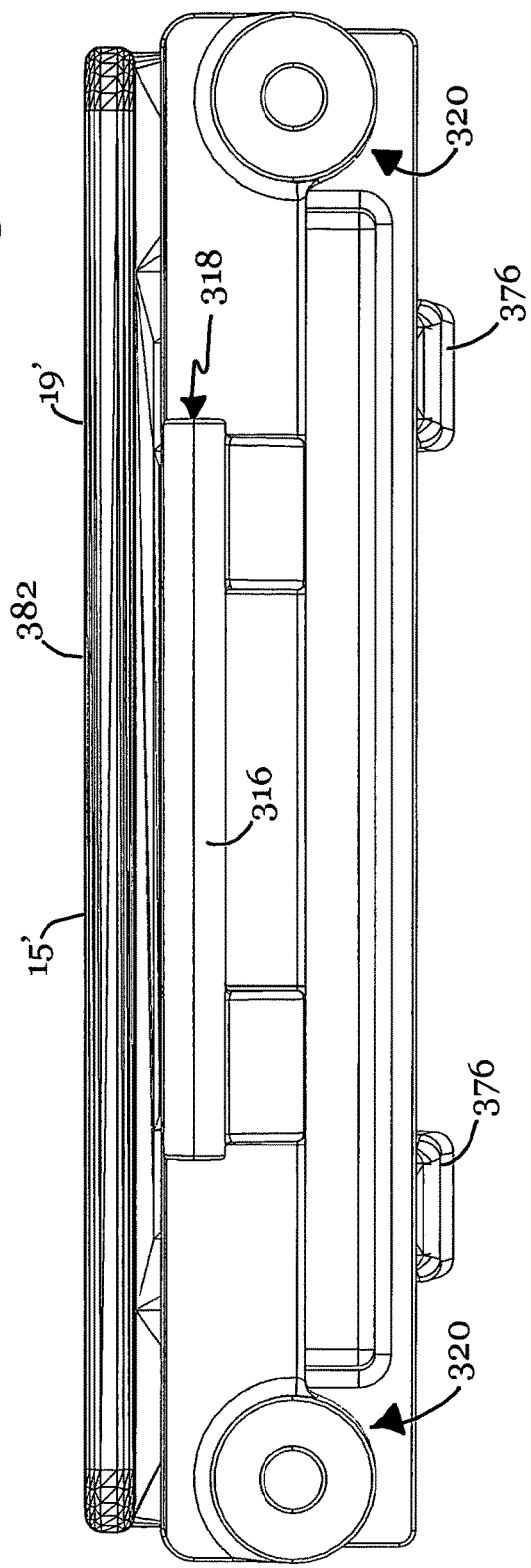
FIG. 108 is an enlarged foot-end view of the supine patient support structure of FIG. 103.
Figure 109:
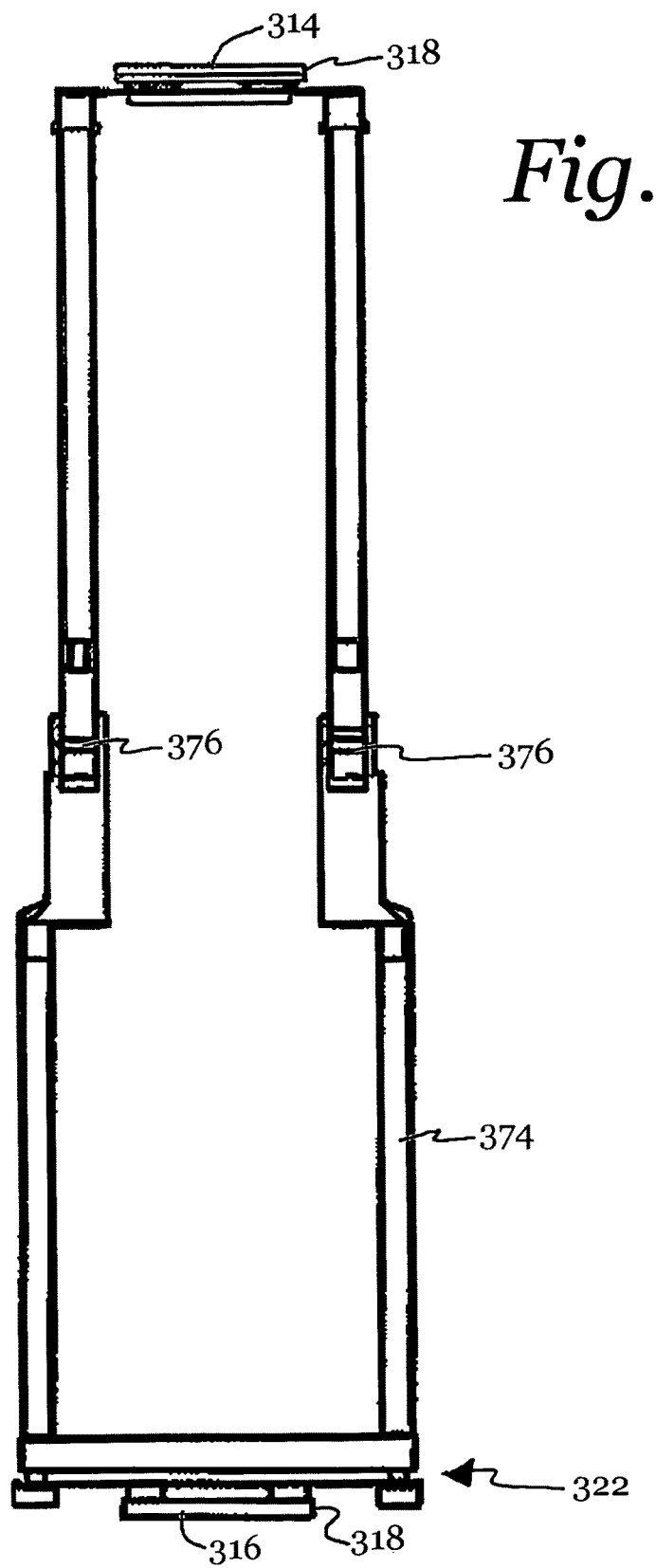
FIG. 109 is a top view of the open breaking frame of the supine patient support structure of FIG. 103, including a pair of spaced opposed hinges.
Figure 110:
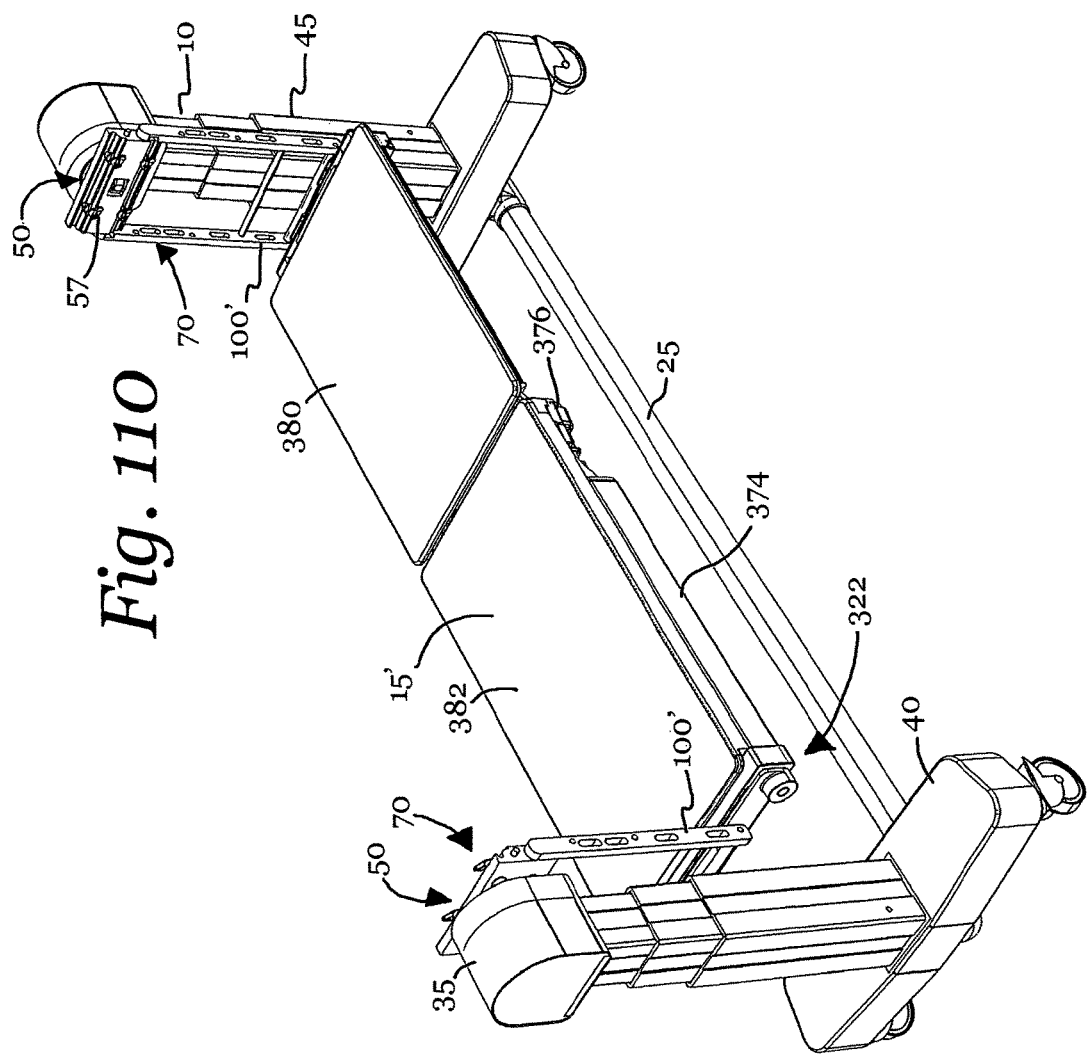
FIG. 110 is perspective view of the supine patient support structure of FIG. 103 attached to a base using extended length ladders.
Figure 111:
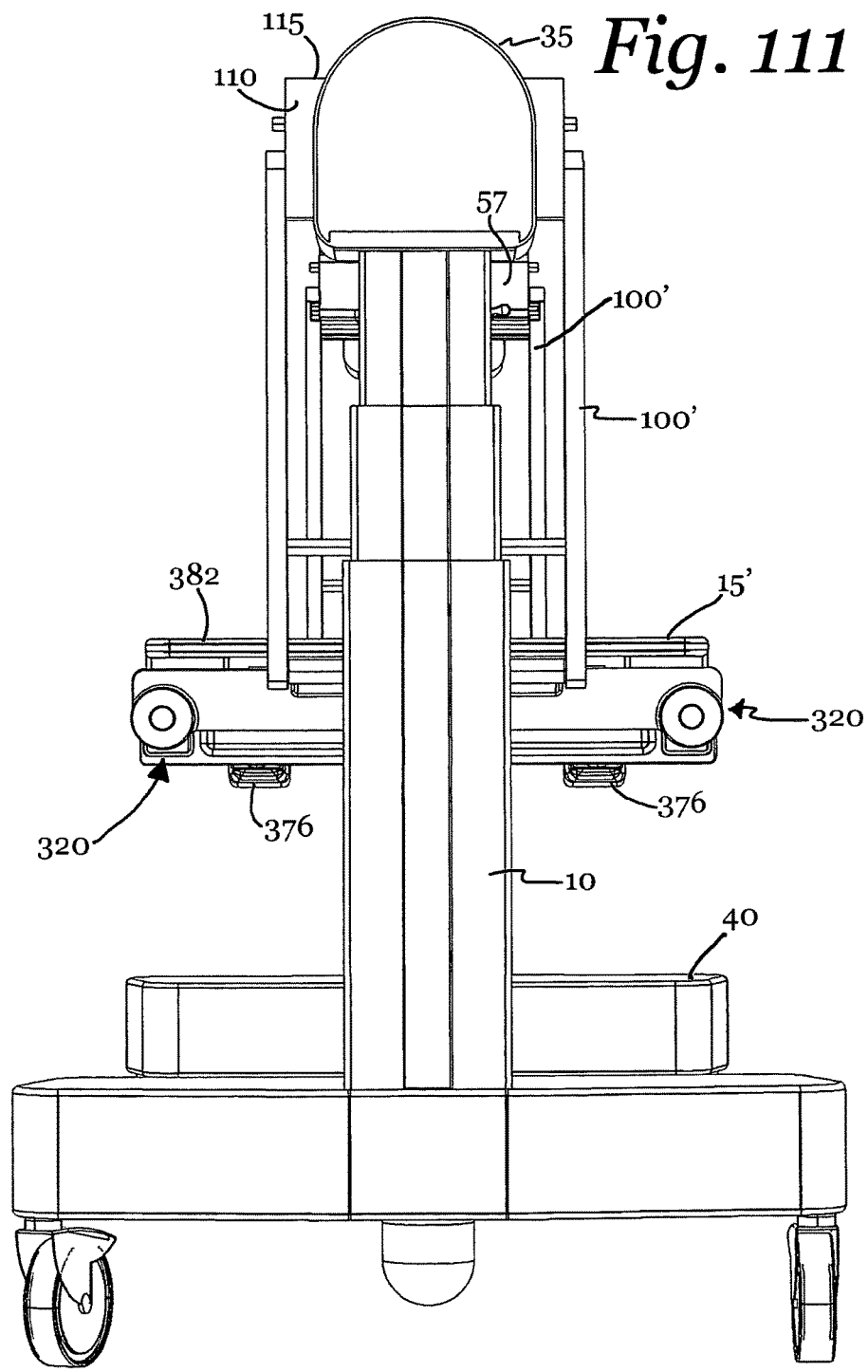
FIG. 111 is a head-end view of the patient positioning support structure of FIG. 110.

Each ladder side member 231, 231' includes inner and outer faces or sides 235, 235' and 236, 236', respectively, and inboard and outboard faces or sides 237, 237' and 238, 238', respectively. As shown in FIGS. 1 and 102, when a ladder 100, 100' is attached to the base 10, the ladder connection block or rotation block 57 and also, or alternatively, to a patient support structure 15°, the inboard faces 237, 237' are positioned toward or closer to the patient support structure 15°. Similarly, the outboard faces 238, 238' are positioned toward the associated, attached or connected vertical translation subassembly 20.

At the upper ends 232, 232', the ladder side members 231, 231' each include an engagement peg receiving groove 239, 239'. The engagement peg receiving groves 239, 239' are cut into the inner faces 235, 235' of the ladder side members 231, 231', and extend from the outboard side 238, 238' toward the inboard side 237, 237' so as to provide a peg-receiving channel 240, 240' with an opening 241, 241' and a peg-engaging chamber 243, 243'. The peg-receiving channel 240, 240' is sized and shaped to removably slidingly receive a ladder engagement peg 195 therein. The two channels 240, 240' are generally or substantially parallel with one another, and are located to as to engage a pair of ladder engagement pegs 195 such as but not limited to pair 200 and pair 205, such as are shown in FIG. 16. The peg-engaging chamber 243, 243' is sized and shaped to lockingly engage the peg 195 received in the channel 240, 240'.

Prior to reversibly or releasably connecting, joining or attaching a patient support structure 15° to the base 10, a pair of ladders 100, 100' must be attached to the base 10. FIGS. 126-133 and FIGS. 152-159 illustrate attaching a standard sized ladder 100 to an upper pair of pegs 200 of a rotation block 57, the steps of which are substantially similar for attachment of a non-standard length ladder 100', such as but not limited to an extended length ladder 100'.

In a first step, shown in FIGS. 126-127, the ladder channel openings 241, 241' are aligned with the block pegs 195, such as the upper pair 200 of pegs 195, such as is indicated by the directional arrow denoted by the numeral 248. The openings 241, 241' are correctly aligned with the upper pair of pegs 200 by orienting, tilting or tipping the ladder 100 such that the lower rail 234 is located more inboard than the upper rail 133. Accordingly, when in this position, the lower rail 234 is spaced or located higher from the floor F than the upper rail 133.

In a second step, shown in FIGS. 128-129, the peg-receiving channel openings 241, 241' are placed, installed or engaged around the upper pegs 200, such that the upper pegs 200 are effectively inserted into the openings 241, 241'. The peg-receiving channels 240, 240' are then slid, moved or placed around the pegs 200, such that the pegs 200 are slid or moved along or through the channels 240, 240', such as by tilting or rotating the lower end of the ladder 100 in an outboard direction, such as is indicated by the directional arrow denoted by the numeral 246. The ladder 100 is moved or tilted until it comes into a vertically aligned orientation or configuration, such as that shown in FIGS. 130 and 131. While the pegs 200 are becoming engaged, the ladder upper rail 133 fits into and engages the ladder connection groove 127 on the front face 105 of the rotation block 57, and the outer surface 205 of the upper rail 133 frictionally engages the groove surface 203. When the ladder 100 is in the vertical orientation, the pegs 200 are substantially engaged by, or located or received within, the respective channel chambers 243, 243'.

It is noted that a pair of opposed ladders 100 or 100' attached to the respective vertical translation subassemblies 20 provide a fail-safe mechanism that prevents improper disconnection of an attached or engaged patient support structure 15° from the base 10. This fail-safe mechanism includes two components. First, the ladders 100 and 100' cannot be disconnected from the base 10 unless no patient support structure 15° is attached thereto. Second, the ladders 100 and 100' must be disconnected or removed from the base 10 by performing the attachment steps in reverse order. Accordingly, the ladder lower ends 233, 233' must be tilted in an inboard direction, before the respective ladder upper ends 232, 232' can be disconnected or disengaged from the rotation block 57. Other fail-safe mechanisms, structures or subassemblies are foreseen.

In some embodiments, the rotation block 57 includes at least one locking mechanism, structure or device, generally 250, adapted to lock the ladder upper rail 133 in the engaged rail-receiving groove 127. In these embodiments, the locking mechanism 250 can be actuated or engaged as an optional step in attaching the ladder 100, 100' to the rotation block 57. FIGS. 132-133 illustrate attaching a ladder 100 to a rotation block 57. Referring to FIGS. 15-20 and 126-133, the rotation block 57 includes upper and lower pairs of lock mechanisms 250. Each lock mechanism 250 includes an inner locking portion 255 and a handle 260 that extends outwardly from the front face 105 of the rotation block 57. The inner locking portion 255 can be swiveled into and out of the opening 265 of the associated rail-receiving groove 127, or ladder connection groove, by manually turning or rotating the associated handle 260 on the front face 105 of the rotation block 57, such that the lock 250 is engaged or closed. It is foreseen that the lock mechanisms 250 could be motorized and controlled by software or otherwise mechanically actuateable.

Closing the locks 250, such as is shown in FIGS. 132 and 133, prevents or blocks removal, disengagement, detachment or disconnection of the upper rail 133 from the engaged, attached or connected first rail-receiving groove 128. To disconnect the ladder 100, 100' from the first rail-receiving groove 128, the lock mechanisms 250 must be opened, disengaged or de-actuated. In embodiments of the patient positioning support system 5 including a lock mechanism 250, it is foreseen that the lock mechanism 250 must be substantially opened prior to attachment or installation of a ladder 100 or 100' with the rotation block 57.

With reference to FIGS. 13, 21, 85-100 and 134-169, it is noted that the patient positioning support system 5 is adapted, configured and arranged for reversible attachment of up to two ladders 100, 100', such as upper and lower ladders, to each rotation block 57. Accordingly, two such ladders 100, 100' attached to a single rotation block 57 are substantially vertically opposed to one another and also co-planar with one another. In contrast, a pair of ladders 100 or 100' attached to the two opposed rotation blocks 57 at either end of the base 10, such as a pair of ladders 100 or 100' attached to either the first rail-receiving grooves 128 or the lower rail-receiving grooves 129, are substantially opposed to and parallel with one another. When the ladder 100, 100' is attached to the block 57, a plane that runs parallel with and through the ladder side members 231, 231' is substantially perpendicular to the floor F. Alternative configurations are foreseen.

In some embodiments, the rotation block 57 is sized, shaped and configured such that when two ladders 100, 100' attached thereto, their upper ends 232, 232' kiss or contact one another. It is foreseen that, in some embodiments, the upper ends 232, 232' may not contact one another, depending upon the locations of the upper and lower pairs 200, 205 of ladder engagement pegs 195.

Attaching two ladders 100, 100' to each of the rotation blocks 57 of the patient positioning support system 5 enables attachment of two patient support structures 15°, such as for example a prone patient support structure 15 and a supine patient support structure 15', such as is described elsewhere herein. For example, a patient can be positioned on a first of two patient support structures 15°, such as for a first surgical procedure, and then transferred to the second of the two patient support structures 15°, such as for performing a second surgical procedure with the patient in a different body position. Such transferring of a patient between the two patient support structures 15° can be performed in numerous ways, including but not limited to a sandwich-and-roll procedure, such as is described below.

The ladders 100, 100' are sized, shaped, configured and arranged for attachment to a patient support structure 15° in addition to the base 10. Each ladder side member 231 or 231' includes a plurality of spaced through-bores 270, 270' joining its respective inner and outer faces 235, 235' and 236, 236'. The through-bores 270, 270' of the opposed ladder side members 231 or 231' are sized, shaped and located or aligned such that pairs of opposed through-bores 270, 270' can removably or reversibly slidingly receive the rod portion 102 of a T-pin 101 therethrough. For example, with reference to FIG. 10, through-bores 275 and 280 are coaxially aligned such that a single, or the same, T-pin 101 is receivable therethrough (e.g., a single T-pin 101 is receivable through both of the through-bores 275 and 280).

Additional aspects of attaching the ladders to the patient support structure 15° are described in greater detail below, with respect to the structure for the patient support structure 15°. Further, additional information regarding ladders can be found in U.S. patent application Ser. No. 13/507,618, filed Jun. 18, 2012, which is incorporated herein by reference.

Roll, Vertical Translation and Yaw Axes

As noted above, the base includes a plurality of axes, including a longitudinally extending roll axis R, at least one vertical axis denoted by the letter Vn, wherein n is an integer indicating, identifying or denoting a particular or specific vertical axis, and at least one yaw axis denoted by the letter Yn, wherein n is an integer indicating a particular or specific yaw axis. The base 10 is configured and arranged for movement with respect to these axes, such as is described below and elsewhere herein.

Roll Axis

The roll axis R extends longitudinally along a length of the patient positioning support system 5. In particular, the roll axis R extends between the outer portions 71 of the rotation shafts. In an exemplary embodiment, when the upper portions 35 of the opposed vertical translation subassemblies 20 are located substantially equidistant from the floor F, such as is shown in FIG. 4, the roll axis R is substantially coaxial with the rotation shafts 56. In another exemplary embodiment, when the upper portions 35 are not equidistant from the floor F, such as is shown in FIGS. 24 and 32, the roll axis R intersects the rotation shaft outer portions 71.

The base 10 is adapted to tilt, roll, turn over, or rotate the patient support structure 15° such as but not limited to the prone patient support structure 15 and the supine patient support structure 15' about or around the roll axis R. The patient support structure 15° can be reversibly rolled or tilted an amount or distance of between about 1-degree and about 237-degrees, such as relative to a plane intersecting the roll axis R wherein the plane is parallel with the floor F, or such as relative to a starting position associated with a plane parallel with the floor F, wherein the plane intersects with the roll axis R. For example, in some embodiments, the patient support structure 15° may be tilted a distance of about 5-degrees, about 10-degrees, about 15-degrees, about 20-degrees, about 25-degrees, about 30-degrees, about 35-degrees, or about 40-degrees about the roll axis R, relative to a starting position associated with a plane parallel with the floor F, wherein the plane intersects with the roll axis R, so as to provide improved access to a surgical site. In a further embodiment, the patient support structure 15° may be tilted a distance of about 45, 50, 55, 60, 65, 70, 75, 80, 85, 90, 95 or 100-degrees about the roll axis R, relative to a starting position associated with a plane parallel with the floor F, wherein the plane intersects with the roll axis R. In some embodiments, the patient support structure 15° may be tilted a distance of about 110, 115, 120, 125, 130, 135, 140, 145, 150, 155, 160, 165, 170, 175 or 180-degrees about the roll axis R, relative to a starting position associated with a plane parallel with the floor F, wherein the plane intersects with the roll axis R. In some embodiments, the patient support structure 15° may be rolled a distance of more than 180-degrees about the roll axis R, relative to a starting position associated with a plane parallel with the floor F, wherein the plane intersects with the roll axis R. In some embodiment, the patient support structure 15° can be rolled clockwise or counter-clockwise, or toward either the left-hand or the right-hand side with respect to the roll axis R. In some circumstances, both the prone and supine patient support structure 15 and 15' may be attached to the base 10 and rolled together with respect to the roll axis R.

Figure 91A:
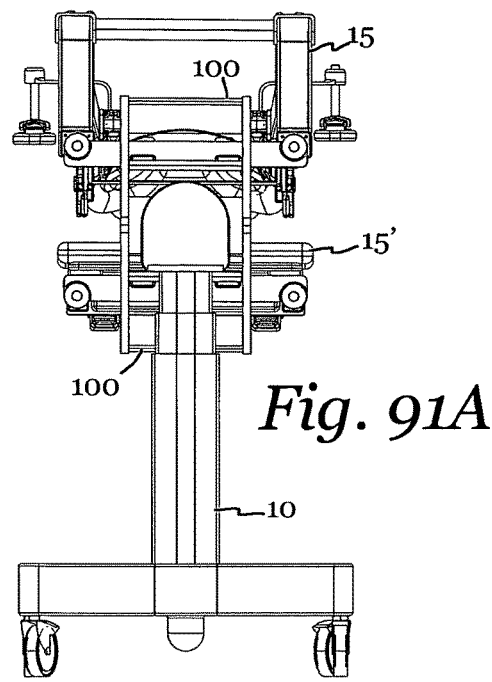
FIG. 91A is foot-end view of the patient positioning support system of FIG. 85, the patient support structures being positioned to begin the sandwich-and-roll procedure to roll a patient over from a supine position to a prone position.
Figure 92A:
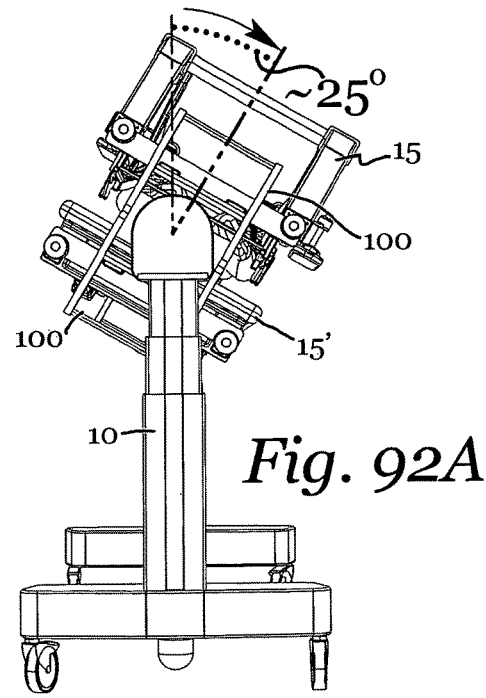
FIG. 92A is a foot-end view of the patient positioning support system of FIG. 91A, wherein the patient support structures has been rolled about 25-degrees.
Figure 93A:
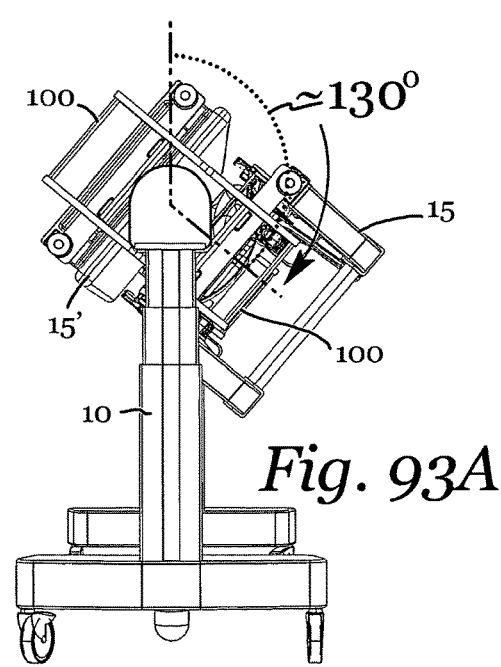
FIG. 93A is a foot-end view of the patient positioning support system of FIG. 91A, wherein the patient support structures has been rolled about 130-degrees.
Figure 94A:
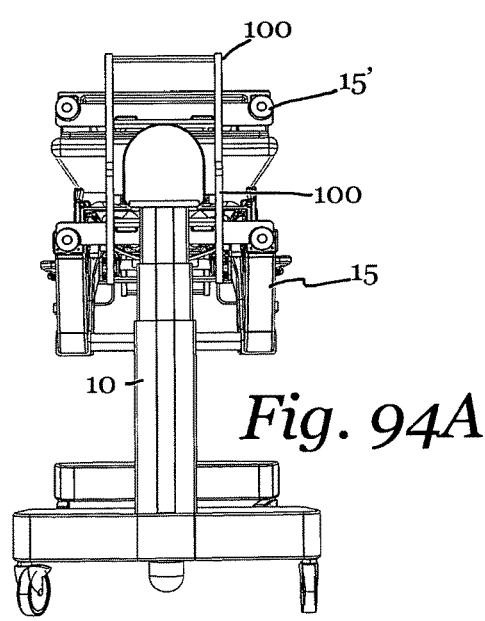
FIG. 94A is a foot-end view of the patient positioning support system of FIG. 91A, wherein the patient support structures has been rolled about 180-degrees.
Figure 91B:
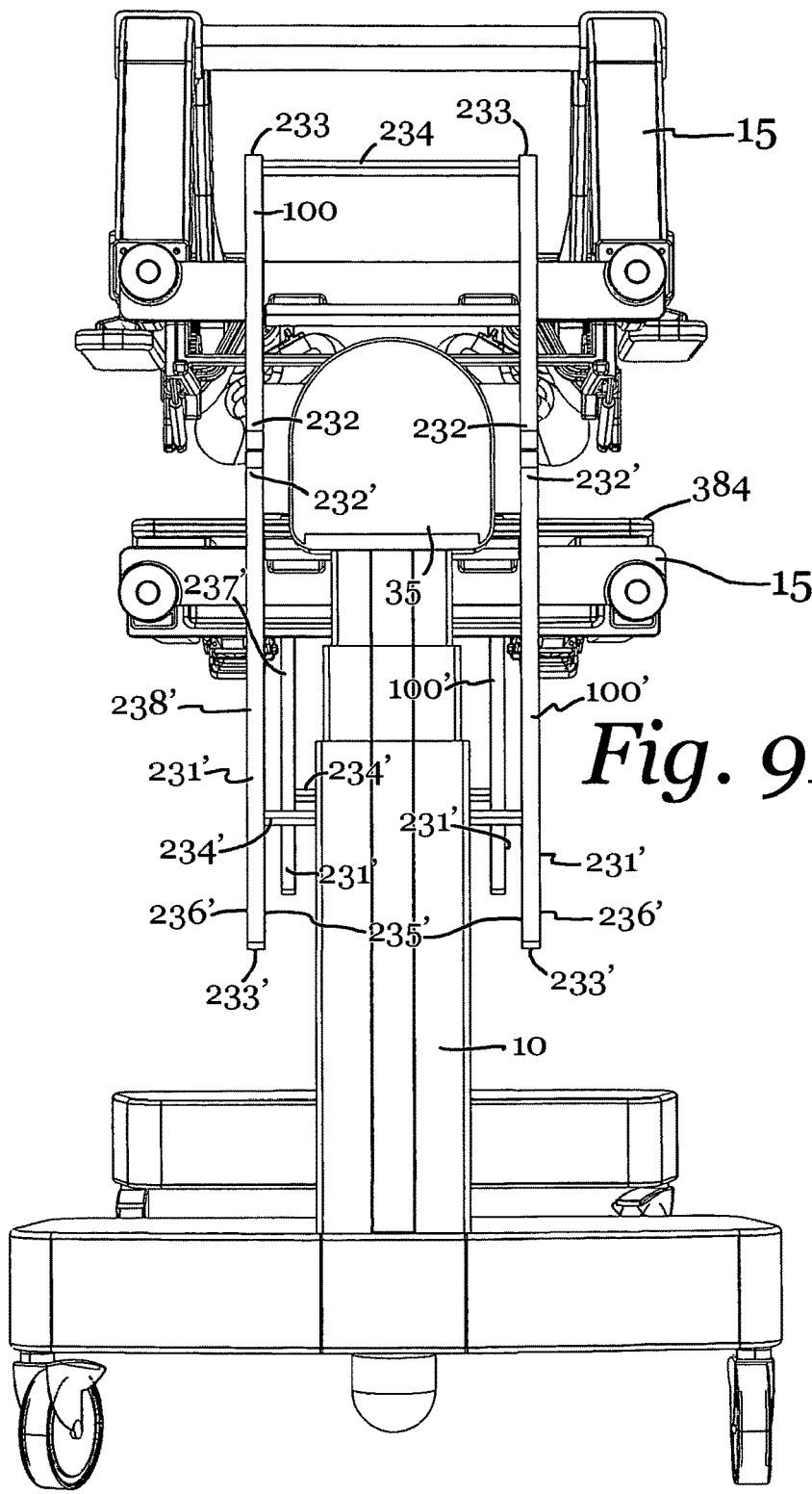
FIG. 91B is head-end view of the patient positioning support system of FIG. 91A, wherein the supine patient support structure is attached to the base by an extended length ladder instead of a standard length ladder.
Figure 92B:
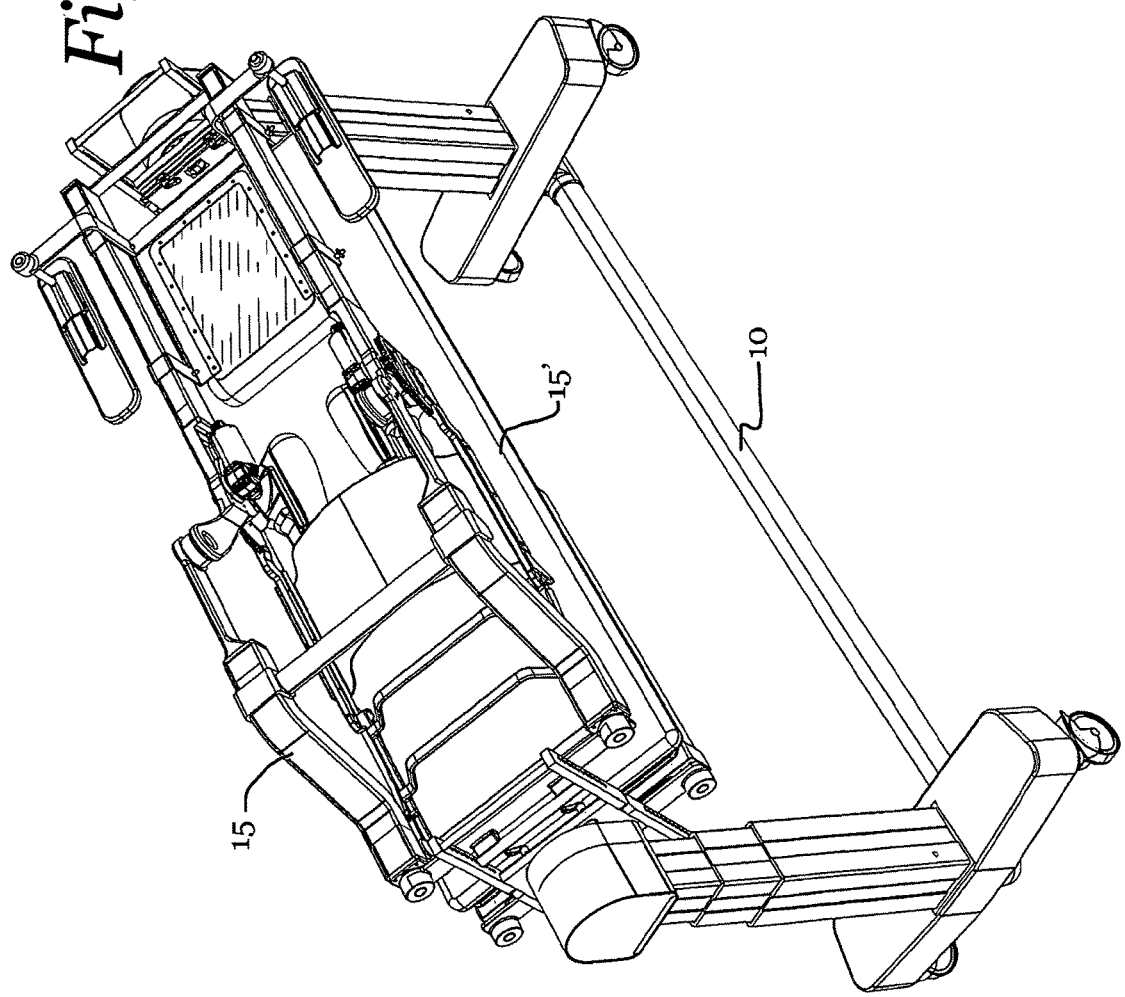
FIG. 92B is a perspective view of the patient positioning support system of FIG. 92A.
Figure 93B:
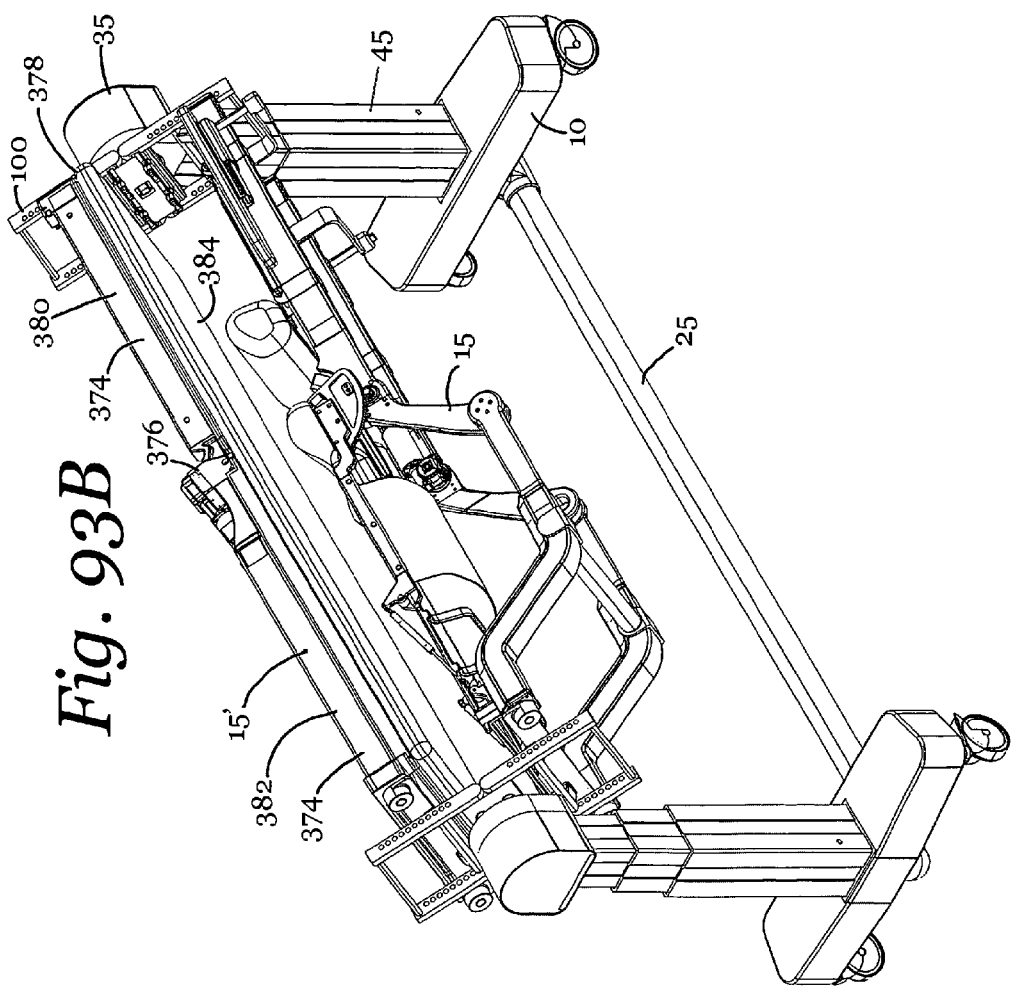
FIG. 93B is a perspective view of the patient positioning support system of FIG. 93A.
Figure 93C:
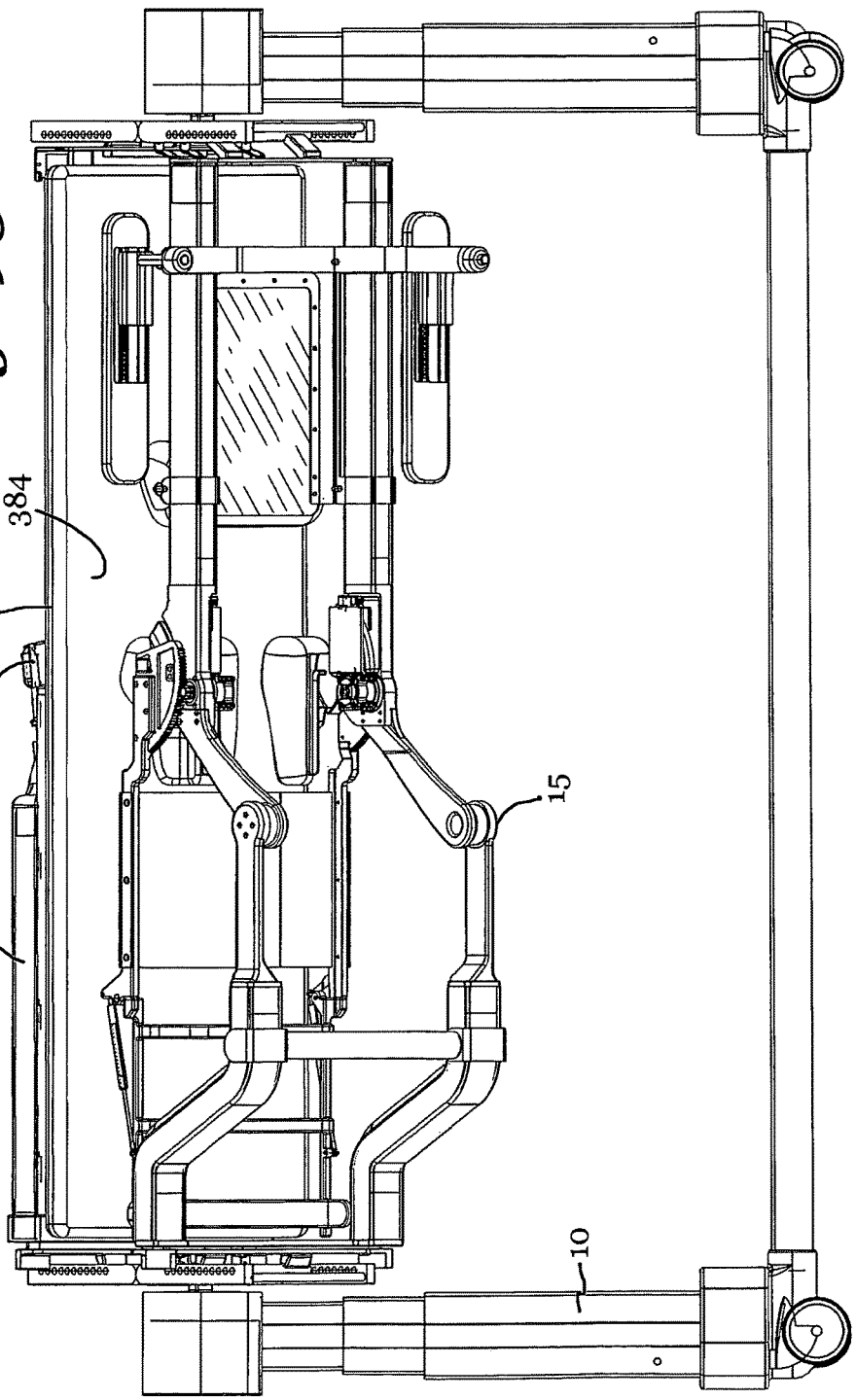
FIG. 93C is a right-side view of the patient positioning support system of FIG. 93A.
Figure 95:
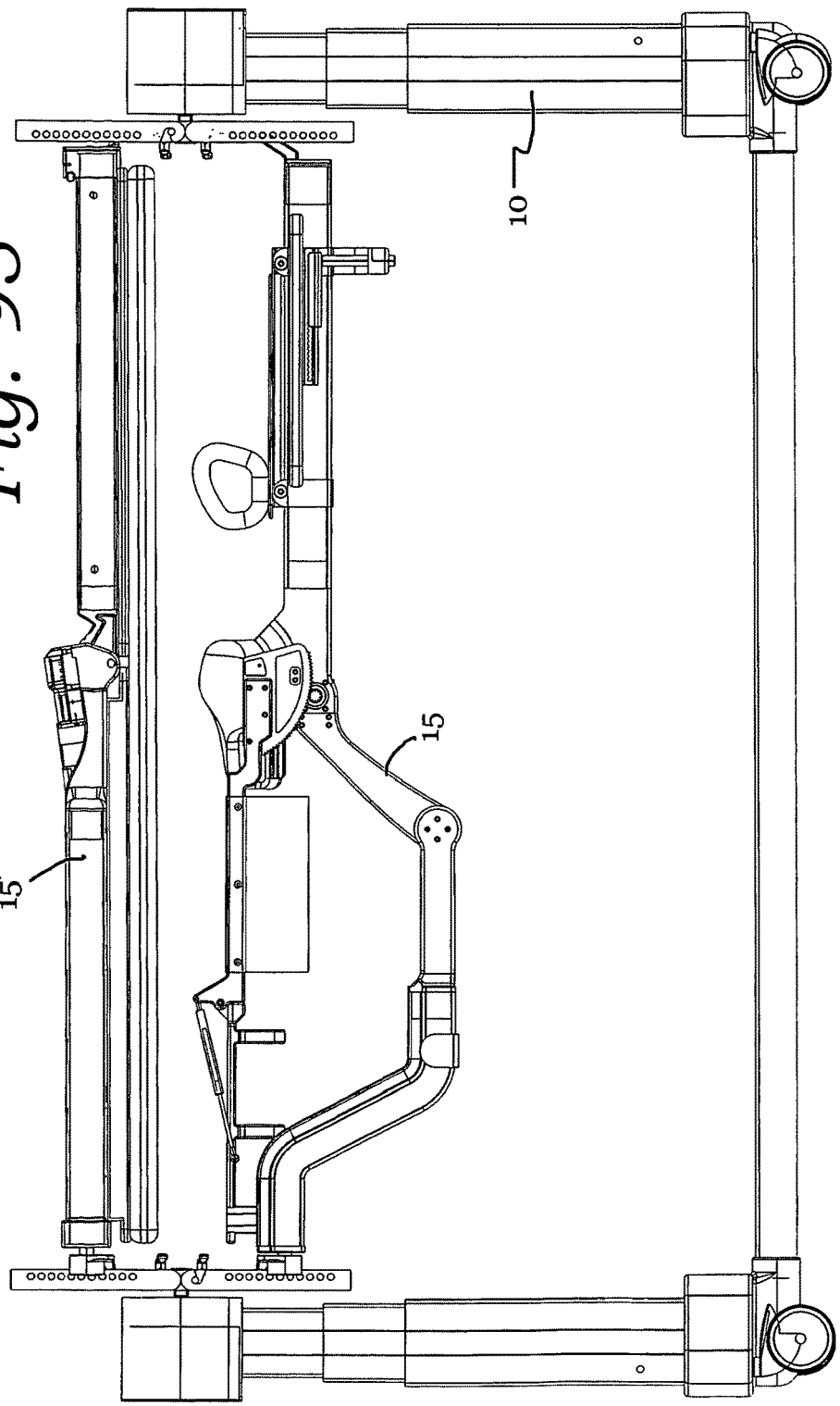
FIG. 95 is a right-side view of the patient positioning support system of FIG. 94A.
Figure 96:
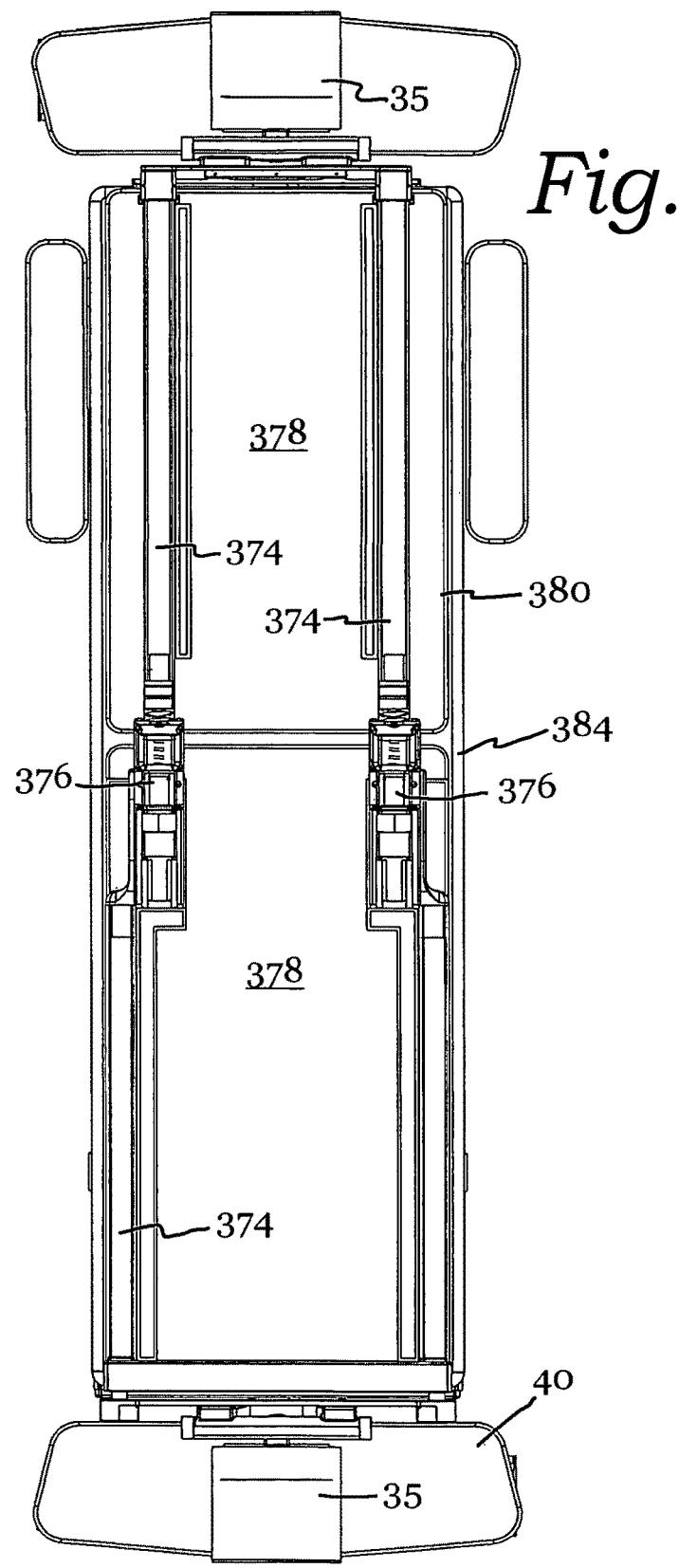
FIG. 96 is a top view of the patient positioning support system of FIG. 94B.
Figure 97:
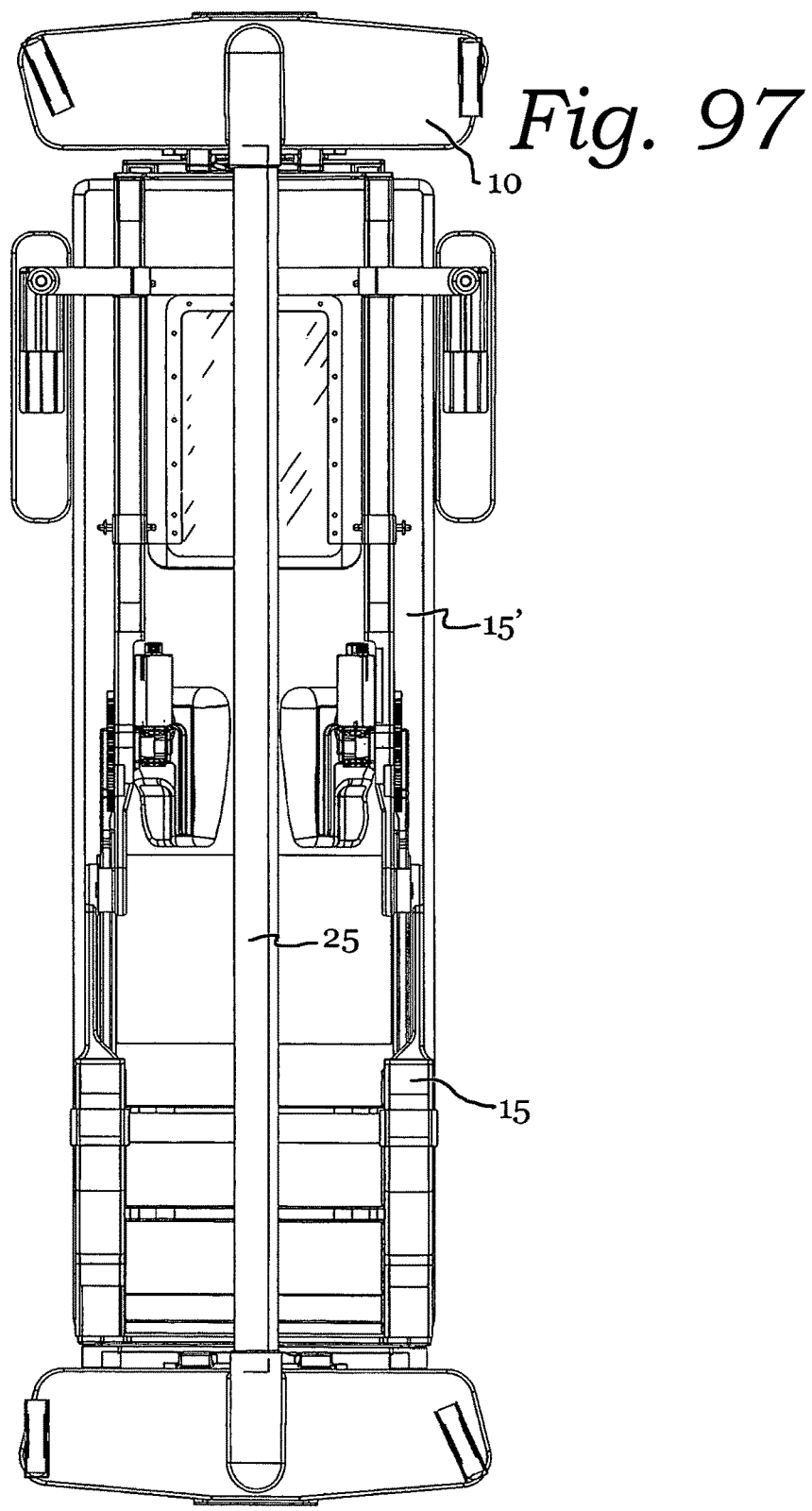
FIG. 97 is a bottom view of the patient positioning support system of FIG. 94B.
Figure 98:
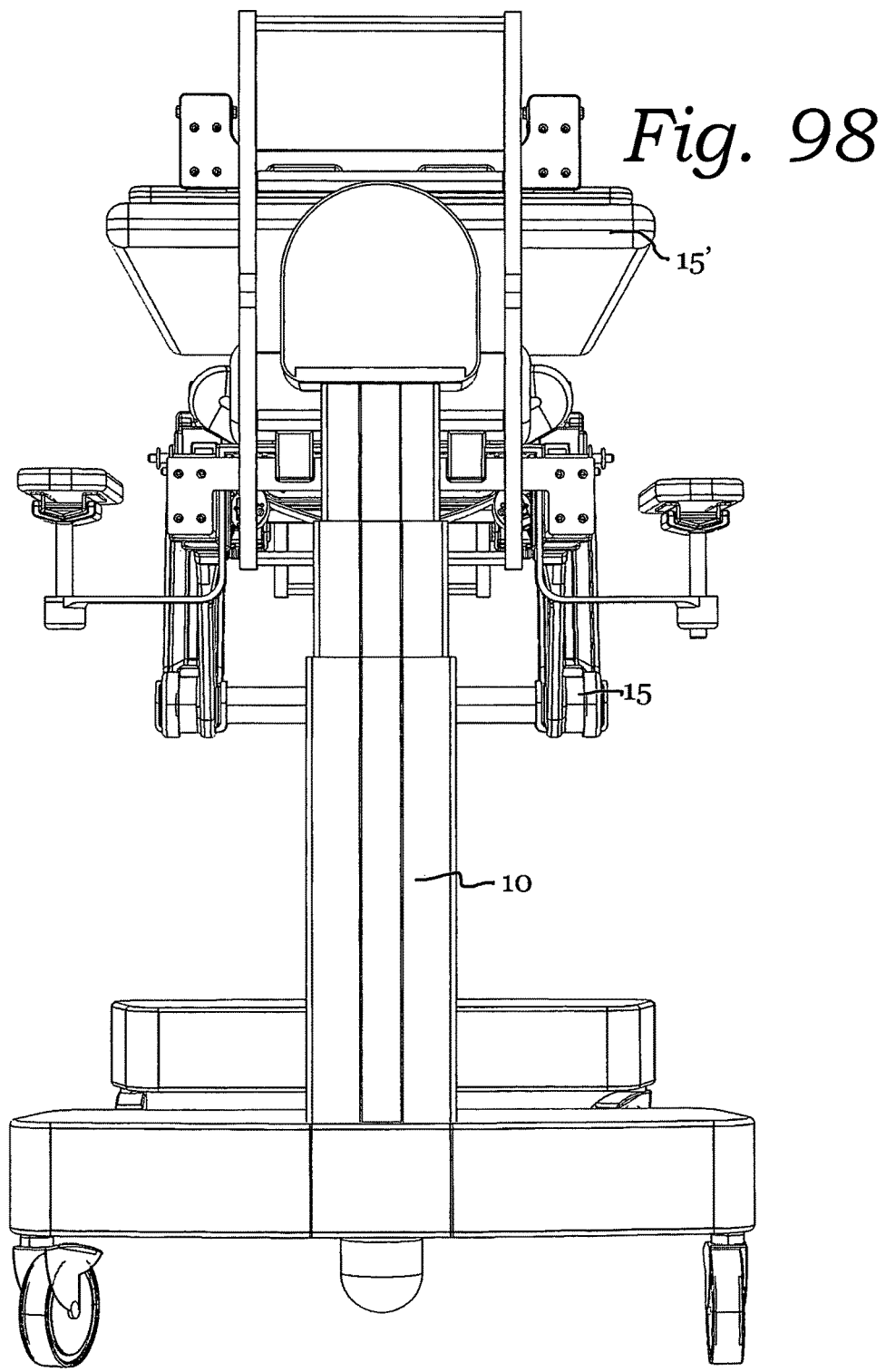
FIG. 98 is a head-end view of the patient positioning support system of FIG. 94B.
Figure 99:
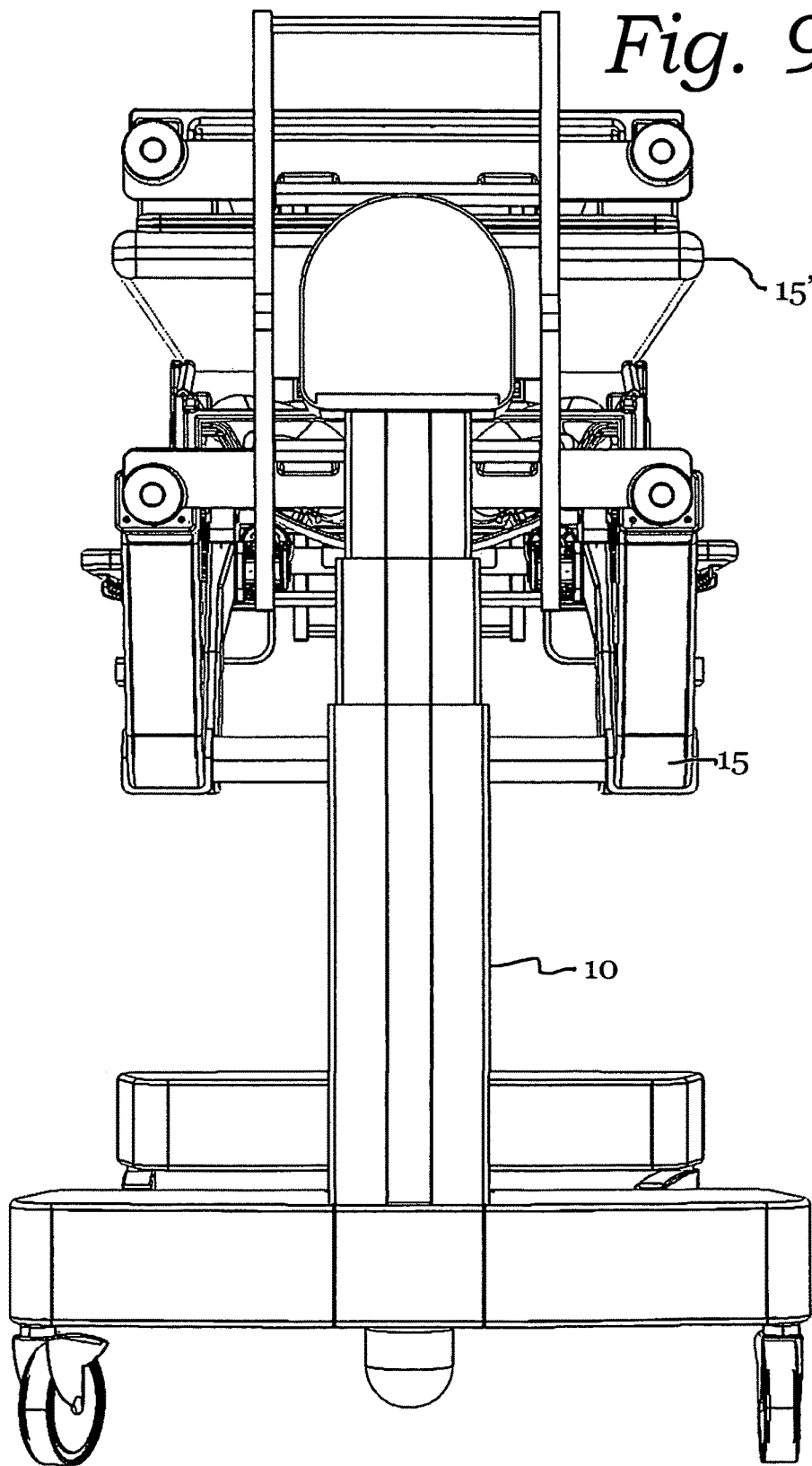
FIG. 99 is a foot-end view of the patient positioning support system of FIG. 94B.
Figure 100:
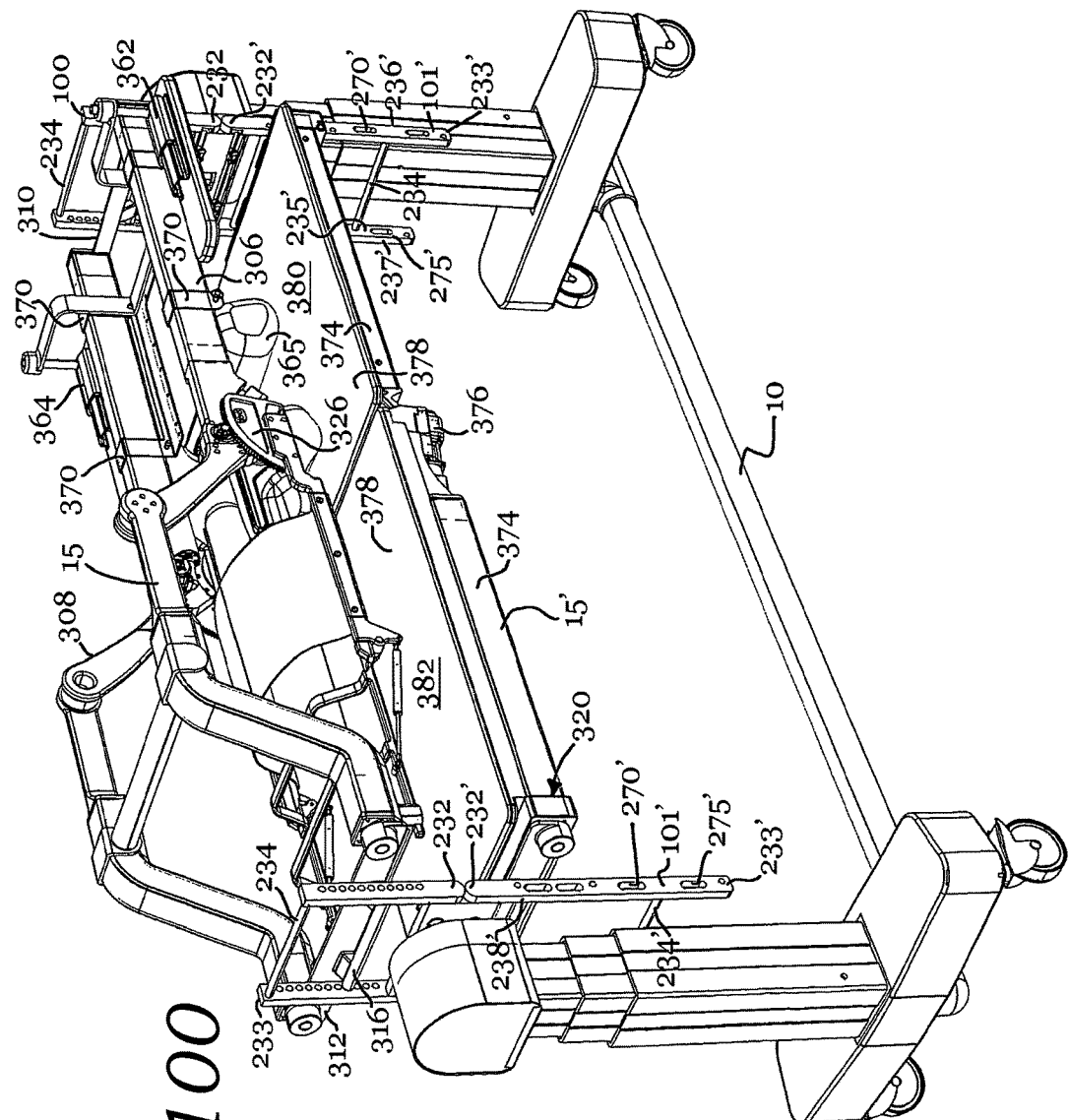
FIG. 100 is a perspective view of the patient positioning support system of FIG. 91A.
Figure 101:
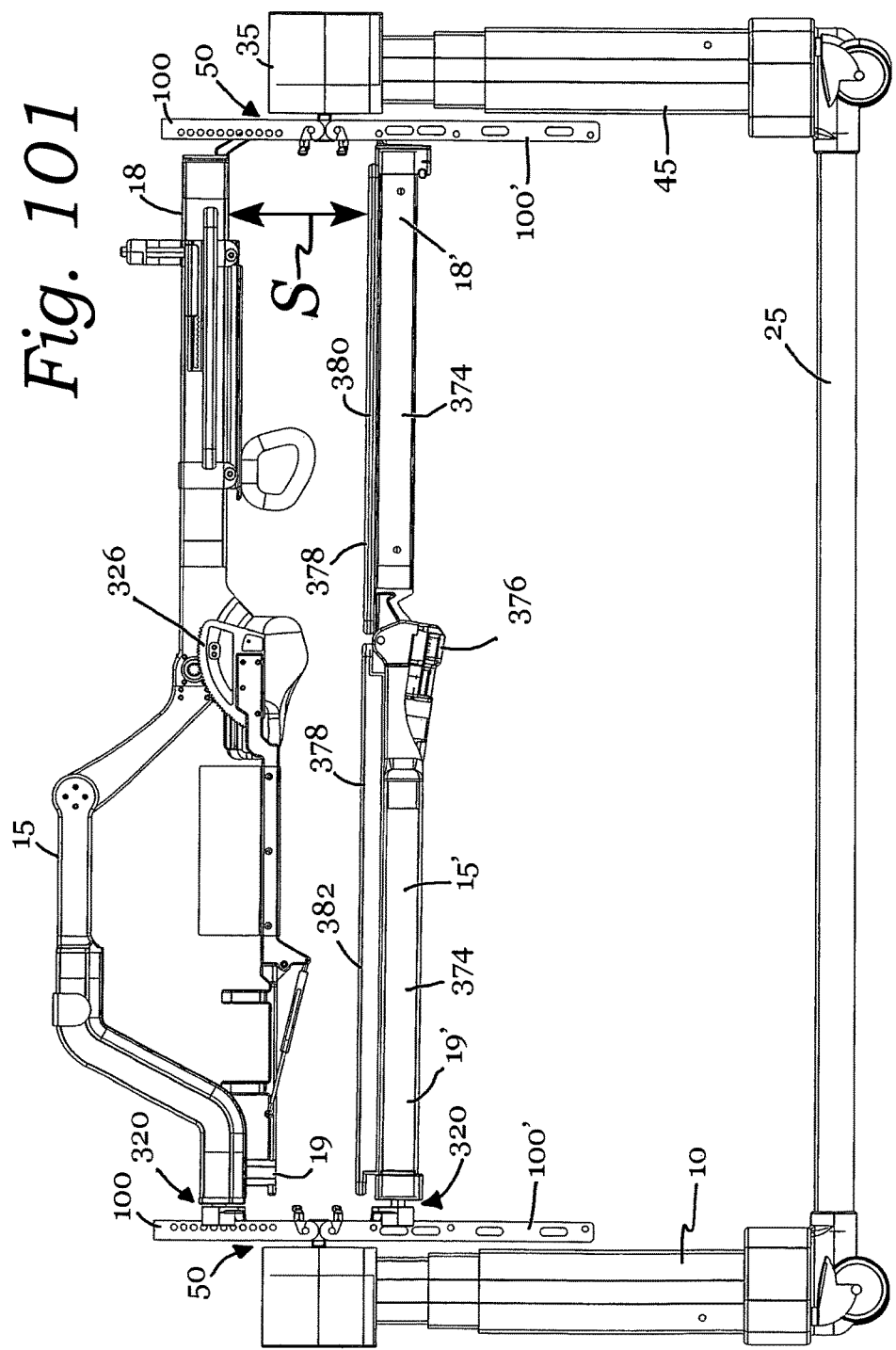
FIG. 101 is a right-side view of the patient positioning support system of FIG. 99.

FIGS. 91A, 92A, 93A and 94A illustrate rolling the prone and supine patient support structures 15, 15' about the roll axis R, in one embodiment, wherein the patient support structures 15, 15' are reversibly attached to a base 10, such as but not limited to during a sandwich-and-roll procedure. In FIG. 91A, the supine patient support structure 15' is below the roll axis R and the prone patient support structure 15 is above the roll axis R. In FIG. 92A, the prone and supine patient support structures 15 and 15' are tilted about the roll axis R, or toward the right of the page, a distance of about 25-degrees. FIGS. 92B and 92C provide alternative views of tilting the prone and supine patient support structures 15 and 15' about 25-degrees around the roll axis R. Then, either the prone and supine patient support structures 15, 15' can be locked in this position, such as for improved access to a surgical site, or they can be rolled farther, such as is described herein. FIGS. 93A-93C illustrate rolling the prone and supine patient support structures 15 and 15' even farther about the roll axis R, a distance of about 130-degrees, such as if the patient is being rolled over in a sandwich-and-roll procedure. FIGS. 94A, 94B and 95 show the positions of the prone and supine patient support structures 15, 15' after completion of a 180-degree roll. In this position, the supine patient support structure 15' is located above the roll axis R and the prone patient support structure 15 is below the roll axis R, and a patient thereon would be facing downward toward the floor F.

In some embodiments, the patient positioning support system 5 is configured and arranged to roll the prone and supine patient support structures 15, 15' a full 360-degrees about the roll axis R in at least one direction, so as to return to the orientation shown in FIG. 91A.

In other embodiments, the base 10 is adapted to roll the patient support structures 15, 15' backwards, or in a reverse direction, about the roll axis R, so as to be rolled a suitable distance, so as to position the patient in an orientation associated therewith, such as but not limited to the positions shown in FIGS. 91A through 95.

Vertical Axes

Each vertical translation subassembly 20 includes a vertical translation axis, which is denoted by V1 or V2. Vertical translation or movement, of at least a portion of the patient positioning support apparatus 5 may occur along one or both of the vertical translation axes V1 and V2. For example, the vertical translation subassembly 20 on the right side of FIG. 2 raises and lowers the associated upper portion 35 along the first vertical translation axis V1. Similarly, the vertical translation subassembly 20 on the left side of FIG. 2 raises and lowers the associated upper portion 35 along the second vertical translation axis V2. Such vertical translation may be synchronous or asynchronous, such as is described in greater detail below.

Figure 50:
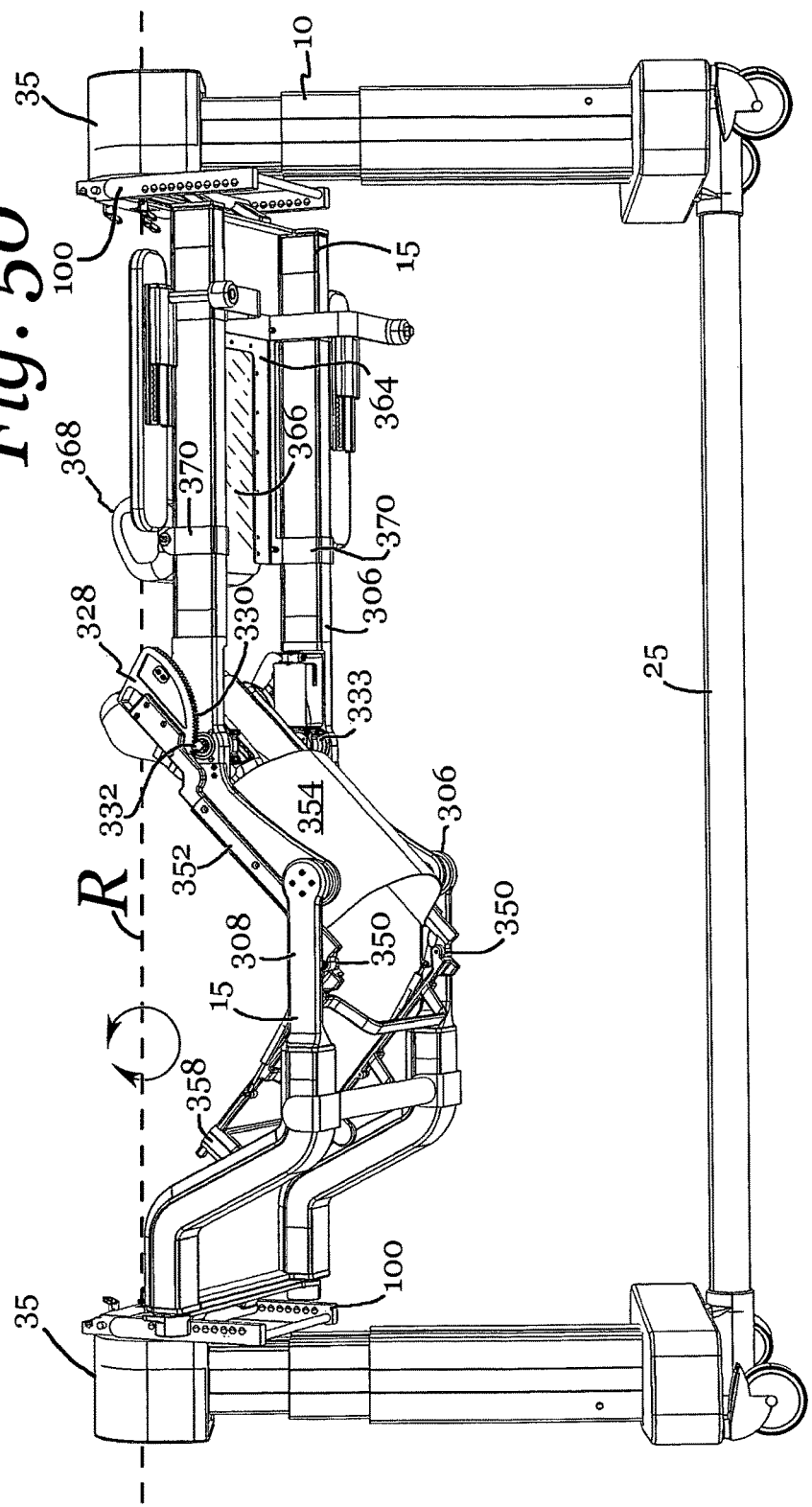
FIG. 50 is a right side view of the patient positioning support system of FIG. 48.
Figure 51:
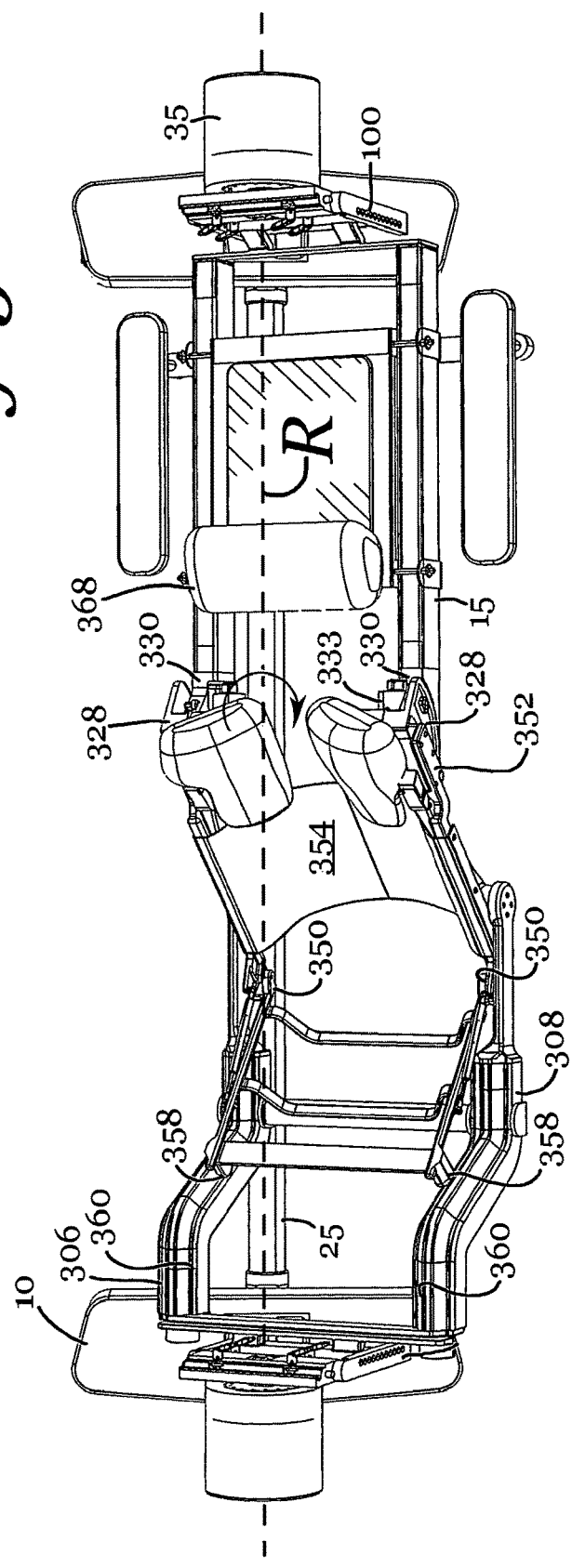
FIG. 51 is a top view of the patient positioning support system of FIG. 48.
Figure 52:
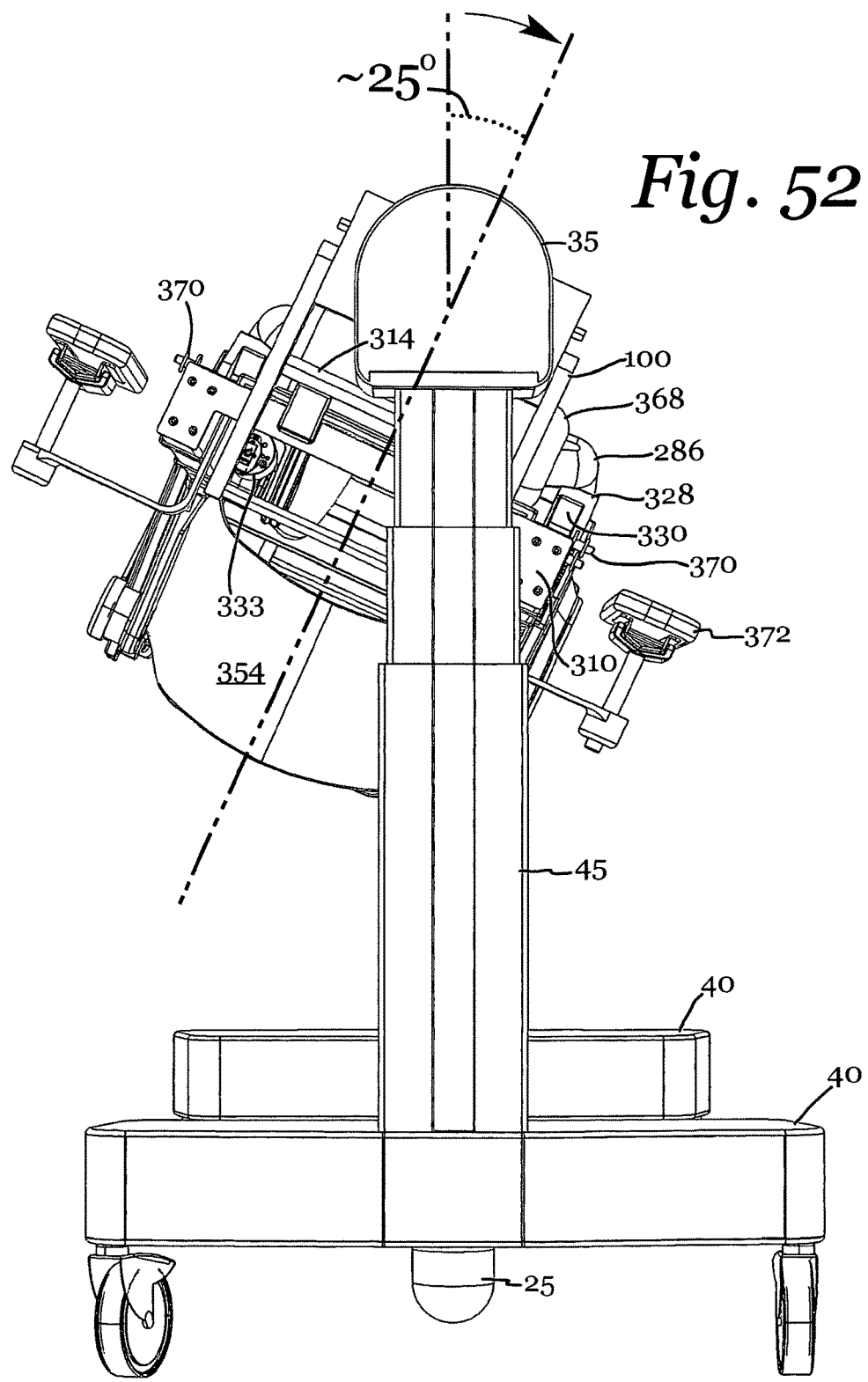
FIG. 52 is a head-end view of the patient positioning support system of FIG. 48.
Figure 53:
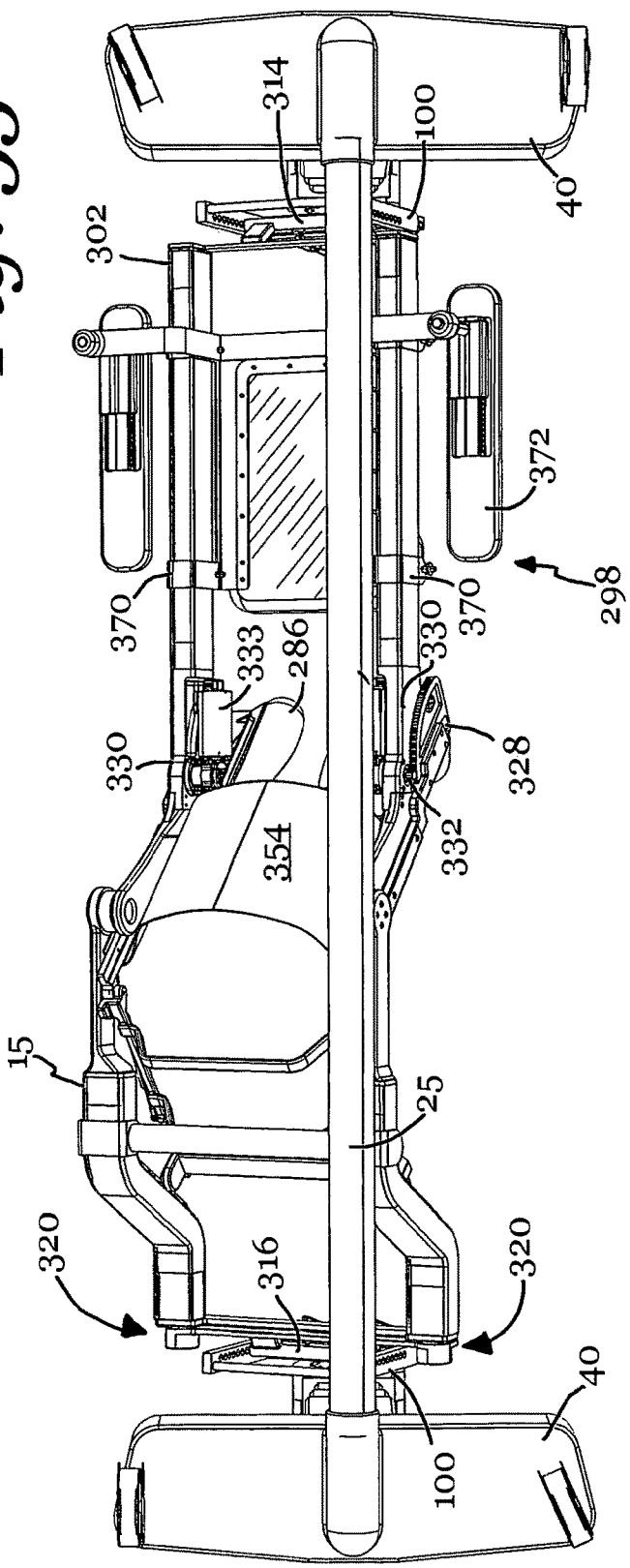
FIG. 53 is a bottom view of the patient positioning support system of FIG. 48.
Figure 54:
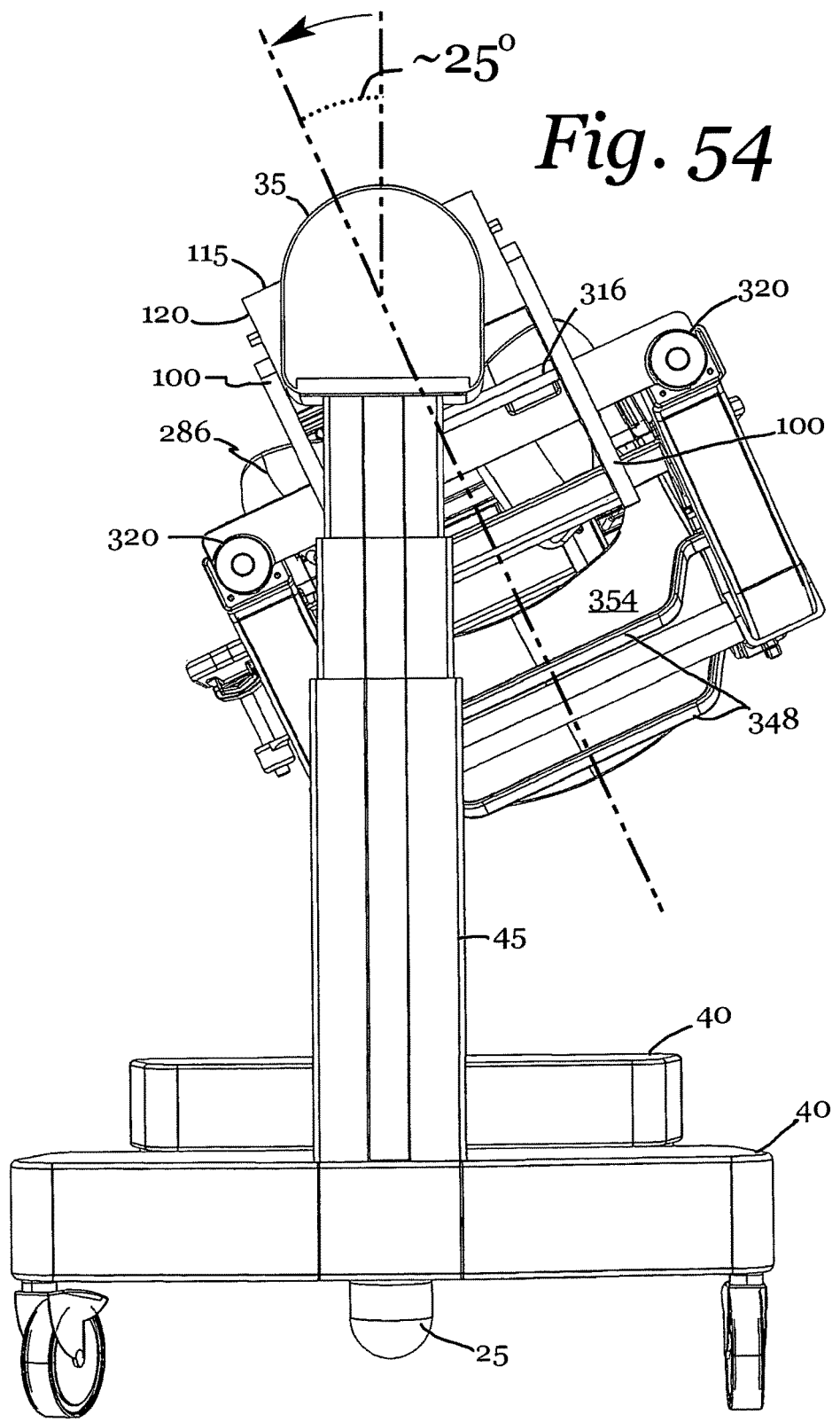
FIG. 54 is a foot-end view of the patient positioning support system of FIG. 48.

Each vertical translation subassembly 20 includes maximum and minimum translation or lift distances. The maximum lift distance is the maximum amount, most or highest the riser assembly 45 can be telescoped outwardly or upwardly, or extended. For example, the maximum lift distance is the highest that the rotation shaft outer portion 71 can be spaced from or above the floor F. In an exemplary embodiment, FIG. 4 shows both of the upper portions 35 positioned at substantially equal distances above the floor F, wherein the distance is about equal to the maximum lift distance described above, and the roll axis R is substantially parallel with the floor F. In another example, FIG. 50 shows both of the vertical translation subassemblies 20 in a maximally outwardly telescoped, raised, opened or fully open configuration, orientation or position with respect to their respective vertical translation axis V1, V2 and also with respect to the floor F.

Figure 45:
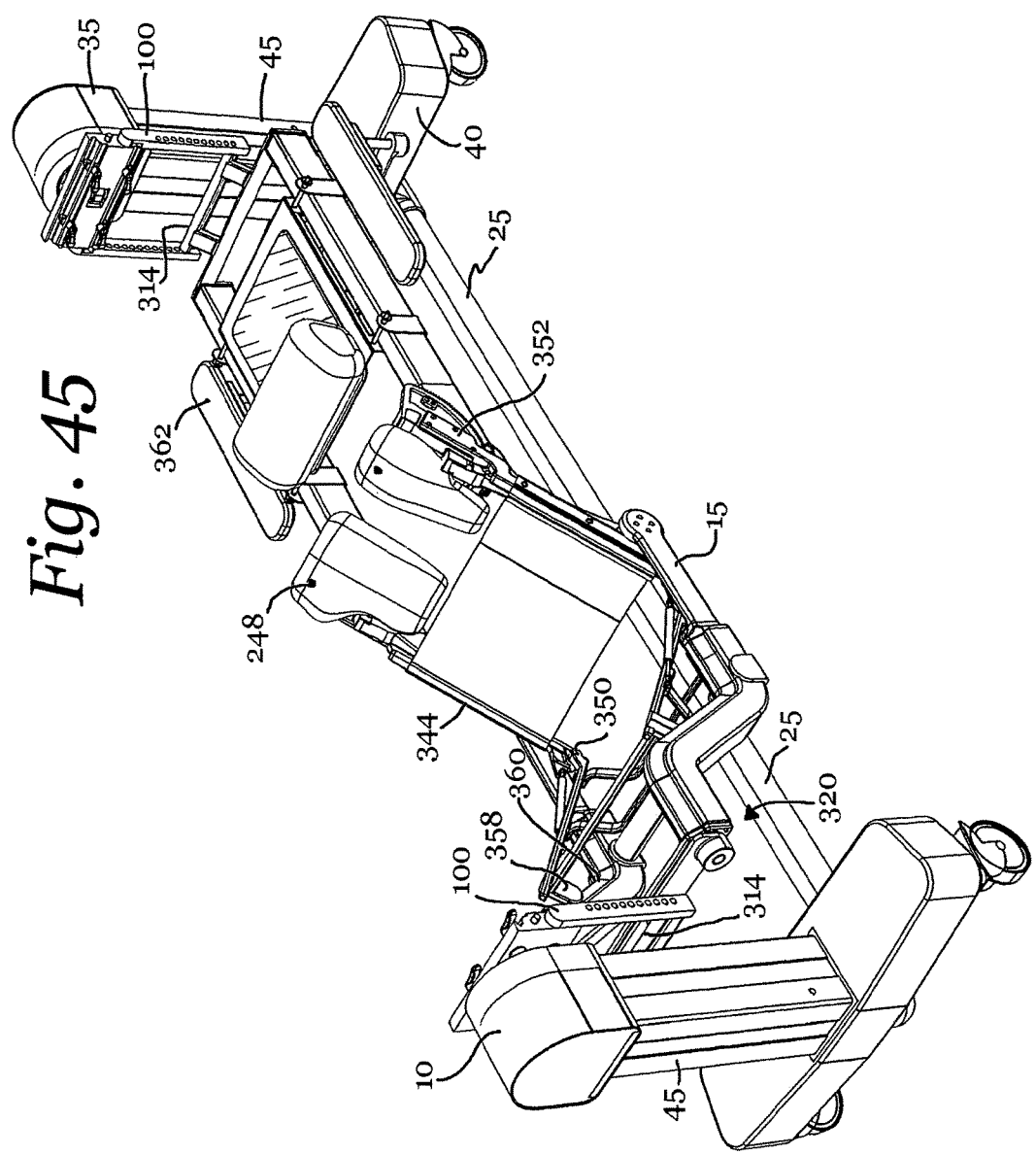
FIG. 45 is an enlarged perspective view of the patient positioning support system of FIG. 39.
Figure 46:
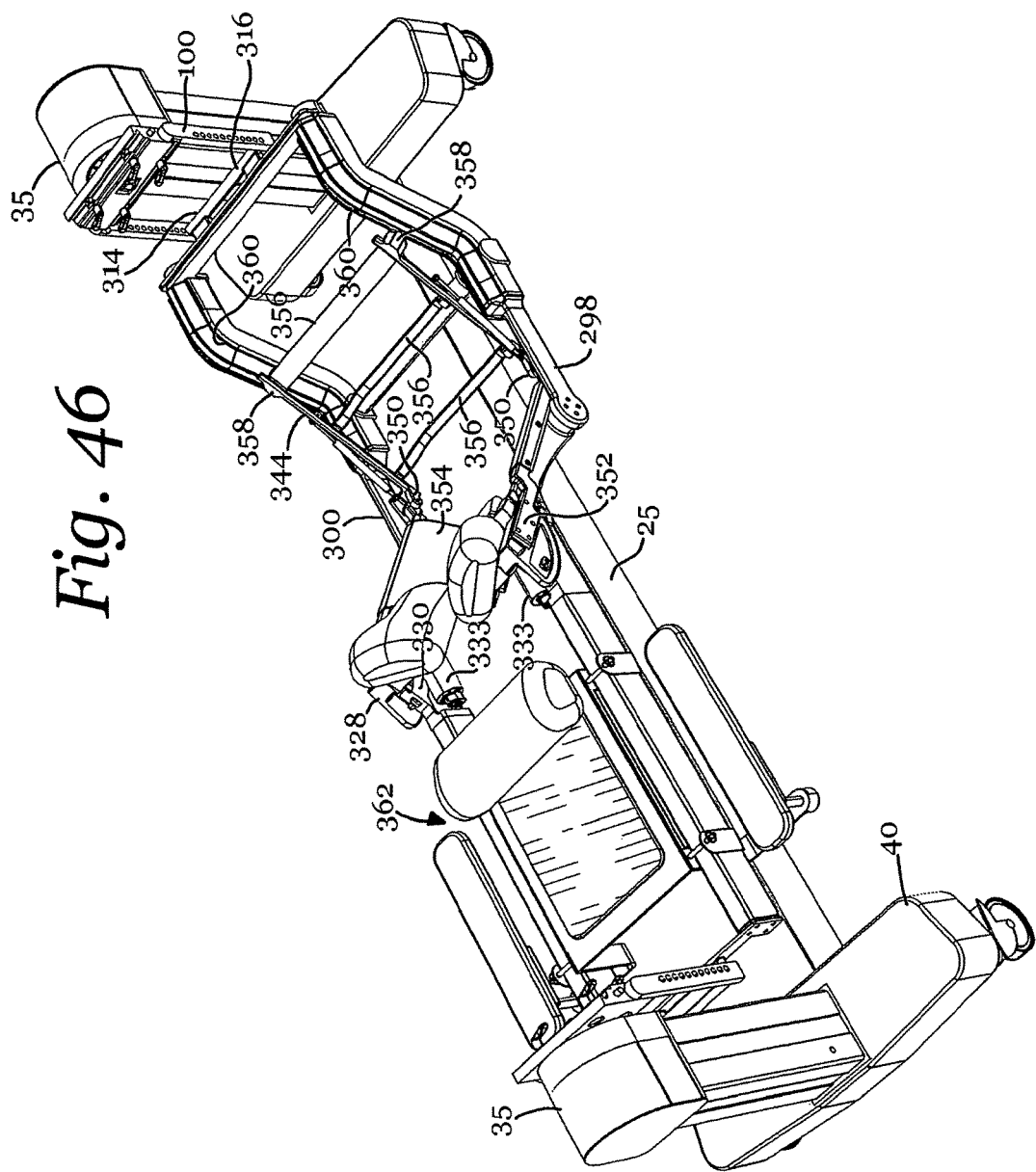
FIG. 46 is an enlarged top perspective view of the patient positioning support system of FIG. 39.
Figure 47:
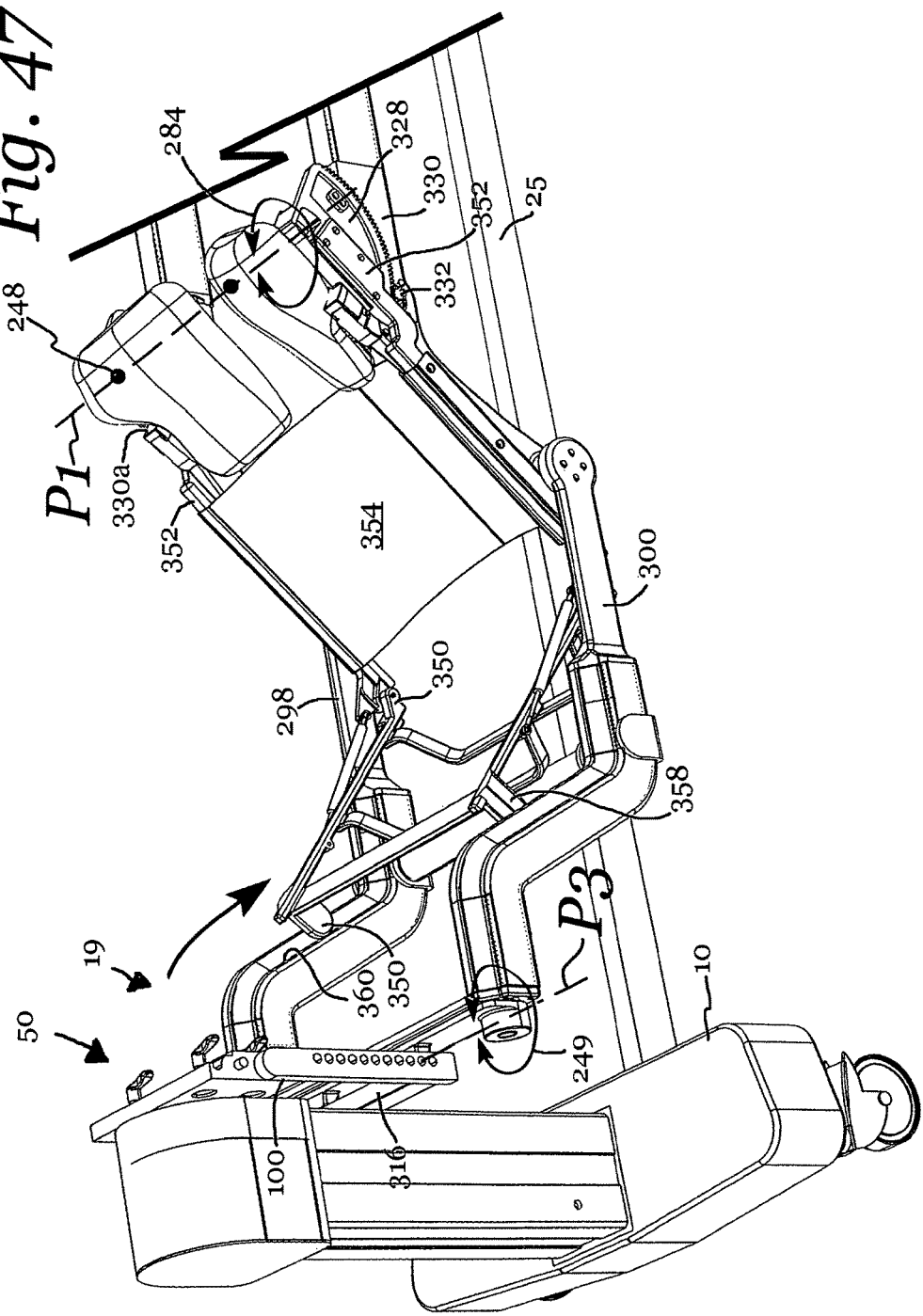
FIG. 47 is another enlarged perspective view of the patient positioning support system of FIG. 39, with portions broken away.
Figure 48:
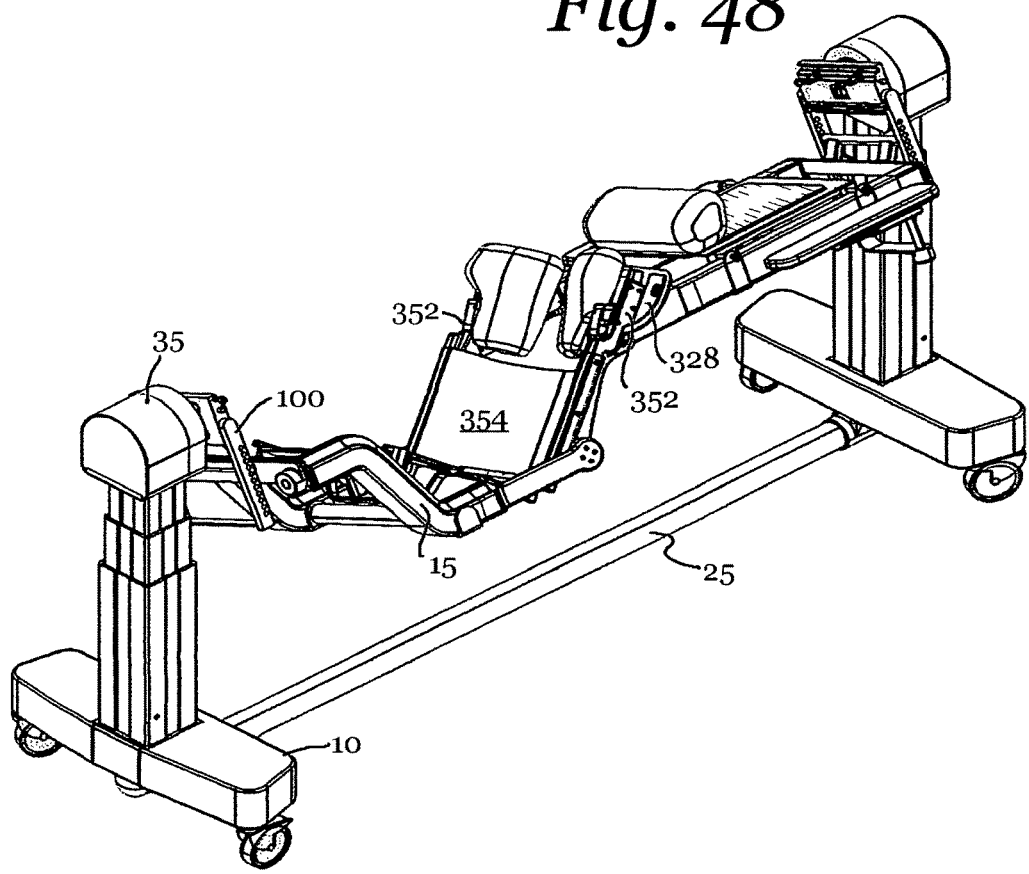
FIG. 48 is a perspective view of the patient positioning support system of FIG. 39, wherein the prone patient support structure is rolled 25-degrees toward the left side of the patient positioning support structure.
Figure 49:
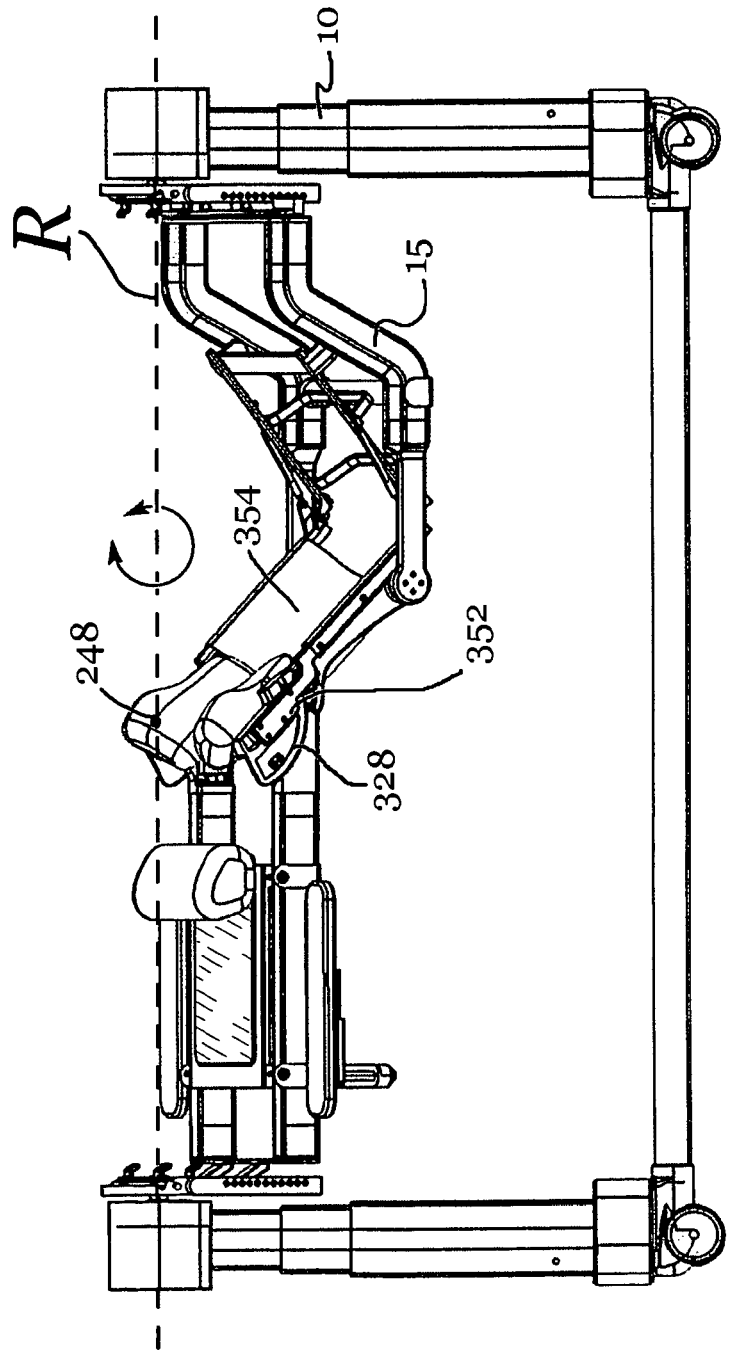
FIG. 49 is a left side view of the patient positioning support system of FIG. 48.

The minimum lift distance is the minimum amount, least, farthest downward, or the lowest the riser assembly 45 can be telescoped downwardly or inwardly, contracted or closed. For example, the minimum lift distance is the lowest height that the rotation shaft outer portion 71 can be spaced, located or extended above the floor F. In an alternative example, shown in FIGS. 1 and 45, both of the vertical translation subassemblies 20 are in a maximally inwardly telescoped, lowered, closed, contracted, or fully closed configuration, orientation or position, with respect to their respective vertical translation axis V1, V2 and also with respect to the floor F, such that the upper portions 35 are both located as close to the floor F as possible.

The vertical translation subassemblies 20 are sized, shaped, arranged, configured, or adapted to move, translate, or lift and lower the rotation shaft outer portion 71 vertically, between the maximum and minimum lift positions. In some embodiments, this vertical translation is incremental. For example, in one embodiment, the vertical translation subassembly 20 includes a ratchet mechanism that controls the intervals of lift, and an operator must select a number of discreet intervals for the upper portion 35 to be moved. In other embodiments this vertical translation is non-incremental, or continuous, between the maximum and minimum lift positions or distances. For example, in an embodiment, the vertical translation subassembly 20 includes a screw-drive mechanism that smoothly lifts and lowers the upper portion 35 an amount determined by an operator, wherein the amount of movement includes no discreet intervals or distances.

Depending upon the desired positioning of the patient, the vertical translation subassemblies 20 can be moved in the same direction or in opposite directions. Further, the vertical translation subassemblies 20 can translate their respective upper portions 35 the same distance or different distances.

In yet another embodiment, both of the vertical translation subassemblies 20 are positionable at substantially equally telescoped positions, relative to their respective vertical translation axis V1, V2 and the floor F, and wherein the telescoped positions are between the fully open and fully closed positions. When in this position, the roll axis R is substantially parallel with the floor F.

In another embodiment, the vertical translation subassemblies 20 are movable in opposite directions, and additionally or alternatively, positionable at different heights. For example, the vertical translation subassemblies 20 can be moved and placed such that one of the upper portions 35 is located farther from the floor F, or higher than, the opposed upper portion 35. For example, FIG. 23 shows the head-end upper portion 35 fully opened, and the foot-end upper portion 35 is closed, such that attached prone patient support structure 15 is positioned in a reverse Trendelenburg position. In this example, the upper portions 35 do not both intersect a single plane running parallel with the floor F; or the upper portions 35 are non-parallel with one another, relative to the floor F.

FIG. 32 shows another example, wherein the head-end vertical translation subassembly 20 is telescoped closed, and the foot-end vertical translation subassembly 20 is fully opened, such that the attached prone patient support structure 15 is in a Trendelenburg position. In yet another example, both of the vertical translation subassemblies 20 are positionable at substantially unequally telescoped positions, relative to their respective vertical translation axis V1, V2 and the floor F, and wherein the telescoped positions are between the fully open and fully closed positions. When in this position, the roll axis R is not substantially parallel with the floor F. Numerous positions of the patient support structure 15º are foreseen, wherein the upper portions 35 are raised to various different heights relative to the floor F.

The vertical translation subassemblies 20 can be operated singly or together, and synchronously or asynchronously. For example, one of the vertical translation subassemblies 20 is telescoped, expanded, lifted or moved, while the opposed vertical translation subassembly 20 is not telescoped or moved, or is held or maintained immobile. In another example, both of the vertical translation subassemblies 20 are moved in the same or opposite directions at the same time, and at the same or different rates of vertical movement. Numerous variations are foreseen.

Operation of the vertical translation subassemblies 20 is generally coordinated and controlled electronically, or synchronized, such as by a computer system that interacts with one or more motion sensors (not shown) associated with various parts of the patient positioning support system 5 and the motorized drives, such as is known in the art. However, it is foreseen that one or more portions or subsystems of the vertical translation subassemblies 20 may be operated manually. Further, in some circumstances, the electronic control of the patient positioning support system 5, or the drive system, can be turned off, or at least temporarily disconnected, so that one or more portions of the patient positioning support system 5 can be moved manually. For example, during a sandwich-and-roll procedure, such as is described elsewhere herein, at least the step of rolling the patient over is usually performed manually by two, three or preferably four or more operators or medical staff, after the drive system, or a clutch, has been temporarily disconnected or released, so as to ensure that the patient is not injured during the procedure. After the roll is completed, the clutch is re-engaged, so that the patient positioning support system 5 can mechanically perform additional movement and positioning of the patient.

Yaw Axes

Figure 37:
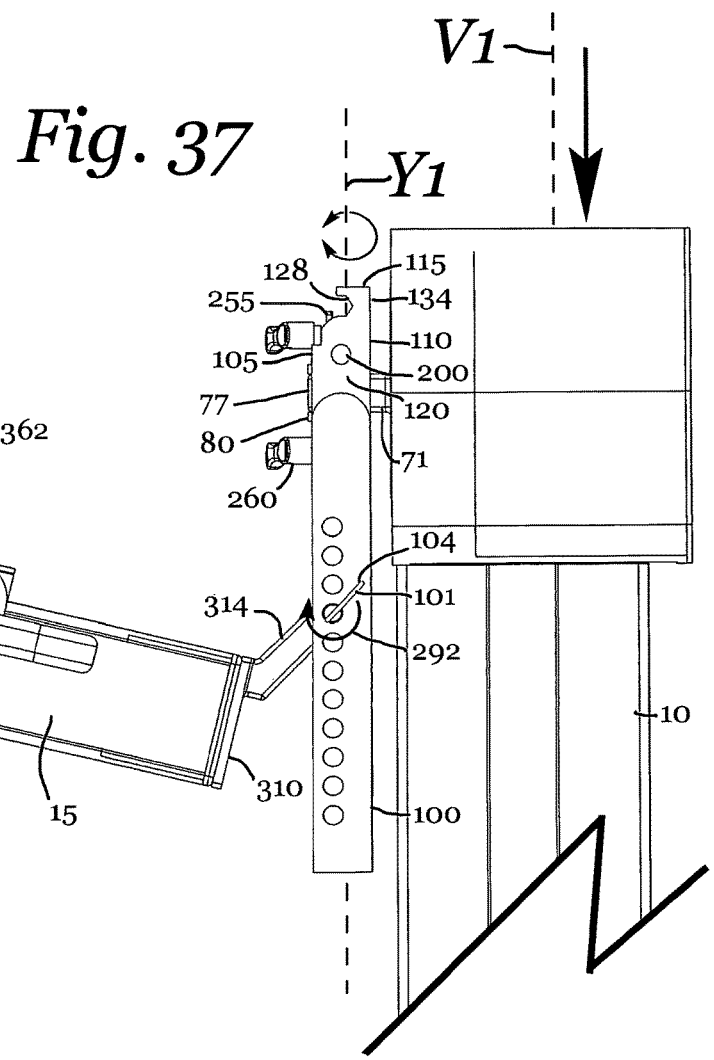
FIG. 37 is an enlarged view of the head-end of the patient positioning support system of FIG. 32, with portions broken away.
Figure 38:
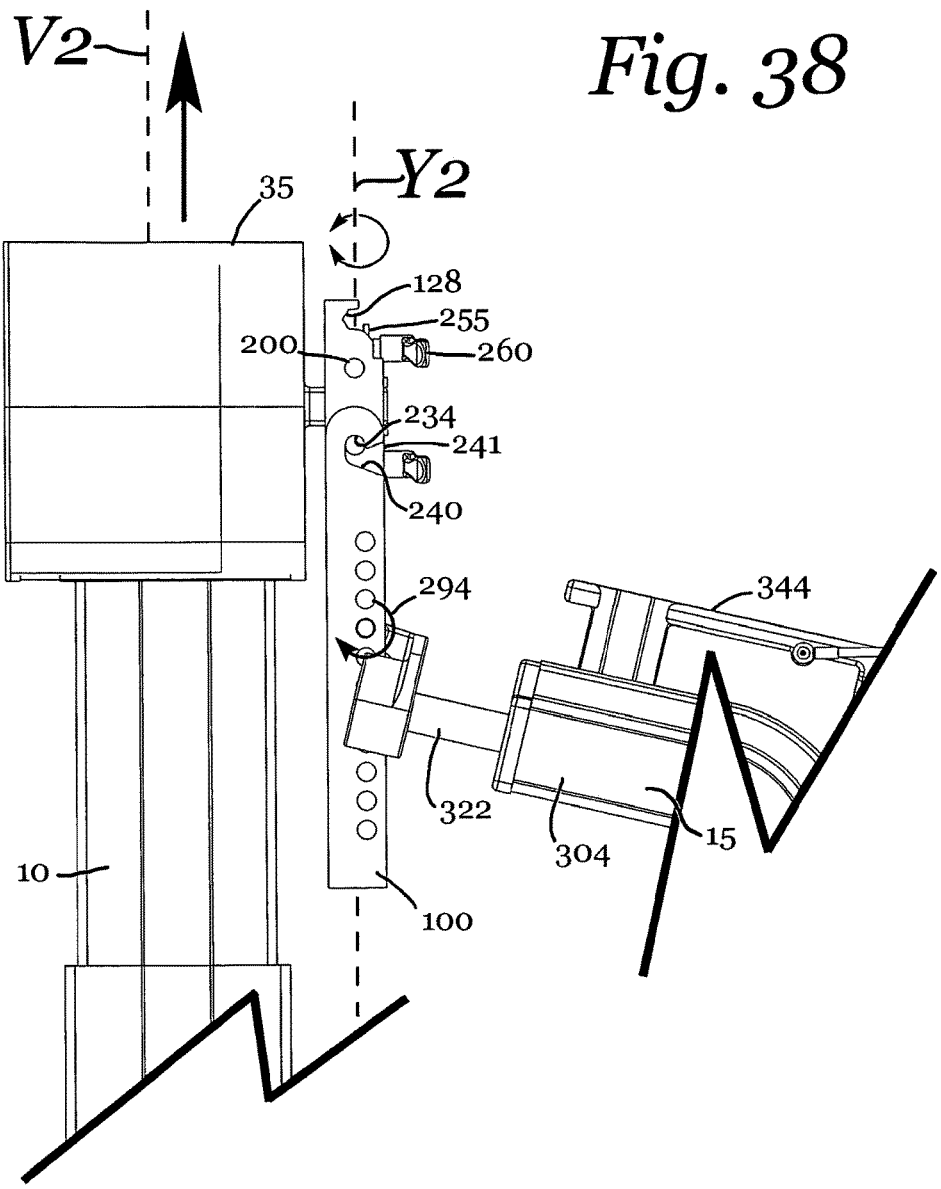
FIG. 38 is an enlarged view of the foot-end of the patient positioning support system of FIG. 32, with portions broken away.

Each of the vertical translation subassemblies 20 includes a yaw axis Yn. For example, in the embodiments shown in FIGS. 2, 37 and 38, the vertical translation subassemblies 20 include the yaw axes Y1 and Y2, respectively. When the patient support structure 15$^\circ$, such as but not limited to a prone patient support structure 15, is substantially parallel with the floor F, and not rolled about the roll axis R, such as is shown in FIG. 4, the yaw axes Y1 and Y2 are substantially perpendicular to the floor F and substantially parallel with the vertical axes V1 and V2. However, when the patient support structure 15$^\circ$ is and rolled about the roll axis R, so as to be non-parallel with the floor F, such as is shown in FIGS. 50-54, the yaw axes Y1 and Y2 are not perpendicular to the floor F or with the vertical axes V1 and V2.

The yaw axes Yn enable rotational movement thereabout of at least a portion of the patient positioning support system 5. Such rotational movement prevents buckling or collapse of the patient positioning support system 5 when the patient support structure 15$^\circ$, such as but not limited to a prone or supine patient support structure 15, 15', is placed in certain positions, such as but not limited to a Trendelenburg or a reverse Trendelenburg position, in conjunction with rotation about the roll axis R, such as is described in greater detail below.

As described below, the rotation block 57 is sized, shaped and arranged to as to rotate or pivot about the associated yaw axis Yn. As the connection block 57 pivots about the yaw axis Yn, the rear face 110 does not substantially contact either the housing front 150 or the rotation plate 65. In some embodiments, the rotation block 57 is spaced a sufficient distance from the rotation plate 65 and additionally or alternatively the housing front 150 so as to substantially prevent such contact therebetween from happening.

In alternative or additional embodiments, the rotation block 57 and the rotation subassembly 50 are sized, shaped and configured to allow or enable the rotation block 57 to be rotated a distance about the yaw axis Yn, so as to prevent the patient positioning support system 5 from collapsing during certain positioning and rolling of the patient support structure 15$^\circ$, such as described elsewhere herein, and also such that the distance of rotation about the yaw axis Yn is not sufficient for the rear face 110 to contact the housing front 150 of the rotation plate 65.

Movement of the Patient Positioning Support Structure with Respect to the Roll, Yaw and Vertical Translation Axes; Active Versus Passive Movement; Simultaneous Versus Sequential Movement The patient positioning support system 5 is adapted for movement with respect to the roll, yaw and vertical translation axes R, Yn and Vn, respectively. With respect to two or more of these axes, such movement may occur simultaneously or sequentially, or occurs at substantially the same time.

In an exemplary embodiment of simultaneous movement with respect to two or more of roll, yaw and vertical translation axes R, Yn and Vn, one of the vertical translation subassemblies 20 may telescope upwardly, so as to lift the attached end of the patient support structure 15$^\circ$, such as but not limited to a prone or supine patient support structure 15 or 15', while the rotation subassembly 50 simultaneously or concurrently rolls the patient support structure 15$^\circ$ a distance of between about 5-degrees and about 25-degrees toward the left-hand side of the patient positioning support system 5.

In other embodiments, movement with respect to two or more of these axes is sequential. The rotation subassembly 50 is movably attached to the connection subassembly 57 so as to enable both rotational movement of at least a portion of the connection subassembly 57 about the roll axis R and also rotational movement of at least a portion of the connection subassembly 57 about an associated yaw axis Yn. In particular, the rotation subassembly 50 is attached to the respective rotation block 57 by an attachment that allows that rotation block 57 to pivot about the yaw axis Yn. It is foreseen that the connection subassembly 57 can be joined or attached to the rotation subassembly 50 using a variety structures or mechanisms known in the art, so long as rotation of the connection subassembly 57 with respect to the roll and yaw axes R, Yn is maintained.

Preferably, such rotation about both the roll and yaw axes R, Yn is smooth and non-incremental. However, in certain embodiments, rotation about the roll axis R is incremental, including a plurality of selectable incremental stops. Further, rotation about the roll axis R may be active, such as mechanically actuated or driven, or rotation about the roll axis R may be passive, such as manually rolling the patient support structure 15$^\circ$ about the roll axis R.

In the illustrated embodiment, such as is shown in FIGS. 14 and 121, the rotation shaft outer portion 71 extends into and optionally through the rotation block through-bore or through-channel 165, and is attached, joined or fixed thereto. Rolling or rotation of the rotation shaft 56, due to actuation of the rotation subassembly 50, causes rotation of the rotation block 57 about the roll axis R, in either a clockwise or a counterclockwise direction. Rolling of the rotation shaft 56 can rotate the rotation block 57 a distance of between about 1-degree and about 237-degrees in either a clockwise or a counter clockwise direction, such that a patient on the patient support structure 15$^\circ$ can be rolled over or tilted, such as is described elsewhere herein.

Patient Support Structure Components and Operation

As described above, the patient positioning support system 5 includes at least one patient support structure 15$^\circ$, such as but not limited to prone and supine patient support structures 15, 15'. In some embodiments, the patient positioning support system 5 includes one or more additional patient support structures, such as but not limited to a patient support structure adapted to hold a patient of a different size, such as but not limited to a pediatric patient, an extra-tall adult patient, and an obese patient. In some embodiments, the patient positioning support system 5 includes one or more additional patient support structures 15$^o$, such as but not limited to a patient support structure adapted for a specific medical procedure, some of which are described in greater detail below. It is foreseen that a patient support structure 15$^o$ may be configured and arranged to include one or more modular or interchangeable portions.

The patient support structure 15$^o$ is suspended above the floor F. In a further embodiment, the patient support structure 15$^o$ is attached to and supported by or suspended by the base 10.

Each patient support structure 15$^o$, such as but not limited to the prone and supine patient support structures 15, 15' described below, includes a plurality of pitch axes, which are denoted by Pn, wherein n is an integer that indicates or denotes a specific or particular pitch axis. For example, as shown in FIGS. 3 and 103, the prone and supine patient support structures 15, 15' each include first, second and third pitch axes, which are denoted by P1, P2 and P3, respectively. The first pitch axis P1 is located between and spaced from the second and third pitch axes P2 and P3. All three pitch axes P1, P2 and P3 run substantially perpendicular to a longitudinal axis of the respective patient support structure 15$^o$ as well as substantially parallel with one another. Depending upon the position of the patient support structure 15$^o$ relative to the floor F, the pitch axes P1, P2 and P3 may be either parallel with the floor F or intersect the floor F.

The patient support structure 15$^o$ is adapted, configured and arranged for rotational movement about each of the pitch axes P1, P2 and P3. In general, the first pitch axis P1 is located so as to be associated with rotational movement at or near a patient's hips. The first pitch axis P1 enables positioning of a patient in a prone position such that the hips are flexed or extended. In contrast, the second and third pitch P2 and P3 axes are associated with rotational movement of the patient support structure 15$^o$ about the respective axis relative to the base 10, and wherein the second pitch axis P2 is associated with head-end of the patient support structure 15$^o$ and P3 is associated with the foot-end of the patient support structure 15$^o$. This enables placing the patient in either a Trendelenburg position or a reverse Trendelenburg position, such as is described in greater detail below.

Prone Patient Support Structure

The prone patient support structure 15 is sized, shaped, configured and arranged, or otherwise adapted, for supporting a patient (not shown) in a prone, or face-down, position during a medical procedure, such as but not limited to imaging and surgical procedures. FIGS. 1, 3-9, 23-101, 121-125, 134-148 and 159-169 illustrate an exemplary prone patient support structure 15, in one embodiment. Alternatively sized, shaped, configured and arranged, or otherwise adapted prone patient support structures 15 are foreseen.

As is most easily seen in FIG. 3, the prone patient support structure 15 of the present invention includes a first pitch or pivot axis P1 that is associated with a virtual pivot point 282. In some embodiments, the virtual pivot point 282 is a pair of virtual pivot points, which may be located so as to be spaced and opposed to one another. The first pitch axis P1 intersects the virtual pivot points 282. At least a portion of the prone patient support structure 15 is rotatable about the first pitch axis P1 wherein such rotational movement is indicated by the double-headed directional arrow 284.

In the exemplary embodiment of FIG. 3, the virtual pivot points 282 are each located at a point of contact between the patient's skin and a surface of a hip-thigh pad 286, also referred to as pelvic pads or pelvic support pads. The hip-thigh pads 286 are sized, shaped and located so as to hold, support and pad the hips or pelvis of a prone patient (not shown) supported on the prone patient support structure 15.

In other embodiments, the virtual pivot points 282 and the associated first pitch axis P1 are located above or below the exemplary virtual pivot points 282 and first pitch axis P1 depicted in FIG. 3. Additionally or alternatively, in some embodiments, the virtual pivot points 282 and the associated first pitch axis P1 are located more toward the head-end 288 or more toward the foot-end 290 of the patient positioning support structure 5, than the exemplary virtual pivot points 282 and first pitch axis P1 depicted in FIG. 3.

The prone patient support structure 15 includes second and third pitch or pivot axes P2 and P3 that are associated with its head and foot-ends, and which are generally denoted by the numerals 288 and 290 respectively. The prone patient support structure 15 is sized, shaped and arranged to provide for rotation of the prone patient support structure 15 about the second pitch axis P2, such as is indicated by the double-headed directional arrow 292. For example, the prone patient support structure 15 is adapted to rotate about the second pitch axis P2 relative to the floor F. Similarly, the prone patient support structure 15 is sized, shaped and arranged to provide for rotation of the prone patient support structure 15 about the third pitch axis P3, such as is indicated by the double-headed directional arrow 294. For example, the prone patient support structure 15 is adapted to rotate about the third pitch axis P3 relative to the floor F.

The maximum amounts of rotation at P2 and P3 is determined by, or dependent upon, the minimum and maximum heights of the vertical translator upper ends, such as but not limited to the min and max heights of the connection subassembly connection to the rotation subassembly.

Figure 31:
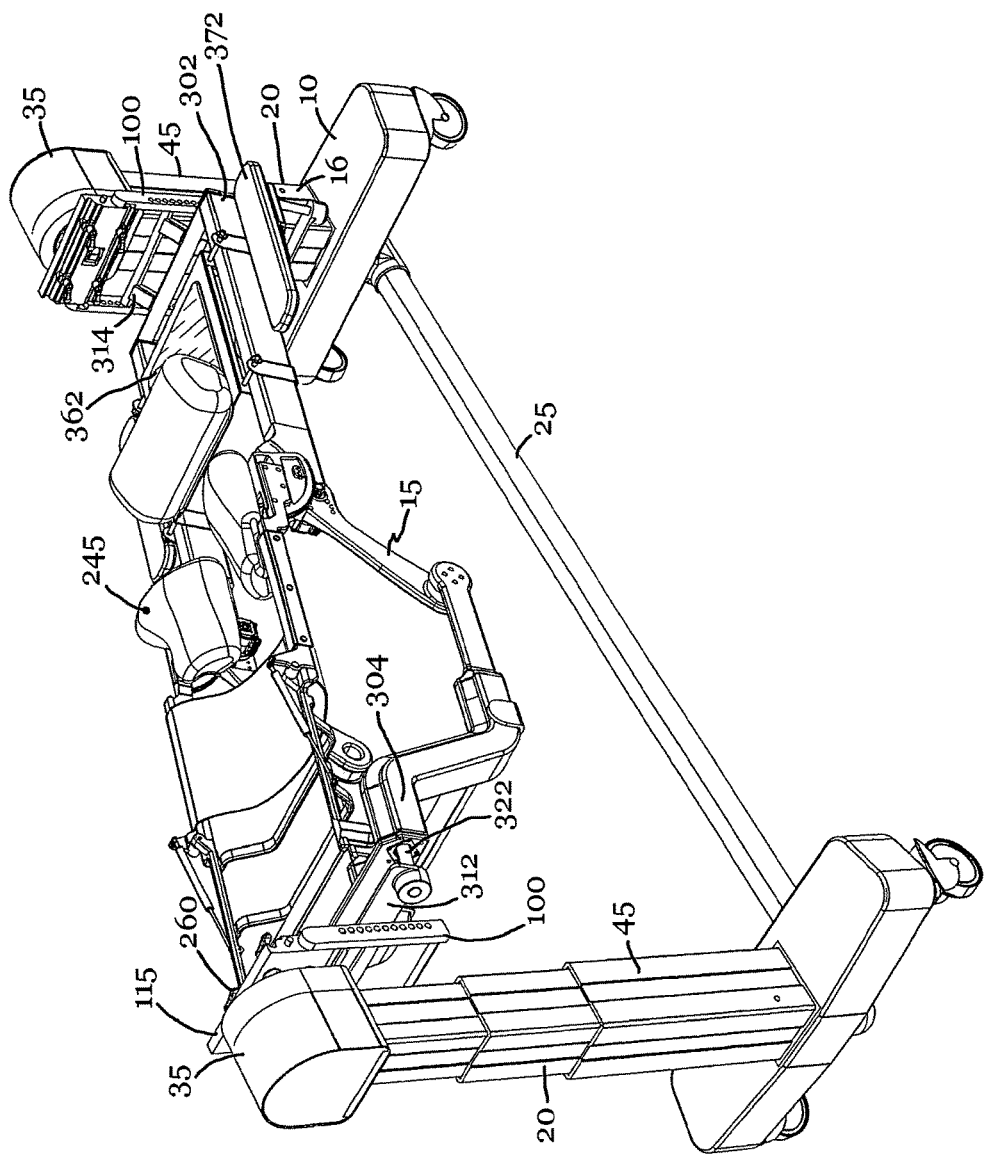
FIG. 31 is a reduced perspective view of the patient positioning support system of FIG. 1, with the patient support structure in a Trendelenburg position.

The prone patient support structure 15 is adapted to pivot, rotate or move about P2 and P3 when reversibly placed in and moved between numerous positions relative to the floor F. For example, in a first position, or orientation, the patient support structure 15 is positioned such that the upper body portion thereof, or the torso of a patient supported thereon is substantially parallel with the floor F. In a second position, the upper body portion of the prone patient support structure 15, or the torso of a patient supported thereon, is substantially non-parallel with the floor F. The patient support structure 15 is movable between the first and second positions. For example the prone patient support structure 15 may be moved to and placed in Trendelenburg and reverse Trendelenburg positions, such as a shown in FIGS. 31 and 23, respectively. When moving the prone patient support structure 15 between the first and second positions, the prone patient support structure 15 must rotate about both P2 and P3. Generally, this pivoting movement about P2 and P3 is simultaneous, thought not necessarily at the same rate. It is foreseen that such movement may be incremental or non-incremental, such as but not limited to between maximally angled Trendelenburg and reverse Trendelenburg positions relative to the floor F. Rotation about the second and third pitch axes P2 and P3 is discussed in greater detail below. It is noted that an infinite number of non-incremental positions exist between the minimum and maximum positions. It is also noted that a finite number of incremental positions exist between the minimum and maximum positions. It is noted that in some embodiments the supine patient support structure 15' is movable in a substantially similar manner to that of the prone patient support structure 15.

Prone Patient Support Structure: Frame

The prone patient support structure 15 includes an open fixed frame 296 that is suspended above the floor F. The frame 296 is substantially rigid and strong, and able to withstand substantial forces applied thereto. Additionally, as much of the frame 296 as possible is radiolucent, so as to not interfere with imaging.

In the illustrated embodiment, the frame 296 is attachable to the base 10, such that the base 10 holds or suspends the frame 296 above the floor F. However, it is foreseen that the frame 296 can also be suspended above the floor F using any other useful structure known in the art, such as but not limited to an attachment structure that connects the frame 296 with the ceiling, with a wall, or with a combination thereof. In some embodiments, the frame 296 is suspended or held above the floor F using another base known in the art. Numerous configurations are foreseen. Further, the illustrated base 10, or any other useful base known in the art, can also suspend either the prone patient support 15 alone or both the prone and supine patient supports 15 and 15' together above the floor F. As described below, the prone and supine patient support structures 15, 15' can both be connected to and disconnected from the base 10.

The prone patient support structure frame 296 includes left-hand and right-hand sides, generally 275 and 300 respectively, a head-end 302 and a foot-end 304. When a prone patient is supported on the prone patient support structure 15, the left side of the patient is near or at the frame left-hand side 298. Similarly, the patient's right side of the patient is located near or at the frame right-hand side 300.

The frame 296 also includes left-hand and right-hand frame portions 306 and 308, respectively, which are spaced and opposed to one another, and extend longitudinally with respect to the prone patient support structure 15. The left-hand and right-hand frame portions 306, 308 are substantially parallel with one another. At the frame head-end 302, the left-hand and right-hand frame portions 306, 308 are joined by a head-end frame member 310. Similarly, at the frame foot-end 304, the left-hand and right-hand frame portions 306, 308 are joined by a foot-end frame member 312. Accordingly, the frame head-end and foot-end frame members 310 and 312 hold or maintain the left-hand and right-hand frame portions 306, 308 in spaced relation to one another.

Each of the head-end and foot-end frame members 310, 312 includes an attachment structure 314 structure adapted for attachment to the base 10 and also to enable angulation of the patient support structure 15 relative to the base 5 at the second and third pivot axes P2 and P3. Attachment of the patient support structure 15 head-end 302 to a vertical translation subassembly 20 using a T-pin 101 and the like is described below. When installed, the T-pin 101 associated with the frame head-end 310 is substantially coaxial with the second pitch axis P2. Similarly, when installed, the T-pin 101 associated with the frame foot-end 312 is substantially coaxial with the third pitch axis P3.

The head-end frame member 310 includes an attachment structure 314 that includes a T-pin engaging member 316 with a through-bore 318 extending therethrough. The through-bore 318 is sized and shaped to reversibly slidingly receive a T-pin 101 therethrough. In the illustrated embodiment, the T-pin engaging member 316 is a substantially cylindrical tube-like portion. However, it is foreseen that the T-pin engaging member 316 my have any other useful shape known in the art. In the illustrated embodiment, the head-end attachment structure 314 is attached to a ladder 100 or 100' by aligning the T-pin engaging member through-bore 318 with a pair of ladder through-bores, such as through-bores 275 and 280, such that the through-bore 318 is located between the through-bores 275 and 280 and the three through-bores 275, 280 and 318 are substantially coaxial. Then, a T-pin 101 is inserted into and through the three through-bores 275, 280 and 318 so as to be engaged thereby. With respect to the head-end 302 of the frame 296, when the T-pin 101 and through-bores 275, 280 and 318 are engaged, they are also coaxial with the second pitch axis P2.

The frame foot-end 304 is connected or attached to a second or foot-end vertical translator 20 in a substantially similar manner to the frame head-end 302. Namely, the foot-end frame member 312 includes another attachment structure 314 that also includes a T-pin engaging member 316 with a through-bore 318 extending therethrough. The through-bore 318 is sized and shaped to reversibly slidingly receive a T-pin 101 therethrough. In the illustrated embodiment, the T-pin engaging member 316 is a substantially cylindrical tube-like portion. However, it is foreseen that the T-pin engaging member 316 my have any other useful shape known in the art. In the illustrated embodiment, the foot-end attachment structure 314 is attached to a ladder 100 or 100' by aligning the T-pin engaging member through-bore 318 with a pair of ladder through-bores, such as through-bores 275 and 280, such that the through-bore 318 is located between the through-bores 275 and 280 and the three through-bores 275, 280 and 318 are substantially coaxial. Then, a T-pin 101 is inserted into and through the three through-bores 275, 280 and 318 so as to be engaged thereby. With respect to the foot-end 304 of the frame 296, when the T-pin 101 and through-bores 275, 280 and 318 are engaged, they are also coaxial with the third pitch axis P3.

Referring to FIGS. 23-38, the T-pin engaging members 316 are sized, shaped and configured to pivot or rotate about an engaged T-pin 101, so as to rotate, pivot, angulate or articulate about the associated pitch axis P2 or P3. For example, with reference to FIG. 29, the head-end T-pin engaging member 316 pivots counter-clockwise about the engaged T-pin 101, as indicated by the arrow 292. In another example, with reference to FIG. 30, the foot-end T-pin engaging member 316 pivots counter clockwise about another T-pin 101, as indicated by the arrow 294. In yet another example, with reference to FIG. 37, the head-end T-pin engaging member 316 pivots clockwise about the engaged T-pin 100, as indicated by the arrow 292. In still another example, with reference to FIG. 38, the foot-end T-pin engaging member 316 pivots clockwise about the T-pin 101, as indicated by the arrow 294.

Figure 11:
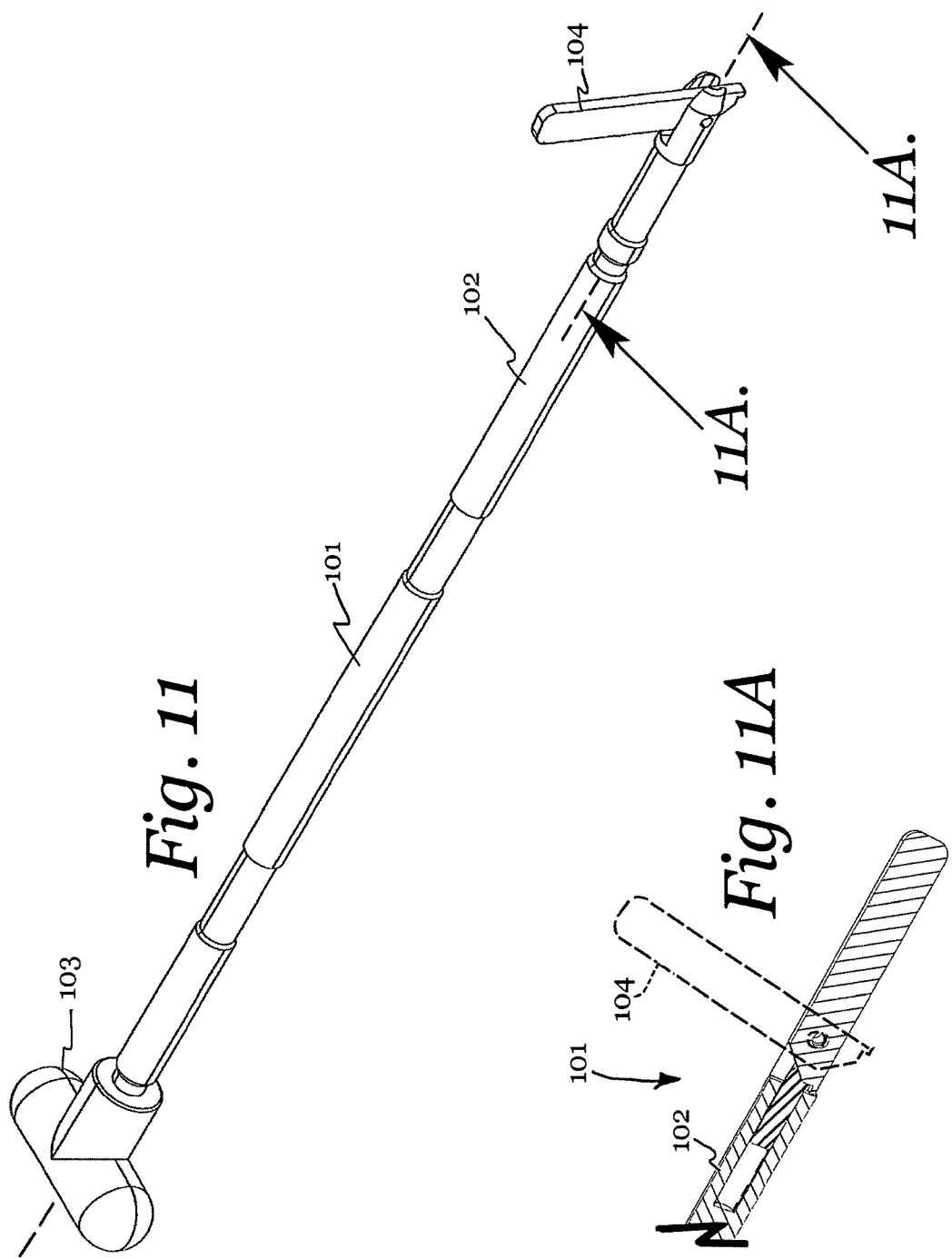
FIG. 11 is an enlarged perspective view of a T-pin of the patient positioning support system of FIG. 1.

An exemplary T-pin 101 is shown in FIGS. 11 and 11A. It is noted that T-pins 101 are used to connect both of the head- and foot-ends 302, 304 of both the prone and supine patient support structures 15, 15' to the vertical translation subassemblies 20 using the ladders 100 and optionally the ladders 100', but such T-pins 101 are not shown in many of the attached figures. Each T-pin 101 includes a shaft 102, a handle 103 and a locking member 104. As shown in FIG. 11A, the locking member is positionable in a locking position, shown in phantom, and a non-locking position. It is foreseen that the patient support structures 15, 15' may include alternatively configured attachment structures 314 and T-pins 101. Additional information about T-pins can be found in co-pending U.S. patent application Ser. No. 13/507,618, filed Jun. 18, 2012.

Translation Compensation Subassembly

As noted above, the patient support structure $15^0$ can be moved to numerous positions wherein said structure is or is not parallel with the floor F. Since the base 10 is fixed in position by the cross-bar 25, such that the vertical translation subassemblies 20 cannot move relative to one another, a change in the height of one or both of the vertical translation subassemblies 20 changes the distance between the rotation subassemblies 50 (e.g., rotation blocks 57, yaw pins 79, etc.). Accordingly, when this distance increases or decreases, the length of the patient support structure 15° must change a similar or complementary amount. The patient support structure 15° changes its length and therefore includes a translation compensation subassembly 320, described below.

Referring now to FIGS. 63 through 66, at their foot-ends 304, the left-hand and right-hand frame portions 306, 308 include an in-frame or in-line translation compensation subassembly, generally 320, also referred to as a lateral translation compensation subassembly. In an exemplary embodiment, each translation compensation subassembly 320 includes a translation bar 322 that joins the foot-end 260 of the associated frame portion 306 or 308 with the foot-end frame member 312. The translation bars 310 are adapted to telescope outwardly and inwardly from the associated frame portions 306, 308, so as to effectively lengthen and shorten the foot-end 304 of the frame 296 when the frame 296 is moved between an orientation generally parallel with the floor F and Trendelenburg and reverse Trendelenburg positions, or when the frame 296 is moved such that the roll axis R moves between orientations that are parallel and non-parallel with the floor F. The translation compensation subassembly 320 also includes a translation driver 324 located within the frame portions 306 or 308 that actuates the telescoping of the translation bar 322.

The frame 296 of the present invention may be adapted to be used with a variety of translation compensation subassemblies, such as but not limited to those described in U.S. Pat. Nos. 7,565,708, 8,060,960, or U.S. Patent Application No. 60/798,288, U.S. patent application Ser. No. 12/803, 173, U.S. patent application Ser. No. 12/803,192, or U.S. patent application Ser. No. 13/317,012, instead of the illustrated translation compensation subassembly 320. However, the in-frame compensation subassembly 320 of the present invention provides the advantage of a low profile.

The translation compensation subassembly 320 of the present invention is actively driven and infinitely adjustable between a maximally outwardly telescoped configuration and a closed configuration. Passive translation compensation mechanisms are foreseen. Translation compensation mechanisms that are not in-line with the frame 296 are also foreseen. It is noted that the supine patient support structure 15' may include a similar translation compensation subassembly 320.

Pivot-Shift Mechanism

Referring again to FIG. 3, as well as FIGS. 65-84, the prone patient support structure 15 includes a pair of spaced opposed radially sliding or gliding joints, generally 326, that provide a pivot-shift mechanism for moving the pelvic pads 286.

The joints 326 are generally centrally located along a length of the frame 296 and cooperate with the frame 296 of the prone patient support structure 15. For example, in the embodiment shown in FIG. 3, the joints 326 are located along the length of the frame 296 so as to be associated with the first pitch axis P1. The joints 326 are spaced and opposed to one another, so as to allow a portion of a patient's body to hang downwardly therebetween. For example, a patent's belly may hang downwardly between the joints 326 when the patient is positioned in a prone position on the prone patient support structure 15. Further, the joints 326 are substantially parallel with one another.

Figure 72:
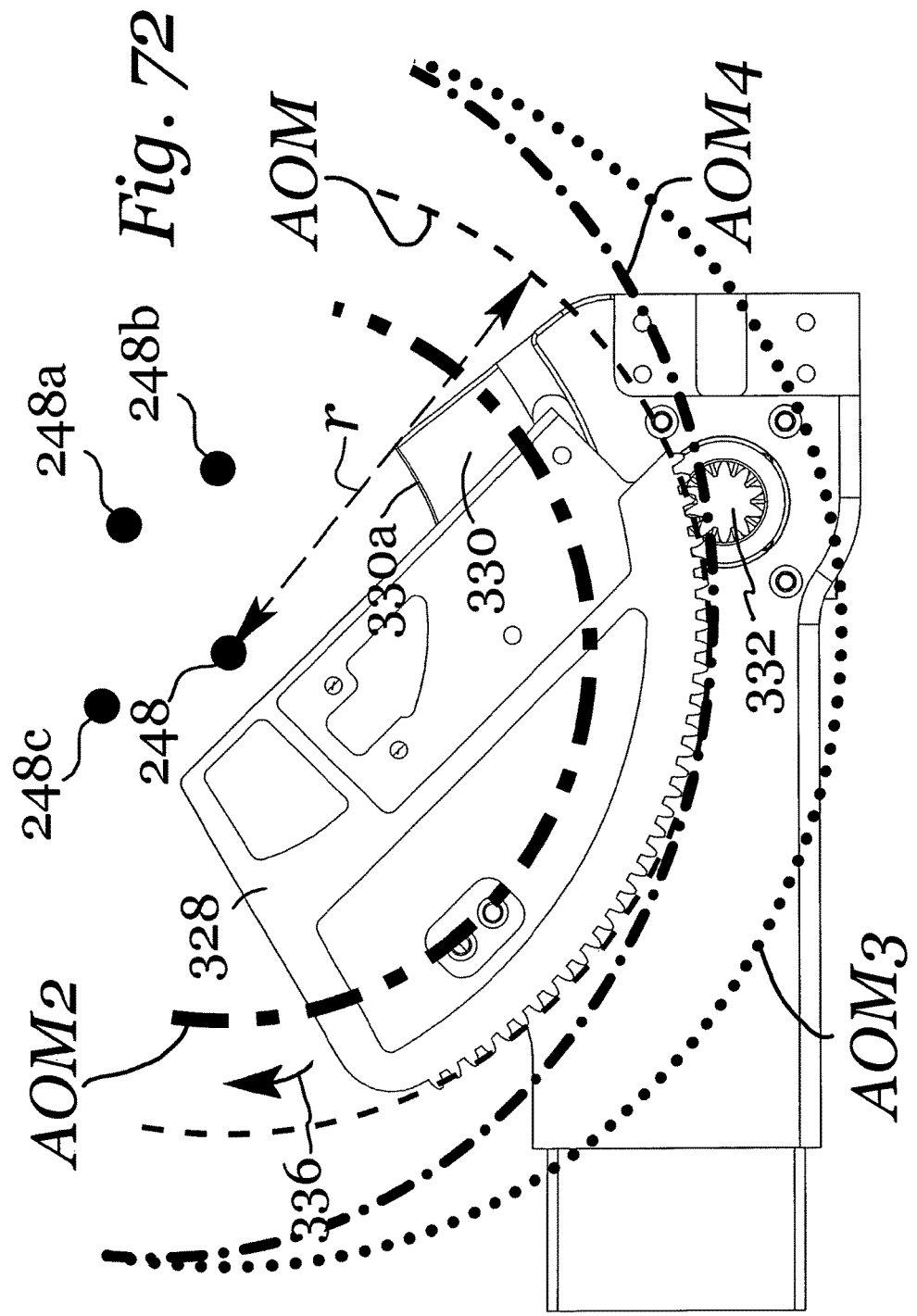
FIG. 72 is yet another enlarged side view of a joint of the prone patient support structure of FIG. 3.
Figure 73:
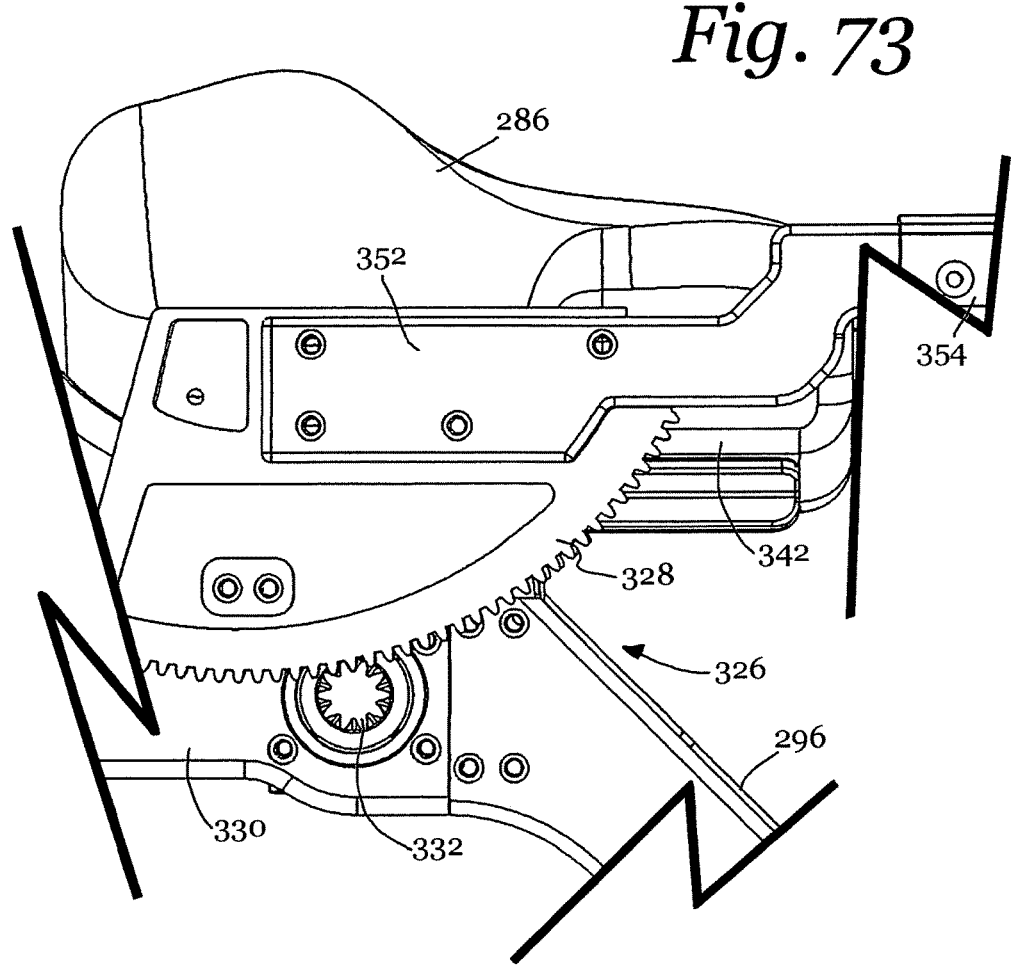
FIG. 73 is an enlarged side view of the prone patient support structure of FIG. 3, with portions broken away.
Figure 74:
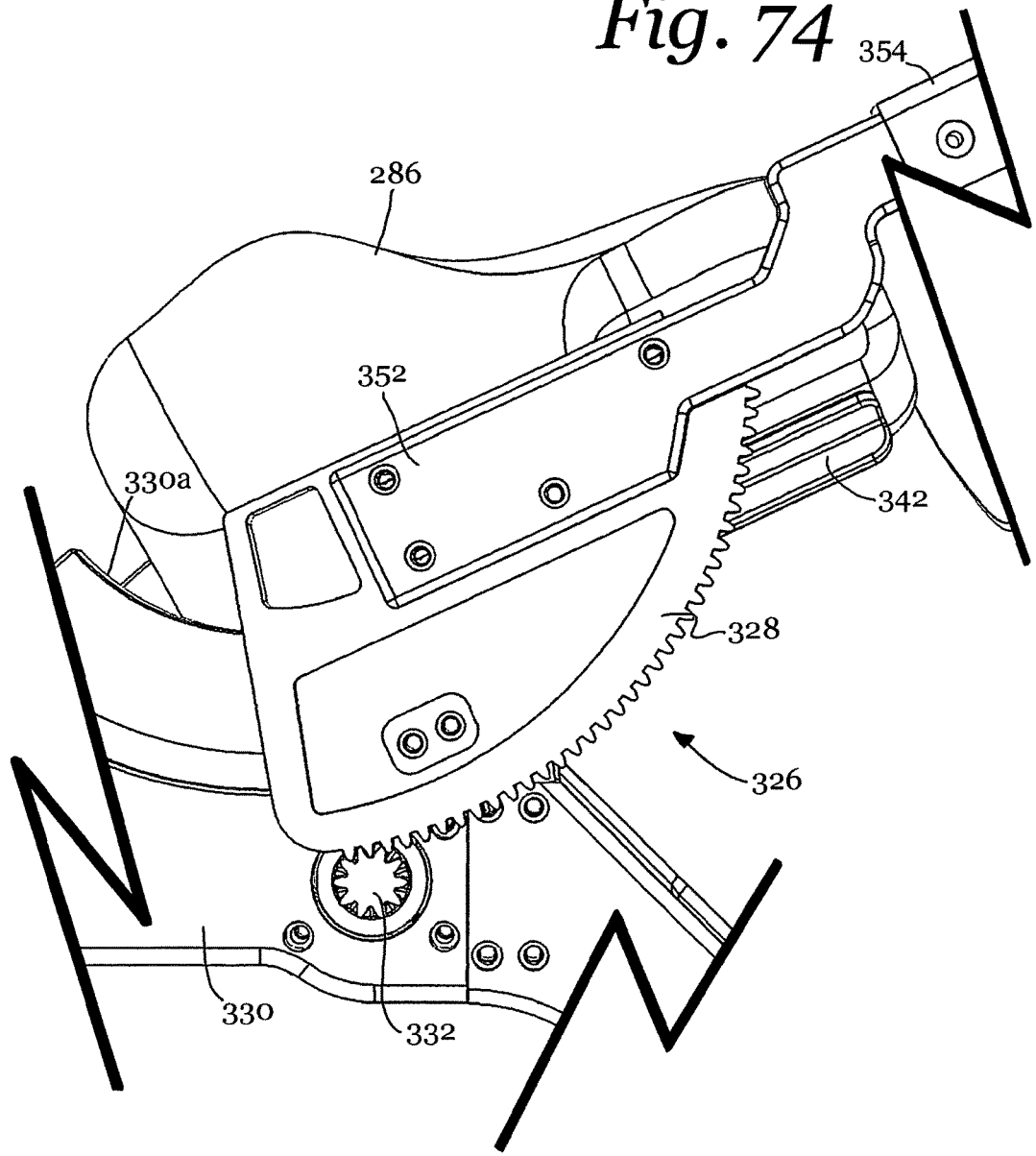
FIG. 74 is another enlarged side view of the prone patient support structure of FIG. 3, with portions broken away.
Figure 75:
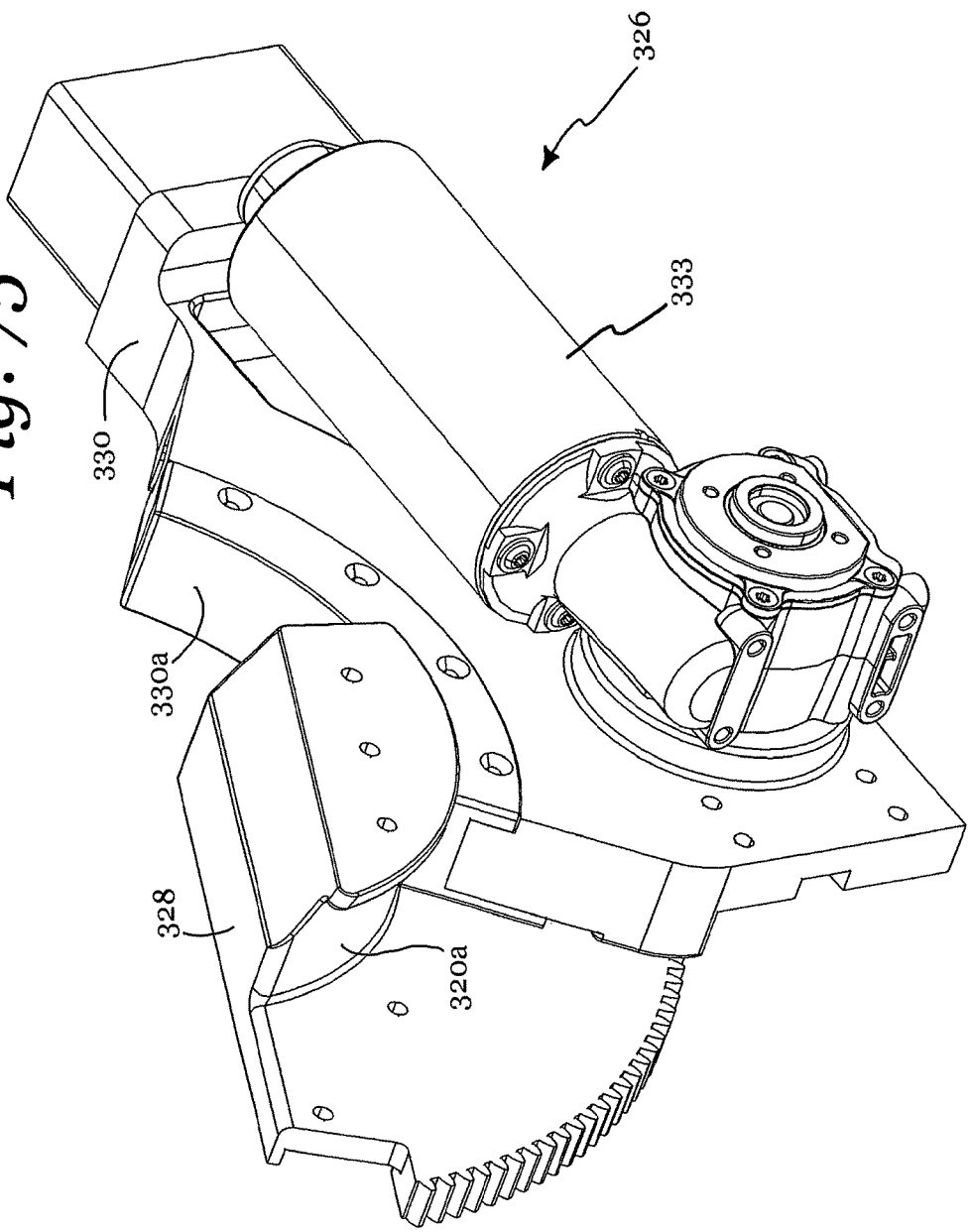
FIG. 75 is an enlarged perspective view of a portion of the joint of the prone patient support structure of FIG. 3, with portions not shown.
Figure 76:
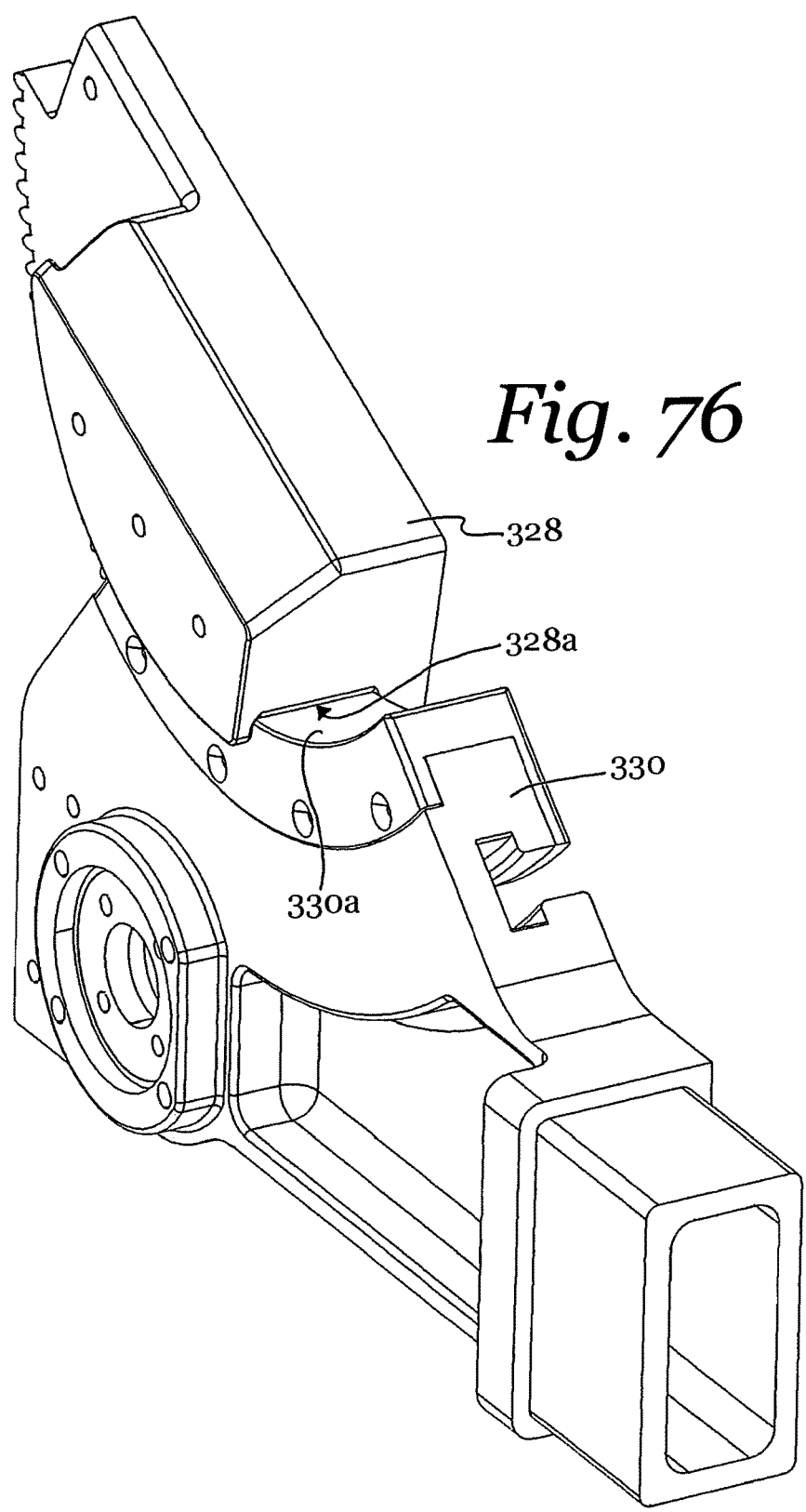
FIG. 76 is a perspective view of a portion of the joint of FIG. 75.
Figure 77:
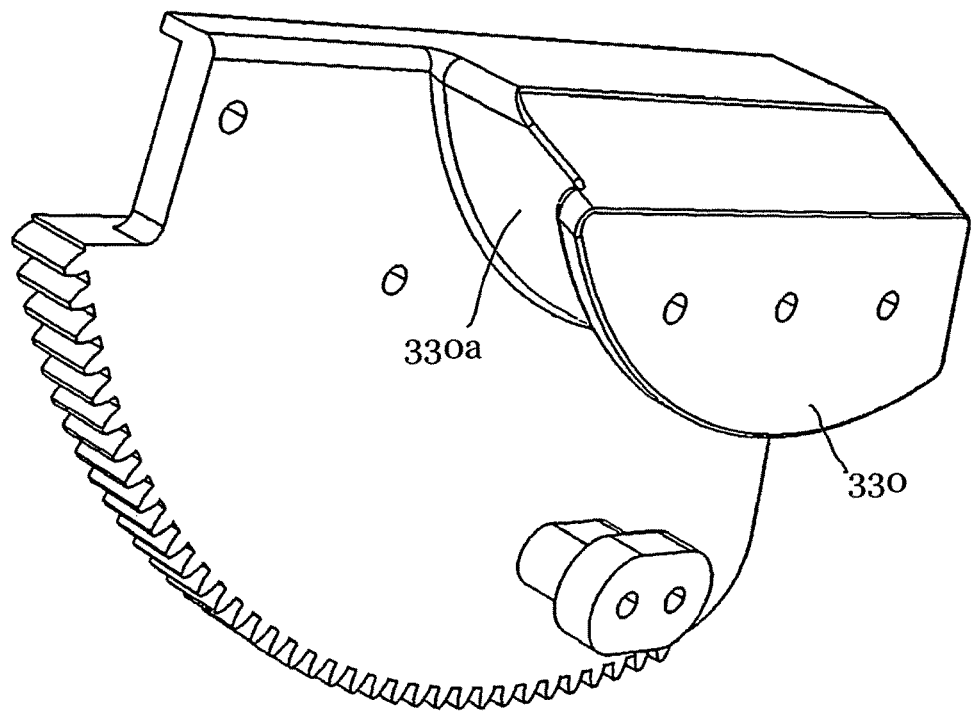
FIG. 77 is an enlarged perspective view of a component of the joint of FIG. 75.
Figure 78:
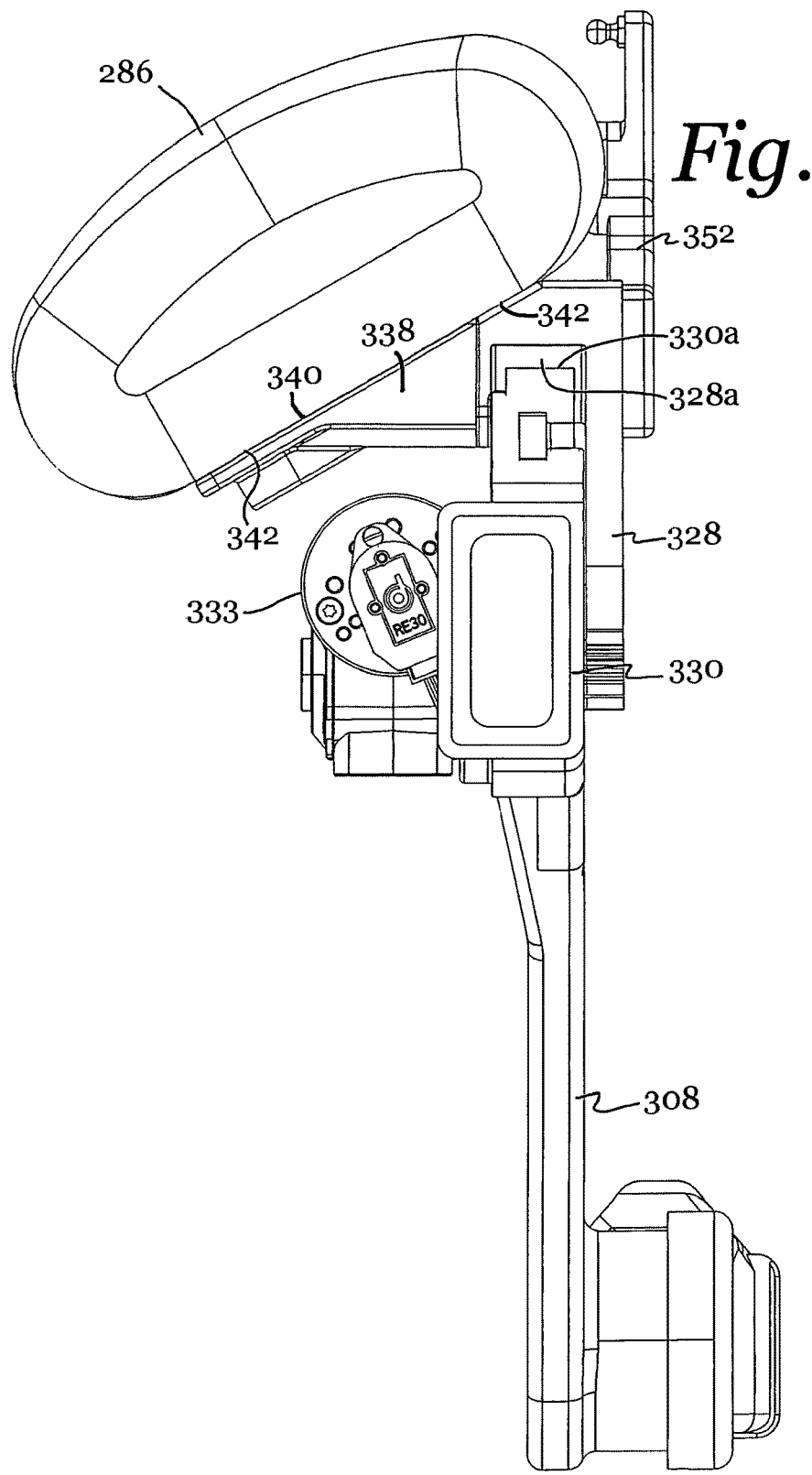
FIG. 78 is an enlarged head-end view of the left-side joint and attached hip-thigh pad of the prone patient support structure of FIG. 3, with portions not shown.
Figure 79:
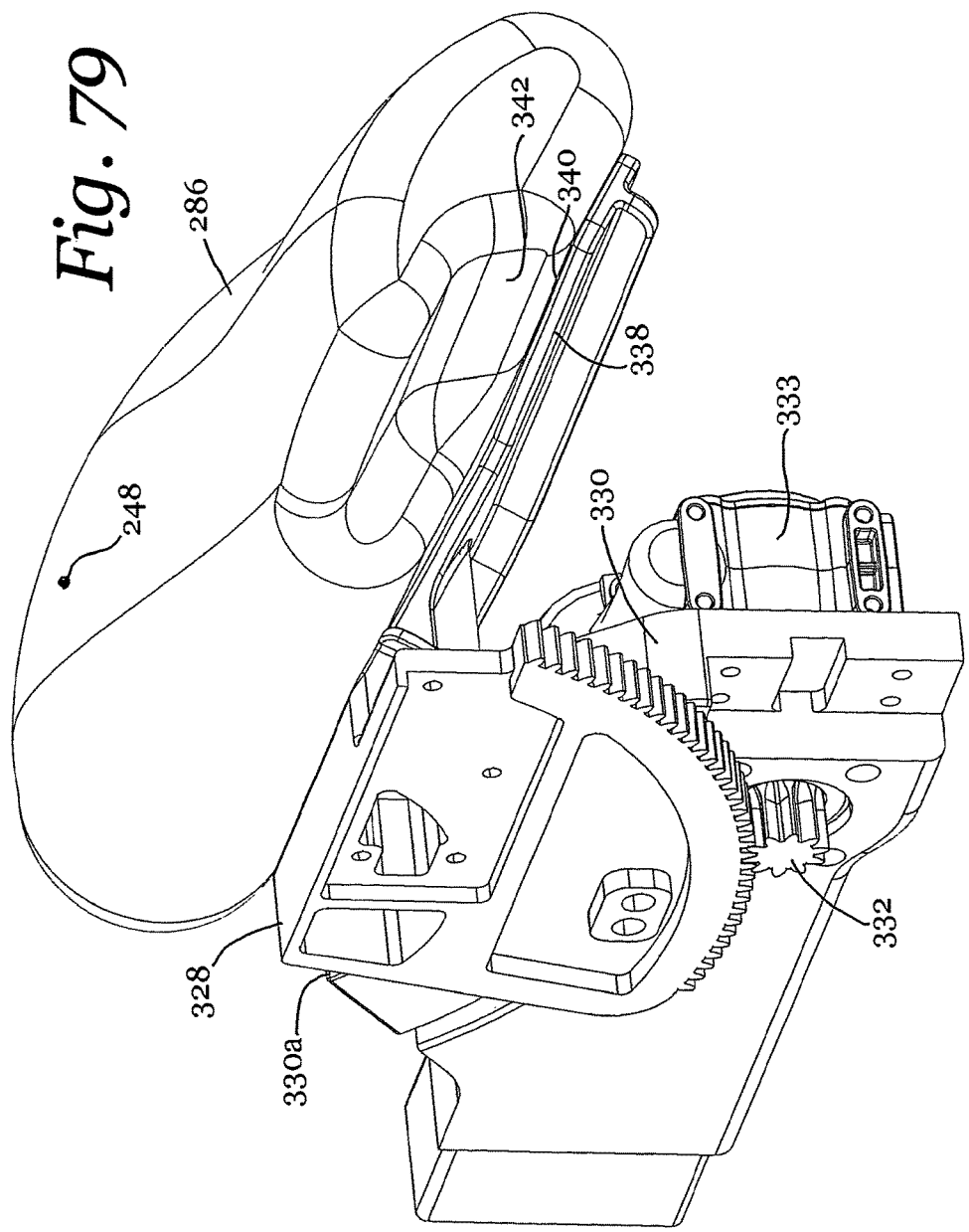
FIG. 79 is an enlarge perspective view of the left-side joint with attached hip-thigh pad, and portions not shown so as to show greater detail thereof.
Figure 80:
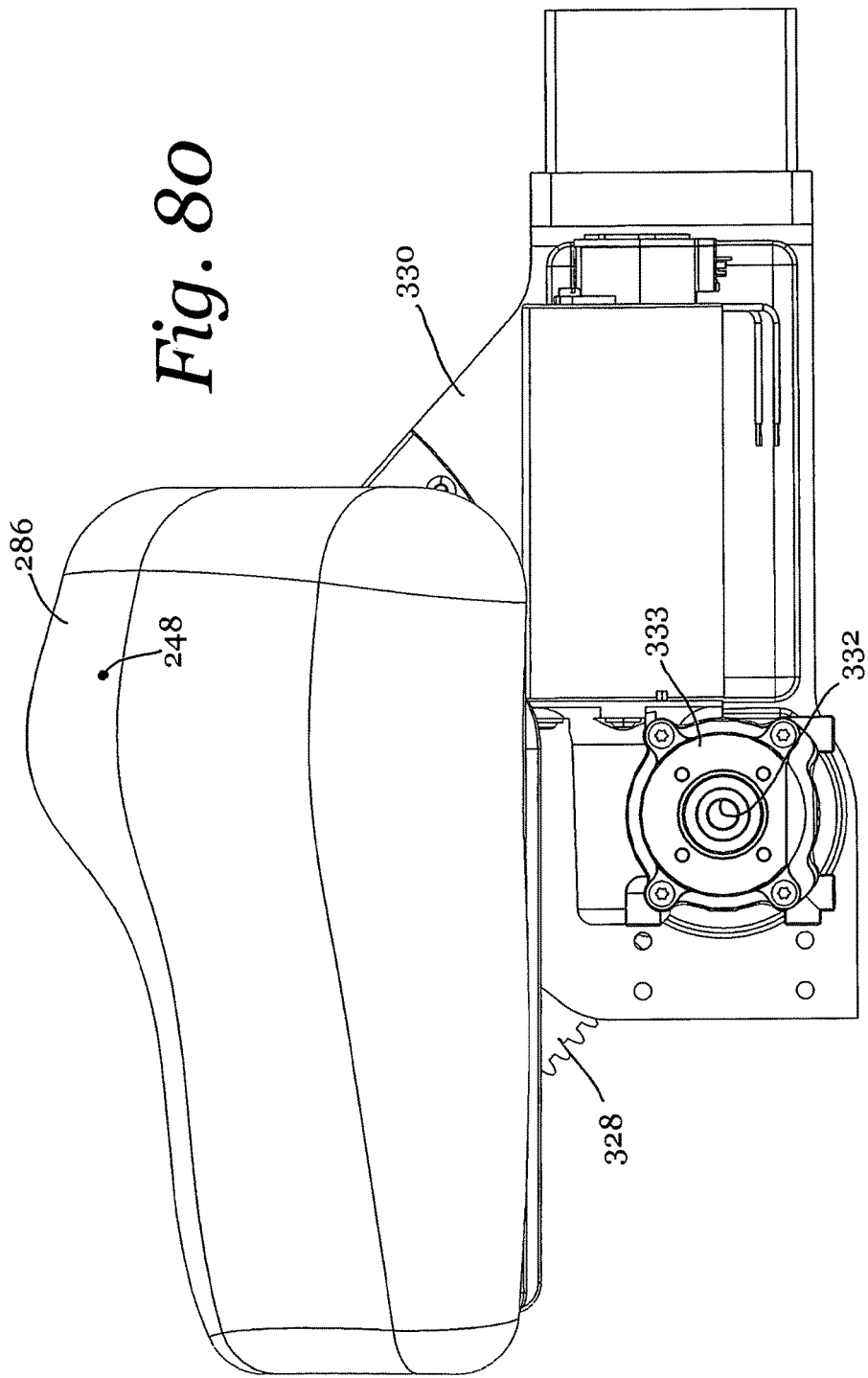
FIG. 80 is an inner side view of the joint of FIG. 79.
Figure 81:
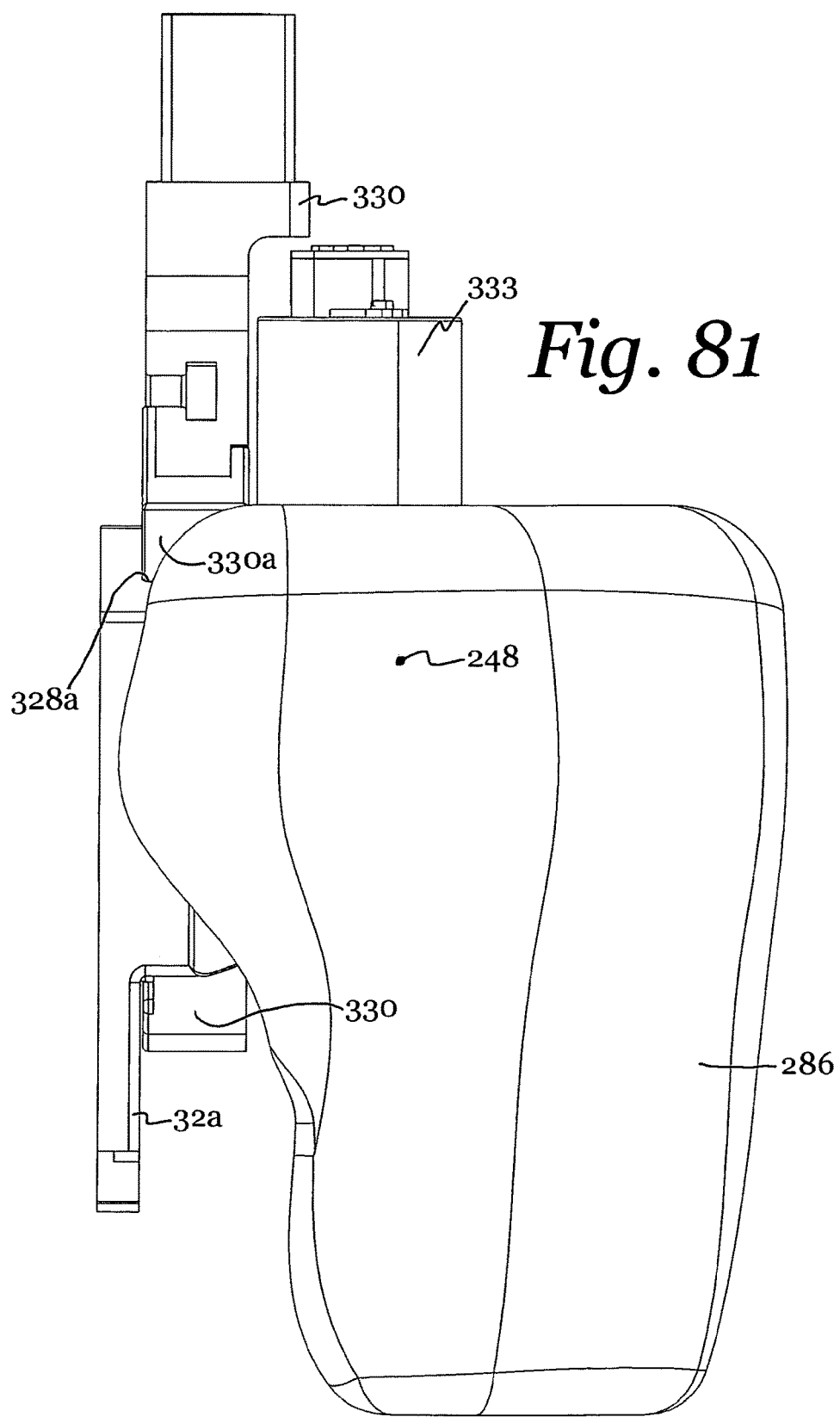
FIG. 81 is a top view of the joint of FIG. 79.
Figure 82:
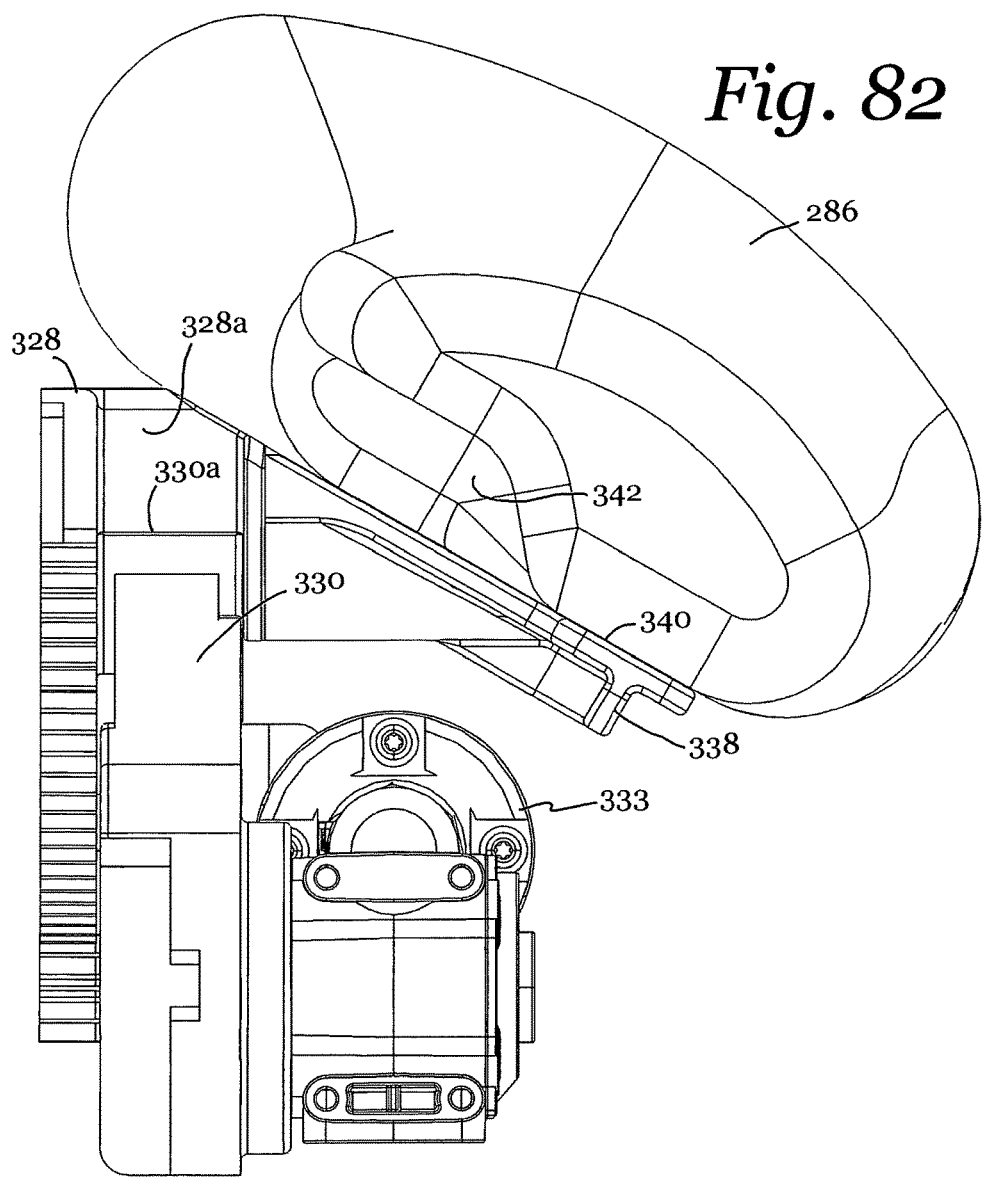
FIG. 82 is a rear view of the joint of FIG. 79.
Figure 83:
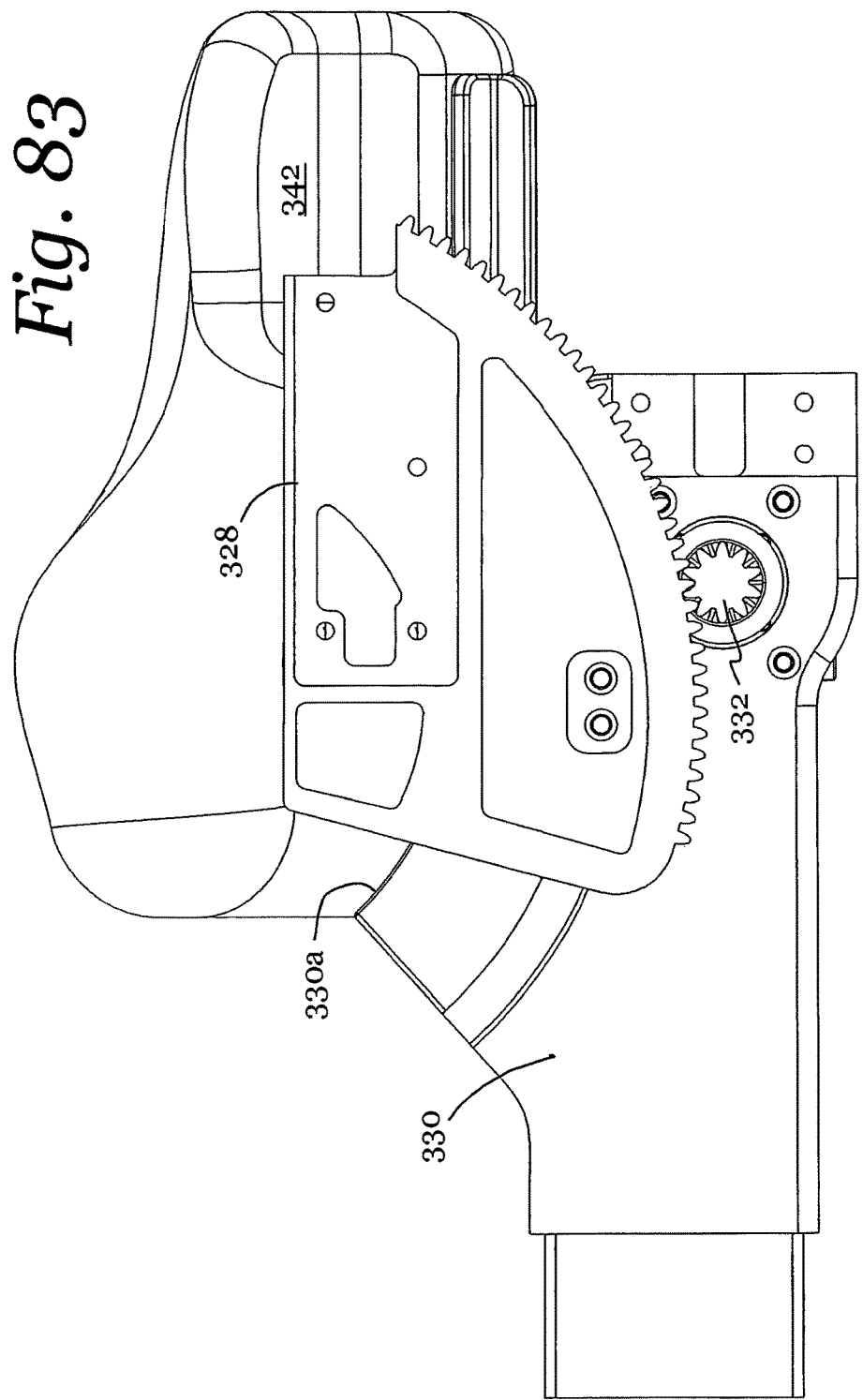
FIG. 83 is an outer side view of the joint of FIG. 79.
Figure 84:
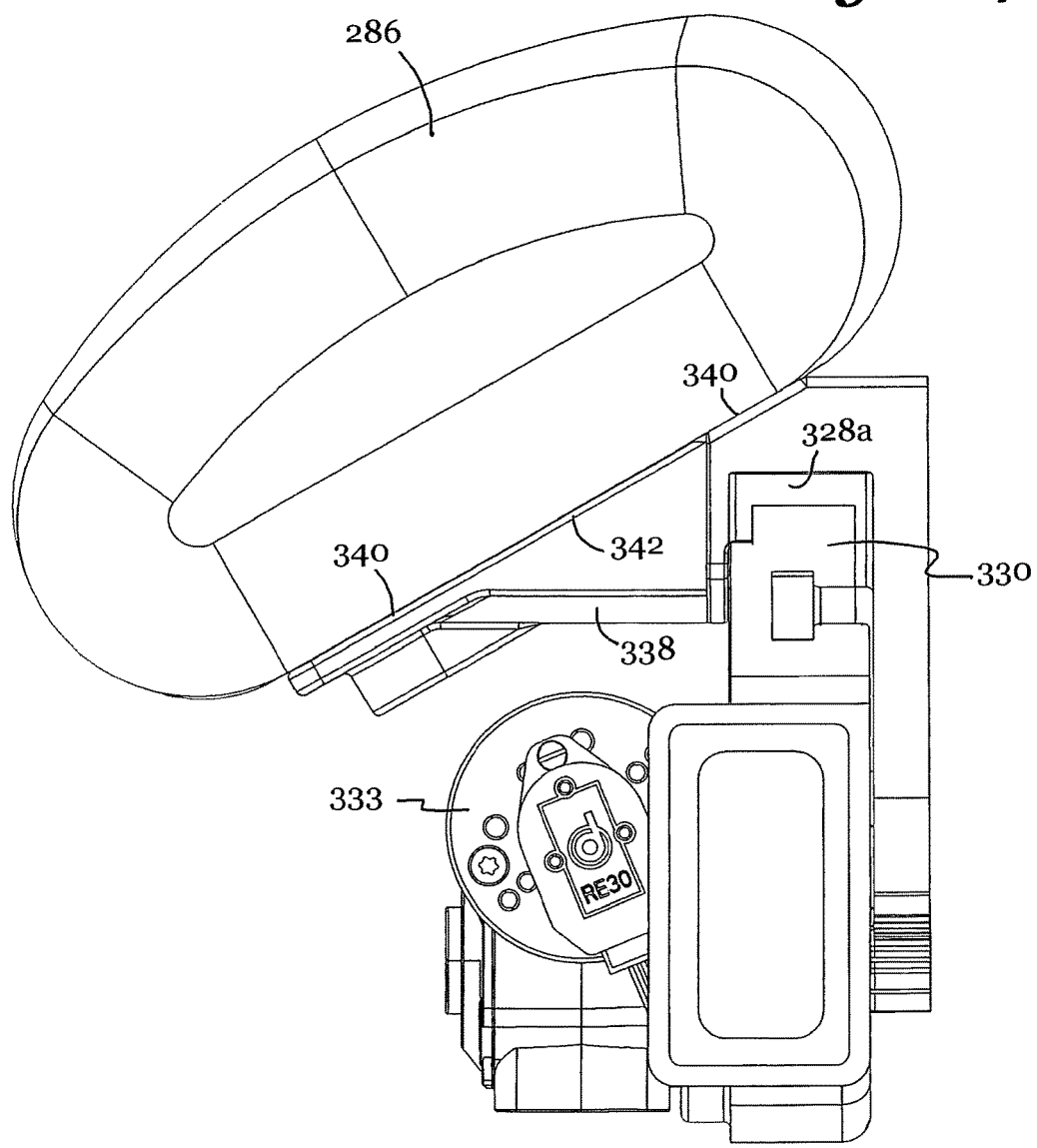
FIG. 84 is a forward view of the joint of FIG. 79.
Figure 85:
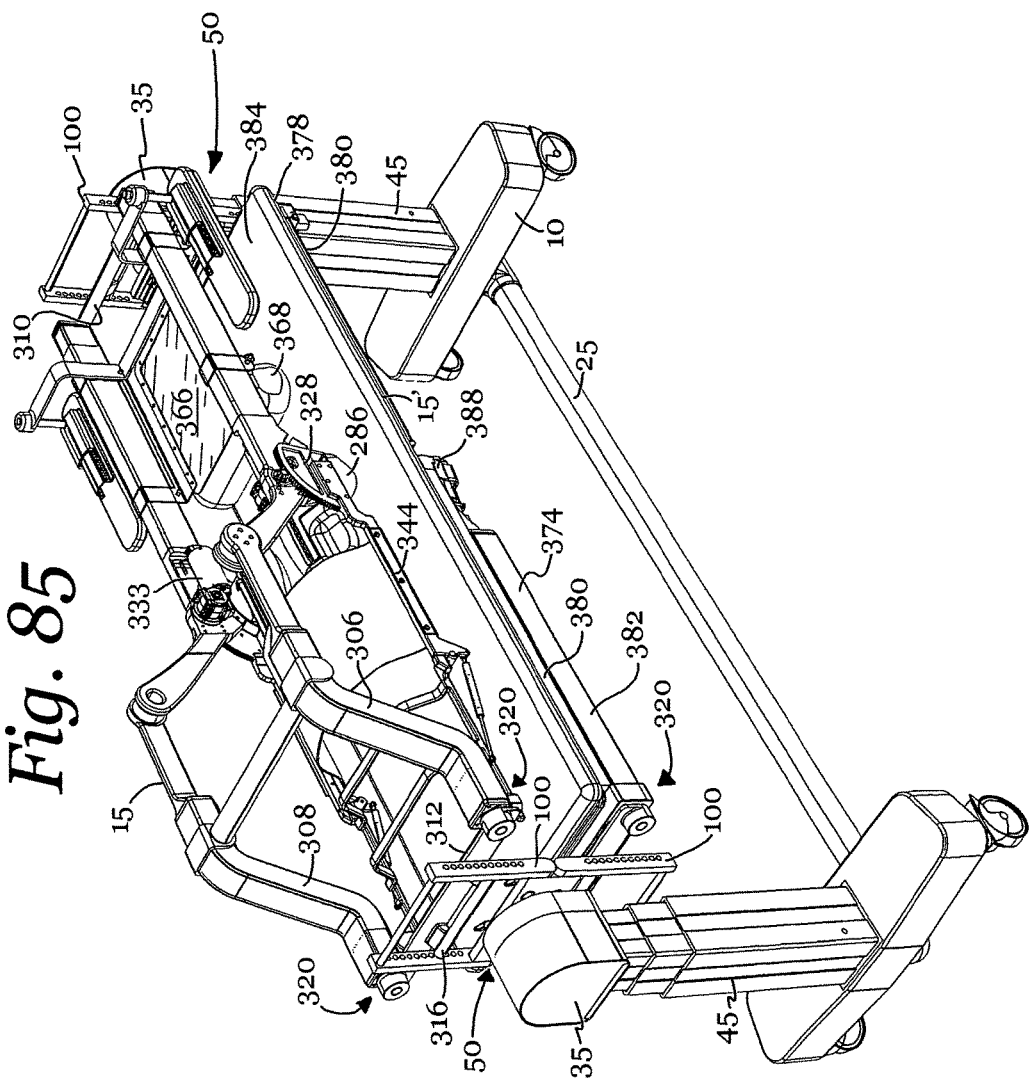
FIG. 85 is a reduced perspective view of the patient positioning support system of FIG. 1, including an attached supine patient support structure, and positioned to perform a sandwich-and-roll procedure, wherein the supine patient support structure is attached to the base by a standard length ladder.
Figure 86:
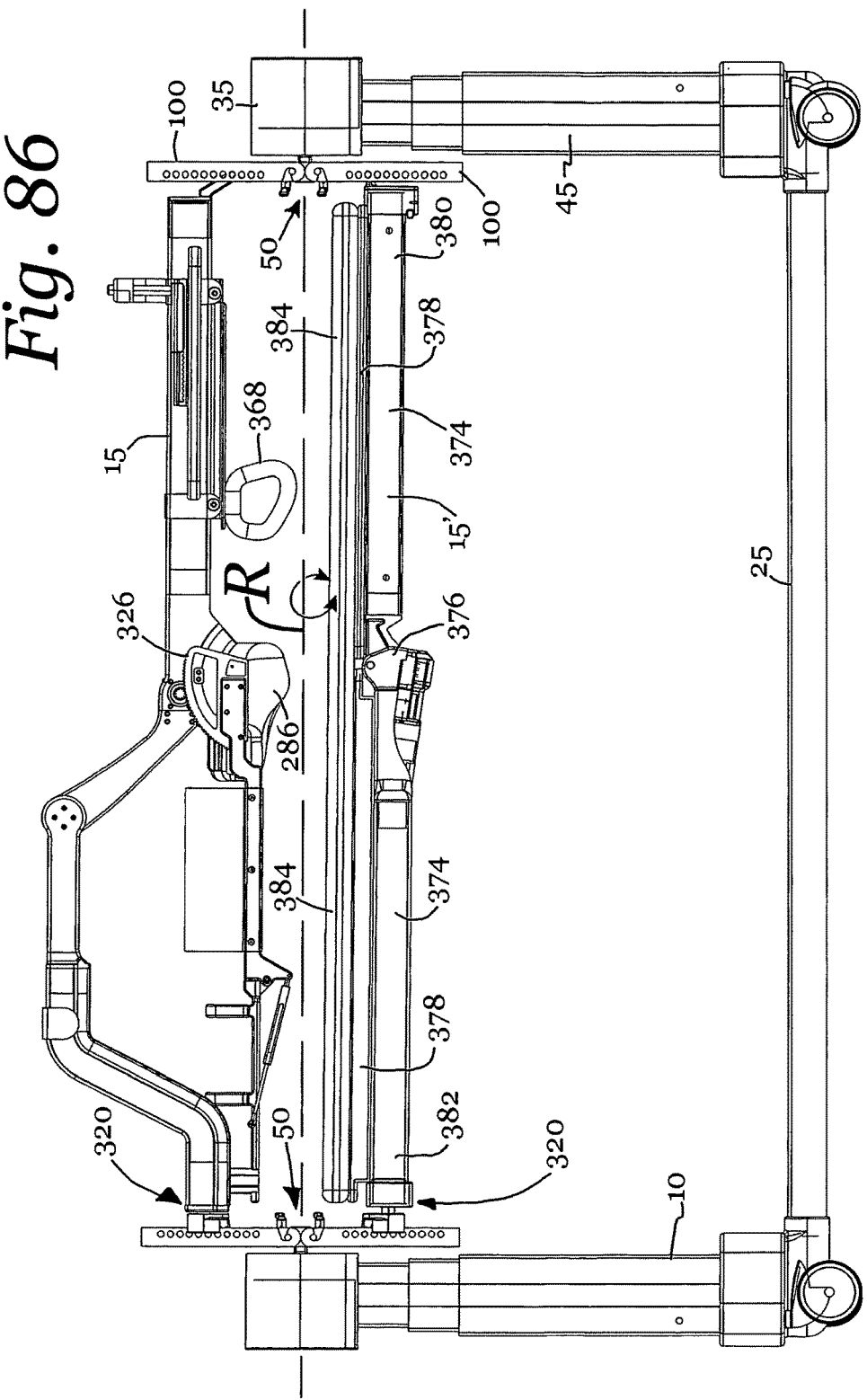
FIG. 86 is a right-side view of the patient positioning support system of FIG. 85.
Figure 87:
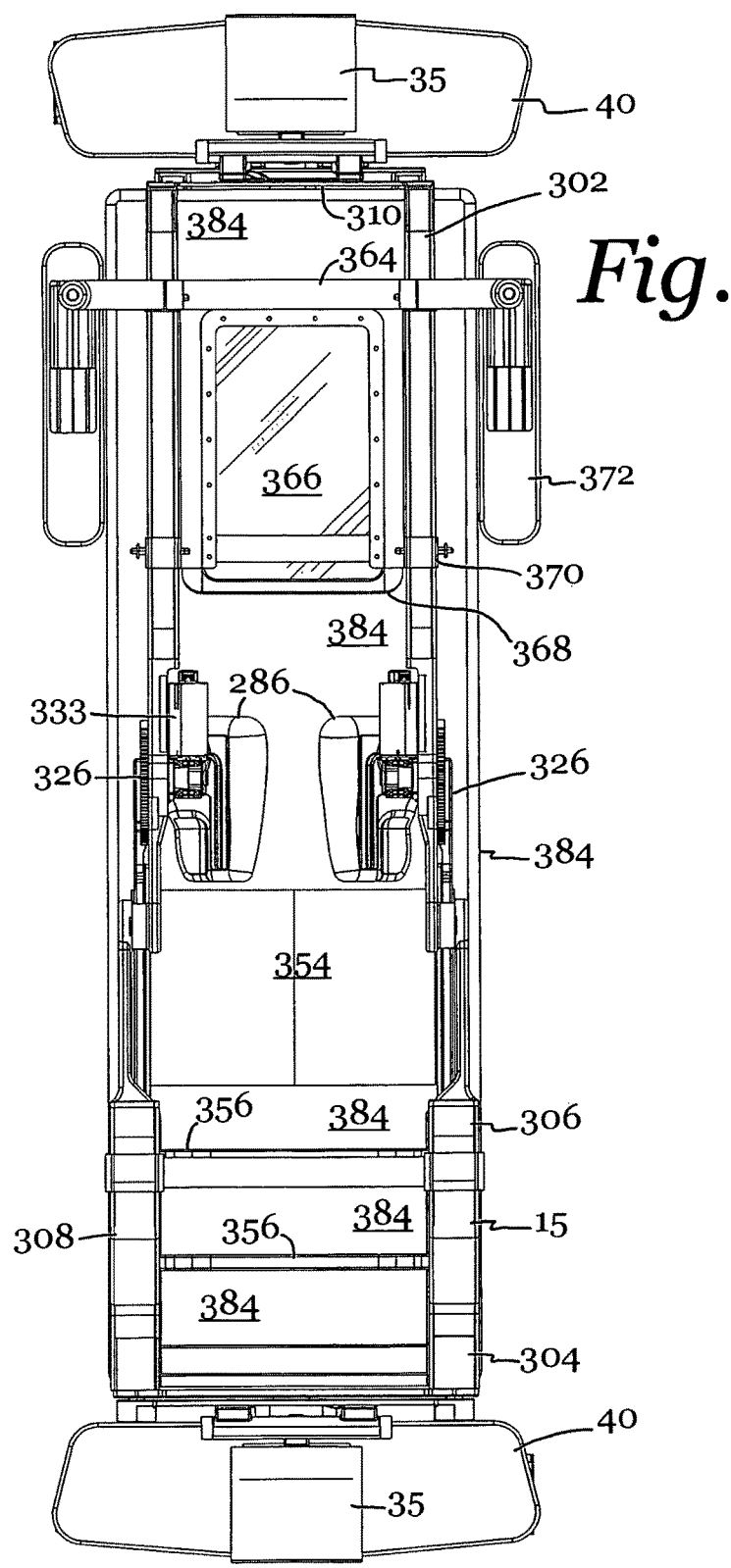
FIG. 87 is a top view of the patient positioning support system of FIG. 85.
Figure 88:
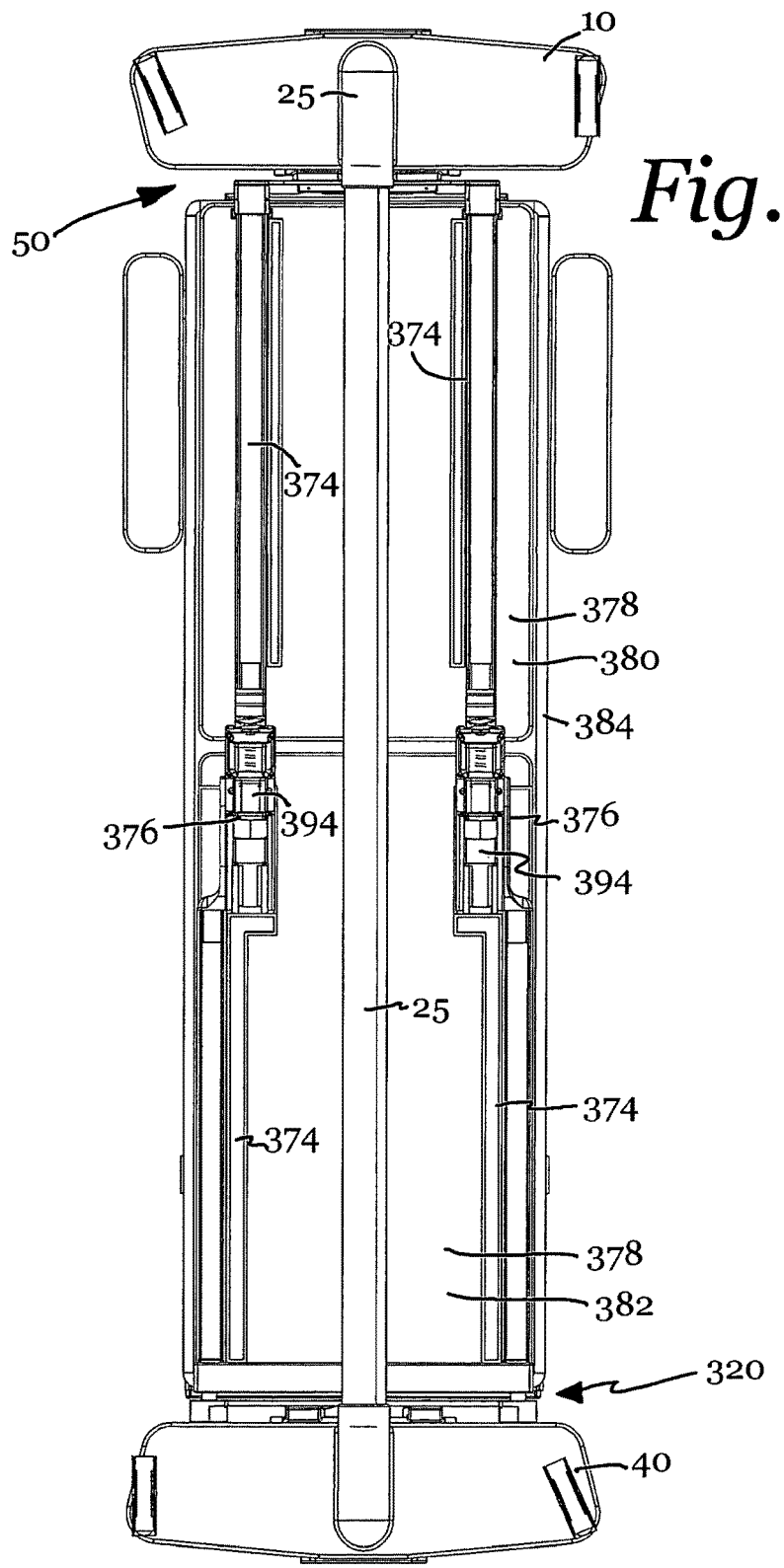
FIG. 88 is a bottom view of the patient positioning support system of FIG. 85.
Figure 89:
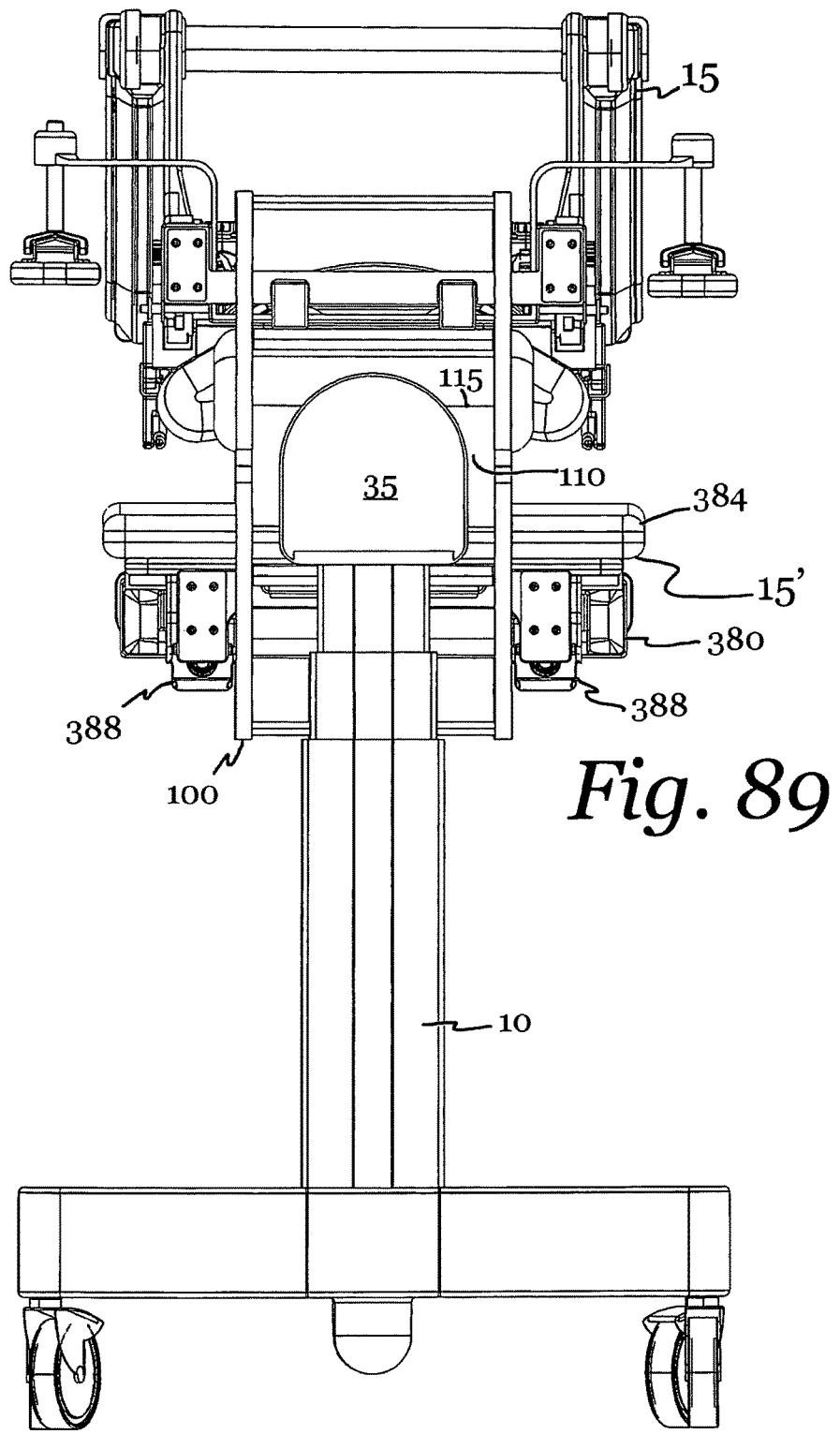
FIG. 89 is a head-end view of the patient positioning support system of FIG. 85.
Figure 90:
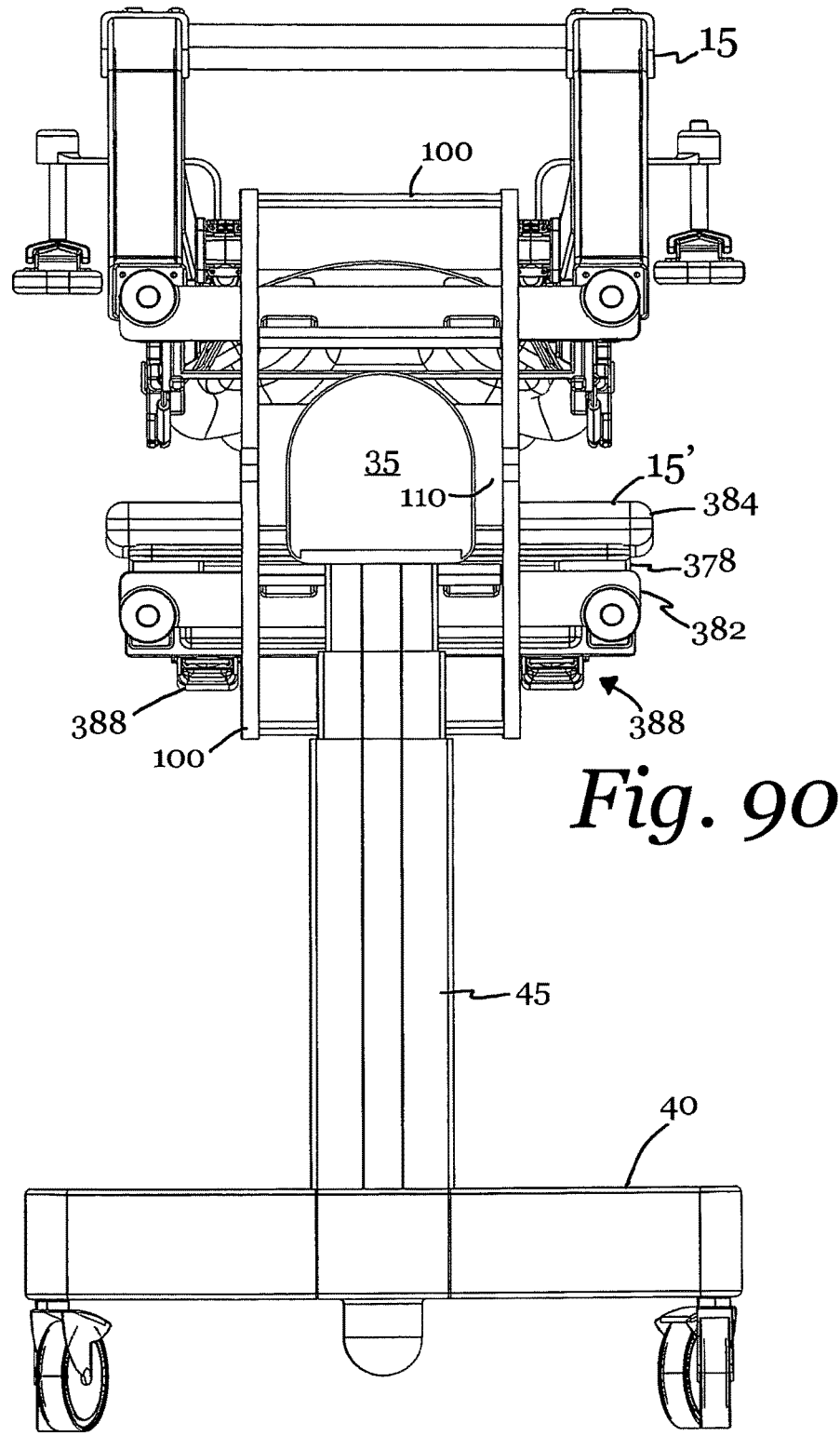
FIG. 90 is a foot-end view of the patient positioning support system of FIG. 85.

Referring to FIG. 72 each joint 326 includes a virtual pivot point 248 and an arc of motion, denoted by AOM, that is spaced a distance, or radius r, from the virtual pivot point 248. The radius r extends from the virtual pivot point 248 to the arc of motion AOM in a plane that is substantially perpendicular to the first pitch axis P1. The radius r defines at least a portion of the arc of motion AOM.

Each joint 326 includes a first joint component 328, a second joint component 330, and a third joint component 332. In the illustrated embodiment, the first and third joint components 328, 332 each include a plurality of ratchet teeth that are adapted such that the teeth 328 of the first joint component 328 cooperatively engage the teeth 332 of the third joint component. The third joint component 322 is connected to a motor 333 that actively drives clockwise and counterclockwise rotation of the third joint component 332, whereby the third joint competent 332 actuates rotary movement of the first joint component 328 with respect to the second joint component 330. It is noted that the first and second joint components 328 and 330 each include a guide track component with a weight-bearing gliding surface, 328a and 330a respectively, where in the guide track components cooperatively sliding mate to enable the first joint component 328 to glide or slide, and therefore rotate, with respect to the second joint component 330 and also about the respective virtual pivot point 248. Alternative joint configurations and components are foreseen so long as the function of moving the joint 326 with respect to the virtual pivot point 248 in maintained.

The joints 326 are movable along the arc of motion AOM. Since each hip-thigh pad 286 is attached to the first joint components 328. Accordingly, movement of the first joint component 328 associated with a hip-thigh pad 286, with respect to the virtual pivot point 248 and the arc of motion AOM glidingly or slidingly moves, pivots or rotates the hip-thigh pad 286 about the virtual pivot point 248 and also a portion of the hip-thigh pad 286 along the arc of motion AOM, such as is described in greater detail below.

Still referring to FIG. 72, it is noted that a joint 326 can be configured such that the virtual pivot point 248 is located higher or lower, or more to the left-hand or the right-hand side of the page, than depicted, such as but not limited to exemplary alternative virtual pivot points 248a, 248b and 248c. Additionally, the arc of motion AOM include alternative shapes than depicted, such as but not limited to exemplary arcs of motion #2, #3 and #4 denoted by AOM2, AOM3 and AOM4, respectively. Accordingly, the radius r of each arc of motion AOM is different. Certain arcs of motion AOM may be shaped such that the radius r of different portions thereof are different, change, or vary.

In some circumstances, the joint 326 is sized, shaped and configured to move the attached hip-thigh pad 286 so as to follow an alternative arc of motion AOM, such as by including at least one of an alternatively located virtual pivot point 248, an alternative length radius r, or an alternatively shaped arc of motion AOM. For example, the prone patient support structure 15 may include joints 326 adapted for use with a pediatric patient, a very tall patient, or a patient with certain spinal anomalies. In some embodiments, the patient positioning support system 5 is provided with at least two prone patient support structures 15, wherein a first of the prone patient support structures 15 includes "standard" joints 326 that are useable with most patients, and a second of the prone patient support structures 15 includes non-standard or alternatively configures joints 326 for use with pediatric patients, very tall patients, patients with certain spinal anomalies, and the like. In some embodiments, the prone patient support structure 15 includes modular joints 326 that are interchangeable to provide the ability to use a single prone patient support structure 15 with adult and pediatric patients, short, medium and tall patients, and the like.

The joints 326 are movable between a first position and a second position with respect to the virtual pivot point 248, the arc of motion AOM and the floor F. The first and second positions are selected by an operator, so as to move the patient's hips between a flexed position, an extended position and a "neutral" position wherein the hips are neither flexed nor extended. For example, in FIG. 70, the first and second joint components 328 and 330 are located and oriented so as to position a patient's hips in a neutral position. In another example, in FIG. 71, the first and second joint components 328 and 330 are located and oriented so as to position a patient's hips in an extended position. In yet another example, in FIG. 72, the first and second joint components 328 and 330 are located and oriented so as to position a patient's hips in a flexed position.

Figure 70:
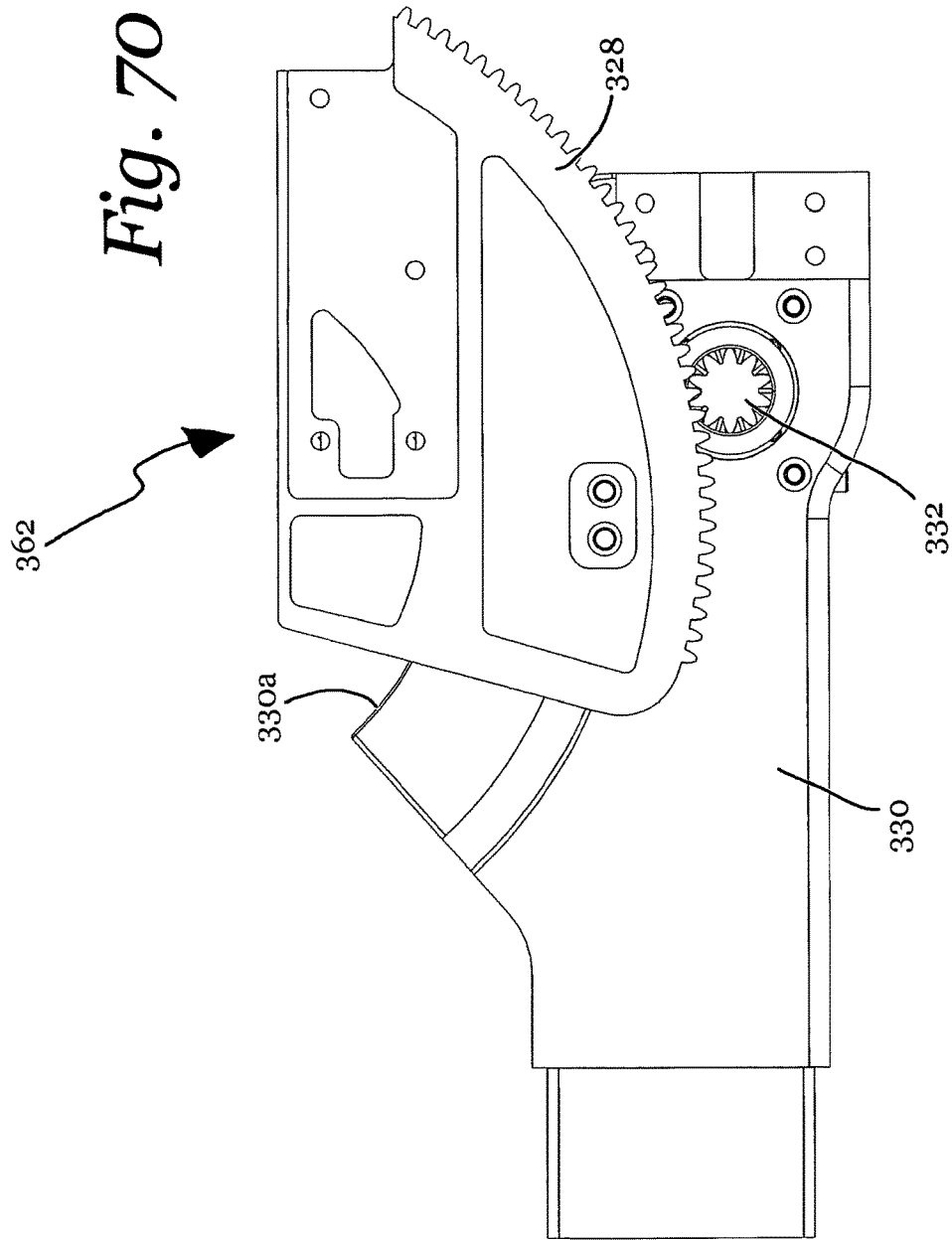
FIG. 70 is an enlarged side view of a joint of the prone patient support structure of FIG. 3.
Figure 71:
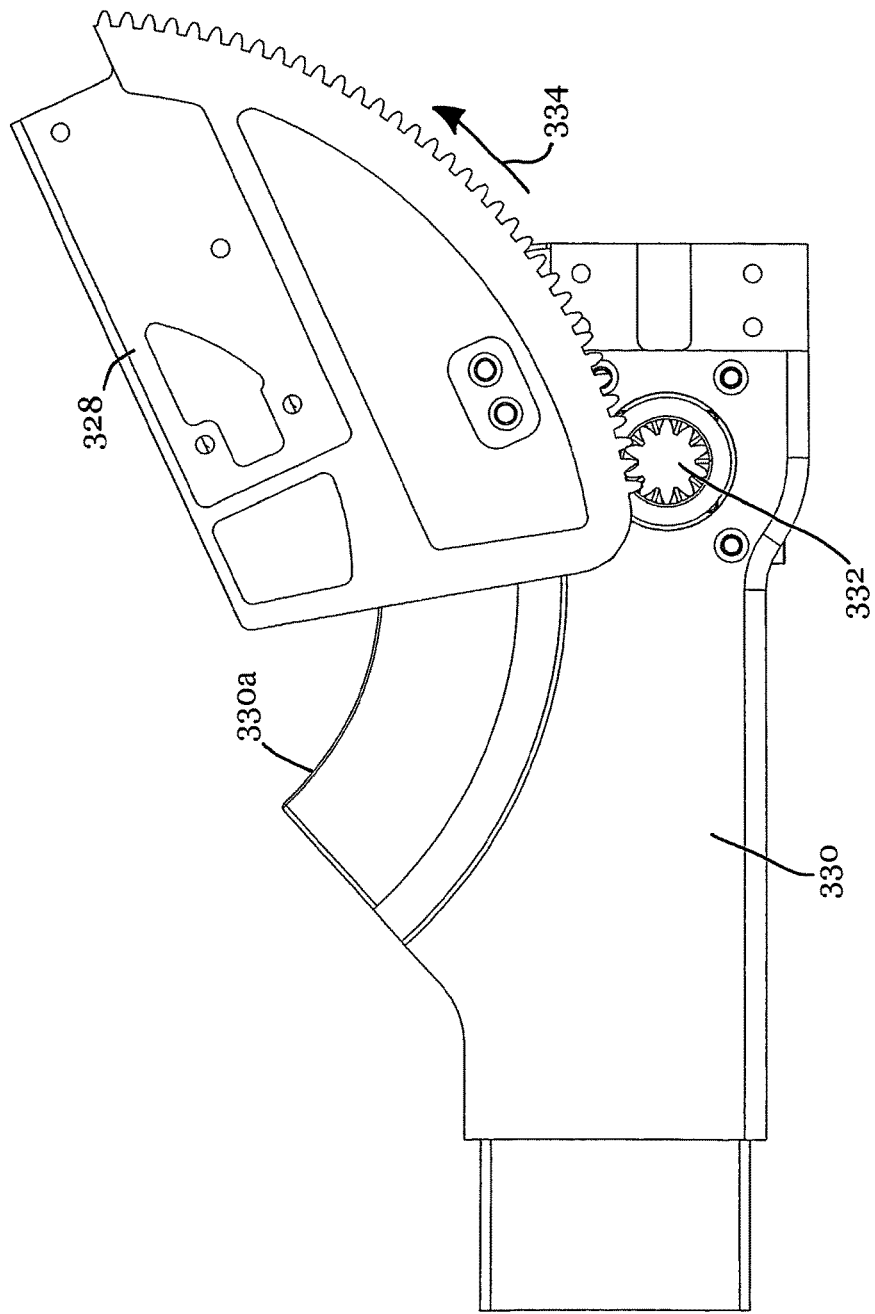
FIG. 71 is another enlarged side view of a joint of the prone patient support structure of FIG. 3.

It is noted that the first joint component 328 may be moved with respect to the second joint component 330, so as to be moved from the orientation or configuration shown in FIG. 70 to the orientation shown in FIG. 71, wherein such movement or motion is indicated by arrow 334. Similarly, the first joint component 328 may be moved with respect to the second joint component 330, so as to be moved from the orientation shown in FIG. 70 to the orientation shown in FIG. 72, wherein such movement or motion is indicated by arrow 336.

The first joint component 328 includes maximum positions, with respect to the second joint component 330 wherein the patient's hips are maximally flexed and maximally extended. The maximum positions are selected so as to cooperate with the patient's biomechanics, such that the patient's spine and additionally or alternatively hips can be flexed and extended a maximum amount. These maximum amounts of flexion and selections are selected so as not to injure the patient, but also to provide a desirable amount of lordosis for a given spinal surgery, such as is known in the art.

In some embodiments, the virtual pivot point 248 is located within a patient supported on the prone patient support structure 15. For example, the joints 326 may be sized, shaped and configured to align the virtual pivot points 282 within the patient, such as near the lumbar spine or on or near the pelvis. Accordingly, in this embodiment, the first pitch axis P1 passes through the patient. For example, in some embodiments, the virtual pivot points 282 are located adjacent to the spine of a patient supported on the patient positioning support system 5.

In some embodiments, the virtual pivot point 248 is located at a contact point between a patient supported on the prone patient support structure 15 and a hip-thigh pad 286. For example, the virtual pivot point 248 may be located where the patient's skin contacts the surface of the hip-thigh pad 286. Since the hip-thigh pads 286 are moldable or compressible, the weight of the patient can cause the hip-thigh pads to be compressed, thereby effectively moving the virtual pivot points 282 above the hip-thigh pads 286 and into the patient's body, in some embodiments. Further, since the patient's belly hangs downward between the hip-thigh pads 286, a virtual pivot point 248 located at a contact point between the patient's skin and a surface of the hip-thigh pad 286 is associated with a first pitch axis P1 that passes through the patient's body.

As discussed above, and with reference to FIGS. 73-84, the hip-thigh pads 286 are joined with the associated joints 326. In particular, the hip-thigh pads 286 are attached to pad mounts 338 of the first joint components 328. It is noted that when the joint is assembled with the frame 296, the pad attachment surfaces 340, of the pad mounts 338, face generally toward, or are oriented toward, the roll axis R, also referred to as being oriented in an inwardly or central direction. The pad attachment surfaces 340 are attached to the undersides 342 of the pads 286. The hip pad undersides 342 are contoured so as to not obstruct movement of the joins 326 or to bang into the frame 296, which could disrupt operation of the joints 326.

The virtual pivot point 248 includes a height or distance, denoted by D1, above the floor F, such as is shown in FIGS. 4, 24, 32, 40, 56, 65-67, 69. The height D1 is substantially constant during, or throughout, movement of the joint 326 with respect to the virtual pivot point 248. In an exemplary embodiment, with reference to FIGS. 4 and 40, wherein the patient positioning support structure 5 is positioned such that the joints 326 are in a neutral position, such that a patient's hips and spine are neither flexed or extended, and the virtual pivot point 248 is spaced a distance D1 above the floor F. The operator adjusts the patient positioning support system 5 such that the virtual pivot point 248 is located at a selected height D1 above the floor F, such as but not limited to 48-inches, for example. The selected height D1 is a convenient and additionally or alternatively comfortable working height for the surgeon to perform the surgery. D1 can be other heights, such as but not limited to a height D1 between minimum and maximum distances above the floor F, wherein the minimum and maximum distances provide a range of selectable infinitely adjustable heights D1. The height D1 is associated with the locations of the upper portions 35 of the vertical translation subassembly 20. Accordingly, the minimum and maximum heights D1 are associated with the vertical translation subassemblies 20 being closed and maximally outwardly telescoped, respectively.

Continuing with the exemplary embodiment above, when the joints 326 are actuated and moved from the neutral position of FIG. 4 to the position shown in FIG. 40, wherein the hips and knees of the patient would be flexed, the height D1 of the virtual pivot point 248 remains unchanged, or stays 48-inches from the floor F. Similarly, if the joints 326 are actuated and moved from the neutral position of FIG. 4 to the position shown in FIG. 56, wherein the hips and knees of the patient would be extended, the height D1 of the virtual pivot point 248 still remains substantially unchanged, or 48-inches from the floor F.

The patient positioning support structure 5 is also configured such that the patient's hips and knees can be kept in the neutral position described above, and also the patient's body can be positioned in either a Trendeleburg position, such as is shown in FIG. 32, or a reverse Trendelenburg position, such as is shown in FIG. 24. When prone patient support structure 15 is moved to the Trendeleburg and reverse Trendeleburg positions, the height D1 remains unchanged, or 48-inches from the floor F.

Figure 65:
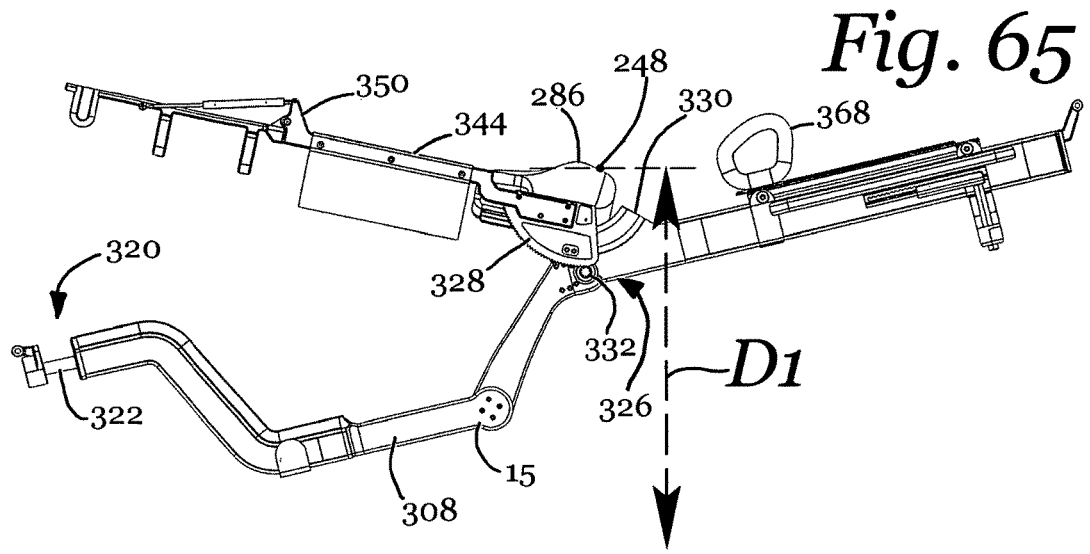
FIG. 65 is an enlarged view of the patient positioning support structure of FIG. 56, with the base not shown.
Figure 66:
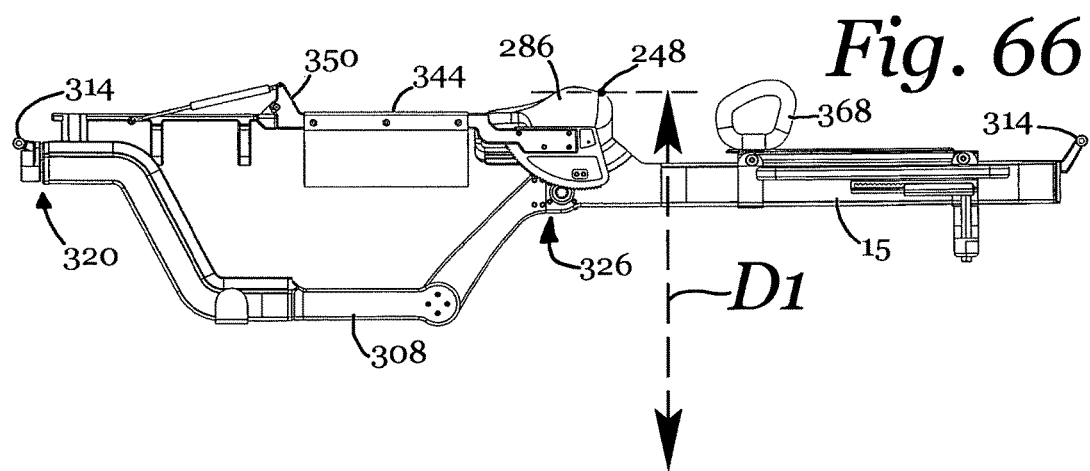
FIG. 66 is an enlarged view of the patient positioning support structure of FIG. 4, with the base not shown.
Figure 67:
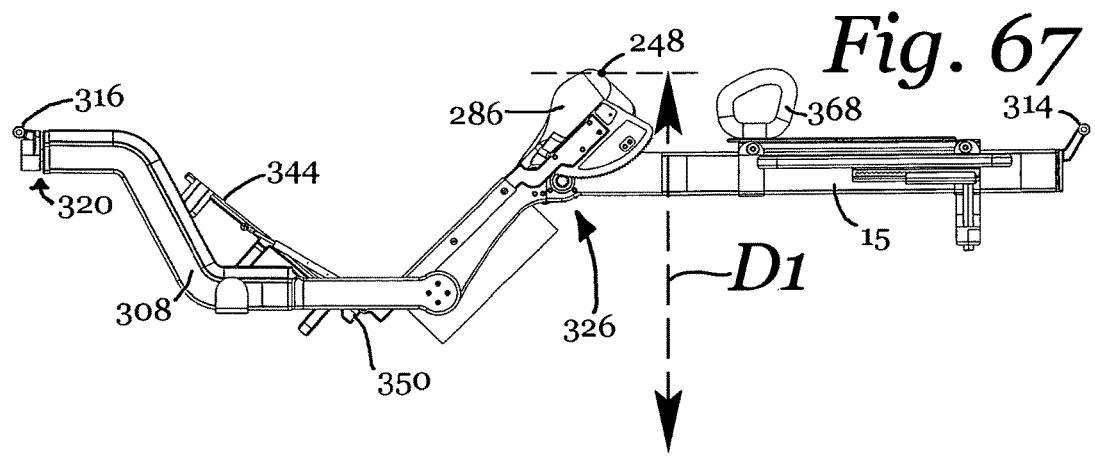
FIG. 67 is an enlarged view of the patient positioning support structure of FIG. 40, with the base not shown.

FIG. 65 depicts the prone patient support structure 15 including joints 326 positioned so as to maximally extend the patient's hips and knees, and the virtual pivot points 282 are located a distance D1 above the floor F. In comparison, FIG. 66 depicts the prone patient support structure 15 including joints 326 positioned so as to maintain the patient's hips and knees in a neutral position, or not flexed or extended, and the virtual pivot points 282 are also located a distance D1 above the floor F, wherein the distance D1 of FIG. 65 is substantially equal to the distance D1 of FIG. 66. In a further comparison, FIG. 67 depicts the prone patient support structure 15 including joints 326 positioned so as to maximally flex the patient's hips and knees, wherein the virtual pivot points 282 are also located a distance D1 above the floor F, and wherein the distance D1 of FIG. 67 is substantially equal to the distances D1 of FIGS. 65 and 66. Thus, as the joints 326 are actuated, they are movable between a plurality of selectable positions, the plurality of selectable positions being between and including the positions shown in FIGS. 70-72 and FIGS. 65-67, without substantially changing the heights D1 of the virtual pivot points 282 of the joints 326.

As noted above, the height D1 of the virtual pivot point 248 is adjustable. The height D1 can be adjusted by actuating one or both of the vertical translation subassemblies 20, so as to move the upper portions 35 upwardly or downwardly with respect to the associated vertical translation axis V1 and V2. Such vertical translation of the upper portions 35 causes vertical translation of the associated connection assembly 75, which in turn is connected with the head-end or foot-end frame members 310 and 312, respectively. At least a portion of each the hip-thigh pad 286 glides along the associated arc of motion AOM, such as, for example, when the associated joint moves to and between the positions shown in FIGS. 70-72 and FIGS. 65-67.

Figure 39:
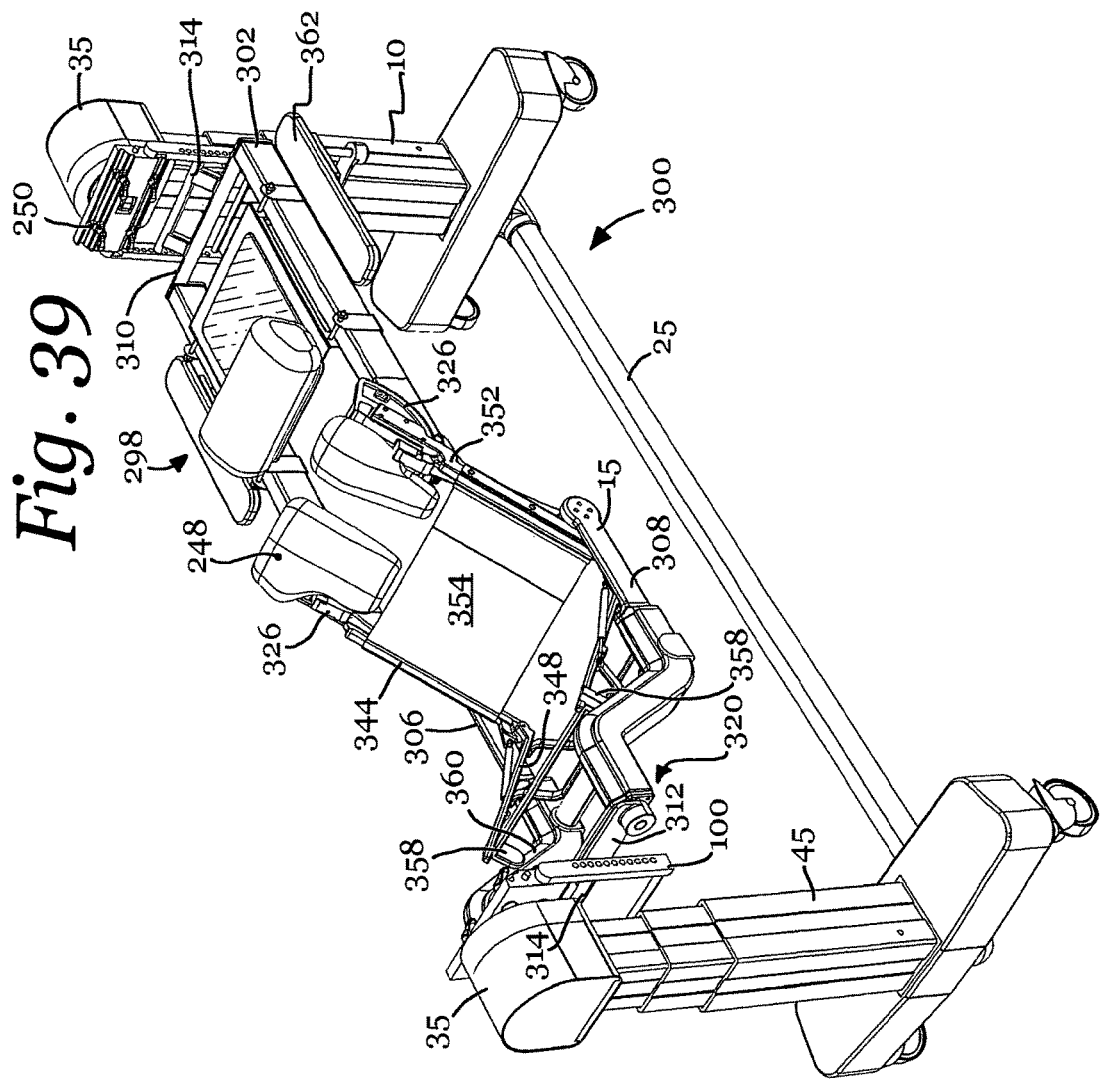
FIG. 39 is a reduced perspective view of the patient positioning support system of FIG. 1, with the patient support structure positioned so as to maximally flex the hips and legs of a patient thereon.
Figure 55:
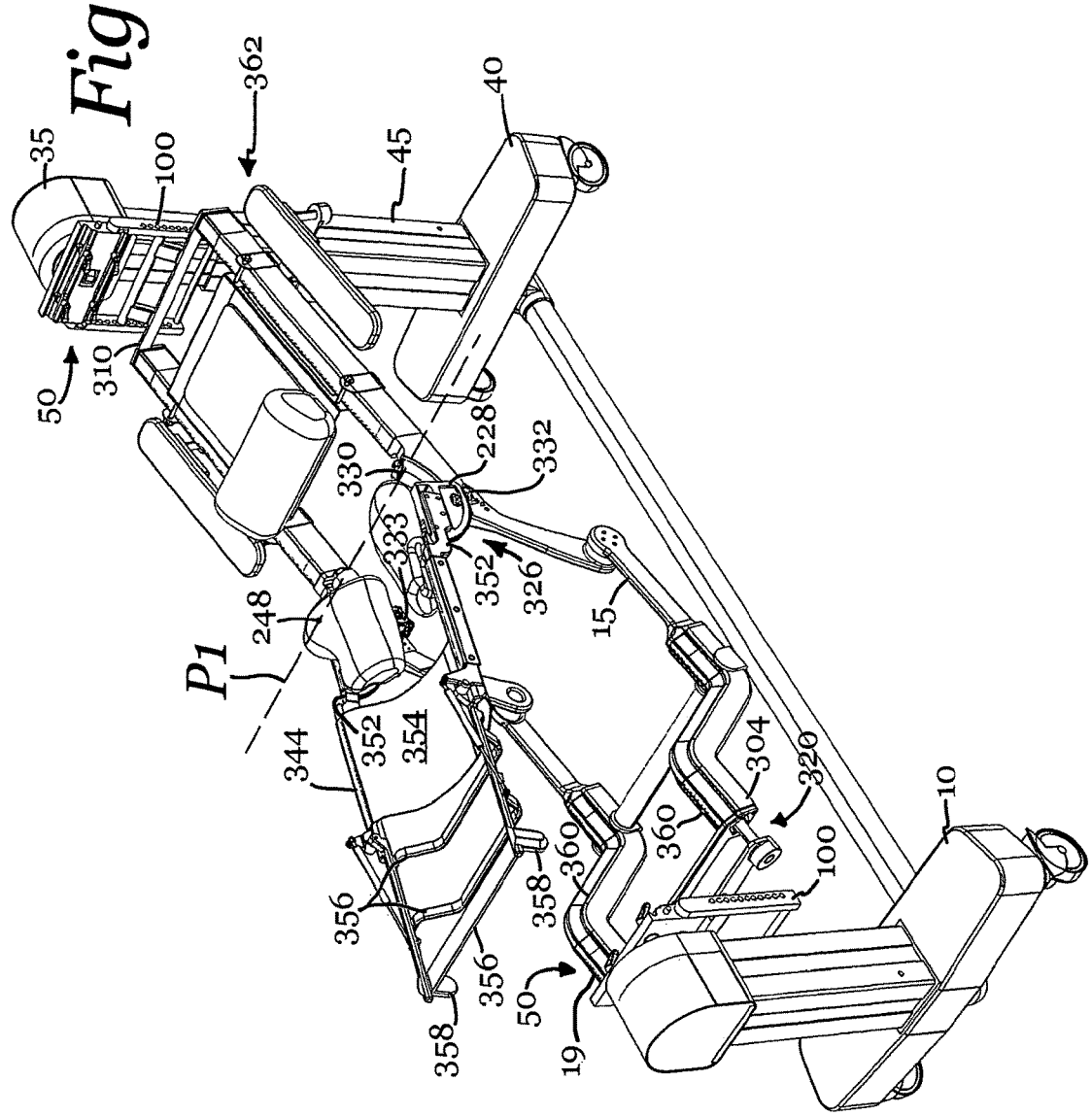
FIG. 55 is a reduced perspective view of the patient positioning support system of FIG. 1, with the patient support structure positioned so as to maximally extend the hips and legs of a patient thereon.
Figure 57A:
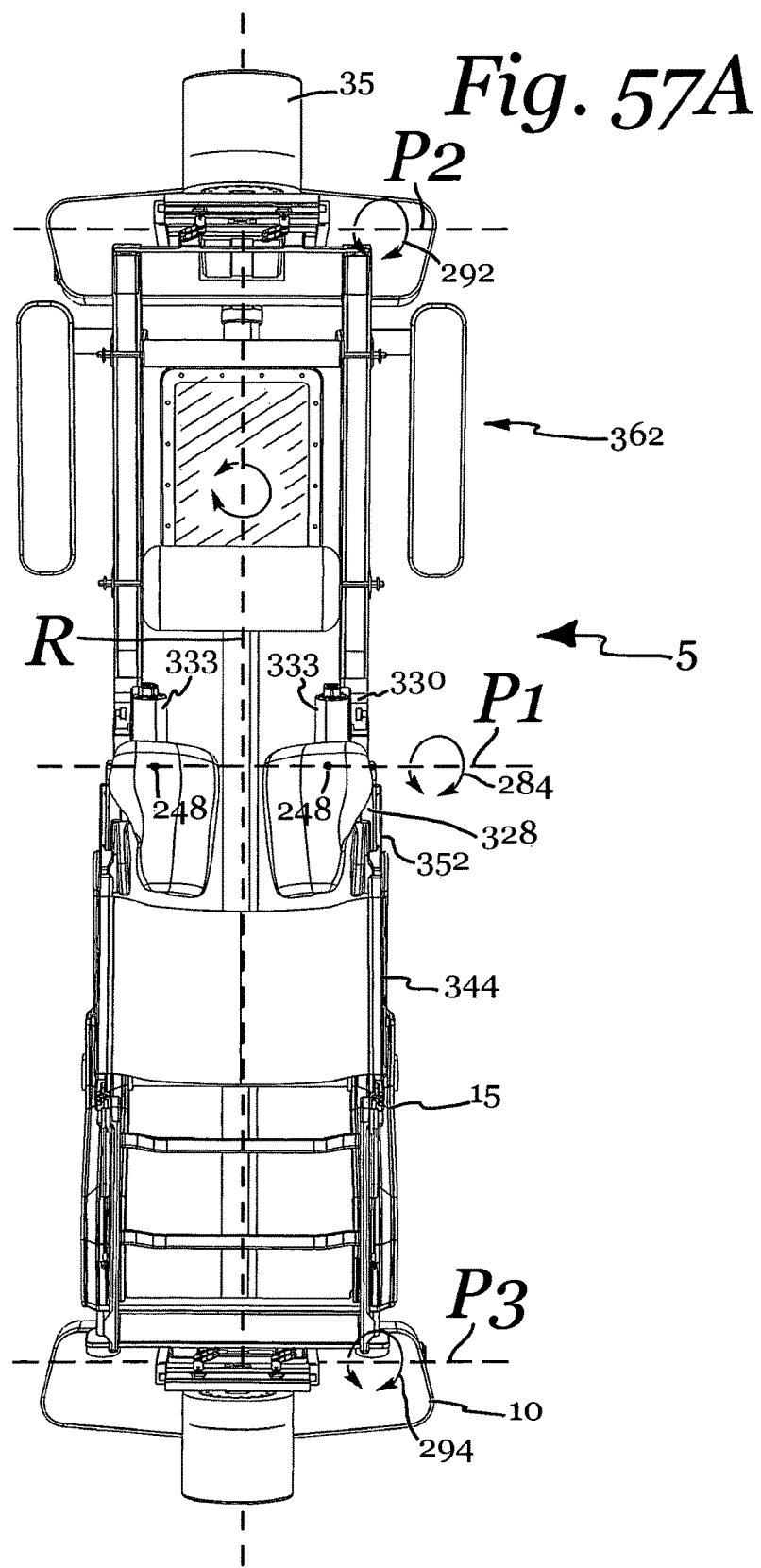
FIG. 57A is top view of the patient positioning support system of FIG. 55.
Figure 57B:
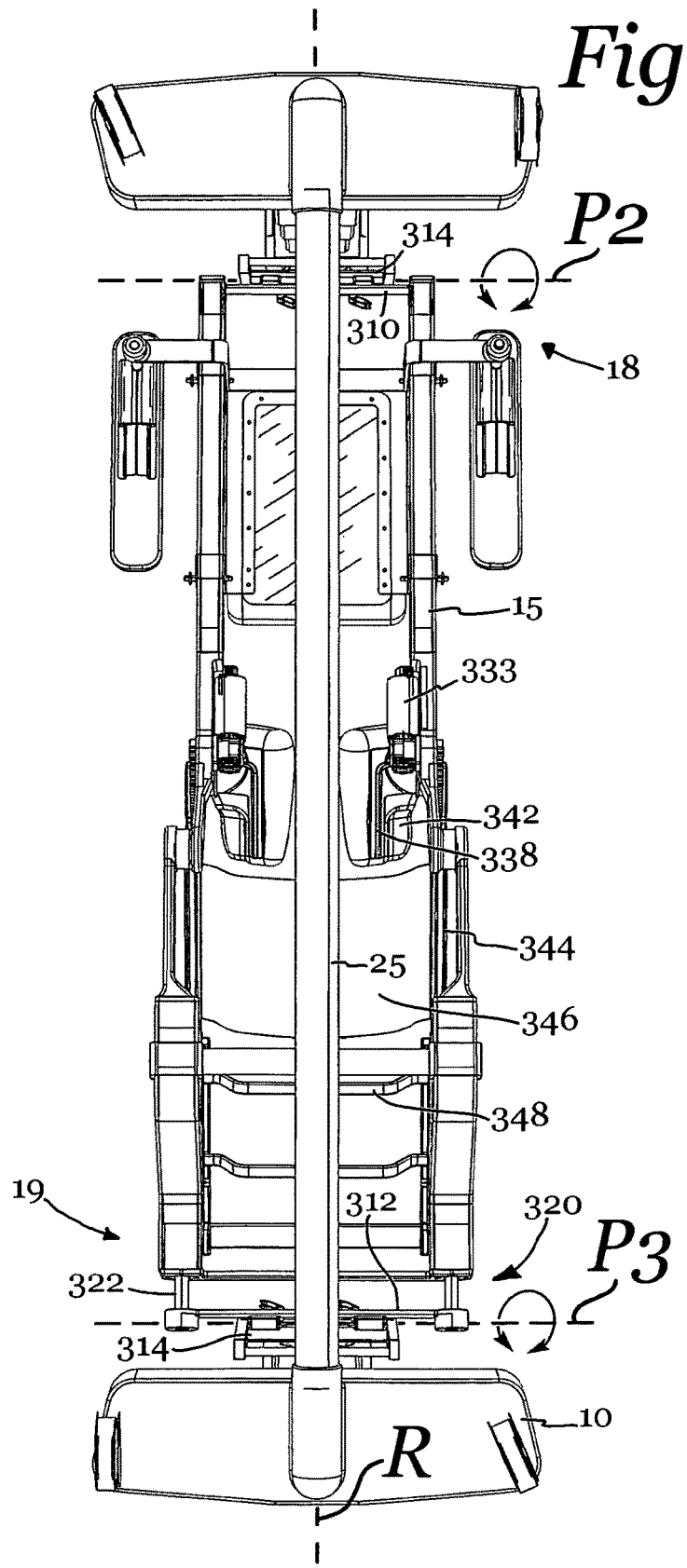
FIG. 57B is a bottom view of the patient positioning support system of FIG. 55.
Figure 58:
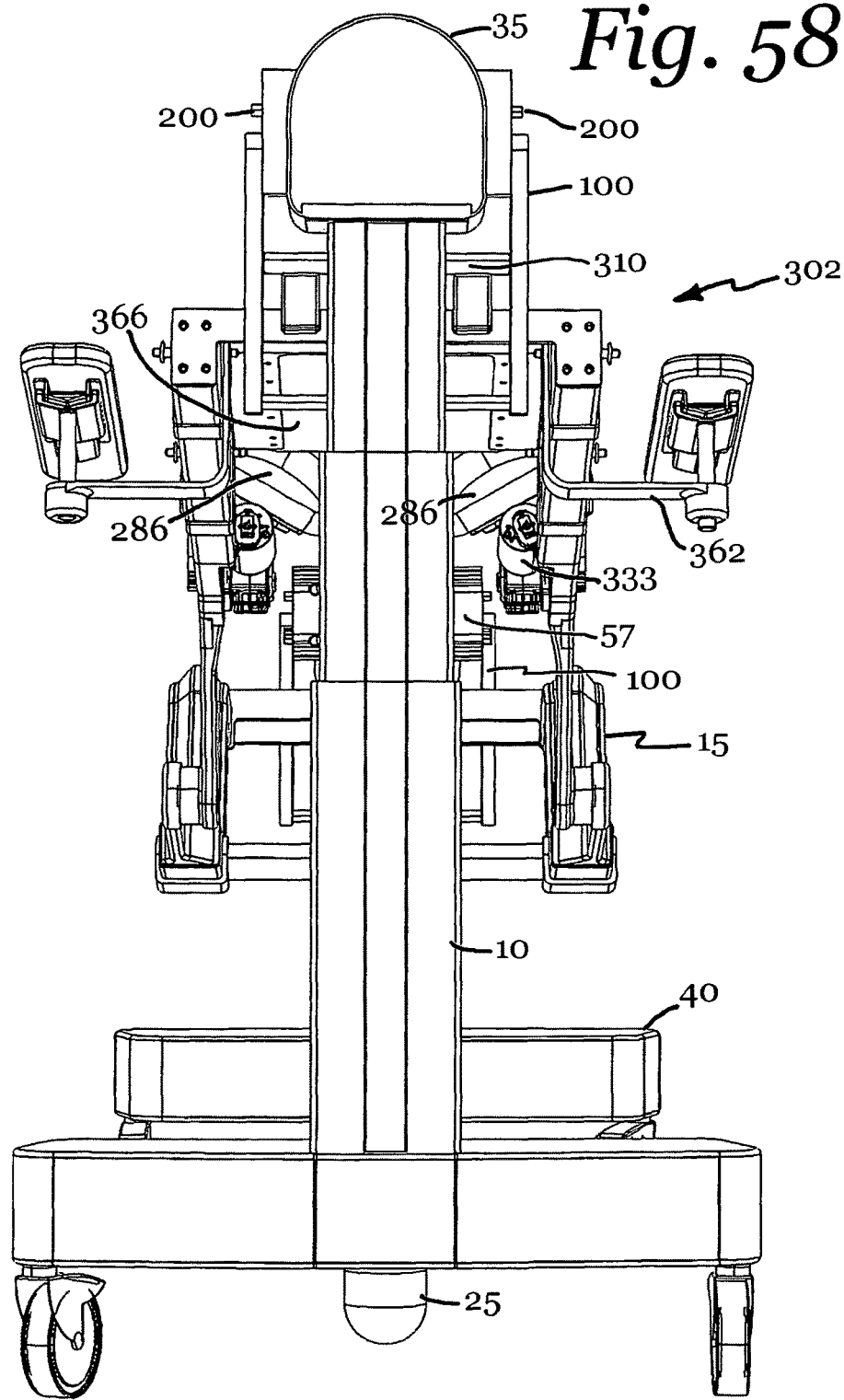
FIG. 58 is head-end view of the patient positioning support system of FIG. 55.
Figure 59:
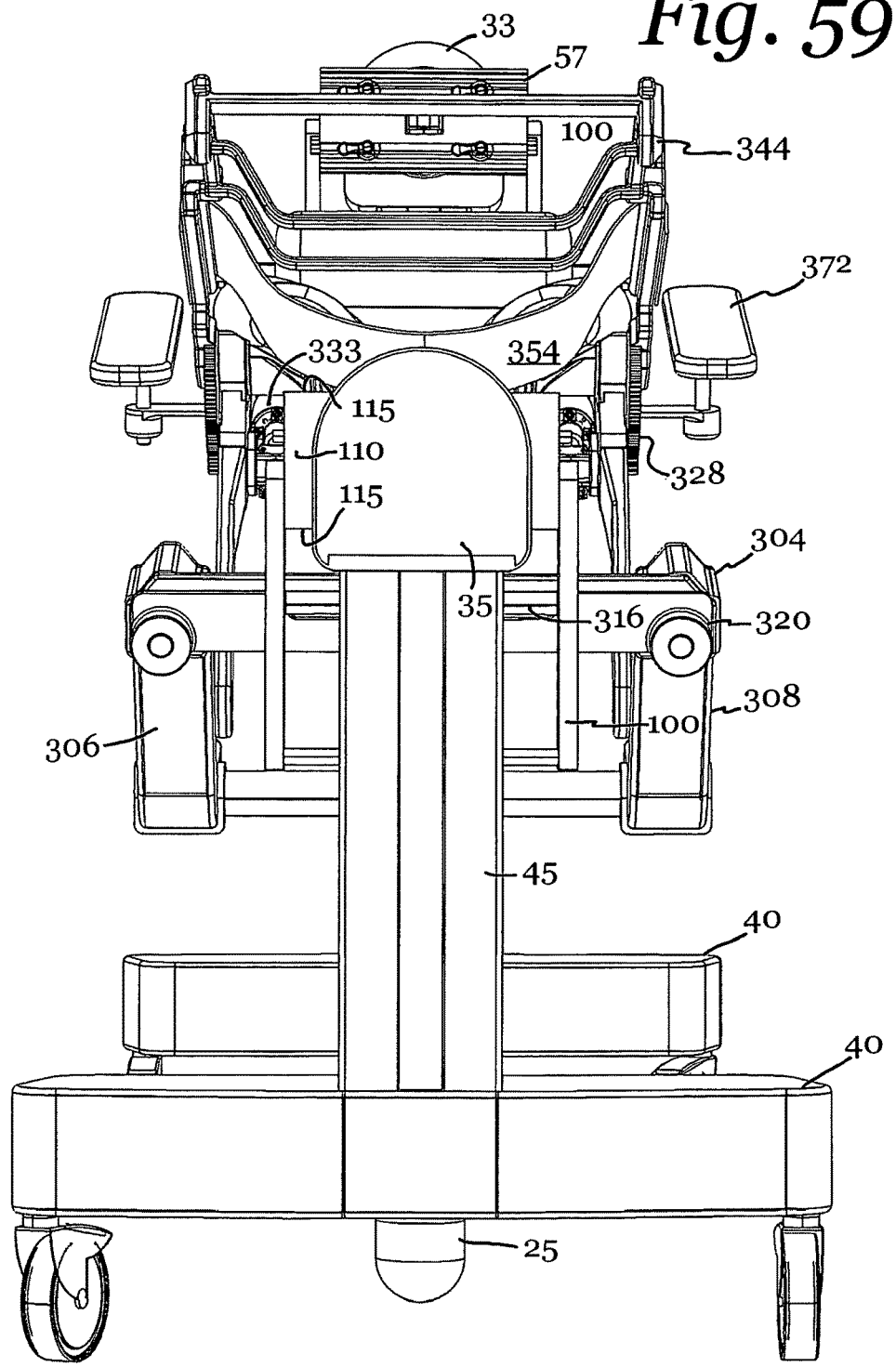
FIG. 59 is foot-end view of the patient positioning support system of FIG. 55.
Figure 60:
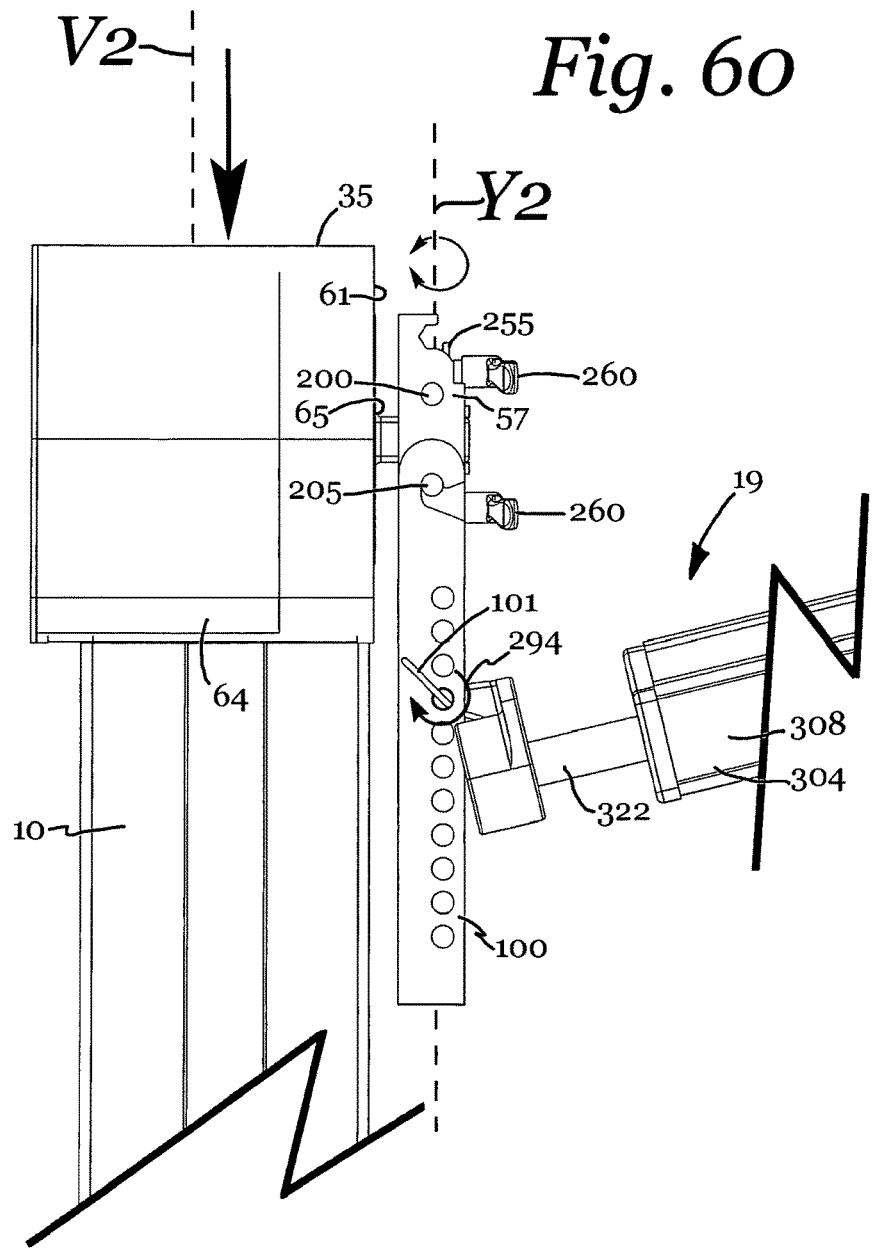
FIG. 60 is an enlarged view of the foot-end of the patient positioning support system of FIG. 56, with portions broken away.
Figure 61:
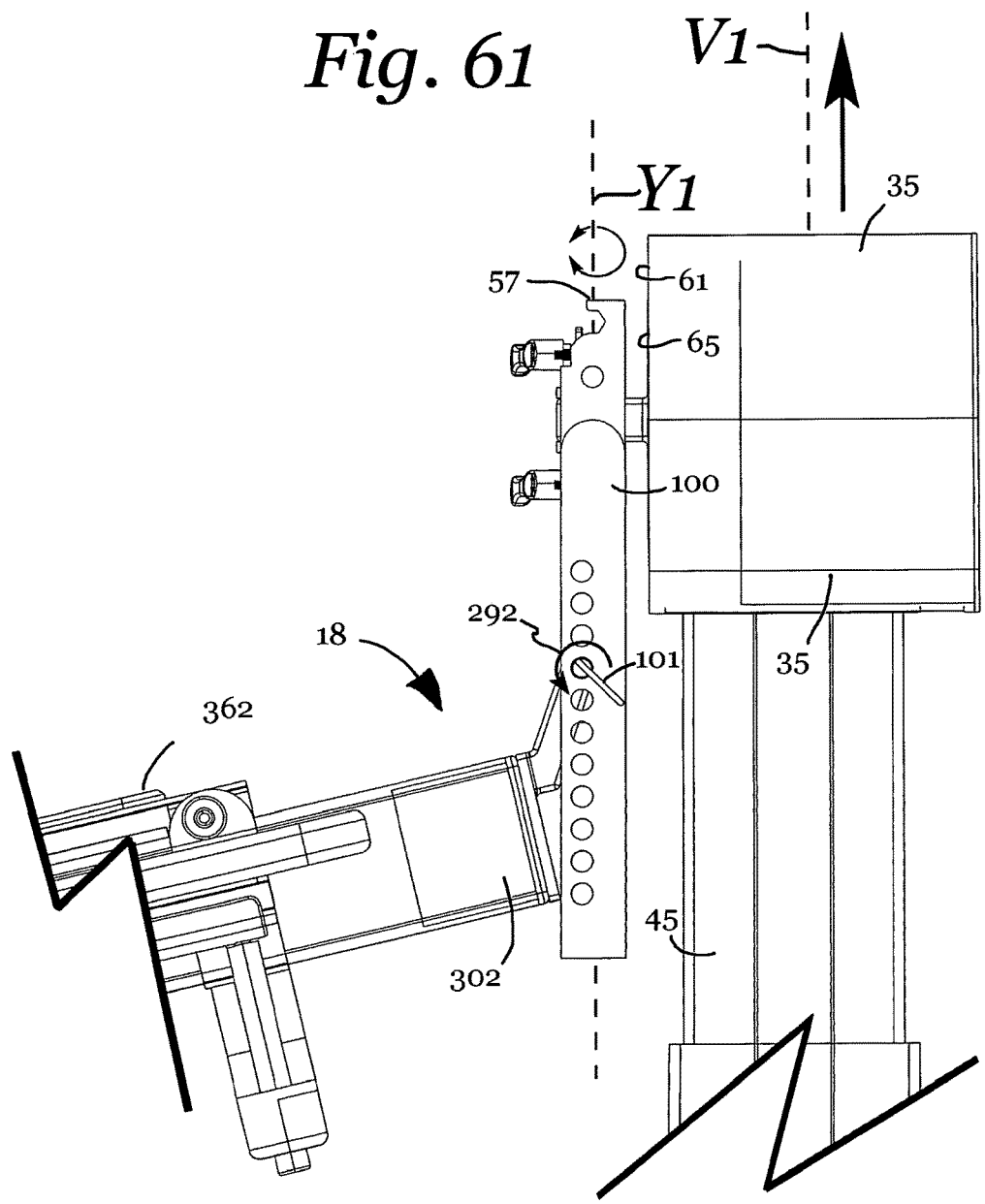
FIG. 61 is an enlarged view of the head-end of the patient positioning support system of FIG. 56, with portions broken away.
Figure 62:
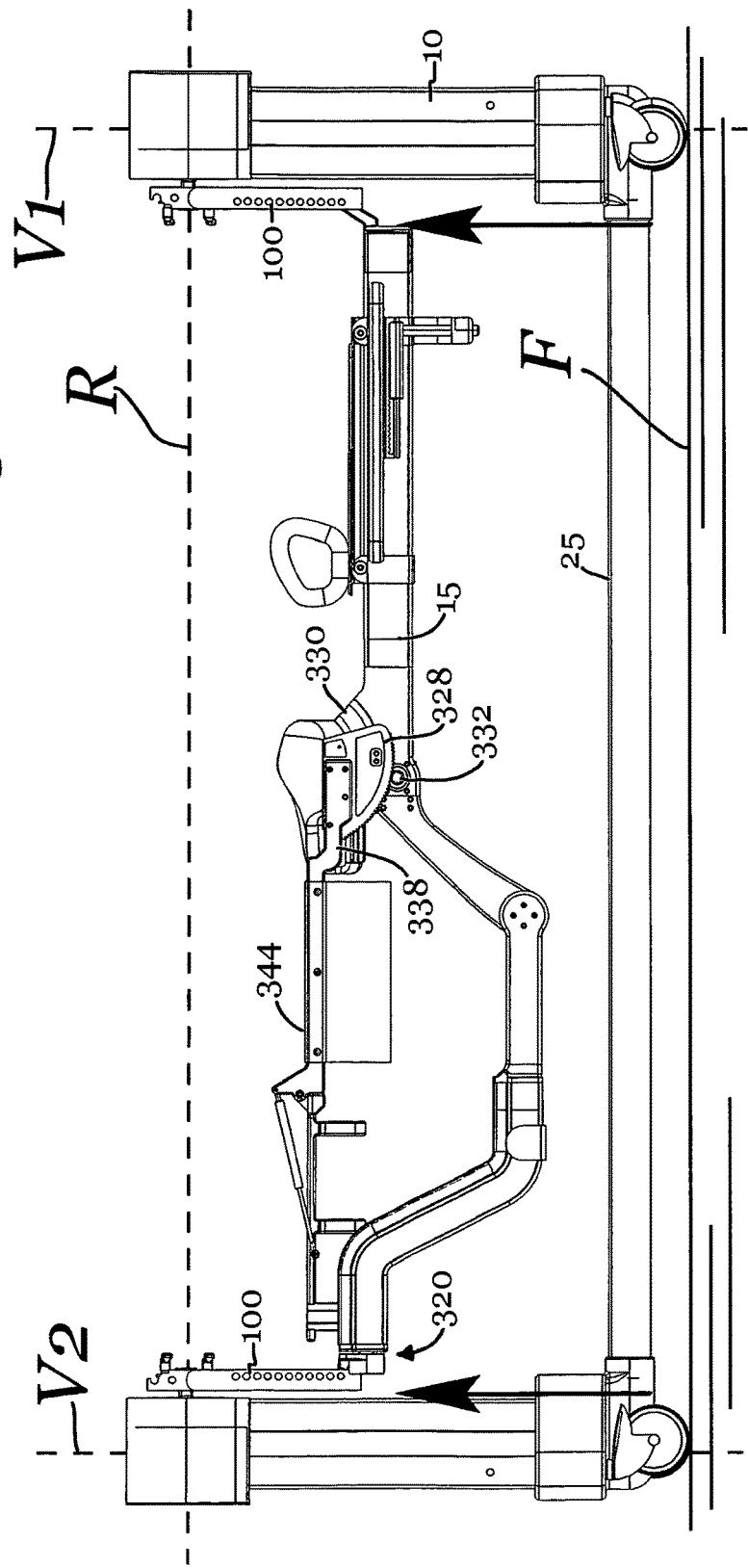
FIG. 62 is a reduced right side view of the patient positioning support system of FIG. 1, with the prone patient support structure attached to the lowest possible position of the ladders.
Figure 63:
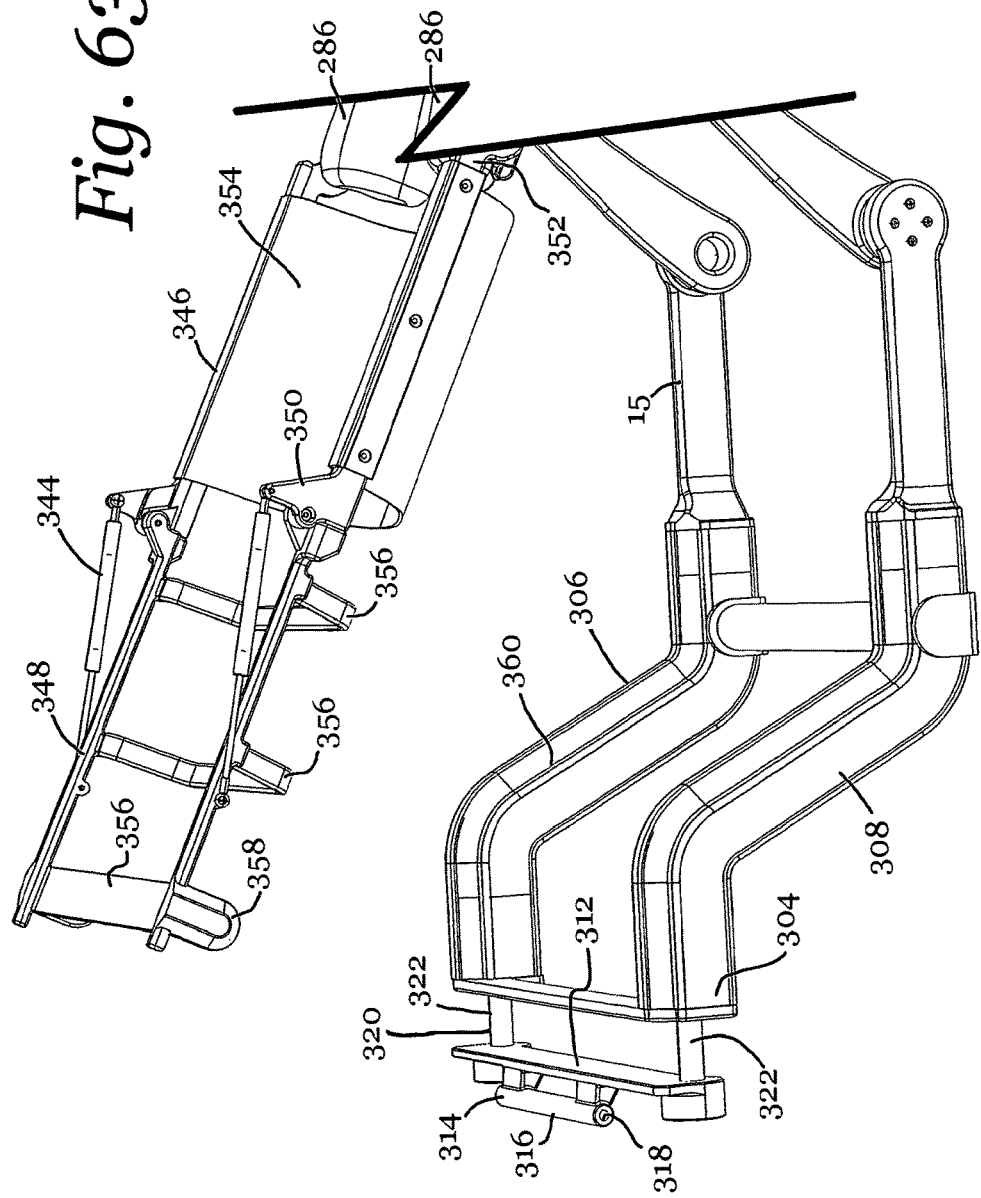
FIG. 63 is an enlarged perspective view of the prone patient positioning support structure of FIG. 55, with portions broken away or not shown.
Figure 64:
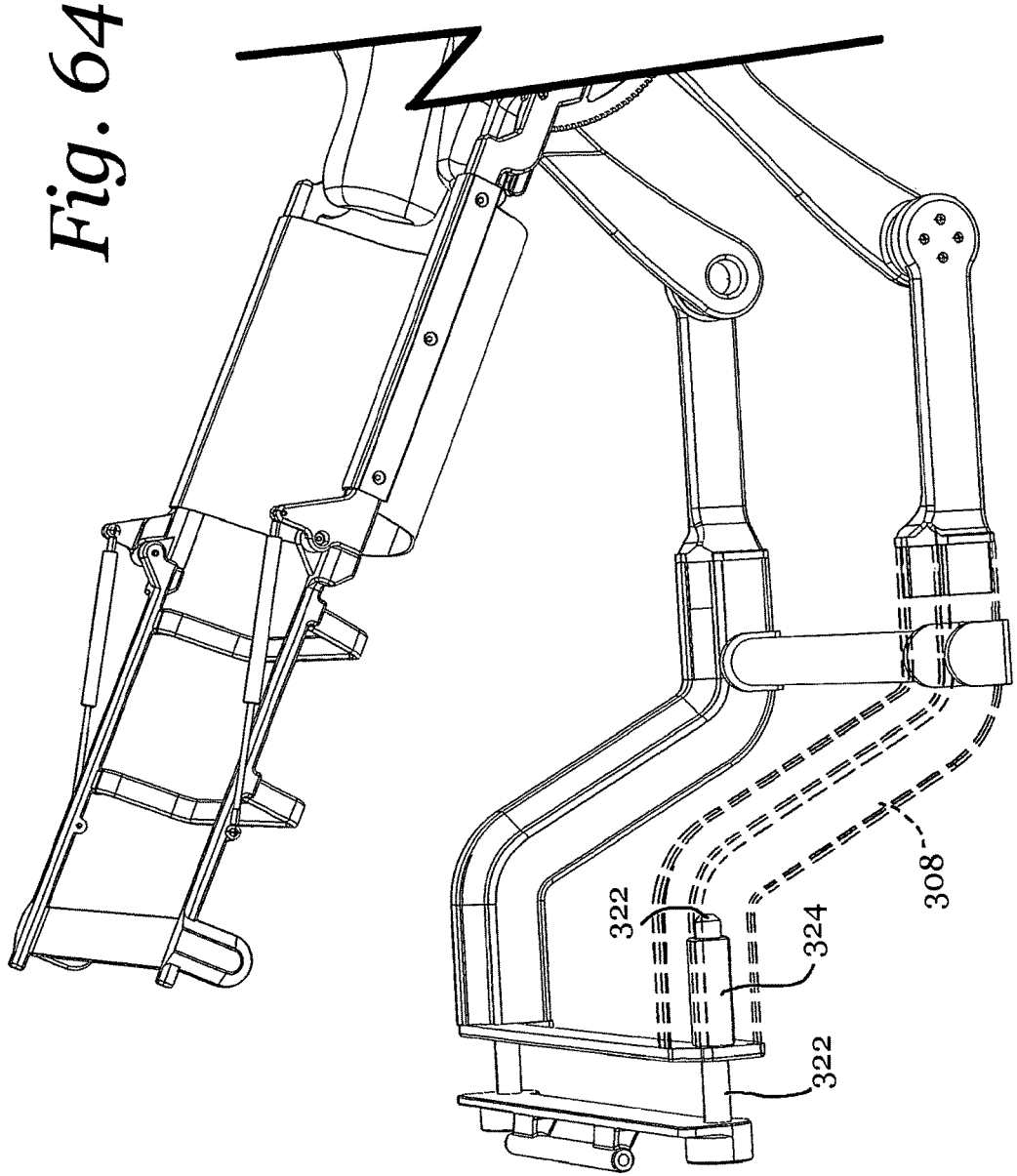
FIG. 64 is a view of FIG. 63 with portions shown in phantom to show additional detail of the foot-end of the frame.

The prone patient support structure 15 includes a lower extremity support structure 344. The lower extremity support structure 344 is adapted to support the legs of the patient on the prone patient support structure 15. The lower extremity support structure 344 is also adapted to move the patient's legs between the neutral, flexed and extended positions, and to support the legs when the legs are in those positions. For example, in FIG. 39, the lower extremity support structure 344 is rotated downwardly by the joints 326, such that the hips would be flexed. In another example, in FIG. 55, the lower extremity support structure 344 is rotated upwardly by the joints 326, such that the hips would be extended.

The lower extremity support structure 344 includes an upper leg support portion or femoral support 346, and a lower leg support portion or lower leg cradle 348 that are joined or pivotably connected by a pair of knee hinges 350, so as to be movable between a first position and a second position; and wherein when in the first position, the femoral support 346 and the lower leg cradle 348 are in a neutral position; and when in the second position, the femoral support 346 and the lower leg cradle 348 are in a flexed position. In some embodiments, the lower leg cradle 348 is non-incrementally adjustable with respect to the femoral support 346 and between the neutral position and a maximally flexed position. In other embodiments, the lower leg cradle 348 is continuously adjustable with respect to the femoral support 346 and between the neutral position and a maximally flexed position. Additionally, in some embodiments, the lower leg cradle 348 is incrementally adjustable with respect to the femoral support 346. In other embodiments, the lower leg cradle 348 is non-incrementally adjustable with respect to the femoral support 346.

The knee hinges 350, also referred to as lower leg hinges, are spaced from and opposed to one another, and also enable flexion and extension of the patient's knees between the first and second positions. The knee hinges 350 may be active, or powered, or the knee hinges 350 may be passive, or un-powered, such as but not limited to spring hinges. The upper leg support portion 346 includes a pair of spaced opposed rails 352 with a thigh support sling 354 suspended therebetween. In some embodiments, the thigh support sling 354 is adjustable, such that the height of the thighs is adjustable. In some embodiments, the thigh support sling 354 is removable, such as for cleaning, replacement and additionally or alternatively adjustment. The thigh support sling 354, like other components of the patient positioning support structure, such as but not limited to the frame 396, the hip-thigh pads 286, and the joints 326 may be covered with a disposable, or washable, covering or drape provided as part of a draping kit, such as is known in the surgical arts. The draping kit may also include one or more pillow structures, for filling the thigh support sling 354, so as to support the thighs in a more preferred orientation.

The spaced opposed rails 352 are fixedly joined with the joint first components 328, such as is shown in FIGS. 65-67. Accordingly, in addition to glidingly moving the hip-thigh pads 286 with respect to the arc of motion AOM, the joints 326 also move, pivot or rotate the rails 352, and therefore the lower extremity support structure 344, about the first pitch axis P1. Accordingly, as the joints 326 move, or are selectively moved, from a neutral position, such as is shown in FIG. 66, to the maximally extended position, and such as is shown in FIG. 65, the patients hips become progressively more extended, until the maximum extended position is reached. The operator can adjust the amount of hip extension, by selecting an extended position of the joints 326. Further, as the joints 326 move, or are selectively moved, from the neutral position, shown in FIG. 66, to the maximally flexed position, such as is shown in FIG. 67, the patients hips become progressively more flexed, until the maximum flexed position is reached. It is noted that, due to the knee hinges 350, the knees are also flexed and extended together with the flexion and extension of the hips. However, it is foreseen that the lower extremity support structure 344 may be configured without knee hinges 350, such that the knees do not flex or extend.

In the illustrated embodiment, the lower leg support portion 348 is a frame adapted for supporting the lower legs of the patient. The lower leg support portion 348 may include one or more cross-pieces 356 adapted for holding pillows or for attachment of the patient's lower legs thereto. Further, in some embodiments, the lower leg support portion 348 includes one or more guide members 358 adapted to guide movement of the lower leg support portion 348 and additionally or alternatively actuation of passive knee hinges 350. In some embodiments, such guide members 358 contact and slide along a guide track 360 of the foot-end portions of the frame 296, or the foot ends 304 of the left-hand and right-hand frame portions 306, 308, such as is shown in FIGS. 44-54. It is foreseen that in some embodiments the frame 296 does not include guide tracks 360. In some embodiments, the knee hinges 350 are actively driven, or powered, such that the knee hinges 350 operate without the need to guide tracks 360 or guide members 358.

In some embodiments, the lower extremity support structure 344 is joined with the joints 326 such that the lower extremity support structure 344 is movable with respect to the virtual pivot point 248 and between the first and second positions, such as described above.

Torso Support Structure

Figure 12:
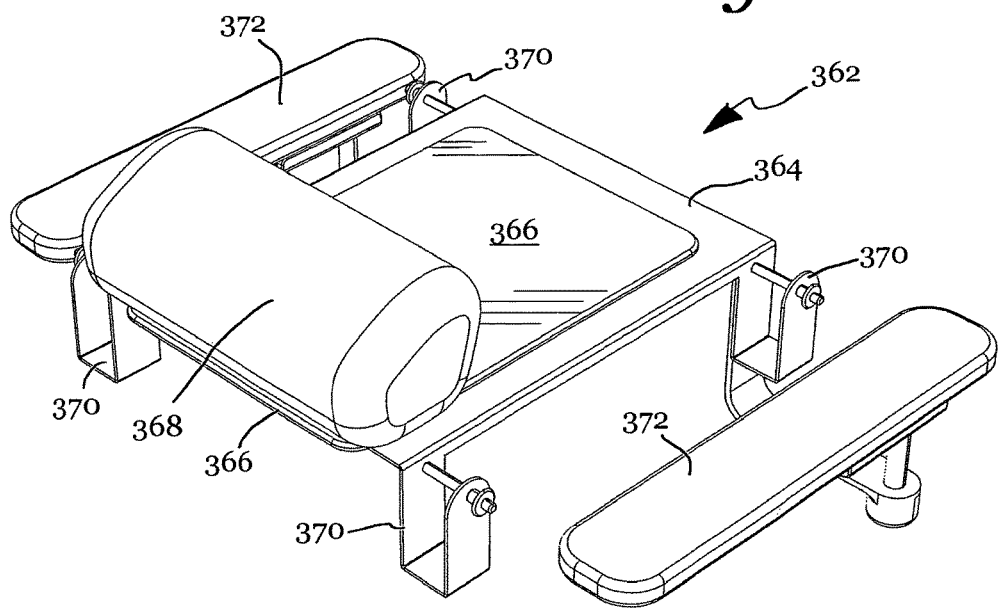
FIG. 12 is an enlarged perspective view of a torso support subassembly of the patient positioning support system of FIG. 1.
Figure 13:
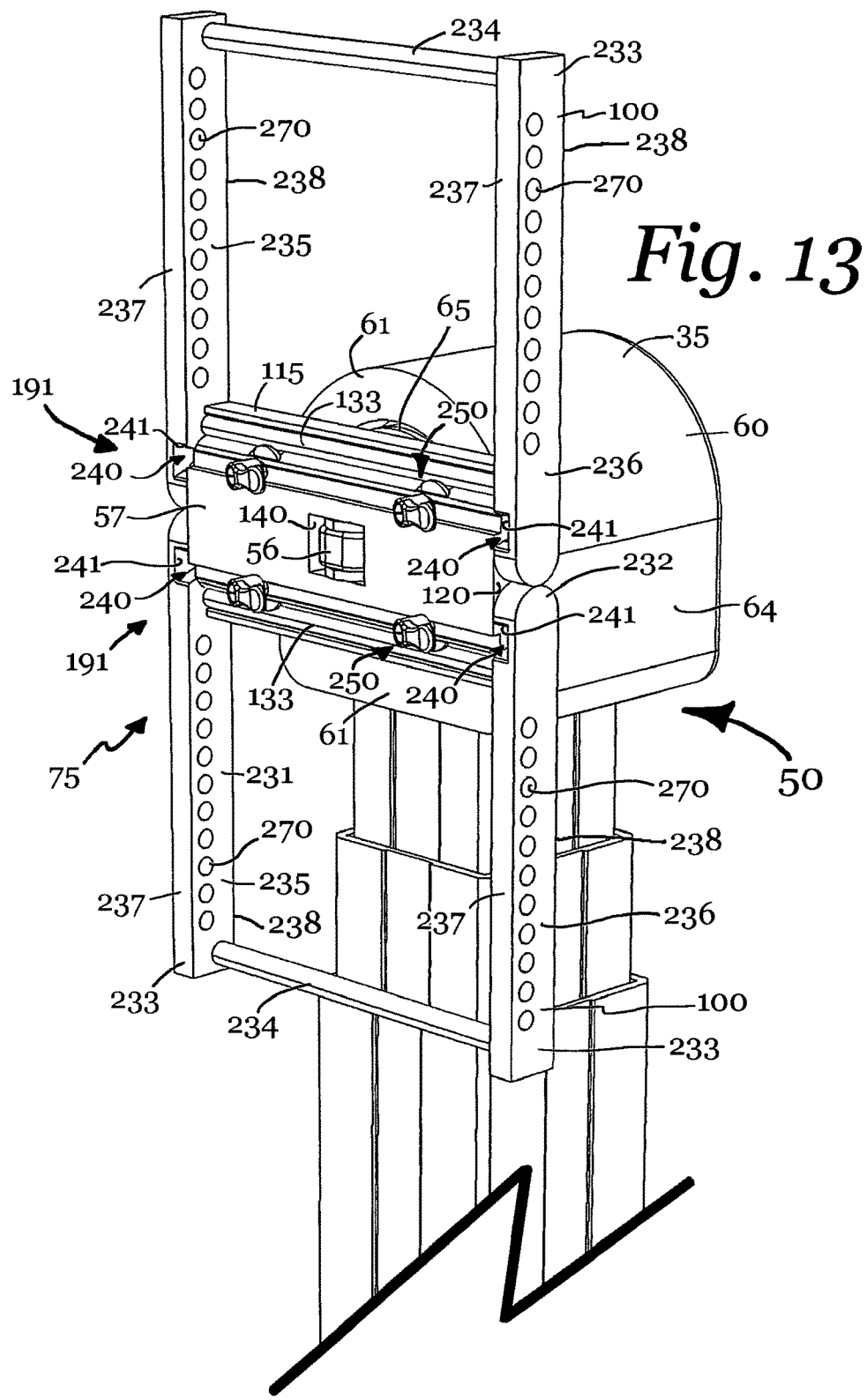
FIG. 13 is an enlarged perspective view of a connection subassembly of the patient positioning support system of FIG. 1, with portions broken away.

The patient positioning support structure 5 of the present invention includes a torso support structure 362 that is received on and attachable to a head-end portion 302 of the frame 296 of the prone patient support structure 15, so as to support the head and torso of a patient thereon. As shown in FIG. 12, the torso support structure 362 includes a support body 364 with a substantially transparent face shield 366, a chest pad 368 attached to the support body 364 and a plurality of lockable brackets 370 that are adapted for releasable connection to the frame 296. A pair of adjustable arm support boards 372, such as are known in the art, is attachable either to the support body 364 or optionally to the frame 296 of the patient support structure 15. A ring-shaped pillow or similar structure (not shown) may be placed on the face shield 366 so as to support the patient's head while simultaneously providing clearance for anesthesia tubing or other equipment. The chest pad 368 is somewhat compressible and substantially radiolucent. In some embodiments, the chest pad 368 includes two or more chest pads 368. The chest pad 368 may be covered with a cover or drape, such as is described elsewhere herein. The position of the chest pad 368 is slidably adjustable along a length of the head-end portion 302 of the frame 296. Accordingly, the torso support structure 362 can be slid or moved along the frame head-end portions 302, or along a length thereof, so as to position the chest pad 368 in a suitable location with respect to the patient's body and biomechanics. Once the chest pad 368 is in a suitable position along the frame 296, the torso support structure 362 can be locked into place on the frame 296, such as by actuating reversibly lockable brackets 370.

Referring to FIGS. 162-165, when the patient positioning support system 5 is being assembled for a sandwich-and-roll procedure, the patient is face up on the supine support structure 15', described below, and the prone patient support structure 15 is positioned over or on top of the patient, such that the patient is sandwiched between the two structures 15 and 15'. Then, the torso support structure 362 is placed onto the frame 296, such that the chest pad 368 is located between the sides of the frame 296, or between the left-hand and right-hand frame portions 306, 308, and against the patient's chest. The location of the chest pad 368 is adjusted by sliding it along the length of the frame 296 upper portion 302. When the desired location of the chest pad 368 is reached, achieved or selected, the brackets 370 are locked or otherwise engaged so as to fix the position of the torso support structure 362 with respect to the frame 296. The patient's arms are positioned and removably attached or strapped onto adjustable arm boards 372 of the torso support structure 362, and then the sandwiched patient can be rolled over about the roll axis R.

Figure 68:
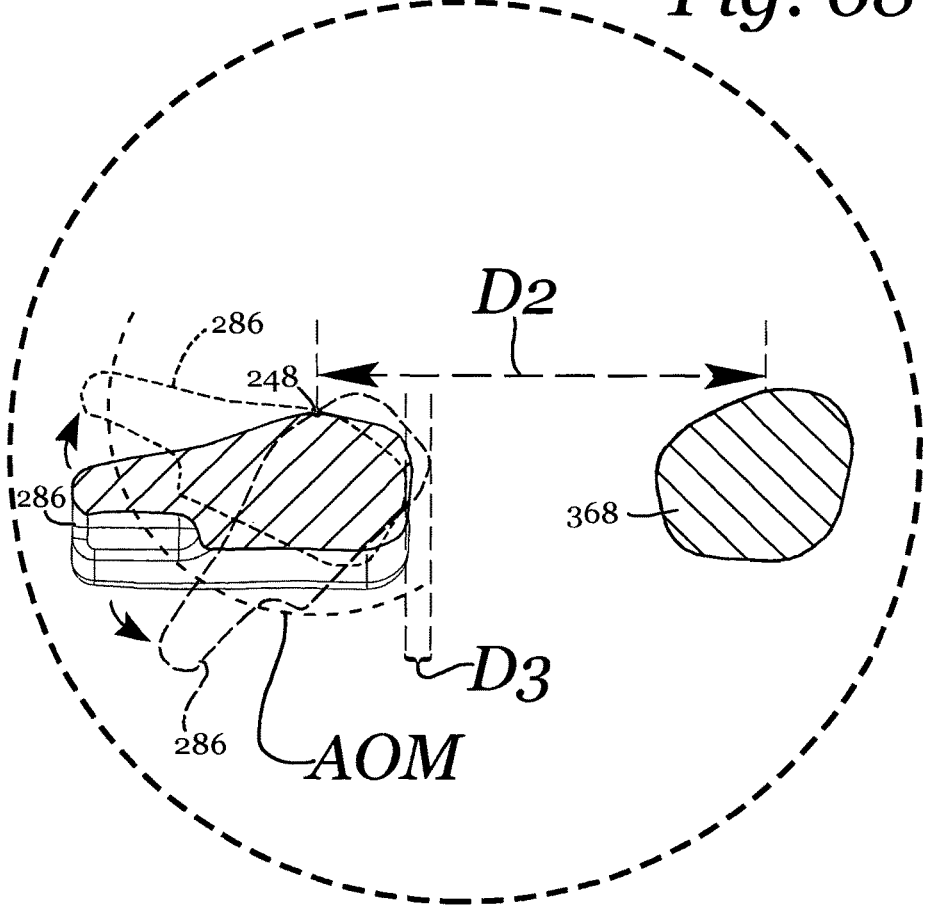
FIG. 68 is an enlarged overlaid cross-sectional schematic of the patient positioning support structures of FIGS. 65, 66 and 67 taken along the line 68-68 of FIG. 5.
Figure 69:
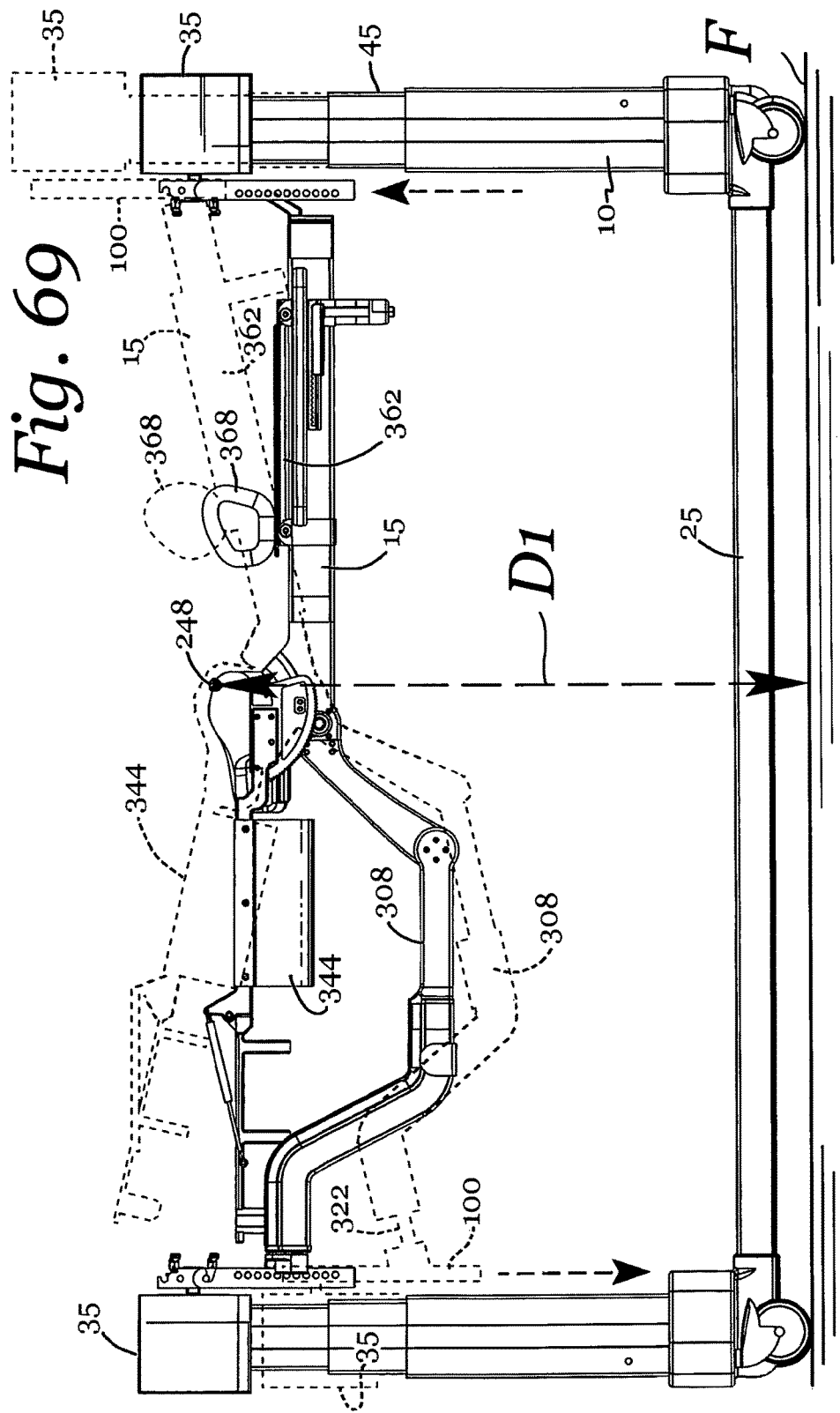
FIG. 69 is an enlarged view of the patient positioning support structure of FIG. 4 overlaid with an enlarged phantom view of the patient positioning support structure of FIG. 56, so as to compare changes in the positions of various parts of the patient positioning support structure when moved between the positions shown in FIGS. 4 and 56.

Referring to FIGS. 65-68, the hip-thigh pads 286 are associated with a lower-body side of the joints 326 and the chest pad 368 is associated with an upper-body side of the joints 326. Accordingly, the hip-thigh pads 286 are opposed to and spaced a distance from the chest pad 368. In particular, the virtual pivot point 248 of each hip-thigh pad 286, or of each joint 326, is spaced a distance D2 from the chest pad 368. As shown in FIG. 68, as the hip-thigh pads 286 are rotated about the pivot point 248, the distance D2 between the pivot point 248 and the chest pad 368 is substantially constant. Additionally, when the joints 326 are moved to an extended or flexed position, even though the distance D2 between the pivot point 248 and the chest pad 368 remains substantially constant, the hip pads 286 may translate laterally, or horizontally, a distance D3 toward the head-end of the patient positioning support system 5. Generally, the distance D3 is relatively small. When the joints 326 return to the neutral position, the hip pads 286 move back to the starting position, such as by laterally or horizontally translating a distance D3 toward the foot-end of the system 5 such as toward the foot end 16' of the base 10 or toward the foot end 19 of the prone patient support structure 15.

Accordingly, in some embodiments, the distance D2 between the chest pad 368 and the hip-thigh pads 286 is substantially constant during movement of the joints 326 between a first position and a second position, or toward and away from the head-end 16 of the base 10 when moving between neutral and angulated positions. In other embodiments, the distance D2 between the chest pad 368 and the hip-thigh pads 286 is slightly variable during movement of the joints 326.

Supine Patient Support Structure

In some embodiments, the present invention includes a supine patient support structure 15' that is suspended above the floor F, such as is illustrated in FIGS. 102-120. In particular, the patient positioning support structure 5 of the present invention includes a base 10 that supports or suspends the supine patient support structure 15' above the floor F. The supine patient support structure 15' is removably attachable to the base 10 using a pair of ladders 100, 100', such as with a pair of standard-length ladders 100 or a pair of extended-length ladders 100', such as is described above with respect to attaching the prone patient support structure 15 to the base 10 using a pair of standard-length ladders 100.

In some embodiments, the supine patient support structure 15' includes an open frame 374 that is articulatable or breakable at a pair of spaced opposed hinges 376, and at least one of a set of body support pads (not shown), such as is known in the art, and a closed table-top 378. The supine patient support structure 15' also includes head- and foot-ends 288', 290', and left-hand and right-hand sides 298', 300'. The closed table-top 378 includes a head portion 380 and a foot portion 382, and may be covered by one or more flat pads 384. In some embodiments, the body support pads, the elongate table pad 384 and the table-top 378 are substantially radiolucent.

The supine patient support structure 15' includes head-end and foot-end ladder connection subassemblies 190'. In some embodiments, the ladder connection subassemblies 190' are configured and arranged so as to be substantially the same in structure and function as the ladder connection subassemblies 190 of the prone patient support structure 15. In other embodiments, other ladder connection subassemblies 190' are used. The ladder subassemblies 190' are attached to either a pair of standard length ladders 100 or a pair of extended length ladders 100' using a pair of T-pins 101, such as is described with respect to the ladder connection subassemblies 190 of the prone patient positioning structure 15. It is noted that the T-pins 101 are coaxial with second and third pitch axes P2 and P3 of the supine patient support structure 15', similar to that described above with respect to the prone patient support structure 15, whereby the supine patient support structure 15' can rotate or pivot about the second and third pitch axes P2 and P3.

The spaced opposed hinges 376 of the supine patient support structure 15' include a first pivot axis P1. As shown in FIGS. 116-120, each hinge 376 includes first and second hinge members 388 and 390, respectively, and a worm drive, generally 392. A shroud or housing 394 covers and protects the worm drive 392. The worm drive 392 is also partially covered by a frame portion 396 that joins the second hinge member 390 with the frame 374 of the supine patient support structure 15'. In some embodiments, the frame 374 includes one or more of the first and second hinge members 388, 390, and the frame portion 396. However, it is foreseen that the hinges 376 may be entirely separate from but connected to the frame 374.

The worm drive 392 is a gear arrangement in which a worm 398, which is a gear in the form of a screw, meshes with a worm gear 400. Like other gear arrangements, a worm drive 392 can reduce rotational speed or allow higher torque to be transmitted. In the illustrated embodiments, the worm drive 392 is actuated by a motor 402 and the amount of pivot about the first pitch axis P1 is selectable.

Figure 112:
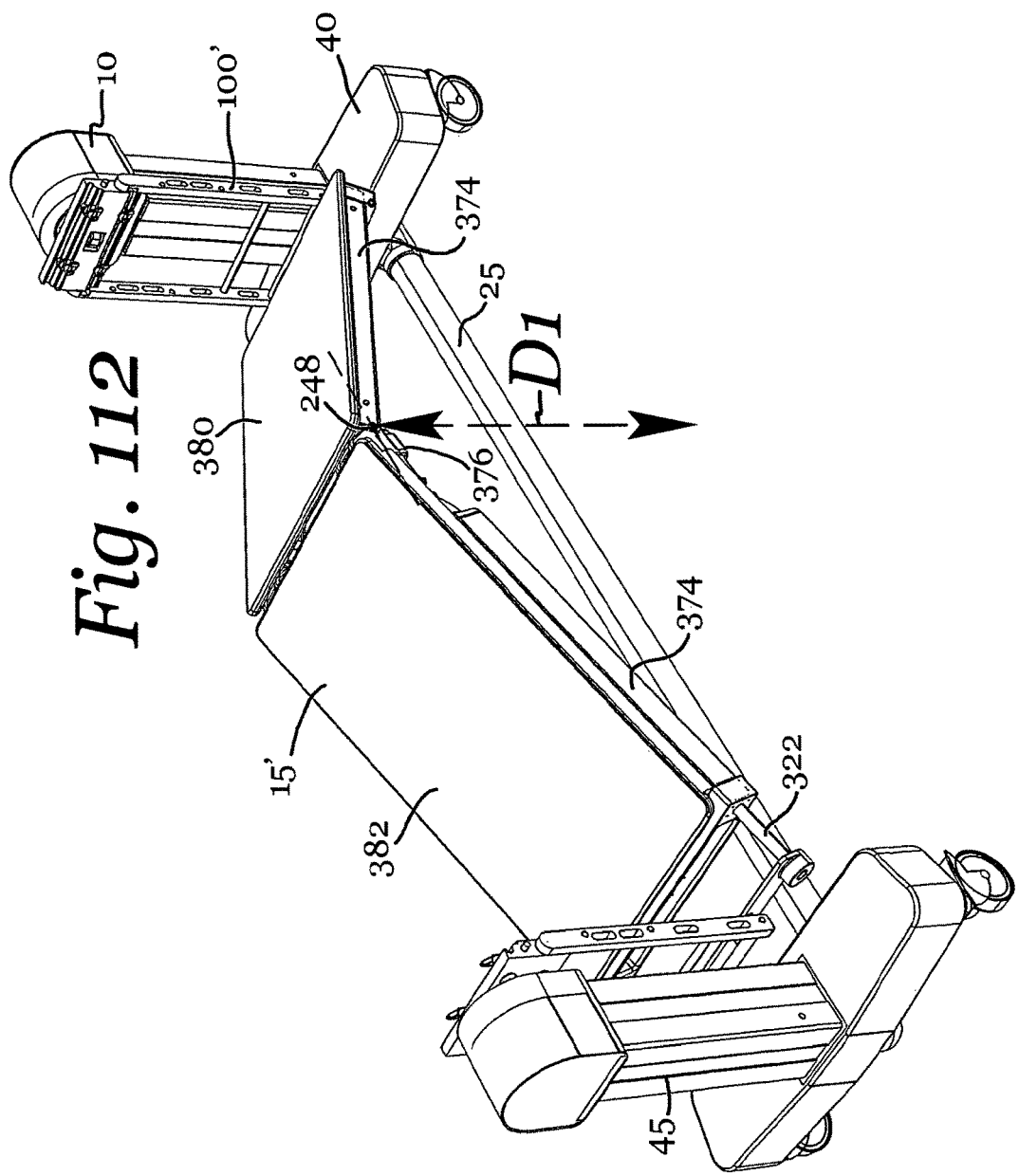
Figure 113:
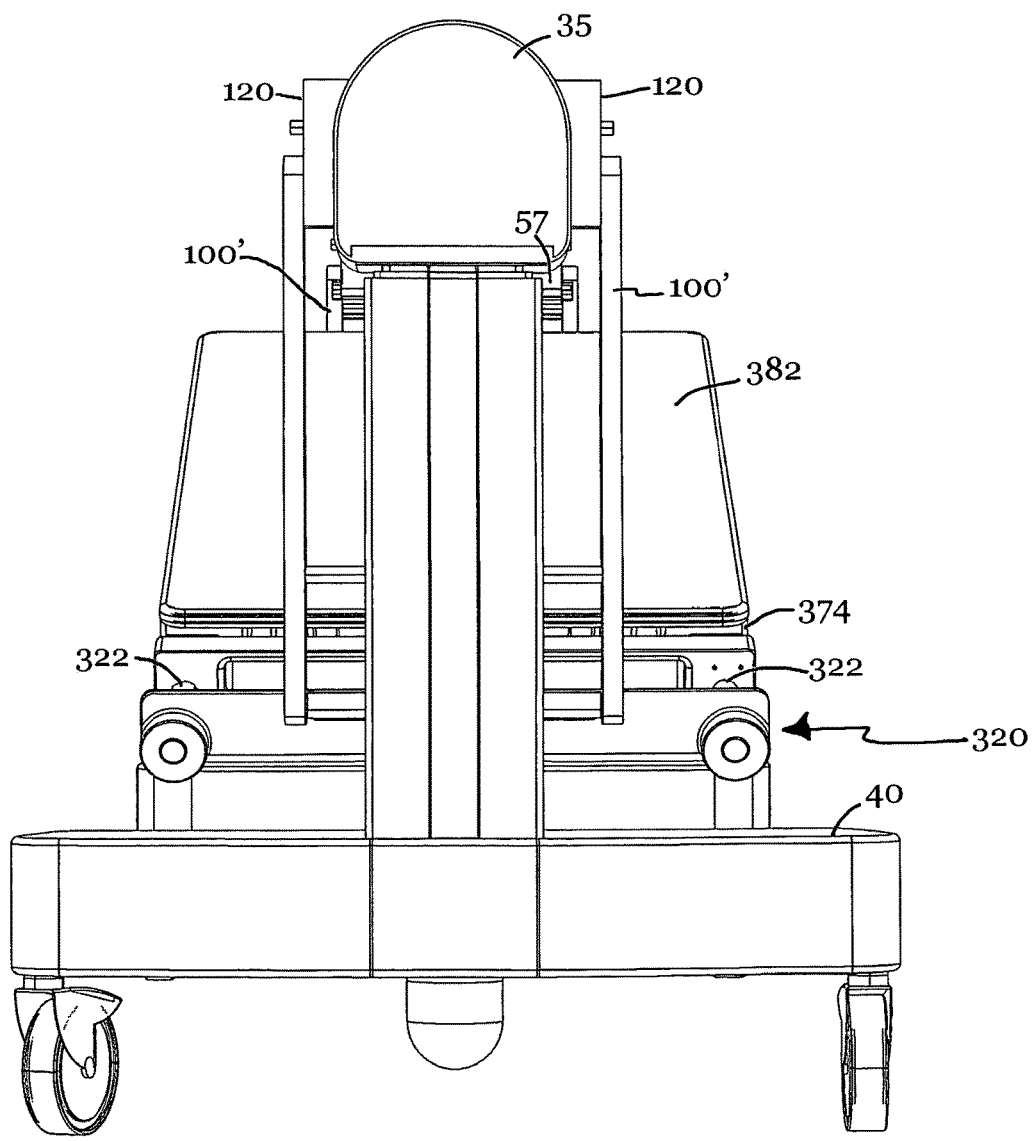

In some embodiments, the supine patient support structure 15' is reversibly positionable in a decubitus position, such as is shown in FIGS. 112-113. In a decubitus position, the patient may be positioned on their side, such that the patient is bent at the waist, with the head and feet lower than the hips. A lateral-decubitus position is essential for certain spinal surgeries, such as is known in the art. When in a decubitus position, the supine patient support structure 15' is joined with the base 10 using the extended-length ladders 100'. The extended-length ladders 100' are useful for positioning the patient in a later-decubitus position while spacing the surgical site, and therefore the first pitch axis P1 and the hinges 376, a suitable distance D4 from the floor F, such that the surgeon can perform the surgery comfortably.

In some embodiments, the patient positioning support system 5 includes a supine patient support structure 15', such as is shown in FIGS. 102-108, that is used for positioning a patient (not shown) in a supine or lateral position, such as is described elsewhere herein.

In another exemplary embodiment of the supine patient support structure 15' shown in FIG. 105, a first pitch axis P1 is associated with the pair of spaced opposed hinges 376. The supine patient support structure 15' also includes second and third pitch axes P2 and P3 that are associated with its head and foot-ends, which are generally denoted by the numerals 18' and 19' respectively.

For convenience, the left and right-hand sides of the supine patient support structure 15' are designated 298' and 300', and are also associated with the left and right sides, respectively of the patient. Accordingly, when the table is configured for a sandwich-and-roll procedure, the two left-hand sides 298 and 298' of the prone and supine patient support structures 15 and 15' are spaced and opposed from each other, on the front and back sides of the patient, such as is shown in FIGS. 92a and 94b-99. Additionally, the two right-hand sides 300 and 300' of the prone and supine patient support structures 15 and 15' are also spaced and opposed from each other, on the front and back sides of the patient.

Figure 114:
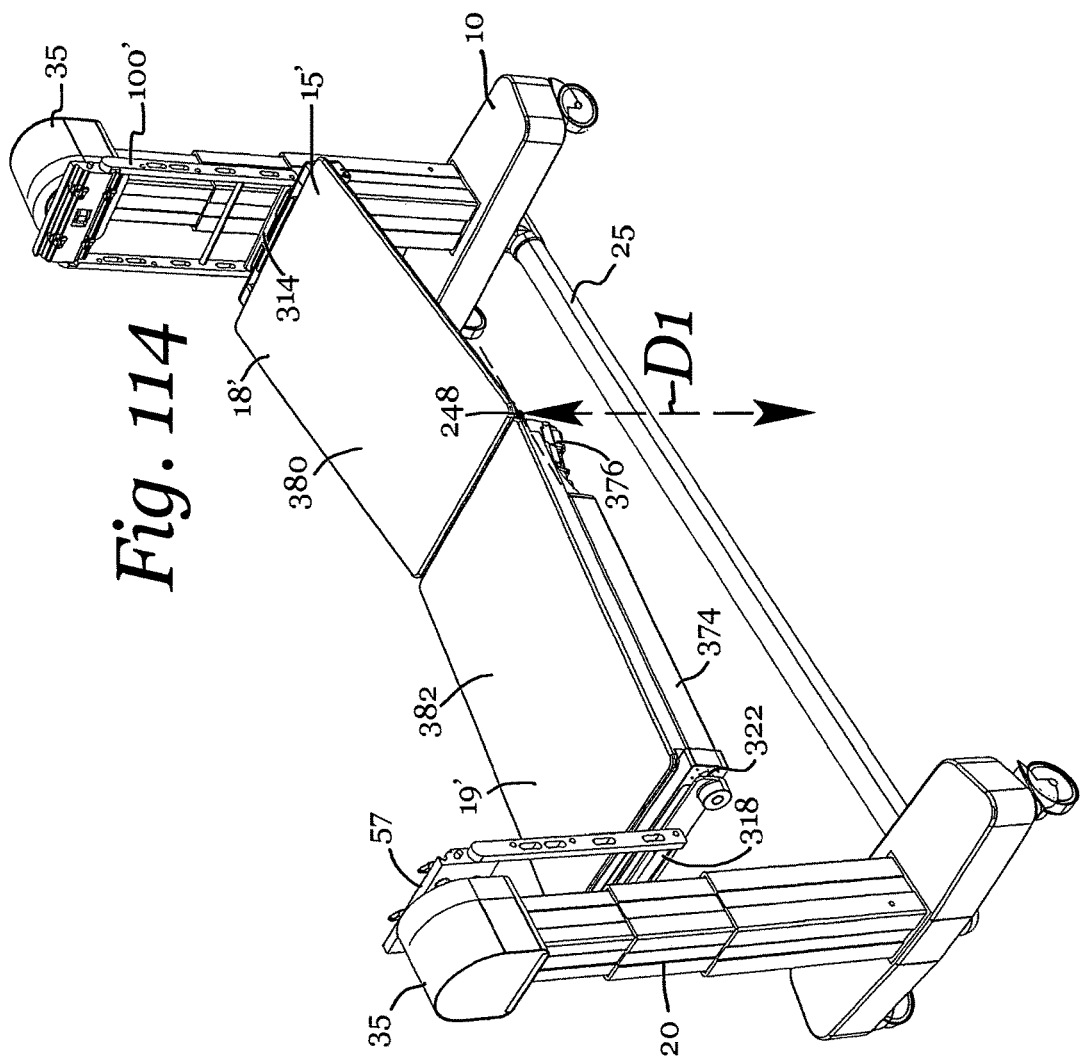
Figure 115:
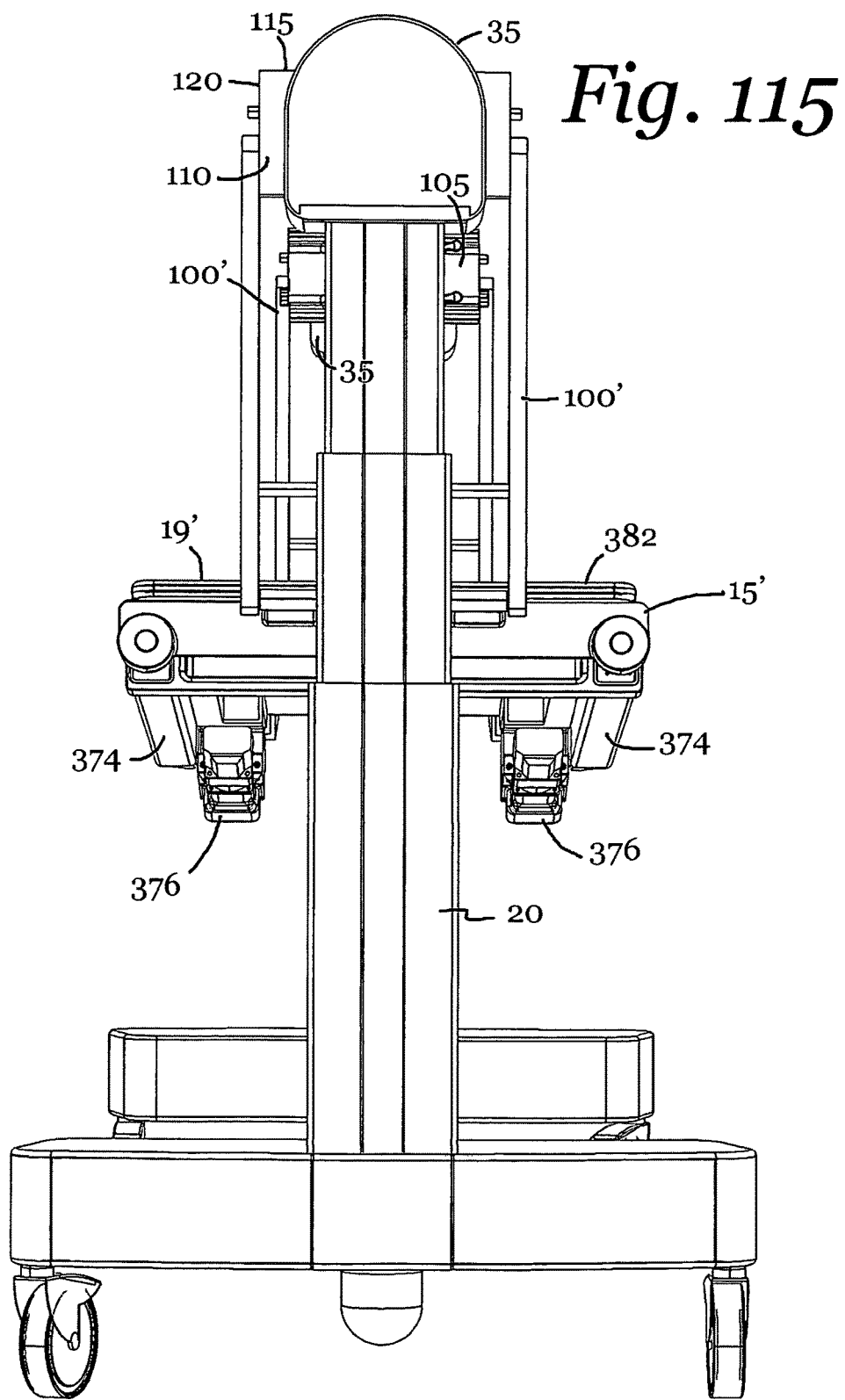
Figure 122:
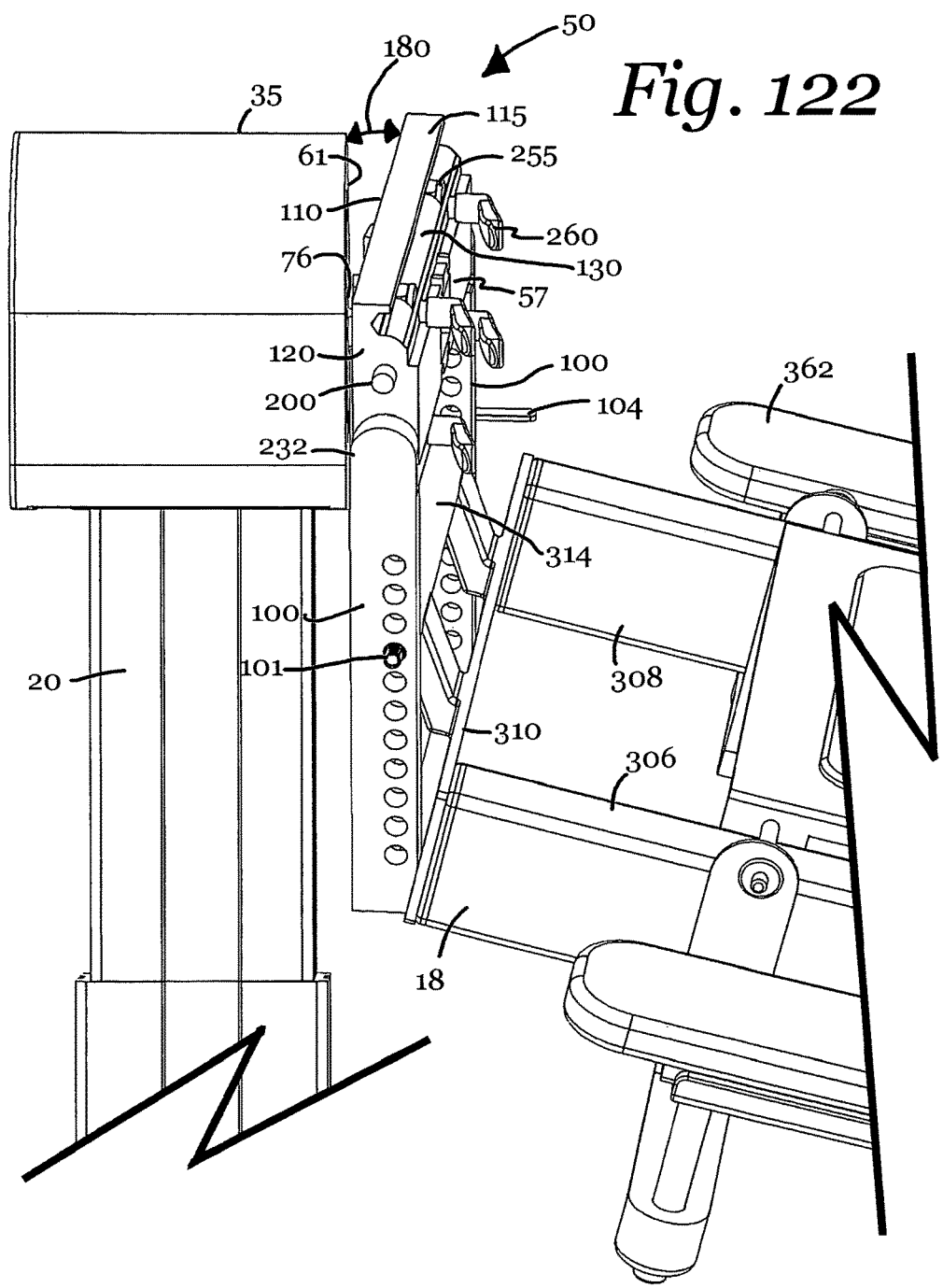
Figure 123:
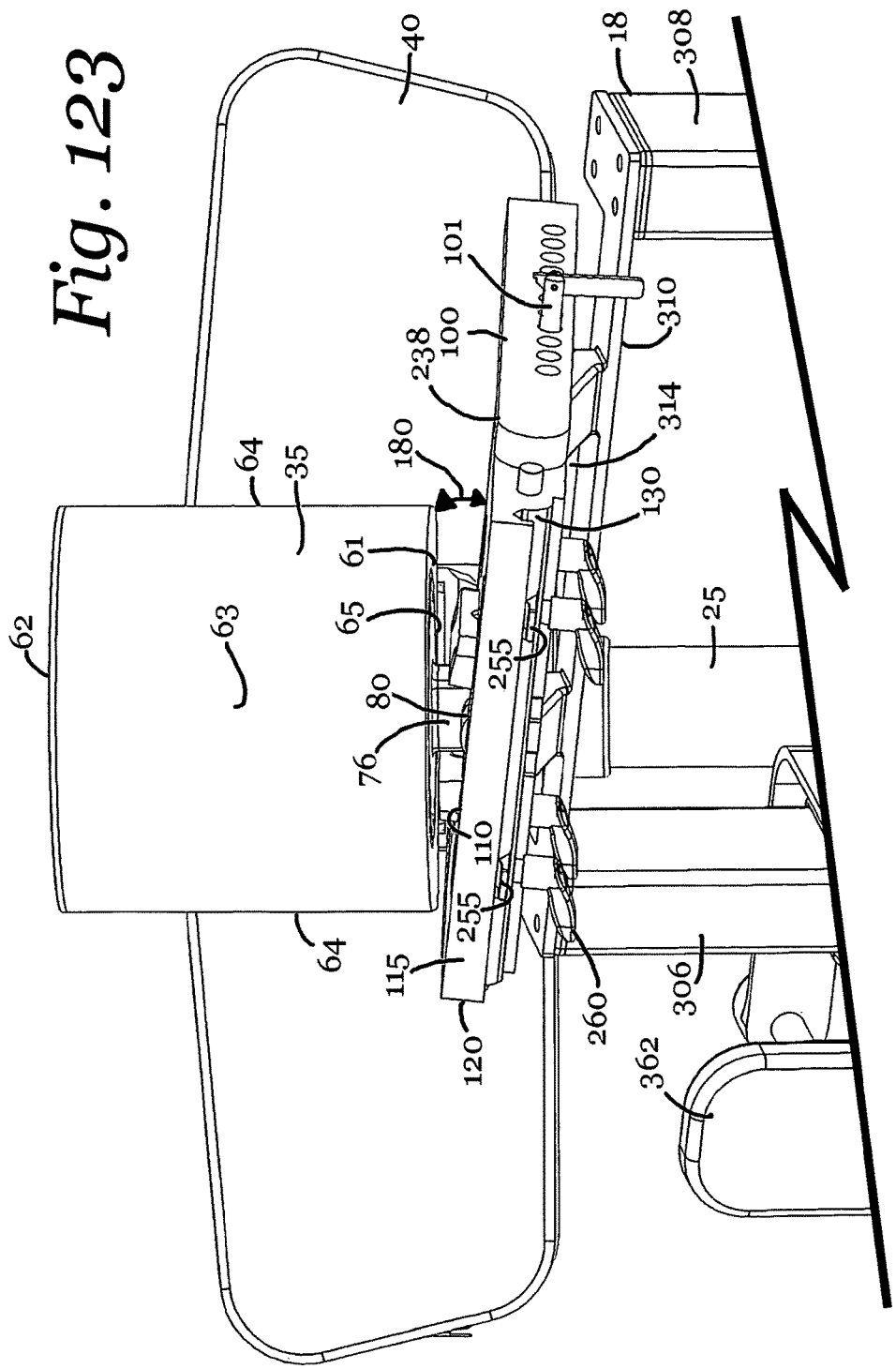

With reference to FIGS. 112 and 114, the vertical translation subassemblies 20 can be raised or upwardly telescoped, such as to raise the ends 18' 19' of the supine patient support structure 15'. While moving to the position shown in FIG. 114, the height of the surgical site D4 is maintainable by pivoting the hinges 376 downwardly.

Still revering to FIGS. 112 and 113, in some embodiments, the supine patient support structure 15' includes an in-frame translation compensation subassembly 320' that is substantially similar to the translation compensation subassembly 320 of the prone patient support structure 15. The in-frame translation compensation subassembly 320' includes a translation bar 322', which is most easily seen in FIG. 112, that is actively extended and retracted, or telescoped at the foot-end 304' of the frame 374. It is foreseen that in some embodiments the supine patient support structure 15' includes a translation compensation subassembly 320' that is located outside of the frame 374. It is foreseen that in some embodiments, the supine patient support structure 15' includes a translation compensation subassembly 320' such as but not limited to translation compensation structures and mechanisms described in U.S. Pat. Nos. 7,152,261, 7,343,635, 7,565,708, 8,060,960, or U.S. Patent Application No. 60/798,288, U.S. patent application Ser. No. 12/803,173, U.S. patent application Ser. No. 12/803,192, or U.S. patent application Ser. No. 13/317,012.

Sandwich-And-Roll Procedure

In some embodiments, such as but not limited to when performing various steps of a sandwich-and-roll procedure, such as is illustrated in FIGS. 85-101 and 134-169, the supine patient support structure 15' is spaced from and opposed to the frame 296 of the prone patient support structure 15. In these embodiments, both the prone and supine patient support structures 15 and 15' are attached to the base 10. When both the prone and supine patient support structures 15 and 15' are attached to the base 10, a patient can be reversibly sandwiched between the structures 15 and 15'. The space S between the prone and supine patient support structures 15 and 15' is adjustable. For example, in some embodiments, the space S can be modified by moving one of the patient support structures 15 or 15' away from, or toward, the opposed patient support structure. For example, a first T-pin 101 associated with a first end of the patient support structure 15 or 15' to be adjusted can be disconnected, such as described elsewhere herein, followed by moving the associated end of the patient support structure upwardly or downwardly a distance, and reconnecting the first T-pin 101; followed by disconnecting a second T-pin 101 associated with the second end of the patient support structure 15 or 15', adjusting the second end of the patient support structure the same distance as the first end, and then reconnecting the second T-pin 101.

Referring now to FIGS. 4-7, and as noted above, the patient positioning support structure 5 of the present invention includes a base 10 with a pair of spaced opposed vertical translation subassemblies 20 that are optionally joined by a cross-bar 25. The patient positioning support structure 5 is adapted such that the vertical translation subassemblies 20 are not substantially laterally movable with respect to one another during operation of the patient positioning support structure 5. The patient positioning support structure 5 also includes a prone patient support structure 15 removably attached to the base 10 by connection subassemblies 75 located at the head- and foot-ends 18, 19 of the prone patient support structure 15. The patient positioning support structure 15 includes a pair of spaced opposed gliding or sliding joints 326. The joints 326 each include a virtual pivot point 248, and arc of motion AOM and a radius r. The joints 326 are attached to hip-thigh pads 286 and are sized, shaped, configured and arranged to slidingly rotate at least a portion of the hip-thigh pads 286 about or around the virtual pivot point 248 and along the arc of motion AOM. Accordingly, the hips of a patient on the prone patient support structure 15 can be flexed and extended about the virtual pivot point 248, thereby enabling flexion and translation of the hips substantially without lateral translation of the patient's torso. The virtual pivot point 248 is associated with a selectable location or height for the surgical site, wherein the height of virtual pivot point 248 is spaced a first distance D1 above the floor F. As the prone patient support structure 15 is manipulated to place the patient in various positions, such as but not limited to flexed or articulated positions and additionally or alternatively Trendelenburg or reverse Trendelenburg positions, the patient positioning support structure 5 is adapted to substantially maintain the first distance D1.

Still referring to FIGS. 4-7, the patient positioning support system 5 includes a roll axis R, about which the prone patient support structure 15 can be tilted or rotated. When the supine patient support structure 15' is attached to the base 10, the supine patient support structure 15' can also be tilted or rotated about the roll axis R. The patient positioning support system 5 includes a pair of vertical translation axes V1 and V2, wherein each of the vertical translation axes V1 and V2 is associated with one of the vertical translation subassemblies 20. Additionally, the patient positioning support system 5 includes a pair of yaw axes Y1 and Y2 associated with the connection subassemblies 75. The yaw axes Y1 and Y2 allow for generally small amounts of rotation of the patient support structure 15 or 15' when the patient support structure 15 or 15' is placed in a Trendelenburg or reverse Trendelenburg position and also tilted about the roll axis R.

The prone patient support structure 15 includes a releasably attachable and lockable torso support structure 362 with a chest pad 368. The location of the chest pad 368 is slidably adjustable along a length of the prone patient support structure 15, as indicated by the straight double-headed arrow above the torso support 580 that is generally parallel with the roll axis R.

As shown in FIGS. 23-30, the patient positioning support system 5 is configured and arranged to move and place the patient support structure 15 or 15' in a reverse Trendelenburg position, such as but not limited to by outwardly telescoping the head-end vertical translation subassembly 20 and alternatively or additionally inwardly telescoping the foot-end vertical translation subassembly 20, such as is indicated by the upward and downward arrows, respectively. It is noted that D1 in FIG. 24 is substantially equal to D1 in FIG. 4. In FIG. 4, the roll axis R is substantially parallel with the floor F. However, in FIG. 24, the roll axis R sloped upwardly from the floor F, moving from left to right across the page. It is noted that when the patient support structure 15 is moved from the position of FIG. 4 to the position shown in FIG. 24, the distance between the virtual pivot point 248 and a point of the chest pad 368 does not change substantially. Also, in the configuration of FIG. 24, the patient support structure 15 had not substantially pivoted about either of the yaw axes Y1 or Y2. In the position shown in FIG. 24, the patient support structure 15 does pivot about the second and third pivot axes P2 and P3, which is most easily in FIGS. 24, 29 and 30, and is indicated by arrows 292 and 294.

FIGS. 31-38 show the patient positioning support structure in a Trendelenburg position. This positioning is achieved by telescoping the vertical translation subassemblies 20 in opposite directions from those associated with placing the patient positioning support structure in a reverse Trendelenburg position. It is noted that D1 of FIG. 32 is substantially equal to D1 of FIGS. 4 and 24.

FIGS. 39-47 illustrate the configuration of the patient positioning support structure 5 with the patient support structure 15 in a neutral position and the joints rotated such that the lower extremity support structure 344, or lower body support structure, is adjusted so as to flex the hips and knees of a patient thereon. Again, D1 of FIG. 40 is substantially equal to D1 of FIGS. 4, 24 and 32.

FIGS. 48-53 illustrate the patient positioning support structure 5 with the patient support structure 15 in a neutral position and the joints rotated such that the lower body support structure 344 is adjusted so as to flex the hips and knees of a patient thereon and also such that the patient support structure 15 is rolled or tilted about, or approximately, 25-degrees about, or around, the roll axis R. Such tilting can proved improved access to the surgical site. The patient support structure 15 can also be tilted when the legs are extended, such as is described elsewhere herein.

FIGS. 55-64 illustrate the patient positioning support structure 5 with the joints 326 rotated such that the lower body support structure 344 is adjusted so as to extend the hips and knees of a patient thereon. It is noted that the distance D1 of FIG. 56 is substantially equal to the distance D1 of FIGS. 4, 24, 32 and 40. To maintain the height D1 while extending the hips, the head-end vertical translator 20 is telescoped upwardly, so as to raise the head-end 18 of the patient support structure 15, and the foot-end vertical translator 20 is telescoped downwardly, so as to lower the foot-end 19 of the patient support structure 15. This changes the roll axis R to a position sloping upwardly, when viewed from the left to the right of the page. Additionally, articulation or rotation occurs about all three pitch axes, P1, P2 and P3.

Methods of Positioning a Patient on the Patient Positioning Support System

The present invention also provides a method of positioning a patient on a patient positioning support system 5 in a prone position, various steps of which are shown in FIGS. 134-169. In one embodiment the method includes a first step of placing a patient on a supine patient support 15' suspended above a floor F by a base structure 10, such that the patient is in a substantially supine position. In a second step, such as is shown in FIGS. 134-139 and 160-169, the patient is sandwiched between the supine patient support 15' and a prone patient support 15 suspended above the supine patient support 15'. Then, the patient is rolled an amount of about 180-degrees with respect to a longitudinally extending roll axis R, such that the patient is in a substantially prone position, such as to but not limited to as is shown in the sequence of FIGS. 134 through 136. After the patient has been transferred to the prone patient support structure 15, the supine patient support 15' is removable.

To roll the patient over, from the position shown in FIG. 134 to the position shown in FIG. 136, the motor or actuation system of the patient positioning support system 5 is disconnected or temporarily inactivated, such as but not limited to by disengaging a clutch, such as is known in the art, and such that a group of personnel can manually roll the patient over. After the patient had been rolled over, the clutch is re-engaged, such that the patient support structure 15 can be further positioned for the surgical procedure that is to be performed.

To return the patient to a supine position, the steps of the method are performed in reverse as was described above. Accordingly, the patient is again sandwiched between the prone and supine patient support structures 15 and 15', and rolled back over to a supine position on the supine patient support structure 15'. When the patient is on the supine patient support structure 15' the patient can be transferred to a gurney or other mobile support structure, or repositioned on the supine patient support structure 15' for a lateral-decubitus surgical procedure.

In a further embodiment, the step of sandwiching the patient between the supine patient support 15' and the prone patient support 15 includes attaching the prone patient support 15 to a pair of spaced opposed connection subassemblies 75, such as by ladders 100 attached to rotation subassemblies 50 associated with the base head-end 16 and foot-end 16'.

FIGS. 170-178 illustrate another embodiment 900 of a breaking supine lateral patient support 15' in another embodiment. As shown in FIG. 170, the patient support 900 includes head-end and foot-end portions 905 and 910 for supporting and positioning a patient in a supine position, such as described herein. The head-end portion 905 includes a frame portion 915 and a solid planar top structure, member or portion 920, or table top, non-removably attached thereto, as well as left and right side accessory attachment members 925. The foot-end portion 910 also includes a frame portion 930 and a solid planar top structure, member or portion 935, or table top, non-removably attached thereto, as well as left and right side accessory attachment members 940. The head end portion 905 is joined with the foot-end portion 910 by a pair of spaced apart opposed hinges, generally 376, such as are described herein. At each of its outboard ends 950, the patient support 900 includes an attachment structure for attachment to a ladder 100 or 100', such as is described elsewhere herein. At the foot outboard end 950, the foot-end frame portion 930 includes an in-line or in-frame, longitudinal translation compensation subassembly, generally 955, that is substantially similar to the translation compensation subassembly 320 described elsewhere herein. The patient support 900 is adapted to support the patient both supine or lateral positions. The patient support 900 includes a pair of space opposed hinges 376, such as is described elsewhere herein. The patient support 900 operates, angulates, breaks or articulates from 0° to about 40° hinge apex in an upward direction. The patient support 900 so as to support the patient when the hinges operate, angulate, break or articulate from 0° to 30° hinge apex in a downward direction. The patient support 900 includes attachment rails 925, 940 for Clark Sockets. The patient support 900 is adapted to function with a patient weight of up to 600-pounds. Additionally, the patient support 900 provides for translation compensation during hinge apex up and down positioning, such as by an in-frame translation compensation subassembly 320, such as is described elsewhere herein. Further, the patient support 900 includes attachment points for attachment to the base structure 10, such as is described above or as described herein.

FIGS. 179-187 illustrate a non-breaking or fixed frame patient support 1000, for supporting a patient in a non-angulated supine, prone or lateral positions. The patient support 1000 includes head-end and foot-end support portions 1005 and 1010. The patient support 1000 also includes a frame portion 1015 and a removably attached solid planar top structure, member or portion 1019, or table top. Reversibly engageable clamps 1020 removably or releasably attach the top structure 1019 to the frame portion 1015. The frame portion 1015 includes a pair of spaced spars 1021 joined at the respective head and foot ends 1022 and 1023, respectively, by head- and foot-end frame cross-members 1024 and 1025, respectively. As shown in FIG. 181, the foot-end frame cross-member 1025 is longer than the head-end cross-member 1024. Accordingly, the frame portion of the foot-end portion 1010 is wider than the frame portion 1015 of the head-end portion 1005. Each of the spars 1021 includes a transition portion 1026 that is contoured so as to curve, bend or bow outwardly when moving along a length of each of the spars 1021, such as along a central portion thereof, when moving along the spar 1021 in a direction from the head end toward the foot end thereof, as indicated by the directional arrow 1027. It is noted that the frame portion 1015 is non-breaking as it includes no hinges.

Each of the left-hand and right-hand sides of the frame portion 1015, of the head-end support portion 1005, includes at least one accessory attachment member 1030, for attachment of accessories for supporting limbs of the patient, such as is known in the art.

At each of its outboard ends 1050, the patient support 1000 includes an attachment structure 1053 for reversible attachment to a ladder 100 or 100', such as is described elsewhere herein. It is foreseen that the ladders 100 or 100' may be integral, and therefore non-removable, with the attachment structures 1053 at one or both of the outboard ends 1050. Alternatively, the attachment structure 1053 may be configured substantially similarly to the attachment structure 314, 316 described above. It is foreseen that in other patient supports described herein, the ladder and the attachment structure may also be integral or non-detachable. At the foot outboard end 1050, the frame portion 1015 includes an in-line or in-frame, longitudinal translation compensation subassembly, generally 1055, that is substantially similar to the translation compensation subassembly 320 described elsewhere herein.

The patient support 1000 is adapted to function or operate with a patient weight up to about 600-pounds. Removable flat tops 1019 are incorporated into the patient support 1000. The patient support 1000 is adapted to provide for supine patient positioning and for prone patient positioning. The patient support 1000 is adapted for attachment of an adjustable chest support structure. The patient support 1000 is adapted for attachment of adjustable pelvic support structures, such as are known in the art. The patient support 1000 is adapted for attachment of adjustable leg supports, such as are known in the art. The flat tops 1019 include rails 1030 for Clark Socket attachments. The patient support 1000 includes attachment points for attachment to the base structure 10, such as at the outboard ends 1050.

FIGS. 188-196 illustrate yet another embodiment 1100 of a breaking supine lateral patient support 15' in another embodiment. As shown in FIG. 188, the patient support 1100 includes head-end and foot-end portions 1105 and 1110 for supporting and positioning a patient in a supine position, such as described herein. The head-end portion 1105 includes a frame portion 1115 and a solid planar top structure, member or portion 1120, or table top, removably attached thereto by reversibly actuatable clamps 1121, as well as left and right side accessory attachment members 1125. The foot-end portion 1110 also includes a frame portion 1130 and a solid planar top structure, member or portion 1135, or table top, removably attached thereto by additional reversibly actuatable clamps 1121, as well as left and right side accessory attachment members 1140. It is noted that in this embodiment, the top structures 1120 and 1135 rest or are attached on top of the respective frame portions 1115 and 1130, and are substantially wider than the respective frame portions 1115 and 1130, such that the hinges are at least partially covered by the frame portions 1115 and 1130. It is foreseen that the top structures 1120 and 1135 may be wider than is shown, so as to support larger than average patients.

The head end portion 1105 is joined with the foot-end portion 1110 by a pair of spaced apart opposed hinges, generally 1145, such as are described herein. At each of its outboard ends 1150, the patient support 1100 includes an attachment structure for attachment to a ladder 100 or 100', such as is described elsewhere herein. At the foot outboard end 1150, the foot-end frame portion 1130 includes an in-line or in-frame, longitudinal translation compensation subassembly, generally 1155, that is substantially similar to the translation compensation subassembly 305 described elsewhere herein.

FIGS. 197-205 illustrate another embodiment of a prone patient support 1200 that is substantially similar to the prone patient support 15 described above. Accordingly, this prone patient support 1200 is numbered the same way as the first prone patient support 15. In this embodiment, the phone patient support 1200 includes modified joints 326, or hinges, and hip-thigh pads 286. In particular, the joints 326 include a motor subassembly 1205 that is moved to an outer side 1210 of the frame 296. This contrasts with the motor subassemblies 333 of the first prone patient support 15, most easily seen in FIGS. 75 and 78, wherein each motor subassembly 333 is located on the inner side of the joints 326 or the frame 296, so as to be located under the respective hip-thigh pads 286. With respect to the hip-thigh pads 286, in addition to being contoured to fit the patient's pelvic region closely while allowing the patient's belly to depend between the joints 326, as is the case with the first prone patient support 15, each hip-thigh pad 286 includes a small forward hip pad 286a. The forward hip pad 286a provides additional support to the patient's pelvis and protects the patient from the forward end of the joint subassembly. Additionally, the hip-thigh pads 286 and the forward hip pads 286a comprise a patient pelvis support assembly that is adapted to position or extend the patient's pelvis at an angle from between about 0° and about 25° under power. Patient chest or torso support 362 is manually adjustable along a length of the frame 296, such as is described elsewhere herein. As described herein, the chest support 362 is manually lockable in place along a length of the frame head-end portion 302, so as to substantially prevent movement along an axis parallel to the patient's centerline, or with respect to the roll axis R. The prone patient support 15 or 1200 is constructed of resilient and strong materials such that a patient weighing up to 600-pound can be safely supported, positioned for a surgical procedure and rolled between prone and supine positions, such as is described above. It is noted that the foot-end portion of the frame 296 is wider than the head-end portion of the frame 296, so as to accommodate the lower extremity support structure 344 between the spars 310, 312 thereof.

The prone patient support 1200 includes attachment subassemblies 314, 316 for attachment to the base structure 10, such as is describe above with respect to the prone patient support 15.

The prone patient support 1200 provides for attachment of an adjustable chest support structure 362, such as is described above.

The patient's lower limbs are supported in a fixed position relative to the patient's pelvis, such as is described above. The prone patient support 1200 provides support to shins and feet during both flexion and extension of patient's hips, such as is described above with respect to the first prone patient support 15. Further, the prone patient support 1200 allows the patient pelvis to rotate about a fixed, virtual axis during flexion and extension, such as pivot axis P1.

FIGS. 206-239 illustrate another patient positioning and support system, generally 5, for supporting and positioning a patient for a surgical procedure, including an off-set base 1310 and a patient support structure 15°. In particular, the off-set base 1310 is sized, shaped, configured and adapted for suspending none, one or both of a prone patient support structure 15 and a supine patient support structure 15' above the floor F at a convenient position and orientation for a medical procedure. It is noted that the off-set base 1310 is similar to the base 10, the description of which is incorporated herein by reference.

The off-set base 1310 includes head and foot-ends 16, 16', left and right-hand sides, and top and bottom sides, which for discussion purposes are denoted relative to the sides of a patient's body when the patient is positioned in a prone position on the prone patient support structure 15. The base 1310 also includes a plurality of axes, including but not limited to a roll axis R, a pitch axis $P_E$, and two vertical translation axes V1°, and V2°, which are most easily seen in FIGS. 206, 207, 212-219, 228 and 230, and are discussed in greater detail below. The patient support structures 15 and 15' each include head and foot ends 18, 18' and 19, 19', respectively, and first, second and third pitch axes which are denoted by P1, P2 and P3 respectively.

FIG. 206 is a perspective view of an off-set base 1310 of the present invention, in an exemplary embodiment. The off-set base 1310 may also be referred to as a base structure or base subassembly. The base 1310 is adapted to support the patient support structure 15° above the floor F. The base 1310 includes structure that is adapted to lift and lower, tilt, roll, rotate and, additionally or alternatively, angulate at least a portion of the patient support structure 15° relative to the floor F, so as to position a patient's body in a desired position for a medical procedure, such as is described in greater detail below. In various embodiments, the movements of the patient positioning support system 5, with respect to the head and foot-ends, left and right-hand sides, and top and bottom sides, as well as with respect to the axes can be one or more of synchronous or sequential, active or passive, powered or non-powered, mechanically linked or synchronized by software, and continuous, such as but not limited to within a range, or incremental, and such as is described in greater detail below.

The base 1310 includes a pair of spaced opposed vertical translation subassemblies 20, also referred to as vertical elevator assemblies, telescoping piers, vertical translators, or the like. In the illustrated embodiment, the vertical translation subassemblies 20 are generally identical and face one another, though it is foreseen that the base 1310 may include only a single vertical translation subassembly 20 and that one or both vertical translation subassemblies 20 may have an alternative structure. For example, one of the vertical translation subassemblies 20 may be constructed such as described in U.S. Pat. Nos. 7,152,261, 7,343,635, 7,565,708, 8,060,960, or U.S. Patent Application No. 60/798,288, U.S. patent application Ser. No. 12/803,173, U.S. patent application Ser. No. 12/803,192, or U.S. patent application Ser. No. 13/317,012, all of which are incorporated by reference herein in their entireties.

In the illustrated embodiment, the cross-bar 25 is a substantially rigid support that joins and holds the vertical translation subassemblies 20 in spaced opposed relation to one another. In a further embodiment, the cross-bar 25 is non-adjustable. However, in some other embodiments, the cross-bar 25 is removable or telescoping, so that the vertical translation subassemblies 20 can be moved closer together, such as for storage. In certain embodiments, the cross-bar 25 is longitudinally adjustable so that the vertical translation subassemblies 20 can be moved closer together or farther apart, such as, for example, to support or hold different patient support structures 15° of various lengths or configurations, such as but not limited to interchangeable or modular patient support structures 15°. In certain other embodiments, there patient positioning support system 5 does not include a cross-bar 25. Numerous cross-bar 25 variations are foreseen.

Regardless of the presence or absence of any such cross-bar 25 described herein or foreseen, the vertical translation subassemblies 20 are substantially laterally non-movable with respect to one another, either closer together or farther apart, once a patient support structure 15° has been attached to or joined with the base 1310, and during use of the patient positioning support system 5.

Referring again to FIGS. 206, 212-219, a vertical translation subassembly 20 of the present invention includes lower and upper portions, generally 30 and 35 respectively, a lower support structure 40, such as a base portion or a foot, and an off-set elevator subassembly 1341 extending therefrom.

The off-set elevator subassembly 1341 extends upwardly from a first end 1342 of the lower support structure 40 and includes at least a primary elevator portion 1343 and optionally a secondary elevator portion 1344. The second end 1342' of the lower support structure 40 extends from the first end 1342 so as to be parallel with the floor F and perpendicular to the roll axis R. The size of the second end 1342', such as but not limited to the length, width, height and weight of the second end 1342', is sufficient to counterbalance the first end 1342 and an attached patient support 15°, so as to substantially prevent collapse of the patient positioning and support system 5. Additionally, as shown in FIG. 206, the off-set elevator subassemblies 1341 are spaced and opposed to one another so as to be located on opposite sides of the roll axis R relative to one another, so as to substantially prevent collapse of the patient positioning and support system 5.

The primary elevator portion 1343 includes a primary vertical translation axis V1° and riser assembly 45 with a mechanical drive system or mechanism (not shown), such as is known in the art, that lifts and lowers the upper portion 35 along the primary vertical translation axis V1° relative to the floor F. Movement of the primary elevator portion 1343 is controlled by a computer (not shown) so as to be synchronized with movements of other portions or components of the patient positioning and support system 5.

The secondary elevator portion 1344 includes a secondary vertical translation axis V2° and a mechanical drive system or mechanism (not shown), such as is known in the art that lifts and lowers an attached rotation subassembly 50, described below, along the secondary vertical translation axis V2° relative to the floor F. Movement of the secondary elevator portion 1344 is controlled by a computer (not shown) so as to be synchronized with movements of other portions or components of the patient positioning and support system 5.

It is noted that, since the primary elevator portion 1343 raises and lowers the secondary elevator portion 1344, the primary elevator portion 1343 also raises and lowers the rotation subassembly 50. It is foreseen that in some embodiments, there is no secondary elevator portion 1344 and the primary elevator portion 1343 lifts and lowers the rotation subassembly 50 directly.

In addition to rolling an attached patient support structure 15° about the roll axis R, such as is described above, the rotation subassembly 50 of the base 1310 enables tilting of the patient support structure 15° about the pitch axis $P_E$, such as is described below. Movement about each of the axes R and $P_E$, is associated with a rotation motor. Accordingly, the rotation subassembly 50 includes first and second mechanical rotation motors 55 and 55' joined with first and second rotation shafts 56 and 56', respectively.

A first rotation motor subassembly includes the first motor and shaft 55, 56, which are associated with the roll axis R and provide for tilting and rolling of an attached patient support structure 15° about the roll axis R. It is noted that the first shaft 56 is coaxial with the roll axis R.

A second rotation motor subassembly includes the second motor and shaft 55', 56', which are associated with the pitch axis $P_E$ and provide for angulating or articulating an attached patient support structure 15° about the pitch axis $P_E$. It is noted that the second shaft 56' is coaxial with the pitch axis $P_E$, perpendicular to the roll axis R and substantially parallel with the floor F. The second shaft 56' is operably joins the first shaft 56 with the secondary elevator portion 1344, so as to rotate the first shaft 56 about the pitch axis $P_E$, thereby moving the first shaft 56, and the associated roll axis R, to an orientation that is non-parallel with, or angulated with respect to, the floor F. Accordingly, the roll axis R to can be moved from a first position or orientation that is substantially parallel with the floor F, such as is shown in FIG. 220, to a second portion or orientation that is not substantially parallel with the floor F, such as is shown in FIGS. 228 and 230, such as when the patient support structure 15° is placed in a Trendelenburg or a reverse Trendelenburg position.

The motors 55, 55' may be any motor known in the art that is strong enough to rotate the patient support structure 15° with respect to the roll axis R and pitch axes $P_E$, and optionally to lock the patient support structure 15° in a tilted or angulated orientation with respect to the floor F. Harmonic motors are particularly useful as the rotation motor due to their strength. Alternatively, the rotation subassembly 50 may be constructed such as described in U.S. Pat. Nos. 7,152,261, 7,343,635, 7,565,708, 8,060,960, or U.S. Patent Application No. 60/798,288, U.S. patent application Ser. No. 12/803,173, U.S. patent application Ser. No. 12/803,192, or U.S. patent application Ser. No. 13/317,012, all of which are incorporated by reference herein in their entireties. Numerous variations are foreseen. Non-motorized rotation subassemblies 50 are also foreseen.

The base 1310 includes a pair of connection subassemblies 57, for reversible attachment with a patient support structure 15°. Each connection subassembly 57 includes a rotation block 57, a ladder 100 and a T-pin 101. The rotation block 57, also referred to as a ladder connection block 57, is reversibly attachable or connectable to at least one ladder structure 100, which in turn is reversibly attachable to an end of the patient support structure 15°. The connection subassemblies 57 provide structure for removably connecting, attaching or joining the base 10 with a patient support structure 15°. In the illustrated embodiment, the head-end and foot-end rotation blocks 57 are substantially identical; however, it is foreseen that one or both of the blocks 57 may have an alternative size, shape and additional or alternative configuration.

The connection subassemblies 57 provide structure for at least some vertical translation, or height adjustment, of an attached patient support structure 15°. Further, the two connection subassemblies 57 cooperate with each other and optionally with the patient support structure 15° to provide structure for a fail-safe structure or mechanism that blocks incorrect detachment of an attached patient support structure 15°, wherein such incorrect detachment can result in catastrophic collapse of at least a portion of the patient positioning support system 5 and patient injury.

Each rotation block 57 is attached to or joined with the first rotation shaft 56, wherein the first rotation shaft is substantially coaxial with the roll axis R. The rotation shafts 56 of the opposed vertical translation subassemblies 20 are rotated in synchronization, toward either the left-hand side or right-hand side of the patient positioning support system 5 and also at the same speed. Each of the rotation shafts 56 rotates an attached block 57 clockwise or counter-clockwise, which in turn rotate a pair of attached ladders 100 about the roll axis R. As the ladders 100 rotated in unison, they cooperatively rotate a patient support structure 15° that is attached therebetween.

It is noted that in the illustrated embodiment, the ladders 100 may be provided in one of two lengths, a standard length ladder and non-standard length ladder, wherein the non-standard length ladder includes an extended length, or a length greater than that of the standard length ladder. It is foreseen that ladders 100 of other, non-standard lengths can be provided. In the illustrated embodiment, pairs of matched ladders 100, or two ladders 100 having substantially the same length, are attached to the opposed rotation blocks 57. It is foreseen that miss-matched pairs of ladders 100 could be attached to the rotation blocks 57.

Prior to reversibly or releasably connecting, joining or attaching a patient support structure 15° to the base 1310, a pair of ladders 100 must be attached to the base 1310.

It is noted that a pair of opposed ladders 100 or 100' attached to the respective vertical translation subassemblies 20 provide a fail-safe mechanism that prevents improper disconnection of an attached or engaged patient support structure 15° from the base 1310. This fail-safe mechanism includes two components. First, the ladders 100 cannot be disconnected from the base 1310 unless no patient support structure 15° is attached thereto. Second, the ladders 100 must be disconnected or removed from the base 1310 by tilting the ladder ends farthest from the attached rotation block 57 in an inboard direction, before the respective ladder upper ends can be disconnected or disengaged from the rotation block 57. Other fail-safe mechanisms, structures or subassemblies are foreseen.

With reference to FIGS. 207, 219 and 222, it is noted that the patient positioning support system 5 is adapted, configured and arranged for reversible attachment of up to two ladders 100, such as upper and lower ladders, to each rotation block 57. Accordingly, two such ladders 100 attached to a single rotation block 57 are substantially vertically opposed to one another and also co-planar with one another. In contrast, a pair of ladders 100 attached to the two opposed rotation blocks 57 at either end of the base 10, are substantially opposed to and parallel with one another. When the ladder 100 is attached to the block 57, a plane that runs parallel with and through the ladder is substantially perpendicular to the floor F. Alternative configurations are foreseen.

In some embodiments, the rotation block 57 is sized, shaped and configured such that when two ladders 100 attached thereto, their upper or connection ends kiss or contact one another. It is foreseen that, in some embodiments, the upper ends may not contact one another.

Attaching two ladders 100 to each of the rotation blocks 57 of the patient positioning support system 5 enables attachment of two patient support structures, such as for example a prone patient support structure 15 and a supine patient support structure 15'. For example, a patient can be positioned on a first of two patient support structures 15°, such as for a first surgical procedure, and then transferred to the second of the two patient support structures 15°, such as for performing a second surgical procedure with the patient in a different body position. Such transferring of a patient between the two patient support structures 15, 15' can be performed in numerous ways, including but not limited to a sandwich-and-roll procedure, such as is described below.

The ladders 100 are sized, shaped, configured and arranged for attachment to a patient support structure 15° in addition to the base 1310.

The roll axis R extends longitudinally along a length of the base 1310 such that, when the upper portions 35 are located substantially equidistant from the floor F, such as is shown in FIG. 220, the roll axis R is substantially coaxial with the upper portion rotation shafts 56. In another example, when the upper portions 35 are not equidistant from the floor F, such as is shown in FIGS. 228 and 330, the roll axis R is still coaxial with the first rotation shafts 56 but is also positioned at an angle with respect to the floor F.

The base 1310 is adapted to tilt, roll, turn over, or rotate the patient support structure 15° about or around the roll axis R. The patient support structure 15° can be reversibly rolled or tilted an amount or distance of between about 1-degree and about 237-degrees, such as relative to a plane intersecting the roll axis R wherein the plane is parallel with the floor F, or such as relative to a starting position associated with a plane parallel with the floor F, wherein the plan intersects with the roll axis R. For example, in some embodiments, the patient support structure 15° may be tilted a distance of about 5-degrees, about 10-degrees, about 15-degrees, about 20-degrees, about 25-degrees, about 30-degrees, about 35-degrees, or about 40-degrees about the roll axis R, relative to a starting position associated with a plane parallel with the floor F, wherein the plane intersects with the roll axis R, such as but not limited to so as to provide improved access to a surgical site. In a further embodiment, the patient support structure 15° may be tilted a distance of about 45, 50, 55, 60, 65, 70, 75, 80, 85, 90, 95 or 100-degrees about the roll axis R, relative to a starting position associated with a plane parallel with the floor wherein the plane intersects with the roll axis R. In some embodiments, the patient support structure 15° may be tilted a distance of about 110, 115, 120, 125, 130, 135, 140, 145, 150, 155, 160, 165, 170, 175 or 180-degrees about the roll axis R, relative to a starting position associated with a plane parallel with the floor F, wherein the plane intersects with the roll axis R. In some embodiments, the patient support structure 15° may be rolled a distance of more than 180-degrees about the roll axis R, relative to a starting position associated with a plane parallel with the floor F, wherein the plane intersects with the roll axis R. In some embodiment, the patient support structure 15° can be rolled clockwise or counter-clockwise, or toward either the left-hand or the right-hand side with respect to the roll axis R.

As is discussed elsewhere herein, the supine patient support structure 15' can also be reversibly tilted or rolled about the roll axis R, either alternatively to or additionally with the prone patient support structure 15.

In some embodiments, the patient positioning support system 5 is configured and arranged to roll the prone and supine patient support structures 15, 15' a full 237-degrees about the roll axis R in at least one direction, so as to return to the orientation shown in FIG. 91A.

In other embodiments, the base 1310 is adapted to roll the patient support structures 15° backwards, or in a reverse direction, about the roll axis R, so as to be rolled a suitable distance, so as to position the patient in an orientation associated therewith, such as but not limited to the positions shown in FIGS. 91A through 95.

Each vertical translation subassembly 20 includes a vertical translation axis associated with each of the primary and secondary elevator portions 1343 and 1344, respectively, which are denoted by V1° and V2°. Vertical translation or movement, of at least a portion of the patient positioning support apparatus 5 may occur along one or both of the vertical axes V1° and V2°, including at one or both of the base head and foot ends 16, 16'. For example, the primary elevator 1343 raises and lowers the associated upper portion 35 and the secondary elevator portion 1344 along the first vertical axis V1°. Similarly, the secondary elevator portion 1344 raises and lowers the rotation assembly 50 along the second vertical axis V2°. Such vertical translation may be synchronous or asynchronous, and is controlled by a computer (not shown) and associated software.

Each vertical translation subassembly 20 includes maximum and minimum vertical translation or lift distances. The maximum lift distance is associated with the maximum amount, most or highest the rotation subassembly 50 can be raised or upwardly lifted, such as is shown in FIG. 234. The minimum lift distance is the minimum amount, least, farthest downward, or the lowest the rotation subassembly 50 can be moved downwardly or lowered, such as is shown in FIG. 221.

The vertical translation subassemblies 20 are sized, shaped, arranged, configured, or adapted to vertically move, translate, or lift and lower the rotation subassembly 50, and therefore an attached end of a patient support structure 15°, between the maximum and minimum lift positions. In some embodiments, this vertical translation is incremental. For example, the vertical translation subassembly 20 may include a ratchet mechanism that controls the intervals of lift, and an operator must select a number of discreet intervals for the upper portion 35 to be moved. In other embodiments, this vertical translation is non-incremental, or continuous, between the maximum and minimum lift positions or distances. For example, the vertical translation subassembly 20 may include a screw-drive mechanism that smoothly lifts and lowers the upper portion 35 an amount determined by an operator, wherein this amount of movement determined includes no discreet intervals or distances.

Depending upon the desired positioning of the patient, the vertical translation subassemblies 20 can be moved in the same direction or in opposite directions. Further, the vertical translation subassemblies 20 can translate their respective upper portions 35 the same distance or different distances. In yet another example, both of the vertical translation subassemblies 20 are positionable at substantially equally raised positions, relative to their respective vertical translation axis $V1°$ and $V2°$ and the floor F, and wherein the raised positions are between the fully open and fully closed positions. When in this position, the roll axis R is substantially parallel with the floor F.

In the embodiment shown in FIG. 220, the secondary elevators 1344 of both the head-end 18 and foot-end 19 vertical translation subassemblies 20 have been fully raised to their maximum height and the primary elevators 1343 have been slightly raised a substantially similar amount, such that the rotation subassemblies are spaced substantially the same height relative to the floor F. Additionally, in the embodiment shown in FIG. 220, the supine patient support structure 15' is raised as high as possible, relative to the floor F. In the embodiment shown in FIG. 221, both the primary and secondary elevators 1343 and 1344 of the head-end and foot-end vertical translation subassemblies 20 have been fully lowered such that the supine patient support structure 15' is lowered close to the floor F and parallel with the floor F. In yet another example, both of the vertical translation subassemblies 20 are positionable at substantially unequally raised positions, relative to their respective vertical translation axis $V1°$ and $V2°$ and the floor F, and wherein the raised positions are between the fully open and fully closed positions. When in this position, the roll axis R is not substantially parallel with the floor F.

In the embodiment shown in FIG. 222, the prone and supine patient support structures 15 and 15' are attached to the base 1310 and positioned for a sandwich-and-roll procedure, such as described elsewhere herein. In the illustrated embodiment, the head-end and foot-end the primary elevator portions 1343 of both vertical translation subassemblies 20 have both been fully lowered, and the secondary elevator portions 1344 have been lowered to an intermediate location such that the rotation subassemblies 50 are spaced approximately equal distances from the floor F. Accordingly, both the prone and supine patient support structures 15 and 15' are substantially parallel with the floor F.

FIGS. 223-224 illustrate and embodiment in which both of the vertical translation subassemblies 20 are actuated so as to raise the supine patient support structure 15' such that the structure 15' is substantially parallel with the floor F. As shown in FIG. 223, the supine patient support structure 15' is rotated or rolled about the roll axis R toward the left-hand side of the 298 of the supine patient support structure 15'. In contrast, FIG. 224 shows the supine patient support structure 15' rotated or rolled about the roll axis R toward the right-hand side of the 300 of the supine patient support structure 15'. It is noted that in the embodiments shown in FIGS. 223-224, there is no rotational movement about the first, second or third pitch axes P1, P2 and P3, respectively, nor about the head-end and foot-end pitch axes PE, which are associated with the second rotation shafts 56 and 56', however there is rotational movement about the roll axis R.

FIG. 225 shows both of the primary and secondary elevators 1343 and 1344 of both of the vertical translation subassemblies 20 lowered and the supine patient support structure 15' broken upwardly or pivoted in a counter-clockwise direction about the first pitch axis P1, as indicated by arrow 284, at the spaced opposed hinges 376. It is noted that FIG. 225 shows the vertical translation subassemblies 20 not moved closer together than in other embodiments of the off-axis base 1310, and the translation bar 322 extended out of the translation compensation subassembly 320 so as to compensate for the increased overall length of the supine patient support structure 15'. FIG. 255 also shows rotational movement associated with the second and third pitch axes P2 and P3, as indicated by arrows 292 and 294, respectively.

In the embodiment shown in FIG. 226, both of the vertical translation subassemblies 20 are maximally raised. Additionally, the supine patient support structure 15' is broken downwardly or such that counter-clockwise rotational movement has occurred about the first pitch axis P1, as indicated by the arrow 284, at the spaced opposed hinges 376. FIG. 226 illustrates counter-clockwise rotational movement at the second axis P2, as indicated by arrow 292, and clockwise rotational movement at the third axis P3, as indicated by arrow 294, such as is described above.

FIG. 227 illustrates another embodiment, wherein in addition to being upwardly broken in a manner similar to that shown in FIG. 225, the supine patient support structure 15' is rolled about the roll axis R toward the left-hand side 298 of the system 5. FIG. 227 further illustrates counter-clockwise rotational movement at the second axis P2, as indicated by arrow 292, and clockwise rotational movement at the third axis P3, as indicated by arrow 294, such as is described above.

Additionally or alternatively, the vertical translation subassemblies 20 are movable in opposite directions, and additionally or alternatively, positionable at different heights. For example, the vertical translation subassemblies 20 can be moved and placed such that one of the upper portions 35 is located farther from the floor F, or higher than, the opposed upper portion 35. For example, FIG. 330 shows the upper portion 35 joined with a head-end of the attached supine patient support structure 15' is fully opened, and the upper portion 35 joined with a foot-end of the supine patient support structure 15' is closed, such that supine patient support structure 15' is positioned in a reverse Trendelenburg position. In this example, the upper portions 23 do not both intersect a single plane running parallel with the floor F; or the upper portions 23 are non-parallel with one another, relative to the floor F.

The vertical translation subassemblies 20 can be operated singly or together, and synchronously or asynchronously. For example, one of the vertical translation subassemblies 20 may be telescoped, or moved, while the opposed vertical translation subassembly 20 is not telescoped or moved, or is held immobile. In another example, both of the vertical translation subassemblies 20 may be moved in the same or opposite directions at the same time. Numerous variations are foreseen.

Operation of the vertical translation subassemblies 20 is generally coordinated and controlled electronically, or synchronized, such as by a computer system that interacts with one or more motion sensors (not shown) associated with various parts of the patient positioning support system 5 and the motorized drives, such as is known in the art. However, it is foreseen that one or more portions or subsystems of the vertical translation subassemblies 20 may be operated manually. Further, in some circumstances, the electronic control of the patient positioning support system 5, or the drive system, can be turned off, or at least temporarily disconnected, so that one or more portions of the patient positioning support system 5 can be moved manually. For example, during a sandwich-and-roll procedure, such as is described elsewhere herein, at least the step of rolling the patient over is usually performed manually by two, three or preferably four or more operators or medical staff, after the drive system, or a clutch, has been temporarily disconnected or released, so as to ensure that the patient is not injured during the procedure. After the roll is completed, the clutch is re-engaged, so that the patient positioning support system 5 can mechanically perform additional movement and positioning of the patient.

FIG. 228 illustrates an embodiment wherein the head-end vertical translation subassembly 20 is lowered to a closed position, and the foot-end vertical translation subassembly 20 is fully opened, such that the supine patient support structure 15' is in a Trendelenburg position. To place the supine patient support structure 15' in the Trendelenburg position shown, the second rotation shafts 56' of the rotation subassemblies 50 have been actuated to cause rotation about axis PE. With respect to the orientation of the system 5 shown in FIG. 228, rotation about the foot-end axis PE, the clockwise rotation is shown, as indicated by arrow 1312. Similarly, the rotation about the head-end axis PE, the clockwise rotation is also shown, as indicated by arrow 1313. It is noted that in the embodiment shown in FIG. 228, there is no rotational movement with respect to the first, second or third rotational axes, P1, P2 and P3 respectively.

In the embodiment shown in FIG. 229, the supine patient support structure 15' is in the Trendelenburg position of FIG. 228 and also rolled toward the left-hand side 298 of the system 5 about the roll axis R.

FIG. 230 illustrates an embodiment in which the supine patient support structure 15' is positioned in a reverse Trendelenburg position by lowering the foot end 19' and raising the head end 18'. In this embodiment, counter-clockwise rotational movement about the foot-end and head-end pitch axes PE is illustrated by arrows 1312 and 1313 respectively. Further, there is no rotational movement with respect to the first, second or third rotational axes, P1, P2 and P3 respectively, or the roll axis R.

In FIG. 231, the supine patient support structure 15' has been positioned in the reverse Trendelenburg position of FIG. 230 and also rolled about the roll axis R toward the right-side 300 of the system 5. It is noted that in the embodiments of FIGS. 230 and 231, the translation compensation subassembly 230 has been actuated to increase the length of the supine patient support structure 15'.

FIGS. 235-239 show positioning of a prone patient support structure 15, such as that described above, attached to or joined with an off-set base 1310 of the illustrated invention.

FIG. 232 illustrates an embodiment wherein the primary elevator portions 1343 of the vertical translation subassemblies 20 are substantially fully lowered and the secondary elevator portions 1344 are partially lowered, such that the roll axis R is substantially parallel with the floor F. Further, there is no rotational movement with respect to the axes PE, P1, P2, P3 or R.

FIG. 233 illustrates an embodiment similar to the embodiment shown in FIG. 232, except that the vertical translation subassemblies 20 have been partially opened or raised, so as to raise the prone patient support structure 15 relative to the floor F. In particular, the secondary elevator portions 1344 have been fully raised and the primary elevator portions 1343 have been partially opened. In the embodiment shown in FIG. 233, there is no rotational movement with respect to the axes PE, P1, P2, P3 or R.

FIG. 234 illustrates a further embodiment similar to the embodiments shown in FIGS. 232 and 233, except that the vertical translation subassemblies 20 have been fully opened or raised, so as to raise the prone patient support structure 15 as high as possible relative to the floor F. In particular, both the primary and secondary elevator portions 1343, 1344 have been fully raised. In the embodiment shown in FIG. 234, there is no rotational movement with respect to the axes PE, P1, P2, P3 or R.

FIG. 235 illustrates an embodiment of the prone patient support structure 15 positioned so as to flex a patient's spine or hips. As shown in FIG. 235, the joints 326 have been actuated so as to produce counter-clockwise rotation about the first pitch axis P1, as indicated by the arrow 284, whereby the lower extremity support structure 344 is rotated downward, and knee hinges 350 are actuated so as to bend the patient's knees, such as is described above. In this embodiment, there is no rotational movement with respect to the axes PE, P2, P3 or R.

FIG. 236 illustrates an embodiment of the prone patient support structure 15 positioned so as to extend a patient's spine or hips. As shown in FIG. 236, the joints 326 have been actuated so as to produce clockwise rotation about the first pitch axis P1, as indicated by the arrow 284, whereby the lower extremity support structure 344 is rotated upward, and knee hinges 350 are actuated so as to straighten the patient's knees, such as is described above. To maintain the virtual pivot points 248 at the same height as is shown in FIG. 235, the head-end 18 of the patient support structure 15 is raised and the foot-end 19 is lowered. In the illustrated embodiment, since there is no rotation about the second and third pitch axes P2, P3, there must be rotational movement about the head-end and foot-end pitch axes PE of the base 1310, such as is described above. Namely, as shown in FIG. 236 and with respect to the orientation of the system 5 depicted in FIG. 236, the rotational movement about the axes PE is counter-clockwise, as is indicated by arrows 1312 and 1313.

FIG. 237 illustrates another embodiment of the prone patient support structure 15 positioned so as to extend a patient's spine or hips, similar to that shown in FIG. 237. In this embodiment, the patient support structure 15 is positioned in the same orientation or configuration as shown in FIG. 236. However the base 1310 is positioned as is shown in FIG. 235. As a result, there is no rotational movement with respect to the axes PE, P2, P3 or R, which causes the lower extremity support structure 344 to be extended upwardly from the floor F.

It is noted that in the embodiments shown in FIGS. 233 and 235-237 the distances D1 and D2 are not changed between embodiments, similar to that which is described above.

FIGS. 238-239 illustrate embodiments similar to that shown in FIG. 233, except that FIG. 238 illustrates rotational movement about the roll axis R toward the left-hand side 298 of the system 5, and FIG. 239 illustrates rotational movement about the roll axis R toward the right-hand side 300 of the system 5.

It is foreseen that, when joined or attached to the off-set base 1310, the prone and supine patient support structures 15 and 15' may be placed in many additional positions, configurations or orientations than are depicted herein in the figures.

FIGS. 240-254 illustrate another embodiment of an off-set base 1410 for supporting a prone or supine patient support structure 15, 15'. The base 1410 is substantially similar to the base 1310, and is therefore numbered in the same manner as the base 1310. Accordingly, the description of the base 1310 is incorporated herein by reference.

The second off-set base 1410 differs from the first off-set base 1310, described above, in that the head-end and foot-end vertical translation subassemblies are different. In particular, the second off-set base 1410 includes two non-identical vertical translation subassemblies 20, a foot-end vertical translation subassembly denoted by 20a and a head-end vertical translation subassembly denoted by 20b.

The foot-end vertical translation subassembly 20a is substantially similar to the vertical translation subassemblies 20 of the base 1310. Notably, the foot-end vertical translation subassembly 20a includes lower and upper portions 30, 35, an lower support or base portion 40, an off-set elevator subassembly, a secondary elevator portion 1444, a telescoping riser assembly 45, a rotation subassembly 50, with a rotation motor 55, rotation shaft 54 and rotation block, a connection subassembly 75 and a standard length ladder 100. Additionally, at least a portion of the foot-end vertical translation subassembly 20a electronics (not shown) is housed in a housing 1460 located on the lower support 40, so as to be located below the rotation motor 55.

In contrast, while the head-end vertical translation subassembly 20b is substantially similar to the vertical translation subassemblies 20 of the base 1310 and to the foot-end vertical translation subassembly 20a, the electronics (head end) of the head-end vertical translation subassembly 20b have been moved from the lower support 40, to another location in the head-end vertical translation subassembly 20b. Advantageously, this relocation of at least some of the electronics provides for greater freedom and space for anesthesia personnel to have greater access to a patient's head. During operation of the base 1410, the patient's head stays substantially in the same location, so as to provide optimal access for anesthesia and to prevent accidental removal of anesthesia equipment from the patient, such as might occur if the patient's head moved away from its initial location, such as for example farther away from the associated vertical translation subassembly 20b.

The rotation subassembly 50, of the head-end vertical translation subassembly 20b, has also been moved out of the way of anesthesia personnel. Most notably the rotation motor 55, and additionally or alternatively portions of the secondary elevator portion 1444, has been moved toward the back and underneath the rotation subassembly. For example, as shown in FIGS. 244, 247 and 248, the rotation motor 55 of the foot-end vertical translation subassembly 20a extends outwardly, perpendicularly to the roll axis R, so as to extend over the lower support 40. Portions of the secondary vertical elevator 1444, such as the motor 1444a, may extend in an outboard or rearward direction, so and to be located adjacent to the outboard side of the lower support 40, when the vertical translation subassembly 20a is in its lowest portion. In contrast, as shown in FIGS. 244, 247 and 248, the rotation motor 55 of the head-end vertical translation subassembly 20b does not extend over the associated lower support 40. The top surface of the lower support 40 includes a downwardly extending recessed portion or area 40a that provides a space, chamber or clearance region, the opening and sides of which are sized and shaped to receive therein the lower end of the motor 1444, 55, whereby the lower end of the motor 1444, 55 is substantially prevented from bumping into the lower support 40 when the vertical translation subassembly 20b is in its lowest position. This enables the rotation block 57 to be lowered closer to the floor than if there was no such recessed portion 40a.

FIGS. 249 through 253, illustrate the modified rotation subassembly 1550, with at least some portions of the rotation motor 55 extending behind and below the rotation subassembly housing 60. The portions of the worm gear drive system, generally 392, are shown. The rotation block 1557 and ladder 100 are similar to the rotation block and ladder described in U.S. Provisional Patent Application No. 61/743,240, which was filed on Aug. 29, 2012 and entitled "Patient Positioning Support Apparatus With Virtual Pivot Sift Pelvic Pads, Upper Body Stabilization And Fail-Safe Table Attachment Mechanism," as well as in U.S. Provisional Patent Application No. 61/849,035, filed on Jan. 17, 2013 and entitled "Patient Positioning Support Apparatus With Virtual Pivot-Shift Pelvic Pads, Upper Body Stabilization And Fail-Safe Table Attachment Mechanism," both of which are incorporated by reference herein in their entirety.

The base 1410 includes a telescoping or retractable cross-bar 25', instead of a stationary cross-bar 25. The telescoping cross-bar 25' can be closed or retracted, such that the vertical translation subassemblies 20 can be moved closer together, such as for storage or for adjusting the distance between the vertical translation subassemblies 20 to accommodate a shorter patient, such as but not limited to a child. When in use, the telescoping cross-bar 25' is reversibly locked, such that the length of the telescoping cross-bar 25' is not changeable. Accordingly, when the base 1410 is in use, the telescoping cross-bar 25' cannot be substantially lengthened or shortened, such that the vertical translation subassemblies 20 remain substantially non-movable, or in substantially in the same location or place. It is foreseen that the telescoping cross-bar 25' may be removable, or the base 1410 may include a non-telescoping cross-bar 25, such as is described elsewhere herein. It is foreseen that the telescoping base 25' may be incorporated into the base of any other patient positioning and support system known in the art.

Referring now to FIGS. 240-254, and in particular to FIGS. 250-254, the rotation block 1557 includes a new fail-safe table attachment subassembly, generally 15135, which includes a ladder engagement pin 15140, that is received into a pin engagement channel, generally 15145, of the block 1557 and also into a pin engagement through-bore 15150 if the ladder 100. Accordingly, the ladder engagement pin 15140 reversibly joins the block 1557 with the ladder 100, such as is shown in FIG. 251. The fail-safe table attachment subassembly 15135 also includes a locking ladder attachment member 15120 attached on the outboard side of the rotation block 1557, and that releasably locks the upper cross-bar 15155 of the ladder 100 into the block's cross-bar receiving groove 15160. The fail-safe table attachment subassembly 15135 includes a reversibly opening, spring-loaded lock member, generally 15165, which includes a housing 15170, a reversibly locking hook member 15175 and a spring member 15180. As shown in FIGS. 252 and 253, the housing includes an inwardly extending housing recess portion or area 15185 that is sized and shaped to house or receive therein the spring 15180 and the inner portion 15190 of the hook member 15175. The housing recess portion 15185 includes a surface 15195. The spring 15180 engages an axle or pin 15200 at each of its ends 15205. The bottom pin 15210 is attached to the hook member inner portion 15190, and the top pin 15251 is located in an upper area of the housing recess portion 15185. The bottom and top pins 15210, 15215 are spaced apart such that the spring 15180 is biased, and therefore pulls the hook member 15175 into a locked position. When the hook member 15175 is in the locked position, its inner engagement surface 15185 engages or contacts the outer surface 15190 of the upper cross-bar 15155, such as is shown in FIG. 251. The spring is sufficiently strong that the hook member 15175 is strongly pulled into the locked position. To release or remove the upper cross-bar 15155 from the channel 15160, the operator must firmly push the hook member 15175 upward or away from the channel 15160 and the cross-bar 15155. Then the ladder can be swung in and inwardly direction, such that the cross-bar is moved out of the channel 15160, such as is shown and described elsewhere herein. When release by the operator, the spring returns the hook member 15175 to the closed position. Installing the ladder 100 onto the rotation block 1557 is performed in the reverse order. Importantly, the operator must open the hook member 15175, such that the cross-bar 15155 can be swung into the channel 15160. It is noted that both of the hook members 15175 associated with a given channel 15160 must be opened simultaneously, in order for the cross-bar 15155 to be inserted into or removed from the respective channel 15160. This failsafe locking structure substantially prevents inappropriate detachment of the ladder from the rotation block, which could result in the patient support falling and a patient thereon being injured, as well as the patient support or the base 1310, 1410 being damaged. It is foreseen that the failsafe table attachment subassembly 15135 may be incorporated into this base 1410, the base 1310, or any other base known in the art that is adapted to reversibly attach to and support a patient support structure.

FIGS. 255a-287 illustrate yet another embodiment 1600 of a patient support structure 15°. The prone patient support structure 1600 is similar to the patient support structures 15° described above, the descriptions of which are incorporated herein by reference. Accordingly, the numbering of components of the patient support structure 1600 will be numbered similarly to the patient support structures 15° described above.

The patient support structure 1600 of the illustrated embodiment is a prone patient support structure 15 with a head-end 18, a foot end 19, a frame 296, left-hand and right-hand sides 298, 300, a head-end 302, a foot-end 304, a left-hand frame portion or spar 306, a right-hand frame portion 308, a head-end frame member 310 that joins the head-ends of the left- and right-hand frame portions 308, 308, a foot-end frame member 312 that joins the foot-ends of the left- and right-hand frame portions 308, 308, an attachment structure 314 for attachment of the head- or foot-ends 302, 304 of the frame 296 with a ladder 100 or 100', a translation compensation subassembly 320 with a translation bar 322, a translation compensation subassembly driver 324, spaced apart opposed joints 326 of a pivot-shift mechanism similar to that described above, hip pads 268, hip pad mounts 338, and a torso support structure 1700 with a support boy or frame 364, a face shield 366, a chest pad 368 and adjustable arm boards 372. The torso support structure 1700 is described in greater detail below, after the description of the patient support structure 1600. It is foreseen that, in certain circumstances, the patient support structure 1600 may include a lower extremity support structure 344 joined with the joints 326, such as is described above. It is noted that the foot-end portion of each of the left-hand and right-hand portions 306, 308 may be wider than the head-end portions thereof, such as but not limited to so as to accommodate a lower extremity support structure 344 therebetween.

FIGS. 255a, 255b, 256 and 257 are forward top perspective views of the patient support structure 1600, including the torso support structure 1700, which may also be referred to as a chest slide or translator. The patient support structure 1600 is a prone patient support structure 15 for use with a base 10, such as is disclosed above, or with any other useful base with a pair of opposed vertical translation subassemblies 20 between which the patient support structure 1600 can be suspended above the floor F, such as but not limited to by connection subassemblies 75 and ladders 100, 100' described above.

The patient support structure 1600 includes a frame 296 with a left-hand frame portion 306 and a right-hand frame portions 308. Each of the left-hand and right-hand frame portions 306, 308 includes a head-end member and a foot-end member joined by a joint 326. The head-end and foot-end members of the left-hand frame portion 306 are denoted by 306A and 306B, respectively. Similarly, the head-end and foot-end members of the right-hand frame portion 308 are denoted by 308A and 308B, respectively. Thus, the left-hand frame portion 306 includes a head-end frame member 306A joined at its inboard end 306A' to the inboard end 306B' of a foot-end frame member 306B by an intervening joint 326. Similarly, the right-hand frame portion 308 includes a head-end frame member 308A joined at its inboard end 308A' to the inboard end 308B' of a foot-end frame member 308B by another intervening joint 326. The outboard end 306A" of the left-hand head-end frame member 306A is joined to the outboard end 308A" of the right-hand head-end frame member 308A by the head-end frame member 310. The outboard end 306B" of the left-hand foot-end frame member 306B is joined to the outboard end 308B" of the right-hand foot-end frame member 308B by the foot-end frame member 312. The head-end frame member 310 and the foot-end frame member 312 hold the left-hand frame portion 306 and the right-hand frame portion 308 in spaced relation to one another such that they are parallel with one another and form an open frame 296. Further, the joints 326 are spaced and opposed to one another such that the belly of a patient support on the patient support structure 1600 can depend or hang downwardly between the joints 326, such as but not limited to when the patient is positioned in a prone position of the patient support structure 1600, such as is described above. It is noted that in the illustrated embodiment the left and right foot-end frame members 306B and 308B are spaced apart a greater distance than are the left and right head-end frame members 306A and 308A, which is more easily seen in FIGS. 268a-269b.

In the illustrated embodiment, a pair of hip-thigh pads 286 are joined with the joins 326, such as by mounts 338, such as in the manner described above with regards to the hip-thigh pads 286. The hip pads 286 are contoured so as to support the patient without creating pressure points and to protect the patient from being pinched in the joints 326. Further, the hip pads 286 are spaced apart so that the patients's belly can hand downwardly therebetween. The hip pads 286 can be covered with disposable drapes. It is foreseen that a sling structure can be joined to the hip pads 286 or the hip pad mounts 338, such as to provide additional support to the patient's torso, or to accommodate a particularly small patient, such as a child, and the like. It is foreseen that in some circumstances, the separate pads 286 can be replaced with a single pad that spans the space between the joints 326, such as so as to prevent the patient's belly from hanging down between the joints 326.

This hip pads 286 and the joints are adapted so as to provide a virtual pivot point 248 and an arc of motion AOM, such as is described above, so as to enable flexion and extension of the patient's hips and spine with respect to the first pivot axis P1, such as is described above. In the illustrated embodiment, the joints 326 include a worm drive 392 with a worm 398 and a worm hear 400, such as is described above. The worm 398 is covered by a shroud 349 or a frame portion 396. The worm 398 is operated by a drive tether subassembly 1602. The drive tether subassembly 1602 includes a first tether member 1604 attached to and optionally integral with, the worm 398 and a second tether member 1606. The first and second tether members 1604 and 1606 are joined by a tether joint 1608, such as but not limited to a universal joint structure. The second tether member 1606 is a shaft that extends longitudinally through the associated foot-end frame member 306B, 308B, such that the second end 1610 of the respective second tether member 1606 joins a driver, such as but not limited to a motor and associated electronics (not shown) located in the outboard ends 306B" and 308B" of the foot-end frame member 306B, 308B. In some embodiments, some or all of the motor and associated electronics that actuate the second tether members 1606 are located in the translation compensation subassembly 320, located at the foot end 19 of the patient support structure 1600. Rotation of the second tether member 1606 actuates rotation of the first tether member 1604, which actuates rotation of the worm 398. Actuation of the worms 398 of the two joints 326 is synchronized so that the joints 326 move at the same rate and in the same direction. Additionally, such actuation of the joints 326 is also synchronized with movement of the translation compensation subassembly 320 and with the base 10, such as is described above.

In the illustrated embodiment, with the exception of the respective joints 326, the left-hand and right-hand frame members 306, 308 include a rectangular cross-section and a through-channel or through-bore that extends from about the respective inboard and outboard ends, which are noted above. These through-channels enable electronics and various mechanical components of the patient support structure 1600 to be located therein and extended therethrough, so that a portion of such electronics and mechanical components can be located at the head and foot-ends 18, 19 of the patient support structure 1600. Adapting or configuring the patient support structure 1600 in this manner enables reduction in the size of the various components, such as but not limited to the joints 326, and the like. Advantageously, this configuration of electronics and mechanical components stream-lines and reduces the profile of the patient support structure 1600, which improves access to the surgical site, prevents breakage and contamination of patient support structure components, and the like. It is foreseen that the spars of the frame 298 may have non-rectangular cross-sections, such as are known in the art. Further, it is foreseen that the through-channels, denoted by 306C and 308C, of the left-hand and right-hand frame portions 306, 308 respectively, also referred to as spars or beams, may have rectangular or non-rectangular cross-sections which may vary along the length of the respective through-channel.

The patient support structure 1600 includes a translation compensation subassembly 320 similar to that described above, with a translation compensation bar 322 that slides in and out of each of the outboard ends 306B" and 308B" of the respective foot-end members 306B, 308B. A portion of the translation driver 324 is associated with translation bar 322. Additional portions of the translation driver 324 are located in a housing 324B at the foot end 19 of the patient support structure 1600. In some embodiments, the foot-end frame member 312 includes the housing 324B and the portions of the translation driver 342 housed therein, such as but not limited to a motor and associated electronics. In the illustrated embodiment, a single motor drives the two translation compensation subassemblies 320. It is foreseen that each translation compensation subassembly 320 may include its own motor. Further, the two translation compensation subassemblies 320 may share a motor, some or all electronic components, and the like. The translation compensation subassemblies 320 are powered as described herein and are synchronized with the other components of the patient support structure 1600, such as but not limited to the joints 326. The translation compensation subassemblies 320 are also synchronized with the base 10, such that the patient support structure 1600 can be positioned in numerous positions for various surgical procedures, such as are described elsewhere herein.

As noted above, the patient support structure 1600 includes a torso support structure 1700, also referred to as a chest slide, a trunk translator and an upper body support and translator. The torso support structure 1700 is similar to the torso support structure 362 described above, the description of which is incorporated herein by reference. In particular, the torso support structure 1700 of the illustrated embodiment includes a support body 364, a transparent face shield 366, a chest pad 368 and adjustable arm boards 372.

As is most easily seen in FIGS. 268a-269b and 267-279b, the support body 364 includes a pair of body slider housings 1702. The slider housings 1702 may be referred to as left-hand and right-hand slider housings, first and second slider housings, or as housing members. The terms left-hand and right-hand refer to the left-hand and right-hand sides of the torso support structure 1700 and correspond to the left and right sides of a patient supported on the torso support structure 1700.

Each slider housing 1702 includes a forward end 1704 and a rear end 1706. The forward end 1704 may be referred to as a first end or an outboard end. The rear end 1706 may be referred to as a second end or an inboard end. The slider housings 1702 are rectangular in cross-section. Accordingly, each slider housing 1702 also includes inner and outer sides, 1708 and 1710 respectively, and upper and lower sides, 1712 and 1714 respectively. However, it is foreseen that the slider housings 1702 may have a non-rectangular cross-section.

The slider housings 1702 each include a through-channel 1716, or through-bore, extending from a first opening 1718 located at the forward end 1704 to a second opening 1720 at the rear end 1706. The through channel 1716 is sized and shaped to slidingly receive a respective left-hand or right-hand head-end member 306A or 308A therethrough, as is described in greater detail below. Since the head-end members 306A, 308A are rectangular in cross-section, the through-channel 1716 is also rectangular in cross-section, with an inner side surface 1722, and outer side surface 1724, and upper side surface 1726 and an outer side surface 1728.

Within each through-channel 1716 is at lest one slider mechanism 1730. In particular, in the illustrated embodiment, each through-channel 1716 includes at least three slider mechanisms 1730. In some embodiments, the through-channel 1716 includes one, two or four slider mechanisms 1730. The slider mechanisms 1730 are located between, or sandwiched between, the head-end member 306A or 308A and a respective side surface of the through-channel 1716. For example, a slider mechanism 1730 is sandwiched between the head-end member 306A, 308A and each of the inner, outer and upper side surfaces 1722, 1724 and 1726 of a respective through-channel 1716. Optionally, a fourth slider mechanism 1730 is sandwiched between the head-end member 306A, 308A and a respective lower side surfaces 1728.

In the illustrated embodiment, the slider mechanisms 1730 extend along the length of the respective inner, outer, upper and lower side surfaces 1722, 1724, 1726 and 1728, and are adapted to enable the torso support structure 1700 to slide along a length of the head-end members 306A, 308A. Namely, the slider mechanisms 1730 are adapted enable the slider housing 1702 to slide or glide along a length of the respective head-end member 306A, 308A, whereby the torso support structure 1700 is slidingly moved along a length of the frame 296 of the patient support structure 1600.

The torso support structure 1700 also includes a translation mechanism, generally 1732, associated with each of the slider housings 1702. Each translation mechanism 1732 is linked, attached to or associated with the head-end frame member 310 of the frame 296. In the illustrated embodiment, as is most easily seen in FIG. 269a, the translation mechanisms 1732 are located on the lower or bottom sides of the respective head-end member 306A, 308A and linked to the lower side 1714 of the respective slider housing 1702 by a tether 1734 described below. It is foreseen that at least a portion of the translation mechanism 1732 may be located elsewhere in or on the torso support structure 1700 or on the patient support structure 1600.

The translation mechanism 1732 includes a driver (not shown) for actuating movement of the torso support structure 1700. A tether 1734 links the driver of the translation mechanism 1732 with the slider housing 1702. The driver drives movement of the tether 1734 in and out of the translation mechanism housing 1736, such as forward and backward, so as to actuate movement of the attached slider housing 1702 along a length of the respective head-end member 306A, 308A. Actuation of the driver, or movement of the tethers 1734, is synchronized with movements of other portions of the patient support structure 1600, such as but not limited to the joints 326. This synchronization is adapted to substantially maintain the distance between the chest pad 368 and the hip-thigh pads 286, or the distance D2 between the chest pad 368 and the virtual pivot points 248, or the first pitch axis P1, which can be most easily seen in FIG. 68.

Each body slider housing 1702 includes a manual adjustment structure, generally 1742, for manually adjusting the distance D2 between the chest pad 368 and the hip-thigh pads 286. In the illustrated embodiment, the manual adjustment structure 1741 includes an adjustment track 1744, or strip, with a series of sequential or incremental selection portions 1744, or openings or through-bores, which is attached to the lower side 1714 of the slider housing 1702.

The head-end of the adjustment track 1744 is attached, joined or linked with the tether 1734. The foot-end of the adjustment track 1744 is associated with the slider housing 1702. The slider housing 1702 is linked to or engaged with the adjustment track 1744 by a selection member 1748, such as a spring-laded pin or handle, that is received through one of the incremental selection portions 1746, such as is most easily seen in FIG. 279a. To adjust the position of the slider housing 1702, the selection member 1748 is pulled out of the respective engaged selection portion 1746, the slider housings 1702 are moved forward or rearward along the head-end members 306, 308 until the desired distance D2 is achieved or reached, and then the selection member 1748 is re-engaged in a new incremental selection portion 1746 that is substantially aligned therewith. Accordingly, the position of the torso support structure 1700 can be incrementally manually adjusted along a length of the frame 296, so as to provide optimal support to a patient's upper body and so as to substantially maintain the distance D2 between the first pitch axis P1 and the torso support structure 1700. Alternative manual adjustment structures 1742 are forseen.

It is noted that the driver of the translation mechanism 1732 includes a motor, such as but not limited to a servo motor, or any other suitably sized and powerful motor known in the art. It is foreseen that the translation mechanism 1732 may include alternative tethers 1734 than are depicted in the figures, such as but not limited to a chain driver structure or a worm drive structure.

It is foreseen that the slider mechanism 1730 may be a single slider mechanism 1730 that surrounds at least three sides of the head-end member 306A or 308A. It is foreseen that numerous alternative slider mechanisms 1730 known in the art may be used instead of the slider mechanisms 1730 described herein.

The forward ends 1704 of the body slider housings 1702 of the support body 364 are joined by a cross-member 1738. In the illustrated embodiment, the cross-member 1738 is substantially rigid, able to support at least the weight of a patient's head and upper body, and resilient or resistant to breakage. In the illustrated embodiment, the cross-member 1738 includes a pair of arms 1740 that wrap around the outer sides 1712 of the slider housings 1702.

It is to be understood that while certain forms of the present invention have been illustrated and described herein, it is not to be limited to the specific forms or arrangement of parts described and shown.

What is claimed is:

1. A base structure for supporting a patient support structure above a floor, the base structure comprising:
a head end support structure comprising a head end lower portion and a head end upper portion, the head end upper portion configured to change elevation relative to the floor;
a foot end support structure opposite the head end support structure and comprising a foot end lower portion and a foot end upper portion, the foot end upper portion configured to change elevation relative to the floor;
a cross-bar extending between the head end support structure and the foot end support structure;
a head end rotation assembly rotatably coupled with the head end support structure, the head end rotation assembly comprising a head end motor, a head end rotation shaft rotatably coupled to the head end motor, and a head end rotation block pivotally coupled to the head end rotation shaft via a head end yaw pin, the head end yaw pin extending through the head end rotation shaft, the head end rotation block configured to operably couple with a head end of the patient support structure, the head end motor configured to rotate the head end shaft, the head end rotation block, and the patient support structure about a head end rotation axis extending through the head end rotation shaft, the head end rotation block configured to pivot about a head end yaw axis extending through the head end yaw pin, the head end rotation axis oriented perpendicular to the head end yaw axis; and a foot end rotation assembly rotatably coupled with the foot end support structure, the foot end rotation assembly comprising a foot end motor, a foot end rotation shaft rotatably coupled to the foot end motor, and a foot end rotation block pivotally coupled to the foot end rotation shaft via a foot end yaw pin, the foot end rotation block configured to operably couple with a foot end of the patient support structure, the foot end motor configured to rotate the foot end shaft, the foot end rotation block, and the patient support structure about a foot end rotation axis extending through the foot end rotation shaft, the foot end rotation block configured to pivot about a foot end yaw axis extending through the foot end yaw pin, the foot end rotation axis oriented perpendicular to the foot end yaw axis.

2. The base structure of claim 1, wherein the head end support structure is configured to vertically translate along a head end vertical translation axis, the foot end support structure is configured to vertically translate along a foot end vertical translation axis, the head end yaw axis being parallel with the head end vertical translation axis when the patient support structure is in a neutral position, the foot end yaw axis being parallel with the foot end vertical translation axis when the patient support structure is in the neutral position.

3. The base structure of claim 1, wherein the head end yaw axis remains oriented perpendicular to the head end rotation axis during rotation of the head end shaft, head end rotation block, and the patient support structure, the foot end yaw axis remains oriented perpendicular to the foot end rotation axis during rotation of the foot end shaft, foot end rotation block, and the patient support structure.

4. The base structure of claim 1, further comprising a head end ladder connection assembly coupled between the head end rotation block and the head end of the patient support structure, the head end of the patient support structure is coupled to the head end ladder connection assembly via a head end T-pin and is configured to pivot about a head end pitch axis extending through the head end T-pin, the head end pitch axis oriented perpendicular to the head end yaw axis, and the base further comprising a foot end ladder connection assembly coupled between the foot end rotation block and the foot end of the patient support structure, the foot end of the patient support structure is coupled to the foot end ladder connection assembly via a foot end T-pin and is configured to pivot about a foot end pitch axis extending through the foot end T-pin, the foot end pitch axis oriented perpendicular to the foot end yaw axis.

5. The base structure of claim 1, further comprising a head end base structure and a foot end base structure, the head end support structure supported on the head end base structure, the foot end support structure supported on the foot end base structure, wherein the cross-bar couples the head end base structure and the foot end base structure, and wherein the head end support structure and the foot end support structure are laterally off-set from each other on opposite sides of the crossbar.

6. The base structure of claim 1, wherein the head end rotation assembly is rotatably coupled with the head end support structure at the head end upper portion, and the foot end rotation assembly is rotatably coupled with the foot end support structure at the foot end upper portion.

7. The base structure of claim 1, further comprising the patient support structure.

8. The base structure of claim 7, wherein the patient support structure comprises a hinge intermediate the head end and foot end.

9. The base structure of claim 1, wherein the head end support structure and the foot end support structure each comprise a motor.

10. The base structure of claim 1, wherein the cross-bar is adjustable lengthwise between the head end support structure and the foot end support structure.

11. A base structure for supporting a patient support structure above a floor, the base structure comprising:

a head end support structure supported on a head end base structure, the head end support structure configured to extend and retract relative to the head end base structure;

a foot end support structure supported on a foot end base structure, the foot end support structure configured to extend and retract relative to the foot end base structure;

a cross-bar coupling the head end support structure and the foot end support structure in spaced-apart relation to each other;

a head end rotation assembly rotatably coupled with the head end support structure and comprising a head end rotation block operably coupled with a head end of the patient support structure, the head end of the patient support structure configured to pivot relative to the head end rotation assembly about a head end pivot axis, the head end rotation assembly comprising a rotation shaft configured to rotate the patient support structure about a head end rotation axis that is perpendicular to the head end pivot axis, the head end rotation block being pivotably coupled to the rotation shaft via a head end yaw pin that extends through the rotation shaft, the head end yaw pin having a head end yaw axis about which the head end rotation block is configured to pivot; and a foot end rotation assembly rotatably coupled with the foot end support structure and comprising a foot end rotation block operably coupled with a foot end of the patient support structure, the foot end of the patient support structure configured to pivot relative to the foot end rotation assembly about a foot end pivot axis, the foot end rotation assembly configured to rotate the patient support structure about a foot end rotation axis that is perpendicular to the foot end pivot axis, the foot end rotation assembly comprising a foot end yaw pin having a foot end yaw axis about which the foot end rotation block is configured to pivot.

12. The base structure of claim 11, wherein the head end yaw axis is oriented perpendicular to the head end pivot axis and the head end rotation axis, and the foot end yaw axis is oriented perpendicular to the foot end pivot axis and the foot end rotation axis.

13. The base structure of claim 11, wherein the head end support structure is configured to vertically translate along a head end vertical translation axis, the foot end support structure is configured to vertically translate along a foot end vertical translation axis, the head end yaw axis being parallel with the head end vertical translation axis when the patient support structure is in a neutral position, the foot end yaw axis being parallel with the foot end vertical translation axis when the patient support structure is in the neutral position.

14. The base structure of claim 11, wherein the head end yaw axis remains oriented perpendicular to the head end rotation axis during rotation of the head end rotation block and the patient support structure, the foot end yaw axis remains oriented perpendicular to the foot end rotation axis during rotation of the foot end rotation block and the patient support structure.

15. The base structure of claim 11, wherein the head end support structure and the foot end support structure are laterally off-set from each other on opposite sides of the cross-bar.

16. The base structure of claim 15, wherein the head end rotation block and the foot end rotation block are centrally positioned on the head end base structure and the foot end base structure, respectively.

17. The base structure of claim 11, further comprising the patient support structure.

18. The base structure of claim 17, wherein the patient support structure comprises a hinge intermediate the head end and foot end.

19. The base structure of claim 11, wherein the head end support structure and the foot end support structure each comprise a motor.

20. The base structure of claim 11, wherein the cross-bar is adjustable lengthwise between the head end support structure and the foot end support structure.

21. A base structure for supporting a patient support structure above a floor, the base structure comprising:
a head end support structure supported on and extending upwardly from a head end base structure;
a foot end support structure supported on and extending upwardly from a foot end base structure;
a cross-bar coupling the head end base structure and the foot end base structure in spaced-apart relation to each other;
a head end rotation assembly coupled to the head end support structure and comprising a head end rotation block rotatably coupled with the head end rotation assembly via a head end rotation shaft, the head end rotation block being operably coupled with a head end of the patient support structure, the head end of the patient support structure pivotally connected to the head end support structure about a head end pivot axis, the patient support structure configured to rotate about a head end rotation axis extending through the head end rotation shaft, and about a head end yaw axis extending through a head end yaw pin that is spaced-apart from an outer end of the patient support structure, the head end yaw pin extending through the head end rotation shaft, the head end yaw pin being positioned between the outer end of the head end of the patient support structure and the head end support structure; and
a foot end rotation assembly coupled to the foot end support structure and comprising a foot end rotation block rotatably coupled with the foot end rotation assembly via a foot end rotation shaft, the foot end rotation block being operably coupled with a foot end of the patient support structure, the foot end of the patient support structure pivotally connected to the foot end support structure about a foot end pivot axis, the patient support structure configured to rotate about a foot end rotation axis extending through the foot end rotation shaft.

22. The base structure of claim 21, wherein the foot end rotation assembly comprises a foot end yaw pin having a foot end yaw axis about which the foot end rotation block is configured to pivot, the foot end yaw pin spaced-apart from an outer end of the foot end of the patient support structure and positioned between the foot end support structure and the outer end of the foot end of the patient support structure.

23. The base structure of claim 21, wherein the head end yaw pin is positioned between a front face of the head end rotation block and the head end support structure.

24. The base structure of claim 21, wherein the head end support structure comprising a head end lower portion and a head end upper portion, the head end lower portion coupled to the head end base structure, the head end upper portion configured to be raised and lowered relative to the head end lower portion, the foot end support structure comprising a foot end lower portion and a foot end upper portion, the foot end lower portion coupled to the foot end base structure, the foot end upper portion configured to be raised and lowered relative to the foot end lower portion.

25. The base structure of claim 21, wherein the head end yaw axis is perpendicular to the head end rotation axis and the head end pivot axis, and wherein the head end yaw axis intersects the head end rotation axis.

26. The base structure of claim 21, wherein the head end rotation assembly further comprises a head end motor to which the head end shaft is rotatably coupled, the head end motor configured to rotate the head end shaft, the head end rotation block, and the patient support structure.

27. A base structure for supporting a patient support structure above a floor, the base structure comprising:
a head end support structure;
a foot end support structure;
a cross-bar coupling the head end support structure and the foot end support structure in spaced-apart relation to each other;
a head end rotation block coupled with the head end support structure, the head end rotation block having a rotation shaft configured to rotate about a head end rotation axis, the head end rotation block configured to operably couple with a head end of the patient support structure;
a head end yaw pin pivotally coupling the head end rotation block and the head end support structure, the head end rotation block configured to pivot about a head end yaw axis extending through the head end yaw pin, the head end yaw axis being perpendicular to the head end rotation axis, the head end yaw pin extending through the rotation shaft, the head end yaw pin being positioned between the head end of the patient support structure and the head end support structure; and
a foot end rotation block coupled with the foot end support structure, the foot end rotation block having a rotation shaft configured to rotate about a foot end rotation axis, the foot end rotation block configured to operably couple with a foot end of the patient support structure.

28. The base structure of claim 27, wherein the head end rotation block is rotatably coupled with the head end support structure via a head end rotation shaft, and the foot end rotation block is rotatably coupled with the foot end support structure via the foot end rotation shaft.

* * * * *